United States Patent
Bernett et al.

(10) Patent No.: US 11,312,770 B2
(45) Date of Patent: Apr. 26, 2022

(54) BISPECIFIC AND MONOSPECIFIC ANTIBODIES USING NOVEL ANTI-PD-1 SEQUENCES

(71) Applicant: Xencor, Inc., Monrovia, CA (US)

(72) Inventors: Matthew Bernett, Monrovia, CA (US); Gregory Moore, Azusa, CA (US); John Desjarlais, Pasadena, CA (US); Michael Hedvat, Encino, CA (US); Christine Bonzon, Los Angeles, CA (US); Alex Nisthal, Monrovia, CA (US); Umesh Muchhal, Monrovia, CA (US)

(73) Assignee: Xencor, Inc., Monrovia, CA (US)

( * ) Notice: Subject to any disclaimer, the term of this patent is extended or adjusted under 35 U.S.C. 154(b) by 283 days.

(21) Appl. No.: 16/184,895

(22) Filed: Nov. 8, 2018

(65) Prior Publication Data

US 2019/0263909 A1     Aug. 29, 2019

Related U.S. Application Data

(60) Provisional application No. 62/658,227, filed on Apr. 16, 2018, provisional application No. 62/598,938, filed on Dec. 14, 2017, provisional application No. 62/583,438, filed on Nov. 8, 2017.

(51) Int. Cl.
| | |
|---|---|
| *C07K 16/28* | (2006.01) |
| *A61P 35/00* | (2006.01) |
| *C07K 16/46* | (2006.01) |
| *A61K 39/395* | (2006.01) |
| *A61K 39/00* | (2006.01) |

(52) U.S. Cl.
CPC .... *C07K 16/2818* (2013.01); *A61K 39/39541* (2013.01); *A61P 35/00* (2018.01); *C07K 16/2803* (2013.01); *C07K 16/2896* (2013.01); *C07K 16/468* (2013.01); *A61K 2039/505* (2013.01); *C07K 2317/31* (2013.01); *C07K 2317/51* (2013.01); *C07K 2317/515* (2013.01); *C07K 2317/524* (2013.01); *C07K 2317/526* (2013.01); *C07K 2317/622* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 3,773,919 A | 11/1973 | Boswell et al. | |
| 4,169,888 A | 10/1979 | Hanka et al. | |
| 4,179,337 A | 12/1979 | Davis et al. | |
| 4,256,746 A | 3/1981 | Miyashita et al. | |
| 4,294,757 A | 10/1981 | Asai | |
| 4,301,144 A | 11/1981 | Iwashita et al. | |
| 4,307,016 A | 12/1981 | Asai et al. | |
| 4,313,946 A | 2/1982 | Powell et al. | |
| 4,315,929 A | 2/1982 | Freedman et al. | |
| 4,322,348 A | 3/1982 | Asai et al. | |
| 4,331,598 A | 5/1982 | Hasegawa et al. | |
| 4,361,650 A | 5/1982 | Asai et al. | |
| 4,362,663 A | 12/1982 | Kida et al. | |
| 4,364,866 A | 12/1982 | Asai et al. | |
| 4,364,935 A | 12/1982 | Kung et al. | |
| 4,371,533 A | 2/1983 | Akimoto et al. | |
| 4,424,219 A | 1/1984 | Hashimoto et al. | |
| 4,450,254 A | 5/1984 | Isley et al. | |
| 4,496,689 A | 1/1985 | Mitra | |
| 4,640,835 A | 2/1987 | Shimizu et al. | |
| 4,670,417 A | 6/1987 | Iwasaki et al. | |
| 4,791,192 A | 12/1988 | Nakagawa et al. | |
| 4,880,935 A | 11/1989 | Thorpe | |
| 4,923,990 A | 5/1990 | Nakano et al. | |
| 4,943,533 A | 7/1990 | Mendelsohn et al. | |
| 4,970,198 A | 11/1990 | Lee et al. | |
| 5,053,394 A | 10/1991 | Ellestad et al. | |
| 5,070,092 A | 12/1991 | Kanda et al. | |
| 5,084,468 A | 1/1992 | Saito et al. | |
| 5,101,038 A | 3/1992 | Nakano et al. | |
| 5,122,368 A | 6/1992 | Greenfield et al. | |
| 5,187,186 A | 2/1993 | Kanda et al. | |
| 5,208,020 A | 5/1993 | Chari et al. | |
| 5,264,586 A | 11/1993 | Nicolaou et al. | |
| 5,384,412 A | 1/1995 | Nicolaou et al. | |
| 5,416,064 A | 5/1995 | Chari et al. | |
| 5,475,092 A | 12/1995 | Chari et al. | |
| 5,500,362 A | 3/1996 | Robinson et al. | |
| 5,530,101 A | 6/1996 | Queen et al. | |
| 5,541,087 A | 7/1996 | Lo et al. | |
| 5,550,246 A | 8/1996 | Nicolaou et al. | |
| 5,558,864 A | 9/1996 | Bendig et al. | |
| 5,585,089 A | 12/1996 | Queen et al. | |

(Continued)

FOREIGN PATENT DOCUMENTS

| | | |
|---|---|---|
| EP | 0425235 B1 | 9/1996 |
| EP | 1752471 | 2/2007 |

(Continued)

OTHER PUBLICATIONS

Callahan et al. (Journal of Leukocyte Biology, 94:41-53, 2013).*

(Continued)

*Primary Examiner* — Nelson B Moseley, II

(74) *Attorney, Agent, or Firm* — Christopher J. Betti; Morgan, Lewis & Bockius, LLP

(57) ABSTRACT

The present invention is directed to bispecific, heterodimeric checkpoint antibodies.

4 Claims, 288 Drawing Sheets

Specification includes a Sequence Listing.

(56) References Cited

U.S. PATENT DOCUMENTS

| | | |
|---|---|---|
| 5,585,097 A | 12/1996 | Bolt et al. |
| 5,585,499 A | 12/1996 | Chari et al. |
| 5,622,929 A | 4/1997 | Willner et al. |
| 5,635,483 A | 6/1997 | Pettit et al. |
| 5,641,780 A | 6/1997 | Amishiro et al. |
| 5,663,149 A | 9/1997 | Pettit et al. |
| 5,677,171 A | 10/1997 | Hudziak et al. |
| 5,693,761 A | 12/1997 | Queen et al. |
| 5,693,762 A | 12/1997 | Queen et al. |
| 5,703,080 A | 12/1997 | Nakakura et al. |
| 5,712,374 A | 1/1998 | Kuntsmann et al. |
| 5,714,586 A | 2/1998 | Kuntsmann et al. |
| 5,726,044 A | 3/1998 | Lo et al. |
| 5,731,168 A | 3/1998 | Carter et al. |
| 5,736,137 A | 4/1998 | Anderson et al. |
| 5,739,116 A | 4/1998 | Hamann et al. |
| 5,767,237 A | 6/1998 | Sakakibara et al. |
| 5,767,285 A | 6/1998 | Hamann et al. |
| 5,770,701 A | 6/1998 | McGahren et al. |
| 5,770,710 A | 6/1998 | McGahren et al. |
| 5,773,001 A | 6/1998 | Hamann et al. |
| 5,780,588 A | 7/1998 | Pettit et al. |
| 5,807,706 A | 9/1998 | Carter et al. |
| 5,821,333 A | 10/1998 | Carter et al. |
| 5,821,337 A | 10/1998 | Carter et al. |
| 5,824,805 A | 10/1998 | King et al. |
| 5,846,545 A | 12/1998 | Chari et al. |
| 5,859,205 A | 1/1999 | Adair et al. |
| 5,877,291 A | 3/1999 | Mezes et al. |
| 5,877,296 A | 3/1999 | Hamann et al. |
| 5,891,996 A | 4/1999 | Mateo de Acosta del Rio et al. |
| 5,892,020 A | 4/1999 | Mezes et al. |
| 5,945,311 A | 8/1999 | Lindhofer et al. |
| 5,968,509 A | 10/1999 | Gorman et al. |
| 6,054,297 A | 4/2000 | Carter et al. |
| 6,071,515 A | 6/2000 | Mezes et al. |
| 6,124,431 A | 9/2000 | Sakakibara et al. |
| 6,180,370 B1 | 1/2001 | Queen et al. |
| 6,214,345 B1 | 4/2001 | Firestone et al. |
| 6,235,883 B1 | 5/2001 | Jakobovits et al. |
| 6,329,507 B1 | 12/2001 | Mezes et al. |
| 6,407,213 B1 | 6/2002 | Carter et al. |
| 6,441,163 B1 | 8/2002 | Chari et al. |
| 6,455,677 B1 | 9/2002 | Park et al. |
| 6,506,883 B2 | 1/2003 | Meteo de Acosta del Rio et al. |
| 6,602,684 B1 | 8/2003 | Umana et al. |
| 6,632,927 B2 | 10/2003 | Adair et al. |
| 6,706,265 B1 | 3/2004 | Bolt et al. |
| 6,716,410 B1 | 4/2004 | Witztum |
| 6,723,538 B2 | 4/2004 | Mack et al. |
| 6,884,869 B2 | 4/2005 | Senter et al. |
| 6,989,452 B2 | 1/2006 | Ng et al. |
| 7,087,600 B2 | 8/2006 | Ng et al. |
| 7,112,324 B1 | 9/2006 | Dorken et al. |
| 7,129,261 B2 | 10/2006 | Ng et al. |
| 7,276,497 B2 | 10/2007 | Chari et al. |
| 7,303,749 B1 | 12/2007 | Chari |
| 7,368,565 B2 | 5/2008 | Chari et al. |
| 7,498,302 B2 | 3/2009 | Ng et al. |
| 7,507,420 B2 | 3/2009 | Ng et al. |
| 7,517,903 B2 | 4/2009 | Chen et al. |
| 7,601,354 B2 | 10/2009 | Chari |
| 7,642,228 B2 | 1/2010 | Carter et al. |
| 7,691,962 B2 | 4/2010 | Boyd et al. |
| 7,695,936 B2 | 4/2010 | Carter et al. |
| 7,696,338 B2 | 4/2010 | Neville, Jr. et al. |
| 7,728,114 B2 | 6/2010 | Mach et al. |
| 8,063,187 B2 | 11/2011 | Chu et al. |
| 8,114,967 B2 | 2/2012 | Bhatt et al. |
| 8,216,805 B2 | 7/2012 | Carter et al. |
| 8,236,308 B2 | 8/2012 | Kischel et al. |
| 8,309,690 B2 | 11/2012 | Allan et al. |
| 8,367,805 B2 | 2/2013 | Chamberlain et al. |
| 8,409,568 B2 | 4/2013 | Gao et al. |
| 8,592,562 B2 | 11/2013 | Kannan et al. |
| 8,637,641 B2 | 1/2014 | Dahiyat et al. |
| 8,946,387 B2 | 2/2015 | Koenig et al. |
| 9,822,181 B2 | 11/2017 | Bonvini et al. |
| 9,856,327 B2 | 1/2018 | Bernett et al. |
| 10,787,518 B2 | 9/2020 | Bernett et al. |
| 2001/0035606 A1 | 11/2001 | Schoen |
| 2002/0076406 A1 | 6/2002 | Leung |
| 2002/0103345 A1 | 8/2002 | Zhu |
| 2002/0131968 A1 | 9/2002 | Waldmann et al. |
| 2003/0003097 A1 | 1/2003 | Reff et al. |
| 2003/0017979 A1 | 1/2003 | Mack et al. |
| 2003/0091561 A1 | 5/2003 | Van de Winekl |
| 2003/0157108 A1 | 8/2003 | Presta |
| 2003/0223999 A1 | 12/2003 | Lindhofer |
| 2004/0018191 A1 | 1/2004 | Wang |
| 2004/0071696 A1 | 4/2004 | Adams et al. |
| 2004/0162411 A1 | 8/2004 | Lanzavecchia |
| 2004/0170626 A1 | 9/2004 | Schuurman |
| 2004/0242851 A1 | 12/2004 | Zhu |
| 2005/0114037 A1 | 5/2005 | Desjarlais et al. |
| 2005/0136050 A1 | 6/2005 | Kufer et al. |
| 2005/0142133 A1 | 6/2005 | Lazar et al. |
| 2005/0176028 A1 | 8/2005 | Hofmeiser et al. |
| 2005/0191702 A1 | 9/2005 | Mack et al. |
| 2005/0238648 A1 | 10/2005 | Jacobs |
| 2005/0238649 A1 | 10/2005 | Doronina |
| 2006/0008883 A1 | 1/2006 | Lazar |
| 2006/0018897 A1 | 1/2006 | Lee et al. |
| 2006/0024298 A1 | 2/2006 | Lazar et al. |
| 2006/0024317 A1 | 2/2006 | Boyd |
| 2006/0073142 A1 | 4/2006 | Chan et al. |
| 2006/0074008 A1 | 4/2006 | Senter |
| 2006/0115481 A1 | 6/2006 | Lindhofer et al. |
| 2006/0121032 A1 | 6/2006 | Dahiyat et al. |
| 2006/0134105 A1 | 6/2006 | Lazar et al. |
| 2006/0235208 A1 | 10/2006 | Lazar |
| 2007/0071675 A1 | 3/2007 | Wu et al. |
| 2007/0105199 A1 | 5/2007 | Yan et al. |
| 2007/0123479 A1 | 5/2007 | Kufer et al. |
| 2007/0148170 A1 | 6/2007 | Desjarlais |
| 2007/0287170 A1 | 12/2007 | Davis et al. |
| 2008/0044413 A1 | 2/2008 | Hammond et al. |
| 2008/0050370 A1 | 2/2008 | Glaser et al. |
| 2008/0138335 A1 | 6/2008 | Takahashi et al. |
| 2008/0213273 A1 | 9/2008 | Burge |
| 2008/0219974 A1 | 9/2008 | Bernett et al. |
| 2008/0242845 A1 | 10/2008 | Lazar et al. |
| 2009/0082213 A1 | 3/2009 | Horowitz et al. |
| 2009/0163699 A1 | 6/2009 | Desjarlais |
| 2009/0214539 A1 | 8/2009 | Grosmaire et al. |
| 2009/0252683 A1 | 10/2009 | Kischel et al. |
| 2009/0252729 A1 | 10/2009 | Farrington et al. |
| 2009/0274692 A1 | 11/2009 | Tan et al. |
| 2009/0311253 A1 | 12/2009 | Ghayur et al. |
| 2009/0317869 A1 | 12/2009 | Alley et al. |
| 2010/0004431 A1 | 1/2010 | Bernett et al. |
| 2010/0015133 A1 | 1/2010 | Igawa et al. |
| 2010/0080814 A1 | 4/2010 | Desjarlais et al. |
| 2010/0150918 A1 | 6/2010 | Kufer et al. |
| 2010/0174053 A1 | 7/2010 | Johnson et al. |
| 2010/0178298 A1 | 7/2010 | Lindhofer |
| 2010/0183554 A1 | 7/2010 | Mach et al. |
| 2010/0226925 A1 | 9/2010 | Dillon et al. |
| 2010/0239567 A1 | 9/2010 | Esue |
| 2010/0239582 A1 | 9/2010 | Humphreys et al. |
| 2010/0256339 A1 | 10/2010 | Bossenmaier et al. |
| 2010/0256340 A1 | 10/2010 | Brinkmann et al. |
| 2010/0298542 A1 | 11/2010 | Igawa et al. |
| 2010/0322933 A1 | 12/2010 | Lindhofer et al. |
| 2010/0330089 A1 | 12/2010 | Damle et al. |
| 2010/0331527 A1 | 12/2010 | Davis et al. |
| 2011/0054151 A1 | 3/2011 | Lazar et al. |
| 2011/0076275 A1 | 3/2011 | Igawa et al. |
| 2011/0177500 A1 | 7/2011 | Winther et al. |
| 2011/0189178 A1 | 8/2011 | Desjarlais et al. |
| 2011/0189209 A1 | 8/2011 | Neville, Jr. et al. |
| 2011/0201032 A1 | 8/2011 | Zeng et al. |
| 2011/0217302 A1 | 9/2011 | Odegard et al. |
| 2011/0262439 A1 | 10/2011 | Kufer et al. |

(56) References Cited

U.S. PATENT DOCUMENTS

| | | |
|---|---|---|
| 2011/0275787 A1 | 11/2011 | Kufer et al. |
| 2011/0293619 A1 | 12/2011 | Kufer et al. |
| 2012/0028304 A1 | 2/2012 | Dahiyat et al. |
| 2012/0034228 A1 | 2/2012 | Kufer et al. |
| 2012/0121597 A1 | 5/2012 | Ho et al. |
| 2012/0149876 A1 | 6/2012 | Von Kreudenstein et al. |
| 2012/0156207 A1 | 6/2012 | Chu et al. |
| 2012/0251531 A1 | 10/2012 | Baehner et al. |
| 2012/0251541 A1 | 10/2012 | Baurin et al. |
| 2013/0089541 A1 | 4/2013 | D'Angelo et al. |
| 2013/0095097 A1 | 4/2013 | Blakenship et al. |
| 2013/0101586 A1 | 4/2013 | Riegler et al. |
| 2013/0115208 A1 | 5/2013 | Ho et al. |
| 2013/0129723 A1 | 5/2013 | Blakenship et al. |
| 2013/0142793 A1 | 6/2013 | Ledbetter et al. |
| 2013/0171095 A1 | 7/2013 | Bernett et al. |
| 2013/0195849 A1 | 8/2013 | Von Kreudenstein et al. |
| 2013/0209355 A1 | 8/2013 | De Weers et al. |
| 2013/0267686 A1 | 10/2013 | Brinkmann |
| 2013/0336981 A1 | 12/2013 | de Kruif et al. |
| 2014/0024111 A1 | 1/2014 | Kannan et al. |
| 2014/0056879 A1 | 2/2014 | Lazar |
| 2014/0072581 A1 | 3/2014 | Dixit et al. |
| 2014/0086916 A1 | 3/2014 | Zha |
| 2014/0212435 A1 | 7/2014 | Moore et al. |
| 2014/0212436 A1 | 7/2014 | Moore et al. |
| 2014/0249297 A1 | 9/2014 | Lazar et al. |
| 2014/0288275 A1 | 9/2014 | Moore et al. |
| 2014/0294759 A1 | 10/2014 | Chu et al. |
| 2014/0294823 A1 | 10/2014 | Moore et al. |
| 2014/0294833 A1 | 10/2014 | Desjarlais et al. |
| 2014/0294835 A1 | 10/2014 | Moore et al. |
| 2014/0294836 A1 | 10/2014 | Chu et al. |
| 2014/0302064 A1 | 10/2014 | Moore |
| 2014/0322217 A1 | 10/2014 | Moore et al. |
| 2014/0356381 A1 | 12/2014 | Moore et al. |
| 2014/0363426 A1* | 12/2014 | Moore ............ C07K 16/2809 424/133.1 |
| 2014/0370013 A1 | 12/2014 | Desjarlais et al. |
| 2014/0370020 A1 | 12/2014 | Kuramochi et al. |
| 2014/0377269 A1 | 12/2014 | Mabry et al. |
| 2014/0377270 A1 | 12/2014 | Moore et al. |
| 2015/0071948 A1 | 3/2015 | Lazar et al. |
| 2015/0259420 A1* | 9/2015 | Triebel ................ A61P 35/00 424/136.1 |
| 2015/0307629 A1 | 10/2015 | Bernett et al. |
| 2016/0060360 A1 | 3/2016 | Moore et al. |
| 2016/0068588 A1 | 3/2016 | Bernett et al. |
| 2016/0176969 A1 | 6/2016 | Bernett et al. |
| 2016/0215063 A1 | 7/2016 | Bernett et al. |
| 2016/0229924 A1 | 8/2016 | Bernett et al. |
| 2017/0020963 A1 | 1/2017 | Qu et al. |
| 2018/0118828 A1 | 5/2018 | Bernett et al. |
| 2018/0127501 A1 | 5/2018 | Bernett et al. |
| 2018/0289771 A1 | 10/2018 | Shan et al. |
| 2019/0382495 A1 | 12/2019 | Bernett et al. |
| 2019/0389954 A1 | 12/2019 | Bernett et al. |

FOREIGN PATENT DOCUMENTS

| | | |
|---|---|---|
| EP | 1829895 | 5/2007 |
| EP | 2006381 | 12/2008 |
| EP | 2009101 A1 | 12/2008 |
| EP | 2194066 | 6/2010 |
| EP | 2202245 A1 | 6/2010 |
| EP | 2522724 | 6/2011 |
| EP | 2155788 | 2/2014 |
| EP | 3252078 | 12/2017 |
| WO | WO8705330 | 9/1987 |
| WO | WO9211018 | 7/1992 |
| WO | WO9321232 | 10/1993 |
| WO | WO9413804 | 5/1994 |
| WO | WO9520045 | 1/1995 |
| WO | WO9640210 | 6/1996 |
| WO | WO96027011 | 9/1996 |
| WO | WO98050431 | 11/1998 |
| WO | WO199937791 | 7/1999 |
| WO | WO99054440 | 10/1999 |
| WO | WO99066951 | 12/1999 |
| WO | WO200061739 A1 | 10/2000 |
| WO | WO200124763 A2 | 4/2001 |
| WO | WO200129246 A1 | 4/2001 |
| WO | WO200162931 A1 | 8/2001 |
| WO | WO200188138 | 11/2001 |
| WO | WO2001083525 | 11/2001 |
| WO | WO2001090192 | 11/2001 |
| WO | WO200216368 | 2/2002 |
| WO | WO200230954 A1 | 4/2002 |
| WO | WO200231140 A1 | 4/2002 |
| WO | WO2002088172 A2 | 7/2002 |
| WO | WO2002062850 | 8/2002 |
| WO | WO2002083180 | 10/2002 |
| WO | WO2002098883 | 12/2002 |
| WO | WO2004010957 | 2/2004 |
| WO | WO2004043493 | 5/2004 |
| WO | WO2004103272 | 12/2004 |
| WO | WO2004106383 | 12/2004 |
| WO | WO2005063816 | 7/2005 |
| WO | WO2005112919 A2 | 12/2005 |
| WO | WO2005118635 | 12/2005 |
| WO | WO2006020258 | 2/2006 |
| WO | WO2006034488 | 3/2006 |
| WO | WO2006036834 | 4/2006 |
| WO | WO2006072620 | 7/2006 |
| WO | WO2006110476 A2 | 10/2006 |
| WO | WO2006106905 | 12/2006 |
| WO | WO2007005612 | 1/2007 |
| WO | WO2007018431 A2 | 2/2007 |
| WO | WO2007033230 | 3/2007 |
| WO | WO2007042261 | 4/2007 |
| WO | WO2007046006 | 4/2007 |
| WO | WO2007047829 | 4/2007 |
| WO | WO2007059404 A2 | 5/2007 |
| WO | WO2007062037 | 5/2007 |
| WO | WO2007084342 | 7/2007 |
| WO | WO2007089149 A2 | 8/2007 |
| WO | WO2007093630 | 8/2007 |
| WO | WO2007098934 | 9/2007 |
| WO | WO2007110205 | 10/2007 |
| WO | WO2007113648 | 10/2007 |
| WO | WO20070147901 | 12/2007 |
| WO | WO2008003103 | 1/2008 |
| WO | WO2008003115 | 1/2008 |
| WO | WO2008003116 | 1/2008 |
| WO | WO2008119096 | 10/2008 |
| WO | WO2008119566 | 10/2008 |
| WO | WO2008124858 | 10/2008 |
| WO | WO2008145142 | 12/2008 |
| WO | WO2008150494 | 12/2008 |
| WO | WO2009000006 | 12/2008 |
| WO | WO2009017394 A1 | 2/2009 |
| WO | WO2009017823 | 2/2009 |
| WO | WO2009030734 | 3/2009 |
| WO | WO2009032782 | 3/2009 |
| WO | WO2009086320 | 7/2009 |
| WO | WO2009089004 | 7/2009 |
| WO | WO2009106096 | 9/2009 |
| WO | WO2009106321 | 9/2009 |
| WO | WO2010028796 | 3/2010 |
| WO | WO2010033736 | 3/2010 |
| WO | WO2010034441 | 4/2010 |
| WO | WO2010037835 | 4/2010 |
| WO | WO2010042904 | 4/2010 |
| WO | WO2010062171 A2 | 6/2010 |
| WO | WO2010085682 | 7/2010 |
| WO | WO2010106180 | 9/2010 |
| WO | WO2010115551 | 10/2010 |
| WO | WO2010115552 | 10/2010 |
| WO | WO2010115553 | 10/2010 |
| WO | WO2010115589 | 10/2010 |
| WO | WO2010119119 | 10/2010 |
| WO | WO20100112193 | 10/2010 |
| WO | WO2010136172 | 12/2010 |

(56) References Cited

FOREIGN PATENT DOCUMENTS

| | | |
|---|---|---|
| WO | WO2010151792 | 12/2010 |
| WO | WO2010151808 | 12/2010 |
| WO | WO2011005621 | 1/2011 |
| WO | WO2011028952 | 3/2011 |
| WO | WO2011036183 | 3/2011 |
| WO | WO2011066342 | 3/2011 |
| WO | WO2011051307 | 5/2011 |
| WO | WO2011063348 | 5/2011 |
| WO | WO2011066501 | 6/2011 |
| WO | WO2011121110 | 10/2011 |
| WO | WO2011131746 | 10/2011 |
| WO | WO2011133886 | 10/2011 |
| WO | WO2011143545 | 11/2011 |
| WO | WO2011159877 | 12/2011 |
| WO | WO2012016227 | 2/2012 |
| WO | WO2012018687 | 2/2012 |
| WO | WO2012032080 | 3/2012 |
| WO | WO2012058768 | 5/2012 |
| WO | WO2012062596 | 5/2012 |
| WO | WO2012107417 | 8/2012 |
| WO | WO2012116453 | 9/2012 |
| WO | WO2012125495 | 9/2012 |
| WO | WO2012125850 | 9/2012 |
| WO | WO2012131555 | 10/2012 |
| WO | WO2012146394 | 11/2012 |
| WO | WO2012146628 | 11/2012 |
| WO | WO2012162067 | 11/2012 |
| WO | WO2013006544 | 1/2013 |
| WO | WO2013016714 | 1/2013 |
| WO | WO2013022855 | 2/2013 |
| WO | WO2013026833 | 2/2013 |
| WO | WO2013033008 | 3/2013 |
| WO | WO2013047748 | 4/2013 |
| WO | WO2013055809 | 4/2013 |
| WO | WO2013063702 | 5/2013 |
| WO | WO2013096828 | 6/2013 |
| WO | WO2013125667 | 8/2013 |
| WO | WO2013164694 | 11/2013 |
| WO | WO2013180201 | 12/2013 |
| WO | WO2014004586 | 1/2014 |
| WO | WO2014012085 | 1/2014 |
| WO | WO2014047231 | 3/2014 |
| WO | WO2014056783 | 4/2014 |
| WO | WO2014079000 | 5/2014 |
| WO | WO2014110601 | 7/2014 |
| WO | WO2014113510 | 7/2014 |
| WO | WO2014145806 | 9/2014 |
| WO | WO2014145907 | 9/2014 |
| WO | WO2014164553 | 10/2014 |
| WO | WO2014207064 | 12/2014 |
| WO | WO2014209804 | 12/2014 |
| WO | WO2015018528 | 2/2015 |
| WO | WO2015026892 | 2/2015 |
| WO | WO2015063339 | 5/2015 |
| WO | WO2015095392 | 6/2015 |
| WO | WO2015095410 | 6/2015 |
| WO | WO2015095423 | 6/2015 |
| WO | WO2015103072 | 7/2015 |
| WO | WO2015143079 | 9/2015 |
| WO | WO2015149077 | 10/2015 |
| WO | WO2015168379 | 11/2015 |
| WO | WO2015184207 | 12/2015 |
| WO | WO2016014984 | 1/2016 |
| WO | WO2016028672 | 2/2016 |
| WO | WO2016028896 | 2/2016 |
| WO | WO2016079050 | 5/2016 |
| WO | WO2016086186 | 6/2016 |
| WO | WO2016086189 | 6/2016 |
| WO | WO2016086196 | 6/2016 |
| WO | WO2016105450 | 6/2016 |
| WO | WO2016110584 | 7/2016 |
| WO | WO2016115274 | 7/2016 |
| WO | WO2016120789 | 8/2016 |
| WO | WO2016141387 | 9/2016 |
| WO | WO2016182751 | 11/2016 |
| WO | WO2017019846 | 2/2017 |
| WO | WO2017112775 | 6/2017 |
| WO | WO2017210443 | 12/2017 |
| WO | WO2017210485 | 12/2017 |
| WO | WO2017214092 | 12/2017 |
| WO | WO2019050521 | 3/2019 |

OTHER PUBLICATIONS

U.S. Appl. No. 12/875,015, 2011-0054151, U.S. Pat. No. 9,493,578, Granted, filed Sep. 2, 2010, Mar. 3, 2011, Nov. 15, 2016.
U.S. Appl. No. 15/279,266, 2017-0058053, Abandoned, filed Sep. 28, 2016, Mar. 2, 2017.
U.S. Appl. No. 16/539,986, Pending, filed Aug. 13, 2019.
U.S. Appl. No. 13/648,951, 2013-0171095, Published, filed Oct. 10, 2012, Jul. 4, 2013.
U.S. Appl. No. 13/194,904, 2012-0028304, U.S. Pat. No. 8,637,641, Granted, filed Jul. 29, 2011, Feb. 2, 2012, Jan. 28, 2014.
U.S. Appl. No. 14/165,487, 2014-0249297, U.S. Pat. No. 9,605,061, Granted, filed Jan. 27, 2014, Sep. 4, 2014, Mar. 28, 2017.
U.S. Appl. No. 15/444,087, 2017-0174757, To Be Aband, filed Feb. 27, 2017, Jun. 22, 2017.
U.S. Appl. No. 13/568,028, Abandoned, filed Aug. 6, 2012.
U.S. Appl. No. 14/853,622, 2016-0068588, Published, filed Sep. 14, 2015, Mar. 10, 2016.
U.S. Appl. No. 13/887,234, Abandoned, filed May 3, 2013.
U.S. Appl. No. 14/156,431, 2014-0212435, Abandoned, filed Jan. 15, 2014, Jul. 15, 2014.
U.S. Appl. No. 14/156,432, 2014-0212436, U.S. Pat. No. 9,738,722, Granted, filed Jan. 15, 2014, Jul. 31, 2014, Aug. 22, 2017.
U.S. Appl. No. 14/808,826, 2016-0060360, Abandoned, filed Jul. 24, 2015, Mar. 3, 2016.
U.S. Appl. No. 15/682,380, 2018-0201686, Abandoned, filed Aug. 21, 2017, Jul. 19, 2018.
U.S. Appl. No. 14/155,248, 2014-0322217, Allowed, filed Jan. 14, 2014, Oct. 30, 2014.
U.S. Appl. No. 14/155,334, 2014-0370013, Published, filed Jan. 14, 2014, Dec. 18, 2014.
U.S. Appl. No. 14/155,344, 2014-0294833, U.S. Pat. No. 9,701,759, Granted, filed Jan. 14, 2014, Oct. 2, 2014, Jul. 11, 2017.
U.S. Appl. No. 14/205,227, 2014-0294835, Abandoned, filed Mar. 11, 2014, Oct. 2, 2014.
U.S. Appl. No. 14/205,248, 2014-0288275, U.S. Pat. No. 9,650,446, Granted, filed Mar. 11, 2014, Sep. 25, 2014, May 16, 2017.
U.S. Appl. No. 15/589,908, 2018-0142040, Published, filed May 8, 2017, May 24, 2018.
U.S. Appl. No. 15/633,629, 2018-0215834, Allowed, filed Jun. 26, 2017, Aug. 2, 2018.
U.S. Appl. No. 14/214,418, 2014-0356381, U.S. Pat. No. 10,106,624, Granted, filed Mar. 14, 2014, Dec. 4, 2014, Oct. 23, 2018.
U.S. Appl. No. 16/137,389, Abandoned, filed Sep. 20, 2018.
U.S. Appl. No. 14/214,475, 2014-0294836, Allowed, filed Mar. 14, 2014, Oct. 2, 2014.
U.S. Appl. No. 14/217,166, 2014-0294759, Allowed, filed Mar. 17, 2014, Oct. 2, 2014.
U.S. Appl. No. 14/200,652, 2014-0302064, Published, filed Mar. 7, 2014, Oct. 9, 2014.
U.S. Appl. No. 14/207,489, 2014-0377270, U.S. Pat. No. 10,131,710, Granted, filed Mar. 12, 2014, Dec. 25, 2014, Nov. 20, 2018.
U.S. Appl. No. 16/162,172, 2019-0270810, Published, filed Oct. 16, 2018, Sep. 5, 2019.
U.S. Appl. No. 14/200,821, 2014-0294823, U.S. Pat. No. 9,605,084, Granted, filed Mar. 7, 2014, Oct. 2, 2014, Mar. 28, 2017.
U.S. Appl. No. 14/216,705, 2014-0363426, Published, filed Mar. 17, 2014, Dec. 11, 2014.
U.S. Appl. No. 15/444,026, 2018-0037668, U.S. Pat. No. 10,287,364, Granted, filed Feb. 27, 2017, Feb. 8, 2018, May 14, 2019.
U.S. Appl. No. 16/364,093, Pending, filed Mar. 25, 2019.
U.S. Appl. No. 14/673,695, 2015-0307629, Transferred, filed Mar. 30, 2015, Oct. 29, 2015.
U.S. Appl. No. 15/786,252, 2018-0094079, Published, filed Oct. 17, 2017, Apr. 5, 2018.

(56) References Cited

OTHER PUBLICATIONS

U.S. Appl. No. 14/952,705, 2016-0176969, Abandoned, filed Nov. 25, 2015, Jun. 23, 2016.
U.S. Appl. No. 14/952,714, 2016-0229924, Published, filed Nov. 25, 2015, Aug. 11, 2016.
U.S. Appl. No. 15/141,350, 2016-0355608, U.S. Pat. No. 10,259,887, Granted, filed Apr. 28, 2016, Dec. 8, 2016, Apr. 16, 2019.
U.S. Appl. No. 15/945,679, 2018-0282432, Published, filed Apr. 4, 2018, Oct. 4, 2018.
U.S. Appl. No. 15/945,681, 2018-0223000, Published, filed Apr. 4, 2018, Aug. 9, 2018.
U.S. Appl. No. 16/354,058, 2019-0202938, Published, filed Mar. 14, 2019, Jul. 4, 2019.
U.S. Appl. No. 14/952,786, 2016-0215063, Transferred, filed Nov. 25, 2015, Jul. 28, 2016.
U.S. Appl. No. 15/779,325, Pending, filed May 25, 2018.
U.S. Appl. No. 14/757,809, 2016-0355600, U.S. Pat. No. 10,428,155, Allowed, filed Dec. 22, 2015, Dec. 8, 2016, Oct. 1, 2019.
U.S. Appl. No. 16/530,946, Pending, filed Aug. 2, 2019.
U.S. Appl. No. 15/063,441, 2017-0037131, U.S. Pat. No. 10,227,411, Granted, filed Mar. 7, 2016, Feb. 9, 2017, Mar. 12, 2019.
U.S. Appl. No. 16/297,255, 2019-0194325, Published, filed Mar. 8, 2019, Jun. 27, 2019.
U.S. Appl. No. 15/372,360, 2017-0320947, U.S. Pat. No. 10,227,410, Granted, filed Dec. 7, 2016, Nov. 9, 2017, Mar. 12, 2019.
U.S. Appl. No. 16/489,539, Pending, filed Aug. 28, 2019.
U.S. Appl. No. 15/623,314, 2018-0118836, Published, filed Jun. 14, 2017, May 3, 2018.
U.S. Appl. No. 16/435,373, Pending, filed Jun. 7, 2019.
U.S. Appl. No. 16/435,375, Pending, filed Jun. 7, 2019.
U.S. Appl. No. 15/611,361, 2017-0349660, Published, filed Jun. 1, 2017, Dec. 7, 2017.
U.S. Appl. No. 15/611,683, 2017-0349657, Published, filed Jun. 1, 2017, Dec. 7, 2017.
U.S. Appl. No. 15/636,590, 2018-0118827, U.S. Pat. No. 10,316,088, Granted, filed Jun. 28, 2017, May 3, 2018, Jun. 11, 2019.
U.S. Appl. No. 16/393,900, 2019-0248898, Published, filed Apr. 24, 2019, Aug. 15, 2019.
U.S. Appl. No. 15/185,958, 2017-0081420, U.S. Pat. No. 9,850,320, Granted, filed Jun. 17, 2016, Mar. 23, 2017, Dec. 26, 2017.
U.S. Appl. No. 15/186,167, 2017-0081424, U.S. Pat. No. 9,856,327, Granted, filed Jun. 17, 2016, Mar. 23, 2017, Jan. 2, 2018.
U.S. Appl. No. 15/691,665, 2018-0127501, Published, filed Aug. 30, 2017, May 10, 2018.
U.S. Appl. No. 16/184,895, 2019-0263909, Published, filed Nov. 8, 2018, Aug. 29, 2019.
U.S. Appl. No. 16/184,929, 2019-0270816, Published, filed Nov. 8, 2018, Sep. 5, 2019.
U.S. Appl. No. 16/375,777, Pending, filed Apr. 4, 2019.
U.S. Appl. No. 12/631,508, filed Dec. 4, 2009, Chari et al.
(No Author Name) "A method for making multispecific antibodies having heteromultimeric and common components", Expert Opinion on Therapeutic Patents, Genentech, Inc. (1999) 9(6): 785-790, pp. 785-790.
"Polythene Glycol and Derivatives for Advanced PEGylation", Catalog 2005-2006, Nektar Therapeutics.
"Xencor Provides Data Updates on XmaB Bispecific Antibody Program and Announces Presentations at Upcoming American Society of Hematology 2014 Annual Meeting", Nov. 6, 2014, XP055255549, retrieved from the internet: http://files.shareholder.com/downloads/AMDA-2B2V8N/0x0x792404/77590b72-837a-4085-bc55-78fa500638dc/XNCR_News_2014_11_6_General_Releases.pdf.
Abbott Laboratories, Strategies and Current Approaches for Improving Drug-Like-Properties During Biologics Drug Candidate Selection, AAPS Webinar—Nov. 10, 2011.
Adams, et al., Avidity-Mediated Enhancement of In vivo Tumor Targeting by Single-Chain Fv Dimers, Clin Cancer Res, 2006, vol. 12(5), pp. 1599-1605, doi:10.1158/1078-0432.CCR-05-2217.
Alberola-Ila et al., Stimulation Through the TCR/CD3 Complex Up-Regulates the CD2 Srface Expression on Human T Lymphocytes, Feb. 15, 1991.
Alibaud et al., A New Monoclonal Anti-CD3? Antibody Reactive on Paraffin Sections, Journal of Histochemistry & Cytochemistry, 2000, vol. 48, p. 1609.
An, et al., IgG2m4, an engineered antibody isotype with reduced Fc function, mAbs, 2009, vol. 1, Issue 6, pp. 572-579, www.landesbioscience.com/journals/mabs/article/10185.
Aplin et al., , Preparation, properties, and applications of carbohydrate conjugates of proteins and lipids, 1981, CRC Crit. Rev. Biochem., pp. 259-306.
Arnett, et al., Crystal structure of a human CD3-ε/δ dimer in complex with a UCHT1 single-chain antibody fragment, PNAS, 2004, vol. 101, No. 46, pp. 16268-16273.
Asano, et al., Cytotoxic enhancement of a bispecific diabody (Db) by format conversion to tandem single-chain variable fragment (taFv): The Case of the hEx3 Diabody, JBC Papers in Press, 2010, http://www.jbc.org/cgi/doi/10.1074/jbc.M110.172957.
Asano, et al., Highly Effective Recombinant Format of a Humanized IgG-like Bispecific Antibody for Cancer Immunotherapy with Retargeting of Lymphocytes to Tumor Cells, The Journal of Biological Chemistry, 2007, vol. 282, No. 38, pp. 27659-27665.
Atwell, et al., Stable Heterodimers from Remodeling the Domain Interface of a Homodimer using a Phage Display Library, J. Mol. Biol., 1997, vol. 270, pp. 26-35.
Baca et al., Antibody humanization using monovalent phage display, 1997, J. Biol. Chem. 272(16):10678-10684.
Baeuerle, et al., Response to Letter, "Correct TandAb protein," Molecular Immunology, 2007, vol. 44, pp. 3084.
Baeuerle, et al., Review—Bispecific T-Cell Engaging Antibodies for Cancer Therapy, Cancer Res, 2009, vol. 69: (12), pp. 4941-4944.
Barbas, et al. In vitro evolution of a neutralizing human antibody to human immunodeficiency virus type 1 to enhance affinity and broaden strain cross-reactivity, 1994, Proc. Nat. Acad. Sci, USA 91:3809-3813.
Bargou et al., Tumor Regression in Cancer Patients by Very Low Doses of a T Cell-Engaging Antibody, Science, 2008, vol. 321, pp. 974-977.
Bhatt, Sea Lane—DDD presentation, "Surrobodies™—A Novel Approach to Bispecifics . . . ," Aug. 8, 2012.
Bibollet-Ruche et al., The Quality of Chimpanzee T-Cell Activation and Simian Immunodeficiency Virus/Human Immunodeficiency Virus Susceptibility Achieved via Antibody-Mediated T-Cell Receptor/CD3 Stimulation Is a Function of the Anti-CD3 Antibody Isotype, Jul. 30, 2008.
Biochemica, Your apoptosis specialist, 1999, No. 2, pp. 34-37 (Roche Molecular Biochemicals).
Bird et al., Single-chain antigen-binding proteins, 1988, Science 242:423-426.
Bluemel, et al., Epitope distance to the target cell membrane and antigen size determine the potency of T cell-mediated lysis by BiTE antibodies specific for a large melanoma surface antigen, Cancer Immunol Immunother, 2010, vol. 59(8), pp. 1197-1209.
Borras, et al., Generic Approach for the Generation of Stable Humanized Single-chain Fv Fragments from Rabbit Monoclonal Antibodies, The Journal of Biological Chemistry, 2010, vol. 285, No. 12, pp. 9054-9066.
Bortoletto, Nicola et al., "Optimizing anti-CD3 affinity for effective T cell targeting against tumor cells.", Eur J Immunol. Nov. 2002;32(11):3102-7.
Boswell et al., Effects of Charge on Antibody Tissue Distribution and Pharmacokinetics, 2010, Bioconjugate Chem, 21(21):2153-2163.
Brandl, et al., Bispecific antibody fragments with CD20 3 CD28 specificity allow effective autologous and allogeneic T-cell activation against malignant cells in peripheral blood and bone marrow cultures from patients with B-cell lineage leukemia and lymphoma, Experimental Hematology, 1999, vol. 27, pp. 1264-1270.
Brinkmann , et al., presentation slideshow—"Roche Penzberg & Roche Glycart, Schlieren: Centers of Excellence for Recombinant Proteins".

(56) References Cited

OTHER PUBLICATIONS

Brinkmann, et al., A recombinant immunotoxin containing a disulfide-stabilized Fv fragment, Proc. Natl. Acad. Sci. USA, 1993, vol. 90, pp. 7538-7542.
Cao, et al., Oligomerization is required for the activity of recombinant soluble LOX-1., FEBS J. Sep. 2009;276(17):4909-20. doi: 10.1111/j.1742-4658.2009.07190.x. Epub Jul. 31, 2009.
Carpenter, et al., Non-Fc Receptor-Binding Humanized Anti-CD3 Antibodies Induce Apoptosis of Activated Human T Cells, J. Immunol., 2000, vol. 165, No. 11, pp. 6205-6213.
Carter et al., Antibody-drug conjugates for cancer therapy, 2008, Cancer J. 14(3):154-169.
Carter et al., Humanization of an anti-p185HER2 antibody for human cancer therapy, 1992, Proc Natl Acad Sci USA 89:4285-9.
Castoldi, et al., Molecular characterization of novel trispecific ErbB-cMet-IGF1R antibodies and their antigen-binding properties, Protein Engineering, Design & Selection, 2012, vol. 25, No. 10, pp. 551-559.
Cemerski, et al., Suppression of mast cell degranulation through a dual-targeting tandem IgE-IgG Fc domain biologic engineered to bind with high affinity to FcγRIIb., Immunol Lett. Mar. 30, 2012;143(1):34-43. doi:10.1016/j.imlet.2012.01.008. Epub Jan. 25, 2012.
Chames et al., Bispecific antibodies for cancer therapy—The light at the end of the tunnel?, mAbs, 2009, vol. 1, Issue 6, pp. 1-9.
Chang, et al., Monoclonal antibodies against oxidized low-density lipoprotein bind to apoptotic cells and inhibit their phagocytosis by elicited macrophages: evidence that oxidation-specific epitopes mediate macrophage recognition., Proc Natl Acad Sci U S A. May 25, 1999;96(11):6353-8.
Chari et al., Immunoconjugates containing novel maytansinoids: promising anticancer drugs, 1992, Cancer Research 52: 127-131.
Chatal, 1989, Monoclonal Antibodies in Immunoscintigraphy, CRC Press (Book Abstract).
Chelius, et al., Structural and functional characterization of the trifunctional antibody catumaxomab, mAbs, 2010, vol. 2, Issue 3, pp. 309-319.
Chichili et al., A CD3×CD123 bispecific DART for redirecting host T cells to myelogenous leukemia: preclinical activity and safety in nonhuman primates., Sci Transl Med. May 27, 2015;7(289):289ra82. doi: 10.1126/scitranslmed.aaa5693.
Chothia et al., Canonical structures for the hypervariable regions of immunoglobulins, 1987, J. Mol. Biol. 196:901-917.
Chothia, et al., Structural Determinants in the Sequences of Immunoglobulin Variable Domain, J. Mol. Biol., 1998, vol. 278, pp. 457-479.
Chu et al., Immunotherapy with Long-Lived Anti-CD123×Anti-CD3 Bispecific Antibodies Stimulates Potent T Cell Mediated Killing of Human AML Cell Lines and of CD123+ Cells In Monkeys: A Potential Therapy for Acute Myelogenous Leukemia, Blood 2014, 124:2316.
Chu et al., Immunotherapy with Long-Lived Anti-CD123×Anti-CD3 Bispecific Antibodies Stimulates Potent T Cell-Mediated Killing of Human B Cell Lines and of Circulating and Lymphoid B Cells in Monkeys: A Potential Therapy for B Cell Lymphomas and Leukemias, Blood 2014, 124:3111.
Chu et al., Inhibition of B cell receptor-mediated activation of primary human B cells by coengagement of CD19 and FcgammaRIIb with Fc-engineered antibodies., Mol Immunol. Sep. 2008;45(15):3926-33. doi: 10.1016/j.molimm.2008.06.027. Epub Aug. 8, 2008.
Chu et al., Reduction of total IgE by targeted coengagement of IgE B-cell receptor and FcγRIIb with Fc-engineered antibody., J Allergy Clin Immunol. Apr. 2012;129(4):1102-15. doi: 10.1016/j.jaci.2011. 11.029. Epub Jan. 16, 2012.
Conrad, et al., TCR and CD3 Antibody Cross-Reactivity in 44 Species, Cytometry Part A, 2007, vol. 71A, pp. 925-933.
Conrath, et al., Antigen Binding and Solubility Effects upon the Veneering of a Camel VHH in Framework-2 to Mimic a VH, J. Mol. Biol. , 2005, vol. 350, pp. 112-125.

Counterman et al., "Volumes of Individual Amino Acid Residues in Gas-Phase Peptide Ions.", J. Am. Chem. Soc., 1999, 121 (16), pp. 4031-4039.
Cuesta, et al., Multivalent antibodies: when design surpasses evolution, Trends in Biotechnology, 2010, vol. 28, No. 7, pp. 355-362, doi:10.1016/j.tibtech.2010.03.007.
D'Argouges, et al., Combination of rituximab with blinatumomab (MT103/MEDI-538), a T cell-engaging CD19-/CD3-bispecific antibody, for highly efficient lysis of human B lymphoma cells, Leukemia Research, 2009, vol. 33, pp. 465-473.
Davies et al., Expression of GnTIII in recombinant anti-CD20 CHO production cell line: expression of antibodies with altered glycoforms leads to an increase in ADCC through higher affinity for FCγRIII, 2001, Biotechnol Bioeng 74:288-294.
Davila, et al., Efficacy and Toxicity Management of 19-28z CAR T Cell Therapy in B Cell Acute Lymphoblastic Leukemia, Sci. Transl. Med., 2014, vol. 6, Issue 224, pp. 1-10, 224ra25.
Davis, et al., SEEDbodies: fusion proteins based on strand-exchange engineered domain (SEED) $C_H3$ heterodimers in an Fc analogue platform for asymmetric binders or immunofusions and bispecific antibodies, Protein Engineering, Design & Selection, 2010, vol. 23, No. 4 pp. 195-202.
De Groot et al., De-Immunization Of Therapeutic Proteins By T-Cell Epitope Modification, 2005, Dev. In Biologicals, 2005, 122:171-194.
De Pascalis et al., Grafting of "abbreviated" complementarity-determining regions containing specificity-determining residues essential for ligand contact to engineer a less immunogenic humanized monoclonal antibody, 2002, J. Immunol. 169:3076-3084.
Del Nagro et al., A critical role for complement C3d and the B cell coreceptor (CD19/CD21) complex in the initiation of inflammatory arthritis., J. Immunol. Oct. 15, 2005;175(8):5379-89.
Demarest et al., Antibody therapeutics, antibody engineering, and the merits of protein stability, Current Opinin in Drug Discovery & Development, 2008 11(5): 675-587, Sep. 11, 2008.
Deyev, et al., Multivalency: the hallmark of antibodies used for optimization of tumor targeting by design, BioEssays, 2008, vol. 30, pp. 904-918.
DiGiammarino et al., Ligand association rates to the inner-variable-domain of a dual-variable-domain immunoglobulin are significantly impacted by linker design, mAbs3:5, 1-8; Sep.-Oct.; 3(5):487-94, Landes Bioscience, Sep. 1, 2011.
DiGiandomenico et al., A multifunctional bispecific antibody protects against Pseudomonas aeruginosa., Sci Transl Med. Nov. 12, 2014;6(262):262ra155. doi: 10.1126/scitranslmed.3009655.
Dixon, et al., Activation of Human T Lymphocytes by Crosslinking of Anti-CD3 Monoclonal Antibodies, Journal of Leukocyte Biology, 1989, vol. 46, pp. 214-220.
Dong et al., A stable IgG-like bispecific antibody targeting the epidermal growth factor receptor and the type I insulin-like growth factor receptor demonstrates superior anti-tumor activity, mAbs 3:3, May-Jun. 2011: 273-288, May 1, 2011.
Doronina , Development of potent monoclonal antibody auristatin conjugates for cancer therapy, 2003, Nat Biotechnol 21(7):778-784.
Dreier, et al., Extremely Potent, Rapid and Costimulation-Independent Cytotoxic T-cell Response Against Lymphoma Cells Catalyzed by a Single-Chain Bispecific Antibody, Int. J. Cancer, 2002, vol. 100, pp. 690-697.
Dreier, et al., T Cell Costimulus-Independent and Very Efficacious Inhibition of Tumor Growth in Mice Bearing Subcutaneous or Leukemic Human B Cell Lymphoma Xenografts by a CD19-/CD3-Bispecific Single-Chain Antibody Construct, The Journal of Immunology, 2003, vol. 170, pp. 4397-4402.
Dubowchik et al., Receptor-mediated and enzyme-dependent targeting of cytotoxic anticancer drugs, 1999, Pharm. Therapeutics 83:67-123.
Ducry et al., Antibody-drug conjugates: linking cytotoxic payloads to monoclonal antibodies, 2010, Bioconjugate Chem. 21:5-13.
Dudgeon, et al., General strategy for the generation of human antibody variable domains with increased aggregation resistance, PNAS Early Edition, 2012, pp. 10879-10884, www.pnas.org/cgi/doi/10.1073/pnas.1202866109 & Supporting Information.

(56) References Cited

OTHER PUBLICATIONS

Duke, et al., Measurement of apoptosis and other forms of cell death, 2004, Curr protocols immunol. 3.17.1-3.17.16.
DukSin et al., Relationship of the structure and biological activity of the natural homologues of tunicamycin, 1982, J. Biol. Chem. 257:3105.
Duval, et al., A Bispecific Antibody Composed of a Nonneutralizing Antibody to the gp41 Immunodominant Region and an Anti-CD89 Antibody Directs Broad Human Immunodeficiency Virus Destruction by Neutrophils, Journal of Virology, 2008, pp. 4671-4674, doi:10.1128/JVI.02499-07.
Edge et al., Deglycosylation of glycoproteins by trifluoromethanesulfonic acid, 1981, Anal. Biochem. 118:131.
Elliott, et al., Antiparallel Conformation of Knob and Hole Aglycosylated Half-Antibody Homodimers Is Mediated by a CH2—CH3 Hydrophobic Interaction, Journal of Molecular Biology, 2014, vol. 426, Issue 9, pp. 1947-1957.
Feldmann et al., Novel Humanized and Highly Efficient Bispecific Antibodies Mediate Killing of Prostate Stem Cell Antigen-Expressing Tumor Cells by CD8+ and CD4+ T cells, Aug. 8, 2012.
Feldmann et al., Retargeting of T Cells to Prostate Stem Cell Antigen Expressing Tumor Cells: Comparison of Different Antibody Formats, Dec. 28, 2010.
Fernandes, et al., T Cell Receptors are Structures Capable of Initiating Signaling in the Absence of Large Conformational Rearrangements, The Journal of Biological Chemistry, 2012, vol. 287, No. 16, pp. 13324-13335.
Fischer, Nicolas et al., "Bispecifc antibodies: molecules that enable novel therapeutic strategies", 2007, vol. 74, pp. 3-14.
Foreman, et al., ErbB3 Inhibitory Surrobodies Inhibit Tumor Cell Proliferation In Vitro and In Vivo, Mol Cancer Ther, 2012, vol. 11(7), pp. 1411-1420.
Foreman, et al., PEGS poster, "ErbB3 Inhibitory Surrobodies Inhibit Tumor Cell Proliferation In Vitro and In Vivo," 2012.
Fraker et al., Crystal structure of peptide cyclo-(D-VAL-L-PRO-L-VAL-D-PRO)$_3$, 1978, Biochem. Biophys. Res. Common. 80(4):849-57.
Francois, et al., Construction of a Bispecific Antibody Reacting with the α-and β-Chains of the Human IL-2 Receptor, The Journal of Immunology, May 15, 1993, vol. 150, No. 10, pp. 4610-4619.
F-star Modular Antibodies Fact Sheet, Apr. 2008, "Modular Antibody Technology" (w/ reference to Ruker WO 2006/072620 A1).
F-star Modular Antibodies Press Release, Mar. 28, 2008, "Antibody Engineering Company F-Star Buys Back Royalty Obligations. TVM Capital Joins Investor Syndicate.".
Fudenberg, et al., Serologic Demonstration of Dual Specificity of Rabbit Bivalent Hybrid Antibody, The Journal of Experimental Medicine, 1964, vol. 119(1), pp. 151-166.
Ganesan, et al., FcγRIIb on Liver Sinusoidal Endothelium Clears Small Immune Complexes, The Journal of Immunology, Nov. 15, 2012, vol. 189 No. 10, pp. 4981-4988.
GenBank AAA38124.1, immunoglobulin heavy-chain VJ region [Mus musculus] Protein/NCBI.
GenBank AAA39180.1, immunoglobulin light-chain VJ region [Mus musculus] Protein/NCBI.
Ghendler et al., One of the CD3ε Subunits within a T Cell Receptor Complex Lies in Close Proximity to the Cβ FG Loop, J. Exp. Med., 1998, vol. 187, No. 9. pp. 1529-1536.
Ghetie et al., Multiple roles for the major histocompatibility complex Class I-related receptor FcRn, 2000, Annu Rev Immunol 18:739-766.
Gilliland, et al., Universal bispecific antibody for targeting tumor cells for destruction by cytotoxic T cells, Proc. Natl. Acad. Sei. USA, 1988, vol. 85, pp. 7719-7723.
Gorman et al., Reshaping a therapeutic CD4 antibody, Proc. Natl. Acad. Sci. USA 88:4181-4185.
Grodzki & Bernstein, "Antibody Purification: Ion-Exchange Chromatography.", Methods Mol Biol 2010 ;588:27-32.

Gunasekaran et al., Enhancing Antibody Fc Heterodimer Formation through Electrostatic Steering Effects, Journal of Biological Chemistry, vol. 285, No. 25, pp. 19637-10946, Apr. 16, 2010 & Supplementary Tables.
Haagen, et al., The Efficacy of CD3×CD19 Bispecific Monoclonal Antibody (BsAb) in a Clonogenic Assay: The Effect of Repeated Addition of BsAb, and Interleukin-2, Blood, 1995, vol. 85, No. 11, pp. 3208-3212.
Hakimuddin et al., A chemical method for the deglycosylation of proteins, 1987, Arch. Biochem. Biophys. 259:52.
Hamel, et al., The Role of the $V_L$- and $V_H$- Segments in the Preferential Reassociation of Immunoglobulin Subunits, Molecular Immunology, 1986, vol. 23, No. 5, pp. 503-510.
Hawkins et al., Selection of phage antibodies by binding affinity mimicking affinity maturation, 1992, J. Mol. Biol. 226:889-896.
Hayden-Ledbetter, et al., CD20-Directed Small Modular Immunopharmaceutical, TRU-015, Depletes Normal and Malignant B Cells, Clin Cancer Res, 2009, vol. 15(8), pp. 2739-2746.
He et al., Humanization and pharmacokinetics of a monoclonal antibody with specificity for both E- and P-selectin, 1998, J. Immunol. 160:1029-1035.
Hennecke et al., "Non-repetitive single-chain Fv linkers selected by selectively infective phage (SIP) technology.", Protein Eng. May 1998;11(5):405-10.
Hernandez-Caselles, et al., A study of CD33 (SIGLEC-3) antigen expression and function on activated human T and NK cells: two isoforms of CD33 are generated by alternative splicing, J. Leukoc. Biol., 2006, vol. 79, pp. 46-58.
Hexham, et al., Influence of relative binding affinity on efficacy in a panel of anti-CD3 scFv immunotoxins, Molecular Immunology, 2001, vol. 38, pp. 397-408.
Hinman et al., Preparation and characterization of monoclonal antibody conjugates of the calicheamicins: a novel and potent family of antitumor antibodies, 1993 Cancer Res. 53:3336-3342.
Hoffmann, et al., Serial killing of tumor cells by cytotoxic T cells redirected with a CD19-/CD3-bispecific single-chain antibody construct, Int. J. Cancer, 2005, vol. 115, pp. 98-104.
Holliger et al., "Diabodies": Small Bivalent and bispecific antibody fragments, 1993, Proc. Natl. Acad. Sci. U.S.A. 90:6444-6448.
Holliger et al., Engineering bispecific antibodies, 1993, Current Opinion Biotechnol. 4:446-449.
Houtenbos, et al., The novel bispecific diabody αCD40/αCD28 strengthens leukaemic dendritic cell-induced T-cell reactivity, British Journal of Haematology, 2008, vol. 142, pp. 273-283.
Hu et al., Minibody: A novel engineered anti-carcinoembryonic antigen antibody fragment (single-chain Fv-$C_H3$) which exhibits rapid, high-level targeting of xenografts, 1996, Cancer Res. 56:3055-3061.
Huston et al., Protein engineering antibody binding sites: recovery of specific activity in an anti-digoxin single-chain Fv analogue produced in *Escherichia coli*, 1988, Proc. Natl. Acad. Sci. U.S.A. 85:5879-5883.
Igawa et al., Reduced elimination of IgG antibodies by engineering the variable region, 2010, PEDS. 23(5): 385-392.
Igawa, $V_H/V_L$ interface engineering to promote selective expression and inhibit conformational isomerization of thrombopoietin receptor agonist single-chain diabody. Protein Engineering, Design & Selection, 2010, vol. 23, No. 8, pp. 667-677.
Ishigaki et al., Impact of Plasma Oxidized Low-Density Lipoprotein Removal on Atherosclerosis., Circulation 118: 75-83, 2008.
Jackson et al., In vitro antibody maturation, 1995, J. Immunol. 154(7):3310-9.
Jäger, et al., The Trifunctional Antibody Ertumaxomab Destroys Tumor Cells That Express Low Levels of Human Epidermal Growth Factor Receptor 2, Cancer Res, 2009, vol. 69(10), pp. 4270-4276.
Jefferis et al., Interaction sites on human IgG-Fc for FcγR: current models, 2002, Immunol Lett 82:57-65.
Jespers, et al., Crystal Structure of HEL4, a Soluble, Refoldable Human $V_H$ Single Domain with a Germ-line Scaffold, J. Mol. Biol., 2004, vol. 337, pp. 893-903.

(56) References Cited

OTHER PUBLICATIONS

Jimenez, et al., A recombinant, fully human, bispecific antibody neutralizes the biological activities mediated by both vascular endothelial growth factor receptors 2 and 3, Mol Cancer Ther, 2005, vol. 4(3), pp. 427-434.
Jin et al. The Design and Engineering of IgG-Like Bispecific Antibodies., Chapter 9, Bispecific Antibodies, pp. 151-169.
Jin, et al., MetMAb, the One-Armed 5D5 Anti-c-Met Antibody, Inhibits Orthotopic Pancreatic Tumor Growth and Improves Survival, Cancer Res 2008, vol. 68, pp. 4360-4368.
Johnson et al., Anti-tumor activity of CC49-doxorubicin immunoconguates, 1995, Anticancer Res. 15:1387-93.
Johnson, et al., Effector Cell Recruitment with Novel Fv-based Dual-affinity Re-targeting Protein Leads to Potent Tumor Cytolysis and in Vivo B-cell Depletion, J. Mol. Biol., 2010, vol. 399, pp. 436-449.
Jones et al., Replacing the complementarity-determining regions in a human antibody with those from a mouse, 1986, Nature 321:522-525.
Jordan et al., Structural understanding of stabilization patterns in engineered bispecific Ig-like antibody molecules, Proteins 2009; 77:832-841, Jun. 19, 2009.
Jung, et al., Design of interchain disulfide bonds in the framework region of the Fv fragment of the monoclonal antibody B3, Proteins, 1994, vol. 19(1), pp. 35-47.
Jung, et al., Target Cell-restricted Triggering of the CD95 (APO-1/Fas) Death Receptor with Bispecific Antibody Fragments, Cancer Research, 2001, vol. 61, pp. 1846-1848.
Jungbluth et al., A monoclonal antibody recognizing human cancers with amplification/overexpression of the human epidermal growth factor receptor, 2003, Proc Natl Acad Sci U S A. 100(2):639-44.
Kabat et al., 1991, Sequences of proteins of immunological interest, Department of Health and Human Services, Bethesda, vol. 1, $5^{th}$ Ed.
Kakutani et al., Accumulation of LOX-1 ligand in plasma and atherosclerotic lesions of Watanabe heritable hyperlipidemic rabbits: identification by a novel enzyme immunoassay.,Biochem Biophys Res Commun. Mar. 23, 2001;282(1):180-5.
Kanakaraj, et al., Simultaneous targeting of TNF and Ang2 with a novel bispecific antibody enhances efficacy in an in vivo model of arthritis, mAbs, 2012, vol. 4, Issue 5, pp. 600-613, http://dx.doi.org/10.4161/mabs.21227 & Supplemental Data.
Kettleborough et al., Humanization of a mouse monoclonal antibody by CDR-grafting: the importance of framework residues on loop conformation, 1991, Protein Eng. 4(7):773-83.
Keyna, et al., Surrogate Light Chain-Dependent Selection of Ig Heavy Chain V Regions, J. Immunol., 1995, vol. 155, pp. 5536-5542.
Kharmate et al., Inhibition of tumor promoting signals by activation of SSTR2 and opioid receptors in human breast cancer cells., Cancer Cell Int. Sep. 23, 2013;13(1):93. doi: 10.1186/1475-2867-13-93.
Kiewe, et al., Phase I Trial of the Trifunctional Anti-HER2×Anti-CD3 Antibody Ertumaxomab in Metastatic Breast Cancer, Clin Cancer Res., 2006, vol. 12(10), pp. 3085-3091.
Kim et al., "Localization of the site of murine IgG1 molecule that is involved in binding the murine intestinal Fc receptor," Eur. J. Immunol., 24:2429-2434, 1994.
Kim et al., Mutational approaches to improve the biophysical properties of human single-domain antibodies., Biochim Biophys Acta. Nov. 2014;1844(11):1983-2001. doi: 10.1016/j.bbapap.2014.07.008. Epub Jul. 24, 2014.
Kipriyanov, et al., Bispecific CD3×CD19 Diabody for T Cell-Mediated Lysis of Malignant Human B Cells, Int. J. Cancer, 1998. vol. 77, pp. 763-772.
Kipriyanov, et al., Bispecific Tandem Diabody for Tumor Therapy with Improved Antigen Binding and Pharmacokinetics, J. Mol. Biol., 1999, vol. 293, pp. 41-56.
Kipriyanov, et al., Effect of Domain Order on the Activity of Bacterially Produced Bispecific Single-chain Fv Antibodies, J. Mol. Biol., 2003, vol. 330, pp. 99-111.
Kipriyanov, et al., Two amino acid mutations in an anti-human CD3 single chain Fv antibody fragment that affect the yield on bacterial secretion but not the affinity, Protein Engineering, 1997, vol. 10, No. 4, pp. 445-453.
Klein et al., Progression of metastatic human prostate cancer to androgen independence in immunodeficient SDIC mice, 1997, Nature Medicine 3:402-408.
Klein, et al., Progress in overcoming the chain association issue in bispecific heterodimeric IgG antibodies, mAbs, Nov.-Dec. 2012, vol. 4, issue 6, pp. 653-663, doi: 10.4161/mabs.21379, Epub Aug. 27, 2012.
Klinger, et al., Immunopharmacologic response of patients with B-lineage acute lymphoblastic leukemia to continuous infusion of T cell-engaging CD19/CD3-bispecific BiTE antibody blinatumomab, Blood, 2012, vol. 119, No. 26, pp. 6226-6233.
Koristka, et al., Retargeting of Human Regulatory T Cells by Single-Chain Bispecific Antibodies, The Journal of Immunology, 2012, vol. 188, pp. 1551-1558, www.jimmunol.org/cgi/doi/10.4049/jimmunol.1101760.
Kostelny, et al., Formation of a Bispecific Antibody by the Use of Leucine Zippers, The Journal of Immunology 1992, vol. 148, pp. 1547-1553.
Krah et al., "Single-domain antibodies for biomedical applications.", Immunopharmacol Immunotoxicol. 2016;38(1):21-8. doi: 10.3109/08923973.2015.1102934. Epub Nov. 9, 2015.
Krauss et al., Specificity grafting of human antibody frameworks selected from a phage display library: generation of a highly stable humanized anti-CD22 single-chain Fv fragment, 2003, Protein Engineering 16(10):753-759.
Krupka, et al., CD33 target validation and sustained depletion of AML blasts in long-term cultures by the bispecific T-cell-engaging antibody AMG 330, Blood, 2014, vol. 123, No. 3, pp. 356-365, Prepublished online Dec. 3, 2013; doi:10.1182/blood-2013-08-523548 & Data Supplement.
Kung, et al., Monoclonal Antibodies Defining Distinctive Human T Cell Surface Antigens, Science, 1979, vol. 206, pp. 347-349.
Kuppen, peter et al., The development and purification of a bispecific antibody for lymphokine-activated killer cell targeting against the rat colon carcinoma CC531., Cancer Immunol Immunother. Jun. 1993;36(6):403-8.
Labrijn, et al., Efficient generation of stable bispecific IgG1 by controlled Fab-arm exchange, www.pnas.org/cgi/doi/10.1073/pnas.1220145110 & Supporting Information.
Laszlo et al., Cellular determinants for preclinical activity of a novel CD33/CD3 bispecific T-cell engager (BiTE) antibody, AMG 330, against human AML, blood 2014 123: 554-561, Dec. 5, 2013.
Lau et al., Conjugation of Doxorubicin to monoclonal anti-carcinoembryonic antigen antibody via novel thiol-directed cross-linking regents, 1995, Bioorg-Med-Chem. 3(10):1299-1304.
Lau et al., Novel doxorubicin-monoclonal anti-carcinoembryonic antigen antibody immunoconjugate activity in vitro, 1995, Bioorg-Med-Chem. 3(10):1305-12.
Lazar Declaration, Dec. 27, 2010, pp. 1-4.
Lewis, et al., Generation of bispecific IgG antibodies by structure-based design of an orthogonal Fab interface, Nature Biotechnology, 2014, doi:10.1038/nbt.2797 & Supplemental Information.
Li, et al., Construction and characterization of a humanized anti-human CD3 monoclonal antibody 12F6 with effective immunoregulation functions, Immunology, 2005, vol. 116, pp. 487-498.
Lindhofer, et al., Preferential Species-Restricted Heavy/Light Chain Pairing in Rat/Mouse Quadromas: Implications for a Single-Step Purification of Bispecific Antibodies, The Journal of Immunology, 1995, vol. 155, pp. 219-225.
Ling, et al., Interspecies Scaling of Therapeutic Monoclonal Antibodies: Initial Look, J Clin Pharmacol, 2009, vol. 49, pp. 1382-1402, doi: 10.1177/0091270009337134.
Link, et al., Production and Characterization of a Bispecific IgG Capable of Inducing T-Cell-Mediated Lysis of Malignant B Cells, Blood, 1993, vol. 81, No. 12, pp. 3343-3349.
Linke, et al., Catumaxomab, Clinical development and future directions, mAbs, 2010, vol. 2, Issue 2, pp. 129-136.
Little, et al., Letter to the Editor, "Flawed TandAb production," Molecular Immunology, 2007, vol. 44, p. 3083.

(56) References Cited

OTHER PUBLICATIONS

Liu et al, Asymmetrical Fc Engineering Greatly Enhances Antibody-dependent Cellular Cytotoxicity (ADCC) Effector Function and Stability of the Modified Antibodies, J. Biol. Chem. 2014, 289: 3571-3590, Dec. 5, 2013.

Liu et al., Eradication of large colon tumor xenografts by targeted delivery of maytansinoids, 1996 Proc. Natl. Acad. Sci. USA 93:8618-8623.

Liu, et al., Crystallization of a Deglycosylated T Cell Receptor (TCR) Complexed with an Anti-TCR Fab Fragment, The Journal of Biological Chemistry, 1996, vol. 271, No. 52, pp. 33639-33646.

Lode et al., Targeted therapy with a novel enediyne antibiotic calicheamicins $o^I{}_1$ effectively suppress growth and dissemination of liver metastases in a syngeneic model of murine neuroblastoma, 1998, Cancer Res. 58:2928.

Löffler, et al., A recombinant bispecific single-chain antibody, CD19×CD3, induces rapid, and high lymphoma-directed cytotoxicity by unstimulated T lymphocytes, Blood, 2000, vol. 95, No. 6, pp. 2098-2103.

Lu, et al., A Fully Human Recombinant IgG-like Bispecific Antibody to Both the Epidermal Growth Factor Receptor and the Insulin-like Growth Factor Receptor for Enhanced Antitumor Activity, The Journal of Biological Chemistry, 2005, vol. 280, No. 20, pp. 19665-19672.

Lu, et al., Di-diabody: a novel tetravalent bispecific antibody molecule by design, Journal of Immunological Methods, 2003, vol. 279, pp. 219-232.

Lu, et al., Fab-scFv fusion protein: an efficient approach to production of bispecific antibody fragments, Journal of Immunological Methods, 2002, vol. 267, pp. 213-226.

Lu, et al., The effect of variable domain orientation and arrangement on the antigen-binding activity of a recombinant human bispecific diabody, Biochemical and Biophysical Research Communications, 2004, vol. 318, pp. 507-513.

Lum, et al., The new face of bispecific antibodies: targeting cancer and much more, Experimental Hematology, 2006, vol. 34, pp. 1-6.

Lutterbuese, et al., AACR Poster, "Conversion of Cetuximab, Panitumumab, Trastuzumab and Omalizumab into T Cell-engaging BiTE Antibodies Creates Novel Drug Candidates of High Potency," 2008.

Lutterbuese, et al., T cell-engaging BiTE antibodies specific for EGFR potently eliminate KRAS- and BRAF-mutated colorectal cancer cells, PNAS Early Edition, 2010, www.pnas.org/cgi/doi/10.1073/pnas.1000976107 & Supporting Information.

Ma, et al., Expression and Characterization of a Divalent Chimeric Anti-Human CD3 Single Chain Antibody, Scand.J.Immunol, 1996, vol. 43, pp. 134-139.

Mabry, et al., A dual-targeting PDGFRβ/NVEGF-A molecule assembled from stable antibody fragments demonstrates anti-angiogenic activity in vitro and in vivo, mAbs, 2010, vol. 2, Issue 1, pp. 20-34; www.landesbioscience.com/Journals/mabs/article/10498 & Supplemental Information.

Mabry, et al., Engineering of stable bispecific antibodies targeting IL-17A and IL-23, Protein Engineering, Design & Selection, 2009, vol. 23, No. 3, pp. 115-127; doi:10.1093/protein/gzp073 & Supplementary Figures 1-8.

Mack, et al., A small bispecific antibody construct expressed as a functional single-chain molecule with high tumor cell cytotoxicity, Proc. Natl. Acad. Sci. USA, 1995, vol. 92, pp. 7021-7025.

Mack, et al., Biologic Properties of a Bispecific Single-Chain Antibody Directed Against 17-1A (EpCAM) and CD3—Tumor Cell-Dependent T Cell Stimulation and Cytotoxic Activity, The Journal of Immunology, 1997, vol. 158, pp. 3965-3970.

MacroGenics Factsheet, Dual Affinity Re-Targeting ("DART") Platform, 2010.

Mandler et al., Immunoconjugates of geldanamycin and anti-HER2 Monoclonal antibodies: antiproliferative activity on human breast carcinoma cell lines, 2000, J. Nat. Cancer Inst. 92(19):1573-1581.

Mandler et al., Modifications in synthesis strategy improve the yield and efficacy of geldanamycin-herceptin immunoconjugates, 2002, Bioconjugate Chem. 13:786-791).

Mandler et al., Synthesis and evaluation of antiproliferative activity of a geldanaymcin-herceptin™ immunoconjugates, 2000, Bioorganic & Med. Chem. Letters 10:1025-1028.

Mandy, et al., Effect of Reduction of Several Disulfide Bonds on the Properties and Recombination of Univalent Fragments of Rabbit Antibody, The Journal of Biological Chemistry, 1963, vol. 238, No. 1, pp. 206-213.

Mandy, et al., Recombination of Univalent Subunits Derived from Rabbit Antibody, The Journal of Biological Chemistry, 1961, vol. 236, No. 12, pp. 3221-3226.

Marks et al., By-passing immunization: building high affinity human antibodies by chain shuffling, 1992, Biotechnology 10:779-783.

Martin, et al., Generation of the Germline Peripheral B Cell Repertoire: VH81X-λ B Cells Are Unable to Complete All Developmental Programs, J. Immunol., 1998, vol. 160, pp. 3748-3758.

Martinez, et al., Characterization of a novel modification on IgG2 light chain: Evidence for the presence of O-linked mannosylation, J. Chromatogr. A, 2007, vol. 1156 pp. 183-187.

Marvin, Bispecifio antibodies for dual-modality cancer therapy: killing two signaling cascades with one stone, Curr Opin Drug Discov Devel, 2006, vol. 9(2), pp. 184-193.

Marvin, et al., Recombinant approaches to IgG-like bispecific antibodies, Acta Pharmacologica Sinica, 2005, vol. 26 (6), pp. 649-658.

Mateo et al, Humanization of a mouse nonoclonal antibody that blocks the epidermal growth factor receptor: recovery of antagonistic activity, 1997, Immunotechnology, 3(1):71-81.

McPhee, Engineering human immunodeficiency virus 1 protease heterodimers as macromolecular inhibitors of viral maturation, Proc. Natl. Acad. Sci. USA, 1996, vol. 93, pp. 11477-11481.

Meijer, et al., Isolation of Human Antibody Repertoires with Preservation of the Natural Heavy and Light Chain Pairing, J. Mol. Biol., 2006, vol. 358, pp. 764-772.

Merchant, et al., An efficient route to human bispecific IgG, Nature Biotechnology, 1998, vol. 16, pp. 677-681.

Mertens, Nico, "Tribodies: Fab-scFv fusion proteins as a platform to create multi-functional pharmaceuticals.", SpringerLink 2011, 135-149.

Metz, et al., Bispecific antibody derivatives with restricted binding functionalities that are activated by proteolytic processing, Protein Engineering, Design & Selection, 2012, vol. 25, No. 10, pp. 571-580.

Metz, et al., Bispecific digoxigenin-binding antibodies for targeted payload delivery, PNAS, 2011, vol. 108, No. 20, pp. 8194-8199.

Michaelson et al., Anti-tumor activity of stability-engineered IgG-like bispecific antibodies targeting TRAIL-R2 and LTbetaR, [mAbs 1:2, 128-141; Mar./Apr. 2009]; Mar. 11, 2009.

Michalk et al., Characterization of a novel single-chain bispecific antibody for retargeting of T cells to tumor cells via the TCR co-receptor CD8., PLoS One. Apr. 21, 2014;9(4):e95517. doi: 10.1371/journal.pone.0095517.

Miller et al., Stability engineering of scFvs for the development of bispecific and multivalent antibodies, PEDS, 2010, vol. 23, No. 7, pp. 549-557 & Supplementary Data.

Miller, biogen idec Stability Engineering and Production of IgG-like Bispecifc Antibodies, AAPS National Biotechnology Conference, Jun. 24 to Jun. 27, 2007.

Milutinovic, et al., Sanford Burnham Medical Research Institute / AACR Poster, #4318, "Development of a novel dual agonist Surrobody™ that simultaneously activates both death receptors DR4 and DR5 and induces cancer cell death with high potency".

Mimoto et al., Engineered antibody Fc variant with selectively enhanced FcγRIIb binding over both FcγRIIa(R131) and FcγRIIa(H131)., Protein Eng Des Sel. Oct. 2013;26(10):589-98. doi: 10.1093/protein/gzt022. Epub Jun. 5, 2013.

Mimoto, et al., Novel asymmetrically engineered antibody Fc variant with superior FcγR binding affinity and specificity compared with afucosylated Fc variant, mAbs, 2013, vol. 5, Issue 2, pp. 229-236.

(56) References Cited

OTHER PUBLICATIONS

Modjtahedi et al, Phase I trial and tumour localization of the anti-EGFR monoclonal antibody ICR62 in head and neck or lung cancer, 1996, Br J Cancer, 73(2):228-35.

Modjtahedi et al., Targeting of cells expressing wild-type EGFR and type-III mutant EGFR (EGFRVIII) by anti-EGFR MaB ICR62: a two-pronged attack for tumor therapy, 2003, Int J Cancer, 105(2):273-80.

Modjtahedi et al., Antitumor activity of combinations of antibodies directed against different epitopes on the extracellular domain of the human EGF receptor, 1993, J. Cell Biophys. 1993, 22(1-3):129-46.

Modjtahedi et al., The human EGF receptor as a target for cancer therapy: six new rat mAbs against the receptor on the breast carcinoma MDA-MB 468, 1993, Br J Cancer. 1993, 67(2):247-53.

Mølhøj, et al., CD19-/CD3-bispecific antibody of the BiTE class is far superior to tandem diabody with respect to redirected tumor cell lysis, Molecular Immunology 2007, vol. 44, pp. 1935-1943.

Moore et al., Tuning T Cell Affinity Improves Efficacy and Safety of Anti-CD38×Anti-CD3 Bispecific Antibodies in Monkeys—a Potential Therapy for Multiple Myeloma., 57th ASH Annual Meeting and Exposition (Dec. 5-8, 2015), American Society of Hematology, Orlando, Florida.

Moore, et al., A novel bispecific antibody format enables simultaneous bivalent and monovalent co-engagement of distinct target antigens., MAbs. Nov.-Dec. 2011; 3(6): 546-557; Published online Nov. 1, 2011. doi: 10.4161/mabs.3.6.18123.

Moore, et al., Application of dual affinity retargeting molecules to achieve optimal redirected T-cell killing of B-cell lymphoma, Blood, 2011, vol. 117, No. 17, pp. 4542-4551.

Moretti et al., BEAT® the bispecific challenge: a novel and efficient platform for the expression of bispecific IgGs. BMC Proceedings 2013 7(Suppl 6):O9.

Morrison, et al., News and Views: Two heads are better than one, Nature Biotechnology, 2007, vol. 25, No. 11, pp. 1233-1234.

Mosmann, 1983, Rapid colorimetric assay for cellular growth and survival: application to proliferation and cytotoxicity assays, J. Immunol. Methods 65:55-63.

Muda, et al., Therapeutic assessment of SEED: a new engineered antibody platform designed to generate mono and bispecific antibodies, Protein Engineering, Design & Selection, 2011, vol. 24, No. 5, pp. 447-454.

Muramatsu et al., Production and characterization of an active single-chain variable fragment antibody recognizing CD25., Cancer Lett. Jul. 28, 2005;225(2):225-36. Epub Jan. 23, 2005.

Murthy et al., Binding of an antagonistic monoclonal antibody to an intact and fragmented EGF-receptor polypeptide, 1987, Arch Biochem Biophys. 252(2):549-60.

Nagorsen, et al., Blinatumomab: A historical perspective, Pharmacology & Therapeutics, 2012, vol. 136, pp. 334-342, http://dx.doi.org/10.1016/j.pharmthera.2012.07.013.

Nelson, et al., Point of View: Antibody fragments—Hope and hype, mAbs, 2010, vol. 2, Issue 1, pp. 77-83.

Neville et al., Enhancement of immunotoxin efficacy by acid-cleavable cross-ling agents utilizing diphtheria toxin and toxin mutants, 1989, Biol. Chem. 264:14653-14661.

Nielsen, et al., Human T cells resistant to complement lysis by bivalent antibody can be efficiently lysed by dimers of monovalent antibody, Blood, 2002, vol. 100, No. 12, pp. 4067-4073.

Nisonoff, et al., Letters to the Editors: Recombination of a Mixture of Univalent Antibody Fragments of Different Specificity, Arch. Biochem. Biophys., 1961, pp. 460-462.

Nisonoff, et al., Quantitative Estimation of the Hybridization of Rabbit Antibodies, Nature, 1962, vol. 194, No. 4826, pp. 355-359.

North, et al., A New Clustering of Antibody CDR Loop Conformations, J. Mol. Biol., 2011, vol. 406, pp. 228-256, doi:10.1016/j.jmb.2010.10.030.

O'Connor et al., Humanization of an antibody against human protein C and calcium-dependence involving framework residues, 1998, Protein Eng 11:321-8.

Olafsen, et al., Covalent disulfide-linked anti-CEA diabody allows site-specific conjugation and radiolabeling for tumor targeting applications, Protein Engineering, Design & Selection, 2004, vol. 17, No. 1, pp. 21-27.

Page et al., 1993, Intermantional. Journal of Oncology 3:473-476.

Panke, et al., Quantification of cell surface proteins with bispecific antibodies, Protein Engineering, Design & Selection, 2013, vol. 26, No. 10, pp. 645-654.

Pessano, et al., The T3/T cell receptor complex: antigenic distinction between the two 20-kd T3 (T3-6 and T3-ε) subunits, The EMBO Journal, 1985, vol. 4, No. 2, pp. 337-344.

Pettit et al., Antineoplastic agents 365. Dolastatin 10 SAR probes, 1998, Anti-Cancer Drug Design 13:243-277.

Pettit et al., Dolastatins 24. Synthesis of (−)-dolastatin 10.I X-ray molecular structure of N,N-dimethylvalyl-valyl-dolaisoleuine tert-butyl ester, 1996, J. Chem. Soc. Perkin Trans. 1 5:859-863.

Pettit et al., Specific activities of dolastatin 10 and peptide derivatives against Cryptococcus neoformans, 1998, Antimicrob. Agents Chemother. 42(11):2961-2965.

Pettit et al., Structure-activity studies with chiral isomers and with segments of the antimitotic marine peptide dolastation 10, 1989, J. Am. Chem. Soc. 111:5463-5465.

Pettit, et al., The dolastatins; 18: Sterospecific synthesis of dolaproine1, 1996, Synthesis 719-725.

Pichler et al., Differences of T-Cell Activation by the Anti-CD3 Antibodies Leu4 and BMA030, Mar. 30, 1987.

Potapov et al., Protein-Protein Recognition: Juxtaposition of Domain and Interface Cores in Immunoglobulins and Other Sandwich-like Proteins, J. Mol. Biol., 2004, vol. 342, pp. 665-679.

Presta et al., Humanization of an anti-vascular endothelial growth factor monoclonal antibody for the therapy of solid tumors and other disorders, 1997, Cancer Res.57(20):4593-9.

Queen et al., A humanized antibody that binds to the interleukin 2 receptor, 1989, Proc Natl Acad Sci, USA 86:10029-33.

Rader et al., A phage display approach for rapid antibody humanization: designed combinatorial V gene libraries, 1998, Proc. Natl. Acad. Sci. USA 95: 8910-8915.

Raghavan et al., Fc receptors and their interactios with immunoglobulins, 1996, Annu Rev Cell Dev Biol 12:181-220.

Rattel, et al., AACR Poster, "Validation of Cynomolgus Monkeys as Relevant Species for Safety Assessment of a Novel Human BiTE Antibody Platform for Cancer Therapy," 2010.

Reddy et al., Elimination of Fc receptor-dependent effector functions of a modified IgG4 monoclonal antibody to human CD4., J Immunol. Feb. 15, 2000;164(4):1925-33.

Reiter et al., Disulfide stabilization of antibody Fv: computer predictions and experimental evaluation, Protein Eng., 1995, vol. 8(12), pp. 1323-1331.

Reiter et al., Engineering interchain disulfide bonds into conserved framework regions of Fv fragments: improved biochemical characteristics of recombinant immunotoxins containing disulfide-stabilized Fv, Protein Eng., 1994, vol. 7(5), pp. 697-704.

Remington's Pharmaceutical Sciences 16th edition, Osol, A. Ed. (1980) (Book Abstract).

Repp, et al., Combined Fc-protein- and Fc-glyco-engineering of scFv-Fc fusion proteins synergistically enhances CD16a binding but does not further enhance NK-cell mediated ADCC, Journal of Immunological Methods, 2011, vol. 373, Issues 1-2, pp. 67-78.

Ridgway, et al., 'Knobs-into-holes' engineering of antibody CH3 domains for heavy chain heterodimerization, Protein Engineering,1996, vol. 9, No. 7, pp. 617-621.

Riechmann et al., Reshaping human antibodies for therapy, 1988, Nature 332:323-329.

Riethmüller, Symmetry breaking: bispecific antibodies, the beginnings, and 50 years on, Cancer Immunity, 2012, vol. 12, p. 12, pp. 1-7.

Rodeck et al., Interactions between growth factor receptors and corresponding monoclonal antibodies in human tumors, 1987, J Cell Biochem. 35(4):315-20.

Roguska et al., Humanization of murine monoclonal antibodies through variable domain resurfacing, 1994, Proc. Natl. Acad. Sci. USA 91:969-973.

(56) References Cited

OTHER PUBLICATIONS

Roosnek, et al., Triggering T Cells by Otherwise Inert Hybrid Anti-CD3/Antitumor Antibodies Requires Encounter with the Specific Target Cell, J. Exp. Med., 1989, vol. 170, pp. 297-302.

Roque et al., Antibodies and genetically engineered related molecules: production and purification, 2004, Biotechnol. Prog. 20:639-654.

Rose, et al., Mutation of Y407 in the CH3 domain dramatically alters glycosylation and structure of human IgG, mAbs, 2013, vol. 5, Issue 2, pp. 219-228.

Rose, et al., Quantitative Analysis of the Interaction Strength and Dynamics of Human IgG4 Half Molecules by Native Mass Spectrometry, Structure, 2011, vol. 19, pp. 1274-1282.

Rosok et al., A combinatorial library strategy for the rapid humanization of anticarcinoma BR 96 Fab, 1996, J. Biol. Chem. 271(37): 22611-22618.

Rossi, et al., A new class of bispecific antibodies to redirect T cells for cancer immunotherapy, mAbs 2014, vol. 6, Issue 2, pp. 381-391.

Roux, et al., Structural analysis of the nurse shark (new) antigen receptor (NAR): Molecular convergence of NAR and unusual mammalian immunoglobulins, Proc. Natl. Acad. Sci. USA, 1998, vol. 95, pp. 11804-11809.

Rudnick, et al., Affinity and Avidity in Antibody-Based Tumor Targeting, Cancer Biotherapy and Radiopharmaceuticals, 2009, vol. 24, No. 2, pp. 155-161, doi: 10.1089/cbr.2009.0627.

Röthlisberger, et al., Domain Interactions in the Fab Fragment: A Comparative Evaluation of the Single-chain Fv and Fab Format Engineered with Variable Domains of Different Stability, J. Mol. Biol., 2005, vol. 347, pp. 773-789.

Salmeron et al., A conformational epitope expressed upon association of CD3-epsilon with either CD3-delta or CD3-gamma is the main target for recognition by anti-CD3 monoclonal antibodies, Nov. 1, 1991.

Sancho et al., CD3– Surface Expression Is Required for CD4-p56ick-mediated Up-regulation of T Cell Antigen Receptor-CD3 Signaling in T Cells, Apr. 16, 1992.

Schaefer, et al., A Two-in-One Antibody against HER3 and EGFR Has Superior Inhibitory Activity Compared with Monospecific Antibodies, Cancer Cell, 2011, vol. 20, pp. 472-486 & Supplemental Information, pp. 1-21.

Schaefer, et al., Immunoglobulin domain crossover as a generic approach for the production of bispecific IgG antibodies, PNAS, 2011, vol. 108, No. 27, pp. 11187-11192.

Schlapschy, et al., Functional humanization of an anti-CD16 Fab fragment: obstacles of switching from murine λ to human λ or κ light chains, Protein Engineering, Design & Selection, 2009, vol. 22, No. 3, pp. 175-188, doi:10.1093/protein/gzn066.

Schlereth, et al., Eradication of Tumors from a Human Colon Cancer Cell Line and from Ovarian Cancer Metastases in Immunodeficient Mice by a Single-Chain Ep-CAM-/CD3-Bispecific Antibody Construct, Cancer Res 2005, vol. 65(7), pp. 2882-2889.

Schlereth, et al., T-cell activation and B-cell depletion in chimpanzees treated with a bispecific anti-CD19/anti-CD3 single-chain antibody construct, Cancer Immunol Immunother, 2006, vol. 55, pp. 503-514, doi:10.1007/s00262-005-0001-1.

Schoonjans, et al., Fab Chains As an Efficient Heterodimerization Scaffold for the Production of Recombinant Bispecific and Trispecific Antibody Derivatives, The Journal of Immunology, 2000, vol. 165, pp. 7050-7057.

Schroder et al., The Peptides, vol. pp 76-136, 1965, Academic Press.

Senter et al., Proceedings of the American Association for Cancer Research, 2004, vol. 45, Abstract No. 623.

Senter, Potent antibody drug conjugates for cancer therapy, 2009, Current Opin. Chem. Biol. 13:235.

Sforzini et al., Targeting of saporin to Hodgkin's lymphoma cells by anti-CD30 and anti-CD25 bispecific antibodies., Br J Haematol. Sep. 1998;102(4):1061-8.

Shalaby, et al., Development of Humanized Bispecific Antibodies Reactive with Cytotoxic Lymphocytes and Tumor Cells Overexpressing the HER2 Protooncogene, J.Exp.Med., 1992, vol. 175, pp. 217-225.

Shan, et al., Characterization of scFv-Ig Constructs Generated from the Anti-CD20 mAb 1F5 Using Linker Peptides of Varying Lengths, J Immunol, 1999, vol. 162, pp. 6589-6595.

Shearman, et al., Construction, Expression and Characterization of Humanized Antibodies Directed Against the Human α/β T Cell Receptor, The Journal of Immunology, 1991, vol. 147, No. 12, pp. 4366-4373.

Shen, et al., Catumaxomab, a rat/murine hybrid trifunctional bispecific monoclonal antibody for the treatment of cancer, Curr Opin Mol Ther, 2008, vol. 10(3), pp. 273-284.

Shen, et al., Single Variable Domain-IgG Fusion: A Novel Recombinant Approach to Fc Domain-Containing Bispecific Antibodies, The Journal of Biological Chemistry, 2006, vol. 281, No. 16, pp. 10706-10714.

Shields et al., Lack of fucose on human IgG1 N-linked oligosaccharide improves binding to human FcγRIII and antibody-dependent cellular toxicity, 2002, J Biol Chem 277:26733-26740.

Shier et al., Identification of functional and structural amino-acid residues by parsimonious mutagenesis, 1995, Gene 169:147-155.

Shinkawa et al., The absence of fucose but not the presence of galactose or bisecting N-acetylglucosamine of human IgG1 complex-type oligosaccharides shows the critical role of enhancing antibody-dependent cellular cytotoxicity, 2003, J Biol Chem 278:3466-3473.

Skehan et al., Identification of functional and structural amino-acid residues by parsimonious mutagenesis, 1990, J. Natl. Cancer Inst. 82(13):1107-12.

Smith et al., Mouse model recapitulating human Fcγ receptor structural and functional diversity., Proc Natl Acad Sci USA. Apr. 17, 2012;109(16):6181-6. doi: 10.1073/pnas.1203954109. Epub Apr. 2, 2012.

Soumyarani et al, Oxidatively modified high density lipoprotein promotes inflammatory response in human monocytes-macrophages by enhanced production of ROS, TNF-α, MMP-9, and MMP-2., Mol Cell Biochem. Jul. 2012;366(1-2):277-85. doi: 10.1007/s11010-012-1306-y. Epub Apr. 17, 2012.

Spies et al., Alternative molecular formats and therapeutic applications for bispecific antibodies., Mol Immunol. Jan. 27, 2015. pii: S0161-5890(15)00005-X. doi: 10.1016/j.molimm.2015.01.003.

Spiess, et al., Bispecific antibodies with natural architecture produced by co-culture of bacteria expressing two distinct half-antibodies, Nature Biotechnology, 2013, doi:10.1038/nbt.2621 & Supplemental Information.

Stamova, Unexpected recombinations in single chain bispecific anti-CD3-anti-CD33 antibodies can be avoided by a novel linker module, Oct. 29, 2011.

Stanfield, et al., Maturation of Shark Single-domain (IgNAR) Antibodies: Evidence for Induced-fit Binding, J. Mol. Biol., 2007, vol. 367, pp. 358-372.

Stewart, et al., Recombinant CD36 inhibits oxLDL-induced ICAM-1-dependent monocyte adhesion., Mol Immunol. Feb. 2006;43(3):255-67.

Strop, P. et al., Generating Bispecific Human IgG1 and IgG2 Antibodies from Any Antibody Pair, J. Mol. Biol., 2012, doi:10.1016/j.jmb.2012.04.020.

Szymkowski et al., Creating the next generation of protein therapeutics through rational drug design, Current opinion in drug discovery & development, Sep. 1, 2005, p. 590, XP055354917, England.

Tabriz et al., Biodistribution mechanisms of therapeutic monoclonal antibodies in health and disease., AAPS J. Mar. 2010;12(1):33-43. doi: 10.1208/S12248-009-9157-5. Epub Nov. 19, 2009.

Tan et al., "Superhumanized" antibodies: reduction of immunogenic potential by complementarity-determining region grafting with human germline sequences: application to an anti-CD28, 2002, J. Immunol. 169:1119-1125.

Tan, Philip, Presentation at PepTalk, Jan. 25, 2013, "Bi-specific ADAPTIR Molecule Targeting CD86 and Delivering Monomeric IL10 to Inhibit Antigen Presenting Cells".

(56) References Cited

OTHER PUBLICATIONS

Tang et al., Selection of linkers for a catalytic single-chain antibody using phage display technology., Journal of Biological Chemistry, American Society for Biochemistry and Molecular Biology, US, vol. 271, No. 26, Jan. 1, 1996, pp. 15682-9258.

Tarcsa et al., Chapter 10 Dual-Variable Domain Immunoglobulin (DVD-Ig™) Technology: A Versatile, Novel Format for the Next Generation of Dual-Targeting Biologics, Bispecific Antibodies 2011, pp. 171-185, 2011.

Teachey, et al., Cytokine release syndrome after blinatumomab treatment related to abnormal macrophage activation and ameliorated with cytokine-directed therapy, Blood, 2013, vol. 121, No. 26, pp. 5154-5157.

Tedgui, et al., Cytokines in atherosclerosis: pathogenic and regulatory pathways., Physiol Rev. Apr. 2006;86(2):515-81.

Terry M., "FDA Places Clinical Hold on AML Drug Co-Developed by Johnson & Johnson (JNJ) and Genmab A/S (Gen Co.)", Biospace 2016, Retrieved from the internet: https://www.biospace.com/article/fda-places-clinical-hold-on-aml-drug-co-developed-by-johnson-and-johnson-and-genmab-a-s-/.

Thompson, et al., An Anti-CD3 Single-chain Immunotoxin with a Truncated Diphtheria Toxin Avoids Inhibition by Pre-existing Antibodies in Human Blood, J.Biol.Chem., 1995, vol. 270, No. 47, pp. 28037-28041.

Thompson, et al., Improved binding of a bivalent single-chain immunotoxin results in increased efficacy for in vivo T-cell depletion, Protein Engineering, 2001, vol. 14, No. 12, pp. 1035-1041.

Thorne, et al., CD36 is a receptor for oxidized high density lipoprotein: implications for the development of atherosclerosis., FEBS Lett. Mar. 20, 2007;581(6):1227-32. Epub Feb. 28, 2007.

Thorpe et al., New coupling agents for the synthesis of immunotoxins containing a hindered disulfide bond with improved stability in Vivo, 1987, Cancer Res. 47:5924-5931.

Thotakura et al., Enzymatic deglycosylating of glycoproteins, 1987, Meth. Enzymol. 138:350.

Thurman et al., Detection of complement activation using monoclonal antibodies against C3d., J Clin Invest. May 2013;123(5):2218-30. doi: 10.1172/JCI65861. Epub Apr. 24, 2013.

Tomlinson et. al., Methods for generating multivalent and bispecific antibody fragments, 2000, Methods Enzymol. 326:461-479.

Topp, et al., Targeted Therapy With the T-Cell-Engaging Antibody Blinatumomab of Chemotherapy-Refractory Minimal Residual Disease in B-Lineage Acute Lymphoblastic Leukemia Patients Results in High Response Rate and Prolonged Leukemia-Free Survival, J Clin Oncol vol. 29, No. 18, pp. 2493-2498.

Traunecker et al., Bispecific single chain molecules (Janusins) target cytotoxic lymphocytes on HIV infected cells, The EMBO Journal, 1991, vol. 1, No. 12, pp. 3655-3659.

Tsurushita et al., Humanization of monoclonal antibodies, 2004, Molecular Biology of B Cells 533-545.

Umaña et al., Engineered glycoforms of an antineuro-blastoma IgG1 with optimized antibody-dependent cellular cytotoxic activity, 1999, Nat Biotechnol 17:176-180.

Valliere-Douglass, et al., O-Fucosylation of an antibody light chain: Characterization of a modification occurring on an IgG1 molecule, Glycobiology, 2009, vol. 19, No. 2, pp. 144-152, doi:10.1093/glycob/cwn116.

Van Boxel, et al., Some lessons from the systematic production and structural analysis of soluble αβ T-cell receptors, Journal of Immunological Methods, 2009, vol. 350, pp. 14-21.

Van Wauwe, et al., OKT3: A Monoclonal Anti-Human T Lymphoctye Antibody with Potent Mitogenic Properties, The Journal of Immunology, 1980, vol. 124, No. 6, pp. 2708-2713.

Verdier, et al., Determination of lymphocyte subsets and cytokine levels in Cynomolgus monkeys, Toxicology, 1995, vol. 105, pp. 81-90.

Verhoeyen et al., Reshaping human antibodies: grafting an antilysozyme activity, 1988, Science, 239:1534-1536.

Veri, et al., Therapeutic Control of B Cell Activation via Recruitment of Fcγ Receptor IIb (CD32B) Inhibitory Function With a Novel Bispecific Antibody Scaffold, Arthritis & Rheumatism, 2010, vol. 62, No. 7, pp. 1933-1943.

Vettermann, et al., Powered by pairing: The surrogate light chain amplifies immunoglobulin heavy chain signaling and pre-selects the antibody repertoire, Seminars in Immunology 18, 2006, pp. 44-55.

Von Kreudenstein, et al., Improving biophysical properties of a bispecific antibody scaffold to aid developability: Quality by molecular design, mAbs, 2013, vol. 5, Issue 5, pp. 1-9, http://dx.doi.org/10.4161/mabs.25632 & Supplemental Material.

Wang et al., Conserved amino acid networks involved in antibody variable domain interactions, Proteins, 2009, vol. 76, pp. 99-114.

Wang et al., Expression and characterization of recombinant soluble monkey CD3 molecules: mapping the FN18 polymorphic epitope, Molecular Immunology, 2004, vol. 40, pp. 1179-1188.

Wang, et al., A block in both early T lymphocyte and natural killer cell development in transgenic mice with high-copy numbers of the human CD3E gene, Proc. Natl. Acad. Sci. USA, 1994, vol. 91, pp. 9402-9406.

Ward, et al., Protein Engineering of Homodimeric Tyrosyl-tRNA Synthetase to Produce Active Heterodimers, The Journal of Biological Chemistry, 1986, vol. 261, No. 21, pp. 9576-9578.

Wawrzynczak et al., Methods for preparing immunotoxins: Effect of the linkage on activity and stability. In Immunoconjugates. Antibody Conjugates in Radio imaging and Therapy of Cancer. (C.-W. Vogel, editor). New York, Oxford University Press, pp. 28-55.

Weatherill, et al., Towards a universal disulphide stabilised single chain Fv format: importance of interchain disulphide bond location and vL-vH orientation, Protein Engineering, Design & Selection, 2012, vol. 25, No. 7. pp. 321-329.

Weiner, et al., The Role of T Cell Activation Bispecific Antibody Therapy in Anti-CD3 X Antitumor, Journal of Immunology, 1994, vol. 152, pp. 2385-2392.

Wesolowski, et al., Single domain antibodies: promising experimental and therapeutic tools in infection and immunity, Med Microbiol Immunol, 2009, vol. 198, pp. 157-174.

Whitlow, et al., An improved linker for single-chain Fv with reduced aggregation and enhanced proteolytic stability, Protein Engineering, 1993, vol. 6 , No. 8, pp. 989-995.

Wigginton et al., An immunoglobulin E-reactive chimeric human immunoglobulin G1 anti-idiotype inhibits basophil degranulation through cross-linking of FcεRI with FcγRIIb., Clinical & Experimental Allergy, 38:313-319.

Wong, et al., The Mechanism of Anti-CD3 Monoclonal Antibodies, Transplantation, 1990, vol. 50, No. 4, pp. 683-689.

Woods, et al., LC-MS characterization and purity assessment of a prototype bispecific antibody, mAbs, 2013, vol. 5, Issue 5, pp. 711-722, http://dx.doi.org/10.4161/mabs.25488.

Woyke et al., In vitro activities and postantifungal effects of the potent dolastation 10 derivative auristatin PHE, 2001, Antimicrob. Agents and Chemother. 45(12):3580-3584.

Wu et al., Molectular construction and optimization of anti-human IL-11α/β dual variable domain immunoglobulin (DVD-Ig™) molecules, [mAbs 1:4, 339-347; Jul./Aug. 2009]; Landes Bioscience, Apr. 10, 2009.

Wu et al., Simultaneous targeting of multiple disease mediators by a dual-variable-domain immunoglobulin, (DVD-Ig™) molecules, Jul.-Aug. 2009; 339-347, Oct. 14, 2007.

Wu et al., Humanization of a murine monoclonal antibody by simultaneous optimization of framework and CDR residues, 1999, J. Mol. Biol. 294:151-162.

Wu, et al., Multimerization of a chimeric anti-CD20 single-chain Fv-Fc fusion protein is mediated through variable domain exchange, Protein Engineering, 2001, vol. 14, No. 12, pp. 1025-1033.

Wucherpfennig, et al., Structural Biology of the T-cell Receptor: Insights into Receptor Assembly, Ligand Recognition, and Initiation of Signaling, Cold Spring Harb Perspect Biol 2010;2:a005140.

Xie, et al., A new format of bispecific antibody: highly efficient heterodimerization, expression and tumor cell lysis, Journal of Immunological Methods, 2005, vol. 296 , pp. 95-101, doi:10.1016/j.jim.2004.11.005.

(56) References Cited

OTHER PUBLICATIONS

Xu, et al., Combinatorial surrobody libraries, PNAS, 2008, vol. 105, No. 31, pp. 10756-10761.
Xu, et al., Rapid optimization and prototyping for therapeutic antibody-like molecules, mAbs, 2013, vol. 5, Issue 2, pp. 237-254.
Xu, et al., Surrobodies with Functional Tails, J. Mol. Biol., 2010, vol. 397, pp. 352-360.
Yang et al., Differential in vitro activation of CD8-CD4+ and CD4-CD8+ T lymphocytes by combinations of anti-CD2 and anti-CD3 antibodies, Apr. 1, 1988.
Yelton et al., Affinity maturation of the BR96 anti-carcinoma antibody by codon-based mutagenesis, 1995, J. Immunol. 155:1994-2004.
Yeung, et al., Engineering human IgG1 affinity to human neonatal Fc receptor: impact of affinity improvement on pharmacokinetics in primates, J Immunol. Jun. 15, 2009;182(12):7663-71. doi: 10.4049/jimmunol.0804182.
Yoshino et al., Upgrading of flow cytometric analysis for absolute counts, cytokines and other antigenic molecules of cynomolgus monkeys (*Macaca fascicularis*) by using anti-human cross-reactive antibodies, Exp. Anim., 2000, vol. 49(2), pp. 97-100.
Yu et al., The biosynthetic gene cluster of the maytansinoids antitumor agent ansamitocin from actinosynnema pretiosum, 2002, PNAS 99:7968-7973.
Zalevsky et al. "Enhanced antibody half-life improves in vivo activity." Nature Biotechnology, vol. 28, No. 2, Feb. 1, 2010, pp. 157-159.
Zamyatnin AA., Amino acid, peptide, and protein volume in solution., *Annu Rev Biophys Bioeng.* 1984;13:145-65.
Zeidler, et al., The Fc-region of a new class of intact bispecific antibody mediates activation of accessory cells and NK cells and induces direct phagocytosis of tumour cells, Br J Cancer, 2000, vol. 83(2), pp. 261-266.
Zhu, et al., Identification of Heavy Chain Residues in a Humanized Anti-CD3 Antibody Important for Efficient Antigen Binding and T Cell Activation, The Journal of Immunology, 1995, vol. 155, pp. 1903-1910.
Zhu, et al., Remodeling domain interfaces to enhance heterodimer formation, Protein Science, 1997, vol. 6, pp. 781-788.
Zeibig et al., Effect of the oxLDL Binding Protein Fc-CD68 on Plaque Extension and Vulnerability in Atherosclerosis., Circulation Research 108: 695-703, 2011.
Zuo, et al., An efficient route to the production of an IgG-like bispecific antibody, Protein Engineering, 2000, vol. 13, No. 5, pp. 361-367.
Sun et al., Anti-CD20/CD3 T cell-dependent bispecific antibody for the treatment of B cell malignancies., Science Translational Medicine May 13, 2015: vol. 7, Issue 287, pp. 287ra70 DOI: 10.1126/scitranslmed.aaa480.
Capizzi et al., Curative chemotherapy for acute myeloid leukemia: the development of high-dose ara-C from the laboratory to bedside., Invest New Drugs. 1996;14(3):249-56.
Giles et al., Intravenous corticosteroids to reduce gemtuzumab ozogamicin infusion reactions. Ann Pharmacother. Sep. 2003;37(9):1182-5.
Duong et al., Targeted treatment of acute myeloid leukemia in older adults: role of gemtuzumab ozogamicin., Clin Interv Aging. 2009;4:197-205. Epub May 14, 2009.
Sun et al., Preclinical Characterization of Combinability and Potential Synergy of Anti-CD20/CD3 T-Cell Dependent Bispecific Antibody with Chemotherapy and PD-1/PD-L1 Blockade., Blood 2016 128:4168.
Gantke et al., Trispecific antibodies for CD16A-directed NK cell engagement and dual-targeting of tumor cells., Protein Eng Des Sel. Sep. 1, 2017;30(9):673-684. doi: 10.1093/protein/gzx043.
Zhang et al., The development of bispecific antibodies and their applications in tumor immune escape., Experimental Hematology & Oncology20176:12.
Krupka et al.,Blockade of the PD-1/PD-L1 axis augments lysis of AML cells by the CD33/CD3 BiTE antibody construct AMG 330: reversing a T-cell-induced immune escape mechanism., Leukemia. Feb. 2016;30(2):484-91. doi: 10.1038/leu.2015.214. Epub Aug. 4, 2015.
Osada et al., CEA/CD3-bispecific T cell-engaging (BiTE) antibody-mediated T lymphocyte cytotoxicity maximized by inhibition of both PD1 and PD-L1., Cancer Immunol Immunother. Jun. 2015;64(6):677-88. doi: 10.1007/s00262-015-1671-y. Epub Mar. 6, 2015.
Masarova et al., Immune Checkpoint Approaches in AML and MDS: A Next Frontier?, The Journal of Targeted Therapies in Cancer, Mar. 6, 2017 (Mar. 6, 2017), XP002784099.
Scott et al., Antibody therapy of cancer., Nat Rev Cancer. Mar. 22, 2012;12(4):278-87. doi: 10.1038/nrc3236.
Clynes et al., Redirected T Cell Cytotoxicity in Cancer Therapy., Annu Rev Med. Jan. 27, 2019;70:437-450. doi: 10.1146/annurev-med-062617-035821. Epub Oct. 31, 2018.
Merchant et al., Monovalent antibody design and mechanism of action of onartuzumab, a MET antagonist with anti-tumor activity as a therapeutic agent., Proc Natl Acad Sci U S A. Aug. 6, 2013;110(32):E2987-96. doi: 10.1073/pnas.1302725110. Epub Jul. 23, 2013.
Fos et al., ICOS ligation recruits the p50alpha PI3K regulatory subunit to the immunological synapse., J Immunol. Aug. 1, 2008;181(3):1969-77.
Sanmamed et al., Agonists of Co-stimulation in Cancer Immunotherapy Directed Against CD137, OX40, GITR, CD27, CD28, and ICOS., Semin Oncol. Aug. 2015;42(4):640-55. doi: 10.1053/j.seminoncol. 2015.05.014. Epub Jun. 11, 2015.
Vieira et al., ICOS-mediated signaling regulates cytokine production by human T cells and provides a unique signal to selectively control the clonal expansion of Th2 helper cells., Eur J Immunol. May 2004;34(5):1282-90.
Carpenter et al., Activation of human B cells by the agonist CD40 antibody CP-870,893 and augmentation with simultaneous toll-like receptor 9 stimulation., J Transl Med. Nov. 11, 2009;7:93. doi: 10.1186/1479-5876-7-93.
Gilboa et al., Use of oligonucleotide aptamer ligands to modulate the function of immune receptors., Clin Cancer Res. Mar. 1, 2013;19(5):1054-62. doi: 10.1158/1078-0432.CCR-12-2067.
Uy et al., Preliminary Results of a Phase 1 Study of Flotetuzumab, a CD123×CD3 Bispecific Dart® Protein, in Patients with Relapsed/Refractory Acute Myeloid Leukemia and Myelodysplastic Syndrome., Blood 2017 130:637.
Vey et al., Interim Results from a Phase 1 First-in-Human study of flotetuzumab, a CD123×CD3 bispecific DART molecule, in AML/MDS., Annals of Oncology (2017) 28 (suppl_5): v355-v371. 10.1093/annonc/mdx373.
Ravandi et al., Complete Responses in Relapsed/Refractory Acute Myeloid Leukemia (AML) Patients on a Weekly Dosing Schedule of XmAb14045, a CD123×CD3 T Cell-Engaging Bispecific Antibody: Initial Results of a Phase 1 Study., Blood 2018 132:763; doi: https://doi.org/10.1182/blood-2018-99-119786.
Bernett et al., Multiple Bispecific Checkpoint Combinations Promote T cell activation., Nov. 11, 2016, retrieved from the internet: http://files.shareholder.com/downloads/AMDA-2B2V8N/0x0x916283/67AE1A8B-40E8-4316-9F79-384D06B2C395/XNCR_SITC_2016_PD1xCTLA4_Poster126_12Nov2016.pdf.
Chichili et al., Co-targeting of PD-1 and CTLA-4 Inhibitory Pathways with Bispecific DART® and TRIDENT™ Molecules., Apr. 4, 2017, retrieved from the internet: http://files.shareholder.com/downloads/AMDA-278VRP/0x0x935572/8CC86417-40BA-41C0-935D-EF1B7DB0B5BB/AACR_2017_-_Co-targeting_PD-1_and_CTLA-4_Inhibitory_Pathways_with_DART_and_TRIDENT_Molecules.pdf.
"Hedvat et al., Dual Blockade of PD-1 and CTLA-4 with Bispecific Antibodies Promotes Human T cell Activation and Proliferation., Nov. 11, 2016, retrieved from the internet: http://files.shareholder.com/downloads/AMDA-2B2V8N/0x0x916284/D8084990-61EC-4DFE-8B76-60CF58B8C06F/CPI_bispecifics.pdf".
Ott et al., CTLA-4 and PD-1/PD-L1 blockade: new immunotherapeutic modalities with durable clinical benefit in melanoma patients., Clin Cancer Res. Oct. 1, 2013;19(19):5300-9. doi: 10.1158/1078-0432. CCR-13-0143.

(56) References Cited

OTHER PUBLICATIONS

Spranger et al., Mechanism of tumor rejection with doublets of CTLA-4, PD-1/PD-L1, or IDO blockade involves restored IL-2 production and proliferation of CD8(+) T cells directly within the tumor microenvironment., J Immunother Cancer. Feb. 18, 2014;2:3. doi: 10.1186/2051-1426-2-3. eCollection 2014.

Madrenas et al., Conversion of CTLA-4 from inhibitor to activator of T cells with a bispecific tandem single-chain Fv ligand., J Immunol. May 15, 2004;172(10):5948-56.

Yokosuka et al., Spatiotemporal basis of CTLA-4 costimulatory molecule-mediated negative regulation of T cell activation., Immunity. Sep. 24, 2010;33(3):326-39. doi: 10.1016/j.immuni.2010.09.006.

Fan et al., Engagement of the ICOS pathway markedly enhances efficacy of CTLA-4 blockade in cancer immunotherapy., J Exp Med. Apr. 7, 2014;211(4):715-25. doi: 10.1084/jem.20130590. Epub Mar. 31, 2014.

Larkin, J. et al. (2015) Combined Nivolumab and Ipilimumab or Monotherapy in Untreated Melanoma. The New England Journal of Medicine 373(1); 23-34 (Year: 2015).

Postow, M.A., et al. (2015) Nivolumab and Ipilimumab versus Ipilimumab in Untreated Melanoma The New England Journal of Medicine 372; 2006-2017 (Year: 2015).

Hodi, F.S., et al. (2017) Two-year overall survival rates from a randomised phase 2 trial evaluating the combination of nivolumab and ipilimumab versus ipilimumab alone in patients with advanced melanoma Lancet Oneal. 17(11 ); 1558-1568 (Year: 2017).

Sheng, J., et al. (2017) Clinical Pharmacology Considerations for the Development of Immune Checkpoint Inhibitors The Journal of Clinical Pharmacology 57(S1 O); S26-S42 (Year: 2017).

Srivastava, P., et al. (2018) Primary amelanotic malignant melanoma of cervix masquerading as squamous cell carcinoma presenting with extensive metastases. BMJ Case Rep (10) 1-4 (Year: 2018).

Lichtenegger et al., Targeting LAG-3 and PD-1 to Enhance T Cell Activation by Antigen-Presenting Cells., Front. Immunol. Feb. 27, 2018; 9: 385; pp. 1-12.

Liang et al., Targeting IFNα to tumor by anti-PD-L1 creates feedforward antitumor responses to overcome checkpoint blockade resistance ., Nat. Commun. Nov. 2, 2018; 9 (1): 4586.

Chen et al., Therapeutic efficacy of an anti-PD-L1 antibody based immunocytokine in a metastatic mouse model of colorectal cancer ., Biochem. Biophys. Res. Commun. Nov. 11, 2016; 480 (2): 160-5.

\* cited by examiner

Bottle-opener

Dual scFv

One-arm central-scFv

One-arm scFv-mAb

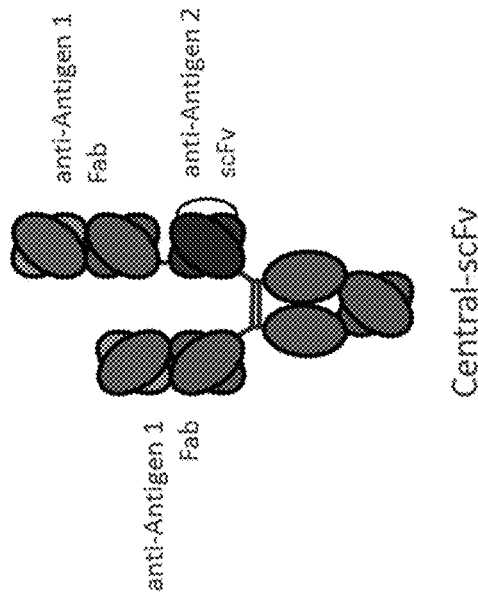
FIG. 1F — Central-scFv
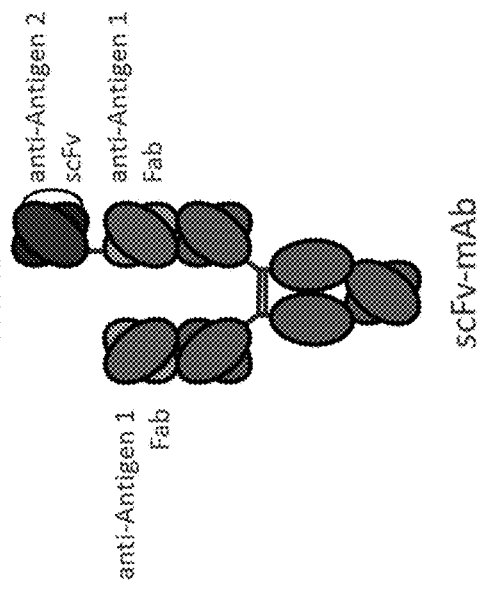
FIG. 1E — scFv-mAb
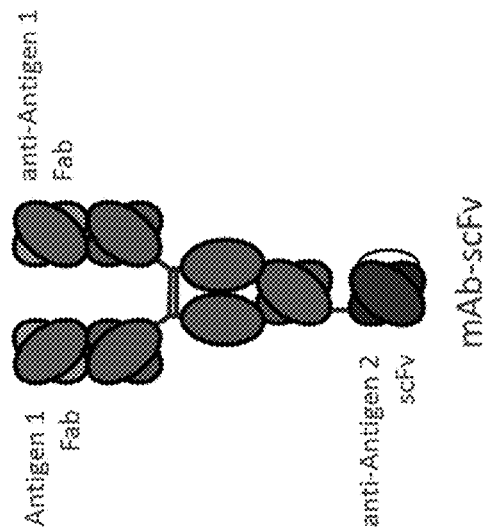
FIG. 1H — mAb-scFv
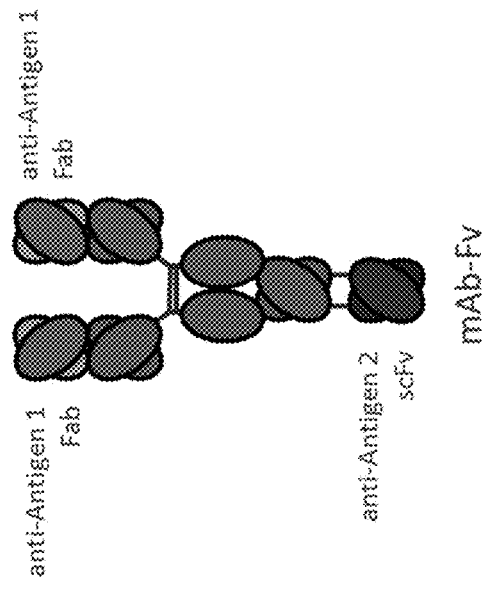
FIG. 1G — mAb-Fv

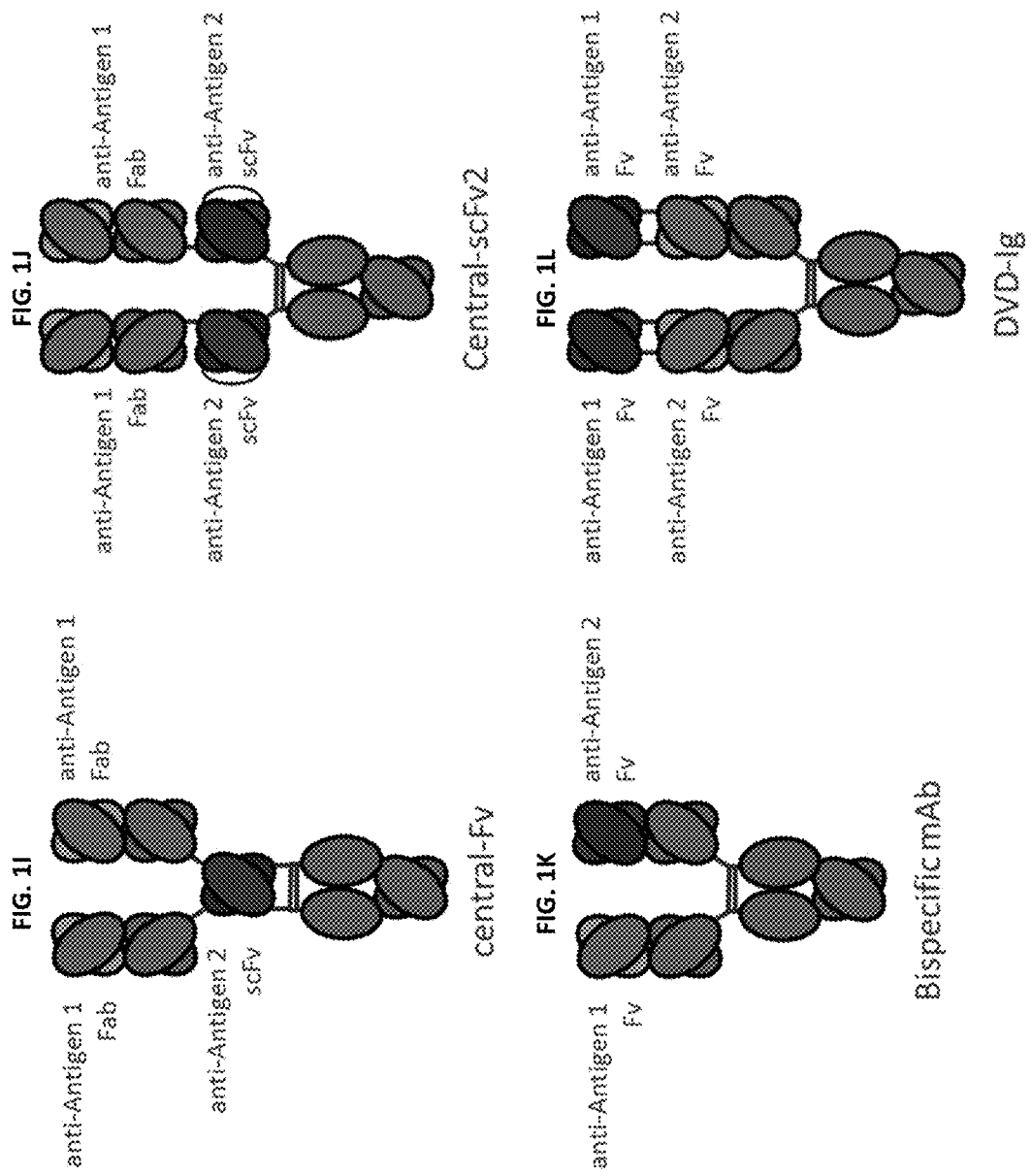

One-arm mAb anti-Antigen 2 Fab

Trident anti-Antigen 1 Fab anti-Antigen 2 scFv anti-Antigen 1 scFv anti-Antigen 2 scFv mAb-(scFv)2

FIG. 2A
antigen sequences

Human PD-1 sequence

>sp|Q15116 SEQ ID NO: 39182
MQIPQAPWPVVWAVLQLGWRPGWFLDSPDRPWNPPTFSPALLVVTEGDNATFTCSFSNTSESFVLNWYRMSPSNQTDKLAAFPEDRSQPGQDCRFRVTQLENGRDFHMSVVRARRNDSG
TYLCGAISLAPKAQIKESLRAELRVTERRAEVPTAHPSPSPRPAGQFQTLVVGVVGGLLGSLVLLVWVLAVICSRAARGTIGARRTGQPLKEDPSAVPVFSVDYGELDFQWREKTPEPP
VPCVPEQTEYATIVFPSGMGTSSPARRGSADGPRSAQPLRPEDGHCSWPL

Human PD-1 sequence, extracellular domain

>sp|Q15116|21-170 SEQ ID NO: 39183
PGWFLDSPDRPWNPPTFSPALLVVTEGDNATFTCSFSNTSESFVLNWYRMSPSNQTDKLAAFPEDRSQPGQDCRFRVTQLPNGRDFHMSVVRARRNDSGTYLCGAISLAPKAQIKESLR
AELRVTERRAEVPTAHPSPSPRPAGQFQTLV

Macaca fascicularis PD-1 sequence

>tr|B0LAJ3 SEQ ID NO: 39184
MQIPQAPWPVVWAVLQLGWRPGWFLESPDRPWNAPTFSPALLVVTEGDNATFTCSFSNASESFVLNWYRMSPSNQTDKLAAFPEDRSQPGQDCRFRVTRLPNGRDFHMSVVRARRNDSG
TYLCGAISLAPKAQIKESLRAELRVTERRAEVPTAHPSPSGLGSIVLLVWVLAVICSRAAQGTIEARRTGQPLKEDPSAVPVFSVDYGELDFQWREKTPEPP
APCVPEQTEYATIVFPSGLGTSSPARRGSADGPRSPRPLRPEDGHCSWPL

Macaca fascicularis PD-1 sequence, extracellular domain (predicted)

>tr|B0LAJ3|21-170 SEQ ID NO: 39185
PGWFLESPDRPWNAPTFSPALLVVTEGDNATFTCSFSNASESFVLNWYRMSPSNQTDKLAAFPEDRSQPGQDCRFRVTRLPNGRDFHMSVVRARRNDSGTYLCGAISLAPKAQIKESLR
AELRVTERRAEVPTAHPSPSPRPAGQFQALV

Human CTLA-4 sequence

>sp|P16410 SEQ ID NO: 39186
MACLGFQRHKAQLNLATRTWPCTLLFFLLFIPVFCKAMHVAQPAVVLASSRGIASFVCEYASPGKATEVRVTVLRQADSQVTEVCAATYMMGNELTFLDDSICTGTSSGNQVNLTIQGL
RAMDTGLYICKVELMYPPPYYLGIGNGTQIYVIDPIN

Human CTLA-4 sequence, extracellular domain

>sp|P16410|36-161 SEQ ID NO: 39187
KAMHVAQPAVVLASSRGIASFVCEYASPGKATEVRVTVLRQADSQVTEVCAATYMMGNELTFLDDSICTGTSSGNQVNLTIQGLRAMDTGLYICKVELMYPPPYYLGIGNGTQIYVIDP
EPCPDSD

FIG. 2B

Macaca fascicularis CTLA-4 sequence

>tr|G7PL88 SEQ ID NO: 39188
MACLGFQRHKARLNLATRTRPYTLLFSLLFIPVFSKAMHVAQPAVVLANSRGIASFVCEYASPGKATEVRVTVLRQADSQVTEVCAATYMMGNELTFLDDSICTGTSSGNQVNLTIQGL
RAMDTGLYICKVELMYPPPYMGIGNGTQIYVIDPEPCPDSDFLLWILAAVSSGLFFYSFLLTAVSLSKMLKKRSPLTTGVYVKMPPTEPECEKQFQPYFIPIN

Macaca fascicularis CTLA-4 sequence, extracellular domain (predicted)

>tr|G7PL88 SEQ ID NO: 39189
KAMHVAQPAVVLANSRGIASFVCEYASPGKATEVRVTVLRQADSQVTEVCAATYMMGNELTFLDDSICTGTSSGNQVNLTIQGLRAMDTGLYICKVELMYPPPYMGIGNGTQIYVIDP
EFCPDSD

Human LAG-3 sequence

>sp|P18627 SEQ ID NO: 39190
MWEAQFLGLLFLQPLWVAPVKPLQPGAEVPVVWAQEGAPAQLPCSPTIPLQDLSLLRRAGVTWQHQPDSGPPAAAPGHPLAPGPHPAAPSSWGPRPRRYTVLSVGPGGLRSGRLPLQPR
VQLDERGRQRGDFSLWLRPARRADAGEYRAAVHLRDRALSCRLRLRLGQASMTASPPGSLRASDWVILNCSFSRPDRPASVHWFRNRGQGRVPVRESPHHHLAESFLFLPQVSPMDSGP
WGCILTYRDGFNVSIMYNLTVLGLEPPTPLTVYAGAGSRVGLPCRLPAGVGTRSFLTAKWTPPGGGPDLLVTGDNGDFTLRLEDVSQAQAGTYTCHIHLQEQQLNATVTLAIITVTPKS
FGSPGSLGKLLCEVTPVSGQERFVWSSLDTPSQRSFSGPWLEAEAQLLSQPWQCQLYQGERLLGAAVYFTELSSPGAQRSGRAPGALPAGHLLLFLILGVLSLLLLVTGAFGFHLWRR
QWRPRRFSALEQGIHPPQAQSKIEELEQEPEPEPEPEPEPEPEPEQL

Human LAG-3 sequence, extracellular domain

>sp|P18627|29-450 SEQ ID NO: 39191
MWEAQFLGLLFLQPLWVAPVKPLQPGAEISVVWAQEGAPAQLPCSPTIPLQDLSLLRRAGVTWQHQPDSGPPAAAPGHPLAPGPHPAAPSSWGPRPRRYTVLSVGPGGLRSGRLPLQPRVQLDERGRQRGDFSLWLRPARRADAGEY
RAAVHLRDRALSCRLRLRLGQASMTASPPGSLRASDWVILNCSFSRPDRPASVHWFRNRGQGRVPVRESPHHHLAESFLFLPQVSPMDSGPWGCILTYRDGFNVSIMYNLTVLGLEPPT
PLTVYAGAGSRVGLPCRLPAGVGTRSFLTAKWTPPGGGPDLLVTGDNGDFTLRLEDVSQAQAGTYTCHIHLQEQQLNATVTLAIITVTPKSFGSPGSLGKLLCEVTPVSGQERFVWSSL
DTPSQRSFSGPWLEAEAQLLSQPWQCQLYQGERLLGAAVYFTELSSPGAQRSGRAPGALPAGHL

Macaca fascicularis LAG-3 sequence (predicted)

>gi|544467815|ref|XP_005570011.1  SEQ ID NO: 39192
MWEAQFLGLLFLQPLWVAPVKPPQPGAEISVVWAQEGAPAQLPCSPTIPLQDLSLLRRAGVTWQHQPDSGPPAAXAPGHPPVPGHRPAAPYSWGPRPRRYTVLSVGPGGLRSGRLPLQPR
VQLDERGRQRGDFSLWLRPARRADAGEYRATVHLRDRALSCRLRLRVGQASMTASPPGSLRTSDWVILNCSFSRPDRPASVHWFRSRGQGRVPVQGSPHHHLAESFLFLPHVGPMDSGL
WGCILTYRDGFNVSIMYNLTVLGLEPATPLITVAGAGSRVELPCRLPPAVGTQSFLTAKWAPPGGGPDFTLRLEDVSQAQAGTYICHIRLQGGQLNATVTLAIITVTPKS
FGSPGSLGKLLCEVTPASGQEHFVWSPLNTPSQRSFSGPWLEAEAQLLSQPWQCQLHQGERLLGAAVYFTELSSPGAQRSGRAPGALRAGHLPLFLILGVLFLLLVTGAFGFHLWRR
QWRPRRFSALEQGIHPPQAQSKIEELEQEPELEPELERELGPEPEPGPEPEPEQL

FIG. 2C

Macaca fascicularis LAG-3 sequence, extracellular domain (predicted)

>gi|544467815|ref|XP_005570011.1|29-450 SEQ ID NO: 39193
ISVVWAQEGAPAQLPCSPTIPLQDLSLLRRAGVTWQHQPDSGPPAXAPGHPPVEGHRPAAPYSWGPREPRRYTVLSVGPGGLRSGRLPLQPRVQLDERGRQRGDFSLWLRPARRADAGEY
RATVHLRDRALSCRLRLRVGQASMTASPPGSLRTSDWVILNCSFSRPDRPASVHWFRSRQGGRVPVQGSPHHHLAESFLFLPHVGPMDSGLWGCILTYRDGFNVSIMYNLTVLGLEPAT
PLTVYAGAGSSRVELPCRLPPAVGTQSFLTAKWAPPGGGPDLLVAGDNGDFTIRLEDVSQAQAGTYICHIRLQGGQQLNATVTLAIITVTPKSFGSPGSLGKLLCEVTPASGQEHFVWSPL
NTPSQRSFSGPWLEAQEAQLLSQPWQCQLHQGERLLGAAVYFTELSSPGAQRSGRAPGALRAGHL

Human BTLA sequence

>sp|Q7Z6A9| SEQ ID NO: 39194
MKTLPAMLGTGKLFWVFFLIPYLDIWNIHGKESCDVQLYIKRQSEHSILAGDPFELECPVKYCANRPHVTWCKLNGTTCVKLEDRQTSWKEEKNISFFILHFEPVLPNDNGSYRCSANF
QSNLIESHSTTLYVTDVKSASERPSKDEMASRPWLLYRLLPLGGLPLLITTCFCLFCCLRRHQGKQNELSDTAGREINLVDAHLKSEQTEASTRQNSQVLLSETGIYDNDPDLCFRMQE
GSEVYSNPCLEENKPGIVYASLNHSVIGPNSRLARNVKEAPTEYASICVRS

Human BTLA sequence, extracellular domain

>sp|Q7Z6A9|31-157 SEQ ID NO: 39195
KESCDVQLYIKRQSEHSILAGDPFELECPVKYCANRPHVTWCKLNGTTCVKLEDRQTSWKEEKNISFFILHFEPVLPNDNGSYRCSANFQSNLIESHSTTLYVTDVKSASERPSKDEMA
SRPWLLYR

Macaca fascicularis BTLA sequence (predicted)

>gi|355574640|gb|EHH51020.1| SEQ ID NO: 39196
MKTLPAMLGSSGRLFWVFLIPYLDIWNIHGKESCDVQLYIKRQSYHSIFAGDRFKLECPVKYCAHRPQVTWCKLNGTTCVKLEGRHTSWKQEKNLSFFILHFEPVLPSDNGSYRCSANF
LSAIIESHSTTLYVTDVKSASERPSKDEMASRPWLLYSLLPLGGLPLLITTCFCLFCFLRRHQGKQNELSDTTRREITLVDVPFKSEQTEASTRQNSQVLLSETGIYDNEPDFCFRMQE
GSEVYSNPCLEENKPGIIYASLNHSIIGLNARQARNVKEAPTEYASICVRS

Macaca fascicularis BTLA sequence, extracellular domain (predicted)

>gi|355574640|gb|EHH51020.1|31-157 SEQ ID NO: 39197
KESCDVQLYIKRQSYHSIFAGDRFKLECPVKYCAHRPQVTWCKLNGTTCVKLEGRHTSWKQEKNLSFFILHFEPVLPSDNGSYRCSANFLSAIIESHSTTLYVTDVKSASERPSKDEMA
SRPWLLYS

Human TIM-3 sequence

>sp|Q8TDQ0| SEQ ID NO: 39198
MFSHLPFDCVLLLLLLLLLTRSSEVEYRAEVGQNAYLPCFYTPAAPGNLVPVCWGKGACPVFECGNVVLRTDERDVNYWTSRYWLNGDFRKGDVSLTIENVTLADSGIYCCRIQIPGIMN
DEKFNLKLVIKPAKVTPAPTRQRDFTAAFPRMLTTRGHGPAETQTLGSLPDINLTIQSTLANELRDSRLANDLRDSGATIRIGIYIGAGICAGLALALIFGALIFKWYSHSKEKIQNLS
LISLANLPPSGLANAVAEGIRSEENIYTIEENVYEVEEPNEYYCYVSSRQQPSQPLGCRFAM

FIG. 2D

Human TIM-3 sequence, extracellular domain

>sp|Q8TDQ0|122-202 SEQ ID NO: 39199
SEVEYRAEVGQNAYLPCFYTPAAPGNLVPVCWGKGACPVFECGNVVLRTDERDVNYWTSRYWLNGDFRKGDVSLTIENVTLADSGIYCCRIQIPGIMNDEKFNLKLVIKPAKVTPAPTR
QRDFTAAFPRMLTTRGHGPAETQTLGSLPDINLTQISTLANELRDSRLANDLRDSGATIRIG

Macaca fascicularis TIM-3 sequence (predicted)

>gi|355750365|gb|EHH54703.1 SEQ ID NO: 39200
MFSHLPFDCVLLLLLLLTRSSEVEYIAEVGQNAYLPCSYTPAPPGNLVPVCWGKGACPVFDCSNVVLRTDNRDVNDRTSGRYWLKGDFHKGDVSLTTIENVTLADSGVYCCRIQIQIPGIM
NDEKHNVKLVVIKPAKVTPAPTLQRDLTSAFPRMLTTGEHGPAETQTPGSLPDVNLTVSNFFCELQIFTLTNELRDSGATIRTAIYIAAGISAGLALALIFGALIFKWYSHSKEKTQNL
SLISLANIPPSGLANAVAEGIRSEENIYTIEEDVYEVEEPNEYYCYVSSGQQPSQPLGCRVAMP

Macaca fascicularis TIM-3 sequence, extracellular domain (predicted)

>gi|355750365|gb|EHH54703.1|22-203 SEQ ID NO: 39201
SEVEYIAEVGQNAYLPCSYTPAPPGNLVPVCWGKGACPVFDCSNVVLRTDNRDVNDRTSGRYWLKGDFHKGDVSLTIENVTLADSGVYCCRIQIPGIMNDEKHNVKLVVIKPAKVTPAP
TLQRDLTSAFPRMLTTGEHGPAETQTPGSLPDVNLTVSNFFCELQIFTLTNELRDSGATIRTA

FIG. 3A
skew variants

| Monomer 1 | Monomer 2 |
|---|---|
| F405A | T394F |
| S364D | Y349K |
| S364E | L368K |
| S364E | Y349K |
| S364F | K370G |
| S364H | Y349K |
| S364H | Y349T |
| S364Y | K370G |
| T411K | K370E |
| V397S/F405A | T394F |
| K370R/T411K | K370E/T411E |
| L351E/S364D | Y349K/L351K |
| L351E/S364E | Y349K/L351K |
| L351E/T366D | L351K/T366K |
| P395T/V397S/F405A | T394F |
| S364D/K370G | S364Y/K370R |
| S364D/T394F | Y349K/F405A |
| S364E/F405A | Y349K/T394F |
| S364E/F405S | Y349K/T394Y |
| S364E/T411E | Y349K/D401K |
| S364H/D401K | Y349T/T411E |
| S364H/F405A | Y349T/T394F |
| S364H/T394F | Y349T/F405A |
| Y349C/S364E | Y349K/S354C |
| L351E/S364D/F405A | Y349K/L351K/T394F |
| L351K/S364H/D401K | Y349T/L351E/T411E |
| S364E/T411E/F405A | Y349K/T394F/D401K |
| S364H/D401K/F405A | Y349T/T394F/T411E |
| S364H/F405A/T411E | Y349T/T394F/D401K |

FIG. 3B

| Monomer 1 | Monomer 2 |
|---|---|
| K370E/T411D | T411K |
| L368E/K409E | L368K |
| Y349T/T394F/S354C | S364H/F405A/Y349C |
| T411E | D401K |
| T411E | D401R/T411R |
| Q347E/K360E | Q347R |
| L368E | S364K |
| L368E/K370S | S364K |
| L368E/K370T | S364K |
| L368E/D401R | S364K |
| L368E/D401N | S364K |
| L368E | E357S/S364K |
| L368E | S364K/K409E |
| L368E | S364K/K409V |
| L368D | S364K |
| L368D/K370S | S364K |
| L368D/K370S | S364K/E357L |
| L368D/K370S | S364K/E357Q |
| T411E/K360E/Q362E | D401K |
| K370S | S364K |
| L368E/K370S | S364K/E357Q |
| K370S | S364K/E357Q |
| T411E/K360D | D401K |
| T411E/K360E | D401K |
| T411E/Q362E | D401K |
| T411E/N390D | D401K |
| T411E | D401K/Q347K |
| T411E | D401K/Q347R |
| T411E/K360D/Q362E | D401K |

FIG. 3C

| Monomer 1 | Monomer 2 |
|---|---|
| K392D/K409D | E356K/D399K |
| K370D/K392D/K409D | E356K/E357K/D399K |
| I199T/N203D/K247Q/R355Q/N384S/K392N/V397M/Q419E/K447_ | Q196K/I199T/P217R/P228R/N276K |
| I199T/N203D/K247Q/R355Q/N384S/K392N/V397M/Q419E/K447_ | Q196K/I199T/N276K |
| N384S/K392N/V397M/Q419E | N276K |
| D221E/P228E/L368E | D221R/P228R/K409R |
| C220E/P228E/L368E | C220R/E224R/P228R/K409R |
| F405L | K409R |
| T366I/K392M/T394W | F405A/Y407V |
| T366V/K409F | L351Y/Y407A |
| T366A/K392E/K409F/T411E | D399R/S400R/Y407A |
| L351K | L351E |
| I199T/N203D/K247Q/R355Q/Q419E/K447_ | Q196K/I199T/P217R/P228R/N276K |
| I199T/N203D/K247Q/R355Q/Q419E/K447_ | Q196K/I199T/N276K |
| I199T N203D K274Q R355Q N384S K392N V397M Q419E DEL447 | |
| N208D Q295E N384D Q418E N421D | |
| N208D Q295E Q418E N421D | |
| Q196K I199T P217R P228R N276K | |
| Q196K I199T N276K | |
| E269Q E272Q E283Q E357Q | |
| E269Q E272Q E283Q | |
| E269Q E272Q | |
| E269Q E283Q | |
| E272Q E283Q | |
| E269Q | |

FIG. 3D

| Monomer 1 | Monomer 2 |
|---|---|
| T411E/K360E/N390D | D401K |
| T411E/Q362E/N390D | D401K |
| T411E/Q347R | D401K/K360D |
| T411E/Q347R | D401K/K360E |
| T411E/K360 | D401K/Q347K |
| T411E/K360D | D401K/Q347R |
| T411E/K360E | D401K/Q347K |
| T411E/K360E | D401K/Q347R |
| T411E/S364K | D401K/K370S |
| T411E/K370S | D401K/S364K |
| Q347E | E357Q |
| Q347E | E357Q/Q362K |
| K360D/Q362E | Q347R |
| K360D/Q362E | D401K |
| K360D/Q362E | Q347R/D401K |
| K360E/Q362E | Q347R |
| K360E/Q362E | D401K |
| K360E/Q362E | Q347R/D401K |
| Q362E/N390D | D401K |
| Q347E/K360D | D401N |
| K360D | Q347R/N390K |
| K360D | N390K/D401N |
| K360E | Y349H |
| K370S/Q347E | S364K |
| K370S/E357L | S364K |
| K370S/E357Q | S364K |
| K370S/Q347E/E357L | S364K |
| K370S/Q347E/E357Q | S364K |

FIG. 3E

| Monomer 1 | Monomer 2 |
|---|---|
| L368D/K370S/Q347E | S364K |
| L368D/K370S/E357L | S364K |
| L368D/K370S/E357Q | S364K |
| L368D/K370S/Q347E/E357L | S364K |
| L368D/K370S/Q347E/E357Q | S364K |
| L368E/K370S/Q347E | S364K |
| L368E/K370S/E357L | S364K |
| L368E/K370S/E357Q | S364K |
| L368E/K370S/Q347E/E357L | S364K |
| L368E/K370S/Q347E/E357Q | S364K |
| L368D/K370T/Q347E | S364K |
| L368D/K370T/E357L | S364K |
| L368D/K370T/E357Q | S364K |
| L368D/K370T/Q347E/E357L | S364K |
| L368D/K370T/Q347E/E357Q | S364K |
| L368E/K370T/Q347E | S364K |
| L368E/K370T/E357L | S364K |
| L368E/K370T/E357Q | S364K |
| L368E/K370T/Q347E/E357L | S364K |
| L368E/K370T/Q347E/E357Q | S364K |
| T411E/Q362E | D401K/T411K |
| T411E/N390D | D401K/T411K |
| T411E/Q362E | D401R/T411R |
| T411E/N390D | D401R/T411R |
| Y407T | T366Y |
| F405A | T394W |
| T366Y/F405A | T394W/Y407T |
| Y407A | T366W |
| T366S/L368A/Y407V | T366W |

FIG. 3F

| Monomer 1 | Monomer 2 |
|---|---|
| T366S/L368A/Y407V/Y349C | T366W/S354C |
| K392D/K409D | E356K/D399K |
| K370D/K392D/K409D | E356K/E357K/D399K |
| I199T/N203D/K247Q/R355Q/N384S/K392N/V397M/Q419E/K447_ | Q196K/I199T/P217R/P228R/N276K |
| I199T/N203D/K247Q/R355Q/N384S/K392N/V397M/Q419E/K447_ | Q196K/I199T/N276K |
| N384S/K392N/V397M/Q419E | N276K |
| D221E/P228E/L368E | D221R/P228R/K409R |
| C220E/P228E/L368E | C220R/E224R/P228R/K409R |
| F405L | K409R |
| T366I/K392M/T394W | F405A/Y407V |
| T366V/K409F | L351Y/Y407A |
| T366A/K392E/K409F/T411E | D399R/S400R/Y407A |
| L351K | L351E |
| I199T/N203D/K247Q/R355Q/Q419E/K447_ | Q196K/I199T/P217R/P228R/N276K |
| I199T/N203D/K247Q/R355Q/Q419E/K447_ | Q196K/I199T/N276K |
| I199T N203D K274Q R355Q N384S K392N V397M Q419E DEL447 | |
| N208D Q295E N384D Q418E N421D | |
| Q295E N384D Q418E N421D | |
| N208D Q295E Q418E N421D | |
| Q295E Q418E N421D | |
| Q196K I199T P217R P228R N276K | |
| Q196K I199T N276K | |
| E269Q E272Q E283Q E357Q | |
| E269Q E272Q E283Q | |
| E269Q E272Q | |
| E269Q E283Q | |
| E272Q E283Q | |
| E269Q | |

FIG. 4
pI variants

| Variant constant region | Substitutions |
|---|---|
| pI_ISO(-) | I199T N203D K274Q R355Q N384S K392N V397M Q419E DEL447 |
| pI_(-)_isosteric_A | N208D Q295E N384D Q418E N421D |
| pI_(-)_isosteric A-Fc only | Q295E N384D Q418E N421D |
| pI_(-)_isosteric_B | N208D Q295E Q418E N421D |
| pI_(-)_isosteric_B-Fc only | Q295E Q418E N421D |
| | |
| pI_ISO(+RR) | Q196K I199T P217R P228R N276K |
| pI_ISO(+) | Q196K I199T N276K |
| pI_(+)_isosteric_A | E269Q E272Q E283Q E357Q |
| pI_(+)_isosteric_B | E269Q E272Q E283Q |
| pI_(+)_isosteric_E269Q/E272Q | E269Q E272Q |
| pI_(+)_isosteric_E269Q/E283Q | E269Q E283Q |
| pI_(+)_isosteric_E272Q/E283Q | E272Q E283Q |
| pI_(+)_isosteric_E269Q | E269Q |

FIG. 5
Ablation variants

| Variant | Variant(s), cont. |
|---|---|
| G236R | P329K |
| S239G | A330L |
| S239K | A330S/P331S |
| S239Q | I332K |
| S239R | I332R |
| V266D | V266D/A327Q |
| S267K | V266D/P329K |
| S267R | S267R/A327Q |
| H268K | S267R/P329K |
| E269R | G236R/L328R |
| 299R | E233P/L234V/L235A/G236del/S239K |
| 299K | E233P/L234V/L235A/G236del/S267K |
| K322A | E233P/L234V/L235A/G236del/S239K/A327G |
| A327G | E233P/L234V/L235A/G236del/S267K/A327G |
| A327L | E233P/L234V/L235A/G236del |
| A327N | S239K/S267K |
| A327Q | 267K/P329K |
| L328E | |
| L328R | |
| P329A | |
| P329H | |

FIG. 6A
useful combinations

| scFv monomer (+) | Fab monomer (-) |
|---|---|
| Heterodimer pI variants S364K/E357Q | Heterodimerization pI variants L368D/K370S |
| Optional scFv charged linker including but not limited to (GKPGS)$_4$ (SEQ ID NO: 39202) | Isosteric pI substitutions N208D/Q295E/N384D/Q418E/N421D |
| FcKO E233P/L234V/L235A/G236del/S267K | FcKO E233P/L234V/L235A/G236del/S267K |
| ± 428L/434S for FcRn | ± 428L/434S for FcRn |
| scFv of ABD of first checkpoint inhibitor (anti-PD-1) | Fv/Fab of the ABD of second checkpoint inhibitor |

FIG. 6B

| scFv monomer | Fab monomer |
|---|---|
| Heterodimer pI variants S364K/E357Q | Heterodimerization pI variants L368D/K370S |
| Optional scFv charged linker including, but not limited to (GKPGS)$_4$(SEQ ID NO: 39202) | pI substitutions I199T N203D K274Q R355Q Q419E K447del |
| FcKO E233P/L234V/L235A/G236del/S267K | FcKO E233P/L234V/L235A/G236del/S267K |
| ± 428L/434S for FcRn (optional) | ± 428L/434S for FcRn (optional) |
| scFv of ABD of first checkpoint inhibitor (anti-PD-1) | Fv/Fab of the ABD of second checkpoint inhibitor |

FIG. 7A
Linkers

Positive charged scFv linkers

| Name | Sequence | Length | Charge | SEQ ID NO: |
|---|---|---|---|---|
| Gly-Ser 15 | GGGGSGGGGSGGGGS | 15 | 0 | 39203 |
| Whitlow linker | GSTSGSGKPGSGEGSTKG | 18 | +1 | 39204 |
| 6paxA_1 (+A) | IRPRAIGGSKPRVA | 14 | +4 | 39205 |
| +B | GKGGSGKGGSGKGGS | 15 | +3 | 39206 |
| +C | GGKGSGGKGSGGKGS | 15 | +3 | 39207 |
| +D | GGGKSGGGKSGGGKS | 15 | +3 | 39208 |
| +E | GKGKSGKGKSGKGKS | 15 | +6 | 39209 |
| +F | GGGKSGGKGSGKGGS | 15 | +3 | 39210 |
| +G | GKPGSGKPGSGKPGS | 15 | +3 | 39211 |
| +H | GKPGSGKPGSGKPGSGKPGS | 20 | +4 | 39202 |
| +I | GKGKSGKGKSGKGKSGKGKS | 20 | +8 | 39212 |

Negative charged scFv linkers

| Name | Sequence | Length | Charge | SEQ ID NO: |
|---|---|---|---|---|
| Gly-Ser 15 | GGGGSGGGGSGGGGSGGGGS | 20 | 0 | 39213 |
| 3hsc_2 (-A) | STAGDTHLGGEDFD | 14 | -4 | 39214 |
| -B | GEGGSGEGGSGEGGS | 15 | -3 | 39215 |
| -C | GGEGSGGEGSGGEGS | 15 | -3 | 39216 |
| -D | GGGESGGGESGGGES | 15 | -3 | 39217 |
| -E | GEGESGEGESGEGES | 15 | -6 | 39218 |
| -F | GGGESGGEGSGEGGS | 15 | -3 | 39219 |
| -G | GEGESGEGESGEGESGEGES | 20 | -8 | 39220 |

FIG. 7B scFv Linkers

| | |
|---|---|
| GGGGSGGGGSGGGGS | (SEQ ID NO: 39203) |
| GGGGSGGGGSGGGGSGGGGS | (SEQ ID NO: 39213) |
| GSTSGSGKPGSGEGSTKG | (SEQ ID NO: 39204) |
| PRGASKSGSASQTGSAPGS | (SEQ ID NO: 39221) |
| GTAAAGAGAAGGAAAGAAG | (SEQ ID NO: 39222) |
| GTSGSSGSGSGGSGSGGGG | (SEQ ID NO: 39223) |
| GKPGSGKPGSGKPGSGKPGS | (SEQ ID NO: 39202) |

FIG. 8
Tms of skews

| XENP | Heterodimer-skewing variant, Chain 1 | Heterodimer-skewing variant, Chain 2 | Heterodimer Yield (%) | CH3 Tm (°C) |
|---|---|---|---|---|
| 12757 | none | none | 52.7 | 83.1 |
| 12758 | L368D/K370S | S364K | 94.4 | 76.6 |
| 12759 | L368D/K370S | S364K/E357L | 90.2 | 77.2 |
| 12760 | L368D/K370S | S364K/E357Q | 95.2 | 77.5 |
| 12761 | T411E/K360E/Q362E | D401K | 85.6 | 80.6 |
| 12496 | L368E/K370S | S364K | 91.5 | n.d. |
| 12511 | K370S | S364K | 59.9 | n.d. |
| 12840 | L368E/K370S | S364K/E357Q | 59.5 | n.d. |
| 12841 | K370S | S364K/E357Q | 90.4 | n.d. |
| 12894 | L368E/K370S | S364K | 41.0 | n.d. |
| 12895 | K370S | S364K | 49.3 | n.d. |
| 12896 | L368E/K370S | S364K/E357Q | 73.9 | n.d. |
| 12901 | K370S | S364K/E357Q | 87.9 | n.d. |

FIG. 9

XENP021575 1C11[PD-1]_H0L0_IgG1_PVA_/S267K Heavy Chain (SEQ ID NOS 39224-39228)
QIQLVQSGPELKKPGETVKISCRASGYTFTHYGMNWVKQAPGKGLKWMGWINTYTGEPTYADDFKGRFAFSLETSASTAYLQINNLKNEDTAT
YFCARDYYGSSPYWGQGTTLTVSS/ASTKGPSVFPLAPSSKSTSGGTAALGCLVKDYFPEPVTVSWNSGALTSGVHTFPAVLQSSGLYSLSSV
VTVPSSSLGTQTYICNVNHKPSNTKVDKKVEPKSCDKTHTCPPCPAPPVAGPSVFLFPPKPKDTLMISRTPEVTCVVVDVKHEDPEVKFNWYV
DGVEVHNAKTKPREEQYNSTYRVVSVLTVLHQDWLNGKEYKCKVSNKALPAPIEKTISKAKGQPREPQVYTLPPSREEMTKNQVSLTCLVKGF
YPSDIAVEWESNGQPENNYKTTPPVLDSDGSFFLYSKLTVDKSRWQQGNVFSCSVMHEALHNHYTQKSLSLSPGK

XENP021575 1C11[PD-1]_H0L0_IgG1_PVA_/S267K Light Chain (SEQ ID NOS 39229-39233)
DVLMTQTPLSLPVSLGDQASISCRSSQSIVHSNGNTYLEWYLQKPGQSPKLLIYKVSNRFSGVPDRFSGSGSGTDFTLKISRVEAEDLGVYYC
FQGSHVPNTFGGGTKLEIK/RTVAAPSVFIFPPSDEQLKSGTASVVCLLNNFYPREAKVQWKVDNALQSGNSQESVTEQDSKDSTYSLSSTLT
LSKADYEKHKVYACEVTHQGLSSPVTKSFNRGEC

FIG. 10

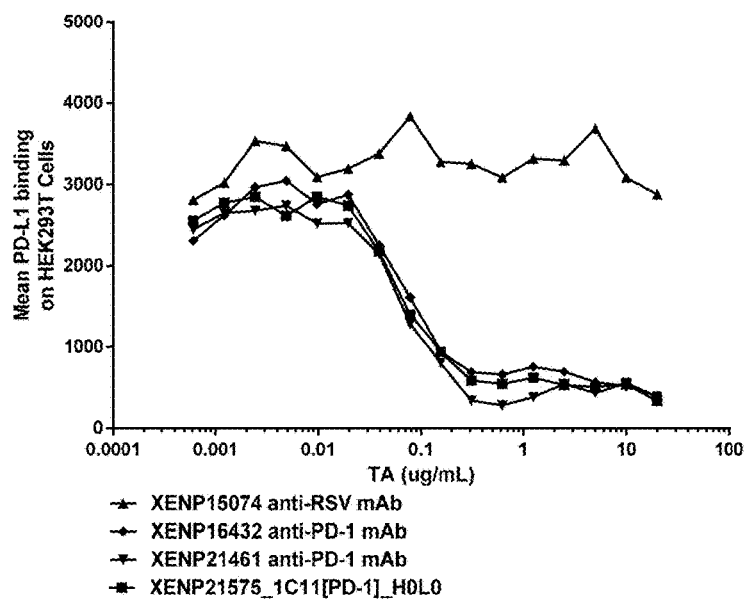

FIG. 13A

>XENP022543 1C11[PD-1]_H1L1_IgG1_PVA_/S267K Heavy Chain (SEQ ID NOS 39234-39238)
QIQLVQSGAEVKKPGASVKVSCKASGYTFTHYGMNWVRQAPGQGLEWMGWINTYTGEPTYADKFQGRVTMTLDTSTS
TAYMELSSLRSEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

>XENP022543 1C11[PD-1]_H1L1_IgG1_PVA_/S267K Light Chain (SEQ ID NOS 39239-39243)
DVLMTQSPLSLPVTPGEPASISCRSSQSIVHSNGNTYLEWYLQKPGQSPQLLIYKVSNRFSGVPDRFSGSGSGTDFT
LKISRVEAEDVGVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XENP022544 1C11[PD-1]_H2L1_IgG1_PVA_/S267K Heavy Chain (SEQ ID NOS 39244-39248)
EIQLLESGGGLVQPGGSLRLSCAASGYTFTHYGMNWVRQAPGKGLEWVSWINTYTGEPTYADSVKGRFTISLDTSKS
TAYLQMNSLRAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

>XENP022544 1C11[PD-1]_H2L1_IgG1_PVA_/S267K Light Chain (SEQ ID NOS 39249-39253)
DVLMTQSPLSLPVTPGEPASISCRSSQSIVHSNGNTYLEWYLQKPGQSPQLLIYKVSNRFSGVPDRFSGSGSGTDFT
LKISRVEAEDVGVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XENP022545 1C11[PD-1]_H3L1_IgG1_PVA_/S267K Heavy Chain (SEQ ID NOS 39254-39258)
QIQLVQSGSELKKPGASVKVSCKASGYTFTHYGMNWVRQAPGQGLEWMGWINTYTGEPTYADGFTGRFVFSLDTSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

>XENP022545 1C11[PD-1]_H3L1_IgG1_PVA_/S267K Light Chain (SEQ ID NOS 39259-39263)
DVLMTQSPLSLPVTPGEPASISCRSSQSIVHSNGNTYLEWYLQKPGQSPQLLIYKVSNRFSGVPDRFSGSGSGTDFT
LKISRVEAEDVGVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XENP022546 1C11[PD-1]_H4L1_IgG1_PVA_/S267K Heavy Chain (SEQ ID NOS 39264-39268)
EVQLLESGGGLVQPGGSLRLSCAASGYTFTHYGMNWVRQAPGKGLEWVSWINTYTGEPTYADSVKGRFTISLDTSKS
TAYLQMNSLRAEDTAVYYCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

>XENP022546 1C11[PD-1]_H4L1_IgG1_PVA_/S267K Light Chain (SEQ ID NOS 39269-39273)
DVLMTQSPLSLPVTPGEPASISCRSSQSIVHSNGNTYLEWYLQKPGQSPQLLIYKVSNRFSGVPDRFSGSGSGTDFT
LKISRVEAEDVGVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

FIG. 13B

>XENP022547 1C11[PD-1]_H1L2_IgG1_PVA_/S267K Heavy Chain (SEQ ID NOS 39274-39278)
QIQLVQSGAEVKKPGASVKVSCKASGYTFTHYGMNWVRQAPGQGLEWMGWINTYTGEPTYADKFQGRVTMTLDTSTS
TAYMELSSLRSEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

>XENP022547 1C11[PD-1]_H1L2_IgG1_PVA_/S267K Light Chain (SEQ ID NOS 39279-39283)
DVLMTQSPLSLPVTLGQPASISCRSSQSIVHSNGNTYLEWYQQRPGQSPRLLIYKVSNRFSGVPDRFSGSGSGTDFT
LKISRVEAEDVGVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XENP022548 1C11[PD-1]_H2L2_IgG1_PVA_/S267K Heavy Chain (SEQ ID NOS 39284-39288)
EIQLLESGGGLVQPGGSLRLSCAASGYTFTHYGMNWVRQAPGKGLEWVSWINTYTGEPTYADSVKGRFTISLDTSKS
TAYLQMNSLRAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

>XENP022548 1C11[PD-1]_H2L2_IgG1_PVA_/S267K Light Chain (SEQ ID NOS 39289-39293)
DVLMTQSPLSLPVTLGQPASISCRSSQSIVHSNGNTYLEWYQQRPGQSPRLLIYKVSNRFSGVPDRFSGSGSGTDFT
LKISRVEAEDVGVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XENP022549 1C11[PD-1]_H3L2_IgG1_PVA_/S267K Heavy Chain (SEQ ID NOS 39294-39298)
QIQLVQSGSELKKPGASVKVSCKASGYTFTHYGMNWVRQAPGQGLEWMGWINTYTGEPTYADGFTGRFVFSLDTSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

>XENP022549 1C11[PD-1]_H3L2_IgG1_PVA_/S267K Light Chain (SEQ ID NOS 39299-39303)
DVLMTQSPLSLPVTLGQPASISCRSSQSIVHSNGNTYLEWYQQRPGQSPRLLIYKVSNRFSGVPDRFSGSGSGTDFT
LKISRVEAEDVGVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XENP022550 1C11[PD-1]_H4L2_IgG1_PVA_/S267K Heavy Chain (SEQ ID NOS 39304-39308)
EVQLLESGGGLVQPGGSLRLSCAASGYTFTHYGMNWVRQAPGKGLEWVSWINTYTGEPTYADSVKGRFTISLDTSKS
TAYLQMNSLRAEDTAVYYCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

>XENP022550 1C11[PD-1]_H4L2_IgG1_PVA_/S267K Light Chain (SEQ ID NOS 39309-39313)
DVLMTQSPLSLPVTLGQPASISCRSSQSIVHSNGNTYLEWYQQRPGQSPRLLIYKVSNRFSGVPDRFSGSGSGTDFT
LKISRVEAEDVGVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

FIG. 13C

>XENP022551 1C11[PD-1]_H1L3_IgG1_PVA_/S267K Heavy Chain (SEQ ID NOS 39314-39318)
QIQLVQSGAEVKKPGASVKVSCKASGYTFTHYGMNWVRQAPGQGLEWMGWINTYTGEPTYADKFQGRVTMTLDTSTS
TAYMELSSLRSEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

>XENP022551 1C11[PD-1]_H1L3_IgG1_PVA_/S267K Light Chain (SEQ ID NOS 39319-39323)
DVLMTQSPDSLAVSLGERATINCKSSQSIVHSNGNTYLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XENP022552 1C11[PD-1]_H2L3_IgG1_PVA_/S267K Heavy Chain (SEQ ID NOS 39324-39328)
EIQLLESGGGLVQPGGSLRLSCAASGYTFTHYGMNWVRQAPGKGLEWVSWINTYTGEPTYADSVKGRFTISLDTSKS
TAYLQMNSLRAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

>XENP022552 1C11[PD-1]_H2L3_IgG1_PVA_/S267K Light Chain (SEQ ID NOS 39329-39333)
DVLMTQSPDSLAVSLGERATINCKSSQSIVHSNGNTYLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XENP022553 1C11[PD-1]_H3L3_IgG1_PVA_/S267K Heavy Chain (SEQ ID NOS 39334-39338)
QIQLVQSGSELKKPGASVKVSCKASGYTFTHYGMNWVRQAPGQGLEWMGWINTYTGEPTYADGFTGRFVFSLDTSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

>XENP022553 1C11[PD-1]_H3L3_IgG1_PVA_/S267K Light Chain (SEQ ID NOS 39339-39343)
DVLMTQSPDSLAVSLGERATINCKSSQSIVHSNGNTYLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XENP022554 1C11[PD-1]_H4L3_IgG1_PVA_/S267K Heavy Chain (SEQ ID NOS 39344-39348)
EVQLLESGGGLVQPGGSLRLSCAASGYTFTHYGMNWVRQAPGKGLEWVSWINTYTGEPTYADSVKGRFTISLDTSKS
TAYLQMNSLRAEDTAVYYCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

>XENP022554 1C11[PD-1]_H4L3_IgG1_PVA_/S267K Light Chain (SEQ ID NOS 39349-39353)
DVLMTQSPDSLAVSLGERATINCKSSQSIVHSNGNTYLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

FIG. 15A

>XENP022538 1C11[PD-1]_H3L3_scFv(GKPGS)4 (SEQ ID NOS 39354-39362 and linker disclosed as SEQ ID NO: 39202)
QIQLVQSGSELKKPGASVKVSCKASGYTFTHYGMNWVRQAPGQGLEWMGWINTYTGEPTYADGFTGRFVFSLDTSVSTAYLQ
ISSLKAEDTAVYFCARDYYGSSPYWGQGTLVTVSS/GKPGSGKPGSGKPGSGKPGS/DVLMTQSPDSLAVSLGERATINCKS
SQSIVHSNGNTYLEWYQQKPGQSPKLLIYKVSNRFSGVPDRFSGSGSGTDFTLTISSLQAEDVAVYYCFQGSHVPNTFGGGT
KVEIK >XENP023577 1C11_H3_L3.1_scFv(GKPGS)4 (SEQ ID NOS 39363-39371 and linker disclosed as SEQ ID NO: 39202)
QIQLVQSGSELKKPGASVKVSCKASGYTFTHYGMNWVRQAPGQGLEWMGWINTYTGEPTYADGFTGRFVFSLDTSVSTAYLQ
ISSLKAEDTAVYFCARDYYGSSPYWGQGTLVTVSS/GKPGSGKPGSGKPGSGKPGS/DILMTQSPDSLAVSLGERATINCKS
SQSIVHSNGNTYLEWYQQKPGQSPKLLIYKVSNRFSGVPDRFSGSGSGTDFTLTISSLQAEDVAVYYCFQGSHVPNTFGGGT
KVEIK >XENP023579 1C11_H3_L3.3_scFv(GKPGS)4 (SEQ ID NOS 39372-39380 and linker disclosed as SEQ ID NO: 39202)
QIQLVQSGSELKKPGASVKVSCKASGYTFTHYGMNWVRQAPGQGLEWMGWINTYTGEPTYADGFTGRFVFSLDTSVSTAYLQ
ISSLKAEDTAVYFCARDYYGSSPYWGQGTLVTVSS/GKPGSGKPGSGKPGSGKPGS/DVVMTQSPDSLAVSLGERATINCKS
SQSIVHSNGNTYLEWYQQKPGQSPKLLIYKVSNRFSGVPDRFSGSGSGTDFTLTISSLQAEDVAVYYCFQGSHVPNTFGGGT
KVEIK >XENP023589 1C11_H3_L3.15_scFv(GKPGS)4 (SEQ ID NOS 39381-39389 and linker disclosed as SEQ ID NO: 39202)
QIQLVQSGSELKKPGASVKVSCKASGYTFTHYGMNWVRQAPGQGLEWMGWINTYTGEPTYADGFTGRFVFSLDTSVSTAYLQ
ISSLKAEDTAVYFCARDYYGSSPYWGQGTLVTVSS/GKPGSGKPGSGKPGSGKPGS/DVLMTQSPDSLSVSLGERATINCKS
SQSIVHSNGNTYLEWYQQKPGQSPKLLIYKVSNRFSGVPDRFSGSGSGTDFTLTISSLQAEDVAVYYCFQGSHVPNTFGGGT
KVEIK >XENP023601 1C11_H3_L3.23_scFv(GKPGS)4 (SEQ ID NOS 39390-39398 and linker disclosed as SEQ ID NO: 39202)
QIQLVQSGSELKKPGASVKVSCKASGYTFTHYGMNWVRQAPGQGLEWMGWINTYTGEPTYADGFTGRFVFSLDTSVSTAYLQ
ISSLKAEDTAVYFCARDYYGSSPYWGQGTLVTVSS/GKPGSGKPGSGKPGSGKPGS/DVLMTQSPDSLAVSLGERVTINCKS
SQSIVHSNGNTYLEWYQQKPGQSPKLLIYKVSNRFSGVPDRFSGSGSGTDFTLTISSLQAEDVAVYYCFQGSHVPNTFGGGT
KVEIK >XENP023605 1C11_H3_L3.28_scFv(GKPGS)4 (SEQ ID NOS 39399-39407 and linker disclosed as SEQ ID NO: 39202)
QIQLVQSGSELKKPGASVKVSCKASGYTFTHYGMNWVRQAPGQGLEWMGWINTYTGEPTYADGFTGRFVFSLDTSVSTAYLQ
ISSLKAEDTAVYFCARDYYGSSPYWGQGTLVTVSS/GKPGSGKPGSGKPGSGKPGS/DVLMTQSPDSLAVSLGERATINCRS
SQSIVHSNGNTYLEWYQQKPGQSPKLLIYKVSNRFSGVPDRFSGSGSGTDFTLTISSLQAEDVAVYYCFQGSHVPNTFGGGT
KVEIK >XENP023609 1C11_H3_L3.32_scFv(GKPGS)4 (SEQ ID NOS 39408-39416 and linker disclosed as SEQ ID NO: 39202)
QIQLVQSGSELKKPGASVKVSCKASGYTFTHYGMNWVRQAPGQGLEWMGWINTYTGEPTYADGFTGRFVFSLDTSVSTAYLQ
ISSLKAEDTAVYFCARDYYGSSPYWGQGTLVTVSS/GKPGSGKPGSGKPGSGKPGS/DVLMTQSPDSLAVSLGERATINCKA
SQSIVHSNGNTYLEWYQQKPGQSPKLLIYKVSNRFSGVPDRFSGSGSGTDFTLTISSLQAEDVAVYYCFQGSHVPNTFGGGT
KVEIK >XENP023615 1C11_H3_L3.46_scFv(GKPGS)4 (SEQ ID NOS 39417-39425 and linker disclosed as SEQ ID NO: 39202)
QIQLVQSGSELKKPGASVKVSCKASGYTFTHYGMNWVRQAPGQGLEWMGWINTYTGEPTYADGFTGRFVFSLDTSVSTAYLQ
ISSLKAEDTAVYFCARDYYGSSPYWGQGTLVTVSS/GKPGSGKPGSGKPGSGKPGS/DVLMTQSPDSLAVSLGERATINCKS
SQSIVHSNGNTYLEWYQQKPGQPPKLLIYKVSNRFSGVPDRFSGSGSGTDFTLTISSLQAEDVAVYYCFQGSHVPNTFGGGT
KVEIK >XENP023616 1C11_H3_L3.47_scFv(GKPGS)4 (SEQ ID NOS 39426-39434 and linker disclosed as SEQ ID NO: 39202)
QIQLVQSGSELKKPGASVKVSCKASGYTFTHYGMNWVRQAPGQGLEWMGWINTYTGEPTYADGFTGRFVFSLDTSVSTAYLQ
ISSLKAEDTAVYFCARDYYGSSPYWGQGTLVTVSS/GKPGSGKPGSGKPGSGKPGS/DVLMTQSPDSLAVSLGERATINCKS
SQSIVHSNGNTYLEWYQQKPGQAPKLLIYKVSNRFSGVPDRFSGSGSGTDFTLTISSLQAEDVAVYYCFQGSHVPNTFGGGT
KVEIK

FIG. 15B

>XENP023624 1C11_H3_L3.57_scFv(GKPGS)4 (SEQ ID NOS 39435-39443 and linker disclosed as SEQ ID NO: 39202)
QIQLVQSGSELKKPGASVKVSCKASGYTFTHYGMNWVRQAPGQGLEWMGWINTYTGEPTYADGFTGRFVFSLDTSVS
TAYLQISSLKAEDTAVYFCARDYYGSSPYWGQGTLVTVSS/GKPGSGKPGSGKPGSGKPGS/DVLMTQSPDSLAVSL
GERATINCKSSQSIVHSNGNTYLEWYQQKPGQSPKLLIYKVSNRFTGVPDRFSGSGSGTDFTLTISSLQAEDVAVYY
CFQGSHVPNTFGGGTKVEIK

>XENP023626 1C11_H3_L3.59_scFv(GKPGS)4 (SEQ ID NOS 39444-39452 and linker disclosed as SEQ ID NO: 39202)
QIQLVQSGSELKKPGASVKVSCKASGYTFTHYGMNWVRQAPGQGLEWMGWINTYTGEPTYADGFTGRFVFSLDTSVS
TAYLQISSLKAEDTAVYFCARDYYGSSPYWGQGTLVTVSS/GKPGSGKPGSGKPGSGKPGS/DVLMTQSPDSLAVSL
GERATINCKSSQSIVHSNGNTYLEWYQQKPGQSPKLLIYKVSNRFSGVPDRFSGSGSGTDFTLTISRLQAEDVAVYY
CFQGSHVPNTFGGGTKVEIK

>XENP023628 1C11_H3_L3.62_scFv(GKPGS)4 (SEQ ID NOS 39453-39461 and linker disclosed as SEQ ID NO: 39202)
QIQLVQSGSELKKPGASVKVSCKASGYTFTHYGMNWVRQAPGQGLEWMGWINTYTGEPTYADGFTGRFVFSLDTSVS
TAYLQISSLKAEDTAVYFCARDYYGSSPYWGQGTLVTVSS/GKPGSGKPGSGKPGSGKPGS/DVLMTQSPDSLAVSL
GERATINCKSSQSIVHSNGNTYLEWYQQKPGQSPKLLIYKVSNRFSGVPDRFSGSGSGTDFTLTISSMQAEDVAVYY
CFQGSHVPNTFGGGTKVEIK

>XENP023629 1C11_H3_L3.63_scFv(GKPGS)4 (SEQ ID NOS 39462-39470 and linker disclosed as SEQ ID NO: 39202)
QIQLVQSGSELKKPGASVKVSCKASGYTFTHYGMNWVRQAPGQGLEWMGWINTYTGEPTYADGFTGRFVFSLDTSVS
TAYLQISSLKAEDTAVYFCARDYYGSSPYWGQGTLVTVSS/GKPGSGKPGSGKPGSGKPGS/DVLMTQSPDSLAVSL
GERATINCKSSQSIVHSNGNTYLEWYQQKPGQSPKLLIYKVSNRFSGVPDRFSGSGSGTDFTLTISSVQAEDVAVYY
CFQGSHVPNTFGGGTKVEIK

>XENP023633 1C11_H3_L3.69_scFv(GKPGS)4 (SEQ ID NOS 39471-39479 and linker disclosed as SEQ ID NO: 39202)
QIQLVQSGSELKKPGASVKVSCKASGYTFTHYGMNWVRQAPGQGLEWMGWINTYTGEPTYADGFTGRFVFSLDTSVS
TAYLQISSLKAEDTAVYFCARDYYGSSPYWGQGTLVTVSS/GKPGSGKPGSGKPGSGKPGS/DVLMTQSPDSLAVSL
GERATINCKSSQSIVHSNGNTYLEWYQQKPGQSPKLLIYKVSNRFSGVPDRFSGSGSGTDFTLTISSLQAEDAAVYY
CFQGSHVPNTFGGGTKVEIK

>XENP023636 1C11_H3_L3.73_scFv(GKPGS)4 (SEQ ID NOS 39480-39488 and linker disclosed as SEQ ID NO: 39202)
QIQLVQSGSELKKPGASVKVSCKASGYTFTHYGMNWVRQAPGQGLEWMGWINTYTGEPTYADGFTGRFVFSLDTSVS
TAYLQISSLKAEDTAVYFCARDYYGSSPYWGQGTLVTVSS/GKPGSGKPGSGKPGSGKPGS/DVLMTQSPDSLAVSL
GERATINCKSSQSIVHSNGNTYLEWYQQKPGQSPKLLIYKVSNRFSGVPDRFSGSGSGTDFTLTISSLQAEDVATYY
CFQGSHVPNTFGGGTKVEIK

>XENP023640 1C11_H3_L3.81_scFv(GKPGS)4 (SEQ ID NOS 39489-39497 and linker disclosed as SEQ ID NO: 39202)
QIQLVQSGSELKKPGASVKVSCKASGYTFTHYGMNWVRQAPGQGLEWMGWINTYTGEPTYADGFTGRFVFSLDTSVS
TAYLQISSLKAEDTAVYFCARDYYGSSPYWGQGTLVTVSS/GKPGSGKPGSGKPGSGKPGS/DVLMTQSPDSLAVSL
GERATINCKSSQSIVHSNGNTYLEWYQQKPGQSPKLLIYKVSNRFSGVPDRFSGSGSGTDFTLTISSLQAEDVAVYY
CFQGSHVPNTFGGQTKVEIK

>XENP023755 1C11_H3.1_L3_scFv(GKPGS)4 (SEQ ID NOS 39498-39506 and linker disclosed as SEQ ID NO: 39202)
QVQLVQSGSELKKPGASVKVSCKASGYTFTHYGMNWVRQAPGQGLEWMGWINTYTGEPTYADGFTGRFVFSLDTSVS
TAYLQISSLKAEDTAVYFCARDYYGSSPYWGQGTLVTVSS/GKPGSGKPGSGKPGSGKPGS/DVLMTQSPDSLAVSL
GERATINCKSSQSIVHSNGNTYLEWYQQKPGQSPKLLIYKVSNRFSGVPDRFSGSGSGTDFTLTISSLQAEDVAVYY
CFQGSHVPNTFGGGTKVEIK

FIG. 15C

>XENP023758 1C11_H3.5_L3_scFv(GKPGS)4 (SEQ ID NOS 39507-39515 and linker disclosed as SEQ ID NO: 39202)
QIQLVQSGAELKKPGASVKVSCKASGYTFTHYGMNWVRQAPGQGLEWMGWINTYTGEPTYADGFTGRFVFSLDTSVS
TAYLQISSLKAEDTAVYFCARDYYGSSPYWGQGTLVTVSS/GKPGSGKPGSGKPGSGKPGS/DVLMTQSPDSLAVSL
GERATINCKSSQSIVHSNGNTYLEWYQQKPGQSPKLLIYKVSNRFSGVPDRFSGSGSGTDFTLTISSLQAEDVAVYY
CFQGSHVPNTFGGGTKVEIK

>XENP023760 1C11_H3.7_L3_scFv(GKPGS)4 (SEQ ID NOS 39516-39524 and linker disclosed as SEQ ID NO: 39202)
QIQLVQSGPELKKPGASVKVSCKASGYTFTHYGMNWVRQAPGQGLEWMGWINTYTGEPTYADGFTGRFVFSLDTSVS
TAYLQISSLKAEDTAVYFCARDYYGSSPYWGQGTLVTVSS/GKPGSGKPGSGKPGSGKPGS/DVLMTQSPDSLAVSL
GERATINCKSSQSIVHSNGNTYLEWYQQKPGQSPKLLIYKVSNRFSGVPDRFSGSGSGTDFTLTISSLQAEDVAVYY
CFQGSHVPNTFGGGTKVEIK

>XENP023765 1C11_H3.18_L3_scFv(GKPGS)4 (SEQ ID NOS 39525-39533 and linker disclosed as SEQ ID NO: 39202)
QIQLVQSGSELKKPGASVKVSCKASGYTFTHYGMNWVRQAPGQGLEWMGWINTYTGEPTYADGFTGRFVFSLDTSVS
TAYLQISSLKAEDTAVYFCARDYYGSSPYWGQGTLVTVSS/GKPGSGKPGSGKPGSGKPGS/DVLMTQSPDSLAVSL
GERATINCKSSQSIVHSNGNTYLEWYQQKPGQSPKLLIYKVSNRFSGVPDRFSGSGSGTDFTLTISSLQAEDVAVYY
CFQGSHVPNTFGGGTKVEIK

>XENP023770 1C11_H3.25_L3_scFv(GKPGS)4 (SEQ ID NOS 39534-39542 and linker disclosed as SEQ ID NO: 39202)
QIQLVQSGSELKKPGASVKVSCKASGYTFTHYGMNWVRQAPGQGLEWMGWINTNTGEPTYADGFTGRFVFSLDTSVS
TAYLQISSLKAEDTAVYFCARDYYGSSPYWGQGTLVTVSS/GKPGSGKPGSGKPGSGKPGS/DVLMTQSPDSLAVSL
GERATINCKSSQSIVHSNGNTYLEWYQQKPGQSPKLLIYKVSNRFSGVPDRFSGSGSGTDFTLTISSLQAEDVAVYY
CFQGSHVPNTFGGGTKVEIK

>XENP023776 1C11_H3.35_L3_scFv(GKPGS)4 (SEQ ID NOS 39543-39551 and linker disclosed as SEQ ID NO: 39202)
QIQLVQSGSELKKPGASVKVSCKASGYTFTHYGMNWVRQAPGQGLEWMGWINTYTGEPTYADKFTGRFVFSLDTSVS
TAYLQISSLKAEDTAVYFCARDYYGSSPYWGQGTLVTVSS/GKPGSGKPGSGKPGSGKPGS/DVLMTQSPDSLAVSL
GERATINCKSSQSIVHSNGNTYLEWYQQKPGQSPKLLIYKVSNRFSGVPDRFSGSGSGTDFTLTISSLQAEDVAVYY
CFQGSHVPNTFGGGTKVEIK

>XENP023779 1C11_H3.41_L3_scFv(GKPGS)4 (SEQ ID NOS 39552-39560 and linker disclosed as SEQ ID NO: 39202)
QIQLVQSGSELKKPGASVKVSCKASGYTFTHYGMNWVRQAPGQGLEWMGWINTYTGEPTYADGFKGRFVFSLDTSVS
TAYLQISSLKAEDTAVYFCARDYYGSSPYWGQGTLVTVSS/GKPGSGKPGSGKPGSGKPGS/DVLMTQSPDSLAVSL
GERATINCKSSQSIVHSNGNTYLEWYQQKPGQSPKLLIYKVSNRFSGVPDRFSGSGSGTDFTLTISSLQAEDVAVYY
CFQGSHVPNTFGGGTKVEIK

>XENP023780 1C11_H3.42_L3_scFv(GKPGS)4 (SEQ ID NOS 39561-39569 and linker disclosed as SEQ ID NO: 39202)
QIQLVQSGSELKKPGASVKVSCKASGYTFTHYGMNWVRQAPGQGLEWMGWINTYTGEPTYADGFQGRFVFSLDTSVS
TAYLQISSLKAEDTAVYFCARDYYGSSPYWGQGTLVTVSS/GKPGSGKPGSGKPGSGKPGS/DVLMTQSPDSLAVSL
GERATINCKSSQSIVHSNGNTYLEWYQQKPGQSPKLLIYKVSNRFSGVPDRFSGSGSGTDFTLTISSLQAEDVAVYY
CFQGSHVPNTFGGGTKVEIK

>XENP023781 1C11_H3.43_L3_scFv(GKPGS)4 (SEQ ID NOS 39570-39578 and linker disclosed as SEQ ID NO: 39202)
QIQLVQSGSELKKPGASVKVSCKASGYTFTHYGMNWVRQAPGQGLEWMGWINTYTGEPTYADGFTGRVVFSLDTSVS
TAYLQISSLKAEDTAVYFCARDYYGSSPYWGQGTLVTVSS/GKPGSGKPGSGKPGSGKPGS/DVLMTQSPDSLAVSL
GERATINCKSSQSIVHSNGNTYLEWYQQKPGQSPKLLIYKVSNRFSGVPDRFSGSGSGTDFTLTISSLQAEDVAVYY
CFQGSHVPNTFGGGTKVEIK

>XENP023786 1C11_H3.50_L3_scFv(GKPGS)4 (SEQ ID NOS 39579-39587 and linker disclosed as SEQ ID NO: 39202)
QIQLVQSGSELKKPGASVKVSCKASGYTFTHYGMNWVRQAPGQGLEWMGWINTYTGEPTYADGFTGRVFSADTSVS
TAYLQISSLKAEDTAVYFCARDYYGSSPYWGQGTLVTVSS/GKPGSGKPGSGKPGSGKPGS/DVLMTQSPDSLAVSL
GERATINCKSSQSIVHSNGNTYLEWYQQKPGQSPKLLIYKVSNRFSGVPDRFSGSGSGTDFTLTISSLQAEDVAVYY
CFQGSHVPNTFGGGTKVEIK

FIG. 15D

>XENP023793 1C11_H3.59_L3_scFv(GKPGS)4 (SEQ ID NOS 39588-39596 and linker disclosed as SEQ ID NO: 39202)
QIQLVQSGSELKKPGASVKVSCKASGYTFTHYGMNWVRQAPGQGLEWMGWINTYTGEPTYADGFTGRFVFSLDTSQSTAYLQ
ISSLKAEDTAVYFCARDYYGSSPYWGQGTLVTVSS/GKPGSGKPGSGKPGSGKPGS/DVLMTQSPDSLAVSLGERATINCKS
SQSIVHSNGNTYLEWYQQKPGQSPKLLIYKVSNRFSGVPDRFSGSGSGTDFTLTISSLQAEDVAVYYCFQGSHVPNTFGGGT
KVEIK

>XENP023796 1C11_H3.62_L3_scFv(GKPGS)4 (SEQ ID NOS 39597-39605 and linker disclosed as SEQ ID NO: 39202)
QIQLVQSGSELKKPGASVKVSCKASGYTFTHYGMNWVRQAPGQGLEWMGWINTYTGEPTYADGFTGRFVFSLDTSVSTIYLQ
ISSLKAEDTAVYFCARDYYGSSPYWGQGTLVTVSS/GKPGSGKPGSGKPGSGKPGS/DVLMTQSPDSLAVSLGERATINCKS
SQSIVHSNGNTYLEWYQQKPGQSPKLLIYKVSNRFSGVPDRFSGSGSGTDFTLTISSLQAEDVAVYYCFQGSHVPNTFGGGT
KVEIK

>XENP023811 1C11_H3.74_L3_scFv(GKPGS)4 (SEQ ID NOS 39606-39614 and linker disclosed as SEQ ID NO: 39202)
QIQLVQSGSELKKPGASVKVSCKASGYTFTHYGMNWVRQAPGQGLEWMGWINTYTGEPTYADGFTGRFVFSLDTSVSTAYLQ
ISSLKAEDTAVYYCARDYYGSSPYWGQGTLVTVSS/GKPGSGKPGSGKPGSGKPGS/DVLMTQSPDSLAVSLGERATINCKS
SQSIVHSNGNTYLEWYQQKPGQSPKLLIYKVSNRFSGVPDRFSGSGSGTDFTLTISSLQAEDVAVYYCFQGSHVPNTFGGGT
KVEIK

>XENP024201 1C11_H3_L3.113_scFv(GKPGS)4 (SEQ ID NOS 39615-39623 and linker disclosed as SEQ ID NO: 39202)
QIQLVQSGSELKKPGASVKVSCKASGYTFTHYGMNWVRQAPGQGLEWMGWINTYTGEPTYADGFTGRFVFSLDTSVSTAYLQ
ISSLKAEDTAVYFCARDYYGSSPYWGQGTLVTVSS/GKPGSGKPGSGKPGSGKPGS/DVLMTQSPDSLAVSLGERATINCKS
SQSIVHSNGNTYLEWYQQKPGKSPKLLIYKVSNRFSGVPDRFSGSGSGTDFTLTISSLQAEDVAVYYCFQGSHVPNTFGGGT
KVEIK

>XENP024207 1C11_H3_L3.122_scFv(GKPGS)4 (SEQ ID NOS 39624-39632 and linker disclosed as SEQ ID NO: 39202)
QIQLVQSGSELKKPGASVKVSCKASGYTFTHYGMNWVRQAPGQGLEWMGWINTYTGEPTYADGFTGRFVFSLDTSVSTAYLQ
ISSLKAEDTAVYFCARDYYGSSPYWGQGTLVTVSS/GKPGSGKPGSGKPGSGKPGS/DVLMTQSPDSLAVSLGERATINCKS
SQSIVHSNGNTYLEWYQQKPGQSPKLLIYKVSNRFSGIPDRFSGSGSGTDFTLTISSLQAEDVAVYYCFQGSHVPNTFGGGT
KVEIK

>XENP024208 1C11_H3_L3.124_scFv(GKPGS)4 (SEQ ID NOS 39633-39641 and linker disclosed as SEQ ID NO: 39202)
QIQLVQSGSELKKPGASVKVSCKASGYTFTHYGMNWVRQAPGQGLEWMGWINTYTGEPTYADGFTGRFVFSLDTSVSTAYLQ
ISSLKAEDTAVYFCARDYYGSSPYWGQGTLVTVSS/GKPGSGKPGSGKPGSGKPGS/DVLMTQSPDSLAVSLGERATINCKS
SQSIVHSNGNTYLEWYQQKPGQSPKLLIYKVSNRFSGVPARFSGSGSGTDFTLTISSLQAEDVAVYYCFQGSHVPNTFGGGT
KVEIK

>XENP024209 1C11_H3_L3.125_scFv(GKPGS)4 (SEQ ID NOS 39642-39650 and linker disclosed as SEQ ID NO: 39202)
QIQLVQSGSELKKPGASVKVSCKASGYTFTHYGMNWVRQAPGQGLEWMGWINTYTGEPTYADGFTGRFVFSLDTSVSTAYLQ
ISSLKAEDTAVYFCARDYYGSSPYWGQGTLVTVSS/GKPGSGKPGSGKPGSGKPGS/DVLMTQSPDSLAVSLGERATINCKS
SQSIVHSNGNTYLEWYQQKPGQSPKLLIYKVSNRFSGVPDRFSGSGSGTDFTLTISSVEAEDVAVYYCFQGSHVPNTFGGGT
KVEIK

>XENP024210 1C11_H3_L3.132_scFv(GKPGS)4 (SEQ ID NOS 39651-39659 and linker disclosed as SEQ ID NO: 39202)
QIQLVQSGSELKKPGASVKVSCKASGYTFTHYGMNWVRQAPGQGLEWMGWINTYTGEPTYADGFTGRFVFSLDTSVSTAYLQ
ISSLKAEDTAVYFCARDYYGSSPYWGQGTLVTVSS/GKPGSGKPGSGKPGSGKPGS/DVLMTQSPDSLAVSLGERATINCKS
SQSIVHSNGNTYLEWYQQKPGQSPKLLIYKVSNRFSGVPDRFSGSGSGTDFTLTISSLQAEDVAVYYCFQGSHVPNTFGPGT
KVEIK

>XENP024211 1C11_H3.78_L3_scFv(GKPGS)4 (SEQ ID NOS 39660-39668 and linker disclosed as SEQ ID NO: 39202)
QIQLVQSGPELKKPGASVKVSCKASGYTFTHYGMNWVRQAPGQGLEWMGWINTNTGEPTYADGFTGRFVFSVDTSQSTAYLQ
ISSLKAEDTAVYFCARDYYGSSPYWGQGTLVTVSS/GKPGSGKPGSGKPGSGKPGS/DVLMTQSPDSLAVSLGERATINCKS
SQSIVHSNGNTYLEWYQQKPGQSPKLLIYKVSNRFSGVPDRFSGSGSGTDFTLTISSLQAEDVAVYYCFQGSHVPNTFGGGT
KVEIK

FIG. 15E

>XENP024212 1C11_H3.80_L3_scFv(GKPGS)4 (SEQ ID NOS 39669-39677 and linker disclosed as SEQ ID NO: 39202)
QIQLVQSGSELKKPGASVKVSCKASGYTFTHYGMNWVRQAPGQGLEWMGWINTNTGEPTYADGFTGRFVFSVDTSQS
TAYLQISSLKAEDTAVYYCARDYYGSSPYWGQGTLVTVSS/GKPGSGKPGSGKPGSGKPGS/DVLMTQSPDSLAVSL
GERATINCKSSQSIVHSNGNTYLEWYQQKPGQSPKLLIYKVSNRFSGVPDRFSGSGSGTDFTLTISSLQAEDVAVYY
CFQGSHVPNTFGGGTKVEIK

>XENP024213 1C11_H3.81_L3_scFv(GKPGS)4 (SEQ ID NOS 39678-39686 and linker disclosed as SEQ ID NO: 39202)
QIQLVQSGSELKKPGASVKVSCKASGYTFTHYGMNWVRQAPGQGLEWMGWINTYTGEPTYADKFKGRFVFSLDTSVS
TAYLQISSLKAEDTAVYFCARDYYGSSPYWGQGTLVTVSS/GKPGSGKPGSGKPGSGKPGS/DVLMTQSPDSLAVSL
GERATINCKSSQSIVHSNGNTYLEWYQQKPGQSPKLLIYKVSNRFSGVPDRFSGSGSGTDFTLTISSLQAEDVAVYY
CFQGSHVPNTFGGGTKVEIK

>XENP024214 1C11_H3.82_L3_scFv(GKPGS)4 (SEQ ID NOS 39687-39695 and linker disclosed as SEQ ID NO: 39202)
QIQLVQSGSELKKPGASVKVSCKASGYTFTHYGMNWVRQAPGQGLEWMGWINTYTGEPTYADKFQGRFVFSLDTSVS
TAYLQISSLKAEDTAVYFCARDYYGSSPYWGQGTLVTVSS/GKPGSGKPGSGKPGSGKPGS/DVLMTQSPDSLAVSL
GERATINCKSSQSIVHSNGNTYLEWYQQKPGQSPKLLIYKVSNRFSGVPDRFSGSGSGTDFTLTISSLQAEDVAVYY
CFQGSHVPNTFGGGTKVEIK

>XENP024215 1C11_H3.83_L3_scFv(GKPGS)4 (SEQ ID NOS 39696-39704 and linker disclosed as SEQ ID NO: 39202)
QIQLVQSGSELKKPGASVKVSCKASGYTFTHYGMNWVRQAPGQGLEWMGWINTNTGEPTYADGFTGRFVFSVDTSQS
TAYLQISSLKAEDTAVYFCARDYYGSSPYWGQGTLVTVSS/GKPGSGKPGSGKPGSGKPGS/DVLMTQSPDSLAVSL
GERATINCKSSQSIVHSNGNTYLEWYQQKPGQSPKLLIYKVSNRFSGVPDRFSGSGSGTDFTLTISSLQAEDVAVYY
CFQGSHVPNTFGGGTKVEIK

>XENP024216 1C11_H3.84_L3_scFv(GKPGS)4 (SEQ ID NOS 39705-39713 and linker disclosed as SEQ ID NO: 39202)
QIQLVQSGSELKKPGASVKVSCKASGYTFTHYGMNWVRQAPGQGLEWMGWINTYTGEPTYADKFKGRFVFSLDTSQS
TAYLQISSLKAEDTAVYFCARDYYGSSPYWGQGTLVTVSS/GKPGSGKPGSGKPGSGKPGS/DVLMTQSPDSLAVSL
GERATINCKSSQSIVHSNGNTYLEWYQQKPGQSPKLLIYKVSNRFSGVPDRFSGSGSGTDFTLTISSLQAEDVAVYY
CFQGSHVPNTFGGGTKVEIK

>XENP024217 1C11_H3.85_L3_scFv(GKPGS)4 (SEQ ID NOS 39714-39722 and linker disclosed as SEQ ID NO: 39202)
QIQLVQSGSELKKPGASVKVSCKASGYTFTHYGMNWVRQAPGQGLEWMGWINTYTGEPTYADKFQGRFVFSLDTSQS
TAYLQISSLKAEDTAVYFCARDYYGSSPYWGQGTLVTVSS/GKPGSGKPGSGKPGSGKPGS/DVLMTQSPDSLAVSL
GERATINCKSSQSIVHSNGNTYLEWYQQKPGQSPKLLIYKVSNRFSGVPDRFSGSGSGTDFTLTISSLQAEDVAVYY
CFQGSHVPNTFGGGTKVEIK

>XENP024218 1C11_H3.86_L3_scFv(GKPGS)4 (SEQ ID NOS 39723-39731 and linker disclosed as SEQ ID NO: 39202)
EIQLVQSGSELKKPGASVKVSCKASGYTFTHYGMNWVRQAPGQGLEWMGWINTYTGEPTYADGFTGRFVFSLDTSVS
TAYLQISSLKAEDTAVYFCARDYYGSSPYWGQGTLVTVSS/GKPGSGKPGSGKPGSGKPGS/DVLMTQSPDSLAVSL
GERATINCKSSQSIVHSNGNTYLEWYQQKPGQSPKLLIYKVSNRFSGVPDRFSGSGSGTDFTLTISSLQAEDVAVYY
CFQGSHVPNTFGGGTKVEIK

>XENP024221 1C11_H3.90_L3_scFv(GKPGS)4 (SEQ ID NOS 39732-39740 and linker disclosed as SEQ ID NO: 39202)
QIQLVQSGSVLKKPGASVKVSCKASGYTFTHYGMNWVRQAPGQGLEWMGWINTYTGEPTYADGFTGRFVFSLDTSVS
TAYLQISSLKAEDTAVYFCARDYYGSSPYWGQGTLVTVSS/GKPGSGKPGSGKPGSGKPGS/DVLMTQSPDSLAVSL
GERATINCKSSQSIVHSNGNTYLEWYQQKPGQSPKLLIYKVSNRFSGVPDRFSGSGSGTDFTLTISSLQAEDVAVYY
CFQGSHVPNTFGGGTKVEIK

>XENP024222 1C11_H3.91_L3_scFv(GKPGS)4 (SEQ ID NOS 39741-39749 and linker disclosed as SEQ ID NO: 39202)
QIQLVQSGSELVKPGASVKVSCKASGYTFTHYGMNWVRQAPGQGLEWMGWINTYTGEPTYADGFTGRFVFSLDTSVS
TAYLQISSLKAEDTAVYFCARDYYGSSPYWGQGTLVTVSS/GKPGSGKPGSGKPGSGKPGS/DVLMTQSPDSLAVSL
GERATINCKSSQSIVHSNGNTYLEWYQQKPGQSPKLLIYKVSNRFSGVPDRFSGSGSGTDFTLTISSLQAEDVAVYY
CFQGSHVPNTFGGGTKVEIK

FIG. 15F

>XENP024226 1C11_H3.95_L3_scFv(GKPGS)4 (SEQ ID NOS 39750-39758 and linker disclosed as SEQ ID NO: 39202)
QIQLVQSGSELKKPGGSVKVSCKASGYTFTHYGMNWVRQAPGQGLEWMGWINTYTGEPTYADGFTGRFVFSLDTSVSTAYLQ
ISSLKAEDTAVYFCARDYYGSSPYWGQGTLVTVSS/GKPGSGKPGSGKPGSGKPGS/DVLMTQSPDSLAVSLGERATINCKS
SQSIVHSNGNTYLEWYQQKPGQSPKLLIYKVSNRFSGVPDRFSGSGSGTDFTLTISSLQAEDVAVYYCFQGSHVPNTFGGGT
KVEIK >XENP024227 1C11_H3.96_L3_scFv(GKPGS)4 (SEQ ID NOS 39759-39767 and linker disclosed as SEQ ID NO: 39202)
QIQLVQSGSELKKPGQSVKVSCKASGYTFTHYGMNWVRQAPGQGLEWMGWINTYTGEPTYADGFTGRFVFSLDTSVSTAYLQ
ISSLKAEDTAVYFCARDYYGSSPYWGQGTLVTVSS/GKPGSGKPGSGKPGSGKPGS/DVLMTQSPDSLAVSLGERATINCKS
SQSIVHSNGNTYLEWYQQKPGQSPKLLIYKVSNRFSGVPDRFSGSGSGTDFTLTISSLQAEDVAVYYCFQGSHVPNTFGGGT
KVEIK >XENP024228 1C11_H3.97_L3_scFv(GKPGS)4 (SEQ ID NOS 39768-39776 and linker disclosed as SEQ ID NO: 39202)
QIQLVQSGSELKKPGESVKVSCKASGYTFTHYGMNWVRQAPGQGLEWMGWINTYTGEPTYADGFTGRFVFSLDTSVSTAYLQ
ISSLKAEDTAVYFCARDYYGSSPYWGQGTLVTVSS/GKPGSGKPGSGKPGSGKPGS/DVLMTQSPDSLAVSLGERATINCKS
SQSIVHSNGNTYLEWYQQKPGQSPKLLIYKVSNRFSGVPDRFSGSGSGTDFTLTISSLQAEDVAVYYCFQGSHVPNTFGGGT
KVEIK >XENP024247 1C11_H3.120_L3_scFv(GKPGS)4 (SEQ ID NOS 39777-39785 and linker disclosed as SEQ ID NO: 39202)
QIQLVQSGSELKKPGASVKVSCKASGYTFTHYGINWVRQAPGQGLEWMGWINTYTGEPTYADGFTGRFVFSLDTSVSTAYLQ
ISSLKAEDTAVYFCARDYYGSSPYWGQGTLVTVSS/GKPGSGKPGSGKPGSGKPGS/DVLMTQSPDSLAVSLGERATINCKS
SQSIVHSNGNTYLEWYQQKPGQSPKLLIYKVSNRFSGVPDRFSGSGSGTDFTLTISSLQAEDVAVYYCFQGSHVPNTFGGGT
KVEIK >XENP024250 1C11_H3.125_L3_scFv(GKPGS)4 (SEQ ID NOS 39786-39794 and linker disclosed as SEQ ID NO: 39202)
QIQLVQSGSELKKPGASVKVSCKASGYTFTHYGMNWVRQPPGQGLEWMGWINTYTGEPTYADGFTGRFVFSLDTSVSTAYLQ
ISSLKAEDTAVYFCARDYYGSSPYWGQGTLVTVSS/GKPGSGKPGSGKPGSGKPGS/DVLMTQSPDSLAVSLGERATINCKS
SQSIVHSNGNTYLEWYQQKPGQSPKLLIYKVSNRFSGVPDRFSGSGSGTDFTLTISSLQAEDVAVYYCFQGSHVPNTFGGGT
KVEIK >XENP024254 1C11_H3.129_L3_scFv(GKPGS)4 (SEQ ID NOS 39795-39803 and linker disclosed as SEQ ID NO: 39202)
QIQLVQSGSELKKPGASVKVSCKASGYTFTHYGMNWVRQAPGQGLEWIGWINTYTGEPTYADGFTGRFVFSLDTSVSTAYLQ
ISSLKAEDTAVYFCARDYYGSSPYWGQGTLVTVSS/GKPGSGKPGSGKPGSGKPGS/DVLMTQSPDSLAVSLGERATINCKS
SQSIVHSNGNTYLEWYQQKPGQSPKLLIYKVSNRFSGVPDRFSGSGSGTDFTLTISSLQAEDVAVYYCFQGSHVPNTFGGGT
KVEIK >XENP024256 1C11_H3.134_L3_scFv(GKPGS)4 (SEQ ID NOS 39804-39812 and linker disclosed as SEQ ID NO: 39202)
QIQLVQSGSELKKPGASVKVSCKASGYTFTHYGMNWVRQAPGQGLEWMGWINTKTGEPTYADGFTGRFVFSLDTSVSTAYLQ
ISSLKAEDTAVYFCARDYYGSSPYWGQGTLVTVSS/GKPGSGKPGSGKPGSGKPGS/DVLMTQSPDSLAVSLGERATINCKS
SQSIVHSNGNTYLEWYQQKPGQSPKLLIYKVSNRFSGVPDRFSGSGSGTDFTLTISSLQAEDVAVYYCFQGSHVPNTFGGGT
KVEIK >XENP024263 1C11_H3.143_L3_scFv(GKPGS)4 (SEQ ID NOS 39813-39821 and linker disclosed as SEQ ID NO: 39202)
QIQLVQSGSELKKPGASVKVSCKASGYTFTHYGMNWVRQAPGQGLEWMGWINTYTGEPYYADGFTGRFVFSLDTSVSTAYLQ
ISSLKAEDTAVYFCARDYYGSSPYWGQGTLVTVSS/GKPGSGKPGSGKPGSGKPGS/DVLMTQSPDSLAVSLGERATINCKS
SQSIVHSNGNTYLEWYQQKPGQSPKLLIYKVSNRFSGVPDRFSGSGSGTDFTLTISSLQAEDVAVYYCFQGSHVPNTFGGGT
KVEIK >XENP024266 1C11_H3.146_L3_scFv(GKPGS)4 (SEQ ID NOS 39822-39830 and linker disclosed as SEQ ID NO: 39202)
QIQLVQSGSELKKPGASVKVSCKASGYTFTHYGMNWVRQAPGQGLEWMGWINTYTGEPTYAPGFTGRFVFSLDTSVSTAYLQ
ISSLKAEDTAVYFCARDYYGSSPYWGQGTLVTVSS/GKPGSGKPGSGKPGSGKPGS/DVLMTQSPDSLAVSLGERATINCKS
SQSIVHSNGNTYLEWYQQKPGQSPKLLIYKVSNRFSGVPDRFSGSGSGTDFTLTISSLQAEDVAVYYCFQGSHVPNTFGGGT
KVEIK

FIG. 15G

>XENP024267 1C11_H3.147_L3_scFv(GKPGS)4 (SEQ ID NOS 39831-39839 and linker disclosed as SEQ ID NO: 39202)
QIQLVQSGSELKKPGASVKVSCKASGYTFTHYGMNWVRQAPGQGLEWMGWINTYTGEPTYATGFTGRFVFSLDTSVSTAYLQ
ISSLKAEDTAVYFCARDYYGSSPYWGQGTLVTVSS/GKPGSGKPGSGKPGSGKPGS/DVLMTQSPDSLAVSLGERATINCKS
SQSIVHSNGNTYLEWYQQKPGQSPKLLIYKVSNRFSGVPDRFSGSGSGTDFTLTISSLQAEDVAVYYCFQGSHVPNTFGGGT
KVEIK

>XENP024268 1C11_H3.148_L3_scFv(GKPGS)4 (SEQ ID NOS 39840-39848 and linker disclosed as SEQ ID NO: 39202)
QIQLVQSGSELKKPGASVKVSCKASGYTFTHYGMNWVRQAPGQGLEWMGWINTYTGEPTYAQKFTGRFVFSLDTSVSTAYLQ
ISSLKAEDTAVYFCARDYYGSSPYWGQGTLVTVSS/GKPGSGKPGSGKPGSGKPGS/DVLMTQSPDSLAVSLGERATINCKS
SQSIVHSNGNTYLEWYQQKPGQSPKLLIYKVSNRFSGVPDRFSGSGSGTDFTLTISSLQAEDVAVYYCFQGSHVPNTFGGGT
KVEIK

>XENP024270 1C11_H3.150_L3_scFv(GKPGS)4 (SEQ ID NOS 39849-39857 and linker disclosed as SEQ ID NO: 39202)
QIQLVQSGSELKKPGASVKVSCKASGYTFTHYGMNWVRQAPGQGLEWMGWINTYTGEPTYADGFTERFVFSLDTSVSTAYLQ
ISSLKAEDTAVYFCARDYYGSSPYWGQGTLVTVSS/GKPGSGKPGSGKPGSGKPGS/DVLMTQSPDSLAVSLGERATINCKS
SQSIVHSNGNTYLEWYQQKPGQSPKLLIYKVSNRFSGVPDRFSGSGSGTDFTLTISSLQAEDVAVYYCFQGSHVPNTFGGGT
KVEIK

>XENP024274 1C11_H3.154_L3_scFv(GKPGS)4 (SEQ ID NOS 39858-39866 and linker disclosed as SEQ ID NO: 39202)
QIQLVQSGSELKKPGASVKVSCKASGYTFTHYGMNWVRQAPGQGLEWMGWINTYTGEPTYADGFTGRFVFSIDTSVSTAYLQ
ISSLKAEDTAVYFCARDYYGSSPYWGQGTLVTVSS/GKPGSGKPGSGKPGSGKPGS/DVLMTQSPDSLAVSLGERATINCKS
SQSIVHSNGNTYLEWYQQKPGQSPKLLIYKVSNRFSGVPDRFSGSGSGTDFTLTISSLQAEDVAVYYCFQGSHVPNTFGGGT
KVEIK

>XENP024278 1C11_H3.158_L3_scFv(GKPGS)4 (SEQ ID NOS 39867-39875 and linker disclosed as SEQ ID NO: 39202)
QIQLVQSGSELKKPGASVKVSCKASGYTFTHYGMNWVRQAPGQGLEWMGWINTYTGEPTYADGFTGRFVFSLDTSVNTAYLQ
ISSLKAEDTAVYFCARDYYGSSPYWGQGTLVTVSS/GKPGSGKPGSGKPGSGKPGS/DVLMTQSPDSLAVSLGERATINCKS
SQSIVHSNGNTYLEWYQQKPGQSPKLLIYKVSNRFSGVPDRFSGSGSGTDFTLTISSLQAEDVAVYYCFQGSHVPNTFGGGT
KVEIK

>XENP024279 1C11_H3.159_L3_scFv(GKPGS)4 (SEQ ID NOS 39876-39884 and linker disclosed as SEQ ID NO: 39202)
QIQLVQSGSELKKPGASVKVSCKASGYTFTHYGMNWVRQAPGQGLEWMGWINTYTGEPTYADGFTGRFVFSLDTSVDTAYLQ
ISSLKAEDTAVYFCARDYYGSSPYWGQGTLVTVSS/GKPGSGKPGSGKPGSGKPGS/DVLMTQSPDSLAVSLGERATINCKS
SQSIVHSNGNTYLEWYQQKPGQSPKLLIYKVSNRFSGVPDRFSGSGSGTDFTLTISSLQAEDVAVYYCFQGSHVPNTFGGGT
KVEIK

>XENP024287 1C11_H3.168_L3_scFv(GKPGS)4 (SEQ ID NOS 39885-39893 and linker disclosed as SEQ ID NO: 39202)
QIQLVQSGSELKKPGASVKVSCKASGYTFTHYGMNWVRQAPGQGLEWMGWINTYTGEPTYADGFTGRFVFSLDTSVSTAYLQ
INSLKAEDTAVYFCARDYYGSSPYWGQGTLVTVSS/GKPGSGKPGSGKPGSGKPGS/DVLMTQSPDSLAVSLGERATINCKS
SQSIVHSNGNTYLEWYQQKPGQSPKLLIYKVSNRFSGVPDRFSGSGSGTDFTLTISSLQAEDVAVYYCFQGSHVPNTFGGGT
KVEIK

>XENP024291 1C11_H3.172_L3_scFv(GKPGS)4 (SEQ ID NOS 39894-39902 and linker disclosed as SEQ ID NO: 39202)
QIQLVQSGSELKKPGASVKVSCKASGYTFTHYGMNWVRQAPGQGLEWMGWINTYTGEPTYADGFTGRFVFSLDTSVSTAYLQ
ISSLKPEDTAVYFCARDYYGSSPYWGQGTLVTVSS/GKPGSGKPGSGKPGSGKPGS/DVLMTQSPDSLAVSLGERATINCKS
SQSIVHSNGNTYLEWYQQKPGQSPKLLIYKVSNRFSGVPDRFSGSGSGTDFTLTISSLQAEDVAVYYCFQGSHVPNTFGGGT
KVEIK

>XENP024372 1C11_H3_L3.86_scFv(GKPGS)4 (SEQ ID NOS 39903-39911 and linker disclosed as SEQ ID NO: 39202)
QIQLVQSGSELKKPGASVKVSCKASGYTFTHYGMNWVRQAPGQGLEWMGWINTYTGEPTYADGFTGRFVFSLDTSVSTAYLQ
ISSLKAEDTAVYFCARDYYGSSPYWGQGTLVTVSS/GKPGSGKPGSGKPGSGKPGS/DVLMTQSPDSLAVSLGERATINCKS
SQSIVHSNGNTYLEWYQQKPGQSPKLLIYKVSNRFTGVPDRFSGSGSGTDFTLTISSVQAEDVATYYCFQGSHVPNTFGQGT
KVEIK

FIG. 15H

>XENP024373 1C11_H3_L3.87_scFv(GKPGS)4 (SEQ ID NOS 39912-39920 and linker disclosed as SEQ ID NO: 39202)
QIQLVQSGSELKKPGASVKVSCKASGYTFTHYGMNWVRQAPGQGLEWMGWINTYTGEPTYADGFTGRFVFSLDTSVSTAYLQ
ISSLKAEDTAVYFCARDYYGSSPYWGQGTLVTVSS/GKPGSGKPGSGKPGSGKPGS/DVVMTQSPDSLAVSLGERVTINCKA
SQSIVHSNGNTYLEWYQQKPGQPPKLLIYKVSNRFSGVPDRFSGSGSGTDFTLTISSLQAEDVAVYYCFQGSHVPNTFGGGT
KVEIK >XENP024374 1C11_H3_L3.90_scFv(GKPGS)4 (SEQ ID NOS 39921-39929 and linker disclosed as SEQ ID NO: 39202)
QIQLVQSGSELKKPGASVKVSCKASGYTFTHYGMNWVRQAPGQGLEWMGWINTYTGEPTYADGFTGRFVFSLDTSVSTAYLQ
ISSLKAEDTAVYFCARDYYGSSPYWGQGTLVTVSS/GKPGSGKPGSGKPGSGKPGS/DVVMTQSPDSLAVSLGERATINCKA
SQSIVHSNGNTYLEWYQQKPGQPPKLLIYKVSNRFSGVPDRFSGSGSGTDFTLTISSVQAEDAATYYCFQGSHVPNTFGQGT
KVEIK >XENP024375 1C11_H3_L3.92_scFv(GKPGS)4 (SEQ ID NOS 39930-39938 and linker disclosed as SEQ ID NO: 39202)
QIQLVQSGSELKKPGASVKVSCKASGYTFTHYGMNWVRQAPGQGLEWMGWINTYTGEPTYADGFTGRFVFSLDTSVSTAYLQ
ISSLKAEDTAVYFCARDYYGSSPYWGQGTLVTVSS/GKPGSGKPGSGKPGSGKPGS/DIVMTQSPDSLAVSLGERVTINCKA
SQSIVHSNGNTYLEWYQQKPGQPPKLLIYKVSNRFTGVPDRFSGSGSGTDFTLTISSLQAEDVAVYYCFQGSHVPNTFGGGT
KVEIK >XENP024376 1C11_H3_L3.94_scFv(GKPGS)4 (SEQ ID NOS 39939-39947 and linker disclosed as SEQ ID NO: 39202)
QIQLVQSGSELKKPGASVKVSCKASGYTFTHYGMNWVRQAPGQGLEWMGWINTYTGEPTYADGFTGRFVFSLDTSVSTAYLQ
ISSLKAEDTAVYFCARDYYGSSPYWGQGTLVTVSS/GKPGSGKPGSGKPGSGKPGS/DILMTQSPDSLAVSLGERATINCKS
SQSIVHSNGNTYLEWYQQKPGQSPKLLIYKVSNRFTGVPDRFSGSGSGTDFTLTISSVQAEDAATYYCFQGSHVPNTFGQGT
KVEIK >XENP024377 1C11_H3_L3.96_scFv(GKPGS)4 (SEQ ID NOS 39948-39956 and linker disclosed as SEQ ID NO: 39202)
QIQLVQSGSELKKPGASVKVSCKASGYTFTHYGMNWVRQAPGQGLEWMGWINTYTGEPTYADGFTGRFVFSLDTSVSTAYLQ
ISSLKAEDTAVYFCARDYYGSSPYWGQGTLVTVSS/GKPGSGKPGSGKPGSGKPGS/DIVMTQSPDSLAVSLGERATINCKA
SQSIVHSNGNTYLEWYQQKPGQPPKLLIYKVSNRFTGVPDRFSGSGSGTDFTLTISSVQAEDAATYYCFQGSHVPNTFGQGT
KVEIK >XENP024378 1C11_H3_L3.105_scFv(GKPGS)4 (SEQ ID NOS 39957-39965 and linker disclosed as SEQ ID NO: 39202)
QIQLVQSGSELKKPGASVKVSCKASGYTFTHYGMNWVRQAPGQGLEWMGWINTYTGEPTYADGFTGRFVFSLDTSVSTAYLQ
ISSLKAEDTAVYFCARDYYGSSPYWGQGTLVTVSS/GKPGSGKPGSGKPGSGKPGS/DVLMTQSPDSLPVTPGEPATINCKS
SQSIVHSNGNTYLEWYQQKPGQSPKLLIYKVSNRFSGVPDRFSGSGSGTDFTLTISSLQAEDVAVYYCFQGSHVPNTFGGGT
KVEIK >XENP024379 1C11_H3_L3.129_scFv(GKPGS)4 (SEQ ID NOS 39966-39974 and linker disclosed as SEQ ID NO: 39202)
QIQLVQSGSELKKPGASVKVSCKASGYTFTHYGMNWVRQAPGQGLEWMGWINTYTGEPTYADGFTGRFVFSLDTSVSTAYLQ
ISSLKAEDTAVYFCARDYYGSSPYWGQGTLVTVSS/GKPGSGKPGSGKPGSGKPGS/DVLMTQSPDSLAVSLGERATINCKS
SQSIVHSNGNTYLEWYQQKPGQSPKLLIYKVSNRFSGVPDRFSGSGSGTDFTLTINSLQAEDAATYYCHQGSHVPNTFGGGT
KVEIK >XENP024380 1C11_H3.176_L3.92_scFv(GKPGS)4 (SEQ ID NOS 39975-39983 and linker disclosed as SEQ ID NO: 39202)
QIQLVQSGPELKKPGASVKVSCKASGYTFTHYGMNWVRQAPGQGLEWMGWINTNTGEPTYADKFTGRVVFSLDTSQSTIYLQ
ISSLKAEDTAVYYCARDYYGSSPYWGQGTLVTVSS/GKPGSGKPGSGKPGSGKPGS/DIVMTQSPDSLAVSLGERVTINCKA
SQSIVHSNGNTYLEWYQQKPGQPPKLLIYKVSNRFTGVPDRFSGSGSGTDFTLTISSLQAEDVAVYYCFQGSHVPNTFGGGT
KVEIK >XENP024381 1C11_H3.176_L3.94_scFv(GKPGS)4 (SEQ ID NOS 39984-39992 and linker disclosed as SEQ ID NO: 39202)
QIQLVQSGPELKKPGASVKVSCKASGYTFTHYGMNWVRQAPGQGLEWMGWINTNTGEPTYADKFTGRVVFSLDTSQSTIYLQ
ISSLKAEDTAVYYCARDYYGSSPYWGQGTLVTVSS/GKPGSGKPGSGKPGSGKPGS/DILMTQSPDSLAVSLGERATINCKS
SQSIVHSNGNTYLEWYQQKPGQSPKLLIYKVSNRFTGVPDRFSGSGSGTDFTLTISSVQAEDAATYYCFQGSHVPNTFGQGT
KVEIK

FIG. 15I

>XENP024382 1C11_H3.176_L3.96_scFv(GKPGS)4 (SEQ ID NOS 39993-40001 and linker disclosed as SEQ ID NO: 39202)
QIQLVQSGPELKKPGASVKVSCKASGYTFTHYGMNWVKQAPGQGLEWMGWINTNTGEPTYADKFTGRVVFSLDTSQSTIYLQISSL
KAEDTAVYFCARDYYGSSPYWGQGTLVTVSS/GKPGSGKPGSGKPGSGKPGS/DIVMTQSPDSLAVSLGERATINCKASQSIVHSN
GNTYLEWYQQKPGQPPKLLIYKVSNRFTGVPDRFSGSGSGTDFTLTISSVQAEDAATYYCFQGSHVPNTFGQGTKVEIK

>XENP024414 1C11[PD-1]_H3_L3.133_scFv(GKPGS)4 (SEQ ID NOS 40002-40010 and linker disclosed as SEQ ID NO: 39202)
QIQLVQSGSELKKPGASVKVSCKASGYTFTHYGMNWVRQAPGQGLEWMGWINTYTGEPTYADGFTGRFVFSLDTSVSTAYLQISSL
KAEDTAVYFCARDYYGSSPYWGQGTLVTVSS/GKPGSGKPGSGKPGSGKPGS/DVVMTQSPDSLAVSLGERVTINCKASQSIVHSN
GNTYLEWYQQKPGQPPKLLIYKVSNRFSGVPDRFSGSGSGTDFTLTISSVQAEDAATYYCFQGSHVPNTFGQGTKVEIK

>XENP024415 1C11[PD-1]_H3_L3.134_scFv(GKPGS)4 (SEQ ID NOS 40011-40019 and linker disclosed as SEQ ID NO: 39202)
QIQLVQSGSELKKPGASVKVSCKASGYTFTHYGMNWVRQAPGQGLEWMGWINTYTGEPTYADGFTGRFVFSLDTSVSTAYLQISSL
KAEDTAVYFCARDYYGSSPYWGQGTLVTVSS/GKPGSGKPGSGKPGSGKPGS/DVVMTQSPDSLAVSLGERVTINCKASQSIVHSN
GNTYLEWYQQKPGQPPKLLIYKVSNRFSGVPDRFSGSGSGTDFTLTISSVEAEDAATYYCFQGSHVPNTFGQGTKVEIK

>XENP024416 1C11[PD-1]_H3_L3.135_scFv(GKPGS)4 (SEQ ID NOS 40020-40028 and linker disclosed as SEQ ID NO: 39202)
QIQLVQSGSELKKPGASVKVSCKASGYTFTHYGMNWVRQAPGQGLEWMGWINTYTGEPTYADGFTGRFVFSLDTSVSTAYLQISSL
KAEDTAVYFCARDYYGSSPYWGQGTLVTVSS/GKPGSGKPGSGKPGSGKPGS/DVVMTQSPDSLAVSLGERVTINCKASQSIVHSN
GNTYLEWYQQKPGQPPKLLIYKVSNRFSGVPDRFSGSGSGTDFTLTISSMQAEDAATYYCFQGSHVPNTFGQGTKVEIK

>XENP024417 1C11[PD-1]_H3_L3.136_scFv(GKPGS)4 (SEQ ID NOS 40029-40037 and linker disclosed as SEQ ID NO: 39202)
QIQLVQSGSELKKPGASVKVSCKASGYTFTHYGMNWVRQAPGQGLEWMGWINTYTGEPTYADGFTGRFVFSLDTSVSTAYLQISSL
KAEDTAVYFCARDYYGSSPYWGQGTLVTVSS/GKPGSGKPGSGKPGSGKPGS/DVVMTQSPDSLAVSLGERITINCKASQSIVHSN
GNTYLEWYQQKPGQPPKLLIYKVSNRFSGVPDRFSGSGSGTDFTLTISSMQAEDAATYYCFQGSHVPNTFGQGTKVEIK

>XENP024418 1C11[PD-1]_H3_L3.137_scFv(GKPGS)4 (SEQ ID NOS 40038-40046 and linker disclosed as SEQ ID NO: 39202)
QIQLVQSGSELKKPGASVKVSCKASGYTFTHYGMNWVRQAPGQGLEWMGWINTYTGEPTYADGFTGRFVFSLDTSVSTAYLQISSL
KAEDTAVYFCARDYYGSSPYWGQGTLVTVSS/GKPGSGKPGSGKPGSGKPGS/DVVMTQSPDSLAVSLGERITINCKASQSIVHSN
GNTYLEWYQQKPGQPPKLLIYKVSNRFSGVPDRFSGSGSGTDFTLTISSVQAEDAATYYCFQGSHVPNTFGQGTKVEIK

>XENP024419 1C11[PD-1]_H3_L3.138_scFv(GKPGS)4 (SEQ ID NOS 40047-40055 and linker disclosed as SEQ ID NO: 39202)
QIQLVQSGSELKKPGASVKVSCKASGYTFTHYGMNWVRQAPGQGLEWMGWINTYTGEPTYADGFTGRFVFSLDTSVSTAYLQISSL
KAEDTAVYFCARDYYGSSPYWGQGTLVTVSS/GKPGSGKPGSGKPGSGKPGS/DVVMTQSPDSLAVSLGERITINCKASQSIVHSN
GNTYLEWYQQKPGQPPKLLIYKVSNRFSGVPDRFSGSGSGTDFTLTISSVEAEDAATYYCFQGSHVPNTFGQGTKVEIK

>XENP024420 1C11[PD-1]_H3_L3.139_scFv(GKPGS)4 (SEQ ID NOS 40056-40064 and linker disclosed as SEQ ID NO: 39202)
QIQLVQSGSELKKPGASVKVSCKASGYTFTHYGMNWVRQAPGQGLEWMGWINTYTGEPTYADGFTGRFVFSLDTSVSTAYLQISSL
KAEDTAVYFCARDYYGSSPYWGQGTLVTVSS/GKPGSGKPGSGKPGSGKPGS/DVVMTQSPDSLAVSLGERATINCKASQSIVHSN
GNTYLEWYQQKPGQPPKLLIYKVSNRFSGIPDRFSGSGSGTDFTLTISSVQAEDAATYYCFQGSHVPNTFGQGTKVEIK

>XENP024421 1C11[PD-1]_H3_L3.140_scFv(GKPGS)4 (SEQ ID NOS 40065-40073 and linker disclosed as SEQ ID NO: 39202)
QIQLVQSGSELKKPGASVKVSCKASGYTFTHYGMNWVRQAPGQGLEWMGWINTYTGEPTYADGFTGRFVFSLDTSVSTAYLQISSL
KAEDTAVYFCARDYYGSSPYWGQGTLVTVSS/GKPGSGKPGSGKPGSGKPGS/DIVMTQSPDSLAVSLGERATINCKASQSIVHSN
GNTYLEWYQQKPGQSPKLLIYKVSNRFSGVPDRFSGSGSGTDFTLTISSVEAEDVATYYCFQGSHVPNTFGQGTKVEIK

FIG. 15J

>XENP024422 1C11[PD-1]_H3_L3.141_scFv(GKPGS)4 (SEQ ID NOS 40074-40082 and linker disclosed as SEQ ID NO: 39202)
QIQLVQSGSELKKPGASVKVSCKASGYTFTHYGMNWVRQAPGQGLEWMGWINTYTGEPTYADGFTGRFVFSLDTSVSTAYLQISSL
KAEDTAVYFCARDYYGSSPYWGQGTLVTVSS/GKPGSGKPGSGKPGSGKPGS/DIVMTQSPDSLAVSLGERATINCKASQSIVHSN
GNTYLEWYQQKPGQPPKLLIYKVSNRFSGVPDRFSGSGSGTDFTLTISSVEAEDVATYYCFQGSHVPNTFGQGTKVEIK

>XENP024423 1C11[PD-1]_H3_L3.142_scFv(GKPGS)4 (SEQ ID NOS 40083-40091 and linker disclosed as SEQ ID NO: 39202)
QIQLVQSGSELKKPGASVKVSCKASGYTFTHYGMNWVRQAPGQGLEWMGWINTYTGEPTYADGFTGRFVFSLDTSVSTAYLQISSL
KAEDTAVYFCARDYYGSSPYWGQGTLVTVSS/GKPGSGKPGSGKPGSGKPGS/DIVMTQSPDSLAVSLGERATINCKASQSIVHSN
GNTYLEWYQQKPGQAPKLLIYKVSNRFSGVPDRFSGSGSGTDFTLTISSVEAEDVATYYCFQGSHVPNTFGQGTKVEIK

>XENP024424 1C11[PD-1]_H3.176_L3_scFv(GKPGS)4 (SEQ ID NOS 40092-40100 and linker disclosed as SEQ ID NO: 39202)
QIQLVQSGSELKKPGASVKVSCKASGYTFTHYGMNWVRQAPGQGLEWMGWINTYTGEPTYAPGFKGRFVFSLDTSVSTAYLQISSL
KAEDTAVYFCARDYYGSSPYWGQGTLVTVSS/GKPGSGKPGSGKPGSGKPGS/DVLMTQSPDSLAVSLGERATINCKSSQSIVHSN
GNTYLEWYQQKPGQSPKLLIYKVSNRFSGVPDRFSGSGSGTDFTLTISSLQAEDVAVYYCFQGSHVPNTFGGGTKVEIK

>XENP024425 1C11[PD-1]_H3.177_L3_scFv(GKPGS)4 (SEQ ID NOS 40101-40109 and linker disclosed as SEQ ID NO: 39202)
QIQLVQSGSELKKPGASVKVSCKASGYTFTHYGMNWVRQAPGQGLEWMGWINTYTGEPTYAPKFTGRFVFSLDTSVSTAYLQISSL
KAEDTAVYFCARDYYGSSPYWGQGTLVTVSS/GKPGSGKPGSGKPGSGKPGS/DVLMTQSPDSLAVSLGERATINCKSSQSIVHSN
GNTYLEWYQQKPGQSPKLLIYKVSNRFSGVPDRFSGSGSGTDFTLTISSLQAEDVAVYYCFQGSHVPNTFGGGTKVEIK

>XENP024426 1C11[PD-1]_H3.178_L3_scFv(GKPGS)4 (SEQ ID NOS 40110-40118 and linker disclosed as SEQ ID NO: 39202)
QIQLVQSGSELKKPGASVKVSCKASGYTFTHYGMNWVRQAPGQGLEWMGWINTYTGEPTYAPKFKERFVFSLDTSVSTAYLQISSL
KAEDTAVYFCARDYYGSSPYWGQGTLVTVSS/GKPGSGKPGSGKPGSGKPGS/DVLMTQSPDSLAVSLGERATINCKSSQSIVHSN
GNTYLEWYQQKPGQSPKLLIYKVSNRFSGVPDRFSGSGSGTDFTLTISSLQAEDVAVYYCFQGSHVPNTFGGGTKVEIK

>XENP024427 1C11[PD-1]_H3.179_L3_scFv(GKPGS)4 (SEQ ID NOS 40119-40127 and linker disclosed as SEQ ID NO: 39202)
QIQLVQSGSELKKPGASVKVSCKASGYTFTHYGMNWVRQAPGQGLEWMGWINTYTGEPTYAPKFTERFVFSLDTSVSTAYLQISSL
KAEDTAVYFCARDYYGSSPYWGQGTLVTVSS/GKPGSGKPGSGKPGSGKPGS/DVLMTQSPDSLAVSLGERATINCKSSQSIVHSN
GNTYLEWYQQKPGQSPKLLIYKVSNRFSGVPDRFSGSGSGTDFTLTISSLQAEDVAVYYCFQGSHVPNTFGGGTKVEIK

>XENP024428 1C11[PD-1]_H3.180_L3_scFv(GKPGS)4 (SEQ ID NOS 40128-40136 and linker disclosed as SEQ ID NO: 39202)
QIQLVQSGSELKKPGASVKVSCKASGYTFTHYGINWVRQAPGQGLEWMGWINTYTGEPTYADGFTGRFVFSVDTSVSTAYLQISSL
KAEDTAVYFCARDYYGSSPYWGQGTLVTVSS/GKPGSGKPGSGKPGSGKPGS/DVLMTQSPDSLAVSLGERATINCKSSQSIVHSN
GNTYLEWYQQKPGQSPKLLIYKVSNRFSGVPDRFSGSGSGTDFTLTISSLQAEDVAVYYCFQGSHVPNTFGGGTKVEIK

>XENP024429 1C11[PD-1]_H3.181_L3_scFv(GKPGS)4 (SEQ ID NOS 40137-40145 and linker disclosed as SEQ ID NO: 39202)
QIQLVQSGSELKKPGASVKVSCKASGYTFTHYGINWVRQAPGQGLEWMGWINTYTGEPTYADGFTGRFVFSIDTSVSTAYLQISSL
KAEDTAVYFCARDYYGSSPYWGQGTLVTVSS/GKPGSGKPGSGKPGSGKPGS/DVLMTQSPDSLAVSLGERATINCKSSQSIVHSN
GNTYLEWYQQKPGQSPKLLIYKVSNRFSGVPDRFSGSGSGTDFTLTISSLQAEDVAVYYCFQGSHVPNTFGGGTKVEIK

>XENP024430 1C11[PD-1]_H3.182_L3_scFv(GKPGS)4 (SEQ ID NOS 40146-40154 and linker disclosed as SEQ ID NO: 39202)
QIQLVQSGSELVKPGESVKVSCKASGYTFTHYGMNWVRQAPGQGLEWMGWINTYTGEPTYADGFTGRFVFSLDTSVSTAYLQISSL
KAEDTAVYFCARDYYGSSPYWGQGTLVTVSS/GKPGSGKPGSGKPGSGKPGS/DVLMTQSPDSLAVSLGERATINCKSSQSIVHSN
GNTYLEWYQQKPGQSPKLLIYKVSNRFSGVPDRFSGSGSGTDFTLTISSLQAEDVAVYYCFQGSHVPNTFGGGTKVEIK

FIG. 15K

>XENP024431 1C11[PD-1]_H3.183_L3_scFv(GKPGS)4 (SEQ ID NOS 40155-40163 and linker disclosed as SEQ ID NO: 39202)
QIQLVQSGSVLKKPGESVKVSCKASGYTFTHYGMNWVRQAPGQGLEWMGWINTYTGEPTYADGFTGRFVFSLDTSVSTAYLQISSL
KAEDTAVYFCARDYYGSSPYWGQGTLVTVSS/GKPGSGKPGSGKPGSGKPGS/DVLMTQSPDSLAVSLGERATINCKSSQSIVHSN
GNTYLEWYQQKPGQSPKLLIYKVSNRFSGVPDRFSGSGSGTDFTLTISSLQAEDVAVYYCFQGSHVPNTFGGGTKVEIK >XENP024432 1C11[PD-1]_H3.184_L3_scFv(GKPGS)4 (SEQ ID NOS 40164-40172 and linker disclosed as SEQ ID NO: 39202)
QIQLVQSGSVLVKPGESVKVSCKASGYTFTHYGMNWVRQAPGQGLEWMGWINTYTGEPTYADGFTGRFVFSLDTSVSTAYLQISSL
KAEDTAVYFCARDYYGSSPYWGQGTLVTVSS/GKPGSGKPGSGKPGSGKPGS/DVLMTQSPDSLAVSLGERATINCKSSQSIVHSN
GNTYLEWYQQKPGQSPKLLIYKVSNRFSGVPDRFSGSGSGTDFTLTISSLQAEDVAVYYCFQGSHVPNTFGGGTKVEIK >XENP024433 1C11[PD-1]_H3.185_L3_scFv(GKPGS)4 (SEQ ID NOS 40173-40181 and linker disclosed as SEQ ID NO: 39202)
EVQLVQSGSELVKPGESVKVSCKASGYTFTHYGINWVRQPPGQGLEWIGWINTYTGEPYYAPKFTERFVFSLDTSQDTAYLQINSL
KAEDTAVYYCARDYYGSSPYWGQGTLVTVSS/GKPGSGKPGSGKPGSGKPGS/DVLMTQSPDSLAVSLGERATINCKSSQSIVHSN
GNTYLEWYQQKPGQSPKLLIYKVSNRFSGVPDRFSGSGSGTDFTLTISSLQAEDVAVYYCFQGSHVPNTFGGGTKVEIK >XENP024434 1C11[PD-1]_H3.186_L3_scFv(GKPGS)4 (SEQ ID NOS 40182-40190 and linker disclosed as SEQ ID NO: 39202)
EVQLVQSGSELVKPGESVKVSCKASGYTFTHYGINWVRQPPGQGLEWMGWINTYTGEPYYAPGFTERFVFSLDTSVDTAYLQINSL
KAEDTAVYYCARDYYGSSPYWGQGTLVTVSS/GKPGSGKPGSGKPGSGKPGS/DVLMTQSPDSLAVSLGERATINCKSSQSIVHSN
GNTYLEWYQQKPGQSPKLLIYKVSNRFSGVPDRFSGSGSGTDFTLTISSLQAEDVAVYYCFQGSHVPNTFGGGTKVEIK >XENP024435 1C11[PD-1]_H3.187_L3_scFv(GKPGS)4 (SEQ ID NOS 40191-40199 and linker disclosed as SEQ ID NO: 39202)
QVQLVQSGSELVKPGESVKVSCKASGYTFTHYGINWVRQPPGQGLEWMGWINTYTGEPYYAPGFTERFVFSLDTSQSTAYLQINSL
KAEDTAVYYCARDYYGSSPYWGQGTLVTVSS/GKPGSGKPGSGKPGSGKPGS/DVLMTQSPDSLAVSLGERATINCKSSQSIVHSN
GNTYLEWYQQKPGQSPKLLIYKVSNRFSGVPDRFSGSGSGTDFTLTISSLQAEDVAVYYCFQGSHVPNTFGGGTKVEIK >XENP024436 1C11[PD-1]_H3.188_L3_scFv(GKPGS)4 (SEQ ID NOS 40200-40208 and linker disclosed as SEQ ID NO: 39202)
QVQLVQSGSELKKPGESVKVSCKASGYTFTHYGINWVRQPPGQGLEWIGWINTYTGEPYYAPGFTGRFVFSLDTSQSTAYLQINSL
KAEDTAVYYCARDYYGSSPYWGQGTLVTVSS/GKPGSGKPGSGKPGSGKPGS/DVLMTQSPDSLAVSLGERATINCKSSQSIVHSN
GNTYLEWYQQKPGQSPKLLIYKVSNRFSGVPDRFSGSGSGTDFTLTISSLQAEDVAVYYCFQGSHVPNTFGGGTKVEIK >XENP024437 1C11[PD-1]_H3.189_L3_scFv(GKPGS)4 (SEQ ID NOS 40209-40217 and linker disclosed as SEQ ID NO: 39202)
QVQLVQSGSELKKPGASVKVSCKASGYTFTHYGINWVRQPPGQGLEWIGWINTYTGEPYYAPKFTGRFVFSLDTSVSTAYLQINSL
KAEDTAVYYCARDYYGSSPYWGQGTLVTVSS/GKPGSGKPGSGKPGSGKPGS/DVLMTQSPDSLAVSLGERATINCKSSQSIVHSN
GNTYLEWYQQKPGQSPKLLIYKVSNRFSGVPDRFSGSGSGTDFTLTISSLQAEDVAVYYCFQGSHVPNTFGGGTKVEIK >XENP024438 1C11[PD-1]_H3.190_L3_scFv(GKPGS)4 (SEQ ID NOS 40218-40226 and linker disclosed as SEQ ID NO: 39202)
QVQLVQSGSVLKKPGGSVKVSCKASGYTFTHYGINWVRQPPGQGLEWIGWINTYTGEPYYAPGFTGRFVFSLDTSQSTAYLQINSL
KAEDTAVYYCARDYYGSSPYWGQGTLVTVSS/GKPGSGKPGSGKPGSGKPGS/DVLMTQSPDSLAVSLGERATINCKSSQSIVHSN
GNTYLEWYQQKPGQSPKLLIYKVSNRFSGVPDRFSGSGSGTDFTLTISSLQAEDVAVYYCFQGSHVPNTFGGGTKVEIK >XENP024439 1C11[PD-1]_H3.191_L3_scFv(GKPGS)4 (SEQ ID NOS 40227-40235 and linker disclosed as SEQ ID NO: 39202)
QVQLVQSGSELVKPGESVKVSCKASGYTFTHYGMNWVRQAPGQGLEWMGWINTYTGEPTYAPGFTGRFVFSLDTSQSTAYLQINSL
KAEDTAVYFCARDYYGSSPYWGQGTLVTVSS/GKPGSGKPGSGKPGSGKPGS/DVLMTQSPDSLAVSLGERATINCKSSQSIVHSN
GNTYLEWYQQKPGQSPKLLIYKVSNRFSGVPDRFSGSGSGTDFTLTISSLQAEDVAVYYCFQGSHVPNTFGGGTKVEIK

FIG. 15L

>XENP024440 1C11[PD-1]_H3.192_L3_scFv(GKPGS)4 (SEQ ID NOS 40236-40244 and linker disclosed as SEQ ID NO: 39202)
EVQLVQSGSVLKKPGESVKVSCKASGYTFTHYGINWVRQAPGQGLEWMGWINTYTGEPTYADGFTERFVFSLDTSVSTAYLQISSL
KAEDTAVYFCARDYYGSSPYWGQGTLVTVSS/GKPGSGKPGSGKPGSGKPGS/DVLMTQSPDSLAVSLGERATINCKSSQSIVHSN
GNTYLEWYQQKPGQSPKLLIYKVSNRFSGVPDRFSGSGSGTDFTLTISSLQAEDVAVYYCFQGSHVPNTFGGGTKVEIK

>XENP024441 1C11[PD-1]_H3.193_L3_scFv(GKPGS)4 (SEQ ID NOS 40245-40253 and linker disclosed as SEQ ID NO: 39202)
QIQLVQSGSELKKPGASVKVSCKASGYTFTHYGMNWVRQPPGQGLEWIGWINTYTGEPTYAPGFTERFVFSLDTSQSTAYLQINSL
KAEDTAVYYCARDYYGSSPYWGQGTLVTVSS/GKPGSGKPGSGKPGSGKPGS/DVLMTQSPDSLAVSLGERATINCKSSQSIVHSN
GNTYLEWYQQKPGQSPKLLIYKVSNRFSGVPDRFSGSGSGTDFTLTISSLQAEDVAVYYCFQGSHVPNTFGGGTKVEIK

>XENP024442 1C11[PD-1]_H3.194_L3_scFv(GKPGS)4 (SEQ ID NOS 40254-40262 and linker disclosed as SEQ ID NO: 39202)
EIQLVQSGSVLKKPGASVKVSCKASGYTFTHYGINWVRQAPGQGLEWIGWINTYTGEPTYADGFTGRFVFSLDTSVSTAYLQISSL
KAEDTAVYFCARDYYGSSPYWGQGTLVTVSS/GKPGSGKPGSGKPGSGKPGS/DVLMTQSPDSLAVSLGERATINCKSSQSIVHSN
GNTYLEWYQQKPGQSPKLLIYKVSNRFSGVPDRFSGSGSGTDFTLTISSLQAEDVAVYYCFQGSHVPNTFGGGTKVEIK

>XENP024443 1C11[PD-1]_H3.195_L3_scFv(GKPGS)4 (SEQ ID NOS 40263-40271 and linker disclosed as SEQ ID NO: 39202)
QIQLVQSGSELKKPGASVKVSCKASGYTFTHYGMNWVRQPPGQGLEWMGWINTYTGEPYYADGFTGRFVFSLDTSVDTAYLQINSL
KAEDTAVYYCARDYYGSSPYWGQGTLVTVSS/GKPGSGKPGSGKPGSGKPGS/DVLMTQSPDSLAVSLGERATINCKSSQSIVHSN
GNTYLEWYQQKPGQSPKLLIYKVSNRFSGVPDRFSGSGSGTDFTLTISSLQAEDVAVYYCFQGSHVPNTFGGGTKVEIK

>XENP024827 1C11_H3.196_L3_scFv(GKPGS)4 (SEQ ID NOS 40272-40280 and linker disclosed as SEQ ID NO: 39202)
EVQLVQSGSELKKPGESVKVSCKASGYTFTHYGINWVRQPPGQGLEWIGWINTYTGEPYYAPGFTGRFVFSLDTSQSTAYLQINSL
KAEDTAVYYCARDYYGSSPYWGQGTLVTVSS/GKPGSGKPGSGKPGSGKPGS/DVLMTQSPDSLAVSLGERATINCKSSQSIVHSN
GNTYLEWYQQKPGQSPKLLIYKVSNRFSGVPDRFSGSGSGTDFTLTISSLQAEDVAVYYCFQGSHVPNTFGGGTKVEIK

>XENP024828 1C11_H3.197_L3_scFv(GKPGS)4 (SEQ ID NOS 40281-40289 and linker disclosed as SEQ ID NO: 39202)
QVQLVQSGSELKKPGASVKVSCKASGYTFTHYGINWVRQPPGQGLEWIGWINTYTGEPYYAPGFTGRFVFSLDTSQSTAYLQINSL
KAEDTAVYYCARDYYGSSPYWGQGTLVTVSS/GKPGSGKPGSGKPGSGKPGS/DVLMTQSPDSLAVSLGERATINCKSSQSIVHSN
GNTYLEWYQQKPGQSPKLLIYKVSNRFSGVPDRFSGSGSGTDFTLTISSLQAEDVAVYYCFQGSHVPNTFGGGTKVEIK

>XENP024829 1C11_H3.198_L3_scFv(GKPGS)4 (SEQ ID NOS 40290-40298 and linker disclosed as SEQ ID NO: 39202)
QVQLVQSGSELKKPGESVKVSCKASGYTFTHYGINWVRQPPGQGLEWIGWINTYTGEPYYADGFTGRFVFSLDTSQSTAYLQINSL
KAEDTAVYYCARDYYGSSPYWGQGTLVTVSS/GKPGSGKPGSGKPGSGKPGS/DVLMTQSPDSLAVSLGERATINCKSSQSIVHSN
GNTYLEWYQQKPGQSPKLLIYKVSNRFSGVPDRFSGSGSGTDFTLTISSLQAEDVAVYYCFQGSHVPNTFGGGTKVEIK

>XENP024830 1C11_H3.199_L3_scFv(GKPGS)4 (SEQ ID NOS 40299-40307 and linker disclosed as SEQ ID NO: 39202)
QVQLVQSGSELKKPGESVKVSCKASGYTFTHYGMNWVRQPPGQGLEWIGWINTYTGEPYYAPGFTGRFVFSLDTSQSTAYLQINSL
KAEDTAVYYCARDYYGSSPYWGQGTLVTVSS/GKPGSGKPGSGKPGSGKPGS/DVLMTQSPDSLAVSLGERATINCKSSQSIVHSN
GNTYLEWYQQKPGQSPKLLIYKVSNRFSGVPDRFSGSGSGTDFTLTISSLQAEDVAVYYCFQGSHVPNTFGGGTKVEIK

>XENP024831 1C11_H3.200_L3_scFv(GKPGS)4 (SEQ ID NOS 40308-40316 and linker disclosed as SEQ ID NO: 39202)
QVQLVQSGSELKKPGESVKVSCKASGYTFTHYGINWVRQPPGQGLEWIGWINTYTGEPYYAPGFTGRFVFSLDTSQSTAYLQINSL
KAEDTAVYFCARDYYGSSPYWGQGTLVTVSS/GKPGSGKPGSGKPGSGKPGS/DVLMTQSPDSLAVSLGERATINCKSSQSIVHSN
GNTYLEWYQQKPGQSPKLLIYKVSNRFSGVPDRFSGSGSGTDFTLTISSLQAEDVAVYYCFQGSHVPNTFGGGTKVEIK

FIG. 15M

>XENP024832 1C11_H3.201_L3_scFv(GKPGS)4 (SEQ ID NOS 40317-40325 and linker disclosed as SEQ ID NO: 39202)
QVQLVQSGSELKKPGESVKVSCKASGYTFTHYGINWVRQPPGQGLEWIGWINTYTGEPYYAPGFTGRFVFSIDTSQSTAYLQ
INSLKAEDTAVYYCARDYYGSSPYWGQGTLVTVSS/GKPGSGKPGSGKPGSGKPGS/DVLMTQSPDSLAVSLGERATINCKS
SQSIVHSNGNTYLEWYQQKPGQSPKLLIYKVSNRFSGVPDRFSGSGSGTDFTLTISSLQAEDVAVYYCFQGSHVPNTFGGGT
KVEIK

>XENP024833 1C11_H3.202_L3_scFv(GKPGS)4 (SEQ ID NOS 40326-40334 and linker disclosed as SEQ ID NO: 39202)
QVQLVQSGSELKKPGESVKVSCKASGYTFTHYGINWVRQAPGQGLEWIGWINTYTGEPYYAPGFTGRFVFSLDTSQSTAYLQ
INSLKAEDTAVYYCARDYYGSSPYWGQGTLVTVSS/GKPGSGKPGSGKPGSGKPGS/DVLMTQSPDSLAVSLGERATINCKS
SQSIVHSNGNTYLEWYQQKPGQSPKLLIYKVSNRFSGVPDRFSGSGSGTDFTLTISSLQAEDVAVYYCFQGSHVPNTFGGGT
KVEIK

>XENP024834 1C11_H3.203_L3_scFv(GKPGS)4 (SEQ ID NOS 40335-40343 and linker disclosed as SEQ ID NO: 39202)
QVQLVQSGSELKKPGESVKVSCKASGYTFTHYGINWVRQPPGQGLEWIGWINTYTGEPYYAPGFTERFVFSLDTSQSTAYLQ
INSLKAEDTAVYYCARDYYGSSPYWGQGTLVTVSS/GKPGSGKPGSGKPGSGKPGS/DVLMTQSPDSLAVSLGERATINCKS
SQSIVHSNGNTYLEWYQQKPGQSPKLLIYKVSNRFSGVPDRFSGSGSGTDFTLTISSLQAEDVAVYYCFQGSHVPNTFGGGT
KVEIK

>XENP024835 1C11_H3.204_L3_scFv(GKPGS)4 (SEQ ID NOS 40344-40352 and linker disclosed as SEQ ID NO: 39202)
QVQLVQSGSELKKPGESVKVSCKASGYTFTHYGINWVRQPPGQGLEWIGWINTYTGEPYYAPGFQGRFVFSLDTSQSTAYLQ
INSLKAEDTAVYYCARDYYGSSPYWGQGTLVTVSS/GKPGSGKPGSGKPGSGKPGS/DVLMTQSPDSLAVSLGERATINCKS
SQSIVHSNGNTYLEWYQQKPGQSPKLLIYKVSNRFSGVPDRFSGSGSGTDFTLTISSLQAEDVAVYYCFQGSHVPNTFGGGT
KVEIK

>XENP024836 1C11_H3.205_L3_scFv(GKPGS)4 (SEQ ID NOS 40353-40361 and linker disclosed as SEQ ID NO: 39202)
QVQLVQSGSELKKPGESVKVSCKASGYTFTHYGINWVRQPPGQGLEWIGWINTYTGEPYYAPGFKGRFVFSLDTSQSTAYLQ
INSLKAEDTAVYYCARDYYGSSPYWGQGTLVTVSS/GKPGSGKPGSGKPGSGKPGS/DVLMTQSPDSLAVSLGERATINCKS
SQSIVHSNGNTYLEWYQQKPGQSPKLLIYKVSNRFSGVPDRFSGSGSGTDFTLTISSLQAEDVAVYYCFQGSHVPNTFGGGT
KVEIK

>XENP024837 1C11_H3.206_L3_scFv(GKPGS)4 (SEQ ID NOS 40362-40370 and linker disclosed as SEQ ID NO: 39202)
QVQLVQSGSELKKPGESVKVSCKASGYTFTHYGINWVRQPPGQGLEWIGWINTYTGEPTYAPGFTGRFVFSLDTSQSTAYLQ
INSLKAEDTAVYYCARDYYGSSPYWGQGTLVTVSS/GKPGSGKPGSGKPGSGKPGS/DVLMTQSPDSLAVSLGERATINCKS
SQSIVHSNGNTYLEWYQQKPGQSPKLLIYKVSNRFSGVPDRFSGSGSGTDFTLTISSLQAEDVAVYYCFQGSHVPNTFGGGT
KVEIK

>XENP024838 1C11_H3.207_L3_scFv(GKPGS)4 (SEQ ID NOS 40371-40379 and linker disclosed as SEQ ID NO: 39202)
QVQLVQSGSELKKPGESVKVSCKASGYTFTHYGINWVRQPPGQGLEWIGWINTYTGEPYYAPGFTGRFVFSLDTSQSTAYLQ
ISSLKAEDTAVYYCARDYYGSSPYWGQGTLVTVSS/GKPGSGKPGSGKPGSGKPGS/DVLMTQSPDSLAVSLGERATINCKS
SQSIVHSNGNTYLEWYQQKPGQSPKLLIYKVSNRFSGVPDRFSGSGSGTDFTLTISSLQAEDVAVYYCFQGSHVPNTFGGGT
KVEIK

>XENP024839 1C11_H3.208_L3_scFv(GKPGS)4 (SEQ ID NOS 40380-40388 and linker disclosed as SEQ ID NO: 39202)
QVQLVQSGSELKKPGESVKVSCKASGYTFTHYGINWVRQPPGQGLEWIGWINTYTGEPYYAPGFTGRFVFSLDTSQDTAYLQ
INSLKAEDTAVYYCARDYYGSSPYWGQGTLVTVSS/GKPGSGKPGSGKPGSGKPGS/DVLMTQSPDSLAVSLGERATINCKS
SQSIVHSNGNTYLEWYQQKPGQSPKLLIYKVSNRFSGVPDRFSGSGSGTDFTLTISSLQAEDVAVYYCFQGSHVPNTFGGGT
KVEIK

>XENP024840 1C11_H3.209_L3_scFv(GKPGS)4 (SEQ ID NOS 40389-40397 and linker disclosed as SEQ ID NO: 39202)
QVQLVQSGSELKKPGESVKVSCKASGYTFTHYGINWVRQPPGQGLEWMGWINTYTGEPYYAPGFTGRFVFSLDTSQSTAYLQ
INSLKAEDTAVYYCARDYYGSSPYWGQGTLVTVSS/GKPGSGKPGSGKPGSGKPGS/DVLMTQSPDSLAVSLGERATINCKS
SQSIVHSNGNTYLEWYQQKPGQSPKLLIYKVSNRFSGVPDRFSGSGSGTDFTLTISSLQAEDVAVYYCFQGSHVPNTFGGGT
KVEIK

FIG. 15N

>XENP024841 1C11_H3.210_L3_scFv(GKPGS)4 (SEQ ID NOS 40398-40406 and linker disclosed as SEQ ID NO: 39202)
QVQLVQSGSELKKPGESVKVSCKASGYTFTHYGINWVRQPPGQGLEWIGWINTYTGEPYYAPGFTGRFVFSLDTSVSTAYLQ
INSLKAEDTAVYYCARDYYGSSPYWGQGTLVTVSS/GKPGSGKPGSGKPGSGKPGS/DVLMTQSPDSLAVSLGERATINCKS
SQSIVHSNGNTYLEWYQQKPGQSPKLLIYKVSNRFSGVPDRFSGSGSGTDFTLTISSLQAEDVAVYYCFQGSHVPNTFGGGT
KVEIK

>XENP024842 1C11_H3.211_L3_scFv(GKPGS)4 (SEQ ID NOS 40407-40415 and linker disclosed as SEQ ID NO: 39202)
QVQLVQSGPELKKPGESVKVSCKASGYTFTHYGINWVRQPPGQGLEWIGWINTYTGEPYYAPGFTGRFVFSLDTSQSTAYLQ
INSLKAEDTAVYYCARDYYGSSPYWGQGTLVTVSS/GKPGSGKPGSGKPGSGKPGS/DVLMTQSPDSLAVSLGERATINCKS
SQSIVHSNGNTYLEWYQQKPGQSPKLLIYKVSNRFSGVPDRFSGSGSGTDFTLTISSLQAEDVAVYYCFQGSHVPNTFGGGT
KVEIK

>XENP024843 1C11_H3.212_L3_scFv(GKPGS)4 (SEQ ID NOS 40416-40424 and linker disclosed as SEQ ID NO: 39202)
QVQLVQSGSELKKPGESVKVSCKASGYTFTHYGINWVRQPPGQGLEWIGWINTYTGEPYYAPGFTGRFVFSLDTSVDTAYLQ
INSLKAEDTAVYYCARDYYGSSPYWGQGTLVTVSS/GKPGSGKPGSGKPGSGKPGS/DVLMTQSPDSLAVSLGERATINCKS
SQSIVHSNGNTYLEWYQQKPGQSPKLLIYKVSNRFSGVPDRFSGSGSGTDFTLTISSLQAEDVAVYYCFQGSHVPNTFGGGT
KVEIK

>XENP024844 1C11_H3.213_L3_scFv(GKPGS)4 (SEQ ID NOS 40425-40433 and linker disclosed as SEQ ID NO: 39202)
QVQLVQSGPELKKPGESVKVSCKASGYTFTHYGINWVRQAPGQGLEWIGWINTYTGEPYYAPGFTGRFVFSLDTSQDTAYLQ
INSLKAEDTAVYYCARDYYGSSPYWGQGTLVTVSS/GKPGSGKPGSGKPGSGKPGS/DVLMTQSPDSLAVSLGERATINCKS
SQSIVHSNGNTYLEWYQQKPGQSPKLLIYKVSNRFSGVPDRFSGSGSGTDFTLTISSLQAEDVAVYYCFQGSHVPNTFGGGT
KVEIK

>XENP024845 1C11_H3.214_L3_scFv(GKPGS)4 (SEQ ID NOS 40434-40442 and linker disclosed as SEQ ID NO: 39202)
QVQLVQSGPELKKPGESVKVSCKASGYTFTHYGINWVRQAPGQGLEWIGWINTYTGEPYYAPGFTGRFVFSIDTSQSTAYLQ
INSLKAEDTAVYYCARDYYGSSPYWGQGTLVTVSS/GKPGSGKPGSGKPGSGKPGS/DVLMTQSPDSLAVSLGERATINCKS
SQSIVHSNGNTYLEWYQQKPGQSPKLLIYKVSNRFSGVPDRFSGSGSGTDFTLTISSLQAEDVAVYYCFQGSHVPNTFGGGT
KVEIK

>XENP024846 1C11_H3.215_L3_scFv(GKPGS)4 (SEQ ID NOS 40443-40451 and linker disclosed as SEQ ID NO: 39202)
QVQLVQSGPELKKPGESVKVSCKASGYTFTHYGINWVRQAPGQGLEWIGWINTYTGEPYYAPGFTGRFVFSLDTSVSTAYLQ
INSLKAEDTAVYYCARDYYGSSPYWGQGTLVTVSS/GKPGSGKPGSGKPGSGKPGS/DVLMTQSPDSLAVSLGERATINCKS
SQSIVHSNGNTYLEWYQQKPGQSPKLLIYKVSNRFSGVPDRFSGSGSGTDFTLTISSLQAEDVAVYYCFQGSHVPNTFGGGT
KVEIK

>XENP024847 1C11_H3.216_L3_scFv(GKPGS)4 (SEQ ID NOS 40452-40460 and linker disclosed as SEQ ID NO: 39202)
QVQLVQSGPELKKPGESVKVSCKASGYTFTHYGINWVRQPPGQGLEWMGWINTYTGEPYYAPGFTGRFVFSIDTSQSTAYLQ
INSLKAEDTAVYYCARDYYGSSPYWGQGTLVTVSS/GKPGSGKPGSGKPGSGKPGS/DVLMTQSPDSLAVSLGERATINCKS
SQSIVHSNGNTYLEWYQQKPGQSPKLLIYKVSNRFSGVPDRFSGSGSGTDFTLTISSLQAEDVAVYYCFQGSHVPNTFGGGT
KVEIK

>XENP024848 1C11_H3.217_L3_scFv(GKPGS)4 (SEQ ID NOS 40461-40469 and linker disclosed as SEQ ID NO: 39202)
QVQLVQSGPELKKPGESVKVSCKASGYTFTHYGINWVRQPPGQGLEWMGWINTYTGEPYYAPGFTGRFVFSLDTSVSTAYLQ
INSLKAEDTAVYYCARDYYGSSPYWGQGTLVTVSS/GKPGSGKPGSGKPGSGKPGS/DVLMTQSPDSLAVSLGERATINCKS
SQSIVHSNGNTYLEWYQQKPGQSPKLLIYKVSNRFSGVPDRFSGSGSGTDFTLTISSLQAEDVAVYYCFQGSHVPNTFGGGT
KVEIK

>XENP024849 1C11_H3.218_L3_scFv(GKPGS)4 (SEQ ID NOS 40470-40478 and linker disclosed as SEQ ID NO: 39202)
QVQLVQSGPELKKPGESVKVSCKASGYTFTHYGINWVRQPPGQGLEWMGWINTYTGEPYYAPGFTGRFVFSLDTSQDTAYLQ
INSLKAEDTAVYYCARDYYGSSPYWGQGTLVTVSS/GKPGSGKPGSGKPGSGKPGS/DVLMTQSPDSLAVSLGERATINCKS
SQSIVHSNGNTYLEWYQQKPGQSPKLLIYKVSNRFSGVPDRFSGSGSGTDFTLTISSLQAEDVAVYYCFQGSHVPNTFGGGT
KVEIK

FIG. 15O

>XENP024850 1C11_H3.219_L3_scFv(GKPGS)4 (SEQ ID NOS 40479-40487 and linker disclosed as SEQ ID NO: 39202)
QVQLVQSGSELKKPGESVKVSCKASGYTFTHYGINWVRQPPGQGLEWIGWINTYTGEPYYAPGFQERFVFSLDTSQSTAYLQINSL
KAEDTAVYYCARDYYGSSPYWGQGTLVTVSS/GKPGSGKPGSGKPGSGKPGS/DVLMTQSPDSLAVSLGERATINCKSSQSIVHSN
GNTYLEWYQQKPGQSPKLLIYKVSNRFSGVPDRFSGSGSGTDFTLTISSLQAEDVAVYYCFQGSHVPNTFGGGTKVEIK >XENP024851 1C11_H3.220_L3_scFv(GKPGS)4 (SEQ ID NOS 40488-40496 and linker disclosed as SEQ ID NO: 39202)
QVQLVQSGSELKKPGESVKVSCKASGYTFTHYGINWVRQPPGQGLEWIGWINTYTGEPYYAPGFKERFVFSLDTSQSTAYLQINSL
KAEDTAVYYCARDYYGSSPYWGQGTLVTVSS/GKPGSGKPGSGKPGSGKPGS/DVLMTQSPDSLAVSLGERATINCKSSQSIVHSN
GNTYLEWYQQKPGQSPKLLIYKVSNRFSGVPDRFSGSGSGTDFTLTISSLQAEDVAVYYCFQGSHVPNTFGGGTKVEIK >XENP024852 1C11_H3.221_L3_scFv(GKPGS)4 (SEQ ID NOS 40497-40505 and linker disclosed as SEQ ID NO: 39202)
EIQLVQSGSELKKPGESVKVSCKASGYTFTHYGINWVRQPPGQGLEWIGWINTYTGEPYYAPGFTGRFVFSLDTSQSTAYLQINSL
KAEDTAVYYCARDYYGSSPYWGQGTLVTVSS/GKPGSGKPGSGKPGSGKPGS/DVLMTQSPDSLAVSLGERATINCKSSQSIVHSN
GNTYLEWYQQKPGQSPKLLIYKVSNRFSGVPDRFSGSGSGTDFTLTISSLQAEDVAVYYCFQGSHVPNTFGGGTKVEIK >XENP024853 1C11[PD-1]_H3_L3.143_scFv(GKPGS)4 (SEQ ID NOS 40506-40514 and linker disclosed as SEQ ID NO: 39202)
QIQLVQSGSELKKPGASVKVSCKASGYTFTHYGMNWVRQAPGQGLEWMGWINTYTGEPTYADGFTGRFVFSLDTSVSTAYLQISSL
KAEDTAVYFCARDYYGSSPYWGQGTLVTVSS/GKPGSGKPGSGKPGSGKPGS/DIVMTQSPDSLAVSLGERVTINCKASQSIVHSN
GNTYLEWYQQKPGQPPKLLIYKVSNRFSGVPDRFSGSGSGTDFTLTISSVEAEDVATYYCFQGSHVPNTFGQGTKVEIK >XENP024854 1C11[PD-1]_H3_L3.144_scFv(GKPGS)4 (SEQ ID NOS 40515-40523 and linker disclosed as SEQ ID NO: 39202)
QIQLVQSGSELKKPGASVKVSCKASGYTFTHYGMNWVRQAPGQGLEWMGWINTYTGEPTYADGFTGRFVFSLDTSVSTAYLQISSL
KAEDTAVYFCARDYYGSSPYWGQGTLVTVSS/GKPGSGKPGSGKPGSGKPGS/DIVMTQSPDSLAVSLGERVTINCKASQSIVHSN
GNTYLEWYQQKPGQPPKLLIYKVSNRFSGVPDRFSGSGSGTDFTLTISSVEAEDAATYYCFQGSHVPNTFGQGTKVEIK >XENP024855 1C11[PD-1]_H3_L3.145_scFv(GKPGS)4 (SEQ ID NOS 40524-40532 and linker disclosed as SEQ ID NO: 39202)
QIQLVQSGSELKKPGASVKVSCKASGYTFTHYGMNWVRQAPGQGLEWMGWINTYTGEPTYADGFTGRFVFSLDTSVSTAYLQISSL
KAEDTAVYFCARDYYGSSPYWGQGTLVTVSS/GKPGSGKPGSGKPGSGKPGS/DIVMTQSPDSLAVSLGERVTINCKASQSIVHSN
GNTYLEWYQQKPGQSPKLLIYKVSNRFSGVPDRFSGSGSGTDFTLTISSVEAEDVATYYCFQGSHVPNTFGQGTKVEIK >XENP024856 1C11[PD-1]_H3_L3.146_scFv(GKPGS)4 (SEQ ID NOS 40533-40541 and linker disclosed as SEQ ID NO: 39202)
QIQLVQSGSELKKPGASVKVSCKASGYTFTHYGMNWVRQAPGQGLEWMGWINTYTGEPTYADGFTGRFVFSLDTSVSTAYLQISSL
KAEDTAVYFCARDYYGSSPYWGQGTLVTVSS/GKPGSGKPGSGKPGSGKPGS/DIVMTQSPDSLAVSLGERVTINCKASQSIVHSN
GNTYLEWYQQKPGQSPKLLIYKVSNRFSGVPDRFSGSGSGTDFTLTISSVEAEDAATYYCFQGSHVPNTFGQGTKVEIK >XENP024857 1C11[PD-1]_H3_L3.147_scFv(GKPGS)4 (SEQ ID NOS 40542-40550 and linker disclosed as SEQ ID NO: 39202)
QIQLVQSGSELKKPGASVKVSCKASGYTFTHYGMNWVRQAPGQGLEWMGWINTYTGEPTYADGFTGRFVFSLDTSVSTAYLQISSL
KAEDTAVYFCARDYYGSSPYWGQGTLVTVSS/GKPGSGKPGSGKPGSGKPGS/DIVMTQSPDSLAVSLGERVTINCKASQSIVHSN
GNTYLEWYQQKPGQAPKLLIYKVSNRFSGVPDRFSGSGSGTDFTLTISSVEAEDVATYYCFQGSHVPNTFGQGTKVEIK >XENP024858 1C11[PD-1]_H3_L3.148_scFv(GKPGS)4 (SEQ ID NOS 40551-40559 and linker disclosed as SEQ ID NO: 39202)
QIQLVQSGSELKKPGASVKVSCKASGYTFTHYGMNWVRQAPGQGLEWMGWINTYTGEPTYADGFTGRFVFSLDTSVSTAYLQISSL
KAEDTAVYFCARDYYGSSPYWGQGTLVTVSS/GKPGSGKPGSGKPGSGKPGS/DIVMTQSPDSLAVSLGERVTINCKASQSIVHSN
GNTYLEWYQQKPGQAPKLLIYKVSNRFSGVPDRFSGSGSGTDFTLTISSVEAEDAATYYCFQGSHVPNTFGQGTKVEIK

FIG. 15P

>XENP025295 1C11_H3.222_L3_scFv(GKPGS)4 (SEQ ID NOS 40560-40568 and linker disclosed as SEQ ID NO: 39202)
QVQLVQSGPELKKPGESVKVSCKASGYTFTHYGINWVRQPPGQGLEWMGWINTYTGEPTYAPGFTGRFVFSIDTSQSTAYLQ
INSLKAEDTAVYYCARDYYGSSPYWGQGTLVTVSS/GKPGSGKPGSGKPGSGKPGS/DVLMTQSPDSLAVSLGERATINCKS
SQSIVHSNGNTYLEWYQQKPGQSPKLLIYKVSNRFSGVPDRFSGSGSGTDFTLTISSLQAEDVAVYYCFQGSHVPNTFGGGT
KVEIK

>XENP025296 1C11_H3.223_L3_scFv(GKPGS)4 (SEQ ID NOS 40569-40577 and linker disclosed as SEQ ID NO: 39202)
QVQLVQSGPELKKPGESVKVSCKASGYTFTHYGINWVRQPPGQGLEWMGWINTYTGEPYYAPGFTERFVFSIDTSQSTAYLQ
INSLKAEDTAVYYCARDYYGSSPYWGQGTLVTVSS/GKPGSGKPGSGKPGSGKPGS/DVLMTQSPDSLAVSLGERATINCKS
SQSIVHSNGNTYLEWYQQKPGQSPKLLIYKVSNRFSGVPDRFSGSGSGTDFTLTISSLQAEDVAVYYCFQGSHVPNTFGGGT
KVEIK

>XENP025301 1C11_H3.224_L3_scFv(GKPGS)4 (SEQ ID NOS 40578-40586 and linker disclosed as SEQ ID NO: 39202)
QVQLVQSGPELKKPGESVKVSCKASGYTFTHYGINWVRQPPGQGLEWMGWINTYTGEPYYAPGFQERFVFSIDTSQSTAYLQ
INSLKAEDTAVYYCARDYYGSSPYWGQGTLVTVSS/GKPGSGKPGSGKPGSGKPGS/DVLMTQSPDSLAVSLGERATINCKS
SQSIVHSNGNTYLEWYQQKPGQSPKLLIYKVSNRFSGVPDRFSGSGSGTDFTLTISSLQAEDVAVYYCFQGSHVPNTFGGGT
KVEIK

>XENP025302 1C11_H3.225_L3_scFv(GKPGS)4 (SEQ ID NOS 40587-40595 and linker disclosed as SEQ ID NO: 39202)
QVQLVQSGPELKKPGESVKVSCKASGYTFTHYGINWVRQAPGQGLEWMGWINTYTGEPYYAPGFTERFVFSLDTSQDTAYLQ
INSLKAEDTAVYYCARDYYGSSPYWGQGTLVTVSS/GKPGSGKPGSGKPGSGKPGS/DVLMTQSPDSLAVSLGERATINCKS
SQSIVHSNGNTYLEWYQQKPGQSPKLLIYKVSNRFSGVPDRFSGSGSGTDFTLTISSLQAEDVAVYYCFQGSHVPNTFGGGT
KVEIK

>XENP025303 1C11_H3.226_L3_scFv(GKPGS)4 (SEQ ID NOS 40596-40604 and linker disclosed as SEQ ID NO: 39202)
QVQLVQSGPELKKPGESVKVSCKASGYTFTHYGINWVRQAPGQGLEWMGWINTYTGEPYYAPGFQERFVFSLDTSQDTAYLQ
INSLKAEDTAVYYCARDYYGSSPYWGQGTLVTVSS/GKPGSGKPGSGKPGSGKPGS/DVLMTQSPDSLAVSLGERATINCKS
SQSIVHSNGNTYLEWYQQKPGQSPKLLIYKVSNRFSGVPDRFSGSGSGTDFTLTISSLQAEDVAVYYCFQGSHVPNTFGGGT
KVEIK

>XENP025304 1C11_H3.227_L3_scFv(GKPGS)4 (SEQ ID NOS 40605-40613 and linker disclosed as SEQ ID NO: 39202)
EVQLVQSGPELKKPGESVKVSCKASGYTFTHYGINWVRQAPGQGLEWMGWINTYTGEPYYAPGFTERFVFSLDTSQDTAYLQ
INSLKAEDTAVYYCARDYYGSSPYWGQGTLVTVSS/GKPGSGKPGSGKPGSGKPGS/DVLMTQSPDSLAVSLGERATINCKS
SQSIVHSNGNTYLEWYQQKPGQSPKLLIYKVSNRFSGVPDRFSGSGSGTDFTLTISSLQAEDVAVYYCFQGSHVPNTFGGGT
KVEIK

>XENP025305 1C11_H3.228_L3_scFv(GKPGS)4 (SEQ ID NOS 40614-40622 and linker disclosed as SEQ ID NO: 39202)
EVQLVQSGPELKKPGESVKVSCKASGYTFTHYGINWVRQAPGQGLEWMGWINTYTGEPYYAPGFQERFVFSLDTSQDTAYLQ
INSLKAEDTAVYYCARDYYGSSPYWGQGTLVTVSS/GKPGSGKPGSGKPGSGKPGS/DVLMTQSPDSLAVSLGERATINCKS
SQSIVHSNGNTYLEWYQQKPGQSPKLLIYKVSNRFSGVPDRFSGSGSGTDFTLTISSLQAEDVAVYYCFQGSHVPNTFGGGT
KVEIK

>XENP025306 1C11_H3.229_L3_scFv(GKPGS)4 (SEQ ID NOS 40623-40631 and linker disclosed as SEQ ID NO: 39202)
QVQLVQSGSELKKPGESVKVSCKASGYTFTHYGINWVRQPPGQGLEWMGWINTYTGEPYYAPGFQERFVFSLDTSQSTAYLQ
INSLKAEDTAVYYCARDYYGSSPYWGQGTLVTVSS/GKPGSGKPGSGKPGSGKPGS/DVLMTQSPDSLAVSLGERATINCKS
SQSIVHSNGNTYLEWYQQKPGQSPKLLIYKVSNRFSGVPDRFSGSGSGTDFTLTISSLQAEDVAVYYCFQGSHVPNTFGGGT
KVEIK

>XENP025307 1C11_H3.230_L3_scFv(GKPGS)4 (SEQ ID NOS 40632-40640 and linker disclosed as SEQ ID NO: 39202)
QVQLVQSGSELKKPGESVKVSCKASGYTFTHYGINWVRQPPGQGLEWMGWINTYTGEPYYAPGFQERFVFSLDTSQDTAYLQ
INSLKAEDTAVYYCARDYYGSSPYWGQGTLVTVSS/GKPGSGKPGSGKPGSGKPGS/DVLMTQSPDSLAVSLGERATINCKS
SQSIVHSNGNTYLEWYQQKPGQSPKLLIYKVSNRFSGVPDRFSGSGSGTDFTLTISSLQAEDVAVYYCFQGSHVPNTFGGGT
KVEIK

FIG. 15Q

>XENP025308 1C11_H3.231_L3_scFv(GKPGS)4 (SEQ ID NOS 40641-40649 and linker disclosed as SEQ ID NO: 39202)
QVQLVQSGSELKKPGESVKVSCKASGYTFTHYGINWVRQPPGQGLEWMGWINTYTGEPTYAPGFTGRFVFSLDTSQSTAYLQ
ISSLKAEDTAVYYCARDYYGSSPYWGQGTLVTVSS/GKPGSGKPGSGKPGSGKPGS/DVLMTQSPDSLAVSLGERATINCKS
SQSIVHSNGNTYLEWYQQKPGQSPKLLIYKVSNRFSGVPDRFSGSGSGTDFTLTISSLQAEDVAVYYCFQGSHVPNTFGGGT
KVEIK

>XENP025309 1C11_H3.232_L3_scFv(GKPGS)4 (SEQ ID NOS 40650-40658 and linker disclosed as SEQ ID NO: 39202)
QVQLVQSGSELKKPGESVKVSCKASGYTFTHYGINWVRQPPGQGLEWMGWINTYTGEPTYAPGFTGRFVFSLDTSQDTAYLQ
INSLKAEDTAVYYCARDYYGSSPYWGQGTLVTVSS/GKPGSGKPGSGKPGSGKPGS/DVLMTQSPDSLAVSLGERATINCKS
SQSIVHSNGNTYLEWYQQKPGQSPKLLIYKVSNRFSGVPDRFSGSGSGTDFTLTISSLQAEDVAVYYCFQGSHVPNTFGGGT
KVEIK

>XENP025310 1C11_H3.233_L3_scFv(GKPGS)4 (SEQ ID NOS 40659-40667 and linker disclosed as SEQ ID NO: 39202)
EVQLVQSGSELKKPGESVKVSCKASGYTFTHYGINWVRQPPGQGLEWMGWINTYTGEPYYAPGFQERFVFSLDTSQSTAYLQ
INSLKAEDTAVYYCARDYYGSSPYWGQGTLVTVSS/GKPGSGKPGSGKPGSGKPGS/DVLMTQSPDSLAVSLGERATINCKS
SQSIVHSNGNTYLEWYQQKPGQSPKLLIYKVSNRFSGVPDRFSGSGSGTDFTLTISSLQAEDVAVYYCFQGSHVPNTFGGGT
KVEIK

>XENP025311 1C11_H3.234_L3_scFv(GKPGS)4 (SEQ ID NOS 40668-40676 and linker disclosed as SEQ ID NO: 39202)
EVQLVQSGSELKKPGESVKVSCKASGYTFTHYGINWVRQPPGQGLEWMGWINTYTGEPYYAPGFQERFVFSLDTSQDTAYLQ
INSLKAEDTAVYYCARDYYGSSPYWGQGTLVTVSS/GKPGSGKPGSGKPGSGKPGS/DVLMTQSPDSLAVSLGERATINCKS
SQSIVHSNGNTYLEWYQQKPGQSPKLLIYKVSNRFSGVPDRFSGSGSGTDFTLTISSLQAEDVAVYYCFQGSHVPNTFGGGT
KVEIK

>XENP025312 1C11_H3.235_L3_scFv(GKPGS)4 (SEQ ID NOS 40677-40685 and linker disclosed as SEQ ID NO: 39202)
EVQLVQSGSELKKPGESVKVSCKASGYTFTHYGINWVRQPPGQGLEWMGWINTYTGEPTYAPGFTGRFVFSLDTSQSTAYLQ
ISSLKAEDTAVYYCARDYYGSSPYWGQGTLVTVSS/GKPGSGKPGSGKPGSGKPGS/DVLMTQSPDSLAVSLGERATINCKS
SQSIVHSNGNTYLEWYQQKPGQSPKLLIYKVSNRFSGVPDRFSGSGSGTDFTLTISSLQAEDVAVYYCFQGSHVPNTFGGGT
KVEIK

>XENP025313 1C11_H3.236_L3_scFv(GKPGS)4 (SEQ ID NOS 40686-40694 and linker disclosed as SEQ ID NO: 39202)
EVQLVQSGSELKKPGESVKVSCKASGYTFTHYGINWVRQPPGQGLEWMGWINTYTGEPTYAPGFTGRFVFSLDTSQDTAYLQ
INSLKAEDTAVYYCARDYYGSSPYWGQGTLVTVSS/GKPGSGKPGSGKPGSGKPGS/DVLMTQSPDSLAVSLGERATINCKS
SQSIVHSNGNTYLEWYQQKPGQSPKLLIYKVSNRFSGVPDRFSGSGSGTDFTLTISSLQAEDVAVYYCFQGSHVPNTFGGGT
KVEIK

>XENP025314 1C11_H3.237_L3_scFv(GKPGS)4 (SEQ ID NOS 40695-40703 and linker disclosed as SEQ ID NO: 39202)
QVQLVQSGSELKKPGESVKVSCKASGYTFTHYGINWVRQAPGQGLEWMGWINTYTGEPYYAPGFTERFVFSLDTSQDTAYLQ
INSLKAEDTAVYYCARDYYGSSPYWGQGTLVTVSS/GKPGSGKPGSGKPGSGKPGS/DVLMTQSPDSLAVSLGERATINCKS
SQSIVHSNGNTYLEWYQQKPGQSPKLLIYKVSNRFSGVPDRFSGSGSGTDFTLTISSLQAEDVAVYYCFQGSHVPNTFGGGT
KVEIK

>XENP025315 1C11_H3.238_L3_scFv(GKPGS)4 (SEQ ID NOS 40704-40712 and linker disclosed as SEQ ID NO: 39202)
QVQLVQSGSELKKPGESVKVSCKASGYTFTHYGINWVRQAPGQGLEWMGWINTYTGEPYYAPGFQERFVFSLDTSQDTAYLQ
INSLKAEDTAVYYCARDYYGSSPYWGQGTLVTVSS/GKPGSGKPGSGKPGSGKPGS/DVLMTQSPDSLAVSLGERATINCKS
SQSIVHSNGNTYLEWYQQKPGQSPKLLIYKVSNRFSGVPDRFSGSGSGTDFTLTISSLQAEDVAVYYCFQGSHVPNTFGGGT
KVEIK

>XENP025316 1C11_H3.213_L3.144_scFv(GKPGS)4 (SEQ ID NOS 40713-40721 and linker disclosed as SEQ ID NO: 39202)
QVQLVQSGPELKKPGESVKVSCKASGYTFTHYGINWVRQAPGQGLEWIGWINTYTGEPYYAPGFTGRFVFSLDTSQDTAYLQ
INSLKAEDTAVYYCARDYYGSSPYWGQGTLVTVSS/GKPGSGKPGSGKPGSGKPGS/DIVMTQSPDSLAVSLGERVTINCKA
SQSIVHSNGNTYLEWYQQKPGQPPKLLIYKVSNRFSGVPDRFSGSGSGTDFTLTISSVEAEDAATYYCFQGSHVPNTFGQGT
KVEIK

FIG. 15R

>XENP025317 1C11_H3.213_L3.148_scFv(GKPGS)4 (SEQ ID NOS 40722-40730 and linker disclosed as SEQ ID NO: 39202)
QVQLVQSGPELKKPGESVKVSCKASGYTFTHYGINWVRQAPGQGLEWIGWINTYTGEPYYAPGFTGRFVFSLDTSQDTAYLQINSL
KAEDTAVYYCARDYYGSSPYWGQGTLVTVSS/GKPGSGKPGSGKPGSGKPGS/DIVMTQSPDSLAVSLGERVTINCKASQSIVHSN
GNTYLEWYQQKPGQAPKLLIYKVSNRFSGVPDRFSGSGSGTDFTLTISSVEAEDAATYYCFQGSHVPNTFGQGTKVEIK

>XENP025318 1C11_H3.216_L3.144_scFv(GKPGS)4 (SEQ ID NOS 40731-40739 and linker disclosed as SEQ ID NO: 39202)
QVQLVQSGPELKKPGESVKVSCKASGYTFTHYGINWVRQPPGQGLEWMGWINTYTGEPYYAPGFTGRFVFSIDTSQSTAYLQINSL
KAEDTAVYYCARDYYGSSPYWGQGTLVTVSS/GKPGSGKPGSGKPGSGKPGS/DIVMTQSPDSLAVSLGERVTINCKASQSIVHSN
GNTYLEWYQQKPGQPPKLLIYKVSNRFSGVPDRFSGSGSGTDFTLTISSVEAEDAATYYCFQGSHVPNTFGQGTKVEIK

>XENP025319 1C11_H3.216_L3.148_scFv(GKPGS)4 (SEQ ID NOS 40740-40748 and linker disclosed as SEQ ID NO: 39202)
QVQLVQSGPELKKPGESVKVSCKASGYTFTHYGINWVRQPPGQGLEWMGWINTYTGEPYYAPGFTGRFVFSIDTSQSTAYLQINSL
KAEDTAVYYCARDYYGSSPYWGQGTLVTVSS/GKPGSGKPGSGKPGSGKPGS/DIVMTQSPDSLAVSLGERVTINCKASQSIVHSN
GNTYLEWYQQKPGQAPKLLIYKVSNRFSGVPDRFSGSGSGTDFTLTISSVEAEDAATYYCFQGSHVPNTFGQGTKVEIK

>XENP025320 1C11_H3.188_L3.144_scFv(GKPGS)4 (SEQ ID NOS 40749-40757 and linker disclosed as SEQ ID NO: 39202)
QVQLVQSGSELKKPGESVKVSCKASGYTFTHYGINWVRQPPGQGLEWIGWINTYTGEPYYAPGFTGRFVFSLDTSQSTAYLQINSL
KAEDTAVYYCARDYYGSSPYWGQGTLVTVSS/GKPGSGKPGSGKPGSGKPGS/DIVMTQSPDSLAVSLGERVTINCKASQSIVHSN
GNTYLEWYQQKPGQPPKLLIYKVSNRFSGVPDRFSGSGSGTDFTLTISSVEAEDAATYYCFQGSHVPNTFGQGTKVEIK

>XENP025321 1C11_H3.188_L3.148_scFv(GKPGS)4 (SEQ ID NOS 40758-40766 and linker disclosed as SEQ ID NO: 39202)
QVQLVQSGSELKKPGESVKVSCKASGYTFTHYGINWVRQPPGQGLEWIGWINTYTGEPYYAPGFTGRFVFSLDTSQSTAYLQINSL
KAEDTAVYYCARDYYGSSPYWGQGTLVTVSS/GKPGSGKPGSGKPGSGKPGS/DIVMTQSPDSLAVSLGERVTINCKASQSIVHSN
GNTYLEWYQQKPGQAPKLLIYKVSNRFSGVPDRFSGSGSGTDFTLTISSVEAEDAATYYCFQGSHVPNTFGQGTKVEIK

>XENP025802 1C11[PD-1]_H3.224_L3.144_scFv(GKPGS)4 (SEQ ID NOS 40767-40775 and linker disclosed as SEQ ID NO: 39202)
QVQLVQSGPELKKPGESVKVSCKASGYTFTHYGINWVRQPPGQGLEWMGWINTYTGEPYYAPGFQERFVFSIDTSQSTAYLQINSL
KAEDTAVYYCARDYYGSSPYWGQGTLVTVSS/GKPGSGKPGSGKPGSGKPGS/DIVMTQSPDSLAVSLGERVTINCKASQSIVHSN
GNTYLEWYQQKPGQPPKLLIYKVSNRFSGVPDRFSGSGSGTDFTLTISSVEAEDAATYYCFQGSHVPNTFGQGTKVEIK

>XENP025803 1C11[PD-1]_H3.224_L3.148_scFv(GKPGS)4 (SEQ ID NOS 40776-40784 and linker disclosed as SEQ ID NO: 39202)
QVQLVQSGPELKKPGESVKVSCKASGYTFTHYGINWVRQPPGQGLEWMGWINTYTGEPYYAPGFQERFVFSIDTSQSTAYLQINSL
KAEDTAVYYCARDYYGSSPYWGQGTLVTVSS/GKPGSGKPGSGKPGSGKPGS/DIVMTQSPDSLAVSLGERVTINCKASQSIVHSN
GNTYLEWYQQKPGQAPKLLIYKVSNRFSGVPDRFSGSGSGTDFTLTISSVEAEDAATYYCFQGSHVPNTFGQGTKVEIK

>XENP025804 1C11[PD-1]_H3.228_L3.144_scFv(GKPGS)4 (SEQ ID NOS 40785-40793 and linker disclosed as SEQ ID NO: 39202)
EVQLVQSGPELKKPGESVKVSCKASGYTFTHYGINWVRQAPGQGLEWMGWINTYTGEPYYAPGFQERFVFSLDTSQDTAYLQINSL
KAEDTAVYYCARDYYGSSPYWGQGTLVTVSS/GKPGSGKPGSGKPGSGKPGS/DIVMTQSPDSLAVSLGERVTINCKASQSIVHSN
GNTYLEWYQQKPGQPPKLLIYKVSNRFSGVPDRFSGSGSGTDFTLTISSVEAEDAATYYCFQGSHVPNTFGQGTKVEIK

>XENP025805 1C11[PD-1]_H3.228_L3.148_scFv(GKPGS)4 (SEQ ID NOS 40794-40802 and linker disclosed as SEQ ID NO: 39202)
EVQLVQSGPELKKPGESVKVSCKASGYTFTHYGINWVRQAPGQGLEWMGWINTYTGEPYYAPGFQERFVFSLDTSQDTAYLQINSL
KAEDTAVYYCARDYYGSSPYWGQGTLVTVSS/GKPGSGKPGSGKPGSGKPGS/DIVMTQSPDSLAVSLGERVTINCKASQSIVHSN
GNTYLEWYQQKPGQAPKLLIYKVSNRFSGVPDRFSGSGSGTDFTLTISSVEAEDAATYYCFQGSHVPNTFGQGTKVEIK

FIG. 15S

>XENP025806 1C11[PD-1]_H3.234_L3.144_scFv(GKPGS)4 (SEQ ID NOS 40803-40811 and linker disclosed as SEQ ID NO: 39202)
EVQLVQSGSELKKPGESVKVSCKASGYTFTHYGINWVRQPPGQGLEWMGWINTYTGEPYYAPGFQERFVFSLDTSQDTAYLQINSL
KAEDTAVYYCARDYYGSSPYWGQGTLVTVSS/GKPGSGKPGSGKPGSGKPGS/DIVMTQSPDSLAVSLGERVTINCKASQSIVHSN
GNTYLEWYQQKPGQPPKLLIYKVSNRFSGVPDRFSGSGSGTDFTLTISSVEAEDAATYYCFQGSHVPNTFGQGTKVEIK

>XENP025807 1C11[PD-1]_H3.234_L3.148_scFv(GKPGS)4 (SEQ ID NOS 40812-40820 and linker disclosed as SEQ ID NO: 39202)
EVQLVQSGSELKKPGESVKVSCKASGYTFTHYGINWVRQPPGQGLEWMGWINTYTGEPYYAPGFQERFVFSLDTSQDTAYLQINSL
KAEDTAVYYCARDYYGSSPYWGQGTLVTVSS/GKPGSGKPGSGKPGSGKPGS/DIVMTQSPDSLAVSLGERVTINCKASQSIVHSN
GNTYLEWYQQKPGQAPKLLIYKVSNRFSGVPDRFSGSGSGTDFTLTISSVEAEDAATYYCFQGSHVPNTFGQGTKVEIK

>XENP025808 1C11[PD-1]_H3.239_L3.144_scFv(GKPGS)4 (SEQ ID NOS 40821-40829 and linker disclosed as SEQ ID NO: 39202)
EVQLVQSGPELKKPGESVKVSCKASGYTFTHYGINWVRQPPGQGLEWMGWINTYTGEPYYAPGFQERFVFSIDTSQSTAYLQINSL
KAEDTAVYYCARDYYGSSPYWGQGTLVTVSS/GKPGSGKPGSGKPGSGKPGS/DVLMTQSPDSLAVSLGERATINCKSSQSIVHSN
GNTYLEWYQQKPGQSPKLLIYKVSNRFSGVPDRFSGSGSGTDFTLTISSLQAEDVAVYYCFQGSHVPNTFGGGTKVEIK

>XENP025809 1C11[PD-1]_H3.240_L3.144_scFv(GKPGS)4 (SEQ ID NOS 40830-40838 and linker disclosed as SEQ ID NO: 39202)
QVQLVQSGPELKKPGESVKVSCKASGYTFTHYGINWVRQPPGQGLEWMGWINTYTGEPYYAPGFQERFVFSIDTSQDTAYLQINSL
KAEDTAVYYCARDYYGSSPYWGQGTLVTVSS/GKPGSGKPGSGKPGSGKPGS/DVLMTQSPDSLAVSLGERATINCKSSQSIVHSN
GNTYLEWYQQKPGQSPKLLIYKVSNRFSGVPDRFSGSGSGTDFTLTISSLQAEDVAVYYCFQGSHVPNTFGGGTKVEIK

>XENP025810 1C11[PD-1]_H3.241_L3.144_scFv(GKPGS)4 (SEQ ID NOS 40839-40847 and linker disclosed as SEQ ID NO: 39202)
EVQLVQSGPELKKPGESVKVSCKASGYTFTHYGINWVRQPPGQGLEWMGWINTYTGEPYYAPGFQERFVFSIDTSQDTAYLQINSL
KAEDTAVYYCARDYYGSSPYWGQGTLVTVSS/GKPGSGKPGSGKPGSGKPGS/DVLMTQSPDSLAVSLGERATINCKSSQSIVHSN
GNTYLEWYQQKPGQSPKLLIYKVSNRFSGVPDRFSGSGSGTDFTLTISSLQAEDVAVYYCFQGSHVPNTFGGGTKVEIK

>XENP025811 1C11[PD-1]_H3.239_L3.148_scFv(GKPGS)4 (SEQ ID NOS 40848-40856 and linker disclosed as SEQ ID NO: 39202)
EVQLVQSGPELKKPGESVKVSCKASGYTFTHYGINWVRQPPGQGLEWMGWINTYTGEPYYAPGFQERFVFSIDTSQSTAYLQINSL
KAEDTAVYYCARDYYGSSPYWGQGTLVTVSS/GKPGSGKPGSGKPGSGKPGS/DVLMTQSPDSLAVSLGERATINCKSSQSIVHSN
GNTYLEWYQQKPGQSPKLLIYKVSNRFSGVPDRFSGSGSGTDFTLTISSLQAEDVAVYYCFQGSHVPNTFGGGTKVEIK

>XENP025812 1C11[PD-1]_H3.240_L3.148_scFv(GKPGS)4 (SEQ ID NOS 40857-40865 and linker disclosed as SEQ ID NO: 39202)
QVQLVQSGPELKKPGESVKVSCKASGYTFTHYGINWVRQPPGQGLEWMGWINTYTGEPYYAPGFQERFVFSIDTSQDTAYLQINSL
KAEDTAVYYCARDYYGSSPYWGQGTLVTVSS/GKPGSGKPGSGKPGSGKPGS/DVLMTQSPDSLAVSLGERATINCKSSQSIVHSN
GNTYLEWYQQKPGQSPKLLIYKVSNRFSGVPDRFSGSGSGTDFTLTISSLQAEDVAVYYCFQGSHVPNTFGGGTKVEIK

>XENP025813 1C11[PD-1]_H3.241_L3.148_scFv(GKPGS)4 (SEQ ID NOS 40866-40874 and linker disclosed as SEQ ID NO: 39202)
EVQLVQSGPELKKPGESVKVSCKASGYTFTHYGINWVRQPPGQGLEWMGWINTYTGEPYYAPGFQERFVFSIDTSQDTAYLQINSL
KAEDTAVYYCARDYYGSSPYWGQGTLVTVSS/GKPGSGKPGSGKPGSGKPGS/DVLMTQSPDSLAVSLGERATINCKSSQSIVHSN
GNTYLEWYQQKPGQSPKLLIYKVSNRFSGVPDRFSGSGSGTDFTLTISSLQAEDVAVYYCFQGSHVPNTFGGGTKVEIK

>XENP025814 1C11[PD-1]_H3.239_L3.125_scFv(GKPGS)4 (SEQ ID NOS 40875-40883 and linker disclosed as SEQ ID NO: 39202)
EVQLVQSGPELKKPGESVKVSCKASGYTFTHYGINWVRQPPGQGLEWMGWINTYTGEPYYAPGFQERFVFSIDTSQSTAYLQINSL
KAEDTAVYYCARDYYGSSPYWGQGTLVTVSS/GKPGSGKPGSGKPGSGKPGS/DVLMTQSPDSLAVSLGERATINCKSSQSIVHSN
GNTYLEWYQQKPGQSPKLLIYKVSNRFSGVPDRFSGSGSGTDFTLTISSVEAEDVAVYYCFQGSHVPNTFGGGTKVEIK

FIG. 15T

>XENP025815 1C11[PD-1]_H3.240_L3.125_scFv(GKPGS)4 (SEQ ID NOS 40884-40892 and linker disclosed as SEQ ID NO: 39202)
QVQLVQSGPELKKPGESVKVSCKASGYTFTHYGINWVRQPPGQGLEWMGWINTYTGEPYYAPGFQERFVFSIDTSQD
TAYLQINSLKAEDTAVYYCARDYYGSSPYWGQGTLVTVSS/GKPGSGKPGSGKPGSGKPGS/DVLMTQSPDSLAVSL
GERATINCKSSQSIVHSNGNTYLEWYQQKPGQSPKLLIYKVSNRFSGVPDRFSGSGSGTDFTLTISSVEAEDVAVYY
CFQGSHVPNTFGGGTKVEIK

>XENP025816 1C11[PD-1]_H3.241_L3.125_scFv(GKPGS)4 (SEQ ID NOS 40893-40901 and linker disclosed as SEQ ID NO: 39202)
EVQLVQSGPELKKPGESVKVSCKASGYTFTHYGINWVRQPPGQGLEWMGWINTYTGEPYYAPGFQERFVFSIDTSQD
TAYLQINSLKAEDTAVYYCARDYYGSSPYWGQGTLVTVSS/GKPGSGKPGSGKPGSGKPGS/DVLMTQSPDSLAVSL
GERATINCKSSQSIVHSNGNTYLEWYQQKPGQSPKLLIYKVSNRFSGVPDRFSGSGSGTDFTLTISSVEAEDVAVYY
CFQGSHVPNTFGGGTKVEIK

>XENP025817 1C11[PD-1]_H3.239_L3.92_scFv(GKPGS)4 (SEQ ID NOS 40902-40910 and linker disclosed as SEQ ID NO: 39202)
EVQLVQSGPELKKPGESVKVSCKASGYTFTHYGINWVRQPPGQGLEWMGWINTYTGEPYYAPGFQERFVFSIDTSQS
TAYLQINSLKAEDTAVYYCARDYYGSSPYWGQGTLVTVSS/GKPGSGKPGSGKPGSGKPGS/DIVMTQSPDSLAVSL
GERVTINCKASQSIVHSNGNTYLEWYQQKPGQPPKLLIYKVSNRFTGVPDRFSGSGSGTDFTLTISSLQAEDVAVYY
CFQGSHVPNTFGGGTKVEIK

>XENP025818 1C11[PD-1]_H3.240_L3.92_scFv(GKPGS)4 (SEQ ID NOS 40911-40919 and linker disclosed as SEQ ID NO: 39202)
QVQLVQSGPELKKPGESVKVSCKASGYTFTHYGINWVRQPPGQGLEWMGWINTYTGEPYYAPGFQERFVFSIDTSQD
TAYLQINSLKAEDTAVYYCARDYYGSSPYWGQGTLVTVSS/GKPGSGKPGSGKPGSGKPGS/DIVMTQSPDSLAVSL
GERVTINCKASQSIVHSNGNTYLEWYQQKPGQPPKLLIYKVSNRFTGVPDRFSGSGSGTDFTLTISSLQAEDVAVYY
CFQGSHVPNTFGGGTKVEIK

>XENP025819 1C11[PD-1]_H3.241_L3.92_scFv(GKPGS)4 (SEQ ID NOS 40920-40928 and linker disclosed as SEQ ID NO: 39202)
EVQLVQSGPELKKPGESVKVSCKASGYTFTHYGINWVRQPPGQGLEWMGWINTYTGEPYYAPGFQERFVFSIDTSQD
TAYLQINSLKAEDTAVYYCARDYYGSSPYWGQGTLVTVSS/GKPGSGKPGSGKPGSGKPGS/DIVMTQSPDSLAVSL
GERVTINCKASQSIVHSNGNTYLEWYQQKPGQPPKLLIYKVSNRFTGVPDRFSGSGSGTDFTLTISSLQAEDVAVYY
CFQGSHVPNTFGGGTKVEIK

FIG. 16A

XENP025322 1C11_H3.223_L3_IgG1_PVA_/S267K Heavy Chain (SEQ ID NOS 40929-40933)
QVQLVQSGPELKKPGESVKVSCKASGYTFT<u>HYGIN</u>WVRQPPGQGLEWMG<u>WINTYTGEPYYAPGFTERF</u>VFSIDTSQSTAYLQINSLKAEDTAVYYCA
RD<u>YYGSSPYW</u>GQGTLVTVSS/ASTKGPSVFPLAPSSKSTSGGTAALGCLVKDYFPEPVTVSWNSGALTSGVHTFPAVLQSSGLYSLSSVVTVPSSSL
GTQTYICNVNHKPSNTKVDKKVEPKSCDKTHTCPPCPAPPVAGPSVFLFPPKPKDTLMISRTPEVTCVVVDVKHEDPEVKFNWYVDGVEVHNAKTKP
REEQYNSTYRVVSVLTVLHQDWLNGKEYKCKVSNKALPAPIEKTISKAKGQPREPQVYTLPPSREEMTKNQVSLTCLVKGFYPSDIAVEWESNGQPE
NNYKTTPPVLDSDGSFFLYSKLTVDKSRWQQGNVFSCSVMHEALHNHYTQKSLSLSPGK

>XENP025322 1C11_H3.223_L3_IgG1_PVA_/S267K Light Chain (SEQ ID NOS 40934-40938)
DVLMTQSPDSLAVSLGERATINC<u>KSSQSIVHSNGNTYLE</u>WYQQKPGQSPKLLIY<u>KVSNRFS</u>GVPDRFSGSGSGTDFTLTISSLQAEDVAVYYC<u>FQGS
HVPNT</u>FGGGTKVEIK/RTVAAPSVFIFPPSDEQLKSGTASVVCLLNNFYPREAKVQWKVDNALQSGNSQESVTEQDSKDSTYSLSSTLTLSKADYEK
HKVYACEVTHQGLSSPVTKSFNRGEC

>XENP025323 1C11_H3.224_L3_IgG1_PVA_/S267K Heavy Chain (SEQ ID NOS 40939-40943)
QVQLVQSGPELKKPGESVKVSCKASGYTFT<u>HYGIN</u>WVRQPPGQGLEWMG<u>WINTYTGEPYYAPGFQERF</u>VFSIDTSQSTAYLQINSLKAEDTAVYYCA
RD<u>YYGSSPYW</u>GQGTLVTVSS/ASTKGPSVFPLAPSSKSTSGGTAALGCLVKDYFPEPVTVSWNSGALTSGVHTFPAVLQSSGLYSLSSVVTVPSSSL
GTQTYICNVNHKPSNTKVDKKVEPKSCDKTHTCPPCPAPPVAGPSVFLFPPKPKDTLMISRTPEVTCVVVDVKHEDPEVKFNWYVDGVEVHNAKTKP
REEQYNSTYRVVSVLTVLHQDWLNGKEYKCKVSNKALPAPIEKTISKAKGQPREPQVYTLPPSREEMTKNQVSLTCLVKGFYPSDIAVEWESNGQPE
NNYKTTPPVLDSDGSFFLYSKLTVDKSRWQQGNVFSCSVMHEALHNHYTQKSLSLSPGK

>XENP025323 1C11_H3.224_L3_IgG1_PVA_/S267K Light Chain (SEQ ID NOS 40944-40948)
DVLMTQSPDSLAVSLGERATINC<u>KSSQSIVHSNGNTYLE</u>WYQQKPGQSPKLLIY<u>KVSNRFS</u>GVPDRFSGSGSGTDFTLTISSLQAEDVAVYYC<u>FQGS
HVPNT</u>FGGGTKVEIK/RTVAAPSVFIFPPSDEQLKSGTASVVCLLNNFYPREAKVQWKVDNALQSGNSQESVTEQDSKDSTYSLSSTLTLSKADYEK
HKVYACEVTHQGLSSPVTKSFNRGEC

>XENP025324 1C11_H3.225_L3_IgG1_PVA_/S267K Heavy Chain (SEQ ID NOS 40949-40953)
QVQLVQSGPELKKPGESVKVSCKASGYTFT<u>HYGIN</u>WVRQAPGQGLEWMG<u>WINTYTGEPYYAPGFTERF</u>VFSLDTSQDTAYLQINSLKAEDTAVYYCA
RD<u>YYGSSPYW</u>GQGTLVTVSS/ASTKGPSVFPLAPSSKSTSGGTAALGCLVKDYFPEPVTVSWNSGALTSGVHTFPAVLQSSGLYSLSSVVTVPSSSL
GTQTYICNVNHKPSNTKVDKKVEPKSCDKTHTCPPCPAPPVAGPSVFLFPPKPKDTLMISRTPEVTCVVVDVKHEDPEVKFNWYVDGVEVHNAKTKP
REEQYNSTYRVVSVLTVLHQDWLNGKEYKCKVSNKALPAPIEKTISKAKGQPREPQVYTLPPSREEMTKNQVSLTCLVKGFYPSDIAVEWESNGQPE
NNYKTTPPVLDSDGSFFLYSKLTVDKSRWQQGNVFSCSVMHEALHNHYTQKSLSLSPGK

>XENP025324 1C11_H3.225_L3_IgG1_PVA_/S267K Light Chain (SEQ ID NOS 40954-40958)
DVLMTQSPDSLAVSLGERATINC<u>KSSQSIVHSNGNTYLE</u>WYQQKPGQSPKLLIY<u>KVSNRFS</u>GVPDRFSGSGSGTDFTLTISSLQAEDVAVYYC<u>FQGS
HVPNT</u>FGGGTKVEIK/RTVAAPSVFIFPPSDEQLKSGTASVVCLLNNFYPREAKVQWKVDNALQSGNSQESVTEQDSKDSTYSLSSTLTLSKADYEK
HKVYACEVTHQGLSSPVTKSFNRGEC

>XENP025325 1C11_H3.226_L3_IgG1_PVA_/S267K Heavy Chain (SEQ ID NOS 40959-40963)
QVQLVQSGPELKKPGESVKVSCKASGYTFT<u>HYGIN</u>WVRQAPGQGLEWMG<u>WINTYTGEPYYAPGFQERF</u>VFSLDTSQDTAYLQINSLKAEDTAVYYCA
RD<u>YYGSSPYW</u>GQGTLVTVSS/ASTKGPSVFPLAPSSKSTSGGTAALGCLVKDYFPEPVTVSWNSGALTSGVHTFPAVLQSSGLYSLSSVVTVPSSSL
GTQTYICNVNHKPSNTKVDKKVEPKSCDKTHTCPPCPAPPVAGPSVFLFPPKPKDTLMISRTPEVTCVVVDVKHEDPEVKFNWYVDGVEVHNAKTKP
REEQYNSTYRVVSVLTVLHQDWLNGKEYKCKVSNKALPAPIEKTISKAKGQPREPQVYTLPPSREEMTKNQVSLTCLVKGFYPSDIAVEWESNGQPE
NNYKTTPPVLDSDGSFFLYSKLTVDKSRWQQGNVFSCSVMHEALHNHYTQKSLSLSPGK

>XENP025325 1C11_H3.226_L3_IgG1_PVA_/S267K Light Chain (SEQ ID NOS 40964-40968)
DVLMTQSPDSLAVSLGERATINC<u>KSSQSIVHSNGNTYLE</u>WYQQKPGQSPKLLIY<u>KVSNRFS</u>GVPDRFSGSGSGTDFTLTISSLQAEDVAVYYC<u>FQGS
HVPNT</u>FGGGTKVEIK/RTVAAPSVFIFPPSDEQLKSGTASVVCLLNNFYPREAKVQWKVDNALQSGNSQESVTEQDSKDSTYSLSSTLTLSKADYEK
HKVYACEVTHQGLSSPVTKSFNRGEC

>XENP025326 1C11_H3.229_L3_IgG1_PVA_/S267K Heavy Chain (SEQ ID NOS 40969-40973)
QVQLVQSGSELKKPGESVKVSCKASGYTFT<u>HYGIN</u>WVRQPPGQGLEWMG<u>WINTYTGEPYYAPGFQERF</u>VFSIDTSQSTAYLQINSLKAEDTAVYYCA
RD<u>YYGSSPYW</u>GQGTLVTVSS/ASTKGPSVFPLAPSSKSTSGGTAALGCLVKDYFPEPVTVSWNSGALTSGVHTFPAVLQSSGLYSLSSVVTVPSSSL
GTQTYICNVNHKPSNTKVDKKVEPKSCDKTHTCPPCPAPPVAGPSVFLFPPKPKDTLMISRTPEVTCVVVDVKHEDPEVKFNWYVDGVEVHNAKTKP
REEQYNSTYRVVSVLTVLHQDWLNGKEYKCKVSNKALPAPIEKTISKAKGQPREPQVYTLPPSREEMTKNQVSLTCLVKGFYPSDIAVEWESNGQPE
NNYKTTPPVLDSDGSFFLYSKLTVDKSRWQQGNVFSCSVMHEALHNHYTQKSLSLSPGK

>XENP025326 1C11_H3.229_L3_IgG1_PVA_/S267K Light Chain (SEQ ID NOS 40974-40978)
DVLMTQSPDSLAVSLGERATINC<u>KSSQSIVHSNGNTYLE</u>WYQQKPGQSPKLLIY<u>KVSNRFS</u>GVPDRFSGSGSGTDFTLTISSLQAEDVAVYYC<u>FQGS
HVPNT</u>FGGGTKVEIK/RTVAAPSVFIFPPSDEQLKSGTASVVCLLNNFYPREAKVQWKVDNALQSGNSQESVTEQDSKDSTYSLSSTLTLSKADYEK
HKVYACEVTHQGLSSPVTKSFNRGEC

>XENP025327 1C11_H3.230_L3_IgG1_PVA_/S267K Heavy Chain (SEQ ID NOS 40979-40983)
QVQLVQSGSELKKPGESVKVSCKASGYTFT<u>HYGIN</u>WVRQPPGQGLEWMG<u>WINTYTGEPYYAPGFQERF</u>VFSLDTSQDTAYLQINSLKAEDTAVYYCA
RD<u>YYGSSPYW</u>GQGTLVTVSS/ASTKGPSVFPLAPSSKSTSGGTAALGCLVKDYFPEPVTVSWNSGALTSGVHTFPAVLQSSGLYSLSSVVTVPSSSL
GTQTYICNVNHKPSNTKVDKKVEPKSCDKTHTCPPCPAPPVAGPSVFLFPPKPKDTLMISRTPEVTCVVVDVKHEDPEVKFNWYVDGVEVHNAKTKP
REEQYNSTYRVVSVLTVLHQDWLNGKEYKCKVSNKALPAPIEKTISKAKGQPREPQVYTLPPSREEMTKNQVSLTCLVKGFYPSDIAVEWESNGQPE
NNYKTTPPVLDSDGSFFLYSKLTVDKSRWQQGNVFSCSVMHEALHNHYTQKSLSLSPGK

FIG. 16B

>XENP025327 1C11_H3.230_L3_IgG1_PVA_/S267K Light Chain (SEQ ID NOS 40984-40988)
DVLMTQSPDSLAVSLGERATINCKSSQSIVHSNGNTYLEWYQQKPGQSPKLLIYKVSNRFSGVPDRFSGSGSGTDFTLTISSLQAEDVAVYYCFQGS
HVPNTFGGGTKVEIK/RTVAAPSVFIFPPSDEQLKSGTASVVCLLNNFYPREAKVQWKVDNALQSGNSQESVTEQDSKDSTYSLSSTLTLSKADYEK
HKVYACEVTHQGLSSPVTKSFNRGEC

>XENP025328 1C11_H3.231_L3_IgG1_PVA_/S267K Heavy Chain (SEQ ID NOS 40989-40993)
QVQLVQSGSELKKPGESVKVSCKASGYTFTHYGINWVRQPPGQGLEWMGWINTYTGEPTYAPGFTGRFVFSLDTSQSTAYLQISSLKAEDTAVYYCA
RDYYGSSPYWGQGTLVTVSS/ASTKGPSVFPLAPSSKSTSGGTAALGCLVKDYFPEPVTVSWNSGALTSGVHTFPAVLQSSGLYSLSSVVTVPSSSL
GTQTYICNVNHKPSNTKVDKKVEPKSCDKTHTCPPCPAPPVAGPSVFLFPPKPKDTLMISRTPEVTCVVVDVKHEDPEVKFNWYVDGVEVHNAKTKP
REEQYNSTYRVVSVLTVLHQDWLNGKEYKCKVSNKALPAPIEKTISKAKGQPREPQVYTLPPSREEMTKNQVSLTCLVKGFYPSDIAVEWESNGQPE
NNYKTTPPVLDSDGSFFLYSKLTVDKSRWQQGNVFSCSVMHEALHNHYTQKSLSLSPGK

>XENP025328 1C11_H3.231_L3_IgG1_PVA_/S267K Light Chain (SEQ ID NOS 40994-40998)
DVLMTQSPDSLAVSLGERATINCKSSQSIVHSNGNTYLEWYQQKPGQSPKLLIYKVSNRFSGVPDRFSGSGSGTDFTLTISSLQAEDVAVYYCFQGS
HVPNTFGGGTKVEIK/RTVAAPSVFIFPPSDEQLKSGTASVVCLLNNFYPREAKVQWKVDNALQSGNSQESVTEQDSKDSTYSLSSTLTLSKADYEK
HKVYACEVTHQGLSSPVTKSFNRGEC

>XENP025329 1C11_H3.232_L3_IgG1_PVA_/S267K Heavy Chain (SEQ ID NOS 40999-41003)
QVQLVQSGSELKKPGESVKVSCKASGYTFTHYGINWVRQPPGQGLEWMGWINTYTGEPTYAPGFTGRFVFSLDTSQDTAYLQINSLKAEDTAVYYCA
RDYYGSSPYWGQGTLVTVSS/ASTKGPSVFPLAPSSKSTSGGTAALGCLVKDYFPEPVTVSWNSGALTSGVHTFPAVLQSSGLYSLSSVVTVPSSSL
GTQTYICNVNHKPSNTKVDKKVEPKSCDKTHTCPPCPAPPVAGPSVFLFPPKPKDTLMISRTPEVTCVVVDVKHEDPEVKFNWYVDGVEVHNAKTKP
REEQYNSTYRVVSVLTVLHQDWLNGKEYKCKVSNKALPAPIEKTISKAKGQPREPQVYTLPPSREEMTKNQVSLTCLVKGFYPSDIAVEWESNGQPE
NNYKTTPPVLDSDGSFFLYSKLTVDKSRWQQGNVFSCSVMHEALHNHYTQKSLSLSPGK

>XENP025329 1C11_H3.232_L3_IgG1_PVA_/S267K Light Chain (SEQ ID NOS 41004-41008)
DVLMTQSPDSLAVSLGERATINCKSSQSIVHSNGNTYLEWYQQKPGQSPKLLIYKVSNRFSGVPDRFSGSGSGTDFTLTISSLQAEDVAVYYCFQGS
HVPNTFGGGTKVEIK/RTVAAPSVFIFPPSDEQLKSGTASVVCLLNNFYPREAKVQWKVDNALQSGNSQESVTEQDSKDSTYSLSSTLTLSKADYEK
HKVYACEVTHQGLSSPVTKSFNRGEC

>XENP025330 1C11_H3.235_L3_IgG1_PVA_/S267K Heavy Chain (SEQ ID NOS 41009-41013)
EVQLVQSGSELKKPGESVKVSCKASGYTFTHYGINWVRQPPGQGLEWMGWINTYTGEPTYAPGFTGRFVFSLDTSQSTAYLQISSLKAEDTAVYYCA
RDYYGSSPYWGQGTLVTVSS/ASTKGPSVFPLAPSSKSTSGGTAALGCLVKDYFPEPVTVSWNSGALTSGVHTFPAVLQSSGLYSLSSVVTVPSSSL
GTQTYICNVNHKPSNTKVDKKVEPKSCDKTHTCPPCPAPPVAGPSVFLFPPKPKDTLMISRTPEVTCVVVDVKHEDPEVKFNWYVDGVEVHNAKTKP
REEQYNSTYRVVSVLTVLHQDWLNGKEYKCKVSNKALPAPIEKTISKAKGQPREPQVYTLPPSREEMTKNQVSLTCLVKGFYPSDIAVEWESNGQPE
NNYKTTPPVLDSDGSFFLYSKLTVDKSRWQQGNVFSCSVMHEALHNHYTQKSLSLSPGK

>XENP025330 1C11_H3.235_L3_IgG1_PVA_/S267K Light Chain (SEQ ID NOS 41014-41018)
DVLMTQSPDSLAVSLGERATINCKSSQSIVHSNGNTYLEWYQQKPGQSPKLLIYKVSNRFSGVPDRFSGSGSGTDFTLTISSLQAEDVAVYYCFQGS
HVPNTFGGGTKVEIK/RTVAAPSVFIFPPSDEQLKSGTASVVCLLNNFYPREAKVQWKVDNALQSGNSQESVTEQDSKDSTYSLSSTLTLSKADYEK
HKVYACEVTHQGLSSPVTKSFNRGEC

>XENP025331 1C11_H3.236_L3_IgG1_PVA_/S267K Heavy Chain (SEQ ID NOS 41019-41023)
EVQLVQSGSELKKPGESVKVSCKASGYTFTHYGINWVRQPPGQGLEWMGWINTYTGEPTYAPGFTGRFVFSLDTSQDTAYLQINSLKAEDTAVYYCA
RDYYGSSPYWGQGTLVTVSS/ASTKGPSVFPLAPSSKSTSGGTAALGCLVKDYFPEPVTVSWNSGALTSGVHTFPAVLQSSGLYSLSSVVTVPSSSL
GTQTYICNVNHKPSNTKVDKKVEPKSCDKTHTCPPCPAPPVAGPSVFLFPPKPKDTLMISRTPEVTCVVVDVKHEDPEVKFNWYVDGVEVHNAKTKP
REEQYNSTYRVVSVLTVLHQDWLNGKEYKCKVSNKALPAPIEKTISKAKGQPREPQVYTLPPSREEMTKNQVSLTCLVKGFYPSDIAVEWESNGQPE
NNYKTTPPVLDSDGSFFLYSKLTVDKSRWQQGNVFSCSVMHEALHNHYTQKSLSLSPGK

>XENP025331 1C11_H3.236_L3_IgG1_PVA_/S267K Light Chain (SEQ ID NOS 41024-41028)
DVLMTQSPDSLAVSLGERATINCKSSQSIVHSNGNTYLEWYQQKPGQSPKLLIYKVSNRFSGVPDRFSGSGSGTDFTLTISSLQAEDVAVYYCFQGS
HVPNTFGGGTKVEIK/RTVAAPSVFIFPPSDEQLKSGTASVVCLLNNFYPREAKVQWKVDNALQSGNSQESVTEQDSKDSTYSLSSTLTLSKADYEK
HKVYACEVTHQGLSSPVTKSFNRGEC

>XENP025332 1C11_H3.237_L3_IgG1_PVA_/S267K Heavy Chain (SEQ ID NOS 41029-41033)
QVQLVQSGSELKKPGESVKVSCKASGYTFTHYGINWVRQAPGQGLEWMGWINTYTGEPYYAPGFTERPVFSLDTSQDTAYLQINSLKAEDTAVYYCA
RDYYGSSPYWGQGTLVTVSS/ASTKGPSVFPLAPSSKSTSGGTAALGCLVKDYFPEPVTVSWNSGALTSGVHTFPAVLQSSGLYSLSSVVTVPSSSL
GTQTYICNVNHKPSNTKVDKKVEPKSCDKTHTCPPCPAPPVAGPSVFLFPPKPKDTLMISRTPEVTCVVVDVKHEDPEVKFNWYVDGVEVHNAKTKP
REEQYNSTYRVVSVLTVLHQDWLNGKEYKCKVSNKALPAPIEKTISKAKGQPREPQVYTLPPSREEMTKNQVSLTCLVKGFYPSDIAVEWESNGQPE
NNYKTTPPVLDSDGSFFLYSKLTVDKSRWQQGNVFSCSVMHEALHNHYTQKSLSLSPGK

>XENP025332 1C11_H3.237_L3_IgG1_PVA_/S267K Light Chain (SEQ ID NOS 41034-41038)
DVLMTQSPDSLAVSLGERATINCKSSQSIVHSNGNTYLEWYQQKPGQSPKLLIYKVSNRFSGVPDRFSGSGSGTDFTLTISSLQAEDVAVYYCFQGS
HVPNTFGGGTKVEIK/RTVAAPSVFIFPPSDEQLKSGTASVVCLLNNFYPREAKVQWKVDNALQSGNSQESVTEQDSKDSTYSLSSTLTLSKADYEK
HKVYACEVTHQGLSSPVTKSFNRGEC

FIG. 16C

>XENP025333 1C11_H3.238_L3_IgG1_PVA_/S267K Heavy Chain (SEQ ID NOS 41039-41043)
QVQLVQSGSELKKPGESVKVSCKASGYTFT<u>HYGIN</u>WVRQAPGQGLEWMG<u>WINTYTGEPYYAPGFQER</u>FVFSLDTSQDTAYLQINSLKAEDTAVYYCA
RD<u>YYGSSPY</u>WGQGTLVTVSS/ASTKGPSVFPLAPSSKSTSGGTAALGCLVKDYFPEPVTVSWNSGALTSGVHTFPAVLQSSGLYSLSSVVTVPSSSL
GTQTYICNVNHKPSNTKVDKKVEPKSCDKTHTCPPCPAPPVAGPSVFLFPPKPKDTLMISRTPEVTCVVVDVKHEDPEVKFNWYVDGVEVHNAKTKP
REEQYNSTYRVVSVLTVLHQDWLNGKEYKCKVSNKALPAPIEKTISKAKGQPREPQVYTLPPSREEMTKNQVSLTCLVKGFYPSDIAVEWESNGQPE
NNYKTTPPVLDSDGSFFLYSKLTVDKSRWQQGNVFSCSVMHEALHNHYTQKSLSLSPGK

>XENP025333 1C11_H3.238_L3_IgG1_PVA_/S267K Light Chain (SEQ ID NOS 41044-41048)
DVLMTQSPDSLAVSLGERATINC<u>KSSQSIVHSNGNTYLE</u>WYQQKPGQSPKLLIY<u>KVSNRF</u>SGVPDRFSGSGSGTDFTLTISSLQAEDVAVYYC<u>FQGS
HVPNT</u>FGGGTKVEIK/RTVAAPSVFIFPPSDEQLKSGTASVVCLLNNFYPREAKVQWKVDNALQSGNSQESVTEQDSKDSTYSLSSTLTLSKADYEK
HKVYACEVTHQGLSSPVTKSFNRGEC

>XENP025334 1C11[PD-1]_H3.188_L3.144_IgG1_PVA_/S267K Heavy Chain (SEQ ID NOS 41049-41053)
QVQLVQSGSELKKPGESVKVSCKASGYTFT<u>HYGIN</u>WVRQPPGQGLEWIG<u>WINTYTGEPYYAPGFTGR</u>FVFSLDTSQSTAYLQINSLKAEDTAVYYCA
RD<u>YYGSSPY</u>WGQGTLVTVSS/ASTKGPSVFPLAPSSKSTSGGTAALGCLVKDYFPEPVTVSWNSGALTSGVHTFPAVLQSSGLYSLSSVVTVPSSSL
GTQTYICNVNHKPSNTKVDKKVEPKSCDKTHTCPPCPAPPVAGPSVFLFPPKPKDTLMISRTPEVTCVVVDVKHEDPEVKFNWYVDGVEVHNAKTKP
REEQYNSTYRVVSVLTVLHQDWLNGKEYKCKVSNKALPAPIEKTISKAKGQPREPQVYTLPPSREEMTKNQVSLTCLVKGFYPSDIAVEWESNGQPE
NNYKTTPPVLDSDGSFFLYSKLTVDKSRWQQGNVFSCSVMHEALHNHYTQKSLSLSPGK

>XENP025334 1C11[PD-1]_H3.188_L3.144_IgG1_PVA_/S267K Light Chain (SEQ ID NOS 41054-41058)
DIVMTQSPDSLAVSLGERVTINC<u>KASQSIVHSNGNTYLE</u>WYQQKPGQPPKLLIY<u>KVSNRF</u>SGVPDRFSGSGSGTDFTLTISSVEAEDAATYYC<u>FQGS
HVPNT</u>FGQGTKVEIK/RTVAAPSVFIFPPSDEQLKSGTASVVCLLNNFYPREAKVQWKVDNALQSGNSQESVTEQDSKDSTYSLSSTLTLSKADYEK
HKVYACEVTHQGLSSPVTKSFNRGEC

>XENP025335 1C11[PD-1]_H3.188_L3.148_IgG1_PVA_/S267K Heavy Chain (SEQ ID NOS 41059-41063)
QVQLVQSGSELKKPGESVKVSCKASGYTFT<u>HYGIN</u>WVRQPPGQGLEWIG<u>WINTYTGEPYYAPGFTGR</u>FVFSLDTSQSTAYLQINSLKAEDTAVYYCA
RD<u>YYGSSPY</u>WGQGTLVTVSS/ASTKGPSVFPLAPSSKSTSGGTAALGCLVKDYFPEPVTVSWNSGALTSGVHTFPAVLQSSGLYSLSSVVTVPSSSL
GTQTYICNVNHKPSNTKVDKKVEPKSCDKTHTCPPCPAPPVAGPSVFLFPPKPKDTLMISRTPEVTCVVVDVKHEDPEVKFNWYVDGVEVHNAKTKP
REEQYNSTYRVVSVLTVLHQDWLNGKEYKCKVSNKALPAPIEKTISKAKGQPREPQVYTLPPSREEMTKNQVSLTCLVKGFYPSDIAVEWESNGQPE
NNYKTTPPVLDSDGSFFLYSKLTVDKSRWQQGNVFSCSVMHEALHNHYTQKSLSLSPGK

>XENP025335 1C11[PD-1]_H3.188_L3.148_IgG1_PVA_/S267K Light Chain (SEQ ID NOS 41064-41068)
DIVMTQSPDSLAVSLGERVTINC<u>KASQSIVHSNGNTYLE</u>WYQQKPGQAPKLLIY<u>KVSNRF</u>SGVPDRFSGSGSGTDFTLTISSVEAEDAATYYC<u>FQGS
HVPNT</u>FGQGTKVEIK/RTVAAPSVFIFPPSDEQLKSGTASVVCLLNNFYPREAKVQWKVDNALQSGNSQESVTEQDSKDSTYSLSSTLTLSKADYEK
HKVYACEVTHQGLSSPVTKSFNRGEC

>XENP025336 1C11[PD-1]_H3.224_L3.144_IgG1_PVA_/S267K Heavy Chain (SEQ ID NOS 41069-41073)
QVQLVQSGPELKKPGESVKVSCKASGYTFT<u>HYGIN</u>WVRQPPGQGLEWMG<u>WINTYTGEPYYAPGFQER</u>FVFSIDTSQSTAYLQINSLKAEDTAVYYCA
RD<u>YYGSSPY</u>WGQGTLVTVSS/ASTKGPSVFPLAPSSKSTSGGTAALGCLVKDYFPEPVTVSWNSGALTSGVHTFPAVLQSSGLYSLSSVVTVPSSSL
GTQTYICNVNHKPSNTKVDKKVEPKSCDKTHTCPPCPAPPVAGPSVFLFPPKPKDTLMISRTPEVTCVVVDVKHEDPEVKFNWYVDGVEVHNAKTKP
REEQYNSTYRVVSVLTVLHQDWLNGKEYKCKVSNKALPAPIEKTISKAKGQPREPQVYTLPPSREEMTKNQVSLTCLVKGFYPSDIAVEWESNGQPE
NNYKTTPPVLDSDGSFFLYSKLTVDKSRWQQGNVFSCSVMHEALHNHYTQKSLSLSPGK

>XENP025336 1C11[PD-1]_H3.224_L3.144_IgG1_PVA_/S267K Light Chain (SEQ ID NOS 41074-41078)
DIVMTQSPDSLAVSLGERVTINC<u>KASQSIVHSNGNTYLE</u>WYQQKPGQPPKLLIY<u>KVSNRF</u>SGVPDRFSGSGSGTDFTLTISSVEAEDAATYYC<u>FQGS
HVPNT</u>FGQGTKVEIK/RTVAAPSVFIFPPSDEQLKSGTASVVCLLNNFYPREAKVQWKVDNALQSGNSQESVTEQDSKDSTYSLSSTLTLSKADYEK
HKVYACEVTHQGLSSPVTKSFNRGEC

>XENP025337 1C11[PD-1]_H3.224_L3.148_IgG1_PVA_/S267K Heavy Chain (SEQ ID NOS 41079-41083)
QVQLVQSGPELKKPGESVKVSCKASGYTFT<u>HYGIN</u>WVRQPPGQGLEWMG<u>WINTYTGEPYYAPGFQER</u>FVFSIDTSQSTAYLQINSLKAEDTAVYYCA
RD<u>YYGSSPY</u>WGQGTLVTVSS/ASTKGPSVFPLAPSSKSTSGGTAALGCLVKDYFPEPVTVSWNSGALTSGVHTFPAVLQSSGLYSLSSVVTVPSSSL
GTQTYICNVNHKPSNTKVDKKVEPKSCDKTHTCPPCPAPPVAGPSVFLFPPKPKDTLMISRTPEVTCVVVDVKHEDPEVKFNWYVDGVEVHNAKTKP
REEQYNSTYRVVSVLTVLHQDWLNGKEYKCKVSNKALPAPIEKTISKAKGQPREPQVYTLPPSREEMTKNQVSLTCLVKGFYPSDIAVEWESNGQPE
NNYKTTPPVLDSDGSFFLYSKLTVDKSRWQQGNVFSCSVMHEALHNHYTQKSLSLSPGK

>XENP025337 1C11[PD-1]_H3.224_L3.148_IgG1_PVA_/S267K Light Chain (SEQ ID NOS 41084-41088)
DIVMTQSPDSLAVSLGERVTINC<u>KASQSIVHSNGNTYLE</u>WYQQKPGQAPKLLIY<u>KVSNRF</u>SGVPDRFSGSGSGTDFTLTISSVEAEDAATYYC<u>FQGS
HVPNT</u>FGQGTKVEIK/RTVAAPSVFIFPPSDEQLKSGTASVVCLLNNFYPREAKVQWKVDNALQSGNSQESVTEQDSKDSTYSLSSTLTLSKADYEK
HKVYACEVTHQGLSSPVTKSFNRGEC

>XENP025338 1C11[PD-1]_H3.226_L3.144_IgG1_PVA_/S267K Heavy Chain (SEQ ID NOS 41089-41093)
QVQLVQSGPELKKPGESVKVSCKASGYTFT<u>HYGIN</u>WVRQAPGQGLEWMG<u>WINTYTGEPYYAPGFQER</u>FVFSLDTSQDTAYLQINSLKAEDTAVYYCA
RD<u>YYGSSPY</u>WGQGTLVTVSS/ASTKGPSVFPLAPSSKSTSGGTAALGCLVKDYFPEPVTVSWNSGALTSGVHTFPAVLQSSGLYSLSSVVTVPSSSL
GTQTYICNVNHKPSNTKVDKKVEPKSCDKTHTCPPCPAPPVAGPSVFLFPPKPKDTLMISRTPEVTCVVVDVKHEDPEVKFNWYVDGVEVHNAKTKP
REEQYNSTYRVVSVLTVLHQDWLNGKEYKCKVSNKALPAPIEKTISKAKGQPREPQVYTLPPSREEMTKNQVSLTCLVKGFYPSDIAVEWESNGQPE
NNYKTTPPVLDSDGSFFLYSKLTVDKSRWQQGNVFSCSVMHEALHNHYTQKSLSLSPGK

FIG. 16D

>XENP025338 1C11[PD-1]_H3.226_L3.144_IgG1_PVA_/S267K Light Chain (SEQ ID NOS 41094-41098)
DIVMTQSPDSLAVSLGERVTINCKASQSIVHSNGNTYLEWYQQKPGQPPKLLIYKVSNRFSGVPDRFSGSGSGTDFTLTISSVEAEDAATYYCFQGS
HVPNTFGQGTKVEIK/RTVAAPSVFIFPPSDEQLKSGTASVVCLLNNFYPREAKVQWKVDNALQSGNSQESVTEQDSKDSTYSLSSTLTLSKADYEK
HKVYACEVTHQGLSSPVTKSFNRGEC

>XENP025339 1C11[PD-1]_H3.226_L3.148_IgG1_PVA_/S267K Heavy Chain (SEQ ID NOS 41099-41103)
QVQLVQSGPELKKPGESVKVSCKASGYTFTHYGINWVRQAPGQGLEWMGWINTYTGEPYYAPGFQERFVFSLDTSQDTAYLQINSLKAEDTAVYYCA
RDYYGSSPYWGQGTLVTVSS/ASTKGPSVFPLAPSSKSTSGGTAALGCLVKDYFPEPVTVSWNSGALTSGVHTFPAVLQSSGLYSLSSVVTVPSSSL
GTQTYICNVNHKPSNTKVDKKVEPKSCDKTHTCPPCPAPPVAGPSVFLFPPKPKDTLMISRTPEVTCVVVDVKHEDPEVKFNWYVDGVEVHNAKTKP
REEQYNSTYRVVSVLTVLHQDWLNGKEYKCKVSNKALPAPIEKTISKAKGQPREPQVYTLPPSREEMTKNQVSLTCLVKGFYPSDIAVEWESNGQPE
NNYKTTPPVLDSDGSFFLYSKLTVDKSRWQQGNVFSCSVMHEALHNHYTQKSLSLSPGK

>XENP025339 1C11[PD-1]_H3.226_L3.148_IgG1_PVA_/S267K Light Chain (SEQ ID NOS 41104-41108)
DIVMTQSPDSLAVSLGERVTINCKASQSIVHSNGNTYLEWYQQKPGQAPKLLIYKVSNRFSGVPDRFSGSGSGTDFTLTISSVEAEDAATYYCFQGS
HVPNTFGQGTKVEIK/RTVAAPSVFIFPPSDEQLKSGTASVVCLLNNFYPREAKVQWKVDNALQSGNSQESVTEQDSKDSTYSLSSTLTLSKADYEK
HKVYACEVTHQGLSSPVTKSFNRGEC

>XENP025340 1C11[PD-1]_H3.188_L3_IgG1_PVA_/S267K Heavy Chain (SEQ ID NOS 41109-41113)
QVQLVQSGSELKKPGESVKVSCKASGYTFTHYGINWVRQPPGQGLEWIGWINTYTGEPYYAPGFTGRFVFSLDTSQSTAYLQINSLKAEDTAVYYCA
RDYYGSSPYWGQGTLVTVSS/ASTKGPSVFPLAPSSKSTSGGTAALGCLVKDYFPEPVTVSWNSGALTSGVHTFPAVLQSSGLYSLSSVVTVPSSSL
GTQTYICNVNHKPSNTKVDKKVEPKSCDKTHTCPPCPAPPVAGPSVFLFPPKPKDTLMISRTPEVTCVVVDVKHEDPEVKFNWYVDGVEVHNAKTKP
REEQYNSTYRVVSVLTVLHQDWLNGKEYKCKVSNKALPAPIEKTISKAKGQPREPQVYTLPPSREEMTKNQVSLTCLVKGFYPSDIAVEWESNGQPE
NNYKTTPPVLDSDGSFFLYSKLTVDKSRWQQGNVFSCSVMHEALHNHYTQKSLSLSPGK

>XENP025340 1C11[PD-1]_H3.188_L3_IgG1_PVA_/S267K Light Chain (SEQ ID NOS 41114-41118)
DVLMTQSPDSLAVSLGERATINCKSSQSIVHSNGNTYLEWYQQKPGQSPKLLIYKVSNRFSGVPDRFSGSGSGTDFTLTISSLQAEDVAVYYCFQGS
HVPNTFGGGTKVEIK/RTVAAPSVFIFPPSDEQLKSGTASVVCLLNNFYPREAKVQWKVDNALQSGNSQESVTEQDSKDSTYSLSSTLTLSKADYEK
HKVYACEVTHQGLSSPVTKSFNRGEC

>XENP025341 1C11[PD-1]_H3_L3.141_IgG1_PVA_/S267K Heavy Chain (SEQ ID NOS 41119-41123)
QIQLVQSGSELKKPGASVKVSCKASGYTFTHYGMNWVRQAPGQGLEWMGWINTYTGEPTYADGFTGRFVFSLDTSVSTAYLQISSLKAEDTAVYFCA
RDYYGSSPYWGQGTLVTVSS/ASTKGPSVFPLAPSSKSTSGGTAALGCLVKDYFPEPVTVSWNSGALTSGVHTFPAVLQSSGLYSLSSVVTVPSSSL
GTQTYICNVNHKPSNTKVDKKVEPKSCDKTHTCPPCPAPPVAGPSVFLFPPKPKDTLMISRTPEVTCVVVDVKHEDPEVKFNWYVDGVEVHNAKTKP
REEQYNSTYRVVSVLTVLHQDWLNGKEYKCKVSNKALPAPIEKTISKAKGQPREPQVYTLPPSREEMTKNQVSLTCLVKGFYPSDIAVEWESNGQPE
NNYKTTPPVLDSDGSFFLYSKLTVDKSRWQQGNVFSCSVMHEALHNHYTQKSLSLSPGK

>XENP025341 1C11[PD-1]_H3_L3.141_IgG1_PVA_/S267K Light Chain (SEQ ID NOS 41124-41128)
DIVMTQSPDSLAVSLGERATINCKASQSIVHSNGNTYLEWYQQKPGQPPKLLIYKVSNRFSGVPDRFSGSGSGTDFTLTISSVEAEDVATYYCFQGS
HVPNTFGQGTKVEIK/RTVAAPSVFIFPPSDEQLKSGTASVVCLLNNFYPREAKVQWKVDNALQSGNSQESVTEQDSKDSTYSLSSTLTLSKADYEK
HKVYACEVTHQGLSSPVTKSFNRGEC

>XENP025342 1C11[PD-1]_H3_L3.142_IgG1_PVA_/S267K Heavy Chain (SEQ ID NOS 41129-41133)
QIQLVQSGSELKKPGASVKVSCKASGYTFTHYGMNWVRQAPGQGLEWMGWINTYTGEPTYADGFTGRFVFSLDTSVSTAYLQISSLKAEDTAVYFCA
RDYYGSSPYWGQGTLVTVSS/ASTKGPSVFPLAPSSKSTSGGTAALGCLVKDYFPEPVTVSWNSGALTSGVHTFPAVLQSSGLYSLSSVVTVPSSSL
GTQTYICNVNHKPSNTKVDKKVEPKSCDKTHTCPPCPAPPVAGPSVFLFPPKPKDTLMISRTPEVTCVVVDVKHEDPEVKFNWYVDGVEVHNAKTKP
REEQYNSTYRVVSVLTVLHQDWLNGKEYKCKVSNKALPAPIEKTISKAKGQPREPQVYTLPPSREEMTKNQVSLTCLVKGFYPSDIAVEWESNGQPE
NNYKTTPPVLDSDGSFFLYSKLTVDKSRWQQGNVFSCSVMHEALHNHYTQKSLSLSPGK

>XENP025342 1C11[PD-1]_H3_L3.142_IgG1_PVA_/S267K Light Chain (SEQ ID NOS 41134-41138)
DIVMTQSPDSLAVSLGERATINCKASQSIVHSNGNTYLEWYQQKPGQAPKLLIYKVSNRFSGVPDRFSGSGSGTDFTLTISSVEAEDVATYYCFQGS
HVPNTFGQGTKVEIK/RTVAAPSVFIFPPSDEQLKSGTASVVCLLNNFYPREAKVQWKVDNALQSGNSQESVTEQDSKDSTYSLSSTLTLSKADYEK
HKVYACEVTHQGLSSPVTKSFNRGEC

>XENP025820 1C11[PD-1]_H3_L3.144_IgG1_PVA_/S267K Heavy Chain (SEQ ID NOS 41139-41143)
QIQLVQSGSELKKPGASVKVSCKASGYTFTHYGMNWVRQAPGQGLEWMGWINTYTGEPTYADGFTGRFVFSLDTSVSTAYLQISSLKAEDTAVYFCA
RDYYGSSPYWGQGTLVTVSS/ASTKGPSVFPLAPSSKSTSGGTAALGCLVKDYFPEPVTVSWNSGALTSGVHTFPAVLQSSGLYSLSSVVTVPSSSL
GTQTYICNVNHKPSNTKVDKKVEPKSCDKTHTCPPCPAPPVAGPSVFLFPPKPKDTLMISRTPEVTCVVVDVKHEDPEVKFNWYVDGVEVHNAKTKP
REEQYNSTYRVVSVLTVLHQDWLNGKEYKCKVSNKALPAPIEKTISKAKGQPREPQVYTLPPSREEMTKNQVSLTCLVKGFYPSDIAVEWESNGQPE
NNYKTTPPVLDSDGSFFLYSKLTVDKSRWQQGNVFSCSVMHEALHNHYTQKSLSLSPGK

>XENP025820 1C11[PD-1]_H3_L3.144_IgG1_PVA_/S267K Light Chain (SEQ ID NOS 41144-41148)
DIVMTQSPDSLAVSLGERVTINCKASQSIVHSNGNTYLEWYQQKPGQPPKLLIYKVSNRFSGVPDRFSGSGSGTDFTLTISSVEAEDAATYYCFQGS
HVPNTFGQGTKVEIK/RTVAAPSVFIFPPSDEQLKSGTASVVCLLNNFYPREAKVQWKVDNALQSGNSQESVTEQDSKDSTYSLSSTLTLSKADYEK
HKVYACEVTHQGLSSPVTKSFNRGEC

FIG. 16E

>XENP025821 1C11[PD-1]_H3_L3.148_IgG1_PVA_/S267K Heavy Chain (SEQ ID NOS 41149-41153)
QIQLVQSGSELKKPGASVKVSCKASGYTFT<u>HYGMN</u>WVRQAPGQGLEWMG<u>WINTYTGEPTYADGFTGR</u>FVFSLDTSVSTAYLQISSLKAEDTAVYFCA
R<u>DYYGSSPY</u>WGQGTLVTVSS/ASTKGPSVFPLAPSSKSTSGGTAALGCLVKDYFPEPVTVSWNSGALTSGVHTFPAVLQSSGLYSLSSVVTVPSSSL
GTQTYICNVNHKPSNTKVDKKVEPKSCDKTHTCPPCPAPPVAGPSVFLFPPKPKDTLMISRTPEVTCVVVDVKHEDPEVKFNWYVDGVEVHNAKTKP
REEQYNSTYRVVSVLTVLHQDWLNGKEYKCKVSNKALPAPIEKTISKAKGQPREPQVYTLPPSREEMTKNQVSLTCLVKGFYPSDIAVEWESNGQPE
NNYKTTPPVLDSDGSFFLYSKLTVDKSRWQQGNVFSCSVMHEALHNHYTQKSLSLSPGK

>XENP025821 1C11[PD-1]_H3_L3.148_IgG1_PVA_/S267K Light Chain (SEQ ID NOS 41154-41158)
DIVMTQSPDSLAVSLGERVTINC<u>KASQSIVHSNGNTYLE</u>WYQQKPGQAPKLLIY<u>KVSNRFS</u>GVPDRFSGSGSGTDFTLTISSVEAEDAATYYC<u>FQGS
HVPNT</u>FGQGTKVEIK/RTVAAPSVFIFPPSDEQLKSGTASVVCLLNNFYPREAKVQWKVDNALQSGNSQESVTEQDSKDSTYSLSSTLTLSKADYEK
HKVYACEVTHQGLSSPVTKSFNRGEC

>XENP025822 1C11[PD-1]_H3.216_L3_IgG1_PVA_/S267K Heavy Chain (SEQ ID NOS 41159-41163)
QVQLVQSGPELKKPGESVKVSCKASGYTFT<u>HYGIN</u>WVRQPPGQGLEWMG<u>WINTYTGEPYYAPGFTGR</u>FVFSIDTSQSTAYLQINSLKAEDTAVYYCA
R<u>DYYGSSPY</u>WGQGTLVTVSS/ASTKGPSVFPLAPSSKSTSGGTAALGCLVKDYFPEPVTVSWNSGALTSGVHTFPAVLQSSGLYSLSSVVTVPSSSL
GTQTYICNVNHKPSNTKVDKKVEPKSCDKTHTCPPCPAPPVAGPSVFLFPPKPKDTLMISRTPEVTCVVVDVKHEDPEVKFNWYVDGVEVHNAKTKP
REEQYNSTYRVVSVLTVLHQDWLNGKEYKCKVSNKALPAPIEKTISKAKGQPREPQVYTLPPSREEMTKNQVSLTCLVKGFYPSDIAVEWESNGQPE
NNYKTTPPVLDSDGSFFLYSKLTVDKSRWQQGNVFSCSVMHEALHNHYTQKSLSLSPGK

>XENP025822 1C11[PD-1]_H3.216_L3_IgG1_PVA_/S267K Light Chain (SEQ ID NOS 41164-41168)
DVLMTQSPDSLAVSLGERATINC<u>KSSQSIVHSNGNTYLE</u>WYQQKPGQSPKLLIY<u>KVSNRFS</u>GVPDRFSGSGSGTDFTLTISSLQAEDVAVYYC<u>FQGS
HVPNT</u>FGGGTKVEIK/RTVAAPSVFIFPPSDEQLKSGTASVVCLLNNFYPREAKVQWKVDNALQSGNSQESVTEQDSKDSTYSLSSTLTLSKADYEK
HKVYACEVTHQGLSSPVTKSFNRGEC

XENP025823 1C11[PD-1]_H3.228_L3_IgG1_PVA_/S267K Heavy Chain (SEQ ID NOS 41169-41173)
EVQLVQSGPELKKPGESVKVSCKASGYTFT<u>HYGIN</u>WVRQAPGQGLEWMG<u>WINTYTGEPYYAPGFQER</u>FVFSLDTSQDTAYLQINSLKAEDTAVYYCA
R<u>DYYGSSPY</u>WGQGTLVTVSS/ASTKGPSVFPLAPSSKSTSGGTAALGCLVKDYFPEPVTVSWNSGALTSGVHTFPAVLQSSGLYSLSSVVTVPSSSL
GTQTYICNVNHKPSNTKVDKKVEPKSCDKTHTCPPCPAPPVAGPSVFLFPPKPKDTLMISRTPEVTCVVVDVKHEDPEVKFNWYVDGVEVHNAKTKP
REEQYNSTYRVVSVLTVLHQDWLNGKEYKCKVSNKALPAPIEKTISKAKGQPREPQVYTLPPSREEMTKNQVSLTCLVKGFYPSDIAVEWESNGQPE
NNYKTTPPVLDSDGSFFLYSKLTVDKSRWQQGNVFSCSVMHEALHNHYTQKSLSLSPGK

>XENP025823 1C11[PD-1]_H3.228_L3_IgG1_PVA_/S267K Light Chain (SEQ ID NOS 41174-41178)
DVLMTQSPDSLAVSLGERATINC<u>KSSQSIVHSNGNTYLE</u>WYQQKPGQSPKLLIY<u>KVSNRFS</u>GVPDRFSGSGSGTDFTLTISSLQAEDVAVYYC<u>FQGS
HVPNT</u>FGGGTKVEIK/RTVAAPSVFIFPPSDEQLKSGTASVVCLLNNFYPREAKVQWKVDNALQSGNSQESVTEQDSKDSTYSLSSTLTLSKADYEK
HKVYACEVTHQGLSSPVTKSFNRGEC

>XENP025824 1C11[PD-1]_H3.234_L3_IgG1_PVA_/S267K Heavy Chain (SEQ ID NOS 41179-41183)
EVQLVQSGSELKKPGESVKVSCKASGYTFT<u>HYGIN</u>WVRQPPGQGLEWMG<u>WINTYTGEPYYAPGFQER</u>FVFSLDTSQDTAYLQINSLKAEDTAVYYCA
R<u>DYYGSSPY</u>WGQGTLVTVSS/ASTKGPSVFPLAPSSKSTSGGTAALGCLVKDYFPEPVTVSWNSGALTSGVHTFPAVLQSSGLYSLSSVVTVPSSSL
GTQTYICNVNHKPSNTKVDKKVEPKSCDKTHTCPPCPAPPVAGPSVFLFPPKPKDTLMISRTPEVTCVVVDVKHEDPEVKFNWYVDGVEVHNAKTKP
REEQYNSTYRVVSVLTVLHQDWLNGKEYKCKVSNKALPAPIEKTISKAKGQPREPQVYTLPPSREEMTKNQVSLTCLVKGFYPSDIAVEWESNGQPE
NNYKTTPPVLDSDGSFFLYSKLTVDKSRWQQGNVFSCSVMHEALHNHYTQKSLSLSPGK

>XENP025824 1C11[PD-1]_H3.234_L3_IgG1_PVA_/S267K Light Chain (SEQ ID NOS 41184-41188)
DVLMTQSPDSLAVSLGERATINC<u>KSSQSIVHSNGNTYLE</u>WYQQKPGQSPKLLIY<u>KVSNRFS</u>GVPDRFSGSGSGTDFTLTISSLQAEDVAVYYC<u>FQGS
HVPNT</u>FGGGTKVEIK/RTVAAPSVFIFPPSDEQLKSGTASVVCLLNNFYPREAKVQWKVDNALQSGNSQESVTEQDSKDSTYSLSSTLTLSKADYEK
HKVYACEVTHQGLSSPVTKSFNRGEC

>XENP025825 1C11[PD-1]_H3.239_L3.144_IgG1_PVA_/S267K Heavy Chain (SEQ ID NOS 41189-41193)
EVQLVQSGPELKKPGESVKVSCKASGYTFT<u>HYGIN</u>WVRQPPGQGLEWMG<u>WINTYTGEPYYAPGFQER</u>FVFSIDTSQSTAYLQINSLKAEDTAVYYCA
R<u>DYYGSSPY</u>WGQGTLVTVSS/ASTKGPSVFPLAPSSKSTSGGTAALGCLVKDYFPEPVTVSWNSGALTSGVHTFPAVLQSSGLYSLSSVVTVPSSSL
GTQTYICNVNHKPSNTKVDKKVEPKSCDKTHTCPPCPAPPVAGPSVFLFPPKPKDTLMISRTPEVTCVVVDVKHEDPEVKFNWYVDGVEVHNAKTKP
REEQYNSTYRVVSVLTVLHQDWLNGKEYKCKVSNKALPAPIEKTISKAKGQPREPQVYTLPPSREEMTKNQVSLTCLVKGFYPSDIAVEWESNGQPE
NNYKTTPPVLDSDGSFFLYSKLTVDKSRWQQGNVFSCSVMHEALHNHYTQKSLSLSPGK

>XENP025825 1C11[PD-1]_H3.239_L3.144_IgG1_PVA_/S267K Light Chain (SEQ ID NOS 41194-41198)
DIVMTQSPDSLAVSLGERVTINC<u>KASQSIVHSNGNTYLE</u>WYQQKPGQPPKLLIY<u>KVSNRFS</u>GVPDRFSGSGSGTDFTLTISSVEAEDAATYYC<u>FQGS
HVPNT</u>FGQGTKVEIK/RTVAAPSVFIFPPSDEQLKSGTASVVCLLNNFYPREAKVQWKVDNALQSGNSQESVTEQDSKDSTYSLSSTLTLSKADYEK
HKVYACEVTHQGLSSPVTKSFNRGEC

>XENP025826 1C11[PD-1]_H3.240_L3.144_IgG1_PVA_/S267K Heavy Chain (SEQ ID NOS 41199-41203)
QVQLVQSGPELKKPGESVKVSCKASGYTFT<u>HYGIN</u>WVRQPPGQGLEWMG<u>WINTYTGEPYYAPGFQER</u>FVFSIDTSQDTAYLQINSLKAEDTAVYYCA
R<u>DYYGSSPY</u>WGQGTLVTVSS/ASTKGPSVFPLAPSSKSTSGGTAALGCLVKDYFPEPVTVSWNSGALTSGVHTFPAVLQSSGLYSLSSVVTVPSSSL
GTQTYICNVNHKPSNTKVDKKVEPKSCDKTHTCPPCPAPPVAGPSVFLFPPKPKDTLMISRTPEVTCVVVDVKHEDPEVKFNWYVDGVEVHNAKTKP
REEQYNSTYRVVSVLTVLHQDWLNGKEYKCKVSNKALPAPIEKTISKAKGQPREPQVYTLPPSREEMTKNQVSLTCLVKGFYPSDIAVEWESNGQPE
NNYKTTPPVLDSDGSFFLYSKLTVDKSRWQQGNVFSCSVMHEALHNHYTQKSLSLSPGK

FIG. 16F

>XENP025826 1C11[PD-1]_H3.240_L3.144_IgG1_PVA_/S267K Light Chain (SEQ ID NOS 41204-41208)
DIVMTQSPDSLAVSLGERVTINCKASQSIVHSNGNTYLEWYQQKPGQPPKLLIYKVSNRFSGVPDRFSGSGSGTDFTLTISSVEAEDAATYYCFQGS
HVPNTFGQGTKVEIK/RTVAAPSVFIFPPSDEQLKSGTASVVCLLNNFYPREAKVQWKVDNALQSGNSQESVTEQDSKDSTYSLSSTLTLSKADYEK
HKVYACEVTHQGLSSPVTKSFNRGEC

>XENP025827 1C11[PD-1]_H3.241_L3.144_IgG1_PVA_/S267K Heavy Chain (SEQ ID NOS 41209-41213)
EVQLVQSGPELKKPGESVKVSCKASGYTFTHYGINWVRQPPGQGLEWMGWINTYTGEPYYAPGFQERFVFSIDTSQDTAYLQINSLKAEDTAVYYCA
RDYYGSSPYWGQGTLVTVSS/ASTKGPSVFPLAPSSKSTSGGTAALGCLVKDYFPEPVTVSWNSGALTSGVHTFPAVLQSSGLYSLSSVVTVPSSSL
GTQTYICNVNHKPSNTKVDKKVEPKSCDKTHTCPPCPAPPVAGPSVFLFPPKPKDTLMISRTPEVTCVVVDVKHEDPEVKFNWYVDGVEVHNAKTKP
REEQYNSTYRVVSVLTVLHQDWLNGKEYKCKVSNKALPAPIEKTISKAKGQPREPQVYTLPPSREEMTKNQVSLTCLVKGFYPSDIAVEWESNGQPE
NNYKTTPPVLDSDGSFFLYSKLTVDKSRWQQGNVFSCSVMHEALHNHYTQKSLSLSPGK

>XENP025827 1C11[PD-1]_H3.241_L3.144_IgG1_PVA_/S267K Light Chain (SEQ ID NOS 41214-41218)
DIVMTQSPDSLAVSLGERVTINCKASQSIVHSNGNTYLEWYQQKPGQPPKLLIYKVSNRFSGVPDRFSGSGSGTDFTLTISSVEAEDAATYYCFQGS
HVPNTFGQGTKVEIK/RTVAAPSVFIFPPSDEQLKSGTASVVCLLNNFYPREAKVQWKVDNALQSGNSQESVTEQDSKDSTYSLSSTLTLSKADYEK
HKVYACEVTHQGLSSPVTKSFNRGEC

>XENP025828 1C11[PD-1]_H3.239_L3.148_IgG1_PVA_/S267K Heavy Chain (SEQ ID NOS 41219-41223)
EVQLVQSGPELKKPGESVKVSCKASGYTFTHYGINWVRQPPGQGLEWMGWINTYTGEPYYAPGFQERFVFSIDTSQSTAYLQINSLKAEDTAVYYCA
RDYYGSSPYWGQGTLVTVSS/ASTKGPSVFPLAPSSKSTSGGTAALGCLVKDYFPEPVTVSWNSGALTSGVHTFPAVLQSSGLYSLSSVVTVPSSSL
GTQTYICNVNHKPSNTKVDKKVEPKSCDKTHTCPPCPAPPVAGPSVFLFPPKPKDTLMISRTPEVTCVVVDVKHEDPEVKFNWYVDGVEVHNAKTKP
REEQYNSTYRVVSVLTVLHQDWLNGKEYKCKVSNKALPAPIEKTISKAKGQPREPQVYTLPPSREEMTKNQVSLTCLVKGFYPSDIAVEWESNGQPE
NNYKTTPPVLDSDGSFFLYSKLTVDKSRWQQGNVFSCSVMHEALHNHYTQKSLSLSPGK

>XENP025828 1C11[PD-1]_H3.239_L3.148_IgG1_PVA_/S267K Light Chain (SEQ ID NOS 41224-41228)
DIVMTQSPDSLAVSLGERVTINCKASQSIVHSNGNTYLEWYQQKPGQAPKLLIYKVSNRFSGVPDRFSGSGSGTDFTLTISSVEAEDAATYYCFQGS
HVPNTFGQGTKVEIK/RTVAAPSVFIFPPSDEQLKSGTASVVCLLNNFYPREAKVQWKVDNALQSGNSQESVTEQDSKDSTYSLSSTLTLSKADYEK
HKVYACEVTHQGLSSPVTKSFNRGEC

>XENP025829 1C11[PD-1]_H3.240_L3.148_IgG1_PVA_/S267K Heavy Chain (SEQ ID NOS 41229-41233)
QVQLVQSGPELKKPGESVKVSCKASGYTFTHYGINWVRQPPGQGLEWMGWINTYTGEPYYAPGFQERFVFSIDTSQDTAYLQINSLKAEDTAVYYCA
RDYYGSSPYWGQGTLVTVSS/ASTKGPSVFPLAPSSKSTSGGTAALGCLVKDYFPEPVTVSWNSGALTSGVHTFPAVLQSSGLYSLSSVVTVPSSSL
GTQTYICNVNHKPSNTKVDKKVEPKSCDKTHTCPPCPAPPVAGPSVFLFPPKPKDTLMISRTPEVTCVVVDVKHEDPEVKFNWYVDGVEVHNAKTKP
REEQYNSTYRVVSVLTVLHQDWLNGKEYKCKVSNKALPAPIEKTISKAKGQPREPQVYTLPPSREEMTKNQVSLTCLVKGFYPSDIAVEWESNGQPE
NNYKTTPPVLDSDGSFFLYSKLTVDKSRWQQGNVFSCSVMHEALHNHYTQKSLSLSPGK

>XENP025829 1C11[PD-1]_H3.240_L3.148_IgG1_PVA_/S267K Light Chain (SEQ ID NOS 41234-41238)
DIVMTQSPDSLAVSLGERVTINCKASQSIVHSNGNTYLEWYQQKPGQAPKLLIYKVSNRFSGVPDRFSGSGSGTDFTLTISSVEAEDAATYYCFQGS
HVPNTFGQGTKVEIK/RTVAAPSVFIFPPSDEQLKSGTASVVCLLNNFYPREAKVQWKVDNALQSGNSQESVTEQDSKDSTYSLSSTLTLSKADYEK
HKVYACEVTHQGLSSPVTKSFNRGEC

>XENP025830 1C11[PD-1]_H3.241_L3.148_IgG1_PVA_/S267K Heavy Chain (SEQ ID NOS 41239-41243)
EVQLVQSGPELKKPGESVKVSCKASGYTFTHYGINWVRQPPGQGLEWMGWINTYTGEPYYAPGFQERFVFSIDTSQDTAYLQINSLKAEDTAVYYCA
RDYYGSSPYWGQGTLVTVSS/ASTKGPSVFPLAPSSKSTSGGTAALGCLVKDYFPEPVTVSWNSGALTSGVHTFPAVLQSSGLYSLSSVVTVPSSSL
GTQTYICNVNHKPSNTKVDKKVEPKSCDKTHTCPPCPAPPVAGPSVFLFPPKPKDTLMISRTPEVTCVVVDVKHEDPEVKFNWYVDGVEVHNAKTKP
REEQYNSTYRVVSVLTVLHQDWLNGKEYKCKVSNKALPAPIEKTISKAKGQPREPQVYTLPPSREEMTKNQVSLTCLVKGFYPSDIAVEWESNGQPE
NNYKTTPPVLDSDGSFFLYSKLTVDKSRWQQGNVFSCSVMHEALHNHYTQKSLSLSPGK

>XENP025830 1C11[PD-1]_H3.241_L3.148_IgG1_PVA_/S267K Light Chain (SEQ ID NOS 41244-41248)
DIVMTQSPDSLAVSLGERVTINCKASQSIVHSNGNTYLEWYQQKPGQAPKLLIYKVSNRFSGVPDRFSGSGSGTDFTLTISSVEAEDAATYYCFQGS
HVPNTFGQGTKVEIK/RTVAAPSVFIFPPSDEQLKSGTASVVCLLNNFYPREAKVQWKVDNALQSGNSQESVTEQDSKDSTYSLSSTLTLSKADYEK
HKVYACEVTHQGLSSPVTKSFNRGEC

>XENP025831 1C11[PD-1]_H3.216_L3.144_IgG1_PVA_/S267K Heavy Chain (SEQ ID NOS 41249-41253)
QVQLVQSGPELKKPGESVKVSCKASGYTFTHYGINWVRQPPGQGLEWMGWINTYTGEPYYAPGFTGRFVFSIDTSQSTAYLQINSLKAEDTAVYYCA
RDYYGSSPYWGQGTLVTVSS/ASTKGPSVFPLAPSSKSTSGGTAALGCLVKDYFPEPVTVSWNSGALTSGVHTFPAVLQSSGLYSLSSVVTVPSSSL
GTQTYICNVNHKPSNTKVDKKVEPKSCDKTHTCPPCPAPPVAGPSVFLFPPKPKDTLMISRTPEVTCVVVDVKHEDPEVKFNWYVDGVEVHNAKTKP
REEQYNSTYRVVSVLTVLHQDWLNGKEYKCKVSNKALPAPIEKTISKAKGQPREPQVYTLPPSREEMTKNQVSLTCLVKGFYPSDIAVEWESNGQPE
NNYKTTPPVLDSDGSFFLYSKLTVDKSRWQQGNVFSCSVMHEALHNHYTQKSLSLSPGK

>XENP025831 1C11[PD-1]_H3.216_L3.144_IgG1_PVA_/S267K Light Chain (SEQ ID NOS 41254-41258)
DIVMTQSPDSLAVSLGERVTINCKASQSIVHSNGNTYLEWYQQKPGQPPKLLIYKVSNRFSGVPDRFSGSGSGTDFTLTISSVEAEDAATYYCFQGS
HVPNTFGQGTKVEIK/RTVAAPSVFIFPPSDEQLKSGTASVVCLLNNFYPREAKVQWKVDNALQSGNSQESVTEQDSKDSTYSLSSTLTLSKADYEK
HKVYACEVTHQGLSSPVTKSFNRGEC

FIG. 16G

>XENP025832 1C11[PD-1]_H3.216_L3.148_IgG1_PVA_/S267K Heavy Chain (SEQ ID NOS 41259-41263)
QVQLVQSGPELKKPGESVKVSCKASGYTFT<u>HYGIN</u>WVRQPPGQGLEWMG<u>WINTYTGEPYYAPGFTG</u>RFVFSIDTSQDTAYLQINSLKAEDTAVYYCA
R<u>DYYGSSPYW</u>GQGTLVTVSS/ASTKGPSVFPLAPSSKSTSGGTAALGCLVKDYFPEPVTVSWNSGALTSGVHTFPAVLQSSGLYSLSSVVTVPSSSL
GTQTYICNVNHKPSNTKVDKKVEPKSCDKTHTCPPCPAPPVAGPSVFLFPPKPKDTLMISRTPEVTCVVVDVKHEDPEVKFNWYVDGVEVHNAKTKP
REEQYNSTYRVVSVLTVLHQDWLNGKEYKCKVSNKALPAPIEKTISKAKGQPREPQVYTLPPSREEMTKNQVSLTCLVKGFYPSDIAVEWESNGQPE
NNYKTTPPVLDSDGSFFLYSKLTVDKSRWQQGNVFSCSVMHEALHNHYTQKSLSLSPGK

>XENP025832 1C11[PD-1]_H3.216_L3.148_IgG1_PVA_/S267K Light Chain (SEQ ID NOS 41264-41268)
DIVMTQSPDSLAVSLGERVTINC<u>KASQSIVHSNGNTYLE</u>WYQQKPGQAPKLLIY<u>KVSNRF</u>SGVPDRFSGSGSGTDFTLTISSVEAEDAATYYC<u>FQGS
HVPNT</u>FGQGTKVEIK/RTVAAPSVFIFPPSDEQLKSGTASVVCLLNNFYPREAKVQWKVDNALQSGNSQESVTEQDSKDSTYSLSSTLTLSKADYEK
HKVYACEVTHQGLSSPVTKSFNRGEC

>XENP025833 1C11[PD-1]_H3.228_L3.144_IgG1_PVA_/S267K Heavy Chain (SEQ ID NOS 41269-41273)
EVQLVQSGPELKKPGESVKVSCKASGYTFT<u>HYGIN</u>WVRQAPGQGLEWMG<u>WINTYTGEPYYAPGFQE</u>RFVFSLDTSQDTAYLQINSLKAEDTAVYYCA
R<u>DYYGSSPYW</u>GQGTLVTVSS/ASTKGPSVFPLAPSSKSTSGGTAALGCLVKDYFPEPVTVSWNSGALTSGVHTFPAVLQSSGLYSLSSVVTVPSSSL
GTQTYICNVNHKPSNTKVDKKVEPKSCDKTHTCPPCPAPPVAGPSVFLFPPKPKDTLMISRTPEVTCVVVDVKHEDPEVKFNWYVDGVEVHNAKTKP
REEQYNSTYRVVSVLTVLHQDWLNGKEYKCKVSNKALPAPIEKTISKAKGQPREPQVYTLPPSREEMTKNQVSLTCLVKGFYPSDIAVEWESNGQPE
NNYKTTPPVLDSDGSFFLYSKLTVDKSRWQQGNVFSCSVMHEALHNHYTQKSLSLSPGK

>XENP025833 1C11[PD-1]_H3.228_L3.144_IgG1_PVA_/S267K Light Chain (SEQ ID NOS 41274-41278)
DIVMTQSPDSLAVSLGERVTINC<u>KASQSIVHSNGNTYLE</u>WYQQKPGQPPKLLIY<u>KVSNRF</u>SGVPDRFSGSGSGTDFTLTISSVEAEDAATYYC<u>FQGS
HVPNT</u>FGQGTKVEIK/RTVAAPSVFIFPPSDEQLKSGTASVVCLLNNFYPREAKVQWKVDNALQSGNSQESVTEQDSKDSTYSLSSTLTLSKADYEK
HKVYACEVTHQGLSSPVTKSFNRGEC

>XENP025834 1C11[PD-1]_H3.228_L3.148_IgG1_PVA_/S267K Heavy Chain (SEQ ID NOS 41279-41283)
EVQLVQSGPELKKPGESVKVSCKASGYTFT<u>HYGIN</u>WVRQAPGQGLEWMG<u>WINTYTGEPYYAPGFQE</u>RFVFSLDTSQDTAYLQINSLKAEDTAVYYCA
R<u>DYYGSSPYW</u>GQGTLVTVSS/ASTKGPSVFPLAPSSKSTSGGTAALGCLVKDYFPEPVTVSWNSGALTSGVHTFPAVLQSSGLYSLSSVVTVPSSSL
GTQTYICNVNHKPSNTKVDKKVEPKSCDKTHTCPPCPAPPVAGPSVFLFPPKPKDTLMISRTPEVTCVVVDVKHEDPEVKFNWYVDGVEVHNAKTKP
REEQYNSTYRVVSVLTVLHQDWLNGKEYKCKVSNKALPAPIEKTISKAKGQPREPQVYTLPPSREEMTKNQVSLTCLVKGFYPSDIAVEWESNGQPE
NNYKTTPPVLDSDGSFFLYSKLTVDKSRWQQGNVFSCSVMHEALHNHYTQKSLSLSPGK

>XENP025834 1C11[PD-1]_H3.228_L3.148_IgG1_PVA_/S267K Light Chain (SEQ ID NOS 41284-41288)
DIVMTQSPDSLAVSLGERVTINC<u>KASQSIVHSNGNTYLE</u>WYQQKPGQAPKLLIY<u>KVSNRF</u>SGVPDRFSGSGSGTDFTLTISSVEAEDAATYYC<u>FQGS
HVPNT</u>FGQGTKVEIK/RTVAAPSVFIFPPSDEQLKSGTASVVCLLNNFYPREAKVQWKVDNALQSGNSQESVTEQDSKDSTYSLSSTLTLSKADYEK
HKVYACEVTHQGLSSPVTKSFNRGEC

XENP025835 1C11[PD-1]_H3.234_L3.144_IgG1_PVA_/S267K Heavy Chain (SEQ ID NOS 41289-41293)
EVQLVQSGSELKKPGESVKVSCKASGYTFT<u>HYGIN</u>WVRQPPGQGLEWMG<u>WINTYTGEPYYAPGFQE</u>RFVFSLDTSQDTAYLQINSLKAEDTAVYYCA
R<u>DYYGSSPYW</u>GQGTLVTVSS/ASTKGPSVFPLAPSSKSTSGGTAALGCLVKDYFPEPVTVSWNSGALTSGVHTFPAVLQSSGLYSLSSVVTVPSSSL
GTQTYICNVNHKPSNTKVDKKVEPKSCDKTHTCPPCPAPPVAGPSVFLFPPKPKDTLMISRTPEVTCVVVDVKHEDPEVKFNWYVDGVEVHNAKTKP
REEQYNSTYRVVSVLTVLHQDWLNGKEYKCKVSNKALPAPIEKTISKAKGQPREPQVYTLPPSREEMTKNQVSLTCLVKGFYPSDIAVEWESNGQPE
NNYKTTPPVLDSDGSFFLYSKLTVDKSRWQQGNVFSCSVMHEALHNHYTQKSLSLSPGK

>XENP025835 1C11[PD-1]_H3.234_L3.144_IgG1_PVA_/S267K Light Chain (SEQ ID NOS 41294-41298)
DIVMTQSPDSLAVSLGERVTINC<u>KASQSIVHSNGNTYLE</u>WYQQKPGQPPKLLIY<u>KVSNRF</u>SGVPDRFSGSGSGTDFTLTISSVEAEDAATYYC<u>FQGS
HVPNT</u>FGQGTKVEIK/RTVAAPSVFIFPPSDEQLKSGTASVVCLLNNFYPREAKVQWKVDNALQSGNSQESVTEQDSKDSTYSLSSTLTLSKADYEK
HKVYACEVTHQGLSSPVTKSFNRGEC

>XENP025836 1C11[PD-1]_H3.234_L3.148_IgG1_PVA_/S267K Heavy Chain (SEQ ID NOS 41299-41303)
EVQLVQSGSELKKPGESVKVSCKASGYTFT<u>HYGIN</u>WVRQFPGQGLEWMG<u>WINTYTGEPYYAPGFQE</u>RFVFSLDTSQDTAYLQINSLKAEDTAVYYCA
R<u>DYYGSSPYW</u>GQGTLVTVSS/ASTKGPSVFPLAPSSKSTSGGTAALGCLVKDYFPEPVTVSWNSGALTSGVHTFPAVLQSSGLYSLSSVVTVPSSSL
GTQTYICNVNHKPSNTKVDKKVEPKSCDKTHTCPPCPAPPVAGPSVFLFPPKPKDTLMISRTPEVTCVVVDVKHEDPEVKFNWYVDGVEVHNAKTKP
REEQYNSTYRVVSVLTVLHQDWLNGKEYKCKVSNKALPAPIEKTISKAKGQPREPQVYTLPPSREEMTKNQVSLTCLVKGFYPSDIAVEWESNGQPE
NNYKTTPPVLDSDGSFFLYSKLTVDKSRWQQGNVFSCSVMHEALHNHYTQKSLSLSPGK

>XENP025836 1C11[PD-1]_H3.234_L3.148_IgG1_PVA_/S267K Light Chain (SEQ ID NOS 41304-41308)
DIVMTQSPDSLAVSLGERVTINC<u>KASQSIVHSNGNTYLE</u>WYQQKPGQAPKLLIY<u>KVSNRF</u>SGVPDRFSGSGSGTDFTLTISSVEAEDAATYYC<u>FQGS
HVPNT</u>FGQGTKVEIK/RTVAAPSVFIFPPSDEQLKSGTASVVCLLNNFYPREAKVQWKVDNALQSGNSQESVTEQDSKDSTYSLSSTLTLSKADYEK
HKVYACEVTHQGLSSPVTKSFNRGEC

>XENP025837 1C11[PD-1]_H3.239_L3.125_IgG1_PVA_/S267K Heavy Chain (SEQ ID NOS 41309-41313)
EVQLVQSGPELKKPGESVKVSCKASGYTFT<u>HYGIN</u>WVRQPPGQGLEWMG<u>WINTYTGEPYYAPGFQE</u>RFVFSIDTSQDTAYLQINSLKAEDTAVYYCA
R<u>DYYGSSPYW</u>GQGTLVTVSS/ASTKGPSVFPLAPSSKSTSGGTAALGCLVKDYFPEPVTVSWNSGALTSGVHTFPAVLQSSGLYSLSSVVTVPSSSL
GTQTYICNVNHKPSNTKVDKKVEPKSCDKTHTCPPCPAPPVAGPSVFLFPPKPKDTLMISRTPEVTCVVVDVKHEDPEVKFNWYVDGVEVHNAKTKP
REEQYNSTYRVVSVLTVLHQDWLNGKEYKCKVSNKALPAPIEKTISKAKGQPREPQVYTLPPSREEMTKNQVSLTCLVKGFYPSDIAVEWESNGQPE
NNYKTTPPVLDSDGSFFLYSKLTVDKSRWQQGNVFSCSVMHEALHNHYTQKSLSLSPGK

FIG. 16H

>XENP025837 1C11[PD-1]_H3.239_L3.125_IgG1_PVA_/S267K Light Chain (SEQ ID NOS 41314-41318)
DVLMTQSPDSLAVSLGERATINCKSSQSIVHSNGNTYLEWYQQKPGQSPKLLIYKVSNRFSGVPDRFSGSGSGTDFTLTISSVEAEDVAVYYCFQGS
HVPNTFGGGTKVEIK/RTVAAPSVFIFPPSDEQLKSGTASVVCLLNNFYPREAKVQWKVDNALQSGNSQESVTEQDSKDSTYSLSSTLTLSKADYEK
HKVYACEVTHQGLSSPVTKSFNRGEC >XENP025838 1C11[PD-1]_H3.240_L3.125_IgG1_PVA_/S267K Heavy Chain (SEQ ID NOS 41319-41323)
QVQLVQSGPELKKPGESVKVSCKASGYTFTHYGINWVRQPPGQGLEWMGWINTYTGEPYYAPGFQERFVFSIDTSQDTAYLQINSLKAEDTAVYYCA
RDYYGSSPYWGQGTLVTVSS/ASTKGPSVFPLAPSSKSTSGGTAALGCLVKDYFPEPVTVSWNSGALTSGVHTFPAVLQSSGLYSLSSVVTVPSSSL
GTQTYICNVNHKPSNTKVDKKVEPKSCDKTHTCPPCPAPPVAGPSVFLFPPKPKDTLMISRTPEVTCVVVDVKHEDPEVKFNWYVDGVEVHNAKTKP
REEQYNSTYRVVSVLTVLHQDWLNGKEYKCKVSNKALPAPIEKTISKAKGQPREPQVYTLPPSREEMTKNQVSLTCLVKGFYPSDIAVEWESNGQPE
NNYKTTPPVLDSDGSFFLYSKLTVDKSRWQQGNVFSCSVMHEALHNHYTQKSLSLSPGK >XENP025838 1C11[PD-1]_H3.240_L3.125_IgG1_PVA_/S267K Light Chain (SEQ ID NOS 41324-41328)
DVLMTQSPDSLAVSLGERATINCKSSQSIVHSNGNTYLEWYQQKPGQSPKLLIYKVSNRFSGVPDRFSGSGSGTDFTLTISSVEAEDVAVYYCFQGS
HVPNTFGGGTKVEIK/RTVAAPSVFIFPPSDEQLKSGTASVVCLLNNFYPREAKVQWKVDNALQSGNSQESVTEQDSKDSTYSLSSTLTLSKADYEK
HKVYACEVTHQGLSSPVTKSFNRGEC >XENP025839 1C11[PD-1]_H3.241_L3.125_IgG1_PVA_/S267K Heavy Chain (SEQ ID NOS 41329-41333)
EVQLVQSGPELKKPGESVKVSCKASGYTFTHYGINWVRQPPGQGLEWMGWINTYTGEPYYAPGFQERFVFSIDTSQDTAYLQINSLKAEDTAVYYCA
RDYYGSSPYWGQGTLVTVSS/ASTKGPSVFPLAPSSKSTSGGTAALGCLVKDYFPEPVTVSWNSGVHTFPAVLQSSGLYSLSSVVTVPSSSL
GTQTYICNVNHKPSNTKVDKKVEPKSCDKTHTCPPCPAPPVAGPSVFLFPPKPKDTLMISRTPEVTCVVVDVKHEDPEVKFNWYVDGVEVHNAKTKP
REEQYNSTYRVVSVLTVLHQDWLNGKEYKCKVSNKALPAPIEKTISKAKGQPREPQVYTLPPSREEMTKNQVSLTCLVKGFYPSDIAVEWESNGQPE
NNYKTTPPVLDSDGSFFLYSKLTVDKSRWQQGNVFSCSVMHEALHNHYTQKSLSLSPGK >XENP025839 1C11[PD-1]_H3.241_L3.125_IgG1_PVA_/S267K Light Chain (SEQ ID NOS 41334-41338)
DVLMTQSPDSLAVSLGERATINCKSSQSIVHSNGNTYLEWYQQKPGQSPKLLIYKVSNRFSGVPDRFSGSGSGTDFTLTISSVEAEDVAVYYCFQGS
HVPNTFGGGTKVEIK/RTVAAPSVFIFPPSDEQLKSGTASVVCLLNNFYPREAKVQWKVDNALQSGNSQESVTEQDSKDSTYSLSSTLTLSKADYEK
HKVYACEVTHQGLSSPVTKSFNRGEC >XENP025840 1C11[PD-1]_H3.239_L3.92_IgG1_PVA_/S267K Heavy Chain (SEQ ID NOS 41339-41343)
EVQLVQSGPELKKPGESVKVSCKASGYTFTHYGINWVRQPPGQGLEWMGWINTYTGEPYYAPGFQERFVFSIDTSQDTAYLQINSLKAEDTAVYYCA
RDYYGSSPYWGQGTLVTVSS/ASTKGPSVFPLAPSSKSTSGGTAALGCLVKDYFPEPVTVSWNSGALTSGVHTFPAVLQSSGLYSLSSVVTVPSSSL
GTQTYICNVNHKPSNTKVDKKVEPKSCDKTHTCPPCPAPPVAGPSVFLFPPKPKDTLMISRTPEVTCVVVDVKHEDPEVKFNWYVDGVEVHNAKTKP
REEQYNSTYRVVSVLTVLHQDWLNGKEYKCKVSNKALPAPIEKTISKAKGQPREPQVYTLPPSREEMTKNQVSLTCLVKGFYPSDIAVEWESNGQPE
NNYKTTPPVLDSDGSFFLYSKLTVDKSRWQQGNVFSCSVMHEALHNHYTQKSLSLSPGK >XENP025840 1C11[PD-1]_H3.239_L3.92_IgG1_PVA_/S267K Light Chain (SEQ ID NOS 41344-41348)
DIVMTQSPDSLAVSLGERVTINCKASQSIVHSNGNTYLEWYQQKPGQPPKLLIYKVSNRFTGVPDRFSGSGSGTDFTLTISSLQAEDVAVYYCFQGS
HVPNTFGGGTKVEIK/RTVAAPSVFIFPPSDEQLKSGTASVVCLLNNFYPREAKVQWKVDNALQSGNSQESVTEQDSKDSTYSLSSTLTLSKADYEK
HKVYACEVTHQGLSSPVTKSFNRGEC >XENP025841 1C11[PD-1]_H3.240_L3.92_IgG1_PVA_/S267K Heavy Chain (SEQ ID NOS 41349-41353)
QVQLVQSGPELKKPGESVKVSCKASGYTFTHYGINWVRQPPGQGLEWMGWINTYTGEPYYAPGFQERFVFSIDTSQDTAYLQINSLKAEDTAVYYCA
RDYYGSSPYWGQGTLVTVSS/ASTKGPSVFPLAPSSKSTSGGTAALGCLVKDYFPEPVTVSWNSGALTSGVHTFPAVLQSSGLYSLSSVVTVPSSSL
GTQTYICNVNHKPSNTKVDKKVEPKSCDKTHTCPPCPAPPVAGPSVFLFPPKPKDTLMISRTPEVTCVVVDVKHEDPEVKFNWYVDGVEVHNAKTKP
REEQYNSTYRVVSVLTVLHQDWLNGKEYKCKVSNKALPAPIEKTISKAKGQPREPQVYTLPPSREEMTKNQVSLTCLVKGFYPSDIAVEWESNGQPE
NNYKTTPPVLDSDGSFFLYSKLTVDKSRWQQGNVFSCSVMHEALHNHYTQKSLSLSPGK >XENP025841 1C11[PD-1]_H3.240_L3.92_IgG1_PVA_/S267K Light Chain (SEQ ID NOS 41354-41358)
DIVMTQSPDSLAVSLGERVTINCKASQSIVHSNGNTYLEWYQQKPGQPPKLLIYKVSNRFTGVPDRFSGSGSGTDFTLTISSLQAEDVAVYYCFQGS
HVPNTFGGGTKVEIK/RTVAAPSVFIFPPSDEQLKSGTASVVCLLNNFYPREAKVQWKVDNALQSGNSQESVTEQDSKDSTYSLSSTLTLSKADYEK
HKVYACEVTHQGLSSPVTKSFNRGEC >XENP025842 1C11[PD-1]_H3.241_L3.92_IgG1_PVA_/S267K Heavy Chain (SEQ ID NOS 41359-41363)
EVQLVQSGPELKKPGESVKVSCKASGYTFTHYGINWVRQPPGQGLEWMGWINTYTGEPYYAPGFQERFVFSIDTSQDTAYLQINSLKAEDTAVYYCA
RDYYGSSPYWGQGTLVTVSS/ASTKGPSVFPLAPSSKSTSGGTAALGCLVKDYFPEPVTVSWNSGALTSGVHTFPAVLQSSGLYSLSSVVTVPSSSL
GTQTYICNVNHKPSNTKVDKKVEPKSCDKTHTCPPCPAPPVAGPSVFLFPPKPKDTLMISRTPEVTCVVVDVKHEDPEVKFNWYVDGVEVHNAKTKP
REEQYNSTYRVVSVLTVLHQDWLNGKEYKCKVSNKALPAPIEKTISKAKGQPREPQVYTLPPSREEMTKNQVSLTCLVKGFYPSDIAVEWESNGQPE
NNYKTTPPVLDSDGSFFLYSKLTVDKSRWQQGNVFSCSVMHEALHNHYTQKSLSLSPGK >XENP025842 1C11[PD-1]_H3.241_L3.92_IgG1_PVA_/S267K Light Chain (SEQ ID NOS 41364-41368)
DIVMTQSPDSLAVSLGERVTINCKASQSIVHSNGNTYLEWYQQKPGQPPKLLIYKVSNRFTGVPDRFSGSGSGTDFTLTISSLQAEDVAVYYCFQGS
HVPNTFGGGTKVEIK/RTVAAPSVFIFPPSDEQLKSGTASVVCLLNNFYPREAKVQWKVDNALQSGNSQESVTEQDSKDSTYSLSSTLTLSKADYEK
HKVYACEVTHQGLSSPVTKSFNRGEC

FIG. 17A

| XENP | Variant Name | K$_D$ (M) | k$_a$ (1/Ms) | k$_d$ (1/s) | VH Variants | VL Variants | T$_m$ (°C) |
|---|---|---|---|---|---|---|---|
| 22538 (22553) | 1C11_H3_L3 | 1.84E-08 | 2.14E+05 | 3.93E-03 | | | 53.5 |
| 23577 | 1C11_H3_L3.1 | 9.95E-09 | 2.40E+05 | 2.38E-03 | | V2I | 53.5 |
| 23579 | 1C11_H3_L3.3 | 1.54E-08 | 1.74E+05 | 2.68E-03 | | L3V | 54.5 |
| 23589 | 1C11_H3_L3.15 | 1.50E-08 | 2.45E+05 | 3.67E-03 | | A12S | 53.5 |
| 23601 | 1C11_H3_L3.23 | 3.87E-08 | 1.26E+05 | 4.90E-03 | | A19V | 54 |
| 23605 | 1C11_H3_L3.28 | 1.57E-08 | 2.16E+05 | 3.39E-03 | | K24R | 53.5 |
| 23609 | 1C11_H3_L3.32 | 2.20E-08 | 2.90E+05 | 6.37E-03 | | S25A | 54 |
| 24201 | 1C11_H3_L3.113 | 1.98E-08 | 1.98E+05 | 3.92E-03 | | Q48K | 54 |
| 23615 | 1C11_H3_L3.46 | 1.88E-08 | 2.51E+05 | 4.73E-03 | | S49P | 54 |
| 23616 | 1C11_H3_L3.47 | 1.21E-08 | 4.26E+05 | 5.14E-03 | | S49A | 54 |
| 23624 | 1C11_H3_L3.57 | 1.45E-08 | 2.55E+05 | 3.68E-03 | | S62T | 53.5 |
| 24207 | 1C11_H3_L3.122 | 1.16E-09 | 5.68E+05 | 6.61E-04 | | V64I | 53.5 |
| 24208 | 1C11_H3_L3.124 | 1.62E-08 | 1.80E+05 | 2.92E-03 | | D66A | 53.5 |
| 23626 | 1C11_H3_L3.59 | 1.03E-08 | 3.41E+05 | 3.52E-03 | | S83R | 53 |
| 23628 | 1C11_H3_L3.62 | 1.55E-08 | 1.68E+05 | 2.60E-03 | | L84M | 54 |
| 23629 | 1C11_H3_L3.63 | 4.51E-08 | 9.98E+04 | 4.50E-03 | | L84V | 55 |
| 24209 | 1C11_H3_L3.125 | 6.81E-09 | 3.50E+05 | 2.38E-03 | | L84V Q85E | 54.5 |
| 23633 | 1C11_H3_L3.69 | 3.38E-08 | 2.04E+05 | 6.91E-03 | | V89A | 54 |
| 23636 | 1C11_H3_L3.73 | 1.19E-08 | 2.22E+05 | 2.65E-03 | | V91T | 54 |
| 23640 | 1C11_H3_L3.81 | 2.33E-08 | 1.51E+05 | 3.52E-03 | | G108Q | 54 |
| 24210 | 1C11_H3_L3.132 | 1.63E-08 | 1.81E+05 | 2.95E-03 | | G108P | 53.5 |
| 24372 | 1C11_H3_L3.86 | 1.94E-08 | 2.06E+05 | 3.98E-03 | | S62T L84V V91T G108Q | 55.5 |
| 24373 | 1C11_H3_L3.87 | 2.17E-08 | 1.60E+05 | 3.48E-03 | | L3V A19V S25A S49P | 56 |
| 24374 | 1C11_H3_L3.90 | 2.50E-08 | 1.70E+05 | 4.26E-03 | | L3V S25A S49P L84V V89A V91T G108Q | 57 |
| 24375 | 1C11_H3_L3.92 | 1.89E-08 | 1.70E+05 | 3.22E-03 | | V2I L3V A19V S25A S49P S62T | 56 |
| 24376 | 1C11_H3_L3.94 | 1.85E-08 | 1.77E+05 | 3.27E-03 | | V2I S62T L84V V89A V91T G108Q | 56 |

FIG. 17B

| XENP | Variant Name | K$_D$ (M) | k$_a$ (1/Ms) | k$_d$ (1/s) | VH Variants | VL Variants | T$_m$ (°C) |
|---|---|---|---|---|---|---|---|
| 24377 | 1C11_H3_L3.96 | 2.65E-08 | 1.63E+05 | 4.33E-03 | | V2I L3V S25A S49P S62T L84V V89A V91T G108Q | 57.5 |
| 24378 | 1C11_H3_L3.105 | 2.04E-08 | 1.88E+05 | 3.85E-03 | | A12P S14T L15P R18P | 71.5 |
| 24379 | 1C11_H3_L3.129 | | | | | S82N V89A V91T F95H | 49.5 |
| 24380 | 1C11_H3.176_L3.92 | | | | D66P T69K | V2I L3V A19V S25A S49P S62T | 59 |
| 24381 | 1C11_H3.176_L3.94 | | | | D66P T69K | V2I S62T L84V V89A V91T G108Q | 60 |
| 24382 | 1C11_H3.176_L3.96 | | | | D66P T69K | V2I L3V S25A S49P S62T L84V V89A V91T G108Q | 62 |
| 24414 | 1C11_H3_L3.133 | | | | | L3V A19V S25A S49P L84V V89A V91T G108Q | 58.5 |
| 24415 | 1C11_H3_L3.134 | | | | | L3V A19V S25A S49P L84V Q85E V89A V91T G108Q | 58 |
| 24416 | 1C11_H3_L3.135 | | | | | L3V A19V S25A S49P L84M V89A V91T G108Q | 57.5 |
| 24417 | 1C11_H3_L3.136 | | | | | L3V A19I S25A S49P L84M V89A V91T G108Q | 57 |

FIG. 17C

| XENP | Variant Name | K_D (M) | k_a (1/Ms) | k_d (1/s) | VH Variants | VL Variants | Tm (°C) |
|---|---|---|---|---|---|---|---|
| 24418 | 1C11_H3_L3.137 | | | | | L3V A19I S25A S49P L84V V89A V91T G108Q | 58 |
| 24419 | 1C11_H3_L3.138 | | | | | L3V A19I S25A S49P L84V Q85E V89A V91T G108Q | 58 |
| 24420 | 1C11_H3_L3.139 | | | | | L3V S25A S49P V64I L84V V89A V91T G108Q | 57.5 |
| 24421 | 1C11_H3_L3.140 | | | | | V2I L3V S25A L84V Q85E V91T G108Q | 56 |
| 24422 | 1C11_H3_L3.141 | 3.37E-08 | 2.63E+05 | 8.87E-03 | | V2I L3V S25A S49P L84V Q85E V91T G108Q | 57 |
| 24423 | 1C11_H3_L3.142 | 3.55E-08 | 2.50E+05 | 8.86E-03 | | V2I L3V S25A S49A L84V Q85E V91T G108Q | 57 |
| 24422 | 1C11_H3_L3.141 | | | | | V2I L3V S25A S49P L84V Q85E V91T G108Q | 56.5 |
| 24853 | 1C11_H3_L3.143 | | | | | V2I L3V A19V S25A S49P L84V Q85E V91T G108Q | 57.5 |
| 24854 | 1C11_H3_L3.144 | | | | | V2I L3V A19V S25A S49P L84V Q85E V89A V91T G108Q | 58.5 |

FIG. 17D

| XENP | Variant Name | K$_D$ (M) | k$_a$ (1/Ms) | k$_d$ (1/s) | VH Variants | VL Variants | T$_m$ (°C) |
|---|---|---|---|---|---|---|---|
| 24855 | 1C11_H3_L3.145 | | | | | V2I L3V A19V S25A L84V Q85E V91T G108Q | 56.5 |
| 24856 | 1C11_H3_L3.146 | | | | | V2I L3V A19V S25A L84V Q85E V89A V91T G108Q | 57.5 |
| 24857 | 1C11_H3_L3.147 | | | | | V2I L3V A19V S25A S49A L84V Q85E V91T G108Q | 57 |
| 24858 | 1C11_H3_L3.148 | | | | | V2I L3V A19V S25A S49A L84V Q85E V89A V91T G108Q | 58 |
| 24218 | 1C11_H3.86_L3 | 1.90E-08 | 1.64E+05 | 3.12E-03 | Q1E | | |
| 23755 | 1C11_H3.1_L3 | 2.42E-08 | 1.57E+05 | 3.80E-03 | I2V | | |
| 23758 | 1C11_H3.5_L3 | 1.91E-08 | 2.48E+05 | 4.73E-03 | S9A | | |
| 23760 | 1C11_H3.7_L3 | 4.19E-08 | 1.76E+05 | 7.37E-03 | S9P | | |
| 24221 | 1C11_H3.90_L3 | 2.53E-08 | 1.68E+05 | 4.24E-03 | E10V | | |
| 24222 | 1C11_H3.91_L3 | 2.47E-08 | 1.72E+05 | 4.26E-03 | K12V | | |
| 24226 | 1C11_H3.95_L3 | 2.00E-08 | 1.92E+05 | 3.84E-03 | A16G | | |
| 24227 | 1C11_H3.96_L3 | 2.30E-08 | 1.74E+05 | 4.00E-03 | A16Q | | |
| 24228 | 1C11_H3.97_L3 | 2.42E-08 | 1.87E+05 | 4.52E-03 | A16E | | |
| 24247 | 1C11_H3.120_L3 | 2.14E-08 | 2.02E+05 | 4.32E-03 | M36I | | |
| 23765 | 1C11_H3.18_L3 | 1.56E-08 | 1.51E+05 | 2.35E-03 | R40K | | |
| 24250 | 1C11_H3.125_L3 | 1.80E-08 | 2.04E+05 | 3.66E-03 | A42P | | |
| 24254 | 1C11_H3.129_L3 | 2.37E-08 | 3.03E+05 | 7.19E-03 | M50I | | |
| 24256 | 1C11_H3.134_L3 | 2.17E-08 | 2.48E+05 | 5.38E-03 | Y56K | | |
| 23770 | 1C11_H3.25_L3 | 3.40E-08 | 1.84E+05 | 6.25E-03 | Y56N | | |
| 24263 | 1C11_H3.143_L3 | 3.19E-08 | 2.02E+05 | 6.46E-03 | T63Y | | |
| 24266 | 1C11_H3.146_L3 | 2.30E-08 | 2.20E+05 | 5.06E-03 | D66P | | |
| 24267 | 1C11_H3.147_L3 | 2.04E-08 | 2.22E+05 | 4.52E-03 | D66T | | |
| 24268 | 1C11_H3.148_L3 | 2.26E-08 | 1.89E+05 | 4.26E-03 | D66Q G67K | | |
| 23776 | 1C11_H3.35_L3 | 6.92E-08 | 6.25E+04 | 4.32E-03 | G67K | | |
| 23779 | 1C11_H3.41_L3 | 3.44E-08 | 1.04E+05 | 3.57E-03 | T69K | | |
| 23780 | 1C11_H3.42_L3 | 2.78E-08 | 1.09E+05 | 3.04E-03 | T69Q | | |

FIG. 17E

| XENP | Variant Name | K$_D$ (M) | k$_a$ (1/Ms) | k$_d$ (1/s) | VH Variants | VL Variants | T$_m$ (°C) |
|---|---|---|---|---|---|---|---|
| 24270 | 1C11_H3.150_L3 | 1.89E-08 | 2.02E+05 | 3.81E-03 | G70E | | |
| 23781 | 1C11_H3.43_L3 | 1.60E-08 | 2.42E+05 | 3.89E-03 | F72V | | |
| 23786 | 1C11_H3.50_L3 | 1.80E-08 | 1.40E+05 | 2.52E-03 | L76V | | |
| 24274 | 1C11_H3.154_L3 | 2.24E-08 | 1.99E+05 | 4.46E-03 | L76I | | |
| 23793 | 1C11_H3.59_L3 | 9.74E-09 | 4.40E+05 | 4.28E-03 | V80Q | | |
| 24279 | 1C11_H3.159_L3 | 2.29E-08 | 2.39E+05 | 5.45E-03 | S81D | | |
| 24278 | 1C11_H3.158_L3 | 1.59E-08 | 2.19E+05 | 3.48E-03 | S81N | | |
| 23796 | 1C11_H3.62_L3 | 1.62E-08 | 3.90E+05 | 6.32E-03 | A83I | | |
| 24287 | 1C11_H3.168_L3 | 2.25E-08 | 1.96E+05 | 4.40E-03 | S88N | | |
| 24291 | 1C11_H3.172_L3 | 2.41E-08 | 2.10E+05 | 5.06E-03 | A92P | | |
| 23811 | 1C11_H3.74_L3 | 3.90E-08 | 2.00E+05 | 7.82E-03 | F99Y | | |
| 24211 | 1C11_H3.78_L3 | 4.75E-08 | 2.37E+05 | 1.13E-02 | S9P Y56N L76V V80Q | | |
| 24212 | 1C11_H3.80_L3 | 3.88E-08 | 2.64E+05 | 1.02E-02 | Y56N L76V V80Q F99Y | | |
| 24213 | 1C11_H3.81_L3 | 2.22E-08 | 1.94E+05 | 4.30E-03 | G67K T69K | | |
| 24214 | 1C11_H3.82_L3 | 1.60E-08 | 1.98E+05 | 3.16E-03 | G67K T69Q | | |
| 24215 | 1C11_H3.83_L3 | 3.57E-08 | 2.71E+05 | 9.67E-03 | Y56N L76V V80Q | | |
| 24216 | 1C11_H3.84_L3 | 2.01E-08 | 1.78E+05 | 3.59E-03 | G67K T69K V80Q | | |
| 24217 | 1C11_H3.85_L3 | 1.78E-08 | 1.92E+05 | 3.41E-03 | G67K T69Q V80Q | | |
| 24424 | 1C11_H3.176_L3 | | | | D66P T69K | | 58 |
| 24425 | 1C11_H3.177_L3 | | | | D66P G67K | | 58.5 |
| 24426 | 1C11_H3.178_L3 | | | | D66P T69K G70E | | 59 |
| 24427 | 1C11_H3.179_L3 | | | | D66P G67K G70E | | 58.5 |
| 24428 | 1C11_H3.180_L3 | | | | M36I L76V | | 55.5 |
| 24429 | 1C11_H3.181_L3 | | | | M36I L76I | | 55.5 |
| 24430 | 1C11_H3.182_L3 | | | | K12V A16E | | 54 |
| 24431 | 1C11_H3.183_L3 | | | | E10V A16E | | 56 |
| 24432 | 1C11_H3.184_L3 | | | | E10V K12V A16E | | 55.5 |
| 24433 | 1C11_H3.185_L3 | | | | Q1E I2V K12V A16E M36I A42P M50I T63Y D66P G67K G70E V80Q S81D S88N F99Y | | 61 |

FIG. 17F

| XENP | Variant Name | K$_D$ (M) | k$_a$ (1/Ms) | k$_d$ (1/s) | VH Variants | VL Variants | T$_m$ (°C) |
|---|---|---|---|---|---|---|---|
| 24434 | 1C11_H3.186_L3 | | | | Q1E I2V K12V A16E M36I A42P T63Y D66P G70E S81D S88N F99Y | | 61.5 |
| 24435 | 1C11_H3.187_L3 | | | | I2V K12V A16E M36I A42P T63Y D66P G70E V80Q S88N F99Y | | 62 |
| 24436 | 1C11_H3.188_L3 | 5.32E-08 | 3.20E+05 | 1.71E-02 | I2V A16E M36I A42P M50I T63Y D66P V80Q S88N F99Y | | 62.5 |
| 24437 | 1C11_H3.189_L3 | | | | I2V M36I A42P M50I T63Y D66P G67K S88N F99Y | | 61 |
| 24438 | 1C11_H3.190_L3 | | | | I2V E10V A16G M36I A42P M50I T63Y D66P V80Q S88N F99Y | | 60.5 |
| 24439 | 1C11_H3.191_L3 | | | | I2V K12V A16E D66P V80Q S88N | | 58.5 |
| 24440 | 1C11_H3.192_L3 | | | | Q1E I2V E10V A16E M36I G70E | | 58 |
| 24441 | 1C11_H3.193_L3 | | | | A42P M50I D66P G70E V80Q S88N F99Y | | 59.5 |
| 24442 | 1C11_H3.194_L3 | | | | Q1E E10V M36I M50I | | 56 |

FIG. 17G

| XENP | Variant Name | K_D (M) | k_a (1/Ms) | k_d (1/s) | VH Variants | VL Variants | T_m (°C) |
|---|---|---|---|---|---|---|---|
| 24443 | 1C11_H3.195_L3 | | | | A42P T63Y S81D S88N | | 55 |
| 24436 | 1C11_H3.188_L3 | | | | I2V A16E M36I A42P M50I T63Y D66P V80Q S88N F99Y | | 61.5 |
| 24827 | 1C11_H3.196_L3 | | | | Q1E I2V A16E M36I A42P M50I T63Y D66P V80Q S88N F99Y | | 61 |
| 24828 | 1C11_H3.197_L3 | | | | I2V M36I A42P M50I T63Y D66P V80Q S88N F99Y | | 60 |
| 24829 | 1C11_H3.198_L3 | | | | I2V A16E M36I A42P M50I T63Y V80Q S88N F99Y | | 59 |
| 24830 | 1C11_H3.199_L3 | | | | I2V A16E A42P M50I T63Y D66P V80Q S88N F99Y | | 60.5 |
| 24831 | 1C11_H3.200_L3 | | | | I2V A16E M36I A42P M50I T63Y D66P V80Q S88N | | 61 |
| 24832 | 1C11_H3.201_L3 | | | | I2V A16E M36I A42P M50I T63Y D66P L76I V80Q S88N F99Y | | 62 |
| 24833 | 1C11_H3.202_L3 | | | | I2V A16E M36I M50I T63Y D66P V80Q S88N F99Y | | 61.5 |

FIG. 17H

| XENP | Variant Name | K$_D$ (M) | k$_a$ (1/Ms) | k$_d$ (1/s) | VH Variants | VL Variants | T$_m$ (°C) |
|---|---|---|---|---|---|---|---|
| 24834 | 1C11_H3.203_L3 | | | | I2V A16E M36I A42P M50I T63Y D66P G70E V80Q S88N F99Y | | 62.5 |
| 24835 | 1C11_H3.204_L3 | | | | I2V A16E M36I A42P M50I T63Y D66P T69Q V80Q S88N F99Y | | 62.5 |
| 24836 | 1C11_H3.205_L3 | | | | I2V A16E M36I A42P M50I T63Y D66P T69K V80Q S88N F99Y | | 62.5 |
| 24837 | 1C11_H3.206_L3 | | | | I2V A16E M36I A42P M50I D66P V80Q S88N F99Y | | 62 |
| 24838 | 1C11_H3.207_L3 | | | | I2V A16E M36I A42P M50I T63Y D66P V80Q F99Y | | 61.5 |
| 24839 | 1C11_H3.208_L3 | | | | I2V A16E M36I A42P M50I T63Y D66P V80Q S81D S88N F99Y | | 61.5 |
| 24840 | 1C11_H3.209_L3 | | | | I2V A16E M36I A42P T63Y D66P V80Q S88N F99Y | | 63 |
| 24841 | 1C11_H3.210_L3 | | | | I2V A16E M36I A42P M50I T63Y D66P S88N F99Y | | 61.5 |

FIG. 17I

| XENP | Variant Name | K^D (M) | k_a (1/Ms) | k_d (1/s) | VH Variants | VL Variants | T_m (°C) |
|---|---|---|---|---|---|---|---|
| 24842 | 1C11_H3.211_L3 | | | | I2V S9P A16E M36I A42P M50I T63Y D66P V80Q S88N F99Y | | 63.5 |
| 24843 | 1C11_H3.212_L3 | | | | I2V A16E M36I A42P M50I T63Y D66P S81D S88N F99Y | | 61 |
| 24844 | 1C11_H3.213_L3 | | | | I2V S9P A16E M36I M50I T63Y D66P V80Q S81D S88N F99Y | | 62.5 |
| 24845 | 1C11_H3.214_L3 | | | | I2V S9P A16E M36I M50I T63Y D66P L76I V80Q S88N F99Y | | 62.5 |
| 24846 | 1C11_H3.215_L3 | | | | I2V S9P A16E M36I M50I T63Y D66P S88N F99Y | | 62.5 |
| 24847 | 1C11_H3.216_L3 | | | | I2V S9P A16E M36I A42P T63Y D66P L76I V80Q S88N F99Y | | 65.5 |
| 24848 | 1C11_H3.217_L3 | | | | I2V S9P A16E M36I A42P T63Y D66P S88N F99Y | | 64 |
| 24849 | 1C11_H3.218_L3 | | | | I2V S9P A16E M36I A42P T63Y D66P V80Q S81D S88N F99Y | | 63.5 |

FIG. 17J

| XENP | Variant Name | K$_D$ (M) | k$_a$ (1/Ms) | k$_d$ (1/s) | VH Variants | VL Variants | T$_m$ (°C) |
|---|---|---|---|---|---|---|---|
| 24850 | 1C11_H3.219_L3 | | | | I2V A16E M36I A42P M50I T63Y D66P T69Q G70E V80Q S88N F99Y | | 63 |
| 24851 | 1C11_H3.220_L3 | | | | I2V A16E M36I A42P M50I T63Y D66P T69K G70E V80Q S88N F99Y | | 62.5 |
| 24852 | 1C11_H3.221_L3 | | | | Q1E A16E M36I A42P M50I T63Y D66P V80Q S88N F99Y | | |
| 25295 | 1C11_H3.222_L3 | | | | I2V S9P A16E M36I A42P D66P L76I V80Q S88N F99Y | | 64 |
| 25296 (25322) | 1C11_H3.223_L3 | 3.21E-08 | | | I2V S9P A16E M36I A42P T63Y D66P G70E L76I V80Q S88N F99Y | | 67 |
| 25301 (25323) | 1C11_H3.224_L3 | 3.06E-08 | | | I2V S9P A16E M36I A42P T63Y D66P T69Q G70E L76I V80Q S88N F99Y | | 67 |
| 25302 (25324) | 1C11_H3.225_L3 | 3.22E-08 | | | I2V S9P A16E M36I T63Y D66P G70E V80Q S81D S88N F99Y | | 64.5 |
| 25303 (25325) | 1C11_H3.226_L3 | 3.35E-08 | | | I2V S9P A16E M36I T63Y D66P T69Q G70E V80Q S81D S88N F99Y | | 64.5 |

FIG. 17K

| XENP | Variant Name | K_D (M) | k_a (1/Ms) | k_d (1/s) | VH Variants | VL Variants | T_m (°C) |
|---|---|---|---|---|---|---|---|
| 25304 | 1C11_H3.227_L3 | | | | Q1E I2V S9P A16E M36I T63Y D66P G70E V80Q S81D S88N F99Y | | 64.5 |
| 25305 | 1C11_H3.228_L3 | | | | Q1E I2V S9P A16E M36I T63Y D66P T69Q G70E V80Q S81D S88N F99Y | | 65 |
| 25306 (25326) | 1C11_H3.229_L3 | 3.79E-08 | | | I2V A16E M36I A42P T63Y D66P T69Q G70E V80Q S88N F99Y | | 64.5 |
| 25307 (25327) | 1C11_H3.230_L3 | 4.19E-08 | | | I2V A16E M36I A42P T63Y D66P T69Q G70E V80Q S81D S88N F99Y | | 64 |
| 25308 (25328) | 1C11_H3.231_L3 | 3.01E-08 | | | I2V A16E M36I A42P D66P V80Q F99Y | | 61.5 |
| 25309 (25329) | 1C11_H3.232_L3 | 3.32E-08 | | | I2V A16E M36I A42P D66P V80Q S81D S88N F99Y | | 61.5 |
| 25310 | 1C11_H3.233_L3 | | | | Q1E I2V A16E M36I A42P T63Y D66P T69Q G70E V80Q S88N F99Y | | 64.5 |
| 25311 | 1C11_H3.234_L3 | | | | Q1E I2V A16E M36I A42P T63Y D66P T69Q G70E V80Q S81D S88N F99Y | | 63.5 |

FIG. 17L

| XENP | Variant Name | K_D (M) | k_a (1/Ms) | k_d (1/s) | VH Variants | VL Variants | T_m (°C) |
|---|---|---|---|---|---|---|---|
| 25312 (25330) | 1C11_H3.235_L3 | 3.14E-08 | | | Q1E I2V A16E M36I A42P D66P V80Q F99Y | | 61.5 |
| 25313 (25331) | 1C11_H3.236_L3 | 3.94E-08 | | | Q1E I2V A16E M36I A42P D66P V80Q S81D S88N F99Y | | 61.5 |
| 25314 (25332) | 1C11_H3.237_L3 | 3.44E-08 | | | I2V A16E M36I T63Y D66P G70E V80Q S81D S88N F99Y | | 63 |
| 25315 (25333) | 1C11_H3.238_L3 | 3.84E-08 | | | I2V A16E M36I T63Y D66P T69Q G70E V80Q S81D S88N F99Y | | 63.5 |
| 25316 | 1C11_H3.213_L3.144 | | | | I2V S9P A16E M36I M50I T63Y D66P V80Q S81D S88N F99Y | | 60, 71.5 |
| 25317 | 1C11_H3.213_L3.148 | | | | I2V S9P A16E M36I M50I T63Y D66P V80Q S81D S88N F99Y | | 59.5, 70.5 |
| 25318 | 1C11_H3.216_L3.144 | | | | I2V S9P A16E M36I A42P T63Y D66P L76I V80Q S88N F99Y | | 73 |
| 25319 | 1C11_H3.216_L3.148 | | | | I2V S9P A16E M36I A42P T63Y D66P L76I V80Q S88N F99Y | | 72.5 |

FIG. 17M

| XENP | Variant Name | K_D (M) | k_a (1/Ms) | k_d (1/s) | VH Variants | VL Variants | T_m (°C) |
|---|---|---|---|---|---|---|---|
| 25320 (25334) | 1C11_H3.188_L3.144 | 5.04E-08 | | | I2V A16E M36I A42P M50I T63Y D66P V80Q S88N F99Y | V2I L3V A19V S25A S49P L84V Q85E V89A V91T G108Q | 60, 71 |
| 25321 (25335) | 1C11_H3.188_L3.148 | 4.13E-08 | | | I2V A16E M36I A42P M50I T63Y D66P V80Q S88N F99Y | V2I L3V A19V S25A S49A L84V Q85E V89A V91T G108Q | 59.5, 70.5 |
| 25802 (25336) | 1C11_H3.224_L3.144 | 3.31E-08 | | | I2V S9P A16E M36I A42P T63Y D66P T69Q G70E L76I V80Q S88N F99Y | V2I L3V A19V S25A S49P L84V Q85E V89A V91T G108Q | |
| 25803 (25337) | 1C11_H3.224_L3.148 | 3.12E-08 | | | I2V S9P A16E M36I A42P T63Y D66P T69Q G70E L76I V80Q S88N F99Y | V2I L3V A19V S25A S49A L84V Q85E V89A V91T G108Q | |
| (25338) | 1C11_H3.226_L3.144 | 4.37E-08 | | | I2V S9P A16E M36I T63Y D66P T69Q G70E V80Q S81D S88N F99Y | V2I L3V A19V S25A S49P L84V Q85E V89A V91T G108Q | |
| (25339) | 1C11_H3.226_L3.148 | 4.18E-08 | | | I2V S9P A16E M36I T63Y D66P T69Q G70E V80Q S81D S88N F99Y | V2I L3V A19V S25A S49A L84V Q85E V89A V91T G108Q | |
| 24436 (25340) | 1C11_H3.188_L3 | 5.32E-08 | | | I2V A16E M36I A42P M50I T63Y D66P V80Q S88N F99Y | | |
| 24422 (25341) | 1C11_H3_L3.141 | 3.37E-08 | | | | V2I L3V S25A S49P L84V Q85E V91T G108Q | |

FIG. 17N

| XENP | Variant Name | K$_D$ (M) | k$_a$ (1/Ms) | k$_d$ (1/s) | VH Variants | VL Variants | T$_m$ (°C) |
|---|---|---|---|---|---|---|---|
| 24423 (25342) | 1C11_H3_L3.142 | 3.55E-08 | | | | V2I L3V S25A S49A L84V Q85E V91T G108Q | |
| 25802 (25336) | 1C11_H3.224_L3.144 | 3.31E-08 | | | I2V S9P A16E M36I A42P T63Y D66P T69Q G70E L76I V80Q S88N F99Y | V2I L3V A19V S25A S49P L84V Q85E V89A V91T G108Q | 74 |
| 25803 (25337) | 1C11_H3.224_L3.148 | 3.12E-08 | | | I2V S9P A16E M36I A42P T63Y D66P T69Q G70E L76I V80Q S88N F99Y | V2I L3V A19V S25A S49A L84V Q85E V89A V91T G108Q | 73.5 |
| 25804 (25833) | 1C11_H3.228_L3.144 | 3.88E-08 | 2.59E+05 | 1.00E-02 | Q1E I2V S9P A16E M36I T63Y D66P T69Q G70E V80Q S81D S88N F99Y | V2I L3V A19V S25A S49P L84V Q85E V89A V91T G108Q | 62, 72.5 |
| 25805 (25834) | 1C11_H3.228_L3.148 | 4.19E-08 | 2.37E+05 | 9.94E-03 | Q1E I2V S9P A16E M36I T63Y D66P T69Q G70E V80Q S81D S88N F99Y | V2I L3V A19V S25A S49A L84V Q85E V89A V91T G108Q | 62, 72 |
| 25806 (25835) | 1C11_H3.234_L3.144 | 2.74E-08 | 2.83E+05 | 7.75E-03 | Q1E I2V A16E M36I A42P T63Y D66P T69Q G70E V80Q S81D S88N F99Y | V2I L3V A19V S25A S49P L84V Q85E V89A V91T G108Q | 60.5, 71.5 |
| 25807 (25836) | 1C11_H3.234_L3.148 | 3.75E-08 | 2.32E+05 | 8.69E-03 | Q1E I2V A16E M36I A42P T63Y D66P T69Q G70E V80Q S81D S88N F99Y | V2I L3V A19V S25A S49A L84V Q85E V89A V91T G108Q | 60.5, 71 |

FIG. 17O

| XENP | Variant Name | K$_D$ (M) | k$_a$ (1/Ms) | k$_d$ (1/s) | VH Variants | VL Variants | T$_m$ (°C) |
|---|---|---|---|---|---|---|---|
| 25808 (25825) | 1C11_H3.239_L3.144 | 4.26E-08 | 2.19E+05 | 9.34E-03 | Q1E I2V S9P A16E M36I A42P T63Y D66P T69Q G70E L76I V80Q S88N F99Y | V2I L3V A19V S25A S49P L84V Q85E V89A V91T G108Q | 74 |
| 25809 (25826) | 1C11_H3.240_L3.144 | 4.31E-08 | 2.43E+05 | 1.05E-02 | I2V S9P A16E M36I A42P T63Y D66P T69Q G70E L76I V80Q S81D S88N F99Y | V2I L3V A19V S25A S49P L84V Q85E V89A V91T G108Q | 73.5 |
| 25810 (25827) | 1C11_H3.241_L3.144 | 4.05E-08 | 2.18E+05 | 8.84E-03 | Q1E I2V S9P A16E M36I A42P T63Y D66P T69Q G70E L76I V80Q S81D S88N F99Y | V2I L3V A19V S25A S49P L84V Q85E V89A V91T G108Q | 73.5 |
| 25811 (25828) | 1C11_H3.239_L3.148 | 4.47E-08 | 2.27E+05 | 1.02E-02 | Q1E I2V S9P A16E M36I A42P T63Y D66P T69Q G70E L76I V80Q S88N F99Y | V2I L3V A19V S25A S49A L84V Q85E V89A V91T G108Q | 73.5 |
| 25812 (25829) | 1C11_H3.240_L3.148 | 2.75E-08 | 3.22E+05 | 8.85E-03 | I2V S9P A16E M36I A42P T63Y D66P T69Q G70E L76I V80Q S81D S88N F99Y | V2I L3V A19V S25A S49A L84V Q85E V89A V91T G108Q | 72.5 |
| 25813 (25830) | 1C11_H3.241_L3.148 | 3.33E-08 | 2.86E+05 | 9.53E-03 | Q1E I2V S9P A16E M36I A42P T63Y D66P T69Q G70E L76I V80Q S81D S88N F99Y | V2I L3V A19V S25A S49A L84V Q85E V89A V91T G108Q | 72.5 |

FIG. 17P

| XENP | Variant Name | K$_D$ (M) | k$_a$ (1/Ms) | k$_d$ (1/s) | VH Variants | VL Variants | T$_m$ (°C) |
|---|---|---|---|---|---|---|---|
| 25814 (25837) | 1C11_H3.239_L3.125 | 4.16E-08 | 3.15E+05 | 1.31E-02 | Q1E I2V S9P A16E M36I A42P T63Y D66P T69Q G70E L76I V80Q S88N F99Y | L84V Q85E | 68 |
| 25815 (25838) | 1C11_H3.240_L3.125 | 5.08E-08 | 2.80E+05 | 1.42E-02 | I2V S9P A16E M36I A42P T63Y D66P T69Q G70E L76I V80Q S81D S88N F99Y | L84V Q85E | 67 |
| 25816 (25839) | 1C11_H3.241_L3.125 | 4.34E-08 | 3.34E+05 | 1.45E-02 | Q1E I2V S9P A16E M36I A42P T63Y D66P T69Q G70E L76I V80Q S81D S88N F99Y | L84V Q85E | 67 |
| 25817 (25840) | 1C11_H3.239_L3.92 | 3.46E-08 | 2.66E+05 | 9.22E-03 | Q1E I2V S9P A16E M36I A42P T63Y D66P T69Q G70E L76I V80Q S88N F99Y | V2I L3V A19V S25A S49P S62T | 71 |
| 25818 (25841) | 1C11_H3.240_L3.92 | 3.15E-08 | 3.01E+05 | 9.49E-03 | I2V S9P A16E M36I A42P T63Y D66P T69Q G70E L76I V80Q S81D S88N F99Y | V2I L3V A19V S25A S49P S62T | 70 |
| 25819 (25842) | 1C11_H3.241_L3.92 | 3.31E-08 | 3.05E+05 | 1.01E-02 | Q1E I2V S9P A16E M36I A42P T63Y D66P T69Q G70E L76I V80Q S81D S88N F99Y | V2I L3V A19V S25A S49P S62T | 70 |

FIG. 17Q

| XENP | Variant Name | K$_D$ (M) | k$_a$ (1/Ms) | k$_d$ (1/s) | VH Variants | VL Variants | T$_m$ (°C) |
|---|---|---|---|---|---|---|---|
| 24854 (25820) | 1C11_H3_L3.144 | 3.01E-08 | 2.20E+05 | 6.61E-03 | | V2I L3V A19V S25A S49P L84V Q85E V89A V91T G108Q | 58.5 |
| 24858 (25821) | 1C11_H3_L3.148 | 2.65E-08 | 2.53E+05 | 6.69E-03 | | V2I L3V A19V S25A S49A L84V Q85E V89A V91T G108Q | 58 |
| 24847 (25822) | 1C11_H3.216_L3 | 3.79E-08 | 2.66E+05 | 1.01E-02 | I2V S9P A16E M36I A42P T63Y D66P L76I V80Q S88N F99Y | | 65.5 |
| 25305 (25823) | 1C11_H3.228_L3 | 3.70E-08 | 3.13E+05 | 1.16E-02 | Q1E I2V S9P A16E M36I T63Y D66P T69Q G70E V80Q S81D S88N F99Y | | 65 |
| 25311 (25824) | 1C11_H3.234_L3 | 3.29E-08 | 3.06E+05 | 1.01E-02 | Q1E I2V A16E M36I A42P T63Y D66P T69Q G70E V80Q S81D S88N F99Y | | 63.5 |
| 25318 (25831) | 1C11_H3.216_L3.144 | 3.87E-08 | 2.57E+05 | 9.93E-03 | I2V S9P A16E M36I A42P T63Y D66P L76I V80Q S88N F99Y | V2I L3V A19V S25A S49P L84V Q85E V89A V91T G108Q | 73 |
| 25319 (25832) | 1C11_H3.216_L3.148 | 4.36E-08 | 2.45E+05 | 1.07E-02 | I2V S9P A16E M36I A42P T63Y D66P L76I V80Q S88N F99Y | V2I L3V A19V S25A S49A L84V Q85E V89A V91T G108Q | 72.5 |

FIG. 18A

>XENP022553 1C11[PD-1]_H3L3_IgG1_PVA_/S267K Heavy Chain (SEQ ID NOS 41369-41373)
QIQLVQSGSELKKPGASVKVSCKASGYTFTHYGMNWVRQAPGQGLEWMGWINTYTGEPTYADGFTGRFVFSLDTSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

>XENP022553 1C11[PD-1]_H3L3_IgG1_PVA_/S267K Light Chain (SEQ ID NOS 41374-41378)
DVLMTQSPDSLAVSLGERATINCKSSQSIVHSNGNTYLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XENP026321 1C11[PD-1]_H3.59_L3.1_IgG1_PVA_/S267K Heavy Chain (SEQ ID NOS 41379-41383)
QIQLVQSGSELKKPGASVKVSCKASGYTFTHYGMNWVRQAPGQGLEWMGWINTYTGEPTYADGFTGRFVFSLDTSQS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

>XENP026321 1C11[PD-1]_H3.59_L3.1_IgG1_PVA_/S267K Light Chain (SEQ ID NOS 41384-41388)
DILMTQSPDSLAVSLGERATINCKSSQSIVHSNGNTYLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XENP026322 1C11[PD-1]_H3.59_L3.38_IgG1_PVA_/S267K Heavy Chain (SEQ ID NOS 41389-41393)
QIQLVQSGSELKKPGASVKVSCKASGYTFTHYGMNWVRQAPGQGLEWMGWINTYTGEPTYADGFTGRFVFSLDTSQS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

>XENP026322 1C11[PD-1]_H3.59_L3.38_IgG1_PVA_/S267K Light Chain (SEQ ID NOS 41394-41398)
DVLMTQSPDSLAVSLGERATINCKSSQSIVHSNGNNYLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XENP026323 1C11[PD-1]_H3.59_L3.51_IgG1_PVA_/S267K Heavy Chain (SEQ ID NOS 41399-41403)
QIQLVQSGSELKKPGASVKVSCKASGYTFTHYGMNWVRQAPGQGLEWMGWINTYTGEPTYADGFTGRFVFSLDTSQS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

>XENP026323 1C11[PD-1]_H3.59_L3.51_IgG1_PVA_/S267K Light Chain (SEQ ID NOS 41404-41408)
DVLMTQSPDSLAVSLGERATINCKSSQSIVHSNGNTYLEWYQQKPGQSPKLLIYSVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

FIG. 18B

>XENP026324 1C11[PD-1]_H3.59_L3.59_IgG1_PVA_/S267K Heavy Chain (SEQ ID NOS 41409-41413)
QIQLVQSGSELKKPGASVKVSCKASGYTFTHYGMNWVRQAPGQGLEWMGWINTYTGEPTYADGFTGRFVFSLDTSQS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

>XENP026324 1C11[PD-1]_H3.59_L3.59_IgG1_PVA_/S267K Light Chain (SEQ ID NOS 41414-41418)
DVLMTQSPDSLAVSLGERATINCKSSQSIVHSNGNTYLEWYQQKPGQSPKLLIYKVSNRFSGVPDRFSGSGSGTDFT
LTISRLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XENP026325 1C11[PD-1]_H3.59_L3.73_IgG1_PVA_/S267K Heavy Chain (SEQ ID NOS 41419-41423)
QIQLVQSGSELKKPGASVKVSCKASGYTFTHYGMNWVRQAPGQGLEWMGWINTYTGEPTYADGFTGRFVFSLDTSQS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

>XENP026325 1C11[PD-1]_H3.59_L3.73_IgG1_PVA_/S267K Light Chain (SEQ ID NOS 41424-41428)
DVLMTQSPDSLAVSLGERATINCKSSQSIVHSNGNTYLEWYQQKPGQSPKLLIYKVSNRFSGVPDRFSGSGSGTDFT
LTISSLQAEDVATYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XENP026326 1C11[PD-1]_H3.59_L3.125_IgG1_PVA_/S267K Heavy Chain (SEQ ID NOS 41429-41433)
QIQLVQSGSELKKPGASVKVSCKASGYTFTHYGMNWVRQAPGQGLEWMGWINTYTGEPTYADGFTGRFVFSLDTSQS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

>XENP026326 1C11[PD-1]_H3.59_L3.125_IgG1_PVA_/S267K Light Chain (SEQ ID NOS 41434-41438)
DVLMTQSPDSLAVSLGERATINCKSSQSIVHSNGNTYLEWYQQKPGQSPKLLIYKVSNRFSGVPDRFSGSGSGTDFT
LTISSVEAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XENP026327 1C11[PD-1]_H3.135_L3.1_IgG1_PVA_/S267K Heavy Chain (SEQ ID NOS 41439-41443)
QIQLVQSGSELKKPGASVKVSCKASGYTFTHYGMNWVRQAPGQGLEWMGWINTYTSEPTYADGFTGRFVFSLDTSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

>XENP026327 1C11[PD-1]_H3.135_L3.1_IgG1_PVA_/S267K Light Chain (SEQ ID NOS 41444-41448)
DILMTQSPDSLAVSLGERATINCKSSQSIVHSNGNTYLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

FIG. 18C

>XENP026328 1C11[PD-1]_H3.135_L3.38_IgG1_PVA_/S267K Heavy Chain (SEQ ID NOS 41449-41453)
QIQLVQSGSELKKPGASVKVSCKASGYTFTHYGMNWVRQAPGQGLEWMGWINTYTSEPTYADGFTGRFVFSLDTSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

>XENP026328 1C11[PD-1]_H3.135_L3.38_IgG1_PVA_/S267K Light Chain (SEQ ID NOS 41454-41458)
DVLMTQSPDSLAVSLGERATINCKSSQSIVHSNGNNYLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XENP026329 1C11[PD-1]_H3.135_L3.51_IgG1_PVA_/S267K Heavy Chain (SEQ ID NOS 41459-41463)
QIQLVQSGSELKKPGASVKVSCKASGYTFTHYGMNWVRQAPGQGLEWMGWINTYTSEPTYADGFTGRFVFSLDTSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

>XENP026329 1C11[PD-1]_H3.135_L3.51_IgG1_PVA_/S267K Light Chain (SEQ ID NOS 41464-41468)
DVLMTQSPDSLAVSLGERATINCKSSQSIVHSNGNTYLEWYQQKPGQSPKLLIYSVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XENP026330 1C11[PD-1]_H3.135_L3.59_IgG1_PVA_/S267K Heavy Chain (SEQ ID NOS 41469-41473)
QIQLVQSGSELKKPGASVKVSCKASGYTFTHYGMNWVRQAPGQGLEWMGWINTYTSEPTYADGFTGRFVFSLDTSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

>XENP026330 1C11[PD-1]_H3.135_L3.59_IgG1_PVA_/S267K Light Chain (SEQ ID NOS 41474-41478)
DVLMTQSPDSLAVSLGERATINCKSSQSIVHSNGNTYLEWYQQKPGQSPKLLIYKVSNRFSGVPDRFSGSGSGTDFT
LTISRLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XENP026331 1C11[PD-1]_H3.135_L3.73_IgG1_PVA_/S267K Heavy Chain (SEQ ID NOS 41479-41483)
QIQLVQSGSELKKPGASVKVSCKASGYTFTHYGMNWVRQAPGQGLEWMGWINTYTSEPTYADGFTGRFVFSLDTSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

>XENP026331 1C11[PD-1]_H3.135_L3.73_IgG1_PVA_/S267K Light Chain (SEQ ID NOS 41484-41488)
DVLMTQSPDSLAVSLGERATINCKSSQSIVHSNGNTYLEWYQQKPGQSPKLLIYKVSNRFSGVPDRFSGSGSGTDFT
LTISSLQAEDVATYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

FIG. 18D

>XENP026332 1C11[PD-1]_H3.135_L3.125_IgG1_PVA_/S267K Heavy Chain (SEQ ID NOS 41489-41493)
QIQLVQSGSELKKPGASVKVSCKASGYTFTHYGMNWVRQAPGQGLEWMGWINTYTSEPTYADGFTGRFVFSLDTSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

>XENP026332 1C11[PD-1]_H3.135_L3.125_IgG1_PVA_/S267K Light Chain (SEQ ID NOS 41494-41498)
DVLMTQSPDSLAVSLGERATINCKSSQSIVHSNGNTYLEWYQQKPGQSPKLLIYKVSNRFSGVPDRFSGSGSGTDFT
LTISSVEAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XENP026333 1C11[PD-1]_H3.138_L3.1_IgG1_PVA_/S267K Heavy Chain (SEQ ID NOS 41499-41503)
QIQLVQSGSELKKPGASVKVSCKASGYTFTHYGMNWVRQAPGQGLEWMGWINTYTGDPTYADGFTGRFVFSLDTSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

>XENP026333 1C11[PD-1]_H3.138_L3.1_IgG1_PVA_/S267K Light Chain (SEQ ID NOS 41504-41508)
DILMTQSPDSLAVSLGERATINCKSSQSIVHSNGNTYLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XENP026334 1C11[PD-1]_H3.138_L3.38_IgG1_PVA_/S267K Heavy Chain (SEQ ID NOS 41509-41513)
QIQLVQSGSELKKPGASVKVSCKASGYTFTHYGMNWVRQAPGQGLEWMGWINTYTGDPTYADGFTGRFVFSLDTSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

>XENP026334 1C11[PD-1]_H3.138_L3.38_IgG1_PVA_/S267K Light Chain (SEQ ID NOS 41514-41518)
DVLMTQSPDSLAVSLGERATINCKSSQSIVHSNGNNYLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XENP026335 1C11[PD-1]_H3.138_L3.51_IgG1_PVA_/S267K Heavy Chain (SEQ ID NOS 41519-41523)
QIQLVQSGSELKKPGASVKVSCKASGYTFTHYGMNWVRQAPGQGLEWMGWINTYTGDPTYADGFTGRFVFSLDTSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

>XENP026335 1C11[PD-1]_H3.138_L3.51_IgG1_PVA_/S267K Light Chain (SEQ ID NOS 41524-41528)
DVLMTQSPDSLAVSLGERATINCKSSQSIVHSNGNTYLEWYQQKPGQSPKLLIYSVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

FIG. 18E

>XENP026336 1C11[PD-1]_H3.138_L3.59_IgG1_PVA_/S267K Heavy Chain (SEQ ID NOS 41529-41533)
QIQLVQSGSELKKPGASVKVSCKASGYTFTHYGMNWVRQAPGQGLEWMGWINTYTGDPTYADGFTGRFVFSLDTSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

>XENP026336 1C11[PD-1]_H3.138_L3.59_IgG1_PVA_/S267K Light Chain (SEQ ID NOS 41534-41538)
DVLMTQSPDSLAVSLGERATINCKSSQSIVHSNGNTYLEWYQQKPGQSPKLLIYKVSNRFSGVPDRFSGSGSGTDFT
LTISRLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XENP026337 1C11[PD-1]_H3.138_L3.73_IgG1_PVA_/S267K Heavy Chain (SEQ ID NOS 41539-41543)
QIQLVQSGSELKKPGASVKVSCKASGYTFTHYGMNWVRQAPGQGLEWMGWINTYTGDPTYADGFTGRFVFSLDTSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

>XENP026337 1C11[PD-1]_H3.138_L3.73_IgG1_PVA_/S267K Light Chain (SEQ ID NOS 41544-41548)
DVLMTQSPDSLAVSLGERATINCKSSQSIVHSNGNTYLEWYQQKPGQSPKLLIYKVSNRFSGVPDRFSGSGSGTDFT
LTISSLQAEDVATYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XENP026338 1C11[PD-1]_H3.138_L3.125_IgG1_PVA_/S267K Heavy Chain (SEQ ID NOS 41549-41553)
QIQLVQSGSELKKPGASVKVSCKASGYTFTHYGMNWVRQAPGQGLEWMGWINTYTGDPTYADGFTGRFVFSLDTSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

>XENP026338 1C11[PD-1]_H3.138_L3.125_IgG1_PVA_/S267K Light Chain (SEQ ID NOS 41554-41558)
DVLMTQSPDSLAVSLGERATINCKSSQSIVHSNGNTYLEWYQQKPGQSPKLLIYKVSNRFSGVPDRFSGSGSGTDFT
LTISSVEAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XENP026339 1C11[PD-1]_H3.155_L3.1_IgG1_PVA_/S267K Heavy Chain (SEQ ID NOS 41559-41563)
QIQLVQSGSELKKPGASVKVSCKASGYTFTHYGMNWVRQAPGQGLEWMGWINTYTGEPTYADGFTGRFVFSLDNSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

>XENP026339 1C11[PD-1]_H3.155_L3.1_IgG1_PVA_/S267K Light Chain (SEQ ID NOS 41564-41568)
DILMTQSPDSLAVSLGERATINCKSSQSIVHSNGNTYLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

FIG. 18F

>XENP026340 1C11[PD-1]_H3.155_L3.38_IgG1_PVA_/S267K Heavy Chain (SEQ ID NOS 41569-41573)
QIQLVQSGSELKKPGASVKVSCKASGYTFTHYGMNWVRQAPGQGLEWMGWINTYTGEPTYADGFTGRFVFSLDNSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

>XENP026340 1C11[PD-1]_H3.155_L3.38_IgG1_PVA_/S267K Light Chain (SEQ ID NOS 41574-41578)
DVLMTQSPDSLAVSLGERATINCKSSQSIVHSNGNNYLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XENP026341 1C11[PD-1]_H3.155_L3.51_IgG1_PVA_/S267K Heavy Chain (SEQ ID NOS 41579-41583)
QIQLVQSGSELKKPGASVKVSCKASGYTFTHYGMNWVRQAPGQGLEWMGWINTYTGEPTYADGFTGRFVFSLDNSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

>XENP026341 1C11[PD-1]_H3.155_L3.51_IgG1_PVA_/S267K Light Chain (SEQ ID NOS 41584-41588)
DVLMTQSPDSLAVSLGERATINCKSSQSIVHSNGNTYLEWYQQKPGQSPKLLIYSVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XENP026342 1C11[PD-1]_H3.155_L3.59_IgG1_PVA_/S267K Heavy Chain (SEQ ID NOS 41589-41593)
QIQLVQSGSELKKPGASVKVSCKASGYTFTHYGMNWVRQAPGQGLEWMGWINTYTGEPTYADGFTGRFVFSLDNSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

>XENP026342 1C11[PD-1]_H3.155_L3.59_IgG1_PVA_/S267K Light Chain (SEQ ID NOS 41594-41598)
DVLMTQSPDSLAVSLGERATINCKSSQSIVHSNGNTYLEWYQQKPGQSPKLLIYKVSNRFSGVPDRFSGSGSGTDFT
LTISRLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XENP026343 1C11[PD-1]_H3.155_L3.73_IgG1_PVA_/S267K Heavy Chain (SEQ ID NOS 41599-41603)
QIQLVQSGSELKKPGASVKVSCKASGYTFTHYGMNWVRQAPGQGLEWMGWINTYTGEPTYADGFTGRFVFSLDNSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

>XENP026343 1C11[PD-1]_H3.155_L3.73_IgG1_PVA_/S267K Light Chain (SEQ ID NOS 41604-41608)
DVLMTQSPDSLAVSLGERATINCKSSQSIVHSNGNTYLEWYQQKPGQSPKLLIYKVSNRFSGVPDRFSGSGSGTDFT
LTISSLQAEDVATYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

FIG. 18G

>XENP026344 1C11[PD-1]_H3.155_L3.125_IgG1_PVA_/S267K Heavy Chain (SEQ ID NOS 41609-41613)
QIQLVQSGSELKKPGASVKVSCKASGYTFTHYGMNWVRQAPGQGLEWMGWINTYTGEPTYADGFTGRFVFSLDNSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

>XENP026344 1C11[PD-1]_H3.155_L3.125_IgG1_PVA_/S267K Light Chain (SEQ ID NOS 41614-41618)
DVLMTQSPDSLAVSLGERATINCKSSQSIVHSNGNTYLEWYQQKPGQSPKLLIYKVSNRFSGVPDRFSGSGSGTDFT
LTISSVEAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

FIG. 19

| XENP | Variant | $K_D$ (M) | $k_a$ (1/Ms) | $k_d$ (1/s) |
|---|---|---|---|---|
| 26321 | 1C11[PD-1]_H3.59_L3.1 | 1.28E-08 | 1.90E+05 | 2.43E-03 |
| 26322 | 1C11[PD-1]_H3.59_L3.38 | 7.15E-09 | 2.13E+05 | 1.52E-03 |
| 26323 | 1C11[PD-1]_H3.59_L3.51 | 1.54E-08 | 2.23E+05 | 3.44E-03 |
| 26324 | 1C11[PD-1]_H3.59_L3.59 | 1.74E-08 | 1.98E+05 | 3.43E-03 |
| 26325 | 1C11[PD-1]_H3.59_L3.73 | 1.86E-08 | 1.92E+05 | 3.56E-03 |
| 26326 | 1C11[PD-1]_H3.59_L3.125 | 1.78E-08 | 2.05E+05 | 3.64E-03 |
| 26327 | 1C11[PD-1]_H3.135_L3.1 | 1.45E-08 | 2.04E+05 | 2.96E-03 |
| 26328 | 1C11[PD-1]_H3.135_L3.38 | 8.90E-09 | 2.19E+05 | 1.94E-03 |
| 26329 | 1C11[PD-1]_H3.135_L3.51 | 1.86E-08 | 2.10E+05 | 3.90E-03 |
| 26330 | 1C11[PD-1]_H3.135_L3.59 | 1.66E-08 | 2.30E+05 | 3.82E-03 |
| 26331 | 1C11[PD-1]_H3.135_L3.73 | 1.81E-08 | 2.10E+05 | 3.81E-03 |
| 26332 | 1C11[PD-1]_H3.135_L3.125 | 1.92E-08 | 2.05E+05 | 3.93E-03 |
| 26333 | 1C11[PD-1]_H3.138_L3.1 | 1.81E-08 | 1.92E+05 | 3.49E-03 |
| 26334 | 1C11[PD-1]_H3.138_L3.38 | 1.33E-08 | 1.99E+05 | 2.64E-03 |
| 26335 | 1C11[PD-1]_H3.138_L3.51 | 2.61E-08 | 2.01E+05 | 5.25E-03 |
| 26336 | 1C11[PD-1]_H3.138_L3.59 | 1.92E-08 | 2.31E+05 | 4.44E-03 |
| 26337 | 1C11[PD-1]_H3.138_L3.73 | 1.94E-08 | 3.26E+05 | 6.32E-03 |
| 26338 | 1C11[PD-1]_H3.138_L3.125 | 2.20E-08 | 3.19E+05 | 7.01E-03 |
| 26339 | 1C11[PD-1]_H3.155_L3.1 | 1.78E-08 | 3.05E+05 | 5.41E-03 |
| 26340 | 1C11[PD-1]_H3.155_L3.38 | 1.42E-08 | 3.20E+05 | 4.55E-03 |
| 26341 | 1C11[PD-1]_H3.155_L3.51 | 2.86E-08 | 2.80E+05 | 8.01E-03 |
| 26342 | 1C11[PD-1]_H3.155_L3.59 | 2.27E-08 | 3.10E+05 | 7.03E-03 |
| 26343 | 1C11[PD-1]_H3.155_L3.73 | 2.55E-08 | 2.91E+05 | 7.41E-03 |
| 26344 | 1C11[PD-1]_H3.155_L3.125 | 2.03E-08 | 3.66E+05 | 7.41E-03 |
| 22553 | 1C11[PD-1]_H3L3 | 1.94E-08 | 3.24E+05 | 6.29E-03 |

FIG. 20A

>XenD17478 1C11[PD-1]_H3_IgG1_PVA_/S267K (SEQ ID NOS 41619-41623)
QIQLVQSGSELKKPGASVKVSCKASGYTFT<u>HYGMN</u>WVRQAPGQGLEWMG<u>WINTYTGEPTYADGFTGRFVFSLDTSVS</u>
TAYLQISSLKAEDTAVYFCAR<u>DYYGSSPYW</u>GQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

>XenD18576 1C11_H3.59_IgG1_PVA_/S267K (SEQ ID NOS 41624-41628)
QIQLVQSGSELKKPGASVKVSCKASGYTFT<u>HYGMN</u>WVRQAPGQGLEWMG<u>WINTYTGEPTYADGFTGRFVFSLDTSQS</u>
TAYLQISSLKAEDTAVYFCAR<u>DYYGSSPYW</u>GQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

>XenD22097 1C11_H3.242_IgG1_PVA_/S267K (SEQ ID NOS 41629-41633)
QIQLVQSGSELKKPGASVKVSCKASAYTFT<u>HYGMN</u>WVRQAPGQGLEWMG<u>WINTYTGEPTYADGFTGRFVFSLDTSVS</u>
TAYLQISSLKAEDTAVYFCAR<u>DYYGSSPYW</u>GQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

>XenD22098 1C11_H3.243_IgG1_PVA_/S267K (SEQ ID NOS 41634-41638)
QIQLVQSGSELKKPGASVKVSCKASSYTFT<u>HYGMN</u>WVRQAPGQGLEWMG<u>WINTYTGEPTYADGFTGRFVFSLDTSVS</u>
TAYLQISSLKAEDTAVYFCAR<u>DYYGSSPYW</u>GQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

>XenD22099 1C11_H3.244_IgG1_PVA_/S267K (SEQ ID NOS 41639-41643)
QIQLVQSGSELKKPGASVKVSCKASTYTFT<u>HYGMN</u>WVRQAPGQGLEWMG<u>WINTYTGEPTYADGFTGRFVFSLDTSVS</u>
TAYLQISSLKAEDTAVYFCAR<u>DYYGSSPYW</u>GQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

>XenD22100 1C11_H3.245_IgG1_PVA_/S267K (SEQ ID NOS 41644-41648)
QIQLVQSGSELKKPGASVKVSCKASGWTFT<u>HYGMN</u>WVRQAPGQGLEWMG<u>WINTYTGEPTYADGFTGRFVFSLDTSVS</u>
TAYLQISSLKAEDTAVYFCAR<u>DYYGSSPYW</u>GQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

FIG. 20B

>XenD22101 1C11_H3.246_IgG1_PVA_/S267K (SEQ ID NOS 41649-41653)
QIQLVQSGSELKKPGASVKVSCKASGLTFTHYGMNWVRQAPGQGLEWMGWINTYTGEPTYADGFTGRFVFSLDTSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

>XenD22102 1C11_H3.247_IgG1_PVA_/S267K (SEQ ID NOS 41654-41658)
QIQLVQSGSELKKPGASVKVSCKASGHTFTHYGMNWVRQAPGQGLEWMGWINTYTGEPTYADGFTGRFVFSLDTSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

>XenD22103 1C11_H3.248_IgG1_PVA_/S267K (SEQ ID NOS 41659-41663)
QIQLVQSGSELKKPGASVKVSCKASGQTFTHYGMNWVRQAPGQGLEWMGWINTYTGEPTYADGFTGRFVFSLDTSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

>XenD22104 1C11_H3.249_IgG1_PVA_/S267K (SEQ ID NOS 41664-41668)
QIQLVQSGSELKKPGASVKVSCKASGDTFTHYGMNWVRQAPGQGLEWMGWINTYTGEPTYADGFTGRFVFSLDTSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

>XenD22105 1C11_H3.250_IgG1_PVA_/S267K (SEQ ID NOS 41669-41673)
QIQLVQSGSELKKPGASVKVSCKASGKTFTHYGMNWVRQAPGQGLEWMGWINTYTGEPTYADGFTGRFVFSLDTSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

>XenD22106 1C11_H3.251_IgG1_PVA_/S267K (SEQ ID NOS 41674-41678)
QIQLVQSGSELKKPGASVKVSCKASGYVFTHYGMNWVRQAPGQGLEWMGWINTYTGEPTYADGFTGRFVFSLDTSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

FIG. 20C

>XenD22107 1C11_H3.252_IgG1_PVA_/S267K (SEQ ID NOS 41679-41683)
QIQLVQSGSELKKPGASVKVSCKASGYAFTHYGMNWVRQAPGQGLEWMGWINTYTGEPTYADGFTGRFVFSLDTSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

>XenD22108 1C11_H3.253_IgG1_PVA_/S267K (SEQ ID NOS 41684-41688)
QIQLVQSGSELKKPGASVKVSCKASGYIFTHYGMNWVRQAPGQGLEWMGWINTYTGEPTYADGFTGRFVFSLDTSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

>XenD22109 1C11_H3.254_IgG1_PVA_/S267K (SEQ ID NOS 41689-41693)
QIQLVQSGSELKKPGASVKVSCKASGYQFTHYGMNWVRQAPGQGLEWMGWINTYTGEPTYADGFTGRFVFSLDTSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

>XenD22110 1C11_H3.255_IgG1_PVA_/S267K (SEQ ID NOS 41694-41698)
QIQLVQSGSELKKPGASVKVSCKASGYTYTHYGMNWVRQAPGQGLEWMGWINTYTGEPTYADGFTGRFVFSLDTSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

>XenD22111 1C11_H3.256_IgG1_PVA_/S267K (SEQ ID NOS 41699-41703)
QIQLVQSGSELKKPGASVKVSCKASGYTWTHYGMNWVRQAPGQGLEWMGWINTYTGEPTYADGFTGRFVFSLDTSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

>XenD22112 1C11_H3.257_IgG1_PVA_/S267K (SEQ ID NOS 41704-41708)
QIQLVQSGSELKKPGASVKVSCKASGYTHTHYGMNWVRQAPGQGLEWMGWINTYTGEPTYADGFTGRFVFSLDTSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

FIG. 20D

>XenD22113 1C11_H3.258_IgG1_PVA_/S267K (SEQ ID NOS 41709-41713)
QIQLVQSGSELKKPGASVKVSCKASGYTFVHYGMNWVRQAPGQGLEWMGWINTYTGEPTYADGFTGRFVFSLDTSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

>XenD22114 1C11_H3.259_IgG1_PVA_/S267K (SEQ ID NOS 41714-41718)
QIQLVQSGSELKKPGASVKVSCKASGYTFAHYGMNWVRQAPGQGLEWMGWINTYTGEPTYADGFTGRFVFSLDTSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

>XenD22115 1C11_H3.260_IgG1_PVA_/S267K (SEQ ID NOS 41719-41723)
QIQLVQSGSELKKPGASVKVSCKASGYTFIHYGMNWVRQAPGQGLEWMGWINTYTGEPTYADGFTGRFVFSLDTSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

>XenD22116 1C11_H3.261_IgG1_PVA_/S267K (SEQ ID NOS 41724-41728)
QIQLVQSGSELKKPGASVKVSCKASGYTFQHYGMNWVRQAPGQGLEWMGWINTYTGEPTYADGFTGRFVFSLDTSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

>XenD22117 1C11_H3.262_IgG1_PVA_/S267K (SEQ ID NOS 41729-41733)
QIQLVQSGSELKKPGASVKVSCKASGYTFTYYGMNWVRQAPGQGLEWMGWINTYTGEPTYADGFTGRFVFSLDTSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

>XenD22118 1C11_H3.263_IgG1_PVA_/S267K (SEQ ID NOS 41734-41738)
QIQLVQSGSELKKPGASVKVSCKASGYTFTQYGMNWVRQAPGQGLEWMGWINTYTGEPTYADGFTGRFVFSLDTSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

FIG. 20E

>XenD22119 1C11_H3.264_IgG1_PVA_/S267K (SEQ ID NOS 41739-41743)
QIQLVQSGSELKKPGASVKVSCKASGYTFTDYGMNWVRQAPGQGLEWMGWINTYTGEPTYADGFTGRFVFSLDTSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

>XenD22120 1C11_H3.265_IgG1_PVA_/S267K (SEQ ID NOS 41744-41748)
QIQLVQSGSELKKPGASVKVSCKASGYTFTRYGMNWVRQAPGQGLEWMGWINTYTGEPTYADGFTGRFVFSLDTSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

>XenD22121 1C11_H3.266_IgG1_PVA_/S267K (SEQ ID NOS 41749-41753)
QIQLVQSGSELKKPGASVKVSCKASGYTFTFYGMNWVRQAPGQGLEWMGWINTYTGEPTYADGFTGRFVFSLDTSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

>XenD22122 1C11_H3.267_IgG1_PVA_/S267K (SEQ ID NOS 41754-41758)
QIQLVQSGSELKKPGASVKVSCKASGYTFTHFGMNWVRQAPGQGLEWMGWINTYTGEPTYADGFTGRFVFSLDTSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

>XenD22123 1C11_H3.268_IgG1_PVA_/S267K (SEQ ID NOS 41759-41763)
QIQLVQSGSELKKPGASVKVSCKASGYTFTHHGMNWVRQAPGQGLEWMGWINTYTGEPTYADGFTGRFVFSLDTSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

>XenD22124 1C11_H3.269_IgG1_PVA_/S267K (SEQ ID NOS 41764-41768)
QIQLVQSGSELKKPGASVKVSCKASGYTFTHLGMNWVRQAPGQGLEWMGWINTYTGEPTYADGFTGRFVFSLDTSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

FIG. 20F

>XenD22125 1C11_H3.270_IgG1_PVA_/S267K (SEQ ID NOS 41769-41773)
QIQLVQSGSELKKPGASVKVSCKASGYTFTHWGMNWVRQAPGQGLEWMGWINTYTGEPTYADGFTGRFVFSLDTSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

>XenD22126 1C11_H3.271_IgG1_PVA_/S267K (SEQ ID NOS 41774-41778)
QIQLVQSGSELKKPGASVKVSCKASGYTFTHYTMNWVRQAPGQGLEWMGWINTYTGEPTYADGFTGRFVFSLDTSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

>XenD22127 1C11_H3.272_IgG1_PVA_/S267K (SEQ ID NOS 41779-41783)
QIQLVQSGSELKKPGASVKVSCKASGYTFTHYQMNWVRQAPGQGLEWMGWINTYTGEPTYADGFTGRFVFSLDTSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

>XenD22128 1C11_H3.273_IgG1_PVA_/S267K (SEQ ID NOS 41784-41788)
QIQLVQSGSELKKPGASVKVSCKASGYTFTHYGLNWVRQAPGQGLEWMGWINTYTGEPTYADGFTGRFVFSLDTSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

>XenD22129 1C11_H3.274_IgG1_PVA_/S267K (SEQ ID NOS 41789-41793)
QIQLVQSGSELKKPGASVKVSCKASGYTFTHYGMNWLRQAPGQGLEWMGWINTYTGEPTYADGFTGRFVFSLDTSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

>XenD22130 1C11_H3.275_IgG1_PVA_/S267K (SEQ ID NOS 41794-41798)
QIQLVQSGSELKKPGASVKVSCKASGYTFTHYGMNWTRQAPGQGLEWMGWINTYTGEPTYADGFTGRFVFSLDTSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

FIG. 20G

>XenD22131 1C11_H3.276_IgG1_PVA_/S267K (SEQ ID NOS 41799-41803)
QIQLVQSGSELKKPGASVKVSCKASGYTFTHYGMNWFRQAPGQGLEWMGWINTYTGEPTYADGFTGRFVFSLDTSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

>XenD22132 1C11_H3.277_IgG1_PVA_/S267K (SEQ ID NOS 41804-41808)
QIQLVQSGSELKKPGASVKVSCKASGYTFTHYGMNWVRQAPGQGLEWMTWINTYTGEPTYADGFTGRFVFSLDTSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

>XenD22133 1C11_H3.278_IgG1_PVA_/S267K (SEQ ID NOS 41809-41813)
QIQLVQSGSELKKPGASVKVSCKASGYTFTHYGMNWVRQAPGQGLEWMDWINTYTGEPTYADGFTGRFVFSLDTSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

>XenD22134 1C11_H3.279_IgG1_PVA_/S267K (SEQ ID NOS 41814-41818)
QIQLVQSGSELKKPGASVKVSCKASGYTFTHYGMNWVRQAPGQGLEWMQWINTYTGEPTYADGFTGRFVFSLDTSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

>XenD22135 1C11_H3.280_IgG1_PVA_/S267K (SEQ ID NOS 41819-41823)
QIQLVQSGSELKKPGASVKVSCKASGYTFTHYGMNWVRQAPGQGLEWMEWINTYTGEPTYADGFTGRFVFSLDTSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

>XenD22136 1C11_H3.281_IgG1_PVA_/S267K (SEQ ID NOS 41824-41828)
QIQLVQSGSELKKPGASVKVSCKASGYTFTHYGMNWVRQAPGQGLEWMGFINTYTGEPTYADGFTGRFVFSLDTSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

FIG. 20H

>XenD22137 1C11_H3.282_IgG1_PVA_/S267K (SEQ ID NOS 41829-41833)
QIQLVQSGSELKKPGASVKVSCKASGYTFTHYGMNWVRQAPGQGLEWMGHINTYTGEPTYADGFTGRFVFSLDTSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

>XenD22138 1C11_H3.283_IgG1_PVA_/S267K (SEQ ID NOS 41834-41838)
QIQLVQSGSELKKPGASVKVSCKASGYTFTHYGMNWVRQAPGQGLEWMGWIQTYTGEPTYADGFTGRFVFSLDTSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

>XenD22139 1C11_H3.284_IgG1_PVA_/S267K (SEQ ID NOS 41839-41843)
QIQLVQSGSELKKPGASVKVSCKASGYTFTHYGMNWVRQAPGQGLEWMGWIETYTGEPTYADGFTGRFVFSLDTSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

>XenD22140 1C11_H3.285_IgG1_PVA_/S267K (SEQ ID NOS 41844-41848)
QIQLVQSGSELKKPGASVKVSCKASGYTFTHYGMNWVRQAPGQGLEWMGWIHTYTGEPTYADGFTGRFVFSLDTSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

>XenD22141 1C11_H3.286_IgG1_PVA_/S267K (SEQ ID NOS 41849-41853)
QIQLVQSGSELKKPGASVKVSCKASGYTFTHYGMNWVRQAPGQGLEWMGWISTYTGEPTYADGFTGRFVFSLDTSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

>XenD22142 1C11_H3.287_IgG1_PVA_/S267K (SEQ ID NOS 41854-41858)
QIQLVQSGSELKKPGASVKVSCKASGYTFTHYGMNWVRQAPGQGLEWMGWINTFTGEPTYADGFTGRFVFSLDTSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

FIG. 201

>XenD22143 1C11_H3.288_IgG1_PVA_/S267K (SEQ ID NOS 41859-41863)
QIQLVQSGSELKKPGASVKVSCKASGYTFTHYGMNWVRQAPGQGLEWMGWINTHTGEPTYADGFTGRFVFSLDTSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

>XenD22144 1C11_H3.289_IgG1_PVA_/S267K (SEQ ID NOS 41864-41868)
QIQLVQSGSELKKPGASVKVSCKASGYTFTHYGMNWVRQAPGQGLEWMGWINTLTGEPTYADGFTGRFVFSLDTSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

>XenD22145 1C11_H3.290_IgG1_PVA_/S267K (SEQ ID NOS 41869-41873)
QIQLVQSGSELKKPGASVKVSCKASGYTFTHYGMNWVRQAPGQGLEWMGWINTWTGEPTYADGFTGRFVFSLDTSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

>XenD22146 1C11_H3.291_IgG1_PVA_/S267K (SEQ ID NOS 41874-41878)
QIQLVQSGSELKKPGASVKVSCKASGYTFTHYGMNWVRQAPGQGLEWMGWINTYVGEPTYADGFTGRFVFSLDTSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

>XenD22147 1C11_H3.292_IgG1_PVA_/S267K (SEQ ID NOS 41879-41883)
QIQLVQSGSELKKPGASVKVSCKASGYTFTHYGMNWVRQAPGQGLEWMGWINTYSGEPTYADGFTGRFVFSLDTSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

>XenD22148 1C11_H3.293_IgG1_PVA_/S267K (SEQ ID NOS 41884-41888)
QIQLVQSGSELKKPGASVKVSCKASGYTFTHYGMNWVRQAPGQGLEWMGWINTYAGEPTYADGFTGRFVFSLDTSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

FIG. 20J

>XenD22149 1C11_H3.294_IgG1_PVA_/S267K (SEQ ID NOS 41889-41893)
QIQLVQSGSELKKPGASVKVSCKASGYTFTHYGMNWVRQAPGQGLEWMGWINTYIGEPTYADGFTGRFVFSLDTSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

>XenD22150 1C11_H3.295_IgG1_PVA_/S267K (SEQ ID NOS 41894-41898)
QIQLVQSGSELKKPGASVKVSCKASGYTFTHYGMNWVRQAPGQGLEWMGWINTYTGQPTYADGFTGRFVFSLDTSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

>XenD22151 1C11_H3.296_IgG1_PVA_/S267K (SEQ ID NOS 41899-41903)
QIQLVQSGSELKKPGASVKVSCKASGYTFTHYGMNWVRQAPGQGLEWMGWINTYTGKPTYADGFTGRFVFSLDTSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

>XenD22152 1C11_H3.297_IgG1_PVA_/S267K (SEQ ID NOS 41904-41908)
QIQLVQSGSELKKPGASVKVSCKASGYTFTHYGMNWVRQAPGQGLEWMGWINTYTGEPTYADGFTGRFVFSLDTSVS
TAYLQISSLKAEDTAVYFCARDFYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

>XenD22153 1C11_H3.298_IgG1_PVA_/S267K (SEQ ID NOS 41909-41913)
QIQLVQSGSELKKPGASVKVSCKASGYTFTHYGMNWVRQAPGQGLEWMGWINTYTGEPTYADGFTGRFVFSLDTSVS
TAYLQISSLKAEDTAVYFCARDQYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

>XenD22154 1C11_H3.299_IgG1_PVA_/S267K (SEQ ID NOS 41914-41918)
QIQLVQSGSELKKPGASVKVSCKASGYTFTHYGMNWVRQAPGQGLEWMGWINTYTGEPTYADGFTGRFVFSLDTSVS
TAYLQISSLKAEDTAVYFCARDHYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

FIG. 20K

>XenD22155 1C11_H3.300_IgG1_PVA_/S267K (SEQ ID NOS 41919-41923)
QIQLVQSGSELKKPGASVKVSCKASGYTFTHYGMNWVRQAPGQGLEWMGWINTYTGEPTYADGFTGRFVFSLDTSVS
TAYLQISSLKAEDTAVYFCARDRYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

>XenD22156 1C11_H3.301_IgG1_PVA_/S267K (SEQ ID NOS 41924-41928)
QIQLVQSGSELKKPGASVKVSCKASGYTFTHYGMNWVRQAPGQGLEWMGWINTYTGEPTYADGFTGRFVFSLDTSVS
TAYLQISSLKAEDTAVYFCARDKYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

>XenD22157 1C11_H3.302_IgG1_PVA_/S267K (SEQ ID NOS 41929-41933)
QIQLVQSGSELKKPGASVKVSCKASGYTFTHYGMNWVRQAPGQGLEWMGWINTYTGEPTYADGFTGRFVFSLDTSVS
TAYLQISSLKAEDTAVYFCARDYWGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

>XenD22158 1C11_H3.303_IgG1_PVA_/S267K (SEQ ID NOS 41934-41938)
QIQLVQSGSELKKPGASVKVSCKASGYTFTHYGMNWVRQAPGQGLEWMGWINTYTGEPTYADGFTGRFVFSLDTSVS
TAYLQISSLKAEDTAVYFCARDYFGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

>XenD22159 1C11_H3.304_IgG1_PVA_/S267K (SEQ ID NOS 41939-41943)
QIQLVQSGSELKKPGASVKVSCKASGYTFTHYGMNWVRQAPGQGLEWMGWINTYTGEPTYADGFTGRFVFSLDTSVS
TAYLQISSLKAEDTAVYFCARDYYASSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

>XenD22160 1C11_H3.305_IgG1_PVA_/S267K (SEQ ID NOS 41944-41948)
QIQLVQSGSELKKPGASVKVSCKASGYTFTHYGMNWVRQAPGQGLEWMGWINTYTGEPTYADGFTGRFVFSLDTSVS
TAYLQISSLKAEDTAVYFCARDYYSSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

FIG. 20L

>XenD22161 1C11_H3.306_IgG1_PVA_/S267K (SEQ ID NOS 41949-41953)
QIQLVQSGSELKKPGASVKVSCKASGYTFTHYGMNWVRQAPGQGLEWMGWINTYTGEPTYADGFTGRFVFSLDTSVS
TAYLQISSLKAEDTAVYFCARDYYGSSPFWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

>XenD22162 1C11_H3.307_IgG1_PVA_/S267K (SEQ ID NOS 41954-41958)
QIQLVQSGSELKKPGASVKVSCKASGYTFTHYGMNWVRQAPGQGLEWMGWINTYTGEPTYADGFTGRFVFSLDTSVS
TAYLQISSLKAEDTAVYFCARDYYGSSPWWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

FIG. 21A

>XenD17482 1C11[PD-1]_L3 (SEQ ID NOS 41959-41963)
DVLMTQSPDSLAVSLGERATINCKSSQSIVHSNGNTYLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XenD18472 1C11_L3.38 (SEQ ID NOS 41964-41968)
DVLMTQSPDSLAVSLGERATINCKSSQSIVHSNGNNYLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XenD22163 1C11[PD-1]_L3.149 (SEQ ID NOS 41969-41973)
DVLMTQSPDSLAVSLGERATINCKSSQSIVYSNGNTYLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XenD22164 1C11[PD-1]_L3.150 (SEQ ID NOS 41974-41978)
DVLMTQSPDSLAVSLGERATINCKSSQSIVQSNGNTYLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XenD22165 1C11[PD-1]_L3.151 (SEQ ID NOS 41979-41983)
DVLMTQSPDSLAVSLGERATINCKSSQSIVDSNGNTYLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XenD22166 1C11[PD-1]_L3.152 (SEQ ID NOS 41984-41988)
DVLMTQSPDSLAVSLGERATINCKSSQSIVFSNGNTYLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XenD22167 1C11[PD-1]_L3.153 (SEQ ID NOS 41989-41993)
DVLMTQSPDSLAVSLGERATINCKSSQSIVTSNGNTYLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XenD22168 1C11[PD-1]_L3.154 (SEQ ID NOS 41994-41998)
DVLMTQSPDSLAVSLGERATINCKSSQSIVKSNGNTYLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XenD22169 1C11[PD-1]_L3.155 (SEQ ID NOS 41999-42003)
DVLMTQSPDSLAVSLGERATINCKSSQSIVHTNGNTYLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XenD22170 1C11[PD-1]_L3.156 (SEQ ID NOS 42004-42008)
DVLMTQSPDSLAVSLGERATINCKSSQSIVHANGNTYLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

FIG. 21B

>XenD22171 1C11[PD-1]_L3.157 (SEQ ID NOS 42009-42013)
DVLMTQSPDSLAVSLGERATINCKSSQSIVHQNGNTYLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XenD22172 1C11[PD-1]_L3.158 (SEQ ID NOS 42014-42018)
DVLMTQSPDSLAVSLGERATINCKSSQSIVHGNGNTYLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XenD22173 1C11[PD-1]_L3.159 (SEQ ID NOS 42019-42023)
DVLMTQSPDSLAVSLGERATINCKSSQSIVHVNGNTYLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XenD22174 1C11[PD-1]_L3.160 (SEQ ID NOS 42024-42028)
DVLMTQSPDSLAVSLGERATINCKSSQSIVHSHGNTYLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XenD22175 1C11[PD-1]_L3.161 (SEQ ID NOS 42029-42033)
DVLMTQSPDSLAVSLGERATINCKSSQSIVHSEGNTYLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XenD22176 1C11[PD-1]_L3.162 (SEQ ID NOS 42034-42038)
DVLMTQSPDSLAVSLGERATINCKSSQSIVHSSGNTYLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XenD22177 1C11[PD-1]_L3.163 (SEQ ID NOS 42039-42043)
DVLMTQSPDSLAVSLGERATINCKSSQSIVHSRGNTYLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XenD22178 1C11[PD-1]_L3.164 (SEQ ID NOS 42044-42048)
DVLMTQSPDSLAVSLGERATINCKSSQSIVHSLGNTYLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XenD22179 1C11[PD-1]_L3.165 (SEQ ID NOS 42049-42053)
DVLMTQSPDSLAVSLGERATINCKSSQSIVHSNANTYLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XenD22180 1C11[PD-1]_L3.166 (SEQ ID NOS 42054-42058)
DVLMTQSPDSLAVSLGERATINCKSSQSIVHSNSNTYLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

FIG. 21C

>XenD22181 1C11[PD-1]_L3.167 (SEQ ID NOS 42059-42063)
DVLMTQSPDSLAVSLGERATINCKSSQSIVHSNTNTYLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XenD22182 1C11[PD-1]_L3.168 (SEQ ID NOS 42064-42068)
DVLMTQSPDSLAVSLGERATINCKSSQSIVHSNQNTYLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XenD22183 1C11[PD-1]_L3.169 (SEQ ID NOS 42069-42073)
DVLMTQSPDSLAVSLGERATINCKSSQSIVHSNGDTYLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XenD22184 1C11[PD-1]_L3.170 (SEQ ID NOS 42074-42078)
DVLMTQSPDSLAVSLGERATINCKSSQSIVHSNGHTYLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XenD22185 1C11[PD-1]_L3.171 (SEQ ID NOS 42079-42083)
DVLMTQSPDSLAVSLGERATINCKSSQSIVHSNGETYLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XenD22186 1C11[PD-1]_L3.172 (SEQ ID NOS 42084-42088)
DVLMTQSPDSLAVSLGERATINCKSSQSIVHSNGRTYLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XenD22187 1C11[PD-1]_L3.173 (SEQ ID NOS 42089-42093)
DVLMTQSPDSLAVSLGERATINCKSSQSIVHSNGNTFLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XenD22188 1C11[PD-1]_L3.174 (SEQ ID NOS 42094-42098)
DVLMTQSPDSLAVSLGERATINCKSSQSIVHSNGNTHLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XenD22189 1C11[PD-1]_L3.175 (SEQ ID NOS 42099-42103)
DVLMTQSPDSLAVSLGERATINCKSSQSIVHSNGNTLLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XenD22190 1C11[PD-1]_L3.176 (SEQ ID NOS 42104-42108)
DVLMTQSPDSLAVSLGERATINCKSSQSIVHSNGNTWLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

FIG. 21D

>XenD22191 1C11[PD-1]_L3.177 (SEQ ID NOS 42109-42113)
DVLMTQSPDSLAVSLGERATINCKSSQSIVHSNGNTQLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XenD22192 1C11[PD-1]_L3.178 (SEQ ID NOS 42114-42118)
DVLMTQSPDSLAVSLGERATINCKSSQSIVHSNGNTYLEWYQQKPGQSPKLLIFKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XenD22193 1C11[PD-1]_L3.179 (SEQ ID NOS 42119-42123)
DVLMTQSPDSLAVSLGERATINCKSSQSIVHSNGNTYLEWYQQKPGQSPKLLIHKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XenD22194 1C11[PD-1]_L3.180 (SEQ ID NOS 42124-42128)
DVLMTQSPDSLAVSLGERATINCKSSQSIVHSNGNTYLEWYQQKPGQSPKLLILKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XenD22195 1C11[PD-1]_L3.181 (SEQ ID NOS 42129-42133)
DVLMTQSPDSLAVSLGERATINCKSSQSIVHSNGNTYLEWYQQKPGQSPKLLIWKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XenD22196 1C11[PD-1]_L3.182 (SEQ ID NOS 42134-42138)
DVLMTQSPDSLAVSLGERATINCKSSQSIVHSNGNTYLEWYQQKPGQSPKLLIQKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XenD22197 1C11[PD-1]_L3.183 (SEQ ID NOS 42139-42143)
DVLMTQSPDSLAVSLGERATINCKSSQSIVHSNGNTYLEWYQQKPGQSPKLLIYKISNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XenD22198 1C11[PD-1]_L3.184 (SEQ ID NOS 42144-42148)
DVLMTQSPDSLAVSLGERATINCKSSQSIVHSNGNTYLEWYQQKPGQSPKLLIYKLSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XenD22199 1C11[PD-1]_L3.185 (SEQ ID NOS 42149-42153)
DVLMTQSPDSLAVSLGERATINCKSSQSIVHSNGNTYLEWYQQKPGQSPKLLIYKSSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XenD22200 1C11[PD-1]_L3.186 (SEQ ID NOS 42154-42158)
DVLMTQSPDSLAVSLGERATINCKSSQSIVHSNGNTYLEWYQQKPGQSPKLLIYKVSDRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

FIG. 21E

>XenD22201 1C11[PD-1]_L3.187 (SEQ ID NOS 42159-42163)
DVLMTQSPDSLAVSLGERATINCKSSQSIVHSNGNTYLEWYQQKPGQSPKLLIYKVSHRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XenD22202 1C11[PD-1]_L3.188 (SEQ ID NOS 42164-42168)
DVLMTQSPDSLAVSLGERATINCKSSQSIVHSNGNTYLEWYQQKPGQSPKLLIYKVSERFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XenD22203 1C11[PD-1]_L3.189 (SEQ ID NOS 42169-42173)
DVLMTQSPDSLAVSLGERATINCKSSQSIVHSNGNTYLEWYQQKPGQSPKLLIYKVSRRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XenD22204 1C11[PD-1]_L3.190 (SEQ ID NOS 42174-42178)
DVLMTQSPDSLAVSLGERATINCKSSQSIVHSNGNTYLEWYQQKPGQSPKLLIYKVSNRFSGVPDRFSGSGSGTDFT
LTISSLQAEDVAVYYCMQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XenD22205 1C11[PD-1]_L3.191 (SEQ ID NOS 42179-42183)
DVLMTQSPDSLAVSLGERATINCKSSQSIVHSNGNTYLEWYQQKPGQSPKLLIYKVSNRFSGVPDRFSGSGSGTDFT
LTISSLQAEDVAVYYCEQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XenD22206 1C11[PD-1]_L3.192 (SEQ ID NOS 42184-42188)
DVLMTQSPDSLAVSLGERATINCKSSQSIVHSNGNTYLEWYQQKPGQSPKLLIYKVSNRFSGVPDRFSGSGSGTDFT
LTISSLQAEDVAVYYCFQASHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XenD22207 1C11[PD-1]_L3.193 (SEQ ID NOS 42189-42193)
DVLMTQSPDSLAVSLGERATINCKSSQSIVHSNGNTYLEWYQQKPGQSPKLLIYKVSNRFSGVPDRFSGSGSGTDFT
LTISSLQAEDVAVYYCFQSSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XenD22208 1C11[PD-1]_L3.194 (SEQ ID NOS 42194-42198)
DVLMTQSPDSLAVSLGERATINCKSSQSIVHSNGNTYLEWYQQKPGQSPKLLIYKVSNRFSGVPDRFSGSGSGTDFT
LTISSLQAEDVAVYYCFQDSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XenD22209 1C11[PD-1]_L3.195 (SEQ ID NOS 42199-42203)
DVLMTQSPDSLAVSLGERATINCKSSQSIVHSNGNTYLEWYQQKPGQSPKLLIYKVSNRFSGVPDRFSGSGSGTDFT
LTISSLQAEDVAVYYCFQTSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XenD22210 1C11[PD-1]_L3.196 (SEQ ID NOS 42204-42208)
DVLMTQSPDSLAVSLGERATINCKSSQSIVHSNGNTYLEWYQQKPGQSPKLLIYKVSNRFSGVPDRFSGSGSGTDFT
LTISSLQAEDVAVYYCFQQSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

FIG. 21F

>XenD22211 1C11[PD-1]_L3.197 (SEQ ID NOS 42209-42213)
DVLMTQSPDSLAVSLGERATINCKSSQSIVHSNGNTYLEWYQQKPGQSPKLLIYKVSNRFSGVPDRFSGSGSGTDFT
LTISSLQAEDVAVYYCFQHSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XenD22212 1C11[PD-1]_L3.198 (SEQ ID NOS 42214-42218)
DVLMTQSPDSLAVSLGERATINCKSSQSIVHSNGNTYLEWYQQKPGQSPKLLIYKVSNRFSGVPDRFSGSGSGTDFT
LTISSLQAEDVAVYYCFQLSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XenD22213 1C11[PD-1]_L3.199 (SEQ ID NOS 42219-42223)
DVLMTQSPDSLAVSLGERATINCKSSQSIVHSNGNTYLEWYQQKPGQSPKLLIYKVSNRFSGVPDRFSGSGSGTDFT
LTISSLQAEDVAVYYCFQRSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XenD22214 1C11[PD-1]_L3.200 (SEQ ID NOS 42224-42228)
DVLMTQSPDSLAVSLGERATINCKSSQSIVHSNGNTYLEWYQQKPGQSPKLLIYKVSNRFSGVPDRFSGSGSGTDFT
LTISSLQAEDVAVYYCFQFSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XenD22215 1C11[PD-1]_L3.201 (SEQ ID NOS 42229-42233)
DVLMTQSPDSLAVSLGERATINCKSSQSIVHSNGNTYLEWYQQKPGQSPKLLIYKVSNRFSGVPDRFSGSGSGTDFT
LTISSLQAEDVAVYYCFQGTHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XenD22216 1C11[PD-1]_L3.202 (SEQ ID NOS 42234-42238)
DVLMTQSPDSLAVSLGERATINCKSSQSIVHSNGNTYLEWYQQKPGQSPKLLIYKVSNRFSGVPDRFSGSGSGTDFT
LTISSLQAEDVAVYYCFQGAHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XenD22217 1C11[PD-1]_L3.203 (SEQ ID NOS 42239-42243)
DVLMTQSPDSLAVSLGERATINCKSSQSIVHSNGNTYLEWYQQKPGQSPKLLIYKVSNRFSGVPDRFSGSGSGTDFT
LTISSLQAEDVAVYYCFQGQHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XenD22218 1C11[PD-1]_L3.204 (SEQ ID NOS 42244-42248)
DVLMTQSPDSLAVSLGERATINCKSSQSIVHSNGNTYLEWYQQKPGQSPKLLIYKVSNRFSGVPDRFSGSGSGTDFT
LTISSLQAEDVAVYYCFQGVHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XenD22219 1C11[PD-1]_L3.205 (SEQ ID NOS 42249-42253)
DVLMTQSPDSLAVSLGERATINCKSSQSIVHSNGNTYLEWYQQKPGQSPKLLIYKVSNRFSGVPDRFSGSGSGTDFT
LTISSLQAEDVAVYYCFQGSYVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XenD22220 1C11[PD-1]_L3.206 (SEQ ID NOS 42254-42258)
DVLMTQSPDSLAVSLGERATINCKSSQSIVHSNGNTYLEWYQQKPGQSPKLLIYKVSNRFSGVPDRFSGSGSGTDFT
LTISSLQAEDVAVYYCFQGSQVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

FIG. 21G

>XenD22221 1C11[PD-1]_L3.207 (SEQ ID NOS 42259-42263)
DVLMTQSPDSLAVSLGERATINCKSSQSIVHSNGNTYLEWYQQKPGQSPKLLIYKVSNRFSGVPDRFSGSGSGTDFT
LTISSLQAEDVAVYYCFQGSDVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XenD22222 1C11[PD-1]_L3.208 (SEQ ID NOS 42264-42268)
DVLMTQSPDSLAVSLGERATINCKSSQSIVHSNGNTYLEWYQQKPGQSPKLLIYKVSNRFSGVPDRFSGSGSGTDFT
LTISSLQAEDVAVYYCFQGSFVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XenD22223 1C11[PD-1]_L3.209 (SEQ ID NOS 42269-42273)
DVLMTQSPDSLAVSLGERATINCKSSQSIVHSNGNTYLEWYQQKPGQSPKLLIYKVSNRFSGVPDRFSGSGSGTDFT
LTISSLQAEDVAVYYCFQGSTVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

FIG. 22A

| Variant Name | HC XenD | LC XenD | VH Variants | VL Variants | $K_D$ (M) | $k_a$ (1/Ms) | $k_d$ (1/s) |
|---|---|---|---|---|---|---|---|
| 1C11_H3L3 | XenD17478 | XenD17482 | - | - | 5.35E-08 | 2.27E+05 | 1.22E-02 |
| 1C11_H3.59_L3.38 | XenD18576 | XenD18472 | V80Q | T37N | 1.57E-08 | 3.08E+05 | 4.83E-03 |
| 1C11_H3.242_L3 | XenD22097 | XenD17482 | G26A | - | 3.65E-08 | 2.92E+05 | 1.07E-02 |
| 1C11_H3.243_L3 | XenD22098 | XenD17482 | G26S | - | 3.08E-08 | 3.96E+05 | 1.22E-02 |
| 1C11_H3.244_L3 | XenD22099 | XenD17482 | G26T | - | 1.46E-08 | 3.82E+05 | 5.56E-03 |
| 1C11_H3.245_L3 | XenD22100 | XenD17482 | Y27W | - | 2.94E-08 | 5.02E+05 | 1.48E-02 |
| 1C11_H3.246_L3 | XenD22101 | XenD17482 | Y27L | - | 8.55E-08 | 5.15E+05 | 4.41E-02 |
| 1C11_H3.247_L3 | XenD22102 | XenD17482 | Y27H | - | 1.38E-07 | 2.73E+05 | 3.76E-02 |
| 1C11_H3.248_L3 | XenD22103 | XenD17482 | Y27Q | - | 1.06E-07 | 3.44E+05 | 3.66E-02 |
| 1C11_H3.249_L3 | XenD22104 | XenD17482 | Y27D | - | 4.70E-08 | 4.63E+05 | 2.18E-02 |
| 1C11_H3.250_L3 | XenD22105 | XenD17482 | Y27K | - | 1.50E-08 | 6.61E+05 | 9.88E-03 |
| 1C11_H3.251_L3 | XenD22106 | XenD17482 | T28V | - | 3.37E-08 | 2.48E+05 | 8.35E-03 |
| 1C11_H3.252_L3 | XenD22107 | XenD17482 | T28A | - | 7.63E-08 | 2.57E+05 | 1.96E-02 |
| 1C11_H3.253_L3 | XenD22108 | XenD17482 | T28I | - | 7.03E-08 | 2.86E+05 | 2.01E-02 |
| 1C11_H3.254_L3 | XenD22109 | XenD17482 | T28Q | - | 8.07E-08 | 2.15E+05 | 1.73E-02 |
| 1C11_H3.255_L3 | XenD22110 | XenD17482 | F29Y | - | 2.81E-08 | 3.45E+05 | 9.70E-03 |
| 1C11_H3.256_L3 | XenD22111 | XenD17482 | F29W | - | 1.86E-08 | 4.70E+05 | 8.73E-03 |
| 1C11_H3.257_L3 | XenD22112 | XenD17482 | F29H | - | 7.52E-08 | 6.83E+05 | 5.14E-02 |
| 1C11_H3.258_L3 | XenD22113 | XenD17482 | T30V | - | 1.56E-08 | 2.99E+05 | 4.68E-03 |
| 1C11_H3.259_L3 | XenD22114 | XenD17482 | T30A | - | 3.48E-08 | 3.72E+05 | 1.29E-02 |
| 1C11_H3.260_L3 | XenD22115 | XenD17482 | T30I | - | 4.18E-08 | 2.64E+05 | 1.11E-02 |
| 1C11_H3.261_L3 | XenD22116 | XenD17482 | T30Q | - | 3.05E-08 | 1.98E+05 | 6.04E-03 |
| 1C11_H3.262_L3 | XenD22117 | XenD17482 | H31Y | - | 5.45E-08 | 3.56E+05 | 1.94E-02 |
| 1C11_H3.263_L3 | XenD22118 | XenD17482 | H31Q | - | 1.15E-07 | 4.80E+05 | 5.49E-02 |
| 1C11_H3.264_L3 | XenD22119 | XenD17482 | H31D | - | 8.37E-08 | 4.58E+05 | 3.83E-02 |
| 1C11_H3.265_L3 | XenD22120 | XenD17482 | H31R | - | 1.60E-07 | 4.80E+05 | 7.66E-02 |
| 1C11_H3.266_L3 | XenD22121 | XenD17482 | H31F | - | 7.75E-08 | 5.45E+05 | 4.22E-02 |
| 1C11_H3.267_L3 | XenD22122 | XenD17482 | Y34F | - | 4.88E-08 | 4.38E+05 | 2.14E-02 |
| 1C11_H3.268_L3 | XenD22123 | XenD17482 | Y34H | - | 6.76E-08 | 2.63E+05 | 1.78E-02 |

FIG. 22B

| Variant Name | HC XenD | LC XenD | VH Variants | VL Variants | K$_D$ (M) | k$_a$ (1/Ms) | k$_d$ (1/s) |
|---|---|---|---|---|---|---|---|
| 1C11_H3.269_L3 | XenD22124 | XenD17482 | Y34L | - | 1.03E-07 | 4.99E+05 | 5.14E-02 |
| 1C11_H3.270_L3 | XenD22125 | XenD17482 | Y34W | - | 6.17E-08 | 4.47E+05 | 2.76E-02 |
| 1C11_H3.271_L3 | XenD22126 | XenD17482 | G35T | - | | | |
| 1C11_H3.272_L3 | XenD22127 | XenD17482 | G35Q | - | | | |
| 1C11_H3.273_L3 | XenD22128 | XenD17482 | M36L | - | 4.82E-08 | 4.15E+05 | 2.00E-02 |
| 1C11_H3.274_L3 | XenD22129 | XenD17482 | V39L | - | 4.14E-08 | 3.21E+05 | 1.33E-02 |
| 1C11_H3.275_L3 | XenD22130 | XenD17482 | V39T | - | | | |
| 1C11_H3.276_L3 | XenD22131 | XenD17482 | V39F | - | 1.42E-07 | 4.07E+05 | 5.76E-02 |
| 1C11_H3.277_L3 | XenD22132 | XenD17482 | G51T | - | | | |
| 1C11_H3.278_L3 | XenD22133 | XenD17482 | G51D | - | | | |
| 1C11_H3.279_L3 | XenD22134 | XenD17482 | G51Q | - | | | |
| 1C11_H3.280_L3 | XenD22135 | XenD17482 | G51E | - | | | |
| 1C11_H3.281_L3 | XenD22136 | XenD17482 | W52F | - | 2.64E-07 | 9.36E+05 | 2.47E-01 |
| 1C11_H3.282_L3 | XenD22137 | XenD17482 | W52H | - | | | |
| 1C11_H3.283_L3 | XenD22138 | XenD17482 | N54Q | - | 2.10E-07 | 6.90E+05 | 1.45E-01 |
| 1C11_H3.284_L3 | XenD22139 | XenD17482 | N54E | - | 1.06E-07 | 1.66E+06 | 1.75E-01 |
| 1C11_H3.285_L3 | XenD22140 | XenD17482 | N54H | - | 2.10E-07 | 1.17E+06 | 2.45E-01 |
| 1C11_H3.286_L3 | XenD22141 | XenD17482 | N54S | - | 1.66E-07 | 7.93E+05 | 1.32E-01 |
| 1C11_H3.287_L3 | XenD22142 | XenD17482 | Y56F | - | 5.24E-08 | 4.32E+05 | 2.26E-02 |
| 1C11_H3.288_L3 | XenD22143 | XenD17482 | Y56H | - | 2.05E-08 | 3.45E+05 | 7.08E-03 |
| 1C11_H3.289_L3 | XenD22144 | XenD17482 | Y56L | - | 9.79E-08 | 3.36E+05 | 3.29E-02 |
| 1C11_H3.290_L3 | XenD22145 | XenD17482 | Y56W | - | 8.91E-08 | 3.37E+05 | 3.00E-02 |
| 1C11_H3.291_L3 | XenD22146 | XenD17482 | T59V | - | 5.44E-08 | 4.71E+05 | 2.56E-02 |
| 1C11_H3.292_L3 | XenD22147 | XenD17482 | T59S | - | 3.16E-08 | 3.08E+05 | 9.72E-03 |
| 1C11_H3.293_L3 | XenD22148 | XenD17482 | T59A | - | 4.33E-08 | 3.67E+05 | 1.59E-02 |
| 1C11_H3.294_L3 | XenD22149 | XenD17482 | T59I | - | 1.53E-07 | 3.40E+05 | 5.22E-02 |
| 1C11_H3.295_L3 | XenD22150 | XenD17482 | E61Q | - | 6.46E-08 | 3.06E+05 | 1.98E-02 |
| 1C11_H3.296_L3 | XenD22151 | XenD17482 | E61K | - | 1.20E-07 | 2.01E+05 | 2.42E-02 |
| 1C11_H3.297_L3 | XenD22152 | XenD17482 | Y110F | - | 3.99E-08 | 3.68E+05 | 1.47E-02 |

FIG. 22C

| Variant Name | HC XenD | LC XenD | VH Variants | VL Variants | $K_D$ (M) | $k_a$ (1/Ms) | $k_d$ (1/s) |
|---|---|---|---|---|---|---|---|
| 1C11_H3.298_L3 | XenD22153 | XenD17482 | Y110Q | - | 4.00E-08 | 3.93E+05 | 1.57E-02 |
| 1C11_H3.299_L3 | XenD22154 | XenD17482 | Y110H | - | 4.16E-08 | 4.67E+05 | 1.94E-02 |
| 1C11_H3.300_L3 | XenD22155 | XenD17482 | Y110R | - | 2.99E-08 | 3.00E+05 | 8.98E-03 |
| 1C11_H3.301_L3 | XenD22156 | XenD17482 | Y110K | - | 7.04E-08 | 4.22E+05 | 2.97E-02 |
| 1C11_H3.302_L3 | XenD22157 | XenD17482 | Y111W | - | 4.23E-07 | 2.37E+05 | 1.00E-01 |
| 1C11_H3.303_L3 | XenD22158 | XenD17482 | Y111F | - | 1.37E-08 | 2.67E+05 | 3.66E-03 |
| 1C11_H3.304_L3 | XenD22159 | XenD17482 | G112A | - | 2.98E-07 | 3.29E+05 | 9.81E-02 |
| 1C11_H3.305_L3 | XenD22160 | XenD17482 | G112S | - | 7.23E-07 | 1.29E+05 | 9.35E-02 |
| 1C11_H3.306_L3 | XenD22161 | XenD17482 | Y116F | - | 3.62E-08 | 3.34E+05 | 1.21E-02 |
| 1C11_H3.307_L3 | XenD22162 | XenD17482 | Y116W | - | 6.87E-08 | 2.99E+05 | 2.05E-02 |
| 1C11_H3_L3.149 | XenD17478 | XenD22163 | - | H31Y | 5.36E-09 | 3.71E+05 | 1.99E-03 |
| 1C11_H3_L3.150 | XenD17478 | XenD22164 | - | H31Q | 1.64E-06 | 1.89E+05 | 3.11E-01 |
| 1C11_H3_L3.151 | XenD17478 | XenD22165 | - | H31D | 1.94E-06 | 1.39E+05 | 2.69E-01 |
| 1C11_H3_L3.152 | XenD17478 | XenD22166 | - | H31F | 2.88E-09 | 4.05E+05 | 1.17E-03 |
| 1C11_H3_L3.153 | XenD17478 | XenD22167 | - | H31T | 2.71E-07 | 1.22E+06 | 3.30E-01 |
| 1C11_H3_L3.154 | XenD17478 | XenD22168 | - | H31K | 8.36E-08 | 3.83E+06 | 3.20E-01 |
| 1C11_H3_L3.155 | XenD17478 | XenD22169 | - | S32T | 7.09E-08 | 2.95E+05 | 2.09E-02 |
| 1C11_H3_L3.156 | XenD17478 | XenD22170 | - | S32A | 4.05E-08 | 3.78E+05 | 1.53E-02 |
| 1C11_H3_L3.157 | XenD17478 | XenD22171 | - | S32Q | 7.70E-08 | 2.89E+05 | 2.22E-02 |
| 1C11_H3_L3.158 | XenD17478 | XenD22172 | - | S32G | 4.47E-08 | 2.52E+05 | 1.13E-02 |
| 1C11_H3_L3.159 | XenD17478 | XenD22173 | - | S32V | 4.54E-08 | 3.28E+05 | 1.49E-02 |
| 1C11_H3_L3.160 | XenD17478 | XenD22174 | - | N33H | 2.46E-08 | 7.40E+05 | 1.82E-02 |
| 1C11_H3_L3.161 | XenD17478 | XenD22175 | - | N33E | 2.51E-08 | 8.32E+05 | 2.09E-02 |
| 1C11_H3_L3.162 | XenD17478 | XenD22176 | - | N33S | 5.26E-08 | 4.53E+05 | 2.38E-02 |
| 1C11_H3_L3.163 | XenD17478 | XenD22177 | - | N33R | 9.95E-08 | 5.83E+05 | 5.80E-02 |
| 1C11_H3_L3.164 | XenD17478 | XenD22178 | - | N33L | 3.48E-08 | 7.39E+05 | 2.57E-02 |
| 1C11_H3_L3.165 | XenD17478 | XenD22179 | - | G34A | 3.22E-08 | 3.04E+05 | 9.76E-03 |
| 1C11_H3_L3.166 | XenD17478 | XenD22180 | - | G34S | 1.88E-08 | 4.56E+05 | 8.57E-03 |
| 1C11_H3_L3.167 | XenD17478 | XenD22181 | - | G34T | 2.52E-08 | 4.26E+05 | 1.07E-02 |

FIG. 22D

| Variant Name | HC XenD | LC XenD | VH Variants | VL Variants | $K_D$ (M) | $k_a$ (1/Ms) | $k_d$ (1/s) |
|---|---|---|---|---|---|---|---|
| 1C11_H3_L3.168 | XenD17478 | XenD22182 | - | G34Q | 1.22E-08 | 4.73E+05 | 5.75E-03 |
| 1C11_H3_L3.169 | XenD17478 | XenD22183 | - | N35D | 4.98E-08 | 3.34E+05 | 1.66E-02 |
| 1C11_H3_L3.170 | XenD17478 | XenD22184 | - | N35H | 3.64E-08 | 3.67E+05 | 1.34E-02 |
| 1C11_H3_L3.171 | XenD17478 | XenD22185 | - | N35E | 5.63E-08 | 3.60E+05 | 2.03E-02 |
| 1C11_H3_L3.172 | XenD17478 | XenD22186 | - | N35R | 3.66E-08 | 2.60E+05 | 9.49E-03 |
| 1C11_H3_L3.173 | XenD17478 | XenD22187 | - | Y38F | 2.69E-07 | 4.99E+05 | 1.34E-01 |
| 1C11_H3_L3.174 | XenD17478 | XenD22188 | - | Y38H | 1.22E-07 | 3.68E+06 | 4.49E-01 |
| 1C11_H3_L3.175 | XenD17478 | XenD22189 | - | Y38L | | | |
| 1C11_H3_L3.176 | XenD17478 | XenD22190 | - | Y38W | 1.90E-06 | 2.95E+05 | 5.61E-01 |
| 1C11_H3_L3.177 | XenD17478 | XenD22191 | - | Y38Q | | | |
| 1C11_H3_L3.178 | XenD17478 | XenD22192 | - | Y55F | 5.59E-08 | 3.80E+05 | 2.13E-02 |
| 1C11_H3_L3.179 | XenD17478 | XenD22193 | - | Y55H | 7.74E-08 | 3.17E+05 | 2.46E-02 |
| 1C11_H3_L3.180 | XenD17478 | XenD22194 | - | Y55L | 5.86E-09 | 8.21E+05 | 4.81E-03 |
| 1C11_H3_L3.181 | XenD17478 | XenD22195 | - | Y55W | 1.12E-07 | 5.20E+05 | 5.83E-02 |
| 1C11_H3_L3.182 | XenD17478 | XenD22196 | - | Y55Q | 1.07E-07 | 3.95E+05 | 4.23E-02 |
| 1C11_H3_L3.183 | XenD17478 | XenD22197 | - | V57I | 4.03E-08 | 3.76E+05 | 1.51E-02 |
| 1C11_H3_L3.184 | XenD17478 | XenD22198 | - | V57L | 4.31E-08 | 4.10E+05 | 1.77E-02 |
| 1C11_H3_L3.185 | XenD17478 | XenD22199 | - | V57S | 4.78E-08 | 3.69E+05 | 1.76E-02 |
| 1C11_H3_L3.186 | XenD17478 | XenD22200 | - | N59D | 3.45E-08 | 4.04E+05 | 1.40E-02 |
| 1C11_H3_L3.187 | XenD17478 | XenD22201 | - | N59H | 6.37E-08 | 3.30E+05 | 2.10E-02 |
| 1C11_H3_L3.188 | XenD17478 | XenD22202 | - | N59E | 6.21E-08 | 4.35E+05 | 2.70E-02 |
| 1C11_H3_L3.189 | XenD17478 | XenD22203 | - | N59R | 1.27E-07 | 3.52E+05 | 4.46E-02 |
| 1C11_H3_L3.190 | XenD17478 | XenD22204 | - | F95M | 6.64E-08 | 3.37E+05 | 2.24E-02 |
| 1C11_H3_L3.191 | XenD17478 | XenD22205 | - | F95E | 4.91E-08 | 5.92E+05 | 2.91E-02 |
| 1C11_H3_L3.192 | XenD17478 | XenD22206 | - | G97A | 1.48E-07 | 3.79E+05 | 5.60E-02 |
| 1C11_H3_L3.193 | XenD17478 | XenD22207 | - | G97S | 2.63E-07 | 3.60E+05 | 9.47E-02 |
| 1C11_H3_L3.194 | XenD17478 | XenD22208 | - | G97D | 4.62E-08 | 4.49E+05 | 2.07E-02 |
| 1C11_H3_L3.195 | XenD17478 | XenD22209 | - | G97T | 3.45E-06 | 6.12E+04 | 2.11E-01 |
| 1C11_H3_L3.196 | XenD17478 | XenD22210 | - | G97Q | 1.27E-07 | 3.19E+05 | 4.05E-02 |

FIG. 22E

| Variant Name | HC XenD | LC XenD | VH Variants | VL Variants | $K_D$ (M) | $k_a$ (1/Ms) | $k_d$ (1/s) |
|---|---|---|---|---|---|---|---|
| 1C11_H3_L3.197 | XenD17478 | XenD22211 | - | G97H | | | |
| 1C11_H3_L3.198 | XenD17478 | XenD22212 | - | G97L | 9.47E-08 | 8.29E+05 | 7.85E-02 |
| 1C11_H3_L3.199 | XenD17478 | XenD22213 | - | G97R | | | |
| 1C11_H3_L3.200 | XenD17478 | XenD22214 | - | G97F | | | |
| 1C11_H3_L3.201 | XenD17478 | XenD22215 | - | S98T | 5.22E-08 | 3.05E+05 | 1.59E-02 |
| 1C11_H3_L3.202 | XenD17478 | XenD22216 | - | S98A | 1.99E-08 | 3.89E+05 | 7.76E-03 |
| 1C11_H3_L3.203 | XenD17478 | XenD22217 | - | S98Q | 3.14E-08 | 6.06E+05 | 1.91E-02 |
| 1C11_H3_L3.204 | XenD17478 | XenD22218 | - | S98V | 1.28E-08 | 4.92E+05 | 6.30E-03 |
| 1C11_H3_L3.205 | XenD17478 | XenD22219 | - | H99Y | 5.46E-08 | 3.89E+05 | 2.13E-02 |
| 1C11_H3_L3.206 | XenD17478 | XenD22220 | - | H99Q | 4.57E-08 | 2.75E+05 | 1.26E-02 |
| 1C11_H3_L3.207 | XenD17478 | XenD22221 | - | H99D | 3.48E-08 | 3.48E+05 | 1.21E-02 |
| 1C11_H3_L3.208 | XenD17478 | XenD22222 | - | H99F | 5.16E-08 | 3.91E+05 | 2.02E-02 |
| 1C11_H3_L3.209 | XenD17478 | XenD22223 | - | H99T | 2.93E-08 | 4.26E+05 | 1.25E-02 |

FIG. 23

| Variant Name | HC XenD | LC XenD | VH Variants | VL Variants | $K_D$ (M) | $k_a$ (1/Ms) | $k_d$ (1/s) |
|---|---|---|---|---|---|---|---|
| 1C11_H3.244_L3 | XenD22099 | XenD17482 | G26T | - | 6.48E-08 | 4.54E+05 | 2.94E-02 |
| 1C11_H3.249_L3 | XenD22104 | XenD17482 | Y27D | - | 6.00E-08 | 4.91E+05 | 2.95E-02 |
| 1C11_H3.250_L3 | XenD22105 | XenD17482 | Y27K | - | 3.16E-07 | 3.65E+05 | 1.15E-01 |
| 1C11_H3.256_L3 | XenD22111 | XenD17482 | F29W | - | 2.95E-08 | 3.07E+05 | 9.05E-03 |
| 1C11_H3.258_L3 | XenD22113 | XenD17482 | T30V | - | 2.53E-08 | 4.16E+05 | 1.05E-02 |
| 1C11_H3.288_L3 | XenD22143 | XenD17482 | Y56H | - | 1.95E-08 | 4.18E+05 | 8.16E-03 |
| 1C11_H3.292_L3 | XenD22147 | XenD17482 | T59S | - | 2.02E-08 | 3.34E+05 | 6.75E-03 |
| 1C11_H3.303_L3 | XenD22158 | XenD17482 | Y111F | - | 1.48E-08 | 3.60E+05 | 5.34E-03 |
| 1C11_H3_L3.149 | XenD17478 | XenD22163 | - | H31Y | 7.35E-09 | 6.55E+05 | 4.82E-03 |
| 1C11_H3_L3.152 | XenD17478 | XenD22166 | - | H31F | 6.27E-09 | 4.55E+05 | 2.85E-03 |
| 1C11_H3_L3.160 | XenD17478 | XenD22174 | - | N33H | 4.29E-07 | 1.95E+05 | 8.37E-02 |
| 1C11_H3_L3.161 | XenD17478 | XenD22175 | - | N33E | 3.33E-07 | 3.51E+05 | 1.17E-01 |
| 1C11_H3_L3.166 | XenD17478 | XenD22180 | - | G34S | 3.14E-08 | 4.25E+05 | 1.34E-02 |
| 1C11_H3_L3.168 | XenD17478 | XenD22182 | - | G34Q | 3.18E-08 | 4.57E+05 | 1.45E-02 |
| 1C11_H3_L3.180 | XenD17478 | XenD22194 | - | Y55L | 1.14E-07 | 3.64E+05 | 4.13E-02 |
| 1C11_H3_L3.186 | XenD17478 | XenD22200 | - | N59D | 6.14E-08 | 4.25E+05 | 2.61E-02 |
| 1C11_H3_L3.191 | XenD17478 | XenD22205 | - | F95E | 5.89E-08 | 4.40E+05 | 2.59E-02 |
| 1C11_H3_L3.194 | XenD17478 | XenD22208 | - | G97D | 1.04E-07 | 2.44E+05 | 2.54E-02 |
| 1C11_H3_L3.202 | XenD17478 | XenD22216 | - | S98A | 2.64E-08 | 3.69E+05 | 9.74E-03 |
| 1C11_H3_L3.204 | XenD17478 | XenD22218 | - | S98V | 2.97E-08 | 3.86E+05 | 1.15E-02 |
| 1C11_H3_L3.207 | XenD17478 | XenD22221 | - | H99D | 3.14E-08 | 2.94E+05 | 9.23E-03 |

FIG. 24A

>XENP026917 1C11[PD-1]_H3.244_L3_IgG1_PVA_/S267K Heavy Chain (SEQ ID NOS 42274-42278)
QIQLVQSGSELKKPGASVKVSCKASTYTFTHYGMNWVRQAPGQGLEWMGWINTYTGEPTYADGFTGRFVFSLDTSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

>XENP026917 1C11[PD-1]_H3.244_L3_IgG1_PVA_/S267K Light Chain (SEQ ID NOS 42279-42283)
DVLMTQSPDSLAVSLGERATINCKSSQSIVHSNGNTYLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XENP026918 1C11[PD-1]_H3.249_L3_IgG1_PVA_/S267K Heavy Chain (SEQ ID NOS 42284-42288)
QIQLVQSGSELKKPGASVKVSCKASGDTFTHYGMNWVRQAPGQGLEWMGWINTYTGEPTYADGFTGRFVFSLDTSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

>XENP026918 1C11[PD-1]_H3.249_L3_IgG1_PVA_/S267K Light Chain (SEQ ID NOS 42289-42293)
DVLMTQSPDSLAVSLGERATINCKSSQSIVHSNGNTYLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XENP026919 1C11[PD-1]_H3.250_L3_IgG1_PVA_/S267K Heavy Chain (SEQ ID NOS 42294-42298)
QIQLVQSGSELKKPGASVKVSCKASGKTFTHYGMNWVRQAPGQGLEWMGWINTYTGEPTYADGFTGRFVFSLDTSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

>XENP026919 1C11[PD-1]_H3.250_L3_IgG1_PVA_/S267K Light Chain (SEQ ID NOS 42299-42303)
DVLMTQSPDSLAVSLGERATINCKSSQSIVHSNGNTYLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XENP026920 1C11[PD-1]_H3.256_L3_IgG1_PVA_/S267K Heavy Chain (SEQ ID NOS 42304-42308)
QIQLVQSGSELKKPGASVKVSCKASGYTWTHYGMNWVRQAPGQGLEWMGWINTYTGEPTYADGFTGRFVFSLDTSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

>XENP026920 1C11[PD-1]_H3.256_L3_IgG1_PVA_/S267K Light Chain (SEQ ID NOS 42309-42313)
DVLMTQSPDSLAVSLGERATINCKSSQSIVHSNGNTYLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

FIG. 24B

>XENP026921 1C11[PD-1]_H3.258_L3_IgG1_PVA_/S267K Heavy Chain (SEQ ID NOS 42314-42318)
QIQLVQSGSELKKPGASVKVSCKASGYTFVHYGMNWVRQAPGQGLEWMGWINTYTGEPTYADGFTGRFVFSLDTSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

>XENP026921 1C11[PD-1]_H3.258_L3_IgG1_PVA_/S267K Light Chain (SEQ ID NOS 42319-42323)
DVLMTQSPDSLAVSLGERATINCKSSQSIVHSNGNTYLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XENP026922 1C11[PD-1]_H3.288_L3_IgG1_PVA_/S267K Heavy Chain (SEQ ID NOS 42324-42328)
QIQLVQSGSELKKPGASVKVSCKASGYTFTHYGMNWVRQAPGQGLEWMGWINTHTGEPTYADGFTGRFVFSLDTSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

>XENP026922 1C11[PD-1]_H3.288_L3_IgG1_PVA_/S267K Light Chain (SEQ ID NOS 42329-42333)
DVLMTQSPDSLAVSLGERATINCKSSQSIVHSNGNTYLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XENP026923 1C11[PD-1]_H3.292_L3_IgG1_PVA_/S267K Heavy Chain (SEQ ID NOS 42334-42338)
QIQLVQSGSELKKPGASVKVSCKASGYTFTHYGMNWVRQAPGQGLEWMGWINTYSGEPTYADGFTGRFVFSLDTSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

>XENP026923 1C11[PD-1]_H3.292_L3_IgG1_PVA_/S267K Light Chain (SEQ ID NOS 42339-42343)
DVLMTQSPDSLAVSLGERATINCKSSQSIVHSNGNTYLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XENP026924 1C11[PD-1]_H3.303_L3_IgG1_PVA_/S267K Heavy Chain (SEQ ID NOS 42344-42348)
QIQLVQSGSELKKPGASVKVSCKASGYTFTHYGMNWVRQAPGQGLEWMGWINTYTGEPTYADGFTGRFVFSLDTSVS
TAYLQISSLKAEDTAVYFCARDYFGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

>XENP026924 1C11[PD-1]_H3.303_L3_IgG1_PVA_/S267K Light Chain (SEQ ID NOS 42349-42353)
DVLMTQSPDSLAVSLGERATINCKSSQSIVHSNGNTYLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

FIG. 24C

>XENP026925 1C11[PD-1]_H3_L3.149_IgG1_PVA_/S267K Heavy Chain (SEQ ID NOS 42354-42358)
QIQLVQSGSELKKPGASVKVSCKASGYTFTHYGMNWVRQAPGQGLEWMGWINTYTGEPTYADGFTGRFVFSLDTSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

>XENP026925 1C11[PD-1]_H3_L3.149_IgG1_PVA_/S267K Light Chain (SEQ ID NOS 42359-42363)
DVLMTQSPDSLAVSLGERATINCKSSQSIVYSNGNTYLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XENP026926 1C11[PD-1]_H3_L3.152_IgG1_PVA_/S267K Heavy Chain (SEQ ID NOS 42364-42368)
QIQLVQSGSELKKPGASVKVSCKASGYTFTHYGMNWVRQAPGQGLEWMGWINTYTGEPTYADGFTGRFVFSLDTSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

>XENP026926 1C11[PD-1]_H3_L3.152_IgG1_PVA_/S267K Light Chain (SEQ ID NOS 42369-42373)
DVLMTQSPDSLAVSLGERATINCKSSQSIVFSNGNTYLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XENP026927 1C11[PD-1]_H3_L3.160_IgG1_PVA_/S267K Heavy Chain (SEQ ID NOS 42374-42378)
QIQLVQSGSELKKPGASVKVSCKASGYTFTHYGMNWVRQAPGQGLEWMGWINTYTGEPTYADGFTGRFVFSLDTSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

>XENP026927 1C11[PD-1]_H3_L3.160_IgG1_PVA_/S267K Light Chain (SEQ ID NOS 42379-42383)
DVLMTQSPDSLAVSLGERATINCKSSQSIVHSHGNTYLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XENP026928 1C11[PD-1]_H3_L3.161_IgG1_PVA_/S267K Heavy Chain (SEQ ID NOS 42384-42388)
QIQLVQSGSELKKPGASVKVSCKASGYTFTHYGMNWVRQAPGQGLEWMGWINTYTGEPTYADGFTGRFVFSLDTSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

>XENP026928 1C11[PD-1]_H3_L3.161_IgG1_PVA_/S267K Light Chain (SEQ ID NOS 42389-42393)
DVLMTQSPDSLAVSLGERATINCKSSQSIVHSEGNTYLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

FIG. 24D

>XENP026929 1C11[PD-1]_H3_L3.166_IgG1_PVA_/S267K Heavy Chain (SEQ ID NOS 42394-42398)
QIQLVQSGSELKKPGASVKVSCKASGYTFTHYGMNWVRQAPGQGLEWMGWINTYTGEPTYADGFTGRFVFSLDTSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

>XENP026929 1C11[PD-1]_H3_L3.166_IgG1_PVA_/S267K Light Chain (SEQ ID NOS 42399-42403)
DVLMTQSPDSLAVSLGERATINCKSSQSIVHSNSNTYLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XENP026930 1C11[PD-1]_H3_L3.168_IgG1_PVA_/S267K Heavy Chain (SEQ ID NOS 42404-42408)
QIQLVQSGSELKKPGASVKVSCKASGYTFTHYGMNWVRQAPGQGLEWMGWINTYTGEPTYADGFTGRFVFSLDTSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

>XENP026930 1C11[PD-1]_H3_L3.168_IgG1_PVA_/S267K Light Chain (SEQ ID NOS 42409-42413)
DVLMTQSPDSLAVSLGERATINCKSSQSIVHSNQNTYLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XENP026931 1C11[PD-1]_H3_L3.180_IgG1_PVA_/S267K Heavy Chain (SEQ ID NOS 42414-42418)
QIQLVQSGSELKKPGASVKVSCKASGYTFTHYGMNWVRQAPGQGLEWMGWINTYTGEPTYADGFTGRFVFSLDTSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

>XENP026931 1C11[PD-1]_H3_L3.180_IgG1_PVA_/S267K Light Chain (SEQ ID NOS 42419-42423)
DVLMTQSPDSLAVSLGERATINCKSSQSIVHSNGNTYLEWYQQKPGQSPKLLILKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XENP026932 1C11[PD-1]_H3_L3.186_IgG1_PVA_/S267K Heavy Chain (SEQ ID NOS 42424-42428)
QIQLVQSGSELKKPGASVKVSCKASGYTFTHYGMNWVRQAPGQGLEWMGWINTYTGEPTYADGFTGRFVFSLDTSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

>XENP026932 1C11[PD-1]_H3_L3.186_IgG1_PVA_/S267K Light Chain (SEQ ID NOS 42429-42433)
DVLMTQSPDSLAVSLGERATINCKSSQSIVHSNGNTYLEWYQQKPGQSPKLLIYKVSDRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

FIG. 24E

>XENP026933 1C11[PD-1]_H3_L3.191_IgG1_PVA_/S267K Heavy Chain (SEQ ID NOS 42434-42438)
QIQLVQSGSELKKPGASVKVSCKASGYTFTHYGMNWVRQAPGQGLEWMGWINTYTGEPTYADGFTGRFVFSLDTSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

>XENP026933 1C11[PD-1]_H3_L3.191_IgG1_PVA_/S267K Light Chain (SEQ ID NOS 42439-42443)
DVLMTQSPDSLAVSLGERATINCKSSQSIVHSNGNTYLEWYQQKPGQSPKLLIYKVSNRFSGVPDRFSGSGSGTDFT
LTISSLQAEDVAVYYCEQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XENP026934 1C11[PD-1]_H3_L3.194_IgG1_PVA_/S267K Heavy Chain (SEQ ID NOS 42444-42448)
QIQLVQSGSELKKPGASVKVSCKASGYTFTHYGMNWVRQAPGQGLEWMGWINTYTGEPTYADGFTGRFVFSLDTSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

>XENP026934 1C11[PD-1]_H3_L3.194_IgG1_PVA_/S267K Light Chain (SEQ ID NOS 42449-42453)
DVLMTQSPDSLAVSLGERATINCKSSQSIVHSNGNTYLEWYQQKPGQSPKLLIYKVSNRFSGVPDRFSGSGSGTDFT
LTISSLQAEDVAVYYCFQDSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XENP026935 1C11[PD-1]_H3_L3.202_IgG1_PVA_/S267K Heavy Chain (SEQ ID NOS 42454-42458)
QIQLVQSGSELKKPGASVKVSCKASGYTFTHYGMNWVRQAPGQGLEWMGWINTYTGEPTYADGFTGRFVFSLDTSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

>XENP026935 1C11[PD-1]_H3_L3.202_IgG1_PVA_/S267K Light Chain (SEQ ID NOS 42459-42463)
DVLMTQSPDSLAVSLGERATINCKSSQSIVHSNGNTYLEWYQQKPGQSPKLLIYKVSNRFSGVPDRFSGSGSGTDFT
LTISSLQAEDVAVYYCFQGAHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XENP026936 1C11[PD-1]_H3_L3.204_IgG1_PVA_/S267K Heavy Chain (SEQ ID NOS 42464-42468)
QIQLVQSGSELKKPGASVKVSCKASGYTFTHYGMNWVRQAPGQGLEWMGWINTYTGEPTYADGFTGRFVFSLDTSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

>XENP026936 1C11[PD-1]_H3_L3.204_IgG1_PVA_/S267K Light Chain (SEQ ID NOS 42469-42473)
DVLMTQSPDSLAVSLGERATINCKSSQSIVHSNGNTYLEWYQQKPGQSPKLLIYKVSNRFSGVPDRFSGSGSGTDFT
LTISSLQAEDVAVYYCFQGVHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

FIG. 24F

>XENP026937 1C11[PD-1]_H3_L3.207_IgG1_PVA_/S267K Heavy Chain (SEQ ID NOS 42474-42478)
QIQLVQSGSELKKPGASVKVSCKASGYTFTHYGMNWVRQAPGQGLEWMGWINTYTGEPTYADGFTGRFVFSLDTSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

>XENP026937 1C11[PD-1]_H3_L3.207_IgG1_PVA_/S267K Light Chain (SEQ ID NOS 42479-42483)
DVLMTQSPDSLAVSLGERATINCKSSQSIVHSNGNTYLEWYQQKPGQSPKLLIYKVSNRFSGVPDRFSGSGSGTDFT
LTISSLQAEDVAVYYCFQGSDVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XENP026938 1C11[PD-1]_H3.308_L3.152_IgG1_PVA_/S267K Heavy Chain (SEQ ID NOS 42484-42488)
QIQLVQSGSELKKPGASVKVSCKASGYTFTHYGMNWVRQAPGQGLEWMGWINTYTSEPTYADGFTGRFVFSLDTSQS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

>XENP026938 1C11[PD-1]_H3.308_L3.152_IgG1_PVA_/S267K Light Chain (SEQ ID NOS 42489-42493)
DVLMTQSPDSLAVSLGERATINCKSSQSIVFSNGNTYLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XENP026939 1C11[PD-1]_H3.59_L3.152_IgG1_PVA_/S267K Heavy Chain (SEQ ID NOS 42494-42498)
QIQLVQSGSELKKPGASVKVSCKASGYTFTHYGMNWVRQAPGQGLEWMGWINTYTGEPTYADGFTGRFVFSLDTSQS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

>XENP026939 1C11[PD-1]_H3.59_L3.152_IgG1_PVA_/S267K Light Chain (SEQ ID NOS 42499-42503)
DVLMTQSPDSLAVSLGERATINCKSSQSIVFSNGNTYLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XENP026940 1C11[PD-1]_H3.303_L3.152_IgG1_PVA_/S267K Heavy Chain (SEQ ID NOS 42504-42508)
QIQLVQSGSELKKPGASVKVSCKASGYTFTHYGMNWVRQAPGQGLEWMGWINTYTGEPTYADGFTGRFVFSLDTSVS
TAYLQISSLKAEDTAVYFCARDYFGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

>XENP026940 1C11[PD-1]_H3.303_L3.152_IgG1_PVA_/S267K Light Chain (SEQ ID NOS 42509-42513)
DVLMTQSPDSLAVSLGERATINCKSSQSIVFSNGNTYLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

FIG. 24G

>XENP026941 1C11[PD-1]_H3.308_L3.180_IgG1_PVA_/S267K Heavy Chain (SEQ ID NOS 42514-42518)
QIQLVQSGSELKKPGASVKVSCKASGYTFTHYGMNWVRQAPGQGLEWMGWINTYTSEPTYADGFTGRFVFSLDTSQS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

>XENP026941 1C11[PD-1]_H3.308_L3.180_IgG1_PVA_/S267K Light Chain (SEQ ID NOS 42519-42523)
DVLMTQSPDSLAVSLGERATINCKSSQSIVHSNGNTYLEWYQQKPGQSPKLLILKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XENP026942 1C11[PD-1]_H3.59_L3.180_IgG1_PVA_/S267K Heavy Chain (SEQ ID NOS 42524-42528)
QIQLVQSGSELKKPGASVKVSCKASGYTFTHYGMNWVRQAPGQGLEWMGWINTYTGEPTYADGFTGRFVFSLDTSQS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

>XENP026942 1C11[PD-1]_H3.59_L3.180_IgG1_PVA_/S267K Light Chain (SEQ ID NOS 42529-42533)
DVLMTQSPDSLAVSLGERATINCKSSQSIVHSNGNTYLEWYQQKPGQSPKLLILKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XENP026943 1C11[PD-1]_H3.303_L3.180_IgG1_PVA_/S267K Heavy Chain (SEQ ID NOS 42534-42538)
QIQLVQSGSELKKPGASVKVSCKASGYTFTHYGMNWVRQAPGQGLEWMGWINTYTGEPTYADGFTGRFVFSLDTSVS
TAYLQISSLKAEDTAVYFCARDYFGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

>XENP026943 1C11[PD-1]_H3.303_L3.180_IgG1_PVA_/S267K Light Chain (SEQ ID NOS 42539-42543)
DVLMTQSPDSLAVSLGERATINCKSSQSIVHSNGNTYLEWYQQKPGQSPKLLILKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XENP026944 1C11[PD-1]_H3.303_L3.210_IgG1_PVA_/S267K Heavy Chain (SEQ ID NOS 42544-42548)
QIQLVQSGSELKKPGASVKVSCKASGYTFTHYGMNWVRQAPGQGLEWMGWINTYTGEPTYADGFTGRFVFSLDTSVS
TAYLQISSLKAEDTAVYFCARDYFGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

>XENP026944 1C11[PD-1]_H3.303_L3.210_IgG1_PVA_/S267K Light Chain (SEQ ID NOS 42549-42553)
DILMTQSPDSLAVSLGERATINCKSSQSIVHSNGNNYLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

FIG. 24H

>XENP026945 1C11[PD-1]_H3.308_L3_IgG1_PVA_/S267K Heavy Chain (SEQ ID NOS 42554-42558)
QIQLVQSGSELKKPGASVKVSCKASGYTFTHYGMNWVRQAPGQGLEWMGWINTYTSEPTYADGFTGRFVFSLDTSQS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

>XENP026945 1C11[PD-1]_H3.308_L3_IgG1_PVA_/S267K Light Chain (SEQ ID NOS 42559-42563)
DVLMTQSPDSLAVSLGERATINCKSSQSIVHSNGNTYLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XENP026946 1C11[PD-1]_H3.59_L3_IgG1_PVA_/S267K Heavy Chain (SEQ ID NOS 42564-42568)
QIQLVQSGSELKKPGASVKVSCKASGYTFTHYGMNWVRQAPGQGLEWMGWINTYTGEPTYADGFTGRFVFSLDTSQS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

>XENP026946 1C11[PD-1]_H3.59_L3_IgG1_PVA_/S267K Light Chain (SEQ ID NOS 42569-42573)
DVLMTQSPDSLAVSLGERATINCKSSQSIVHSNGNTYLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XENP026947 1C11[PD-1]_H3.135_L3_IgG1_PVA_/S267K Heavy Chain (SEQ ID NOS 42574-42578)
QIQLVQSGSELKKPGASVKVSCKASGYTFTHYGMNWVRQAPGQGLEWMGWINTYTSEPTYADGFTGRFVFSLDTSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

>XENP026947 1C11[PD-1]_H3.135_L3_IgG1_PVA_/S267K Light Chain (SEQ ID NOS 42579-42583)
DVLMTQSPDSLAVSLGERATINCKSSQSIVHSNGNTYLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XENP026949 1C11[PD-1]_H3.308_L3.210_IgG1_PVA_/S267K Heavy Chain (SEQ ID NOS 42584-42588)
QIQLVQSGSELKKPGASVKVSCKASGYTFTHYGMNWVRQAPGQGLEWMGWINTYTSEPTYADGFTGRFVFSLDTSQS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

>XENP026949 1C11[PD-1]_H3.308_L3.210_IgG1_PVA_/S267K Light Chain (SEQ ID NOS 42589-42593)
DILMTQSPDSLAVSLGERATINCKSSQSIVHSNGNNYLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

FIG. 24I

>XENP026950 1C11[PD-1]_H3_L3.210_IgG1_PVA_/S267K Heavy Chain (SEQ ID NOS 42594-42598)
QIQLVQSGSELKKPGASVKVSCKASGYTFTHYGMNWVRQAPGQGLEWMGWINTYTGEPTYADGFTGRFVFSLDTSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

>XENP026950 1C11[PD-1]_H3_L3.210_IgG1_PVA_/S267K Light Chain (SEQ ID NOS 42599-42603)
DILMTQSPDSLAVSLGERATINCKSSQSIVHSNGNNYLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XENP026951 1C11[PD-1]_H3_L3.1_IgG1_PVA_/S267K Heavy Chain (SEQ ID NOS 42604-42608)
QIQLVQSGSELKKPGASVKVSCKASGYTFTHYGMNWVRQAPGQGLEWMGWINTYTGEPTYADGFTGRFVFSLDTSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

>XENP026951 1C11[PD-1]_H3_L3.1_IgG1_PVA_/S267K Light Chain (SEQ ID NOS 42609-42613)
DILMTQSPDSLAVSLGERATINCKSSQSIVHSNGNTYLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XENP026952 1C11[PD-1]_H3_L3.38_IgG1_PVA_/S267K Heavy Chain (SEQ ID NOS 42614-42618)
QIQLVQSGSELKKPGASVKVSCKASGYTFTHYGMNWVRQAPGQGLEWMGWINTYTGEPTYADGFTGRFVFSLDTSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

>XENP026952 1C11[PD-1]_H3_L3.38_IgG1_PVA_/S267K Light Chain (SEQ ID NOS 42619-42623)
DVLMTQSPDSLAVSLGERATINCKSSQSIVHSNGNNYLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XENP026953 1C11[PD-1]_H3_L3.125_IgG1_PVA_/S267K Heavy Chain (SEQ ID NOS 42624-42628)
QIQLVQSGSELKKPGASVKVSCKASGYTFTHYGMNWVRQAPGQGLEWMGWINTYTGEPTYADGFTGRFVFSLDTSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

>XENP026953 1C11[PD-1]_H3_L3.125_IgG1_PVA_/S267K Light Chain (SEQ ID NOS 42629-42633)
DVLMTQSPDSLAVSLGERATINCKSSQSIVHSNGNTYLEWYQQKPGQSPKLLIYKVSNRFSGVPDRFSGSGSGTDFT
LTISSVEAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

FIG. 24J

>XENP026954 1C11[PD-1]_H3.308_L3.38_IgG1_PVA_/S267K Heavy Chain (SEQ ID NOS 42634-42638)
QIQLVQSGSELKKPGASVKVSCKASGYTFTHYGMNWVRQAPGQGLEWMGWINTYTSEPTYADGFTGRFVFSLDTSQS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

>XENP026954 1C11[PD-1]_H3.308_L3.38_IgG1_PVA_/S267K Light Chain (SEQ ID NOS 42639-42643)
DVLMTQSPDSLAVSLGERATINCKSSQSIVHSNGNNYLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XENP026955 1C11[PD-1]_H3.59_L3.210_IgG1_PVA_/S267K Heavy Chain (SEQ ID NOS 42644-42648)
QIQLVQSGSELKKPGASVKVSCKASGYTFTHYGMNWVRQAPGQGLEWMGWINTYTGEPTYADGFTGRFVFSLDTSQS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

>XENP026955 1C11[PD-1]_H3.59_L3.210_IgG1_PVA_/S267K Light Chain (SEQ ID NOS 42649-42653)
DILMTQSPDSLAVSLGERATINCKSSQSIVHSNGNNYLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

FIG. 25

| XENP | Variant Name | K_D (M) | k_a (1/Ms) | k_d (1/s) |
|---|---|---|---|---|
| 22553 | 1C11_H3L3 | 2.98E-08 | 3.70E+05 | 1.10E-02 |
| 26322 | 1C11_H3.59_L3.38 | 1.27E-08 | 3.13E+05 | 3.99E-03 |
| 26917 | 1C11_H3.244_L3 | 6.48E-08 | 4.54E+05 | 2.94E-02 |
| 26918 | 1C11_H3.249_L3 | 6.00E-08 | 4.91E+05 | 2.95E-02 |
| 26919 | 1C11_H3.250_L3 | 3.16E-07 | 3.65E+05 | 1.15E-01 |
| 26920 | 1C11_H3.256_L3 | 2.95E-08 | 3.07E+05 | 9.05E-03 |
| 26921 | 1C11_H3.258_L3 | 2.53E-08 | 4.16E+05 | 1.05E-02 |
| 26922 | 1C11_H3.288_L3 | 1.95E-08 | 4.18E+05 | 8.16E-03 |
| 26923 | 1C11_H3.292_L3 | 2.02E-08 | 3.34E+05 | 6.75E-03 |
| 26924 | 1C11_H3.303_L3 | 1.48E-08 | 3.60E+05 | 5.34E-03 |
| 26925 | 1C11_H3_L3.149 | 7.35E-09 | 6.55E+05 | 4.82E-03 |
| 26926 | 1C11_H3_L3.152 | 6.27E-09 | 4.55E+05 | 2.85E-03 |
| 26927 | 1C11_H3_L3.160 | 4.29E-07 | 1.95E+05 | 8.37E-02 |
| 26928 | 1C11_H3_L3.161 | 3.33E-07 | 3.51E+05 | 1.17E-01 |
| 26929 | 1C11_H3_L3.166 | 3.14E-08 | 4.25E+05 | 1.34E-02 |
| 26930 | 1C11_H3_L3.168 | 3.18E-08 | 4.57E+05 | 1.45E-02 |
| 26931 | 1C11_H3_L3.180 | 1.14E-07 | 3.64E+05 | 4.13E-02 |
| 26932 | 1C11_H3_L3.186 | 6.14E-08 | 4.25E+05 | 2.61E-02 |
| 26933 | 1C11_H3_L3.191 | 5.89E-08 | 4.40E+05 | 2.59E-02 |
| 26934 | 1C11_H3_L3.194 | 1.04E-07 | 2.44E+05 | 2.54E-02 |
| 26935 | 1C11_H3_L3.202 | 2.64E-08 | 3.69E+05 | 9.74E-03 |
| 26936 | 1C11_H3_L3.204 | 2.97E-08 | 3.86E+05 | 1.15E-02 |
| 26937 | 1C11_H3_L3.207 | 3.14E-08 | 2.94E+05 | 9.23E-03 |
| 26938 | 1C11_H3.308_L3.152 | 1.42E-08 | 1.79E+05 | 2.53E-03 |
| 26939 | 1C11_H3.59_L3.152 | 1.56E-08 | 4.02E+05 | 6.25E-03 |
| 26940 | 1C11_H3.303_L3.152 | 3.41E-09 | 5.18E+05 | 1.77E-03 |
| 26941 | 1C11_H3.308_L3.180 | 4.34E-08 | 4.97E+05 | 2.16E-02 |
| 26942 | 1C11_H3.59_L3.180 | 5.74E-08 | 4.45E+05 | 2.55E-02 |
| 26943 | 1C11_H3.303_L3.180 | 4.20E-08 | 3.53E+05 | 1.48E-02 |
| 26944 | 1C11_H3.303_L3.210 | 1.04E-08 | 4.14E+05 | 4.28E-03 |
| 26945 | 1C11_H3.308_L3 | 3.22E-08 | 4.00E+05 | 1.29E-02 |
| 26946 | 1C11_H3.59_L3 | 3.71E-08 | 4.90E+05 | 1.81E-02 |
| 26947 | 1C11_H3.135_L3 | 4.76E-08 | 3.75E+05 | 1.79E-02 |
| 26949 | 1C11_H3.308_L3.210 | 2.37E-08 | 2.84E+05 | 6.71E-03 |
| 26950 | 1C11_H3_L3.210 | 1.98E-08 | 2.25E+05 | 4.45E-03 |
| 26951 | 1C11_H3_L3.1 | 4.71E-08 | 2.38E+05 | 1.12E-02 |
| 26952 | 1C11_H3_L3.38 | 2.85E-08 | 3.44E+05 | 9.79E-03 |
| 26953 | 1C11_H3_L3.125 | 5.60E-08 | 4.16E+05 | 2.33E-02 |
| 26954 | 1C11_H3.308_L3.38 | 2.29E-08 | 3.31E+05 | 7.58E-03 |
| 26955 | 1C11_H3.59_L3.210 | 1.98E-08 | 2.89E+05 | 5.72E-03 |

FIG. 26

| XENP | Variant | human PD-1 $K_D$ (M) | cyno PD-1 $K_D$ (M) |
|---|---|---|---|
| 21461 | Pembrolizumab_H0L0 | 4.48E-09 | 1.17E-09 |
| 16432 | Nivolumab_H0L0 | 4.46E-09 | 4.09E-09 |
| 21575 | 1C11[PD-1]_H0L0 | 8.65E-09 | 1.39E-08 |
| 22553 | 1C11[PD-1]_H3L3 | 8.35E-09 | 1.23E-08 |
| 25842 | 1C11[PD-1]_H3.241_L3.92 | 7.74E-09 | 1.30E-08 |
| 26917 | 1C11[PD-1]_H3.244_L3 | 1.19E-08 | 1.94E-08 |
| 26322 | 1C11[PD-1]_H3.59_L3.38 | 3.77E-09 | 7.73E-09 |
| 26926 | 1C11[PD-1]_H3_L3.152 | 1.69E-09 | 2.33E-09 |
| 26940 | 1C11[PD-1]_H3.303_L3.152 | 1.31E-09 | 3.00E-09 |

FIG. 28

| | XENP16432 | XENP21575 | XENP22553 | XENP25842 | XENP26322 | XENP26917 | XENP26926 | XENP26940 | PD-L1-Fc | PD-L2-Fc |
|---|---|---|---|---|---|---|---|---|---|---|
| XENP16432 | 0.0008 | 0.0553 | 0.0653 | 0.0607 | 0.132 | 0.0459 | 0.1326 | 0.1929 | -0.0025 | -0.119 |
| XENP21575 | 0.0584 | 0.0807 | 0.0025 | 0.0243 | 0.0355 | 0.0079 | 0.065 | 0.0814 | -0.326 | -0.1936 |
| XENP22553 | 0.0727 | 0.0387 | -0.0066 | -0.0015 | 0.0835 | 0.0106 | 0.0829 | 0.0944 | -0.3022 | -0.1241 |
| XENP25842 | -0.0139 | 0.0935 | 0.0539 | 0.092 | 0.1061 | 0.0052 | 0.0927 | 0.0912 | -0.2328 | -0.1453 |
| XENP26322 | -0.0127 | 0.0611 | -0.0109 | 0.0546 | 0.0272 | 0.0027 | 0.0696 | 0.0735 | -0.219 | -0.2475 |
| XENP26917 | 0.0612 | 0.0288 | 0.0871 | 0.0536 | 0.098 | 0.0973 | 0.1607 | 0.1785 | -0.1353 | -0.0908 |
| XENP26926 | 0.0433 | 0.0663 | 0.0585 | 0.0752 | 0.0562 | 0.0201 | 0.0742 | 0.0928 | 0.0126 | -0.0549 |
| XENP26940 | 0.0647 | -0.0082 | 0.0118 | 0.0841 | 0.0382 | -0.0409 | 0.0501 | 0.0553 | -0.0156 | -0.1703 |
| PD-L1-Fc | 0.7541 | 0.8013 | 0.7233 | 0.7269 | 0.723 | 0.7341 | 0.7119 | 0.7638 | 0.4631 | 0.4469 |
| PD-L2-Fc | 0.4908 | 0.5313 | 0.4743 | 0.5087 | 0.4643 | 0.519 | 0.5255 | 0.5282 | -0.2147 | 0.0984 |
| HBS-EP | 1 | 1 | 1 | 1 | 1 | 1 | 1 | 1 | 1 | 1 |

FIG. 33

XENP026842 Nivolumab_H0L0_IgG1_ PVA_/S267K/M428L/N434S Heavy Chain (SEQ ID NOS 42654-42658)

QVQLVESGGGVVQPGRSLRLDCKASGITFS<u>NSGMH</u>WVRQAPGKGLEWVA<u>VIWYDGSKRYYADSVKGRFTI</u>SRDNSKNTLFLQMNSLRAEDTAVYYCAT<u>NDDY</u>WGQGTLVTVSS/ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPPVAGPSVFLFPPKPKDTLMISRTPEVTCVVVDVKHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVLHEALHSHYTQKSLSLSPGK

XENP016432 Nivolumab_H0L0_IgG1_P PVA_/S267K/M428L/N434S Light Chain (SEQ ID NOS 42659-42663)

EIVLTQSPATLSLSPGERATLSC<u>RASQSVSSYLA</u>WYQQKPGQAPRLLIY<u>DASNRAT</u>GIPARFSGSGSGTDFTLTISSLEPEDFAVYYC<u>QQSSNWPRT</u>FGQGTKVEIK/RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC

FIG. 40A

>XENP27643 1C11_H3_L3.211_IgG1_PVA_/S267K
Heavy Chain (SEQ ID NOS 42664-42668)
QIQLVQSGSELKKPGASVKVSCKASGYTFTHYGMNWVRQAPGQGLEWMGWINTYTGEPTYADGFTGRFVFSLDTSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

Light Chain (SEQ ID NOS 42669-42673)
DVLMTQSPDSLAVSLGERATINCKSSQSIVHSNGNTYLEWYQQKPGQSPELLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XENP27644 1C11_H3_L3.212_IgG1_PVA_/S267K
Heavy Chain (SEQ ID NOS 42674-42678)
QIQLVQSGSELKKPGASVKVSCKASGYTFTHYGMNWVRQAPGQGLEWMGWINTYTGEPTYADGFTGRFVFSLDTSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

Light Chain (SEQ ID NOS 42679-42683)
DVLMTQSPDSLAVSLGERATINCKSSQSIVHSNGNTYLEWYQQKPGQSPQLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XENP27645 1C11_H3_L3.213_IgG1_PVA_/S267K
Heavy Chain (SEQ ID NOS 42684-42688)
QIQLVQSGSELKKPGASVKVSCKASGYTFTHYGMNWVRQAPGQGLEWMGWINTYTGEPTYADGFTGRFVFSLDTSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

Light Chain (SEQ ID NOS 42689-42693)
DVLMTQSPDSLAVSLGERATINCKSSQSIVHSNGNTYLEWYQQKPGQSPTLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XENP27646 1C11_H3_L3.214_IgG1_PVA_/S267K
Heavy Chain (SEQ ID NOS 42694-42698)
QIQLVQSGSELKKPGASVKVSCKASGYTFTHYGMNWVRQAPGQGLEWMGWINTYTGEPTYADGFTGRFVFSLDTSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

FIG. 40B

Light Chain (SEQ ID NOS 42699-42703)
DVLMTQSPDSLAVSLGERATINCKSSQSIVISNGNTYLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XENP27647 1C11_H3_L3.215_IgG1_PVA_/S267K
Heavy Chain (SEQ ID NOS 42704-42708)
QIQLVQSGSELKKPGASVKVSCKASGYTFTHYGMNWVRQAPGQGLEWMGWINTYTGEPTYADGFTGRFVFSLDTSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

Light Chain (SEQ ID NOS 42709-42713)
DVLMTQSPDSLAVSLGERATINCKSSQSIVLSNGNTYLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XENP27648 1C11_H3_L3.216_IgG1_PVA_/S267K
Heavy Chain (SEQ ID NOS 42714-42718)
QIQLVQSGSELKKPGASVKVSCKASGYTFTHYGMNWVRQAPGQGLEWMGWINTYTGEPTYADGFTGRFVFSLDTSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

Light Chain (SEQ ID NOS 42719-42723)
DVLMTQSPDSLAVSLGERATINCKSSQSIVVSNGNTYLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XENP27649 1C11_H3_L3.217_IgG1_PVA_/S267K
Heavy Chain (SEQ ID NOS 42724-42728)
QIQLVQSGSELKKPGASVKVSCKASGYTFTHYGMNWVRQAPGQGLEWMGWINTYTGEPTYADGFTGRFVFSLDTSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

Light Chain (SEQ ID NOS 42729-42733)
DVLMTQSPDSLAVSLGERATINCKSSQSIVFSNGNNYLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

FIG. 40C

>XENP27650 1C11_H3_L3.218_IgG1_PVA_/S267K
Heavy Chain (SEQ ID NOS 42734-42738)
QIQLVQSGSELKKPGASVKVSCKASGYTFTHYGMNWVRQAPGQGLEWMGWINTYTGEPTYADGFTGRFVFSLDTSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

Light Chain (SEQ ID NOS 42739-42743)
DVLMTQSPDSLAVSLGERATINCKSSQSIVYSNGNNYLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XENP27651 1C11_H3_L3.219_IgG1_PVA_/S267K
Heavy Chain (SEQ ID NOS 42744-42748)
QIQLVQSGSELKKPGASVKVSCKASGYTFTHYGMNWVRQAPGQGLEWMGWINTYTGEPTYADGFTGRFVFSLDTSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

Light Chain (SEQ ID NOS 42749-42753)
DILMTQSPDSLAVSLGERATINCKSSQSIVFSNGNNYLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XENP27652 1C11_H3_L3.220_IgG1_PVA_/S267K
Heavy Chain (SEQ ID NOS 42754-42758)
QIQLVQSGSELKKPGASVKVSCKASGYTFTHYGMNWVRQAPGQGLEWMGWINTYTGEPTYADGFTGRFVFSLDTSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

Light Chain (SEQ ID NOS 42759-42763)
DILMTQSPDSLAVSLGERATINCKSSQSIVYSNGNNYLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XENP27839 1C11_H3.309_L3_IgG1_PVA_/S267K
Heavy Chain (SEQ ID NOS 42764-42768)
QIQLVQSESELKKPGASVKVSCKASGYTFTHYGMNWVRQAPGQGLEWMGWINTYTGEPTYADGFTGRFVFSLDTSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

FIG. 40D

Light Chain (SEQ ID NOS 42769-42773)
DVLMTQSPDSLAVSLGERATINCKSSQSIVHSNGNTYLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XENP27840 1C11_H3.310_L3_IgG1_PVA_/S267K
Heavy Chain (SEQ ID NOS 42774-42778)
QIQLVQSSSELKKPGASVKVSCKASGYTFTHYGMNWVRQAPGQGLEWMGWINTYTGEPTYADGFTGRFVFSLDTSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

Light Chain (SEQ ID NOS 42779-42783)
DVLMTQSPDSLAVSLGERATINCKSSQSIVHSNGNTYLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XENP27841 1C11_H3.311_L3_IgG1_PVA_/S267K
Heavy Chain (SEQ ID NOS 42784-42788)
QIQLVQSVSELKKPGASVKVSCKASGYTFTHYGMNWVRQAPGQGLEWMGWINTYTGEPTYADGFTGRFVFSLDTSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

Light Chain (SEQ ID NOS 42789-42793)
DVLMTQSPDSLAVSLGERATINCKSSQSIVHSNGNTYLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XENP27842 1C11_H3.312_L3_IgG1_PVA_/S267K
Heavy Chain (SEQ ID NOS 42794-42798)
QIQLVQSGSELTKPGASVKVSCKASGYTFTHYGMNWVRQAPGQGLEWMGWINTYTGEPTYADGFTGRFVFSLDTSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

Light Chain (SEQ ID NOS 42799-42803)
DVLMTQSPDSLAVSLGERATINCKSSQSIVHSNGNTYLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

FIG. 40E

>XENP27843 1C11_H3.313_L3_IgG1_PVA_/S267K
Heavy Chain (SEQ ID NOS 42804-42808)
QIQLVQSGSELQKPGASVKVSCKASGYTFT<u>HYGMN</u>WVRQAPGQGLEWMG<u>WINTYTGEPTYADGFT</u>GRFVFSLDTSVS
TAYLQISSLKAEDTAVYFCAR<u>DYYGSSPY</u>WGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

Light Chain (SEQ ID NOS 42809-42813)
DVLMTQSPDSLAVSLGERATINC<u>KSSQSIVHSNGNTYLE</u>WYQQKPGQSPKLLIY<u>KVSNRFS</u>GVPDRFSGSGSGTDFT
LTISSLQAEDVAVYYC<u>FQGSHVPNT</u>FGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XENP27844 1C11_H3.314_L3_IgG1_PVA_/S267K
Heavy Chain (SEQ ID NOS 42814-42818)
QIQLVQSGSELYKPGASVKVSCKASGYTFT<u>HYGMN</u>WVRQAPGQGLEWMG<u>WINTYTGEPTYADGFT</u>GRFVFSLDTSVS
TAYLQISSLKAEDTAVYFCAR<u>DYYGSSPY</u>WGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

Light Chain (SEQ ID NOS 42819-42823)
DVLMTQSPDSLAVSLGERATINC<u>KSSQSIVHSNGNTYLE</u>WYQQKPGQSPKLLIY<u>KVSNRFS</u>GVPDRFSGSGSGTDFT
LTISSLQAEDVAVYYC<u>FQGSHVPNT</u>FGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XENP27845 1C11_H3.315_L3_IgG1_PVA_/S267K
Heavy Chain (SEQ ID NOS 42824-42828)
QIQLVQSGSELLKPGASVKVSCKASGYTFT<u>HYGMN</u>WVRQAPGQGLEWMG<u>WINTYTGEPTYADGFT</u>GRFVFSLDTSVS
TAYLQISSLKAEDTAVYFCAR<u>DYYGSSPY</u>WGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

Light Chain (SEQ ID NOS 42829-42833)
DVLMTQSPDSLAVSLGERATINC<u>KSSQSIVHSNGNTYLE</u>WYQQKPGQSPKLLIY<u>KVSNRFS</u>GVPDRFSGSGSGTDFT
LTISSLQAEDVAVYYC<u>FQGSHVPNT</u>FGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XENP27846 1C11_H3.316_L3_IgG1_PVA_/S267K
Heavy Chain (SEQ ID NOS 42834-42838)
QIQLVQSGSELKKPGASVSVSCKASGYTFT<u>HYGMN</u>WVRQAPGQGLEWMG<u>WINTYTGEPTYADGFT</u>GRFVFSLDTSVS
TAYLQISSLKAEDTAVYFCAR<u>DYYGSSPY</u>WGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

FIG. 40F

Light Chain (SEQ ID NOS 42839-42843)
DVLMTQSPDSLAVSLGERATINCKSSQSIVHSNGNTYLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XENP27847 1C11_H3.317_L3_IgG1_PVA_/S267K
Heavy Chain (SEQ ID NOS 42844-42848)
QIQLVQSGSELKKPGASVTVSCKASGYTFTHYGMNWVRQAPGQGLEWMGWINTYTGEPTYADGFTGRFVFSLDTSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

Light Chain (SEQ ID NOS 42849-42853)
DVLMTQSPDSLAVSLGERATINCKSSQSIVHSNGNTYLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XENP27848 1C11_H3.318_L3_IgG1_PVA_/S267K
Heavy Chain (SEQ ID NOS 42854-42858)
QIQLVQSGSELVKPGASVTVSCKASGYTFTHYGMNWVRQAPGQGLEWMGWINTYTGEPTYADGFTGRFVFSLDTSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

Light Chain (SEQ ID NOS 42859-42863)
DVLMTQSPDSLAVSLGERATINCKSSQSIVHSNGNTYLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XENP27849 1C11_H3.319_L3_IgG1_PVA_/S267K
Heavy Chain (SEQ ID NOS 42864-42868)
QIQLVQSGSELKKPGASVKVSCKASGYTFTHYGMNWVRQAPGQGLEWMGWINTYTGEPTYADGFTGRFVFSLDTSQS
TAYLQISSLKAEDTAVYFCARDYFGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

Light Chain (SEQ ID NOS 42869-42873)
DVLMTQSPDSLAVSLGERATINCKSSQSIVHSNGNTYLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

FIG. 40G

>XENP27850_1C11_H3.320_L3_IgG1_PVA_/S267K
Heavy Chain (SEQ ID NOS 42874-42878)
QIQLVQSGSELKKPGASVKVSCKASGYTFTHYGMNWVRQAPGQGLEWMGWINTHTGEPTYADGFTGRFVFSLDTSVS
TAYLQISSLKAEDTAVYFCARDYFGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

Light Chain (SEQ ID NOS 42879-42883)
DVLMTQSPDSLAVSLGERATINCKSSQSIVHSNGNTYLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XENP27851_1C11_H3.321_L3_IgG1_PVA_/S267K
Heavy Chain (SEQ ID NOS 42884-42888)
QIQLVQSGSELKKPGASVKVSCKASGYTFTHYGMNWVRQAPGQGLEWMGWINTYSGEPTYADGFTGRFVFSLDTSVS
TAYLQISSLKAEDTAVYFCARDYFGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

Light Chain (SEQ ID NOS 42889-42893)
DVLMTQSPDSLAVSLGERATINCKSSQSIVHSNGNTYLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XENP27852_1C11_H3.322_L3_IgG1_PVA_/S267K
Heavy Chain (SEQ ID NOS 42894-42898)
QIQLVQSGSELKKPGASVKVSCKASGYTFTHYGMNWVRQAPGQGLEWMGWINTYTSEPTYADGFTGRFVFSLDTSVS
TAYLQISSLKAEDTAVYFCARDYFGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

Light Chain (SEQ ID NOS 42899-42903)
DVLMTQSPDSLAVSLGERATINCKSSQSIVHSNGNTYLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XENP27853_1C11_H3.323_L3_IgG1_PVA_/S267K
Heavy Chain (SEQ ID NOS 42904-42908)
QIQLVQSGSELKKPGASVKVSCKASGYTFTHYGMNWVRQAPGQGLEWMGWINTHSGEPTYADGFTGRFVFSLDTSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

FIG. 40H

Light Chain (SEQ ID NOS 42909-42913)
DVLMTQSPDSLAVSLGERATINCKSSQSIVHSNGNTYLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XENP27854 1C11_H3.324_L3_IgG1_PVA_/S267K
Heavy Chain (SEQ ID NOS 42914-42918)
QIQLVQSGSELKKPGASVKVSCKASGYTFTHYGMNWVRQAPGQGLEWMGWINTHSGEPTYADGFTGRFVFSLDTSVS
TAYLQISSLKAEDTAVYFCARDYFGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

Light Chain (SEQ ID NOS 42919-42923)
DVLMTQSPDSLAVSLGERATINCKSSQSIVHSNGNTYLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XENP27855 1C11_H3.325_L3_IgG1_PVA_/S267K
Heavy Chain (SEQ ID NOS 42924-42928)
QIQLVQSGSELKKPGASVKVSCKASGYTFTHYGMNWVRQAPGQGLEWMGWINTHSGEPTYADGFTGRFVFSLDTSQS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

Light Chain (SEQ ID NOS 42929-42933)
DVLMTQSPDSLAVSLGERATINCKSSQSIVHSNGNTYLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XENP27856 1C11_H3.326_L3_IgG1_PVA_/S267K
Heavy Chain (SEQ ID NOS 42934-42938)
QIQLVQSGSELKKPGASVKVSCKASGYTFTHYGMNWVRQAPGQGLEWMGWINTHSGEPTYADGFTGRFVFSLDTSQS
TAYLQISSLKAEDTAVYFCARDYFGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

Light Chain (SEQ ID NOS 42939-42943)
DVLMTQSPDSLAVSLGERATINCKSSQSIVHSNGNTYLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

FIG. 40I

>XENP27857_1C11_H3.319_L3.152_IgG1_PVA_/S267K
Heavy Chain (SEQ ID NOS 42944-42948)
QIQLVQSGSELKKPGASVKVSCKASGYTFTHYGMNWVRQAPGQGLEWMGWINTYTGEPTYADGFTGRFVFSLDTSQS
TAYLQISSLKAEDTAVYFCARDYFGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

Light Chain (SEQ ID NOS 42949-42953)
DVLMTQSPDSLAVSLGERATINCKSSQSIVFSNGNTYLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XENP27858_1C11_H3.320_L3.152_IgG1_PVA_/S267K
Heavy Chain (SEQ ID NOS 42954-42958)
QIQLVQSGSELKKPGASVKVSCKASGYTFTHYGMNWVRQAPGQGLEWMGWINTHTGEPTYADGFTGRFVFSLDTSVS
TAYLQISSLKAEDTAVYFCARDYFGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

Light Chain (SEQ ID NOS 42959-42963)
DVLMTQSPDSLAVSLGERATINCKSSQSIVFSNGNTYLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XENP27859_1C11_H3.321_L3.152_IgG1_PVA_/S267K
Heavy Chain (SEQ ID NOS 42964-42968)
QIQLVQSGSELKKPGASVKVSCKASGYTFTHYGMNWVRQAPGQGLEWMGWINTYSGEPTYADGFTGRFVFSLDTSVS
TAYLQISSLKAEDTAVYFCARDYFGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

Light Chain (SEQ ID NOS 42969-42973)
DVLMTQSPDSLAVSLGERATINCKSSQSIVFSNGNTYLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XENP27860_1C11_H3.322_L3.152_IgG1_PVA_/S267K
Heavy Chain (SEQ ID NOS 42974-42978)
QIQLVQSGSELKKPGASVKVSCKASGYTFTHYGMNWVRQAPGQGLEWMGWINTYSEPTYADGFTGRFVFSLDTSVS
TAYLQISSLKAEDTAVYFCARDYFGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

FIG. 40J

Light Chain (SEQ ID NOS 42979-42983)
DVLMTQSPDSLAVSLGERATINCKSSQSIVFSNGNTYLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XENP27861 1C11_H3.323_L3.152_IgG1_PVA_/S267K
Heavy Chain (SEQ ID NOS 42984-42988)
QIQLVQSGSELKKPGASVKVSCKASGYTFTHYGMNWVRQAPGQGLEWMGWINTHSGEPTYADGFTGRFVFSLDTSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

Light Chain (SEQ ID NOS 42989-42993)
DVLMTQSPDSLAVSLGERATINCKSSQSIVFSNGNTYLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XENP27862 1C11_H3.324_L3.152_IgG1_PVA_/S267K
Heavy Chain (SEQ ID NOS 42994-42998)
QIQLVQSGSELKKPGASVKVSCKASGYTFTHYGMNWVRQAPGQGLEWMGWINTHSGEPTYADGFTGRFVFSLDTSVS
TAYLQISSLKAEDTAVYFCARDYFGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

Light Chain (SEQ ID NOS 42999-43003)
DVLMTQSPDSLAVSLGERATINCKSSQSIVFSNGNTYLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XENP27863 1C11_H3.325_L3.152_IgG1_PVA_/S267K
Heavy Chain (SEQ ID NOS 43004-43008)
QIQLVQSGSELKKPGASVKVSCKASGYTFTHYGMNWVRQAPGQGLEWMGWINTHSGEPTYADGFTGRFVFSLDTSQS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

Light Chain (SEQ ID NOS 43009-43013)
DVLMTQSPDSLAVSLGERATINCKSSQSIVFSNGNTYLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

FIG. 40K

>XENP27864_1C11_H3.326_L3.152_IgG1_PVA_/S267K
Heavy Chain (SEQ ID NOS 43014-43018)
QIQLVQSGSELKKPGASVKVSCKASGYTFTHYGMNWVRQAPGQGLEWMGWINTHSGEPTYADGFTGRFVFSLDTSQS
TAYLQISSLKAEDTAVYFCARDYFGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

Light Chain (SEQ ID NOS 43019-43023)
DVLMTQSPDSLAVSLGERATINCKSSQSIVFSNGNTYLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XENP27865_1C11_H3.319_L3.220_IgG1_PVA_/S267K
Heavy Chain (SEQ ID NOS 43024-43028)
QIQLVQSGSELKKPGASVKVSCKASGYTFTHYGMNWVRQAPGQGLEWMGWINTYTGEPTYADGFTGRFVFSLDTSQS
TAYLQISSLKAEDTAVYFCARDYFGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

Light Chain (SEQ ID NOS 43029-43033)
DILMTQSPDSLAVSLGERATINCKSSQSIVYSNGNNYLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XENP27866_1C11_H3.320_L3.220_IgG1_PVA_/S267K
Heavy Chain (SEQ ID NOS 43034-43038)
QIQLVQSGSELKKPGASVKVSCKASGYTFTHYGMNWVRQAPGQGLEWMGWINTHTGEPTYADGFTGRFVFSLDTSVS
TAYLQISSLKAEDTAVYFCARDYFGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

Light Chain (SEQ ID NOS 43039-43043)
DILMTQSPDSLAVSLGERATINCKSSQSIVYSNGNNYLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XENP27867_1C11_H3.321_L3.220_IgG1_PVA_/S267K
Heavy Chain (SEQ ID NOS 43044-43048)
QIQLVQSGSELKKPGASVKVSCKASGYTFTHYGMNWVRQAPGQGLEWMGWINTYSGEPTYADGFTGRFVFSLDTSVS
TAYLQISSLKAEDTAVYFCARDYFGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

FIG. 40L

Light Chain (SEQ ID NOS 43049-43053)
DILMTQSPDSLAVSLGERATINCKSSQSIVYSNGNNYLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XENP27868 1C11_H3.322_L3.220_IgG1_PVA_/S267K
Heavy Chain (SEQ ID NOS 43054-43058)
QIQLVQSGSELKKPGASVKVSCKASGYTFTHYGMNWVRQAPGQGLEWMGWINTYTSEPTYADGFTGRFVFSLDTSVS
TAYLQISSLKAEDTAVYFCARDYFGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

Light Chain (SEQ ID NOS 43059-43063)
DILMTQSPDSLAVSLGERATINCKSSQSIVYSNGNNYLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XENP27869 1C11_H3.323_L3.220_IgG1_PVA_/S267K
Heavy Chain (SEQ ID NOS 43064-43068)
QIQLVQSGSELKKPGASVKVSCKASGYTFTHYGMNWVRQAPGQGLEWMGWINTHSGEPTYADGFTGRFVFSLDTSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

Light Chain (SEQ ID NOS 43069-43073)
DILMTQSPDSLAVSLGERATINCKSSQSIVYSNGNNYLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XENP27870 1C11_H3.324_L3.220_IgG1_PVA_/S267K
Heavy Chain (SEQ ID NOS 43074-43078)
QIQLVQSGSELKKPGASVKVSCKASGYTFTHYGMNWVRQAPGQGLEWMGWINTHSGEPTYADGFTGRFVFSLDTSVS
TAYLQISSLKAEDTAVYFCARDYFGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

Light Chain (SEQ ID NOS 43079-43083)
DILMTQSPDSLAVSLGERATINCKSSQSIVYSNGNNYLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

FIG. 40M

>XENP27871_1C11_H3.325_L3.220_IgG1_PVA_/S267K
Heavy Chain (SEQ ID NOS 43084-43088)
QIQLVQSGSELKKPGASVKVSCKASGYTFTHYGMNWVRQAPGQGLEWMGWINTHSGEPTYADGFTGRFVFSLDTSQS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

Light Chain (SEQ ID NOS 43089-43093)
DILMTQSPDSLAVSLGERATINCKSSQSIVYSNGNNYLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XENP27872_1C11_H3.326_L3.220_IgG1_PVA_/S267K
Heavy Chain (SEQ ID NOS 43094-43098)
QIQLVQSGSELKKPGASVKVSCKASGYTFTHYGMNWVRQAPGQGLEWMGWINTHSGEPTYADGFTGRFVFSLDTSQS
TAYLQISSLKAEDTAVYFCARDYFGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

Light Chain (SEQ ID NOS 43099-43103)
DILMTQSPDSLAVSLGERATINCKSSQSIVYSNGNNYLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XENP27959_1C11_H3.303_L3.219_IgG1_PVA_/S267K
Heavy Chain (SEQ ID NOS 43104-43108)
QIQLVQSGSELKKPGASVKVSCKASGYTFTHYGMNWVRQAPGQGLEWMGWINTYTGEPTYADGFTGRFVFSLDTSVS
TAYLQISSLKAEDTAVYFCARDYFGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

Light Chain (SEQ ID NOS 43109-43113)
DILMTQSPDSLAVSLGERATINCKSSQSIVFSNGNNYLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XENP27960_1C11_H3.303_L3.220_IgG1_PVA_/S267K
Heavy Chain (SEQ ID NOS 43114-43118)
QIQLVQSGSELKKPGASVKVSCKASGYTFTHYGMNWVRQAPGQGLEWMGWINTYTGEPTYADGFTGRFVFSLDTSVS
TAYLQISSLKAEDTAVYFCARDYFGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

FIG. 40N

Light Chain (SEQ ID NOS 43119-43123)
DILMTQSPDSLAVSLGERATINCKSSQSIVYSNGNNYLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XENP27961 1C11_H3.320_L3.219_IgG1_PVA_/S267K
Heavy Chain (SEQ ID NOS 43124-43128)
QIQLVQSGSELKKPGASVKVSCKASGYTFTHYGMNWVRQAPGQGLEWMGWINTHTGEPTYADGFTGRFVFSLDTSVS
TAYLQISSLKAEDTAVYFCARDYFGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

Light Chain (SEQ ID NOS 43129-43133)
DILMTQSPDSLAVSLGERATINCKSSQSIVFSNGNNYLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XENP27962 1C11_H3.323_L3.219_IgG1_PVA_/S267K
Heavy Chain (SEQ ID NOS 43134-43138)
QIQLVQSGSELKKPGASVKVSCKASGYTFTHYGMNWVRQAPGQGLEWMGWINTHSGEPTYADGFTGRFVFSLDTSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

Light Chain (SEQ ID NOS 43139-43143)
DILMTQSPDSLAVSLGERATINCKSSQSIVFSNGNNYLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XENP27963 1C11_H3.324_L3.219_IgG1_PVA_/S267K
Heavy Chain (SEQ ID NOS 43144-43148)
QIQLVQSGSELKKPGASVKVSCKASGYTFTHYGMNWVRQAPGQGLEWMGWINTHSGEPTYADGFTGRFVFSLDTSVS
TAYLQISSLKAEDTAVYFCARDYFGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

Light Chain (SEQ ID NOS 43149-43153)
DILMTQSPDSLAVSLGERATINCKSSQSIVFSNGNNYLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

FIG. 400

>XENP28024 1C11_H3.327_L3.220_IgG1_PVA_/S267K
Heavy Chain (SEQ ID NOS 43154-43158)
QIQLVQSGSELLKPGASVKVSCKASGYTFT<u>HYGMN</u>WVRQAPGQGLEWMG<u>WINTHTGEPTYADGFTG</u>RFVFSLDTSVS
TAYLQISSLKAEDTAVYFCAR<u>DYFGSSPY</u>WGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

Light Chain (SEQ ID NOS 43159-43163)
DILMTQSPDSLAVSLGERATINC<u>KSSQSIVYSNGNNYLE</u>WYQQKPGQSPKLLIY<u>KVSNRFS</u>GVPDRFSGSGSGTDFT
LTISSLQAEDVAVYYC<u>FQGSHVPNT</u>FGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC >XENP28025 1C11_H3.328_L3.220_IgG1_PVA_/S267K
Heavy Chain (SEQ ID NOS 43164-43168)
QIQLVQSGSELKKPGASVSVSCKASGYTFT<u>HYGMN</u>WVRQAPGQGLEWMG<u>WINTHTGEPTYADGFTG</u>RFVFSLDTSVS
TAYLQISSLKAEDTAVYFCAR<u>DYFGSSPY</u>WGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

Light Chain (SEQ ID NOS 43169-43173)
DILMTQSPDSLAVSLGERATINC<u>KSSQSIVYSNGNNYLE</u>WYQQKPGQSPKLLIY<u>KVSNRFS</u>GVPDRFSGSGSGTDFT
LTISSLQAEDVAVYYC<u>FQGSHVPNT</u>FGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC >XENP28026 1C11_H3.329_L3.220_IgG1_PVA_/S267K
Heavy Chain (SEQ ID NOS 43174-43178)
QIQLVQSGSELLKPGASVSVSCKASGYTFT<u>HYGMN</u>WVRQAPGQGLEWMG<u>WINTHTGEPTYADGFTG</u>RFVFSLDTSVS
TAYLQISSLKAEDTAVYFCAR<u>DYFGSSPY</u>WGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

Light Chain (SEQ ID NOS 43179-43183)
DILMTQSPDSLAVSLGERATINC<u>KSSQSIVYSNGNNYLE</u>WYQQKPGQSPKLLIY<u>KVSNRFS</u>GVPDRFSGSGSGTDFT
LTISSLQAEDVAVYYC<u>FQGSHVPNT</u>FGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC >XENP28027 1C11_H3.330_L3.220_IgG1_PVA_/S267K
Heavy Chain (SEQ ID NOS 43184-43188)
QIQLVQSGSELLKPGASVKVSCKASGYTFT<u>HYGMN</u>WVRQAPGQGLEWMG<u>WINTHSGEPTYADGFTG</u>RFVFSLDTSVS
TAYLQISSLKAEDTAVYFCAR<u>DYYGSSPY</u>WGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

FIG. 40P

Light Chain (SEQ ID NOS 43189-43193)
DILMTQSPDSLAVSLGERATINCKSSQSIVYSNGNNYLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XENP28028 1C11_H3.331_L3.220_IgG1_PVA_/S267K
Heavy Chain (SEQ ID NOS 43194-43198)
QIQLVQSGSELKKPGASVSVSCKASGYTFTHYGMNWVRQAPGQGLEWMGWINTHSGEPTYADGFTGRFVFSLDTSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

Light Chain (SEQ ID NOS 43199-43203)
DILMTQSPDSLAVSLGERATINCKSSQSIVYSNGNNYLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XENP28029 1C11_H3.332_L3.220_IgG1_PVA_/S267K
Heavy Chain (SEQ ID NOS 43204-43208)
QIQLVQSGSELLKPGASVSVSCKASGYTFTHYGMNWVRQAPGQGLEWMGWINTHSGEPTYADGFTGRFVFSLDTSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

Light Chain (SEQ ID NOS 43209-43213)
DILMTQSPDSLAVSLGERATINCKSSQSIVYSNGNNYLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XENP28030 1C11_H3.333_L3.220_IgG1_PVA_/S267K
Heavy Chain (SEQ ID NOS 43214-43218)
QIQLVQSGSELLKPGASVKVSCKASGYTFTHYGMNWVRQAPGQGLEWMGWINTHSGEPTYADGFTGRFVFSLDTSVS
TAYLQISSLKAEDTAVYFCARDYFGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

Light Chain (SEQ ID NOS 43219-43223)
DILMTQSPDSLAVSLGERATINCKSSQSIVYSNGNNYLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

FIG. 40Q

>XENP28031_1C11_H3.334_L3.220_IgG1_PVA_/S267K
Heavy Chain (SEQ ID NOS 43224-43228)
QIQLVQSGSELKKPGASVSVSCKASGYTFTHYGMNWVRQAPGQGLEWMGWINTHSGEPTYADGFTGRFVFSLDTSVS
TAYLQISSLKAEDTAVYFCARDYFGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

Light Chain (SEQ ID NOS 43229-43233)
DILMTQSPDSLAVSLGERATINCKSSQSIVYSNGNNYLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC >XENP28032_1C11_H3.335_L3.220_IgG1_PVA_/S267K
Heavy Chain (SEQ ID NOS 43234-43238)
QIQLVQSGSELLKPGASVSVSCKASGYTFTHYGMNWVRQAPGQGLEWMGWINTHSGEPTYADGFTGRFVFSLDTSVS
TAYLQISSLKAEDTAVYFCARDYFGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

Light Chain (SEQ ID NOS 43239-43243)
DILMTQSPDSLAVSLGERATINCKSSQSIVYSNGNNYLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC >XENP28033_1C11_H3.336_L3.220_IgG1_PVA_/S267K
Heavy Chain (SEQ ID NOS 43244-43248)
QIQLVQSGSELLKPGASVKVSCKASGYTFTHYGMNWVRQAPGQGLEWMGWINTYTGEPTYADGFTGRFVFSLDTSVS
TAYLQISSLKAEDTAVYFCARDYFGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

Light Chain (SEQ ID NOS 43249-43253)
DILMTQSPDSLAVSLGERATINCKSSQSIVYSNGNNYLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC >XENP28034_1C11_H3.337_L3.220_IgG1_PVA_/S267K
Heavy Chain (SEQ ID NOS 43254-43258)
QIQLVQSGSELKKPGASVSVSCKASGYTFTHYGMNWVRQAPGQGLEWMGWINTYTGEPTYADGFTGRFVFSLDTSVS
TAYLQISSLKAEDTAVYFCARDYFGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

FIG. 40R

Light Chain (SEQ ID NOS 43259-43263)
DILMTQSPDSLAVSLGERATINCKSSQSIVYSNGNNYLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XENP28035 1C11_H3.338_L3.220_IgG1_PVA_/S267K
Heavy Chain (SEQ ID NOS 43264-43268)
QIQLVQSGSELLKPGASVSVSCKASGYTFTHYGMNWVRQAPGQGLEWMGWINTYTGEPTYADGFTGRFVFSLDTSVS
TAYLQISSLKAEDTAVYFCARDYFGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

Light Chain (SEQ ID NOS 43269-43273)
DILMTQSPDSLAVSLGERATINCKSSQSIVYSNGNNYLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XENP28651 1C11_H3.327_L3.152_IgG1_PVA_/S267K
Heavy Chain (SEQ ID NOS 43274-43278)
QIQLVQSGSELLKPGASVKVSCKASGYTFTHYGMNWVRQAPGQGLEWMGWINTHTGEPTYADGFTGRFVFSLDTSVS
TAYLQISSLKAEDTAVYFCARDYFGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

Light Chain (SEQ ID NOS 43279-43283)
DVLMTQSPDSLAVSLGERATINCKSSQSIVFSNGNTYLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XENP28652 1C11_H3.328_L3.152_IgG1_PVA_/S267K
Heavy Chain (SEQ ID NOS 43284-43288)
QIQLVQSGSELKKPGASVSVSCKASGYTFTHYGMNWVRQAPGQGLEWMGWINTHTGEPTYADGFTGRFVFSLDTSVS
TAYLQISSLKAEDTAVYFCARDYFGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

Light Chain (SEQ ID NOS 43289-43293)
DVLMTQSPDSLAVSLGERATINCKSSQSIVFSNGNTYLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

FIG. 40S

>XENP28653_1C11_H3.329_L3.152_IgG1_PVA_/S267K
Heavy Chain (SEQ ID NOS 43294-43298)
QIQLVQSGSELLKPGASVSVSCKASGYTFTHYGMNWVRQAPGQGLEWMGWINTHTGEPTYADGFTGRFVFSLDTSVS
TAYLQISSLKAEDTAVYFCARDYFGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

Light Chain (SEQ ID NOS 43299-43303)
DVLMTQSPDSLAVSLGERATINCKSSQSIVFSNGNTYLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XENP28654_1C11_H3.23_L3_IgG1_PVA_/S267K
Heavy Chain (SEQ ID NOS 43304-43308)
QIQLVQSGSELKKPGASVKVSCKASGYTFTHYGMNWVRQAPGQGLEWMGYINTYTGEPTYADGFTGRFVFSLDTSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

Light Chain (SEQ ID NOS 43309-43313)
DVLMTQSPDSLAVSLGERATINCKSSQSIVHSNGNTYLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XENP28655_1C11_H3.28_L3_IgG1_PVA_/S267K
Heavy Chain (SEQ ID NOS 43314-43318)
QIQLVQSGSELKKPGASVKVSCKASGYTFTHYGMNWVRQAPGQGLEWMGWINTYTGETTYADGFTGRFVFSLDTSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

Light Chain (SEQ ID NOS 43319-43323)
DVLMTQSPDSLAVSLGERATINCKSSQSIVHSNGNTYLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XENP28656_1C11_H3.35_L3_IgG1_PVA_/S267K
Heavy Chain (SEQ ID NOS 43324-43328)
QIQLVQSGSELKKPGASVKVSCKASGYTFTHYGMNWVRQAPGQGLEWMGWINTYTGEPTYADKFTGRFVFSLDTSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

FIG. 40T

Light Chain (SEQ ID NOS 43329-43333)
DVLMTQSPDSLAVSLGERATINCKSSQSIVHSNGNTYLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XENP28657 1C11_H3_L3.71_IgG1_PVA_/S267K
Heavy Chain (SEQ ID NOS 43334-43338)
QIQLVQSGSELKKPGASVKVSCKASGYTFTHYGMNWVRQAPGQGLEWMGWINTYTGEPTYADGFTGRFVFSLDTSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

Light Chain (SEQ ID NOS 43339-43343)
DVLMTQSPDSLAVSLGERATINCKSSQSIVHSNGNTYLEWYQQKPGQSPKLLIYKVSNRFSGVPDRFSGSGSGTDFT
LTISSLQAEDIAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XENP28658 1C11_H3_L3.74_IgG1_PVA_/S267K
Heavy Chain (SEQ ID NOS 43344-43348)
QIQLVQSGSELKKPGASVKVSCKASGYTFTHYGMNWVRQAPGQGLEWMGWINTYTGEPTYADGFTGRFVFSLDTSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

Light Chain (SEQ ID NOS 43349-43353)
DVLMTQSPDSLAVSLGERATINCKSSQSIVHSNGNTYLEWYQQKPGQSPKLLIYKVSNRFSGVPDRFSGSGSGTDFT
LTISSLQAEDVAVYYCQQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XENP28659 1C11_H3_L3.77_IgG1_PVA_/S267K
Heavy Chain (SEQ ID NOS 43354-43358)
QIQLVQSGSELKKPGASVKVSCKASGYTFTHYGMNWVRQAPGQGLEWMGWINTYTGEPTYADGFTGRFVFSLDTSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

Light Chain (SEQ ID NOS 43359-43363)
DVLMTQSPDSLAVSLGERATINCKSSQSIVHSNGNTYLEWYQQKPGQSPKLLIYKVSNRFSGVPDRFSGSGSGTDFT
LTISSLQAEDVAVYYCFQYSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

FIG. 40U

>XENP29029_1C11_H3.246_L3_IgG1_PVA_/S267K
Heavy Chain (SEQ ID NOS 43364-43368)
QIQLVQSGSELKKPGASVKVSCKASGLTFTHYGMNWVRQAPGQGLEWMGWINTYTGEPTYADGFTGRFVFSLDTSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

Light Chain (SEQ ID NOS 43369-43373)
DVLMTQSPDSLAVSLGERATINCKSSQSIVHSNGNTYLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XENP29030_1C11_H3.247_L3_IgG1_PVA_/S267K
Heavy Chain (SEQ ID NOS 43374-43378)
QIQLVQSGSELKKPGASVKVSCKASGHTFTHYGMNWVRQAPGQGLEWMGWINTYTGEPTYADGFTGRFVFSLDTSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

Light Chain (SEQ ID NOS 43379-43383)
DVLMTQSPDSLAVSLGERATINCKSSQSIVHSNGNTYLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XENP29031_1C11_H3.248_L3_IgG1_PVA_/S267K
Heavy Chain (SEQ ID NOS 43384-43388)
QIQLVQSGSELKKPGASVKVSCKASGQTFTHYGMNWVRQAPGQGLEWMGWINTYTGEPTYADGFTGRFVFSLDTSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

Light Chain (SEQ ID NOS 43389-43393)
DVLMTQSPDSLAVSLGERATINCKSSQSIVHSNGNTYLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XENP29032_1C11_H3.254_L3_IgG1_PVA_/S267K
Heavy Chain (SEQ ID NOS 43394-43398)
QIQLVQSGSELKKPGASVKVSCKASGYQFTHYGMNWVRQAPGQGLEWMGWINTYTGEPTYADGFTGRFVFSLDTSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

FIG. 40V

Light Chain (SEQ ID NOS 43399-43403)
DVLMTQSPDSLAVSLGERATINCKSSQSIVHSNGNTYLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XENP29033 1C11_H3.263_L3_IgG1_PVA_/S267K
Heavy Chain (SEQ ID NOS 43404-43408)
QIQLVQSGSELKKPGASVKVSCKASGYTFTQYGMNWVRQAPGQGLEWMGWINTYTGEPTYADGFTGRFVFSLDTSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

Light Chain (SEQ ID NOS 43409-43413)
DVLMTQSPDSLAVSLGERATINCKSSQSIVHSNGNTYLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XENP29034 1C11_H3.264_L3_IgG1_PVA_/S267K
Heavy Chain (SEQ ID NOS 43414-43418)
QIQLVQSGSELKKPGASVKVSCKASGYTFTDYGMNWVRQAPGQGLEWMGWINTYTGEPTYADGFTGRFVFSLDTSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

Light Chain (SEQ ID NOS 43419-43423)
DVLMTQSPDSLAVSLGERATINCKSSQSIVHSNGNTYLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XENP29035 1C11_H3.265_L3_IgG1_PVA_/S267K
Heavy Chain (SEQ ID NOS 43424-43428)
QIQLVQSGSELKKPGASVKVSCKASGYTFTRYGMNWVRQAPGQGLEWMGWINTYTGEPTYADGFTGRFVFSLDTSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

Light Chain (SEQ ID NOS 43429-43433)
DVLMTQSPDSLAVSLGERATINCKSSQSIVHSNGNTYLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

FIG. 40W

>XENP29036_1C11_H3.269_L3_IgG1_PVA_/S267K
Heavy Chain (SEQ ID NOS 43434-43438)
QIQLVQSGSELKKPGASVKVSCKASGYTFTHLGMNWVRQAPGQGLEWMGWINTYTGEPTYADGFTGRFVFSLDTSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

Light Chain (SEQ ID NOS 43439-43443)
DVLMTQSPDSLAVSLGERATINCKSSQSIVHSNGNTYLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XENP29037_1C11_H3.276_L3_IgG1_PVA_/S267K
Heavy Chain (SEQ ID NOS 43444-43448)
QIQLVQSGSELKKPGASVKVSCKASGYTFTHYGMNWFRQAPGQGLEWMGWINTYTGEPTYADGFTGRFVFSLDTSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

Light Chain (SEQ ID NOS 43449-43453)
DVLMTQSPDSLAVSLGERATINCKSSQSIVHSNGNTYLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XENP29038_1C11_H3.283_L3_IgG1_PVA_/S267K
Heavy Chain (SEQ ID NOS 43454-43458)
QIQLVQSGSELKKPGASVKVSCKASGYTFTHYGMNWVRQAPGQGLEWMGWIQTYTGEPTYADGFTGRFVFSLDTSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

Light Chain (SEQ ID NOS 43459-43463)
DVLMTQSPDSLAVSLGERATINCKSSQSIVHSNGNTYLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XENP29039_1C11_H3.284_L3_IgG1_PVA_/S267K
Heavy Chain (SEQ ID NOS 43464-43468)
QIQLVQSGSELKKPGASVKVSCKASGYTFTHYGMNWVRQAPGQGLEWMGWIETYTGEPTYADGFTGRFVFSLDTSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

FIG. 40X

Light Chain (SEQ ID NOS 43469-43473)
DVLMTQSPDSLAVSLGERATINCKSSQSIVHSNGNTYLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XENP29040 1C11_H3.285_L3_IgG1_PVA_/S267K
Heavy Chain (SEQ ID NOS 43474-43478)
QIQLVQSGSELKKPGASVKVSCKASGYTFTHYGMNWVRQAPGQGLEWMGWIHTYTGEPTYADGFTGRFVFSLDTSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

Light Chain (SEQ ID NOS 43479-43483)
DVLMTQSPDSLAVSLGERATINCKSSQSIVHSNGNTYLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XENP29041 1C11_H3.286_L3_IgG1_PVA_/S267K
Heavy Chain (SEQ ID NOS 43484-43488)
QIQLVQSGSELKKPGASVKVSCKASGYTFTHYGMNWVRQAPGQGLEWMGWISTYTGEPTYADGFTGRFVFSLDTSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

Light Chain (SEQ ID NOS 43489-43493)
DVLMTQSPDSLAVSLGERATINCKSSQSIVHSNGNTYLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XENP29042 1C11_H3.289_L3_IgG1_PVA_/S267K
Heavy Chain (SEQ ID NOS 43494-43498)
QIQLVQSGSELKKPGASVKVSCKASGYTFTHYGMNWVRQAPGQGLEWMGWINTLTGEPTYADGFTGRFVFSLDTSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

Light Chain (SEQ ID NOS 43499-43503)
DVLMTQSPDSLAVSLGERATINCKSSQSIVHSNGNTYLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

FIG. 40Y

>XENP29043_1C11_H3.290_L3_IgG1_PVA_/S267K
Heavy Chain (SEQ ID NOS 43504-43508)
QIQLVQSGSELKKPGASVKVSCKASGYTFTHYGMNWVRQAPGQGLEWMGWINTWTGEPTYADGFTGRFVFSLDTSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

Light Chain (SEQ ID NOS 43509-43513)
DVLMTQSPDSLAVSLGERATINCKSSQSIVHSNGNTYLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XENP29044_1C11_H3.294_L3_IgG1_PVA_/S267K
Heavy Chain (SEQ ID NOS 43514-43518)
QIQLVQSGSELKKPGASVKVSCKASGYTFTHYGMNWVRQAPGQGLEWMGWINTYIGEPTYADGFTGRFVFSLDTSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

Light Chain (SEQ ID NOS 43519-43523)
DVLMTQSPDSLAVSLGERATINCKSSQSIVHSNGNTYLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XENP29045_1C11_H3.296_L3_IgG1_PVA_/S267K
Heavy Chain (SEQ ID NOS 43524-43528)
QIQLVQSGSELKKPGASVKVSCKASGYTFTHYGMNWVRQAPGQGLEWMGWINTYTGKPTYADGFTGRFVFSLDTSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

Light Chain (SEQ ID NOS 43529-43533)
DVLMTQSPDSLAVSLGERATINCKSSQSIVHSNGNTYLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XENP29046_1C11_H3_L3.155_IgG1_PVA_/S267K
Heavy Chain (SEQ ID NOS 43534-43538)
QIQLVQSGSELKKPGASVKVSCKASGYTFTHYGMNWVRQAPGQGLEWMGWINTYTGEPTYADGFTGRFVFSLDTSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

FIG. 40Z

Light Chain (SEQ ID NOS 43539-43543)
DVLMTQSPDSLAVSLGERATINCKSSQSIVHTNGNTYLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XENP29047_1C11_H3_L3.157_IgG1_PVA_/S267K
Heavy Chain (SEQ ID NOS 43544-43548)
QIQLVQSGSELKKPGASVKVSCKASGYTFTHYGMNWVRQAPGQGLEWMGWINTYTGEPTYADGFTGRFVFSLDTSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

Light Chain (SEQ ID NOS 43549-43553)
DVLMTQSPDSLAVSLGERATINCKSSQSIVHQNGNTYLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XENP29048_1C11_H3_L3.163_IgG1_PVA_/S267K
Heavy Chain (SEQ ID NOS 43554-43558)
QIQLVQSGSELKKPGASVKVSCKASGYTFTHYGMNWVRQAPGQGLEWMGWINTYTGEPTYADGFTGRFVFSLDTSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

Light Chain (SEQ ID NOS 43559-43563)
DVLMTQSPDSLAVSLGERATINCKSSQSIVHSRGNTYLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XENP29049_1C11_H3_L3.173_IgG1_PVA_/S267K
Heavy Chain (SEQ ID NOS 43564-43568)
QIQLVQSGSELKKPGASVKVSCKASGYTFTHYGMNWVRQAPGQGLEWMGWINTYTGEPTYADGFTGRFVFSLDTSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

Light Chain (SEQ ID NOS 43569-43573)
DVLMTQSPDSLAVSLGERATINCKSSQSIVHSNGNTFLEWYQQKPGQSPKLLIYKVSNRFSGVPDRFSGSGSGTDFT
LTISSLQAEDVAVYYCFQGSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

FIG. 40AA

>XENP29050 1C11_H3_L3.181_IgG1_PVA_/S267K
Heavy Chain (SEQ ID NOS 43574-43578)
QIQLVQSGSELKKPGASVKVSCKASGYTFT<u>HYGMN</u>WVRQAPGQGLEWMG<u>WINTYTGEPTYADGFTGRFVFSLDTSVS
TAYLQISSLKAEDTAVYFCARDYYGSSPYW</u>GQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

Light Chain (SEQ ID NOS 43579-43583)
DVLMTQSPDSLAVSLGERATINC<u>KSSQSIVHSNGNTYLE</u>WYQQKPGQSPKLLIW<u>KVSNRF</u>SGVPDRFSGSGSGTDFT
LTISSLQAEDVAVYYC<u>FQGSHVPNT</u>FGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XENP29051_1C11_H3_L3.182_IgG1_PVA_/S267K
Heavy Chain (SEQ ID NOS 43584-43588)
QIQLVQSGSELKKPGASVKVSCKASGYTFT<u>HYGMN</u>WVRQAPGQGLEWMG<u>WINTYTGEPTYADGFTGRFVFSLDTSVS
TAYLQISSLKAEDTAVYFCARDYYGSSPYW</u>GQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

Light Chain (SEQ ID NOS 43589-43593)
DVLMTQSPDSLAVSLGERATINC<u>KSSQSIVHSNGNTYLE</u>WYQQKPGQSPKLLIQ<u>KVSNRF</u>SGVPDRFSGSGSGTDFT
LTISSLQAEDVAVYYC<u>FQGSHVPNT</u>FGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XENP29052_1C11_H3_L3.189_IgG1_PVA_/S267K
Heavy Chain (SEQ ID NOS 43594-43598)
QIQLVQSGSELKKPGASVKVSCKASGYTFT<u>HYGMN</u>WVRQAPGQGLEWMG<u>WINTYTGEPTYADGFTGRFVFSLDTSVS
TAYLQISSLKAEDTAVYFCARDYYGSSPYW</u>GQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

Light Chain (SEQ ID NOS 43599-43603)
DVLMTQSPDSLAVSLGERATINC<u>KSSQSIVHSNGNTYLE</u>WYQQKPGQSPKLLIY<u>KVSRRF</u>SGVPDRFSGSGSGTDFT
LTISSLQAEDVAVYYC<u>FQGSHVPNT</u>FGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XENP29053_1C11_H3_L3.192_IgG1_PVA_/S267K
Heavy Chain (SEQ ID NOS 43604-43608)
QIQLVQSGSELKKPGASVKVSCKASGYTFT<u>HYGMN</u>WVRQAPGQGLEWMG<u>WINTYTGEPTYADGFTGRFVFSLDTSVS
TAYLQISSLKAEDTAVYFCARDYYGSSPYW</u>GQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

FIG. 40BB

Light Chain (SEQ ID NOS 43609-43613)
DVLMTQSPDSLAVSLGERATINCKSSQSIVHSNGNTYLEWYQQKPGQSPKLLIYKVSNRFSGVPDRFSGSGSGTDFT
LTISSLQAEDVAVYYCFQASHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XENP29054 1C11_H3_L3.193_IgG1_PVA_/S267K
Heavy Chain (SEQ ID NOS 43614-43618)
QIQLVQSGSELKKPGASVKVSCKASGYTFTHYGMNWVRQAPGQGLEWMGWINTYTGEPTYADGFTGRFVFSLDTSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

Light Chain (SEQ ID NOS 43619-43623)
DVLMTQSPDSLAVSLGERATINCKSSQSIVHSNGNTYLEWYQQKPGQSPKLLIYKVSNRFSGVPDRFSGSGSGTDFT
LTISSLQAEDVAVYYCFQSSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XENP29055 1C11_H3_L3.196_IgG1_PVA_/S267K
Heavy Chain (SEQ ID NOS 43624-43628)
QIQLVQSGSELKKPGASVKVSCKASGYTFTHYGMNWVRQAPGQGLEWMGWINTYTGEPTYADGFTGRFVFSLDTSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

Light Chain (SEQ ID NOS 43629-43633)
DVLMTQSPDSLAVSLGERATINCKSSQSIVHSNGNTYLEWYQQKPGQSPKLLIYKVSNRFSGVPDRFSGSGSGTDFT
LTISSLQAEDVAVYYCFQQSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

>XENP29056 1C11_H3_L3.198_IgG1_PVA_/S267K
Heavy Chain (SEQ ID NOS 43634-43638)
QIQLVQSGSELKKPGASVKVSCKASGYTFTHYGMNWVRQAPGQGLEWMGWINTYTGEPTYADGFTGRFVFSLDTSVS
TAYLQISSLKAEDTAVYFCARDYYGSSPYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

Light Chain (SEQ ID NOS 43639-43643)
DVLMTQSPDSLAVSLGERATINCKSSQSIVHSNGNTYLEWYQQKPGQSPKLLIYKVSNRFSGVPDRFSGSGSGTDFT
LTISSLQAEDVAVYYCFQLSHVPNTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

FIG. 41

|  | | Human PD-1 | | |
|---|---|---|---|---|
| TA | Variant | $K_D$ (M) | $k_a$ (1/Ms) | $k_d$ (1/s) |
| XENP27643 | 1C11_H3_L3.211 | 2.95E-08 | 3.57E+05 | 1.05E-02 |
| XENP27644 | 1C11_H3_L3.212 | 2.57E-08 | 3.75E+05 | 9.63E-03 |
| XENP27645 | 1C11_H3_L3.213 | 3.32E-08 | 3.16E+05 | 1.05E-02 |
| XENP27646 | 1C11_H3_L3.214 | 7.26E-08 | 4.75E+05 | 3.45E-02 |
| XENP27647 | 1C11_H3_L3.215 | 7.90E-08 | 7.89E+05 | 6.23E-02 |
| XENP27648 | 1C11_H3_L3.216 | 1.25E-07 | 7.64E+05 | 9.52E-02 |
| XENP27649 | 1C11_H3_L3.217 | 7.18E-09 | 3.81E+05 | 2.73E-03 |
| XENP27650 | 1C11_H3_L3.218 | 5.80E-09 | 3.53E+05 | 2.05E-03 |
| XENP27651 | 1C11_H3_L3.219 | 6.72E-09 | 3.40E+05 | 2.29E-03 |
| XENP27652 | 1C11_H3_L3.220 | 5.02E-09 | 3.43E+05 | 1.72E-03 |
| XENP16432 | Nivolumab_H0L0 | 1.02E-08 | 3.38E+05 | 3.43E-03 |

FIG. 42

| | | Human PD-1 | | |
|---|---|---|---|---|
| TA | Variant | $K_D$ (M) | $k_a$ (1/Ms) | $k_d$ (1/s) |
| XENP27839 | 1C11_H3.309_L3 | 4.63E-08 | 3.02E+05 | 1.40E-02 |
| XENP27840 | 1C11_H3.310_L3 | 6.02E-08 | 2.84E+05 | 1.71E-02 |
| XENP27841 | 1C11_H3.311_L3 | 5.30E-08 | 3.06E+05 | 1.62E-02 |
| XENP27842 | 1C11_H3.312_L3 | 5.07E-08 | 3.31E+05 | 1.68E-02 |
| XENP27843 | 1C11_H3.313_L3 | 4.92E-08 | 3.14E+05 | 1.54E-02 |
| XENP27844 | 1C11_H3.314_L3 | 4.93E-08 | 3.85E+05 | 1.90E-02 |
| XENP27845 | 1C11_H3.315_L3 | 3.15E-08 | 3.40E+05 | 1.07E-02 |
| XENP27846 | 1C11_H3.316_L3 | 3.77E-08 | 3.51E+05 | 1.32E-02 |
| XENP27847 | 1C11_H3.317_L3 | 5.04E-08 | 3.41E+05 | 1.72E-02 |
| XENP27848 | 1C11_H3.318_L3 | 7.16E-08 | 2.84E+05 | 2.03E-02 |
| XENP27849 | 1C11_H3.319_L3 | 2.44E-08 | 3.31E+05 | 8.07E-03 |
| XENP27850 | 1C11_H3.320_L3 | 1.60E-08 | 2.96E+05 | 4.73E-03 |
| XENP27851 | 1C11_H3.321_L3 | 1.19E-08 | 3.95E+05 | 4.70E-03 |
| XENP27852 | 1C11_H3.322_L3 | 1.91E-08 | 3.17E+05 | 6.06E-03 |
| XENP27853 | 1C11_H3.323_L3 | 1.25E-08 | 3.87E+05 | 4.81E-03 |
| XENP27854 | 1C11_H3.324_L3 | 7.17E-09 | 4.18E+05 | 3.00E-03 |
| XENP27855 | 1C11_H3.325_L3 | 1.67E-08 | 4.03E+05 | 6.74E-03 |
| XENP27856 | 1C11_H3.326_L3 | 1.16E-08 | 3.67E+05 | 4.25E-03 |
| XENP27857 | 1C11_H3.319_L3.152 | 8.51E-09 | 3.15E+05 | 2.68E-03 |
| XENP27858 | 1C11_H3.320_L3.152 | 5.66E-09 | 3.75E+05 | 2.12E-03 |
| XENP27859 | 1C11_H3.321_L3.152 | 5.60E-09 | 3.40E+05 | 1.90E-03 |
| XENP27860 | 1C11_H3.322_L3.152 | 8.41E-09 | 3.09E+05 | 2.60E-03 |
| XENP27861 | 1C11_H3.323_L3.152 | 4.39E-09 | 3.82E+05 | 1.68E-03 |
| XENP27862 | 1C11_H3.324_L3.152 | 3.46E-09 | 4.06E+05 | 1.41E-03 |
| XENP27863 | 1C11_H3.325_L3.152 | 6.61E-09 | 4.88E+05 | 3.23E-03 |
| XENP27864 | 1C11_H3.326_L3.152 | 6.12E-09 | 5.02E+05 | 3.07E-03 |
| XENP27865 | 1C11_H3.319_L3.220 | 5.46E-09 | 3.37E+05 | 1.84E-03 |
| XENP27866 | 1C11_H3.320_L3.220 | 4.13E-09 | 3.44E+05 | 1.42E-03 |
| XENP27867 | 1C11_H3.321_L3.220 | 5.89E-09 | 4.50E+05 | 2.65E-03 |
| XENP27868 | 1C11_H3.322_L3.220 | 7.13E-09 | 4.00E+05 | 2.85E-03 |
| XENP27869 | 1C11_H3.323_L3.220 | 4.70E-09 | 3.86E+05 | 1.82E-03 |
| XENP27870 | 1C11_H3.324_L3.220 | 4.48E-09 | 4.26E+05 | 1.91E-03 |
| XENP27871 | 1C11_H3.325_L3.220 | 5.34E-09 | 5.44E+05 | 2.90E-03 |
| XENP27872 | 1C11_H3.326_L3.220 | 3.91E-09 | 3.78E+05 | 1.48E-03 |
| XENP22553 | 1C11_H3L3 | 6.19E-08 | 3.04E+05 | 1.88E-02 |
| XENP26940 | 1C11_H3.303_L3.152 | 7.36E-09 | 3.67E+05 | 2.70E-03 |

FIG. 43

| | | Human PD-1 | | |
|---|---|---|---|---|
| TA | Variant | $K_D$ (M) | $k_a$ (1/Ms) | $k_d$ (1/s) |
| XENP22553 | 1C11_H3L3 | 1.54E-08 | 3.17E+05 | 4.87E-03 |
| XENP26940 | 1C11_H3.303_L3.152 | 6.74E-09 | 2.57E+05 | 1.73E-03 |
| XENP27858 | 1C11_H3.320_L3.152 | 3.07E-09 | 3.23E+05 | 9.91E-04 |
| XENP27861 | 1C11_H3.323_L3.152 | 4.14E-09 | 4.74E+05 | 1.97E-03 |
| XENP27862 | 1C11_H3.324_L3.152 | 4.48E-09 | 3.25E+05 | 1.46E-03 |
| XENP27959 | 1C11_H3.303_L3.219 | 3.58E-09 | 2.56E+05 | 9.14E-04 |
| XENP27960 | 1C11_H3.303_L3.220 | 2.30E-09 | 2.47E+05 | 5.68E-04 |
| XENP27961 | 1C11_H3.320_L3.219 | 2.75E-09 | 3.28E+05 | 9.01E-04 |
| XENP27962 | 1C11_H3.323_L3.219 | 2.32E-09 | 3.60E+05 | 8.34E-04 |
| XENP27963 | 1C11_H3.324_L3.219 | 2.96E-09 | 3.71E+05 | 1.10E-03 |

FIG. 44

|  | | Human PD-1 | | |
| --- | --- | --- | --- | --- |
| TA | Variant | $K_D$ (M) | $k_a$ (1/Ms) | $k_d$ (1/s) |
| XENP28024 | 1C11_H3.327_L3.220 | 1.39E-09 | 2.35E+05 | 3.25E-04 |
| XENP28025 | 1C11_H3.328_L3.220 | 1.85E-09 | 2.17E+05 | 4.02E-04 |
| XENP28026 | 1C11_H3.329_L3.220 | 1.78E-09 | 2.50E+05 | 4.45E-04 |
| XENP28027 | 1C11_H3.330_L3.220 | 2.18E-09 | 3.03E+05 | 6.61E-04 |
| XENP28028 | 1C11_H3.331_L3.220 | 2.15E-09 | 3.42E+05 | 7.35E-04 |
| XENP28029 | 1C11_H3.332_L3.220 | 2.57E-09 | 2.94E+05 | 7.56E-04 |
| XENP28030 | 1C11_H3.333_L3.220 | 2.37E-09 | 2.71E+05 | 6.44E-04 |
| XENP28031 | 1C11_H3.334_L3.220 | 2.43E-09 | 2.56E+05 | 6.21E-04 |
| XENP28032 | 1C11_H3.335_L3.220 | 2.11E-09 | 2.45E+05 | 5.18E-04 |
| XENP28033 | 1C11_H3.336_L3.220 | 5.29E-09 | 1.79E+05 | 9.50E-04 |
| XENP28034 | 1C11_H3.337_L3.220 | 2.92E-09 | 2.82E+05 | 8.23E-04 |
| XENP28035 | 1C11_H3.338_L3.220 | 5.54E-09 | 2.55E+05 | 1.41E-03 |
| XENP22553 | 1C11_H3L3 | 1.80E-08 | 2.13E+05 | 3.82E-03 |
| XENP26940 | 1C11_H3.303_L3.152 | 5.18E-09 | 1.41E+05 | 7.28E-04 |
| XENP27960 | 1C11_H3.303_L3.220 | 3.35E-09 | 2.45E+05 | 8.19E-04 |
| XENP27866 | 1C11_H3.320_L3.220 | 3.26E-09 | 3.67E+05 | 1.20E-03 |
| XENP27869 | 1C11_H3.323_L3.220 | 4.13E-09 | 2.55E+05 | 1.05E-03 |
| XENP27870 | 1C11_H3.324_L3.220 | 7.56E-09 | 2.41E+05 | 1.82E-03 |
| XENP27959 | 1C11_H3.303_L3.219 | 6.47E-09 | 1.82E+05 | 1.17E-03 |
| XENP27961 | 1C11_H3.320_L3.219 | 4.22E-09 | 2.60E+05 | 1.10E-03 |
| XENP27962 | 1C11_H3.323_L3.219 | 4.58E-09 | 3.95E+05 | 1.81E-03 |
| XENP27963 | 1C11_H3.324_L3.219 | 4.63E-09 | 2.73E+05 | 1.27E-03 |

FIG. 45

|  |  | Human PD-1 | | | Cynomolgus PD-1 | | |
| --- | --- | --- | --- | --- | --- | --- | --- |
| TA | Variant | KD (M) | ka (1/Ms) | kd (1/s) | KD (M) | ka (1/Ms) | kd (1/s) |
| XENP28651 | 1C11_H3.327_L3.152 | 4.14E-09 | 2.03E+05 | 8.41E-04 | 5.23E-09 | 3.38E+05 | 1.77E-03 |
| XENP28652 | 1C11_H3.328_L3.152 | 7.74E-09 | 1.77E+05 | 1.37E-03 | 1.10E-08 | 2.63E+05 | 2.89E-03 |
| XENP28653 | 1C11_H3.329_L3.152 | 4.95E-09 | 1.93E+05 | 9.55E-04 | 7.78E-09 | 3.59E+05 | 2.79E-03 |

FIG. 49A

XenCS500: PD-1 X ICOS

[ICOS]_H0L0_Fab-1C11[PD-1]_H3.234_L3.144-scFv(GKPGS)4-IgG1_pI(-)_Isosteric_A_/PVA_/S267K/L368D/K370S-Fc(216)_IgG1_C220S/PVA_/S267K/S364K/E357Q Fab Chain 1 – [ICOS]_H0_ IgG1_pI(-)_Isosteric_A_/PVA_/S267K/L368D/K370S (SEQ ID NOS 43644-43648)

QVQLVQSGAEVKKPGASVKVSCKASGYTFTGYYMHWVRQAPGQGLEWMGWINPHSGGTNYAQKFQGRVTMTRDTSISTAYME
LSRLRSDDTAVYYCARTYYYDSSGYYHDAFDIWGQGTMVTVSS/ASTKGPSVFPLAPSSKSTSGGTAALGCLVKDYFPEPVTVSWNSGAL
TSGVHTFPAVLQSSGLYSLSSVVTVPSSSLGTQTYICNVNHKPSDTKVDKKVEPKSCDKTHTCPPCPAPPVAGPSVFLFPPKPKDTLMISRTPEVTCVV
VDVKHEDPEVKFNWYVDGVEVHNAKTKPREEEYNSTYRVVSVLTVLHQDWLNGKEYKCKVSNKALPAPIEKTISKAKGQPREPQVYTLPPSREEMTKNQ
VSLTCDVSGFYPSDIAVEWESDGQPENNYKTTPPVLDSDGSFFLYSKLTVDKSRWEQGDVFSCSVMHEALHNHYTQKSLSLSPGK

VH ICOS H0L0 (SEQ ID NOS 43645-43648)
QVQLVQSGAEVKKPGASVKVSCKASGYTFTGYYMHWVRQAPGQGLEWMGWINPHSGGTNYAQKFQGRVTMTRDTSISTAYME
LSRLRSDDTAVYYCARTYYYDSSGYYHDAFDIWGQGTMVTVSS scFv Chain 2 – 1C11[PD-1]_H3.234_L3.144_scFv(GKPGS)4_Fc(216)_IgG1_C220S/PVA_/S267K/S364K/E357Q (SEQ ID NOS 43649-43658 and linker disclosed as SEQ ID NO: 39202)

EVQLVQSGSELKKPGESVKVSCKASGYTFTHYGINWVRQPPGQGLEWMGWINTYTGEPYYAPGFQERFVFSLDTSQDTAYLQ
INSLKAEDTAVYYCARDYYGSSPYWGQGTLVTVSS/GKPGSGKPGSGKPGSGKPGS/DIVMTQSPDSLAVSLGERVTINCKA
SQSIVHSNGNTYLEWYQQKPGQPPKLLIYKVSNRFSGVPDRFSGSGSGTDFTLTISSVEAEDAATYYCFQGSHVPNTFGQGT
KVEIK/EPKSSDKTHTCPPCPAPPVAGPSVFLFPPKPKDTLMISRTPEVTCVVVDVKHEDPEVKFNWYVDGVEVHNAKTKPR
EEQYNSTYRVVSVLTVLHQDWLNGKEYKCKVSNKALPAPIEKTISKAKGQPREPQVYTLPPSREQMTKNQVKLTCLVKGFYP
SDIAVEWESNGQPENNYKTTPPVLDSDGSFFLYSKLTVDKSRWQQGNVFSCSVMHEALHNHYTQKSLSLSPGK

Light Chain 3 – [ICOS]_L0 (SEQ ID NOS 43659-43663)

DIQMTQSPSSVSASVGDRVTITCRASQGISRLLAWYQQKPGKAPKLLIYVASSLQSGVPSRFSGSGSGTDFTLTISSLQPED
FATYYCQQANSFPWTFGQGTKVEIK/RTVAAPSVFIFPPSDEQLKSGTASVVCLLNNFYPREAKVQWKVDNALQSGNSQESV
TEQDSKDSTYSLSSTLTLSKADYEKHKVYACEVTHQGLSSPVTKSFNRGEC

VL ICOS H0L0 (SEQ ID NOS 43660-43663)
DIQMTQSPSSVSASVGDRVTITCRASQGISRLLAWYQQKPGKAPKLLIYVASSLQSGVPSRFSGSGSGTDFTLTISSLQPED
FATYYCQQANSFPWTFGQGTKVEIK

XenCS501: PD-1 X ICOS
> [ICOS]_H0.66_L0_Fab-1C11[PD-1]_H3.234_L3.144-scFv(GKPGS)4-IgG1_pI(-)_Isosteric_A_/PVA_/S267K/L368D/K370S-Fc(216)_IgG1_C220S/PVA_/S267K/S364K/E357Q Fab Chain 1 – [ICOS]_H0.66_ IgG1_pI(-)_Isosteric_A_/PVA_/S267K/L368D/K370S (SEQ ID NOS 43664-43668)

QVQLVQSGAEVKKPGASVKVSCKASGYTFTGYYMHWVRQAPGQGLEWMGWINPHSGETIYAQKFQGRVTMTRDTSISTAYME
LSSLRSEDTAVYYCARTYYYDTSGYYHDAFDVWGQGTMVTVSS/ASTKGPSVFPLAPSSKSTSGGTAALGCLVKDYFPEPVT
VSWNSGALTSGVHTFPAVLQSSGLYSLSSVVTVPSSSLGTQTYICNVNHKPSDTKVDKKVEPKSCDKTHTCPPCPAPPVAGP
SVFLFPPKPKDTLMISRTPEVTCVVVDVKHEDPEVKFNWYVDGVEVHNAKTKPREEEYNSTYRVVSVLTVLHQDWLNGKEYK
CKVSNKALPAPIEKTISKAKGQPREPQVYTLPPSREEMTKNQVSLTCDVSGFYPSDIAVEWESDGQPENNYKTTPPVLDSDG
SFFLYSKLTVDKSRWEQGDVFSCSVMHEALHNHYTQKSLSLSPGK

FIG. 49B

VH_ICOS_H0.66_L0 (SEQ ID NOS 43665-43668)
QVQLVQSGAEVKKPGASVKVSCKASGYTFTGYYMHWVRQAPGQGLEWMGWINPHSGETIYAQKFQGRVTMTRDTSIS
TAYMELSSLRSEDTAVYYCARTYYYDTSGYYHDAFDVWGQGTMVTVSS scFv Chain 2 – 1C11[PD-1]_H3.234_L3.144_scFv(GKPGS)4_Fc(216)_IgG1_C220S/PVA_/S267K/S364K/E357Q (SEQ ID NOS 43669-43678 and linker disclosed as SEQ ID NO: 39202)
EVQLVQSGSELKKPGESVKVSCKASGYTFTHYGINWVRQPPGQGLEWMGWINTYTGEPYYAPGFQERFVFSLDTSQD
TAYLQINSLKAEDTAVYYCARDYYGSSPYWGQGTLVTVSS/GKPGSGKPGSGKPGSGKPGS/DIVMTQSPDSLAVSL
GERVTINCKASQSIVHSNGNTYLEWYQQKPGQPPKLLIYKVSNRFSGVPDRFSGSGSGTDFTLTISSVEAEDAATYY
CFQGSHVPNTFGQGTKVEIK/EPKSSDKTHTCPPCPAPPVAGPSVFLFPPKPKDTLMISRTPEVTCVVVDVKHEDPE
VKFNWYVDGVEVHNAKTKPREEQYNSTYRVVSVLTVLHQDWLNGKEYKCKVSNKALPAPIEKTISKAKGQPREPQVY
TLPPSREQMTKNQVKLTCLVKGFYPSDIAVEWESNGQPENNYKTTPPVLDSDGSFFLYSKLTVDKSRWQQGNVFSCS
VMHEALHNHYTQKSLSLSPGK

Light Chain 3 – [ICOS]_L0 (SEQ ID NOS 43679-43683)
DIQMTQSPSSVSASVGDRVTITCRASQGISRLLAWYQQKPGKAPKLLIYVASSLQSGVPSRFSGSGSGTDFTLTISS
LQPEDFATYYCQQANSFPWTFGQGTKVEIK/RTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSPVTKSFNRGEC

VL_ICOS_H0.66_L0 (SEQ ID NOS 43680-43683)
DIQMTQSPSSVSASVGDRVTITCRASQGISRLLAWYQQKPGKAPKLLIYVASSLQSGVPSRFSGSGSGTDFTLTISS
LQPEDFATYYCQQANSFPWTFGQGTKVEIK

XenCS502: PD-1 X CTLA-4

> [CTLA-4]_H3_L0.22_Fab-1C11[PD-1]_H3.234_L3.144_scFv(GKPGS)4-IgG1_pI(-)_Isosteric_A_/PVA_/S267K/L368D/K370S-Fc(216)_IgG1_C220S/PVA_/S267K/S364K/E357Q

Fab Chain 1 - [CTLA-4]_H3_IgG1_pI(-)_Isosteric_A_/PVA_/S267K/L368D/K370S (SEQ ID NOS 43684-43688)
EVQLVESGGGLVKPGGSLRLSCAASGFTFSSYTMHWVRQAPGKGLEWVSFISYDGNNKYYADSVKGRFTISRDNAKN
SLYLQMNSLRAEDTAVYYCARTGWLGPFDYWGQGTLVTVSS/ASTKGPSVFPLAPSSKSTSGGTAALGCLVKDYFPE
PVTVSWNSGALTSGVHTFPAVLQSSGLYSLSSVVTVPSSSLGTQTYICNVNHKPSDTKVDKKVEPKSCDKTHTCPPC
PAPPVAGPSVFLFPPKPKDTLMISRTPEVTCVVVDVKHEDPEVKFNWYVDGVEVHNAKTKPREEEYNSTYRVVSVLT
VLHQDWLNGKEYKCKVSNKALPAPIEKTISKAKGQPREPQVYTLPPSREEMTKNQVSLTCDVSGFYPSDIAVEWESD
GQPENNYKTTPPVLDSDGSFFLYSKLTVDKSRWEQGDVFSCSVMHEALHNHYTQKSLSLSPGK scFv Chain 2 - 1C11[PD-1]_H3.234_L3.144_scFv(GKPGS)4_Fc(216)_IgG1_C220S/PVA_/S267K/S364K/E357Q (SEQ ID NOS 43689-43698 and linker disclosed as SEQ ID NO: 39202)
EVQLVQSGSELKKPGESVKVSCKASGYTFTHYGINWVRQPPGQGLEWMGWINTYTGEPYYAPGFQERFVFSLDTSQD
TAYLQINSLKAEDTAVYYCARDYYGSSPYWGQGTLVTVSS/GKPGSGKPGSGKPGSGKPGS/DIVMTQSPDSLAVSL
GERVTINCKASQSIVHSNGNTYLEWYQQKPGQPPKLLIYKVSNRFSGVPDRFSGSGSGTDFTLTISSVEAEDAATYY
CFQGSHVPNTFGQGTKVEIK/EPKSSDKTHTCPPCPAPPVAGPSVFLFPPKPKDTLMISRTPEVTCVVVDVKHEDPE
VKFNWYVDGVEVHNAKTKPREEQYNSTYRVVSVLTVLHQDWLNGKEYKCKVSNKALPAPIEKTISKAKGQPREPQVY
TLPPSREQMTKNQVKLTCLVKGFYPSDIAVEWESNGQPENNYKTTPPVLDSDGSFFLYSKLTVDKSRWQQGNVFSCS
VMHEALHNHYTQKSLSLSPGK

FIG. 49C

Light Chain 3 - [CTLA-4]_L0.22 (SEQ ID NOS 43699-43703)
EIVLTQSPGTLSLSPGERATLSCRASQSVSSSYLAWYQQKPGQAPRLLIYGAFSRATGIPDRFSGSGSGTDFTLTIS
RLEPEDFAVYYCQQYGSSPWTFGQGTKVEIK/RTVAAPSVFIFPPSDEQLKSGTASVVCLLNNFYPREAKVQWKVDN
ALQSGNSQESVTEQDSKDSTYSLSSTLTLSKADYEKHKVYACEVTHQGLSSPVTKSFNRGEC

```
CS503: PD-1 X LAG-3
```
> 7G8_H3.30_L1.34_[LAG-3]_Fab-1C11[PD-1]_H3.234_L3.144_scFv(GKPGS)4-IgG1_pI(-)_Isosteric_A_/PVA_/S267K/L368D/K370S-Fc(216)_IgG1_C220S/PVA_/S267K/S364K/E357Q

Fab Chain 1 – 7G8_H3.30_ IgG1_pI(-)_Isosteric_A_/PVA_/S267K/L368D/K370S (SEQ ID NOS 43704-43708)
EVQLVESGGGLVQPGGSLRLSCAASGFTFDDAWMSWVRQAPGKGLEWVAEISTKANNHATYYAESVKGRFTISRDDS
KSSVYLQMNSLRAEDTAVYYCTRLATWDWYFDVWGQGTTVTVSS/ASTKGPSVFPLAPSSKSTSGGTAALGCLVKDY
FPEPVTVSWNSGALTSGVHTFPAVLQSSGLYSLSSVVTVPSSSLGTQTYICNVNHKPSDTKVDKKVEPKSCDKTHTC
PPCPAPPVAGPSVFLFPPKPKDTLMISRTPEVTCVVVDVKHEDPEVKFNWYVDGVEVHNAKTKPREEEYNSTYRVVS
VLTVLHQDWLNGKEYKCKVSNKALPAPIEKTISKAKGQPREPQVYTLPPSREEMTKNQVSLTCDVSGFYPSDIAVEW
ESDGQPENNYKTTPPVLDSDGSFFLYSKLTVDKSRWEQGDVFSCSVMHEALHNHYTQKSLSLSPGK scFv Chain 2 –1C11[PD-1]_H3.234_L3.144_scFv(GKPGS)4_Fc(216)_IgG1_C220S/PVA_/S267K/S364K/E357Q (SEQ ID NOS 43709-43718 and linker disclosed as SEQ ID NO: 39202)
EVQLVQSGSELKKPGESVKVSCKASGYTFTHYGINWVRQPPGQGLEWMGWINTYTGEPYYAPGFQERFVFSLDTSQD
TAYLQINSLKAEDTAVYYCARDYYGSSPYWGQGTLVTVSS/GKPGSGKPGSGKPGSGKPGS/DIVMTQSPDSLAVSL
GERVTINCKASQSIVHSNGNTYLEWYQQKPGQPPKLLIYKVSNRFSGVPDRFSGSGSGTDFTLTISSVEAEDAATYY
CFQGSHVPNTFGQGTKVEIK/EPKSSDKTHTCPPCPAPPVAGPSVFLFPPKPKDTLMISRTPEVTCVVVDVKHEDPE
VKFNWYVDGVEVHNAKTKPREEQYNSTYRVVSVLTVLHQDWLNGKEYKCKVSNKALPAPIEKTISKAKGQPREPQVY
TLPPSREQMTKNQVKLTCLVKGFYPSDIAVEWESNGQPENNYKTTPPVLDSDGSFFLYSKLTVDKSRWQQGNVFSCS
VMHEALHNHYTQKSLSLSPGK

Light Chain 3 – 7G8_L1.34 (SEQ ID NOS 43719-43723)
DIVLTQSPSSLSASVGDRVTITCRASQSVDYDGDSYMNWYQQKPGKPPKLLIYAASELESGIPARFSGSGSGTDFTL
TISSLQPEDFATYYCQQSNEDPFTFGSGTKLEIK/RTVAAPSVFIFPPSDEQLKSGTASVVCLLNNFYPREAKVQWK
VDNALQSGNSQESVTEQDSKDSTYSLSSTLTLSKADYEKHKVYACEVTHQGLSSPVTKSFNRGEC XenCs504: PD-1 X LAG-3
> 2A11_H1.144_L2.142_[LAG-3]_Fab-1C11[PD-1]_H3.234_L3.144_scFv(GKPGS)4-IgG1_pI(-)_Isosteric_A_/PVA_/S267K/L368D/K370S-Fc(216)_IgG1_C220S/PVA_/S267K/S364K/E357Q

Fab Chain 1 – 2A11_H1.144_ IgG1_pI(-)_Isosteric_A_/PVA_/S267K/L368D/K370S (SEQ ID NOS 43724-43728)
EVQLVQSGAEVKKPGATVKISCKASGFNIKDYFMHWVQQAPGKGLEWMGWIDPELGDTEYAPKFQGRVTITADTSTN
TAYMELSSLRSEDTAVYYCYARGVYQALDYWGQGTLVTVSS/ASTKGPSVFPLAPSSKSTSGGTAALGCLVKDYFPE
PVTVSWNSGALTSGVHTFPAVLQSSGLYSLSSVVTVPSSSLGTQTYICNVNHKPSDTKVDKKVEPKSCDKTHTCPPC
PAPPVAGPSVFLFPPKPKDTLMISRTPEVTCVVVDVKHEDPEVKFNWYVDGVEVHNAKTKPREEEYNSTYRVVSVLT
VLHQDWLNGKEYKCKVSNKALPAPIEKTISKAKGQPREPQVYTLPPSREEMTKNQVSLTCDVSGFYPSDIAVEWESD
GQPENNYKTTPPVLDSDGSFFLYSKLTVDKSRWEQGDVFSCSVMHEALHNHYTQKSLSLSPGK

FIG. 49D scFv Chain 2 – 1C11[PD-1]_H3.234_L3.144_scFv(GKPGS)4_Fc(216)_IgG1_C220S/PVA_/S267K/S364K/E357Q (SEQ ID NOS 43729-43738 and linker disclosed as SEQ ID NO: 39202)

EVQLVQSGSELKKPGESVKVSCKASGYTFTHYGINWVRQPPGQGLEWMGWINTYTGEPYYAPGFQERFVFSLDTSQD
TAYLQINSLKAEDTAVYYCARDYYGSSPYWGQGTLVTVSS/GKPGSGKPGSGKPGSGKPGS/DIVMTQSPDSLAVSL
GERVTINCKASQSIVHSNGNTYLEWYQQKPGQPPKLLIYKVSNRFSGVPDRFSGSGSGTDFTLTISSVEAEDAATYY
CFQGSHVPNTFGQGTKVEIK/EPKSSDKTHTCPPCPAPPVAGPSVFLFPPKPKDTLMISRTPEVTCVVVDVKHEDPE
VKFNWYVDGVEVHNAKTKPREEQYNSTYRVVSVLTVLHQDWLNGKEYKCKVSNKALPAPIEKTISKAKGQPREPQVY
TLPPSREQMTKNQVKLTCLVKGFYPSDIAVEWESNGQPENNYKTTPPVLDSDGSFFLYSKLTVDKSRWQQGNVFSCS
VMHEALHNHYTQKSLSLSPGK

Light Chain 3 – 2A11_L2.142 (SEQ ID NOS 43739-43743)

DIQMTQSPAFLSVTPGEKVTITCQASQDIGNYLNWFQQKPGQTVKLLIYFTSYLHSGVPSRFSGSGSGTDYTFTISS
LEAEDAATYFCQQGNTLPYTFGGGTKVEIK/RTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSPVTKSFNRGEC

XenCS505: PD-1 X TIM-3

> 3H3_H1_L2.1_Fab-1C11[PD-1]_H3.234_L3.144-scFv(GKPGS)4-IgG1_pI(-)_Isosteric_A_/PVA_/S267K/L368D/K370S-Fc(216)_IgG1_C220S/PVA_/S267K/S364K/E357Q

Fab Chain 1 – 3H3_H1_ IgG1_pI(-)_Isosteric_A_/PVA_/S267K/L368D/K370S (SEQ ID NOS 43744-43748)

QVTLKESGPVLVKPTETLTLTCTVSGFSLNGYGVNWVRQPPGKGLEWLAMIWGDGSTDYNSALKSRLTISKDNSKSQ
VVLTMTNMDPVDTATYYCARSYYTSDEDYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSDTKVDKKVEPKSCDKTHTCPPCP
APPVAGPSVFLFPPKPKDTLMISRTPEVTCVVVDVKHEDPEVKFNWYVDGVEVHNAKTKPREEEYNSTYRVVSVLTV
LHQDWLNGKEYKCKVSNKALPAPIEKTISKAKGQPREPQVYTLPPSREEMTKNQVSLTCDVSGFYPSDIAVEWESDG
QPENNYKTTPPVLDSDGSFFLYSKLTVDKSRWEQGDVFSCSVMHEALHNHYTQKSLSLSPGK scFv Chain 2 – 1C11[PD-1]_H3.234_L3.144_scFv(GKPGS)4_Fc(216)_IgG1_C220S/PVA_/S267K/S364K/E357Q (SEQ ID NOS 43749-43758 and linker disclosed as SEQ ID NO: 39202)

EVQLVQSGSELKKPGESVKVSCKASGYTFTHYGINWVRQPPGQGLEWMGWINTYTGEPYYAPGFQERFVFSLDTSQD
TAYLQINSLKAEDTAVYYCARDYYGSSPYWGQGTLVTVSS/GKPGSGKPGSGKPGSGKPGS/DIVMTQSPDSLAVSL
GERVTINCKASQSIVHSNGNTYLEWYQQKPGQPPKLLIYKVSNRFSGVPDRFSGSGSGTDFTLTISSVEAEDAATYY
CFQGSHVPNTFGQGTKVEIK/EPKSSDKTHTCPPCPAPPVAGPSVFLFPPKPKDTLMISRTPEVTCVVVDVKHEDPE
VKFNWYVDGVEVHNAKTKPREEQYNSTYRVVSVLTVLHQDWLNGKEYKCKVSNKALPAPIEKTISKAKGQPREPQVY
TLPPSREQMTKNQVKLTCLVKGFYPSDIAVEWESNGQPENNYKTTPPVLDSDGSFFLYSKLTVDKSRWQQGNVFSCS
VMHEALHNHYTQKSLSLSPGK

Light Chain 3 – 3H3_L2.1 (SEQ ID NOS 43759-43763)

DIVMTQSPDSLAVSLGERATINCKSSQSLLNSRTRKNYLAWYQQKPGQSPKLLIYWASTRESGVPDRFTGSGSGTDF
TLTISSLQAEDVAVYYCKQSYSLRTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

FIG. 49E

XENCS:506 PD-1 X BTLA

> 9C6_H1.1_L1_[BTLA]_Fab-1C11[PD-1]_H3.234_L3.144_scFv(GKPGS)4-IgG1_pI(-
)_Isosteric_A_/PVA_/S267K/L368D/K370S-Fc(216)_IgG1_C220S/PVA_/S267K/S364K/E357Q

Fab Chain 1 – 9C6_H1.1_ IgG1_pI(-)_Isosteric_A_/PVA_/S267K/L368D/K370S (SEQ ID NOS 43764-43768)
QVQLKESGAEVKKPGASVKVSCKVSGFSLTGYGVNWVRQAPGQGLEWMGMIWIDGSTDYNSKFQGRVTMTKDNSKST
VYMELSSLRSEDTAVYYCARDRPDGRAMDYWGQGTMVTVSS/ASTKGPSVFPLAPSSKSTSGGTAALGCLVKDYFPE
PVTVSWNSGALTSGVHTFPAVLQSSGLYSLSSVVTVPSSSLGTQTYICNVNHKPSDTKVDKKVEPKSCDKTHTCPPC
PAPPVAGPSVFLFPPKPKDTLMISRTPEVTCVVVDVKHEDPEVKFNWYVDGVEVHNAKTKPREEEYNSTYRVVSVLT
VLHQDWLNGKEYKCKVSNKALPAPIEKTISKAKGQPREPQVYTLPPSREEMTKNQVSLTCDVSGFYPSDIAVEWESD
GQPENNYKTTPPVLDSDGSFFLYSKLTVDKSRWEQGDVFSCSVMHEALHNHYTQKSLSLSPGK scFv Chain 2 – 1C11[PD-1]_H3.234_L3.144_scFv(GKPGS)4_Fc(216)_IgG1_C220S/PVA_/S267K/S364K/E357Q (SEQ
ID NOS 43769-43778 and linker disclosed as SEQ ID NO: 39202)
EVQLVQSGSELKKPGESVKVSCKASGYTFTHYGINWVRQPPGQGLEWMGWINTYTGEPYYAPGFQERFVFSLDTSQD
TAYLQINSLKAEDTAVYYCARDYYGSSPYWGQGTLVTVSS/GKPGSGKPGSGKPGSGKPGS/DIVMTQSPDSLAVSL
GERVTINCKASQSIVHSNGNTYLEWYQQKPGQPPKLLIYKVSNRFSGVPDRFSGSGSGTDFTLTISSVEAEDAATYY
CFQGSHVPNTFGQGTKVEIK/EPKSSDKTHTCPPCPAPPVAGPSVFLFPPKPKDTLMISRTPEVTCVVVDVKHEDPE
VKFNWYVDGVEVHNAKTKPREEQYNSTYRVVSVLTVLHQDWLNGKEYKCKVSNKALPAPIEKTISKAKGQPREPQVY
TLPPSREQMTKNQVKLTCLVKGFYPSDIAVEWESNGQPENNYKTTPPVLDSDGSFFLYSKLTVDKSRWQQGNVFSCS
VMHEALHNHYTQKSLSLSPGK

Light Chain 3 – 9C6_L1 (SEQ ID NOS 43779-43783)
SIVMTQSPDSLAVSLGERATINCKASQSVSNDVAWYQQKPGQSPKLLIYYASNRYTGVPDRFTGSGYGTDFTLTISS
LQAEDVAVYFCQQDYSSPTFGGGTKLEIK/RTVAAPSVFIFPPSDEQLKSGTASVVCLLNNFYPREAKVQWKVDNAL
QSGNSQESVTEQDSKDSTYSLSSTLTLSKADYEKHKVYACEVTHQGLSSPVTKSFNRGEC XENCS507 PD-1 X ICOS
> [ICOS]_H0L0_Fab-1C11[PD-1]_H3.240_L3.148-scFv(GKPGS)4-IgG1_pI(-
)_Isosteric_A_/PVA_/S267K/L368D/K370S-Fc(216)_IgG1_C220S/PVA_/S267K/S364K/E357Q

Fab Chain 1 – [ICOS]_H0_ IgG1_pI(-)_Isosteric_A_/PVA_/S267K/L368D/K370S (SEQ ID NOS 43784-43788)
QVQLVQSGAEVKKPGASVKVSCKASGYTFTGYYMHWVRQAPGQGLEWMGWINPHSGGTNYAQKFQGRVTMTRDTSIS
TAYMELSRLRSDDTAVYYCARTYYYDSSGYYHDAFDIWGQGTMVTVSS/ASTKGPSVFPLAPSSKSTSGGTAALGCLVKDYFP
EPVTVSWNSGALTSGVHTFPAVLQSSGLYSLSSVVTVPSSSLGTQTYICNVNHKPSDTKVDKKVEPKSCDKTHTCPPCPAPPVAGPSVFLFPP
KPKDTLMISRTPEVTCVVVDVKHEDPEVKFNWYVDGVEVHNAKTKPREEEYNSTYRVVSVLTVLHQDWLNGKEYKCKVSNKALPAPIEKTISK
AKGQPREPQVYTLPPSREEMTKNQVSLTCDVSGFYPSDIAVEWESDGQPENNYKTTPPVLDSDGSFFLYSKLTVDKSRWEQGDVFSCSVMHEA
LHNHYTQKSLSLSPGK

FIG. 49F scFv Chain 2 – 1C11[PD-1]_H3.240_L3.148_scFv(GKPGS)4_Fc(216)_IgG1_C220S/PVA_/S267K/S364K/E357Q (SEQ ID NOS 43789-43798 and linker disclosed as SEQ ID NO: 39202)
QVQLVQSGPELKKPGESVKVSCKASGYTFT<u>HYGIN</u>WVRQPPGQGLEWMG<u>WINTYTGEPYYAPGFQER</u>FVFSIDTSQD
TAYLQINSLKAEDTAVYYCARD<u>YYGSSPY</u>WGQGTLVTVSS/<u>GKPGSGKPGSGKPGSGKPGS</u>/DVLMTQSPDSLAVSL
GERATINCK<u>SSQSIVHSNGNTYLE</u>WYQQKPGQSPKLLIY<u>KVSNRFS</u>GVPDRFSGSGSGTDFTLTISSLQAEDVAVYY
C<u>FQGSHVPNT</u>FGGGTKVEIK/EPKSSDKTHTCPPCPAPPVAGPSVFLFPPKPKDTLMISRTPEVTCVVVDVKHEDPE
VKFNWYVDGVEVHNAKTKPREEQYNSTYRVVSVLTVLHQDWLNGKEYKCKVSNKALPAPIEKTISKAKGQPREPQVY
TLPPSREQMTKNQVKLTCLVKGFYPSDIAVEWESNGQPENNYKTTPPVLDSDGSFFLYSKLTVDKSRWQQGNVFSCS
VMHEALHNHYTQKSLSLSPGK

Light Chain 3 – [ICOS]_L0 (SEQ ID NOS 43799-43803)
DIQMTQSPSSVSASVGDRVTITC<u>RASQGISRLLA</u>WYQQKPGKAPKLLIY<u>VASSLQS</u>GVPSRFSGSGSGTDFTLTISS
LQPEDFATYYC<u>QQANSFPWT</u>FGQGTKVEIK/RTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSPVTKSFNRGEC XENCS508 PD-1 X ICOS
>[ICOS]_H0.66_L0_Fab-1C11[PD-1]_H3.240_L3.148-scFv(GKPGS)4-IgG1_pI(-)_Isosteric_A_/PVA_/S267K/L368D/K370S-Fc(216)_IgG1_C220S/PVA_/S267K/S364K/E357Q

Fab Chain 1 – [ICOS]_H0.66_IgG1_pI(-)_Isosteric_A_/PVA_/S267K/L368D/K370S (SEQ ID NOS 43804-43808)
QVQLVQSGAEVKKPGASVKVSCKASGYTFT<u>GYYMH</u>WVRQAPGQGLEWMG<u>WINPHSGETIYAQKFQG</u>RVTMTRDTSIS
TAYMELSSLRSEDTAVYYCART<u>YYYDTSGYYHDAFDV</u>WGQGTMVTVSS/ASTKGPSVFPLAPSSKSTSGGTAALGCL
VKDYFPEPVTVSWNSGALTSGVHTFPAVLQSSGLYSLSSVVTVPSSSLGTQTYICNVNHKPSDTKVDKKVEPKSCDK
THTCPPCPAPPVAGPSVFLFPPKPKDTLMISRTPEVTCVVVDVKHEDPEVKFNWYVDGVEVHNAKTKPREEEYNSTY
RVVSVLTVLHQDWLNGKEYKCKVSNKALPAPIEKTISKAKGQPREPQVYTLPPSREEMTKNQVSLTCDVSGFYPSDI
AVEWESDGQPENNYKTTPPVLDSDGSFFLYSKLTVDKSRWEQGDVFSCSVMHEALHNHYTQKSLSLSPGK scFv Chain 2 – 1C11[PD-1]_H3.240_L3.148_scFv(GKPGS)4_Fc(216)_IgG1_C220S/PVA_/S267K/S364K/E357Q (SEQ ID NOS 43809-43818 and linker disclosed as SEQ ID NO: 39202)
QVQLVQSGPELKKPGESVKVSCKASGYTFT<u>HYGIN</u>WVRQPPGQGLEWMG<u>WINTYTGEPYYAPGFQER</u>FVFSIDTSQD
TAYLQINSLKAEDTAVYYCARD<u>YYGSSPY</u>WGQGTLVTVSS/<u>GKPGSGKPGSGKPGSGKPGS</u>/DVLMTQSPDSLAVSL
GERATINCK<u>SSQSIVHSNGNTYLE</u>WYQQKPGQSPKLLIY<u>KVSNRFS</u>GVPDRFSGSGSGTDFTLTISSLQAEDVAVYY
C<u>FQGSHVPNT</u>FGGGTKVEIK/EPKSSDKTHTCPPCPAPPVAGPSVFLFPPKPKDTLMISRTPEVTCVVVDVKHEDPE
VKFNWYVDGVEVHNAKTKPREEQYNSTYRVVSVLTVLHQDWLNGKEYKCKVSNKALPAPIEKTISKAKGQPREPQVY
TLPPSREQMTKNQVKLTCLVKGFYPSDIAVEWESNGQPENNYKTTPPVLDSDGSFFLYSKLTVDKSRWQQGNVFSCS
VMHEALHNHYTQKSLSLSPGK

Light Chain 3 – [ICOS]_L0 (SEQ ID NOS 43819-43823)
DIQMTQSPSSVSASVGDRVTITC<u>RASQGISRLLA</u>WYQQKPGKAPKLLIY<u>VASSLQS</u>GVPSRFSGSGSGTDFTLTISS
LQPEDFATYYC<u>QQANSFPWT</u>FGQGTKVEIK/RTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSPVTKSFNRGEC

FIG. 49G

```
XENCS509 PD-1 X CTLA-4
>[CTLA-4]_H3_L0.22_Fab-1C11[PD-1]_H3.240_L3.148_scFv(GKPGS)4-IgG1_pI(-
)_Isosteric_A_/PVA_/S267K/L368D/K370S-Fc(216)_IgG1_C220S/PVA_/S267K/S364K/E357Q
```

Fab Chain 1 - [CTLA-4]_H3_ IgG1_pI(-)_Isosteric_A_/PVA_/S267K/L368D/K370S (SEQ ID NOS 43824-43828)
EVQLVESGGGLVKPGGSLRLSCAASGFTFSSYTMHWVRQAPGKGLEWVSFISYDGNNKYYADSVKGRFTISRDNAKN
SLYLQMNSLRAEDTAVYYCARTGWLGPFDYWGQGTLVTVSS/ASTKGPSVFPLAPSSKSTSGGTAALGCLVKDYFPE
PVTVSWNSGALTSGVHTFPAVLQSSGLYSLSSVVTVPSSSLGTQTYICNVNHKPSDTKVDKKVEPKSCDKTHTCPPC
PAPPVAGPSVFLFPPKPKDTLMISRTPEVTCVVVDVKHEDPEVKFNWYVDGVEVHNAKTKPREEEYNSTYRVVSVLT
VLHQDWLNGKEYKCKVSNKALPAPIEKTISKAKGQPREPQVYTLPPSREEMTKNQVSLTCDVSGFYPSDIAVEWESD
GQPENNYKTTPPVLDSDGSFFLYSKLTVDKSRWEQGDVFSCSVMHEALHNHYTQKSLSLSPGK scFv Chain 2 - 1C11[PD-1]_H3.240_L3.148_scFv(GKPGS)4_Fc(216)_IgG1_C220S/PVA_/S267K/S364K/E357Q (SEQ ID NOS 43829-43838 and linker disclosed as SEQ ID NO: 39202)
QVQLVQSGPELKKPGESVKVSCKASGYTFTHYGINWVRQPPGQGLEWMGWINTYTGEPYYAPGFQERFVFSIDTSQD
TAYLQINSLKAEDTAVYYCARDYYGSSPYWGQGTLVTVSS/GKPGSGKPGSGKPGSGKPGS/DVLMTQSPDSLAVSL
GERATINCKSSQSIVHSNGNTYLEWYQQKPGQSPKLLIYKVSNRFSGVPDRFSGSGSGTDFTLTISSLQAEDVAVYY
CFQGSHVPNTFGGGTKVEIK/EPKSSDKTHTCPPCPAPPVAGPSVFLFPPKPKDTLMISRTPEVTCVVVDVKHEDPE
VKFNWYVDGVEVHNAKTKPREEQYNSTYRVVSVLTVLHQDWLNGKEYKCKVSNKALPAPIEKTISKAKGQPREPQVY
TLPPSREQMTKNQVKLTCLVKGFYPSDIAVEWESNGQPENNYKTTPPVLDSDGSFFLYSKLTVDKSRWQQGNVFSCS
VMHEALHNHYTQKSLSLSPGK

Light Chain 3 - [CTLA-4]_L0.22 (SEQ ID NOS 43839-43843)
EIVLTQSPGTLSLSPGERATLSCRASQSVSSSYLAWYQQKPGQAPRLLIYGAFSRATGIPDRFSGSGSGTDFTLTIS
RLEPEDFAVYYCQQYGSSPWTFGQGTKVEIK/RTVAAPSVFIFPPSDEQLKSGTASVVCLLNNFYPREAKVQWKVDN
ALQSGNSQESVTEQDSKDSTYSLSSTLTLSKADYEKHKVYACEVTHQGLSSPVTKSFNRGEC

```
XENCs510PD-1 X LAG-3
>7G8_H3.30_L1.34_[LAG-3]_Fab-1C11[PD-1]_H3.240_L3.148_scFv(GKPGS)4-IgG1_pI(-
)_Isosteric_A_/PVA_/S267K/L368D/K370S-Fc(216)_IgG1_C220S/PVA_/S267K/S364K/E357Q
```

Fab Chain 1 – 7G8_H3.30_ IgG1_pI(-)_Isosteric_A_/PVA_/S267K/L368D/K370S (SEQ ID NOS 43844-43848)
EVQLVESGGGLVQPGGSLRLSCAASGFTFDDAWMSWVRQAPGKGLEWVAEISTKANNHATYYAESVKGRFTISRDDS
KSSVYLQMNSLRAEDTAVYYCTRLATWDWYFDVWGQGTTVTVSS/ASTKGPSVFPLAPSSKSTSGGTAALGCLVKDY
FPEPVTVSWNSGALTSGVHTFPAVLQSSGLYSLSSVVTVPSSSLGTQTYICNVNHKPSDTKVDKKVEPKSCDKTHTC
PPCPAPPVAGPSVFLFPPKPKDTLMISRTPEVTCVVVDVKHEDPEVKFNWYVDGVEVHNAKTKPREEEYNSTYRVVS
VLTVLHQDWLNGKEYKCKVSNKALPAPIEKTISKAKGQPREPQVYTLPPSREEMTKNQVSLTCDVSGFYPSDIAVEW
ESDGQPENNYKTTPPVLDSDGSFFLYSKLTVDKSRWEQGDVFSCSVMHEALHNHYTQKSLSLSPGK

FIG. 49H scFv Chain 2 – 1C11[PD-1]_H3.240_L3.148_scFv(GKPGS)4_Fc(216)_IgG1_C220S/PVA_/S267K/S364K/E357Q (SEQ ID NOS 43849-43858 and linker disclosed as SEQ ID NO: 39202)
QVQLVQSGPELKKPGESVKVSCKASGYTFTHYGINWVRQPPGQGLEWMGWINTYTGEPYYAPGFQERFVFSIDTSQD
TAYLQINSLKAEDTAVYYCARDYYGSSPYWGQGTLVTVSS/GKPGSGKPGSGKPGSGKPGS/DVLMTQSPDSLAVSL
GERATINCKSSQSIVHSNGNTYLEWYQQKPGQSPKLLIYKVSNRFSGVPDRFSGSGSGTDFTLTISSLQAEDVAVYY
CFQGSHVPNTFGGGTKVEIK/EPKSSDKTHTCPPCPAPPVAGPSVFLFPPKPKDTLMISRTPEVTCVVVDVKHEDPE
VKFNWYVDGVEVHNAKTKPREEQYNSTYRVVSVLTVLHQDWLNGKEYKCKVSNKALPAPIEKTISKAKGQPREPQVY
TLPPSREQMTKNQVKLTCLVKGFYPSDIAVEWESNGQPENNYKTTPPVLDSDGSFFLYSKLTVDKSRWQQGNVFSCS
VMHEALHNHYTQKSLSLSPGK

Light Chain 3 – 7G8_L1.34 (SEQ ID NOS 43859-43863)
DIVLTQSPSSLSASVGDRVTITCRASQSVDYDGDSYMNWYQQKPGKPPKLLIYAASELESGIPARFSGSGSGTDFTL
TISSLQPEDFATYYCQQSNEDPFTFGSGTKLEIK/RTVAAPSVFIFPPSDEQLKSGTASVVCLLNNFYPREAKVQWK
VDNALQSGNSQESVTEQDSKDSTYSLSSTLTLSKADYEKHKVYACEVTHQGLSSPVTKSFNRGEC XENCS511 PD-1 X LAG-3
> 2A11_H1.144_L2.142_[LAG-3]_Fab-1C11[PD-1]_H3.240_L3.148_scFv(GKPGS)4-IgG1_pI(-)_Isosteric_A_/PVA_/S267K/L368D/K370S-Fc(216)_IgG1_C220S/PVA_/S267K/S364K/E357Q

Fab Chain 1 – 2A11_H1.144_IgG1_pI(-)_Isosteric_A_/PVA_/S267K/L368D/K370S (SEQ ID NOS 43864-43868)
EVQLVQSGAEVKKPGATVKISCKASGFNIKDYFMHWVQQAPGKGLEWMGWIDPELGDTEYAPKFQGRVTITADTSTN
TAYMELSSLRSEDTAVYYCYARGVYQALDYWGQGTLVTVSS/ASTKGPSVFPLAPSSKSTSGGTAALGCLVKDYFPE
PVTVSWNSGALTSGVHTFPAVLQSSGLYSLSSVVTVPSSSLGTQTYICNVNHKPSDTKVDKKVEPKSCDKTHTCPPC
PAPPVAGPSVFLFPPKPKDTLMISRTPEVTCVVVDVKHEDPEVKFNWYVDGVEVHNAKTKPREEEYNSTYRVVSVLT
VLHQDWLNGKEYKCKVSNKALPAPIEKTISKAKGQPREPQVYTLPPSREEMTKNQVSLTCDVSGFYPSDIAVEWESD
GQPENNYKTTPPVLDSDGSFFLYSKLTVDKSRWEQGDVFSCSVMHEALHNHYTQKSLSLSPGK scFv Chain 2 – 1C11[PD-1]_H3.240_L3.148_scFv(GKPGS)4_Fc(216)_IgG1_C220S/PVA_/S267K/S364K/E357Q (SEQ ID NOS 43869-43878 and linker disclosed as SEQ ID NO: 39202)
QVQLVQSGPELKKPGESVKVSCKASGYTFTHYGINWVRQPPGQGLEWMGWINTYTGEPYYAPGFQERFVFSIDTSQD
TAYLQINSLKAEDTAVYYCARDYYGSSPYWGQGTLVTVSS/GKPGSGKPGSGKPGSGKPGS/DVLMTQSPDSLAVSL
GERATINCKSSQSIVHSNGNTYLEWYQQKPGQSPKLLIYKVSNRFSGVPDRFSGSGSGTDFTLTISSLQAEDVAVYY
CFQGSHVPNTFGGGTKVEIK/EPKSSDKTHTCPPCPAPPVAGPSVFLFPPKPKDTLMISRTPEVTCVVVDVKHEDPE
VKFNWYVDGVEVHNAKTKPREEQYNSTYRVVSVLTVLHQDWLNGKEYKCKVSNKALPAPIEKTISKAKGQPREPQVY
TLPPSREQMTKNQVKLTCLVKGFYPSDIAVEWESNGQPENNYKTTPPVLDSDGSFFLYSKLTVDKSRWQQGNVFSCS
VMHEALHNHYTQKSLSLSPGK

Light Chain 3 – 2A11_L2.142 (SEQ ID NOS 43879-43883)
DIQMTQSPAFLSVTPGEKVTITCQASQDIGNYLNWFQQKPGQTVKLLIYFTSYLHSGVPSRFSGSGSGTDYTFTISS
LEAEDAATYFCQQGNTLPYTFGGGTKVEIK/RTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSPVTKSFNRGEC

FIG. 49I

```
XENCS512 PD-1 X TIM-3
> 3H3_H1_L2.1_Fab-1C11[PD-1]_H3.240_L3.148-scFv(GKPGS)4-IgG1_pI(-
)_Isosteric_A_/PVA_/S267K/L368D/K370S-Fc(216)_IgG1_C220S/PVA_/S267K/S364K/E357Q
```

Chain 1 – 3H3_H1_ IgG1_pI(-)_Isosteric_A_/PVA_/S267K/L368D/K370S (SEQ ID NOS 43884-43888)
QVTLKESGPVLVKPTETLTLTCTVSGFSLNGYGVNWVRQPPGKGLEWLAMIWGDGSTDYNSALKSRLTISKDNSKSQ
VVLTMTNMDPVDTATYYCARSYYTSDEDYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSDTKVDKKVEPKSCDKTHTCPPCP
APPVAGPSVFLFPPKPKDTLMISRTPEVTCVVVDVKHEDPEVKFNWYVDGVEVHNAKTKPREEEYNSTYRVVSVLTV
LHQDWLNGKEYKCKVSNKALPAPIEKTISKAKGQPREPQVYTLPPSREEMTKNQVSLTCDVSGFYPSDIAVEWESDG
QPENNYKTTPPVLDSDGSFFLYSKLTVDKSRWEQGDVFSCSVMHEALHNHYTQKSLSLSPGK

Chain 2 – 1C11[PD-1]_H3.240_L3.148_scFv(GKPGS)4_Fc(216)_IgG1_C220S/PVA_/S267K/S364K/E357Q (SEQ ID NOS 43889-43898 and linker disclosed as SEQ ID NO: 39202)
QVQLVQSGPELKKPGESVKVSCKASGYTFTHYGINWVRQPPGQGLEWMGWINTYTGEPYYAPGFQERFVFSIDTSQD
TAYLQINSLKAEDTAVYYCARDYYGSSPYWGQGTLVTVSS/GKPGSGKPGSGKPGSGKPGS/DVLMTQSPDSLAVSL
GERATINCKSSQSIVHSNGNTYLEWYQQKPGQSPKLLIYKVSNRFSGVPDRFSGSGSGTDFTLTISSLQAEDVAVYY
CFQGSHVPNTFGGGTKVEIK/EPKSSDKTHTCPPCPAPPVAGPSVFLFPPKPKDTLMISRTPEVTCVVVDVKHEDPE
VKFNWYVDGVEVHNAKTKPREEQYNSTYRVVSVLTVLHQDWLNGKEYKCKVSNKALPAPIEKTISKAKGQPREPQVY
TLPPSREQMTKNQVKLTCLVKGFYPSDIAVEWESNGQPENNYKTTPPVLDSDGSFFLYSKLTVDKSRWQQGNVFSCS
VMHEALHNHYTQKSLSLSPGK

Chain 3 – 3H3_L2.1 (SEQ ID NOS 43899-43903)
DIVMTQSPDSLAVSLGERATINCKSSQSLLNSRTRKNYLAWYQQKPGQSPKLLIYWASTRESGVPDRFTGSGSGTDF
TLTISSLQAEDVAVYYCKQSYSLRTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

```
XENCS513 PD-1 X BTLA
> 9C6_H1.1_L1_[BTLA]_Fab-1C11[PD-1]_H3.240_L3.148_scFv(GKPGS)4-IgG1_pI(-
)_Isosteric_A_/PVA_/S267K/L368D/K370S-Fc(216)_IgG1_C220S/PVA_/S267K/S364K/E357Q
```

Chain 1 – 9C6_H1.1_ IgG1_pI(-)_Isosteric_A_/PVA_/S267K/L368D/K370S (SEQ ID NOS 43904-43908)
QVQLKESGAEVKKPGASVKVSCKVSGFSLTGYGVNWVRQAPGQGLEWMGMIWIDGSTDYNSKFQGRVTMTKDNSKST
VYMELSSLRSEDTAVYYCARDRPDGRAMDYWGQGTMVTVSS/ASTKGPSVFPLAPSSKSTSGGTAALGCLVKDYFPE
PVTVSWNSGALTSGVHTFPAVLQSSGLYSLSSVVTVPSSSLGTQTYICNVNHKPSDTKVDKKVEPKSCDKTHTCPPC
PAPPVAGPSVFLFPPKPKDTLMISRTPEVTCVVVDVKHEDPEVKFNWYVDGVEVHNAKTKPREEEYNSTYRVVSVLT
VLHQDWLNGKEYKCKVSNKALPAPIEKTISKAKGQPREPQVYTLPPSREEMTKNQVSLTCDVSGFYPSDIAVEWESD
GQPENNYKTTPPVLDSDGSFFLYSKLTVDKSRWEQGDVFSCSVMHEALHNHYTQKSLSLSPGK

FIG. 49J

Chain 2 – 1C11[PD-1]_H3.240_L3.148_scFv(GKPGS)4_Fc(216)_IgG1_C220S/PVA_/S267K/S364K/E357Q (SEQ ID NOS 43909-43918 and linker disclosed as SEQ ID NO: 39202)
QVQLVQSGPELKKPGESVKVSCKASGYTFTHYGINWVRQPPGQGLEWMGWINTYTGEPYYAPGFQERFVFSIDTSQD
TAYLQINSLKAEDTAVYYCARDYYGSSPYWGQGTLVTVSS/GKPGSGKPGSGKPGSGKPGS/DVLMTQSPDSLAVSL
GERATINCKSSQSIVHSNGNTYLEWYQQKPGQSPKLLIYKVSNRFSGVPDRFSGSGSGTDFTLTISSLQAEDVAVYY
CFQGSHVPNTFGGGTKVEIK/EPKSSDKTHTCPPCPAPPVAGPSVFLFPPKPKDTLMISRTPEVTCVVVDVKHEDPE
VKFNWYVDGVEVHNAKTKPREEQYNSTYRVVSVLTVLHQDWLNGKEYKCKVSNKALPAPIEKTISKAKGQPREPQVY
TLPPSREQMTKNQVKLTCLVKGFYPSDIAVEWESNGQPENNYKTTPPVLDSDGSFFLYSKLTVDKSRWQQGNVFSCS
VMHEALHNHYTQKSLSLSPGK

Chain 3 – 9C6_L1 (SEQ ID NOS 43919-43923)
SIVMTQSPDSLAVSLGERATINCKASQSVSNDVAWYQQKPGQSPKLLIYYASNRYTGVPDRFTGSGYGTDFTLTISS
LQAEDVAVYFCQQDYSSPTFGGGTKLEIK/RTVAAPSVFIFPPSDEQLKSGTASVVCLLNNFYPREAKVQWKVDNAL
QSGNSQESVTEQDSKDSTYSLSSTLTLSKADYEKHKVYACEVTHQGLSSPVTKSFNRGEC XENCS514 PD_1 X ICOS
> [ICOS]_H0L0_Fab-1C11[PD-1]_H3.241_L3.148-scFv(GKPGS)4-IgG1_pI(-
)_Isosteric_A_/PVA_/S267K/L368D/K370S-Fc(216)_IgG1_C220S/PVA_/S267K/S364K/E357Q

Chain 1 – [ICOS]_H0_IgG1_pI(-)_Isosteric_A_/PVA_/S267K/L368D/K370S (SEQ ID NOS 43924-43928)
QVQLVQSGAEVKKPGASVKVSCKASGYTFTGYYMHWVRQAPGQGLEWMGWINPHSGGTNYAQKFQGRVTMTRDTSIS
TAYMELSRLRSDDTAVYYCARTYYYDSSGYYHDAFDIWGQGTMVTVSS/ASTKGPSVFPLAPSSKSTSGGTAALGCLVKDYFP
EPVTVSWNSGALTSGVHTFPAVLQSSGLYSLSSVVTVPSSSLGTQTYICNVNHKPSDTKVDKKVEPKSCDKTHTCPPCPAPPVAGPSVFLFPP
KPKDTLMISRTPEVTCVVVDVKHEDPEVKFNWYVDGVEVHNAKTKPREEEYNSTYRVVSVLTVLHQDWLNGKEYKCKVSNKALPAPIEKTISK
AKGQPREPQVYTLPPSREEMTKNQVSLTCDVSGFYPSDIAVEWESDGQPENNYKTTPPVLDSDGSFFLYSKLTVDKSRWEQGDVFSCSVMHEA
LHNHYTQKSLSLSPGK

Chain 2 – 1C11[PD-1]_H3.241_L3.148_scFv(GKPGS)4_Fc(216)_IgG1_C220S/PVA_/S267K/S364K/E357Q (SEQ ID NOS 43929-43938 and linker disclosed as SEQ ID NO: 39202)
EVQLVQSGPELKKPGESVKVSCKASGYTFTHYGINWVRQPPGQGLEWMGWINTYTGEPYYAPGFQERFVFSIDTSQD
TAYLQINSLKAEDTAVYYCARDYYGSSPYWGQGTLVTVSS/GKPGSGKPGSGKPGSGKPGS/DVLMTQSPDSLAVSL
GERATINCKSSQSIVHSNGNTYLEWYQQKPGQSPKLLIYKVSNRFSGVPDRFSGSGSGTDFTLTISSLQAEDVAVYY
CFQGSHVPNTFGGGTKVEIK/EPKSSDKTHTCPPCPAPPVAGPSVFLFPPKPKDTLMISRTPEVTCVVVDVKHEDPE
VKFNWYVDGVEVHNAKTKPREEQYNSTYRVVSVLTVLHQDWLNGKEYKCKVSNKALPAPIEKTISKAKGQPREPQVY
TLPPSREQMTKNQVKLTCLVKGFYPSDIAVEWESNGQPENNYKTTPPVLDSDGSFFLYSKLTVDKSRWQQGNVFSCS
VMHEALHNHYTQKSLSLSPGK

Chain 3 – [ICOS]_L0 (SEQ ID NOS 43939-43943)
DIQMTQSPSSVSASVGDRVTITCRASQGISRLLAWYQQKPGKAPKLLIYVASSLQSGVPSRFSGSGSGTDFTLTISS
LQPEDFATYYCQQANSFPWTFGQGTKVEIK/RTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSPVTKSFNRGEC

FIG. 49K

```
XENCS515 PD_1 X ICOS
```
> [ICOS]_H0.66_L0_Fab-1C11[PD-1]_H3.241_L3.148-scFv(GKPGS)4-IgG1_pI(-)_Isosteric_A_/PVA_/S267K/L368D/K370S-Fc(216)_IgG1_C220S/PVA_/S267K/S364K/E357Q

Chain 1 – [ICOS]_H0.66_ IgG1_pI(-)_Isosteric_A_/PVA_/S267K/L368D/K370S (SEQ ID NOS 43944-43948)
QVQLVQSGAEVKKPGASVKVSCKASGYTFT<u>GYYMH</u>WVRQAPGQGLEWMG<u>WINPHSGETIYAQKFQG</u>RVTMTRDTSISTAYME
LSSLRSEDTAVYYCAR<u>TYYYDTSGYYHDAFDV</u>WGQGTMVTVSS/ASTKGPSVFPLAPSSKSTSGGTAALGCLVKDYFPEPVT
VSWNSGALTSGVHTFPAVLQSSGLYSLSSVVTVPSSSLGTQTYICNVNHKPSDTKVDKKVEPKSCDKTHTCPPCPAPPVAGP
SVFLFPPKPKDTLMISRTPEVTCVVVDVKHEDPEVKFNWYVDGVEVHNAKTKPREEEYNSTYRVVSVLTVLHQDWLNGKEYK
CKVSNKALPAPIEKTISKAKGQPREPQVYTLPPSREEMTKNQVSLTCDVSGFYPSDIAVEWESDGQPENNYKTTPPVLDSDG
SFFLYSKLTVDKSRWEQGDVFSCSVMHEALHNHYTQKSLSLSPGK

Chain 2 – 1C11[PD-1]_H3.241_L3.148_scFv(GKPGS)4_Fc(216)_IgG1_C220S/PVA_/S267K/S364K/E357Q (SEQ ID NOS 43949-43958 and linker disclosed as SEQ ID NO: 39202)
EVQLVQSGPELKKPGESVKVSCKASGYTFT<u>HYGIN</u>WVRQPPGQGLEWMG<u>WINTYTGEPYYAPGFQER</u>FVFSIDTSQDTAYLQ
INSLKAEDTAVYYCAR<u>DYYGSSPYW</u>GQGTLVTVSS/<u>GKPGSGKPGSGKPGSGKPGS</u>/DVLMTQSPDSLAVSLGERATINCK<u>S
SQSIVHSNGNTYLE</u>WYQQKPGQSPKLLIY<u>KVSNRFS</u>GVPDRFSGSGSGTDFTLTISSLQAEDVAVYYC<u>FQGSHVPNTF</u>GGGT
KVEIK/EPKSSDKTHTCPPCPAPPVAGPSVFLFPPKPKDTLMISRTPEVTCVVVDVKHEDPEVKFNWYVDGVEVHNAKTKPR
EEQYNSTYRVVSVLTVLHQDWLNGKEYKCKVSNKALPAPIEKTISKAKGQPREPQVYTLPPSREQMTKNQVKLTCLVKGFYP
SDIAVEWESNGQPENNYKTTPPVLDSDGSFFLYSKLTVDKSRWQQGNVFSCSVMHEALHNHYTQKSLSLSPGK

Chain 3 – [ICOS]_L0 (SEQ ID NOS 43959-43963)
DIQMTQSPSSVSASVGDRVTITCR<u>ASQGISRLLA</u>WYQQKPGKAPKLLIY<u>VASSLQS</u>GVPSRFSGSGSGTDFTLTISSLQPED
FATYYC<u>QQANSFPWT</u>FGQGTKVEIK/RTVAAPSVFIFPPSDEQLKSGTASVVCLLNNFYPREAKVQWKVDNALQSGNSQESV
TEQDSKDSTYSLSSTLTLSKADYEKHKVYACEVTHQGLSSPVTKSFNRGEC

```
XENCS516 PD-1 X CTLA-4
```
> [CTLA-4]_H3_L0.22_Fab-1C11[PD-1]_H3.241_L3.148_scFv(GKPGS)4-IgG1_pI(-)_Isosteric_A_/PVA_/S267K/L368D/K370S-Fc(216)_IgG1_C220S/PVA_/S267K/S364K/E357Q

Chain 1 - [CTLA-4]_H3_ IgG1_pI(-)_Isosteric_A_/PVA_/S267K/L368D/K370S (SEQ ID NOS 43964-43968)
EVQLVESGGGLVKPGGSLRLSCAASGFTFS<u>SYTMH</u>WVRQAPGKGLEWVS<u>FISYDGNNKYYADSVKG</u>RFTISRDNAKNSLYLQ
MNSLRAEDTAVYYCAR<u>TGWLGPFDY</u>WGQGTLVTVSS/ASTKGPSVFPLAPSSKSTSGGTAALGCLVKDYFPEPVTVSWNSGA
LTSGVHTFPAVLQSSGLYSLSSVVTVPSSSLGTQTYICNVNHKPSDTKVDKKVEPKSCDKTHTCPPCPAPPVAGPSVFLFPP
KPKDTLMISRTPEVTCVVVDVKHEDPEVKFNWYVDGVEVHNAKTKPREEEYNSTYRVVSVLTVLHQDWLNGKEYKCKVSNKA
LPAPIEKTISKAKGQPREPQVYTLPPSREEMTKNQVSLTCDVSGFYPSDIAVEWESDGQPENNYKTTPPVLDSDGSFFLYSK
LTVDKSRWEQGDVFSCSVMHEALHNHYTQKSLSLSPGK

Chain 2 - 1C11[PD-1]_H3.241_L3.148_scFv(GKPGS)4_Fc(216)_IgG1_C220S/PVA_/S267K/S364K/E357Q (SEQ ID NOS 43969-43978 and linker disclosed as SEQ ID NO: 39202)
EVQLVQSGPELKKPGESVKVSCKASGYTFT<u>HYGIN</u>WVRQPPGQGLEWMG<u>WINTYTGEPYYAPGFQER</u>FVFSIDTSQDTAYLQ
INSLKAEDTAVYYCAR<u>DYYGSSPYW</u>GQGTLVTVSS/<u>GKPGSGKPGSGKPGSGKPGS</u>/DVLMTQSPDSLAVSLGERATINCK<u>S
SQSIVHSNGNTYLE</u>WYQQKPGQSPKLLIY<u>KVSNRFS</u>GVPDRFSGSGSGTDFTLTISSLQAEDVAVYYC<u>FQGSHVPNTF</u>GGGT
KVEIK/EPKSSDKTHTCPPCPAPPVAGPSVFLFPPKPKDTLMISRTPEVTCVVVDVKHEDPEVKFNWYVDGVEVHNAKTKPR
EEQYNSTYRVVSVLTVLHQDWLNGKEYKCKVSNKALPAPIEKTISKAKGQPREPQVYTLPPSREQMTKNQVKLTCLVKGFYP
SDIAVEWESNGQPENNYKTTPPVLDSDGSFFLYSKLTVDKSRWQQGNVFSCSVMHEALHNHYTQKSLSLSPGK

FIG. 49L

Chain 3 - [CTLA-4]_L0.22 (SEQ ID NOS 43979-43983)
EIVLTQSPGTLSLSPGERATLSCRASQSVSSSYLAWYQQKPGQAPRLLIYGAFSRATGIPDRFSGSGSGTDFTLTIS
RLEPEDFAVYYCQQYGSSPWTFGQGTKVEIK/RTVAAPSVFIFPPSDEQLKSGTASVVCLLNNFYPREAKVQWKVDN
ALQSGNSQESVTEQDSKDSTYSLSSTLTLSKADYEKHKVYACEVTHQGLSSPVTKSFNRGEC XENCS517 PD_1 X LAG-3
> 7G8_H3.30_L1.34_[LAG-3]_Fab-1C11[PD-1]_H3.241_L3.148_scFv(GKPGS)4-IgG1_pI(-
)_Isosteric_A_/PVA_/S267K/L368D/K370S-Fc(216)_IgG1_C220S/PVA_/S267K/S364K/E357Q

Chain 1 – 7G8_H3.30_ IgG1_pI(-)_Isosteric_A_/PVA_/S267K/L368D/K370S (SEQ ID NOS 43984-43988)
EVQLVESGGGLVQPGGSLRLSCAASGFTFDDAWMSWVRQAPGKGLEWVAEISTKANNHATYYAESVKGRFTISRDDS
KSSVYLQMNSLRAEDTAVYYCTRLATWDWYFDVWGQGTTVTVSS/ASTKGPSVFPLAPSSKSTSGGTAALGCLVKDY
FPEPVTVSWNSGALTSGVHTFPAVLQSSGLYSLSSVVTVPSSSLGTQTYICNVNHKPSDTKVDKKVEPKSCDKTHTC
PPCPAPPVAGPSVFLFPPKPKDTLMISRTPEVTCVVVDVKHEDPEVKFNWYVDGVEVHNAKTKPREEEYNSTYRVVS
VLTVLHQDWLNGKEYKCKVSNKALPAPIEKTISKAKGQPREPQVYTLPPSREEMTKNQVSLTCDVSGFYPSDIAVEW
ESDGQPENNYKTTPPVLDSDGSFFLYSKLTVDKSRWEQGDVFSCSVMHEALHNHYTQKSLSLSPGK

Chain 2 –1C11[PD-1]_H3.241_L3.148_scFv(GKPGS)4_Fc(216)_IgG1_C220S/PVA_/S267K/S364K/E357Q (SEQ ID NOS 43989-43998 and linker disclosed as SEQ ID NO: 39202)
EVQLVQSGPELKKPGESVKVSCKASGYTFTHYGINWVRQPPGQGLEWMGWINTYTGEPYYAPGFQERFVFSIDTSQD
TAYLQINSLKAEDTAVYYCARDYYGSSPYWGQGTLVTVSS/GKPGSGKPGSGKPGSGKPGS/DVLMTQSPDSLAVSL
GERATINCKSSQSIVHSNGNTYLEWYQQKPGQSPKLLIYKVSNRFSGVPDRFSGSGSGTDFTLTISSLQAEDVAVYY
CFQGSHVPNTFGGGTKVEIK/EPKSSDKTHTCPPCPAPPVAGPSVFLFPPKPKDTLMISRTPEVTCVVVDVKHEDPE
VKFNWYVDGVEVHNAKTKPREEQYNSTYRVVSVLTVLHQDWLNGKEYKCKVSNKALPAPIEKTISKAKGQPREPQVY
TLPPSREQMTKNQVKLTCLVKGFYPSDIAVEWESNGQPENNYKTTPPVLDSDGSFFLYSKLTVDKSRWQQGNVFSCS
VMHEALHNHYTQKSLSLSPGK

Chain 3 – 7G8_L1.34 (SEQ ID NOS 43999-44003)
DIVLTQSPSSLSASVGDRVTITCRASQSVDYDGDSYMNWYQQKPGKPPKLLIYAASELESGIPARFSGSGSGTDFTL
TISSLQPEDFATYYCQQSNEDPFTFGSGTKLEIK/RTVAAPSVFIFPPSDEQLKSGTASVVCLLNNFYPREAKVQWK
VDNALQSGNSQESVTEQDSKDSTYSLSSTLTLSKADYEKHKVYACEVTHQGLSSPVTKSFNRGEC XENCS518 PD_1 X LAG-3
> 2A11_H1.144_L2.142_[LAG-3]_Fab-1C11[PD-1]_H3.241_L3.148_scFv(GKPGS)4-IgG1_pI(-
)_Isosteric_A_/PVA_/S267K/L368D/K370S-Fc(216)_IgG1_C220S/PVA_/S267K/S364K/E357Q

Chain 1 – 2A11_H1.144_ IgG1_pI(-)_Isosteric_A_/PVA_/S267K/L368D/K370S (SEQ ID NOS 44004-44008)
EVQLVQSGAEVKKPGATVKISCKASGFNIKDYFMHWVQQAPGKGLEWMGWIDPELGDTEYAPKFQGRVTITADTSTN
TAYMELSSLRSEDTAVYYCYARGVYQALDYWGQGTLVTVSS/ASTKGPSVFPLAPSSKSTSGGTAALGCLVKDYFPE
PVTVSWNSGALTSGVHTFPAVLQSSGLYSLSSVVTVPSSSLGTQTYICNVNHKPSDTKVDKKVEPKSCDKTHTCPPC
PAPPVAGPSVFLFPPKPKDTLMISRTPEVTCVVVDVKHEDPEVKFNWYVDGVEVHNAKTKPREEEYNSTYRVVSVLT
VLHQDWLNGKEYKCKVSNKALPAPIEKTISKAKGQPREPQVYTLPPSREEMTKNQVSLTCDVSGFYPSDIAVEWESD
GQPENNYKTTPPVLDSDGSFFLYSKLTVDKSRWEQGDVFSCSVMHEALHNHYTQKSLSLSPGK

FIG. 49M

Chain 2 – 1C11[PD-1]_H3.241_L3.148_scFv(GKPGS)4_Fc(216)_IgG1_C220S/PVA_/S267K/S364K/E357Q (SEQ ID NOS 44009-44018 and linker disclosed as SEQ ID NO: 39202)
EVQLVQSGPELKKPGESVKVSCKASGYTFTHYGINWVRQPPGQGLEWMGWINTYTGEPYYAPGFQERFVFSIDTSQD
TAYLQINSLKAEDTAVYYCARDYYGSSPYWGQGTLVTVSS/GKPGSGKPGSGKPGSGKPGS/DVLMTQSPDSLAVSL
GERATINCKSSQSIVHSNGNTYLEWYQQKPGQSPKLLIYKVSNRFSGVPDRFSGSGSGTDFTLTISSLQAEDVAVYY
CFQGSHVPNTFGGGTKVEIK/EPKSSDKTHTCPPCPAPPVAGPSVFLFPPKPKDTLMISRTPEVTCVVVDVKHEDPE
VKFNWYVDGVEVHNAKTKPREEQYNSTYRVVSVLTVLHQDWLNGKEYKCKVSNKALPAPIEKTISKAKGQPREPQVY
TLPPSREQMTKNQVKLTCLVKGFYPSDIAVEWESNGQPENNYKTTPPVLDSDGSFFLYSKLTVDKSRWQQGNVFSCS
VMHEALHNHYTQKSLSLSPGK

Chain 3 – 2A11_L2.142 (SEQ ID NOS 44019-44023)
DIQMTQSPAFLSVTPGEKVTITCQASQDIGNYLNWFQQKPGQTVKLLIYFTSYLHSGVPSRFSGSGSGTDYTFTISS
LEAEDAATYFCQQGNTLPYTFGGGTKVEIK/RTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSPVTKSFNRGEC XENCS519 PD-1 X TIM-3
**> 3H3_H1_L2.1_Fab-1C11[PD-1]_H3.241_L3.148-scFv(GKPGS)4-IgG1_pI(-
)_Isosteric_A_/PVA_/S267K/L368D/K370S-Fc(216)_IgG1_C220S/PVA_/S267K/S364K/E357Q**

Chain 1 – 3H3_H1_ IgG1_pI(-)_Isosteric_A_/PVA_/S267K/L368D/K370S (SEQ ID NOS 44024-44028)
QVTLKESGPVLVKPTETLTLTCTVSGFSLNGYGVNWVRQPPGKGLEWLAMIWGDGSTDYNSALKSRLTISKDNSKSQ
VVLTMTNMDPVDTATYYCARSYYTSDEDYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSDTKVDKKVEPKSCDKTHTCPPCP
APPVAGPSVFLFPPKPKDTLMISRTPEVTCVVVDVKHEDPEVKFNWYVDGVEVHNAKTKPREEEYNSTYRVVSVLTV
LHQDWLNGKEYKCKVSNKALPAPIEKTISKAKGQPREPQVYTLPPSREEMTKNQVSLTCDVSGFYPSDIAVEWESDG
QPENNYKTTPPVLDSDGSFFLYSKLTVDKSRWEQGDVFSCSVMHEALHNHYTQKSLSLSPGK

Chain 2 – 1C11[PD-1]_H3.241_L3.148_scFv(GKPGS)4_Fc(216)_IgG1_C220S/PVA_/S267K/S364K/E357Q (SEQ ID NOS 44029-44038 and linker disclosed as SEQ ID NO: 39202)
EVQLVQSGPELKKPGESVKVSCKASGYTFTHYGINWVRQPPGQGLEWMGWINTYTGEPYYAPGFQERFVFSIDTSQD
TAYLQINSLKAEDTAVYYCARDYYGSSPYWGQGTLVTVSS/GKPGSGKPGSGKPGSGKPGS/DVLMTQSPDSLAVSL
GERATINCKSSQSIVHSNGNTYLEWYQQKPGQSPKLLIYKVSNRFSGVPDRFSGSGSGTDFTLTISSLQAEDVAVYY
CFQGSHVPNTFGGGTKVEIK/EPKSSDKTHTCPPCPAPPVAGPSVFLFPPKPKDTLMISRTPEVTCVVVDVKHEDPE
VKFNWYVDGVEVHNAKTKPREEQYNSTYRVVSVLTVLHQDWLNGKEYKCKVSNKALPAPIEKTISKAKGQPREPQVY
TLPPSREQMTKNQVKLTCLVKGFYPSDIAVEWESNGQPENNYKTTPPVLDSDGSFFLYSKLTVDKSRWQQGNVFSCS
VMHEALHNHYTQKSLSLSPGK

Chain 3 – 3H3_L2.1 (SEQ ID NOS 44039-44043)
DIVMTQSPDSLAVSLGERATINCKSSQSLLNSRTRKNYLAWYQQKPGQSPKLLIYWASTRESGVPDRFTGSGSGTDF
TLTISSLQAEDVAVYYCKQSYSLRTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

FIG. 49N

XENCS520 PD-1 X BTLA
> 9C6_H1.1_L1_[BTLA]_Fab-1C11[PD-1]_H3.241_L3.148_scFv(GKPGS)4-IgG1_pI(-)_Isosteric_A_/PVA_/S267K/L368D/K370S-Fc(216)_IgG1_C220S/PVA_/S267K/S364K/E357Q

Chain 1 – 9C6_H1.1_ IgG1_pI(-)_Isosteric_A_/PVA_/S267K/L368D/K370S (SEQ ID NOS 44044-44048)
QVQLKESGAEVKKPGASVKVSCKVSGFSLTGYGVNWVRQAPGQGLEWMGMIWIDGSTDYNSKFQGRVTMTKDNSKST
VYMELSSLRSEDTAVYYCARDRPDGRAMDYWGQGTMVTVSS/ASTKGPSVFPLAPSSKSTSGGTAALGCLVKDYFPE
PVTVSWNSGALTSGVHTFPAVLQSSGLYSLSSVVTVPSSSLGTQTYICNVNHKPSDTKVDKKVEPKSCDKTHTCPPC
PAPPPVAGPSVFLFPPKPKDTLMISRTPEVTCVVVDVKHEDPEVKFNWYVDGVEVHNAKTKPREEEYNSTYRVVSVLT
VLHQDWLNGKEYKCKVSNKALPAPIEKTISKAKGQPREPQVYTLPPSREEMTKNQVSLTCDVSGFYPSDIAVEWESD
GQPENNYKTTPPVLDSDGSFFLYSKLTVDKSRWEQGDVFSCSVMHEALHNHYTQKSLSLSPGK

Chain 2 – 1C11[PD-1]_H3.241_L3.148_scFv(GKPGS)4_Fc(216)_IgG1_C220S/PVA_/S267K/S364K/E357Q (SEQ ID
NOS 44049-44058 and linker disclosed as SEQ ID NO: 39202)
EVQLVQSGPELKKPGESVKVSCKASGYTFTHYGINWVRQPPGQGLEWMGWINTYTGEPYYAPGFQERFVFSIDTSQD
TAYLQINSLKAEDTAVYYCARDYYGSSPYWGQGTLVTVSS/GKPGSGKPGSGKPGSGKPGS/DVLMTQSPDSLAVSL
GERATINCKSSQSIVHSNGNTYLEWYQQKPGQSPKLLIYKVSNRFSGVPDRFSGSGSGTDFTLTISSLQAEDVAVYY
CFQGSHVPNTFGGGTKVEIK/EPKSSDKTHTCPPCPAPPVAGPSVFLFPPKPKDTLMISRTPEVTCVVVDVKHEDPE
VKFNWYVDGVEVHNAKTKPREEQYNSTYRVVSVLTVLHQDWLNGKEYKCKVSNKALPAPIEKTISKAKGQPREPQVY
TLPPSREQMTKNQVKLTCLVKGFYPSDIAVEWESNGQPENNYKTTPPVLDSDGSFFLYSKLTVDKSRWQQGNVFSCS
VMHEALHNHYTQKSLSLSPGK

Chain 3 – 9C6_L1 (SEQ ID NOS 44059-44063)
SIVMTQSPDSLAVSLGERATINCKASQSVSNDVAWYQQKPGQSPKLLIYYASNRYTGVPDRFTGSGYGTDFTLTISS
LQAEDVAVYFCQQDYSSPTFGGGTKLEIK/RTVAAPSVFIFPPSDEQLKSGTASVVCLLNNFYPREAKVQWKVDNAL
QSGNSQESVTEQDSKDSTYSLSSTLTLSKADYEKHKVYACEVTHQGLSSPVTKSFNRGEC XENCS521 PD-1 X ICOS
> [ICOS]_H0L0_Fab-1C11[PD-1]_H3.241_L3.92-scFv(GKPGS)4-IgG1_pI(-)_Isosteric_A_/PVA_/S267K/L368D/K370S-Fc(216)_IgG1_C220S/PVA_/S267K/S364K/E357Q

Chain 1 – [ICOS]_H0_ IgG1_pI(-)_Isosteric_A_/PVA_/S267K/L368D/K370S (SEQ ID NOS 44064-44068)
QVQLVQSGAEVKKPGASVKVSCKASGYTFTGYYMHWVRQAPGQGLEWMGWINPHSGGTNYAQKFQGRVTMTRDTSIS
TAYMELSRLRSDDTAVYYCARTYYYDSSGYYHDAFDIWGQGTMVTVSS/ASTKGPSVFPLAPSSKSTSGGTAALGCLVKDYFP
EPVTVSWNSGALTSGVHTFPAVLQSSGLYSLSSVVTVPSSSLGTQTYICNVNHKPSDTKVDKKVEPKSCDKTHTCPPCPAPPVAGPSVFLFPP
KPKDTLMISRTPEVTCVVVDVKHEDPEVKFNWYVDGVEVHNAKTKPREEEYNSTYRVVSVLTVLHQDWLNGKEYKCKVSNKALPAPIEKTISK
AKGQPREPQVYTLPPSREEMTKNQVSLTCDVSGFYPSDIAVEWESDGQPENNYKTTPPVLDSDGSFFLYSKLTVDKSRWEQGDVFSCSVMHEA
LHNHYTQKSLSLSPGK

FIG. 49O

Chain 2 – 1C11[PD-1]_H3.241_L3.92_scFv(GKPGS)4_Fc(216)_IgG1_C220S/PVA_/S267K/S364K/E357Q (SEQ ID NOS 44069-44078 and linker disclosed as SEQ ID NO: 39202)
EVQLVQSGPELKKPGESVKVSCKASGYTFTHYGINWVRQPPGQGLEWMGWINTYTGEPYYAPGFQERFVFSIDTSQD
TAYLQINSLKAEDTAVYYCARDYYGSSPYWGQGTLVTVSS/GKPGSGKPGSGKPGSGKPGS/DIVMTQSPDSLAVSL
GERVTINCKASQSIVHSNGNTYLEWYQQKPGQPPKLLIYKVSNRFTGVPDRFSGSGSGTDFTLTISSLQAEDVAVYY
CFQGSHVPNTFGGGTKVEIK/EPKSSDKTHTCPPCPAPPVAGPSVFLFPPKPKDTLMISRTPEVTCVVVDVKHEDPE
VKFNWYVDGVEVHNAKTKPREEQYNSTYRVVSVLTVLHQDWLNGKEYKCKVSNKALPAPIEKTISKAKGQPREPQVY
TLPPSREQMTKNQVKLTCLVKGFYPSDIAVEWESNGQPENNYKTTPPVLDSDGSFFLYSKLTVDKSRWQQGNVFSCS
VMHEALHNHYTQKSLSLSPGK

Chain 3 – [ICOS]_L0 (SEQ ID NOS 44079-44083)
DIQMTQSPSSVSASVGDRVTITCRASQGISRLLAWYQQKPGKAPKLLIYVASSLQSGVPSRFSGSGSGTDFTLTISS
LQPEDFATYYCQQANSFPWTFGQGTKVEIK/RTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSPVTKSFNRGEC

```
XENCS522 PD-1 X ICOS
```
> [ICOS]_H0.66_L0_Fab-1C11[PD-1]_H3.241_L3.92-scFv(GKPGS)4-IgG1_pI(-
)_Isosteric_A_/PVA_/S267K/L368D/K370S-Fc(216)_IgG1_C220S/PVA_/S267K/S364K/E357Q

Chain 1 – [ICOS]_H0.66_IgG1_pI(-)_Isosteric_A_/PVA_/S267K/L368D/K370S (SEQ ID NOS 44084-44088)
QVQLVQSGAEVKKPGASVKVSCKASGYTFTGYYMHWVRQAPGQGLEWMGWINPHSGETIYAQKFQGRVTMTRDTSIS
TAYMELSSLRSEDTAVYYCARTYYYDTSGYYHDAFDVWGQGTMVTVSS/ASTKGPSVFPLAPSSKSTSGGTAALGCL
VKDYFPEPVTVSWNSGALTSGVHTFPAVLQSSGLYSLSSVVTVPSSSLGTQTYICNVNHKPSDTKVDKKVEPKSCDK
THTCPPCPAPPVAGPSVFLFPPKPKDTLMISRTPEVTCVVVDVKHEDPEVKFNWYVDGVEVHNAKTKPREEEYNSTY
RVVSVLTVLHQDWLNGKEYKCKVSNKALPAPIEKTISKAKGQPREPQVYTLPPSREEMTKNQVSLTCDVSGFYPSDI
AVEWESDGQPENNYKTTPPVLDSDGSFFLYSKLTVDKSRWEQGDVFSCSVMHEALHNHYTQKSLSLSPGK

Chain 2 – 1C11[PD-1]_H3.241_L3.92_scFv(GKPGS)4_Fc(216)_IgG1_C220S/PVA_/S267K/S364K/E357Q (SEQ ID NOS 44089-44098 and linker disclosed as SEQ ID NO: 39202)
EVQLVQSGPELKKPGESVKVSCKASGYTFTHYGINWVRQPPGQGLEWMGWINTYTGEPYYAPGFQERFVFSIDTSQD
TAYLQINSLKAEDTAVYYCARDYYGSSPYWGQGTLVTVSS/GKPGSGKPGSGKPGSGKPGS/DIVMTQSPDSLAVSL
GERVTINCKASQSIVHSNGNTYLEWYQQKPGQPPKLLIYKVSNRFTGVPDRFSGSGSGTDFTLTISSLQAEDVAVYY
CFQGSHVPNTFGGGTKVEIK/EPKSSDKTHTCPPCPAPPVAGPSVFLFPPKPKDTLMISRTPEVTCVVVDVKHEDPE
VKFNWYVDGVEVHNAKTKPREEQYNSTYRVVSVLTVLHQDWLNGKEYKCKVSNKALPAPIEKTISKAKGQPREPQVY
TLPPSREQMTKNQVKLTCLVKGFYPSDIAVEWESNGQPENNYKTTPPVLDSDGSFFLYSKLTVDKSRWQQGNVFSCS
VMHEALHNHYTQKSLSLSPGK

Chain 3 – [ICOS]_L0 (SEQ ID NOS 44099-44103)
DIQMTQSPSSVSASVGDRVTITCRASQGISRLLAWYQQKPGKAPKLLIYVASSLQSGVPSRFSGSGSGTDFTLTISS
LQPEDFATYYCQQANSFPWTFGQGTKVEIK/RTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSPVTKSFNRGEC

FIG. 49P

XENCS523 PD-1 X CTLA-4
> [CTLA-4]_H3_L0.22_Fab-1C11[PD-1]_H3.241_L3.92_scFv(GKPGS)4-IgG1_pI(-
)_Isosteric_A_/PVA_/S267K/L368D/K370S-Fc(216)_IgG1_C220S/PVA_/S267K/S364K/E357Q

Chain 1 - [CTLA-4]_H3_ IgG1_pI(-)_Isosteric_A_/PVA_/S267K/L368D/K370S (SEQ ID NOS 44104-44108)
EVQLVESGGGLVKPGGSLRLSCAASGFTFSSYTMHWVRQAPGKGLEWVSFISYDGNNKYYADSVKGRFTISRDNAKNSLYLQ
MNSLRAEDTAVYYCARTGWLGPFDYWGQGTLVTVSS/ASTKGPSVFPLAPSSKSTSGGTAALGCLVKDYFPEPVTVSWNSGA
LTSGVHTFPAVLQSSGLYSLSSVVTVPSSSLGTQTYICNVNHKPSDTKVDKKVEPKSCDKTHTCPPCPAPPVAGPSVFLFPP
KPKDTLMISRTPEVTCVVVDVKHEDPEVKFNWYVDGVEVHNAKTKPREEEYNSTYRVVSVLTVLHQDWLNGKEYKCKVSNKA
LPAPIEKTISKAKGQPREPQVYTLPPSREEMTKNQVSLTCDVSGFYPSDIAVEWESDGQPENNYKTTPPVLDSDGSFFLYSK
LTVDKSRWEQGDVFSCSVMHEALHNHYTQKSLSLSPGK

Chain 2 - 1C11[PD-1]_H3.241_L3.92_scFv(GKPGS)4_Fc(216)_IgG1_C220S/PVA_/S267K/S364K/E357Q (SEQ ID NOS 44109-44118 and linker disclosed as SEQ ID NO: 39202)
EVQLVQSGPELKKPGESVKVSCKASGYTFTHYGINWVRQPPGQGLEWMGWINTYTGEPYYAPGFQERFVFSIDTSQDTAYLQ
INSLKAEDTAVYYCARDYYGSSPYWGQGTLVTVSS/GKPGSGKPGSGKPGSGKPGS/DIVMTQSPDSLAVSLGERVTINCKA
SQSIVHSNGNTYLEWYQQKPGQPPKLLIYKVSNRFTGVPDRFSGSGSGTDFTLTISSLQAEDVAVYYCFQGSHVPNTFGGGT
KVEIK/EPKSSDKTHTCPPCPAPPVAGPSVFLFPPKPKDTLMISRTPEVTCVVVDVKHEDPEVKFNWYVDGVEVHNAKTKPR
EEQYNSTYRVVSVLTVLHQDWLNGKEYKCKVSNKALPAPIEKTISKAKGQPREPQVYTLPPSREQMTKNQVKLTCLVKGFYP
SDIAVEWESNGQPENNYKTTPPVLDSDGSFFLYSKLTVDKSRWQQGNVFSCSVMHEALHNHYTQKSLSLSPGK

Chain 3 - [CTLA-4]_L0.22 (SEQ ID NOS 44119-44123)
EIVLTQSPGTLSLSPGERATLSCRASQSVSSSYLAWYQQKPGQAPRLLIYGAFSRATGIPDRFSGSGSGTDFTLTISRLEPE
DFAVYYCQQYGSSPWTFGQGTKVEIK/RTVAAPSVFIFPPSDEQLKSGTASVVCLLNNFYPREAKVQWKVDNALQSGNSQES
VTEQDSKDSTYSLSSTLTLSKADYEKHKVYACEVTHQGLSSPVTKSFNRGEC XENCS524 PD-1 X LAG-3
> 7G8_H3.30_L1.34_[LAG-3]_Fab-1C11[PD-1]_H3.241_L3.92_scFv(GKPGS)4-IgG1_pI(-
)_Isosteric_A_/PVA_/S267K/L368D/K370S-Fc(216)_IgG1_C220S/PVA_/S267K/S364K/E357Q

Chain 1 – 7G8_H3.30_ IgG1_pI(-)_Isosteric_A_/PVA_/S267K/L368D/K370S (SEQ ID NOS 44124-44128)
EVQLVESGGGLVQPGGSLRLSCAASGFTFDDAWMSWVRQAPGKGLEWVAEISTKANNHATYYAESVKGRFTISRDDSKSSVY
LQMNSLRAEDTAVYYCTRLATWDWYFDVWGQGTTVTVSS/ASTKGPSVFPLAPSSKSTSGGTAALGCLVKDYFPEPVTVSWN
SGALTSGVHTFPAVLQSSGLYSLSSVVTVPSSSLGTQTYICNVNHKPSDTKVDKKVEPKSCDKTHTCPPCPAPPVAGPSVFL
FPPKPKDTLMISRTPEVTCVVVDVKHEDPEVKFNWYVDGVEVHNAKTKPREEEYNSTYRVVSVLTVLHQDWLNGKEYKCKVS
NKALPAPIEKTISKAKGQPREPQVYTLPPSREEMTKNQVSLTCDVSGFYPSDIAVEWESDGQPENNYKTTPPVLDSDGSFFL
YSKLTVDKSRWEQGDVFSCSVMHEALHNHYTQKSLSLSPGK

Chain 2 –1C11[PD-1]_H3.241_L3.92_scFv(GKPGS)4_Fc(216)_IgG1_C220S/PVA_/S267K/S364K/E357Q (SEQ ID NOS 44129-44138 and linker disclosed as SEQ ID NO: 39202)
EVQLVQSGPELKKPGESVKVSCKASGYTFTHYGINWVRQPPGQGLEWMGWINTYTGEPYYAPGFQERFVFSIDTSQDTAYLQ
INSLKAEDTAVYYCARDYYGSSPYWGQGTLVTVSS/GKPGSGKPGSGKPGSGKPGS/DIVMTQSPDSLAVSLGERVTINCKA
SQSIVHSNGNTYLEWYQQKPGQPPKLLIYKVSNRFTGVPDRFSGSGSGTDFTLTISSLQAEDVAVYYCFQGSHVPNTFGGGT
KVEIK/EPKSSDKTHTCPPCPAPPVAGPSVFLFPPKPKDTLMISRTPEVTCVVVDVKHEDPEVKFNWYVDGVEVHNAKTKPR
EEQYNSTYRVVSVLTVLHQDWLNGKEYKCKVSNKALPAPIEKTISKAKGQPREPQVYTLPPSREQMTKNQVKLTCLVKGFYP
SDIAVEWESNGQPENNYKTTPPVLDSDGSFFLYSKLTVDKSRWQQGNVFSCSVMHEALHNHYTQKSLSLSPGK

FIG. 49Q

Chain 3 – 7G8_L1.34 (SEQ ID NOS 44139-44143)
DIVLTQSPSSLSASVGDRVTITCRASQSVDYDGDSYMNWYQQKPGKPPKLLIYAASELESGIPARFSGSGSGTDFTL
TISSLQPEDFATYYCQQSNEDPFTFGSGTKLEIK/RTVAAPSVFIFPPSDEQLKSGTASVVCLLNNFYPREAKVQWK
VDNALQSGNSQESVTEQDSKDSTYSLSSTLTLSKADYEKHKVYACEVTHQGLSSPVTKSFNRGEC

XENCS525 PD-1 X LAG-3

> 2A11_H1.144_L2.142_[LAG-3]_Fab-1C11[PD-1]_H3.241_L3.92_scFv(GKPGS)4-IgG1_pI(-)_Isosteric_A_/PVA_/S267K/L368D/K370S-Fc(216)_IgG1_C220S/PVA_/S267K/S364K/E357Q

Chain 1 – 2A11_H1.144_ IgG1_pI(-)_Isosteric_A_/PVA_/S267K/L368D/K370S (SEQ ID NOS 44144-44148)
EVQLVQSGAEVKKPGATVKISCKASGFNIKDYFMHWVQQAPGKGLEWMGWIDPELGDTEYAPKFQGRVTITADTSTN
TAYMELSSLRSEDTAVYYCYARGVYQALDYWGQGTLVTVSS/ASTKGPSVFPLAPSSKSTSGGTAALGCLVKDYFPE
PVTVSWNSGALTSGVHTFPAVLQSSGLYSLSSVVTVPSSSLGTQTYICNVNHKPSDTKVDKKVEPKSCDKTHTCPPC
PAPPVAGPSVFLFPPKPKDTLMISRTPEVTCVVVDVKHEDPEVKFNWYVDGVEVHNAKTKPREEEYNSTYRVVSVLT
VLHQDWLNGKEYKCKVSNKALPAPIEKTISKAKGQPREPQVYTLPPSREEMTKNQVSLTCDVSGFYPSDIAVEWESD
GQPENNYKTTPPVLDSDGSFFLYSKLTVDKSRWEQGDVFSCSVMHEALHNHYTQKSLSLSPGK

Chain 2 – 1C11[PD-1]_H3.241_L3.92_scFv(GKPGS)4_Fc(216)_IgG1_C220S/PVA_/S267K/S364K/E357Q (SEQ ID NOS 44149-44158 and linker disclosed as SEQ ID NO: 39202)
EVQLVQSGPELKKPGESVKVSCKASGYTFTHYGINWVRQPPGQGLEWMGWINTYTGEPYYAPGFQERFVFSIDTSQD
TAYLQINSLKAEDTAVYYCARDYYGSSPYWGQGTLVTVSS/GKPGSGKPGSGKPGSGKPGS/DIVMTQSPDSLAVSL
GERVTINCKASQSIVHSNGNTYLEWYQQKPGQPPKLLIYKVSNRFTGVPDRFSGSGSGTDFTLTISSLQAEDVAVYY
CFQGSHVPNTFGGGTKVEIK/EPKSSDKTHTCPPCPAPPVAGPSVFLFPPKPKDTLMISRTPEVTCVVVDVKHEDPE
VKFNWYVDGVEVHNAKTKPREEQYNSTYRVVSVLTVLHQDWLNGKEYKCKVSNKALPAPIEKTISKAKGQPREPQVY
TLPPSREQMTKNQVKLTCLVKGFYPSDIAVEWESNGQPENNYKTTPPVLDSDGSFFLYSKLTVDKSRWQQGNVFSCS
VMHEALHNHYTQKSLSLSPGK

Chain 3 – 2A11_L2.142 (SEQ ID NOS 44159-44163)
DIQMTQSPAFLSVTPGEKVTITCQASQDIGNYLNWFQQKPGQTVKLLIYFTSYLHSGVPSRFSGSGSGTDYTFTISS
LEAEDAATYFCQQGNTLPYTFGGGTKVEIK/RTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSPVTKSFNRGEC

XENCS526 PD-1 X TIM-3

> 3H3_H1_L2.1_Fab-1C11[PD-1]_H3.241_L3.92-scFv(GKPGS)4-IgG1_pI(-)_Isosteric_A_/PVA_/S267K/L368D/K370S-Fc(216)_IgG1_C220S/PVA_/S267K/S364K/E357Q

Chain 1 – 3H3_H1_ IgG1_pI(-)_Isosteric_A_/PVA_/S267K/L368D/K370S (SEQ ID NOS 44164-44168)
QVTLKESGPVLVKPTETLTLTCTVSGFSLNGYGVNWVRQPPGKGLEWLAMIWGDGSTDYNSALKSRLTISKDNSKSQ
VVLTMTNMDPVDTATYYCARSYYTSDEDYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSDTKVDKKVEPKSCDKTHTCPPCP
APPVAGPSVFLFPPKPKDTLMISRTPEVTCVVVDVKHEDPEVKFNWYVDGVEVHNAKTKPREEEYNSTYRVVSVLTV
LHQDWLNGKEYKCKVSNKALPAPIEKTISKAKGQPREPQVYTLPPSREEMTKNQVSLTCDVSGFYPSDIAVEWESDG
QPENNYKTTPPVLDSDGSFFLYSKLTVDKSRWEQGDVFSCSVMHEALHNHYTQKSLSLSPGK

FIG. 49R

Chain 2 – 1C11[PD-1]_H3.241_L3.92_scFv(GKPGS)4_Fc(216)_IgG1_C220S/PVA_/S267K/S364K/E357Q (SEQ ID NOS 44169-44178 and linker disclosed as SEQ ID NO: 39202)
EVQLVQSGPELKKPGESVKVSCKASGYTFTHYGINWVRQPPGQGLEWMGWINTYTGEPYYAPGFQERFVFSIDTSQD
TAYLQINSLKAEDTAVYYCARDYYGSSPYWGQGTLVTVSS/GKPGSGKPGSGKPGSGKPGS/DIVMTQSPDSLAVSL
GERVTINCKASQSIVHSNGNTYLEWYQQKPGQPPKLLIYKVSNRFTGVPDRFSGSGSGTDFTLTISSLQAEDVAVYY
CFQGSHVPNTFGGGTKVEIK/EPKSSDKTHTCPPCPAPPVAGPSVFLFPPKPKDTLMISRTPEVTCVVVDVKHEDPE
VKFNWYVDGVEVHNAKTKPREEQYNSTYRVVSVLTVLHQDWLNGKEYKCKVSNKALPAPIEKTISKAKGQPREPQVY
TLPPSREQMTKNQVKLTCLVKGFYPSDIAVEWESNGQPENNYKTTPPVLDSDGSFFLYSKLTVDKSRWQQGNVFSCS
VMHEALHNHYTQKSLSLSPGK

Chain 3 – 3H3_L2.1 (SEQ ID NOS 44179-44183)
DIVMTQSPDSLAVSLGERATINCKSSQSLLNSRTRKNYLAWYQQKPGQSPKLLIYWASTRESGVPDRFTGSGSGTDF
TLTISSLQAEDVAVYYCKQSYSLRTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

XENCS527 PD-1 X BTLA

> 9C6_H1.1_L1_[BTLA]_Fab-1C11[PD-1]_H3.241_L3.92_scFv(GKPGS)4-IgG1_pI(-)_Isosteric_A_/PVA_/S267K/L368D/K370S-Fc(216)_IgG1_C220S/PVA_/S267K/S364K/E357Q

Chain 1 – 9C6_H1.1_IgG1_pI(-)_Isosteric_A_/PVA_/S267K/L368D/K370S (SEQ ID NOS 44184-44188)
QVQLKESGAEVKKPGASVKVSCKVSGFSLTGYGVNWVRQAPGQGLEWMGMIWIDGSTDYNSKFQGRVTMTKDNSKST
VYMELSSLRSEDTAVYYCARDRPDGRAMDYWGQGTMVTVSS/ASTKGPSVFPLAPSSKSTSGGTAALGCLVKDYFPE
PVTVSWNSGALTSGVHTFPAVLQSSGLYSLSSVVTVPSSSLGTQTYICNVNHKPSDTKVDKKVEPKSCDKTHTCPPC
PAPPVAGPSVFLFPPKPKDTLMISRTPEVTCVVVDVKHEDPEVKFNWYVDGVEVHNAKTKPREEEYNSTYRVVSVLT
VLHQDWLNGKEYKCKVSNKALPAPIEKTISKAKGQPREPQVYTLPPSREEMTKNQVSLTCDVSGFYPSDIAVEWESD
GQPENNYKTTPPVLDSDGSFFLYSKLTVDKSRWEQGDVFSCSVMHEALHNHYTQKSLSLSPGK

Chain 2 – 1C11[PD-1]_H3.241_L3.92_scFv(GKPGS)4_Fc(216)_IgG1_C220S/PVA_/S267K/S364K/E357Q (SEQ ID NOS 44189-44198 and linker disclosed as SEQ ID NO: 39202)
EVQLVQSGPELKKPGESVKVSCKASGYTFTHYGINWVRQPPGQGLEWMGWINTYTGEPYYAPGFQERFVFSIDTSQD
TAYLQINSLKAEDTAVYYCARDYYGSSPYWGQGTLVTVSS/GKPGSGKPGSGKPGSGKPGS/DIVMTQSPDSLAVSL
GERVTINCKASQSIVHSNGNTYLEWYQQKPGQPPKLLIYKVSNRFTGVPDRFSGSGSGTDFTLTISSLQAEDVAVYY
CFQGSHVPNTFGGGTKVEIK/EPKSSDKTHTCPPCPAPPVAGPSVFLFPPKPKDTLMISRTPEVTCVVVDVKHEDPE
VKFNWYVDGVEVHNAKTKPREEQYNSTYRVVSVLTVLHQDWLNGKEYKCKVSNKALPAPIEKTISKAKGQPREPQVY
TLPPSREQMTKNQVKLTCLVKGFYPSDIAVEWESNGQPENNYKTTPPVLDSDGSFFLYSKLTVDKSRWQQGNVFSCS
VMHEALHNHYTQKSLSLSPGK

Chain 3 – 9C6_L1 (SEQ ID NOS 44199-44203)
SIVMTQSPDSLAVSLGERATINCKASQSVSNDVAWYQQKPGQSPKLLIYYASNRYTGVPDRFTGSGYGTDFTLTISS
LQAEDVAVYFCQQDYSSPTFGGGTKLEIK/RTVAAPSVFIFPPSDEQLKSGTASVVCLLNNFYPREAKVQWKVDNAL
QSGNSQESVTEQDSKDSTYSLSSTLTLSKADYEKHKVYACEVTHQGLSSPVTKSFNRGEC

FIG. 49S

```
XENCS528 PD-1 X ICOS (Xtend)
```

> [ICOS]_H0L0_Fab-1C11[PD-1]_H3.234_L3.144-scFv(GKPGS)4-IgG1_pI(-)_Isosteric_A_/PVA_/S267K/L368D/K370S/M428L/N434S-Fc(216)_IgG1_C220S/PVA_/S267K/S364K/E357Q/M428L/N434S

Chain 1 – [ICOS]_H0_ IgG1_pI(-)_Isosteric_A_/PVA_/S267K/L368D/K370S/M428L/N434S (SEQ ID NOS 44204-44208)

QVQLVQSGAEVKKPGASVKVSCKASGYTFTGYYMHWVRQAPGQGLEWMGWINPHSGGTNYAQKFQGRVTMTRDTSIS
TAYMELSRLRSDDTAVYYCARTYYYDSSGYYHDAFDIWGQGTMVTVSS/ASTKGPSVFPLAPSSKSTSGGTAALGCLVKDYFP
EPVTVSWNSGALTSGVHTFPAVLQSSGLYSLSSVVTVPSSSLGTQTYICNVNHKPSDTKVDKKVEPKSCDKTHTCPPCPAPPVAGPSVFLFPP
KPKDTLMISRTPEVTCVVVDVKHEDPEVKFNWYVDGVEVHNAKTKPREEEYNSTYRVVSVLTVLHQDWLNGKEYKCKVSNKALPAPIEKTISK
AKGQPREPQVYTLPPSREEMTKNQVSLTCDVSGFYPSDIAVEWESDGQPENNYKTTPPVLDSDGSFFLYSKLTVDKSRWQEGDVFSCSVLHEA
LHSHYTQKSLSLSPGK

Chain 2 – 1C11[PD-1]_H3.234_L3.144_scFv(GKPGS)4_Fc(216)_IgG1_C220S/PVA_/S267K/S364K/E357Q/M428L/N434S (SEQ ID NOS 44209-44218 and linker disclosed as SEQ ID NO: 39202)

EVQLVQSGSELKKPGESVKVSCKASGYTFTHYGINWVRQPPGQGLEWMGWINTYTGEPYYAPGFQERFVFSLDTSQD
TAYLQINSLKAEDTAVYYCARDYYGSSPYWGQGTLVTVSS/GKPGSGKPGSGKPGSGKPGS/DIVMTQSPDSLAVSL
GERVTINCKASQSIVHSNGNTYLEWYQQKPGQPPKLLIYKVSNRFSGVPDRFSGSGSGTDFTLTISSVEAEDAATYY
CFQGSHVPNTFGQGTKVEIK/EPKSSDKTHTCPPCPAPPVAGPSVFLFPPKPKDTLMISRTPEVTCVVVDVKHEDPE
VKFNWYVDGVEVHNAKTKPREEQYNSTYRVVSVLTVLHQDWLNGKEYKCKVSNKALPAPIEKTISKAKGQPREPQVY
TLPPSREQMTKNQVKLTCLVKGFYPSDIAVEWESNGQPENNYKTTPPVLDSDGSFFLYSKLTVDKSRWQQGNVFSCS
VLHEALHSHYTQKSLSLSPGK

Chain 3 – [ICOS]_L0 (SEQ ID NOS 44219-44223)

DIQMTQSPSSVSASVGDRVTITCRASQGISRLLAWYQQKPGKAPKLLIYVASSLQSGVPSRFSGSGSGTDFTLTISS
LQPEDFATYYCQQANSFPWTFGQGTKVEIK/RTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSPVTKSFNRGEC

```
XENCS529 PD-1 X ICOS (Xtend)
```

> [ICOS]_H0.66_L0_Fab-1C11[PD-1]_H3.234_L3.144-scFv(GKPGS)4-IgG1_pI(-)_Isosteric_A_/PVA_/S267K/L368D/K370S/M428L/N434S-Fc(216)_IgG1_C220S/PVA_/S267K/S364K/E357Q/M428L/N434S

Chain 1 – [ICOS]_H0.66_ IgG1_pI(-)_Isosteric_A_/PVA_/S267K/L368D/K370S/M428L/N434S (SEQ ID NOS 44224-44228)

QVQLVQSGAEVKKPGASVKVSCKASGYTFTGYYMHWVRQAPGQGLEWMGWINPHSGETIYAQKFQGRVTMTRDTSIS
TAYMELSSLRSEDTAVYYCARTYYYDTSGYYHDAFDVWGQGTMVTVSS/ASTKGPSVFPLAPSSKSTSGGTAALGCL
VKDYFPEPVTVSWNSGALTSGVHTFPAVLQSSGLYSLSSVVTVPSSSLGTQTYICNVNHKPSDTKVDKKVEPKSCDK
THTCPPCPAPPVAGPSVFLFPPKPKDTLMISRTPEVTCVVVDVKHEDPEVKFNWYVDGVEVHNAKTKPREEEYNSTY
RVVSVLTVLHQDWLNGKEYKCKVSNKALPAPIEKTISKAKGQPREPQVYTLPPSREEMTKNQVSLTCDVSGFYPSDI
AVEWESDGQPENNYKTTPPVLDSDGSFFLYSKLTVDKSRWQEGDVFSCSVLHEALHSHYTQKSLSLSPGK

FIG. 49T

Chain 2 – 1C11[PD-1]_H3.234_L3.144_scFv(GKPGS)4_Fc(216)_IgG1_C220S/PVA_/S267K/S364K/E357Q/M428L/N434S (SEQ ID NOS 44229-44238 and linker disclosed as SEQ ID NO: 39202)

EVQLVQSGSELKKPGESVKVSCKASGYTFTHYGINWVRQPPGQGLEWMGWINTYTGEPYYAPGFQERFVFSLDTSQD
TAYLQINSLKAEDTAVYYCARDYYGSSPYWGQGTLVTVSS/GKPGSGKPGSGKPGSGKPGS/DIVMTQSPDSLAVSL
GERVTINCKASQSIVHSNGNTYLEWYQQKPGQPPKLLIYKVSNRFSGVPDRFSGSGSGTDFTLTISSVEAEDAATYY
CFQGSHVPNTFGQGTKVEIK/EPKSSDKTHTCPPCPAPPVAGPSVFLFPPKPKDTLMISRTPEVTCVVVDVKHEDPE
VKFNWYVDGVEVHNAKTKPREEQYNSTYRVVSVLTVLHQDWLNGKEYKCKVSNKALPAPIEKTISKAKGQPREPQVY
TLPPSREQMTKNQVKLTCLVKGFYPSDIAVEWESNGQPENNYKTTPPVLDSDGSFFLYSKLTVDKSRWQQGNVFSCS
VLHEALHSHYTQKSLSLSPGK

Chain 3 – [ICOS]_L0 (SEQ ID NOS 44239-44243)

DIQMTQSPSSVSASVGDRVTITCRASQGISRLLAWYQQKPGKAPKLLIYVASSLQSGVPSRFSGSGSGTDFTLTISS
LQPEDFATYYCQQANSFPWTFGQGTKVEIK/RTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSPVTKSFNRGEC

XENCS530 PD-1 X CTLA-4 (Xtend)

>[CTLA-4]_H3_L0.22_Fab-1C11[PD-1]_H3.234_L3.144_scFv(GKPGS)4-IgG1_pI(-)_Isosteric_A_/PVA_/S267K/L368D/K370S/M428L/N434S-Fc(216)_IgG1_C220S/PVA_/S267K/S364K/E357Q/M428L/N434S

Chain 1 - [CTLA-4]_H3_IgG1_pI(-)_Isosteric_A_/PVA_/S267K/L368D/K370S/M428L/N434S (SEQ ID NOS 44244-44248)

EVQLVESGGGLVKPGGSLRLSCAASGFTFSSYTMHWVRQAPGKGLEWVSFISYDGNNKYYADSVKGRFTISRDNAKN
SLYLQMNSLRAEDTAVYYCARTGWLGPFDYWGQGTLVTVSS/ASTKGPSVFPLAPSSKSTSGGTAALGCLVKDYFPE
PVTVSWNSGALTSGVHTFPAVLQSSGLYSLSSVVTVPSSSLGTQTYICNVNHKPSDTKVDKKVEPKSCDKTHTCPPC
PAPPVAGPSVFLFPPKPKDTLMISRTPEVTCVVVDVKHEDPEVKFNWYVDGVEVHNAKTKPREEEYNSTYRVVSVLT
VLHQDWLNGKEYKCKVSNKALPAPIEKTISKAKGQPREPQVYTLPPSREEMTKNQVSLTCDVSGFYPSDIAVEWESD
GQPENNYKTTPPVLDSDGSFFLYSKLTVDKSRWEQGDVFSCSVLHEALHSHYTQKSLSLSPGK

Chain 2 - 1C11[PD-1]_H3.234_L3.144_scFv(GKPGS)4_Fc(216)_IgG1_C220S/PVA_/S267K/S364K/E357Q/M428L/N434S (SEQ ID NOS 44249-44258 and linker disclosed as SEQ ID NO: 39202)

EVQLVQSGSELKKPGESVKVSCKASGYTFTHYGINWVRQPPGQGLEWMGWINTYTGEPYYAPGFQERFVFSLDTSQD
TAYLQINSLKAEDTAVYYCARDYYGSSPYWGQGTLVTVSS/GKPGSGKPGSGKPGSGKPGS/DIVMTQSPDSLAVSL
GERVTINCKASQSIVHSNGNTYLEWYQQKPGQPPKLLIYKVSNRFSGVPDRFSGSGSGTDFTLTISSVEAEDAATYY
CFQGSHVPNTFGQGTKVEIK/EPKSSDKTHTCPPCPAPPVAGPSVFLFPPKPKDTLMISRTPEVTCVVVDVKHEDPE
VKFNWYVDGVEVHNAKTKPREEQYNSTYRVVSVLTVLHQDWLNGKEYKCKVSNKALPAPIEKTISKAKGQPREPQVY
TLPPSREQMTKNQVKLTCLVKGFYPSDIAVEWESNGQPENNYKTTPPVLDSDGSFFLYSKLTVDKSRWQQGNVFSCS
VLHEALHSHYTQKSLSLSPGK

Chain 3 - [CTLA-4]_L0.22 (SEQ ID NOS 44259-44263)

EIVLTQSPGTLSLSPGERATLSCRASQSVSSSYLAWYQQKPGQAPRLLIYGAFSRATGIPDRFSGSGSGTDFTLTIS
RLEPEDFAVYYCQQYGSSPWTFGQGTKVEIK/RTVAAPSVFIFPPSDEQLKSGTASVVCLLNNFYPREAKVQWKVDN
ALQSGNSQESVTEQDSKDSTYSLSSTLTLSKADYEKHKVYACEVTHQGLSSPVTKSFNRGEC

FIG. 49U

XENCS531 PD-1 X LAG-3 (Xtend)

<u>> 7G8_H3.30_L1.34_[LAG-3]_Fab-1C11[PD-1]_H3.234_L3.144_scFv(GKPGS)4-IgG1_pI(-
)_Isosteric_A_/PVA_/S267K/L368D/K370S/M428L/N434S-
Fc(216)_IgG1_C220S/PVA_/S267K/S364K/E357Q/M428L/N434S</u>

Chain 1 – 7G8_H3.30_ IgG1_pI(-)_Isosteric_A_/PVA_/S267K/L368D/K370S/M428L/N434S (SEQ ID NOS 44264-44268)
EVQLVESGGGLVQPGGSLRLSCAASGFTFD<u>D</u>A<u>WMS</u>WVRQAPGKGLEWVA<u>EISTKANNHATYYAESVKG</u>RFTISRDDS
KSSVYLQMNSLRAEDTAVYYCTR<u>LATWDWYFDV</u>WGQGTTVTVSS/ASTKGPSVFPLAPSSKSTSGGTAALGCLVKDY
FPEPVTVSWNSGALTSGVHTFPAVLQSSGLYSLSSVVTVPSSSLGTQTYICNVNHKPSDTKVDKKVEPKSCDKTHTC
PPCPAPPVAGPSVFLFPPKPKDTLMISRTPEVTCVVVDVKHEDPEVKFNWYVDGVEVHNAKTKPREEEYNSTYRVVS
VLTVLHQDWLNGKEYKCKVSNKALPAPIEKTISKAKGQPREPQVYTLPPSREEMTKNQVSLTCDVSGFYPSDIAVEW
ESDGQPENNYKTTPPVLDSDGSFFLYSKLTVDKSRWEQGDVFSCSVLHEALHSHYTQKSLSLSPGK

**Chain 2 –1C11[PD-
1]_H3.234_L3.144_scFv(GKPGS)4_Fc(216)_IgG1_C220S/PVA_/S267K/S364K/E357Q/M428L/N434S** (SEQ ID NOS
44269-44278 and linker disclosed as SEQ ID NO: 39202)
EVQLVQSGSELKKPGESVKVSCKASGYTFT<u>HYGIN</u>WVRQPPGQGLEWMG<u>WINTYTGEPYYAPGFQE</u>RFVFSLDTSQD
TAYLQINSLKAEDTAVYYCARD<u>YYGSSPY</u>WGQGTLVTVSS/<u>GKPGSGKPGSGKPGSGKPGS</u>/DIVMTQSPDSLAVSL
GERVTINC<u>KASQSIVHSNGNTYLE</u>WYQQKPGQPPKLLIY<u>KVSNRFS</u>GVPDRFSGSGSGTDFTLTISSVEAEDAATYY
C<u>FQGSHVPNT</u>FGQGTKVEIK/EPKSSDKTHTCPPCPAPPVAGPSVFLFPPKPKDTLMISRTPEVTCVVVDVKHEDPE
VKFNWYVDGVEVHNAKTKPREEQYNSTYRVVSVLTVLHQDWLNGKEYKCKVSNKALPAPIEKTISKAKGQPREPQVY
TLPPSREQMTKNQVKLTCLVKGFYPSDIAVEWESNGQPENNYKTTPPVLDSDGSFFLYSKLTVDKSRWQQGNVFSCS
VLHEALHSHYTQKSLSLSPGK

Chain 3 – 7G8_L1.34 (SEQ ID NOS 44279-44283)
DIVLTQSPSSLSASVGDRVTITC<u>RASQSVDYDGDSYMN</u>WYQQKPGKPPKLLIY<u>AASELES</u>GIPARFSGSGSGTDFTL
TISSLQPEDFATYYC<u>QQSNEDPFT</u>FGSGTKLEIK/RTVAAPSVFIFPPSDEQLKSGTASVVCLLNNFYPREAKVQWK
VDNALQSGNSQESVTEQDSKDSTYSLSSTLTLSKADYEKHKVYACEVTHQGLSSPVTKSFNRGEC XENCS532 PD-1 X LAG-3 (Xtend)

<u>> 2A11_H1.144_L2.142_[LAG-3]_Fab-1C11[PD-1]_H3.234_L3.144_scFv(GKPGS)4-IgG1_pI(-
)_Isosteric_A_/PVA_/S267K/L368D/K370S/M428L/N434S-
Fc(216)_IgG1_C220S/PVA_/S267K/S364K/E357Q/M428L/N434S</u>

Chain 1 – 2A11_H1.144_ IgG1_pI(-)_Isosteric_A_/PVA_/S267K/L368D/K370S/M428L/N434S (SEQ ID NOS 44284-44288)
EVQLVQSGAEVKKPGATVKISCKASGFNIK<u>DYFMH</u>WVQQAPGKGLEWMG<u>WIDPELGDTEYAPKFQG</u>RVTITADTSTN
TAYMELSSLRSEDTAVYYCY<u>ARGVYQALDY</u>WGQGTLVTVSS/ASTKGPSVFPLAPSSKSTSGGTAALGCLVKDYFPE
PVTVSWNSGALTSGVHTFPAVLQSSGLYSLSSVVTVPSSSLGTQTYICNVNHKPSDTKVDKKVEPKSCDKTHTCPPC
PAPPVAGPSVFLFPPKPKDTLMISRTPEVTCVVVDVKHEDPEVKFNWYVDGVEVHNAKTKPREEEYNSTYRVVSVLT
VLHQDWLNGKEYKCKVSNKALPAPIEKTISKAKGQPREPQVYTLPPSREEMTKNQVSLTCDVSGFYPSDIAVEWESD
GQPENNYKTTPPVLDSDGSFFLYSKLTVDKSRWEQGDVFSCSVLHEALHSHYTQKSLSLSPGK

FIG. 49V

Chain 2 – 1C11[PD-1]_H3.234_L3.144_scFv(GKPGS)4_Fc(216)_IgG1_C220S/PVA_/S267K/S364K/E357Q/M428L/N434S (SEQ ID NOS 44289-44298 and linker disclosed as SEQ ID NO: 39202)EVQLVQSGSELKKPGESVKVSCKASGYTFTHYGINWVRQPPGQGLEWMGWINTYTGEPYYAPGFQERFVFSLD
TSQDTAYLQINSLKAEDTAVYYCARDYYGSSPYWGQGTLVTVSS/GKPGSGKPGSGKPGSGKPGS/DIVMTQSPDSL
AVSLGERVTINCKASQSIVHSNGNTYLEWYQQKPGQPPKLLIYKVSNRFSGVPDRFSGSGSGTDFTLTISSVEAEDA
ATYYCFQGSHVPNTFGQGTKVEIK/EPKSSDKTHTCPPCPAPPVAGPSVFLFPPKPKDTLMISRTPEVTCVVVDVKH
EDPEVKFNWYVDGVEVHNAKTKPREEQYNSTYRVVSVLTVLHQDWLNGKEYKCKVSNKALPAPIEKTISKAKGQPRE
PQVYTLPPSREQMTKNQVKLTCLVKGFYPSDIAVEWESNGQPENNYKTTPPVLDSDGSFFLYSKLTVDKSRWQQGNV
FSCSVLHEALHSHYTQKSLSLSPGK

Chain 3 – 2A11_L2.142 (SEQ ID NOS 44299-44303)
DIQMTQSPAFLSVTPGEKVTITCQASQDIGNYLNWFQQKPGQTVKLLIYFTSYLHSGVPSRFSGSGSGTDYTFTISS
LEAEDAATYFCQQGNTLPYTFGGGTKVEIK/RTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSPVTKSFNRGEC XENCS533 PD-1 X TIM-3 (Xtend)

> 3H3_H1_L2.1_Fab-1C11[PD-1]_H3.234_L3.144-scFv(GKPGS)4-IgG1_pI(-)_Isosteric_A_/PVA_/S267K/L368D/K370S/M428L/N434S-Fc(216)_IgG1_C220S/PVA_/S267K/S364K/E357Q/M428L/N434S

Chain 1 – 3H3_H1_IgG1_pI(-)_Isosteric_A_/PVA_/S267K/L368D/K370S/M428L/N434S (SEQ ID NOS 44304-44308)
QVTLKESGPVLVKPTETLTLTCTVSGFSLNGYGVNWVRQPPGKGLEWLAMIWGDGSTDYNSALKSRLTISKDNSKSQ
VVLTMTNMDPVDTATYYCARSYYTSDEDYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSDTKVDKKVEPKSCDKTHTCPPCP
APPVAGPSVFLFPPKPKDTLMISRTPEVTCVVVDVKHEDPEVKFNWYVDGVEVHNAKTKPREEEYNSTYRVVSVLTV
LHQDWLNGKEYKCKVSNKALPAPIEKTISKAKGQPREPQVYTLPPSREEMTKNQVSLTCDVSGFYPSDIAVEWESDG
QPENNYKTTPPVLDSDGSFFLYSKLTVDKSRWEQGDVFSCSVLHEALHSHYTQKSLSLSPGK

Chain 2 – 1C11[PD-1]_H3.234_L3.144_scFv(GKPGS)4_Fc(216)_IgG1_C220S/PVA_/S267K/S364K/E357Q/M428L/N434S (SEQ ID NOS 44309-44318 and linker disclosed as SEQ ID NO: 39202)
EVQLVQSGSELKKPGESVKVSCKASGYTFTHYGINWVRQPPGQGLEWMGWINTYTGEPYYAPGFQERFVFSLDTSQD
TAYLQINSLKAEDTAVYYCARDYYGSSPYWGQGTLVTVSS/GKPGSGKPGSGKPGSGKPGS/DIVMTQSPDSLAVSL
GERVTINCKASQSIVHSNGNTYLEWYQQKPGQPPKLLIYKVSNRFSGVPDRFSGSGSGTDFTLTISSVEAEDAATYY
CFQGSHVPNTFGQGTKVEIK/EPKSSDKTHTCPPCPAPPVAGPSVFLFPPKPKDTLMISRTPEVTCVVVDVKHEDPE
VKFNWYVDGVEVHNAKTKPREEQYNSTYRVVSVLTVLHQDWLNGKEYKCKVSNKALPAPIEKTISKAKGQPREPQVY
TLPPSREQMTKNQVKLTCLVKGFYPSDIAVEWESNGQPENNYKTTPPVLDSDGSFFLYSKLTVDKSRWQQGNVFSCS
VLHEALHSHYTQKSLSLSPGK

Chain 3 – 3H3_L2.1 (SEQ ID NOS 44319-44323)
DIVMTQSPDSLAVSLGERATINCKSSQSLLNSRTRKNYLAWYQQKPGQSPKLLIYWASTRESGVPDRFTGSGSGTDF
TLTISSLQAEDVAVYYCKQSYSLRTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

FIG. 49W

```
XENCS534 PD-1 X BTLA (Xtend)
```

**> 9C6_H1.1_L1_[BTLA]_Fab-1C11[PD-1]_H3.234_L3.144_scFv(GKPGS)4-IgG1_pI(-
)_Isosteric_A_/PVA_/S267K/L368D/K370S/M428L/N434S-
Fc(216)_IgG1_C220S/PVA_/S267K/S364K/E357Q/M428L/N434S**

Chain 1 – 9C6_H1.1_ IgG1_pI(-)_Isosteric_A_/PVA_/S267K/L368D/K370S/M428L/N434S (SEQ ID NOS 44324-44328)
QVQLKESGAEVKKPGASVKVSCKVSGFSLT<u>GYGVN</u>WVRQAPGQGLEWMG<u>MIWIDGSTDYNSKFQ</u>GRVTMTKDNSKST
VYMELSSLRSEDTAVYYCARD<u>RPDGRAMDY</u>WGQGTMVTVSS/ASTKGPSVFPLAPSSKSTSGGTAALGCLVKDYFPE
PVTVSWNSGALTSGVHTFPAVLQSSGLYSLSSVVTVPSSSLGTQTYICNVNHKPSDTKVDKKVEPKSCDKTHTCPPC
PAPPVAGPSVFLFPPKPKDTLMISRTPEVTCVVVDVKHEDPEVKFNWYVDGVEVHNAKTKPREEEYNSTYRVVSVLT
VLHQDWLNGKEYKCKVSNKALPAPIEKTISKAKGQPREPQVYTLPPSREEMTKNQVSLTCDVSGFYPSDIAVEWESD
GQPENNYKTTPPVLDSDGSFFLYSKLTVDKSRWEQGDVFSCSVLHEALHSHYTQKSLSLSPGK

**Chain 2 – 1C11[PD-
1]_H3.234_L3.144_scFv(GKPGS)4_Fc(216)_IgG1_C220S/PVA_/S267K/S364K/E357Q/M428L/N434S** (SEQ ID NOS 44329-44338 and linker disclosed as SEQ ID NO: 39202)
EVQLVQSGSELKKPGESVKVSCKASGYTFT<u>HYGIN</u>WVRQPPGQGLEWMG<u>WINTYTGEPYYAPGFQE</u>RFVFSLDTSQD
TAYLQINSLKAEDTAVYYCARD<u>YYGSSPYW</u>GQGTLVTVSS/GKPGSGKPGSGKPGSGKPGS/DIVMTQSPDSLAVSL
GERVTINC<u>KASQSIVHSNGNTYLE</u>WYQQKPGQPPKLLIY<u>KVSNRFS</u>GVPDRFSGSGSGTDFTLTISSVEAEDAATYY
C<u>FQGSHVPNTF</u>GQGTKVEIK/EPKSSDKTHTCPPCPAPPVAGPSVFLFPPKPKDTLMISRTPEVTCVVVDVKHEDPE
VKFNWYVDGVEVHNAKTKPREEQYNSTYRVVSVLTVLHQDWLNGKEYKCKVSNKALPAPIEKTISKAKGQPREPQVY
TLPPSREQMTKNQVKLTCLVKGFYPSDIAVEWESNGQPENNYKTTPPVLDSDGSFFLYSKLTVDKSRWQQGNVFSCS
VLHEALHSHYTQKSLSLSPGK

Chain 3 – 9C6_L1 (SEQ ID NOS 44339-44343)
SIVMTQSPDSLAVSLGERATINC<u>KASQSVSNDVAW</u>YQQKPGQSPKLLIY<u>YASNRYT</u>GVPDRFTGSGYGTDFTLTISS
LQAEDVAVYFC<u>QQDYSSPTF</u>GGGTKLEIK/RTVAAPSVFIFPPSDEQLKSGTASVVCLLNNFYPREAKVQWKVDNAL
QSGNSQESVTEQDSKDSTYSLSSTLTLSKADYEKHKVYACEVTHQGLSSPVTKSFNRGEC

```
XENCS535 PD-1 X ICOS (Xtend)
```

**> [ICOS]_H0L0_Fab-1C11[PD-1]_H3.240_L3.148-scFv(GKPGS)4-IgG1_pI(-
)_Isosteric_A_/PVA_/S267K/L368D/K370S/M428L/N434S-
Fc(216)_IgG1_C220S/PVA_/S267K/S364K/E357Q/M428L/N434S**

Chain 1 – [ICOS]_H0_ IgG1_pI(-)_Isosteric_A_/PVA_/S267K/L368D/K370S/M428L/N434S (SEQ ID NOS 44344-44348)
QVQLVQSGAEVKKPGASVKVSCKASGYTFT<u>GYYMH</u>WVRQAPGQGLEWMG<u>WINPHSGGTNYAQKFQ</u>GRVTMTRDTSIS
TAYMELSRLRSDDTAVYYCART<u>YYYDSSGYYHDAFDI</u>WGQGTMVTVSS/ASTKGPSVFPLAPSSKSTSGGTAALGCLVKDYFP
EPVTVSWNSGALTSGVHTFPAVLQSSGLYSLSSVVTVPSSSLGTQTYICNVNHKPSDTKVDKKVEPKSCDKTHTCPPCPAPPVAGPSVFLFPP
KPKDTLMISRTPEVTCVVVDVKHEDPEVKFNWYVDGVEVHNAKTKPREEEYNSTYRVVSVLTVLHQDWLNGKEYKCKVSNKALPAPIEKTISK
AKGQPREPQVYTLPPSREEMTKNQVSLTCDVSGFYPSDIAVEWESDGQPENNYKTTPPVLDSDGSFFLYSKLTVDKSRWEQGDVFSCSVLHEA
LHSHYTQKSLSLSPGK

FIG. 49X

Chain 2 – 1C11[PD-1]_H3.240_L3.148_scFv(GKPGS)4_Fc(216)_IgG1_C220S/PVA_/S267K/S364K/E357Q/M428L/N434S (SEQ ID NOS 44349-44358 and linker disclosed as SEQ ID NO: 39202)
QVQLVQSGPELKKPGESVKVSCKASGYTFTHYGINWVRQPPGQGLEWMGWINTYTGEPYYAPGFQERFVFSIDTSQD
TAYLQINSLKAEDTAVYYCARDYYGSSPYWGQGTLVTVSS/GKPGSGKPGSGKPGSGKPGS/DVLMTQSPDSLAVSL
GERATINCKSSQSIVHSNGNTYLEWYQQKPGQSPKLLIYKVSNRFSGVPDRFSGSGSGTDFTLTISSLQAEDVAVYY
CFQGSHVPNTFGGGTKVEIK/EPKSSDKTHTCPPCPAPPVAGPSVFLFPPKPKDTLMISRTPEVTCVVVDVKHEDPE
VKFNWYVDGVEVHNAKTKPREEQYNSTYRVVSVLTVLHQDWLNGKEYKCKVSNKALPAPIEKTISKAKGQPREPQVY
TLPPSREQMTKNQVKLTCLVKGFYPSDIAVEWESNGQPENNYKTTPPVLDSDGSFFLYSKLTVDKSRWQQGNVFSCS
VLHEALHSHYTQKSLSLSPGK

Chain 3 – [ICOS]_L0 (SEQ ID NOS 44359-44363)
DIQMTQSPSSVSASVGDRVTITCRASQGISRLLAWYQQKPGKAPKLLIYVASSLQSGVPSRFSGSGSGTDFTLTISS
LQPEDFATYYCQQANSFPWTFGQGTKVEIK/RTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSPVTKSFNRGEC

```
XENCS536 PD-1 X ICOS (Xtend)
```

> [ICOS]_H0.66_L0_Fab-1C11[PD-1]_H3.240_L3.148-scFv(GKPGS)4-IgG1_pI(-)_Isosteric_A_/PVA_/S267K/L368D/K370S/M428L/N434S-Fc(216)_IgG1_C220S/PVA_/S267K/S364K/E357Q/M428L/N434S

Chain 1 – [ICOS]_H0.66_IgG1_pI(-)_Isosteric_A_/PVA_/S267K/L368D/K370S/M428L/N434S (SEQ ID NOS 44364-44368)
QVQLVQSGAEVKKPGASVKVSCKASGYTFTGYYMHWVRQAPGQGLEWMGWINPHSGETIYAQKFQGRVTMTRDTSIS
TAYMELSSLRSEDTAVYYCARTYYYDTSGYYHDAFDVWGQGTMVTVSS/ASTKGPSVFPLAPSSKSTSGGTAALGCL
VKDYFPEPVTVSWNSGALTSGVHTFPAVLQSSGLYSLSSVVTVPSSSLGTQTYICNVNHKPSDTKVDKKVEPKSCDK
THTCPPCPAPPVAGPSVFLFPPKPKDTLMISRTPEVTCVVVDVKHEDPEVKFNWYVDGVEVHNAKTKPREEEYNSTY
RVVSVLTVLHQDWLNGKEYKCKVSNKALPAPIEKTISKAKGQPREPQVYTLPPSREEMTKNQVSLTCDVSGFYPSDI
AVEWESDGQPENNYKTTPPVLDSDGSFFLYSKLTVDKSRWEQGDVFSCSVLHEALHSHYTQKSLSLSPGK

Chain 2 – 1C11[PD-1]_H3.240_L3.148_scFv(GKPGS)4_Fc(216)_IgG1_C220S/PVA_/S267K/S364K/E357Q/M428L/N434S (SEQ ID NOS 44369-44378 and linker disclosed as SEQ ID NO: 39202)
QVQLVQSGPELKKPGESVKVSCKASGYTFTHYGINWVRQPPGQGLEWMGWINTYTGEPYYAPGFQERFVFSIDTSQD
TAYLQINSLKAEDTAVYYCARDYYGSSPYWGQGTLVTVSS/GKPGSGKPGSGKPGSGKPGS/DVLMTQSPDSLAVSL
GERATINCKSSQSIVHSNGNTYLEWYQQKPGQSPKLLIYKVSNRFSGVPDRFSGSGSGTDFTLTISSLQAEDVAVYY
CFQGSHVPNTFGGGTKVEIK/EPKSSDKTHTCPPCPAPPVAGPSVFLFPPKPKDTLMISRTPEVTCVVVDVKHEDPE
VKFNWYVDGVEVHNAKTKPREEQYNSTYRVVSVLTVLHQDWLNGKEYKCKVSNKALPAPIEKTISKAKGQPREPQVY
TLPPSREQMTKNQVKLTCLVKGFYPSDIAVEWESNGQPENNYKTTPPVLDSDGSFFLYSKLTVDKSRWQQGNVFSCS
VLHEALHSHYTQKSLSLSPGK

Chain 3 – [ICOS]_L0 (SEQ ID NOS 44379-44383)
DIQMTQSPSSVSASVGDRVTITCRASQGISRLLAWYQQKPGKAPKLLIYVASSLQSGVPSRFSGSGSGTDFTLTISS
LQPEDFATYYCQQANSFPWTFGQGTKVEIK/RTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSPVTKSFNRGEC

FIG. 49Y

```
XENCS537 PD-1 X CTLA-4
```

> [CTLA-4]_H3_L0.22_Fab-1C11[PD-1]_H3.240_L3.148_scFv(GKPGS)4-IgG1_pI(-
)_Isosteric_A_/PVA_/S267K/L368D/K370S/M428L/N434S-
Fc(216)_IgG1_C220S/PVA_/S267K/S364K/E357Q/M428L/N434S

Chain 1 - [CTLA-4]_H3_ IgG1_pI(-)_Isosteric_A_/PVA_/S267K/L368D/K370S/M428L/N434S (SEQ ID NOS 44384-44388)

EVQLVESGGGLVKPGGSLRLSCAASGFTFSSYTMHWVRQAPGKGLEWVSFISYDGNNKYYADSVKGRFTISRDNAKN
SLYLQMNSLRAEDTAVYYCARTGWLGPFDYWGQGTLVTVSS/ASTKGPSVFPLAPSSKSTSGGTAALGCLVKDYFPE
PVTVSWNSGALTSGVHTFPAVLQSSGLYSLSSVVTVPSSSLGTQTYICNVNHKPSDTKVDKKVEPKSCDKTHTCPPC
PAPPPVAGPSVFLFPPKPKDTLMISRTPEVTCVVVDVKHEDPEVKFNWYVDGVEVHNAKTKPREEEYNSTYRVVSVLT
VLHQDWLNGKEYKCKVSNKALPAPIEKTISKAKGQPREPQVYTLPPSREEMTKNQVSLTCDVSGFYPSDIAVEWESD
GQPENNYKTTPPVLDSDGSFFLYSKLTVDKSRWEQGDVFSCSVLHEALHSHYTQKSLSLSPGK

Chain 2 - 1C11[PD-1]_H3.240_L3.148_scFv(GKPGS)4_Fc(216)_IgG1_C220S/PVA_/S267K/S364K/E357Q/M428L/N434S (SEQ ID NOS 44389-44398 and linker disclosed as SEQ ID NO: 39202)

QVQLVQSGPELKKPGESVKVSCKASGYTFTHYGINWVRQPPGQGLEWMGWINTYTGEPYYAPGFQERFVFSIDTSQD
TAYLQINSLKAEDTAVYYCARDYYGSSPYWGQGTLVTVSS/GKPGSGKPGSGKPGSGKPGS/DVLMTQSPDSLAVSL
GERATINCKSSQSIVHSNGNTYLEWYQQKPGQSPKLLIYKVSNRFSGVPDRFSGSGSGTDFTLTISSLQAEDVAVYY
CFQGSHVPNTFGGGTKVEIK/EPKSSDKTHTCPPCPAPPVAGPSVFLFPPKPKDTLMISRTPEVTCVVVDVKHEDPE
VKFNWYVDGVEVHNAKTKPREEQYNSTYRVVSVLTVLHQDWLNGKEYKCKVSNKALPAPIEKTISKAKGQPREPQVY
TLPPSREQMTKNQVKLTCLVKGFYPSDIAVEWESNGQPENNYKTTPPVLDSDGSFFLYSKLTVDKSRWQQGNVFSCS
VLHEALHSHYTQKSLSLSPGK

Chain 3 - [CTLA-4]_L0.22 (SEQ ID NOS 44399-44403)
EIVLTQSPGTLSLSPGERATLSCRASQSVSSSYLAWYQQKPGQAPRLLIYGAFSRATGIPDRFSGSGSGTDFTLTIS
RLEPEDFAVYYCQQYGSSPWTFGQGTKVEIK/RTVAAPSVFIFPPSDEQLKSGTASVVCLLNNFYPREAKVQWKVDN
ALQSGNSQESVTEQDSKDSTYSLSSTLTLSKADYEKHKVYACEVTHQGLSSPVTKSFNRGEC

```
XENCS538 PD-1 X LAG-3 (Xtend)
```

> 7G8_H3.30_L1.34_[LAG-3]_Fab-1C11[PD-1]_H3.240_L3.148_scFv(GKPGS)4-IgG1_pI(-
)_Isosteric_A_/PVA_/S267K/L368D/K370S/M428L/N434S-
Fc(216)_IgG1_C220S/PVA_/S267K/S364K/E357Q/M428L/N434S

Chain 1 – 7G8_H3.30_ IgG1_pI(-)_Isosteric_A_/PVA_/S267K/L368D/K370S/M428L/N434S (SEQ ID NOS 44404-44408)

EVQLVESGGGLVQPGGSLRLSCAASGFTFDDAWMSWVRQAPGKGLEWVAEISTKANNHATYYAESVKGRFTISRDDS
KSSVYLQMNSLRAEDTAVYYCTRLATWDWYFDVWGQGTTVTVSS/ASTKGPSVFPLAPSSKSTSGGTAALGCLVKDY
FPEPVTVSWNSGALTSGVHTFPAVLQSSGLYSLSSVVTVPSSSLGTQTYICNVNHKPSDTKVDKKVEPKSCDKTHTC
PPCPAPPVAGPSVFLFPPKPKDTLMISRTPEVTCVVVDVKHEDPEVKFNWYVDGVEVHNAKTKPREEEYNSTYRVVS
VLTVLHQDWLNGKEYKCKVSNKALPAPIEKTISKAKGQPREPQVYTLPPSREEMTKNQVSLTCDVSGFYPSDIAVEW
ESDGQPENNYKTTPPVLDSDGSFFLYSKLTVDKSRWEQGDVFSCSVLHEALHSHYTQKSLSLSPGK

FIG. 49Z

Chain 2 –1C11[PD-1]_H3.240_L3.148_scFv(GKPGS)4_Fc(216)_IgG1_C220S/PVA_/S267K/S364K/E357Q/M428L/N434S
(SEQ ID NOS 44409-44418 and linker disclosed as SEQ ID NO: 39202)
QVQLVQSGPELKKPGESVKVSCKASGYTFT<u>HYGIN</u>WVRQPPGQGLEWMG<u>WINTYTGEPYYAPGFQE</u>RFVFSIDTSQDTAYLQ
INSLKAEDTAVYYCAR<u>DYYGSSPYW</u>GQGTLVTVSS/<u>GKPGSGKPGSGKPGSGKPGS</u>/DVLMTQSPDSLAVSLGERATINCK<u>S
SQSIVHSNGNTYLE</u>WYQQKPGQSPKLLIY<u>KVSNRF</u>SGVPDRFSGSGSGTDFTLTISSLQAEDVAVYYC<u>FQGSHVPNTF</u>GGGT
KVEIK/EPKSSDKTHTCPPCPAPPVAGPSVFLFPPKPKDTLMISRTPEVTCVVVDVKHEDPEVKFNWYVDGVEVHNAKTKPR
EEQYNSTYRVVSVLTVLHQDWLNGKEYKCKVSNKALPAPIEKTISKAKGQPREPQVYTLPPSREQMTKNQVKLTCLVKGFYP
SDIAVEWESNGQPENNYKTTPPVLDSDGSFFLYSKLTVDKSRWQQGNVFSCSVLHEALHSHYTQKSLSLSPGK

Chain 3 – 7G8_L1.34 (SEQ ID NOS 44419-44423)
DIVLTQSPSSLSASVGDRVTITC<u>RASQSVDYDGDSYMN</u>WYQQKPGKPPKLLIY<u>AASELES</u>GIPARFSGSGSGTDFTLTISSL
QPEDFATYYC<u>QQSNEDPFT</u>FGSGTKLEIK/RTVAAPSVFIFPPSDEQLKSGTASVVCLLNNFYPREAKVQWKVDNALQSGNS
QESVTEQDSKDSTYSLSSTLTLSKADYEKHKVYACEVTHQGLSSPVTKSFNRGEC XENCS539 PD-1 X LAG-3 (Xtend)

> 2A11_H1.144_L2.142_[LAG-3]_Fab-1C11[PD-1]_H3.240_L3.148_scFv(GKPGS)4-IgG1_pI(-)_Isosteric_A_/PVA_/S267K/L368D/K370S/M428L/N434S-Fc(216)_IgG1_C220S/PVA_/S267K/S364K/E357Q/M428L/N434S

Chain 1 – 2A11_H1.144_ IgG1_pI(-)_Isosteric_A_/PVA_/S267K/L368D/K370S/M428L/N434S (SEQ ID NOS 44424-44428)
EVQLVQSGAEVKKPGATVKISCKASGFNIK<u>DYFMH</u>WVQQAPGKGLEWMG<u>WIDPELGDTEYAPKFQG</u>RVTITADTSTNTAYME
LSSLRSEDTAVYYCYAR<u>GVYQALDY</u>WGQGTLVTVSS/ASTKGPSVFPLAPSSKSTSGGTAALGCLVKDYFPEPVTVSWNSGA
LTSGVHTFPAVLQSSGLYSLSSVVTVPSSSLGTQTYICNVNHKPSDTKVDKKVEPKSCDKTHTCPPCPAPPVAGPSVFLFPP
KPKDTLMISRTPEVTCVVVDVKHEDPEVKFNWYVDGVEVHNAKTKPREEEYNSTYRVVSVLTVLHQDWLNGKEYKCKVSNKA
LPAPIEKTISKAKGQPREPQVYTLPPSREEMTKNQVSLTCDVSGFYPSDIAVEWESDGQPENNYKTTPPVLDSDGSFFLYSK
LTVDKSRWEQGDVFSCSVLHEALHSHYTQKSLSLSPGK

Chain 2 – 1C11[PD-1]_H3.240_L3.148_scFv(GKPGS)4_Fc(216)_IgG1_C220S/PVA_/S267K/S364K/E357Q/M428L/N434S
(SEQ ID NOS 44429-44438 and linker disclosed as SEQ ID NO: 39202)
QVQLVQSGPELKKPGESVKVSCKASGYTFT<u>HYGIN</u>WVRQPPGQGLEWMG<u>WINTYTGEPYYAPGFQE</u>RFVFSIDTSQDTAYLQ
INSLKAEDTAVYYCAR<u>DYYGSSPYW</u>GQGTLVTVSS/<u>GKPGSGKPGSGKPGSGKPGS</u>/DVLMTQSPDSLAVSLGERATINCK<u>S
SQSIVHSNGNTYLE</u>WYQQKPGQSPKLLIY<u>KVSNRF</u>SGVPDRFSGSGSGTDFTLTISSLQAEDVAVYYC<u>FQGSHVPNTF</u>GGGT
KVEIK/EPKSSDKTHTCPPCPAPPVAGPSVFLFPPKPKDTLMISRTPEVTCVVVDVKHEDPEVKFNWYVDGVEVHNAKTKPR
EEQYNSTYRVVSVLTVLHQDWLNGKEYKCKVSNKALPAPIEKTISKAKGQPREPQVYTLPPSREQMTKNQVKLTCLVKGFYP
SDIAVEWESNGQPENNYKTTPPVLDSDGSFFLYSKLTVDKSRWQQGNVFSCSVLHEALHSHYTQKSLSLSPGK

Chain 3 – 2A11_L2.142 (SEQ ID NOS 44439-44443)
DIQMTQSPAFLSVTPGEKVTITCQA<u>SQDIGNYLN</u>WFQQKPGQTVKLLIY<u>FTSYLHS</u>GVPSRFSGSGSGTDYTFTISSLEAED
AATYFC<u>QQGNTLPYT</u>FGGGTKVEIK/RTVAAPSVFIFPPSDEQLKSGTASVVCLLNNFYPREAKVQWKVDNALQSGNSQESV
TEQDSKDSTYSLSSTLTLSKADYEKHKVYACEVTHQGLSSPVTKSFNRGEC

FIG. 49AA

```
XENCS540 PD-1 X TIM-3 (Xtend)
```

**> 3H3_H1_L2.1_Fab-1C11[PD-1]_H3.240_L3.148-scFv(GKPGS)4-IgG1_pI(-
)_Isosteric_A_/PVA_/S267K/L368D/K370S/M428L/N434S-
Fc(216)_IgG1_C220S/PVA_/S267K/S364K/E357Q/M428L/N434S**

Chain 1 – 3H3_H1_ IgG1_pI(-)_Isosteric_A_/PVA_/S267K/L368D/K370S/M428L/N434S (SEQ ID NOS 44444-44448)
QVTLKESGPVLVKPTETLTLTCTVSGFSLNGYGVNWVRQPPGKGLEWLAMIWGDGSTDYNSALKSRLTISKDNSKSQ
VVLTMTNMDPVDTATYYCARSYYTSDEDYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSDTKVDKKVEPKSCDKTHTCPPCP
APPVAGPSVFLFPPKPKDTLMISRTPEVTCVVVDVKHEDPEVKFNWYVDGVEVHNAKTKPREEEYNSTYRVVSVLTV
LHQDWLNGKEYKCKVSNKALPAPIEKTISKAKGQPREPQVYTLPPSREEMTKNQVSLTCDVSGFYPSDIAVEWESDG
QPENNYKTTPPVLDSDGSFFLYSKLTVDKSRWEQGDVFSCSVLHEALHSHYTQKSLSLSPGK

**Chain 2 – 1C11[PD-
1]_H3.240_L3.148_scFv(GKPGS)4_Fc(216)_IgG1_C220S/PVA_/S267K/S364K/E357Q/M428L/N434S** (SEQ ID NOS
44449-44458 and linker disclosed as SEQ ID NO: 39202)
QVQLVQSGPELKKPGESVKVSCKASGYTFTHYGINWVRQPPGQGLEWMGWINTYTGEPYYAPGFQERFVFSIDTSQD
TAYLQINSLKAEDTAVYYCARDYYGSSPYWGQGTLVTVSS/GKPGSGKPGSGKPGSGKPGS/DVLMTQSPDSLAVSL
GERATINCKSSQSIVHSNGNTYLEWYQQKPGQSPKLLIYKVSNRFSGVPDRFSGSGSGTDFTLTISSLQAEDVAVYY
CFQGSHVPNTFGGGTKVEIK/EPKSSDKTHTCPPCPAPPVAGPSVFLFPPKPKDTLMISRTPEVTCVVVDVKHEDPE
VKFNWYVDGVEVHNAKTKPREEQYNSTYRVVSVLTVLHQDWLNGKEYKCKVSNKALPAPIEKTISKAKGQPREPQVY
TLPPSREQMTKNQVKLTCLVKGFYPSDIAVEWESNGQPENNYKTTPPVLDSDGSFFLYSKLTVDKSRWQQGNVFSCS
VLHEALHSHYTQKSLSLSPGK

Chain 3 – 3H3_L2.1 (SEQ ID NOS 44459-44463)
DIVMTQSPDSLAVSLGERATINCKSSQSLLNSRTRKNYLAWYQQKPGQSPKLLIYWASTRESGVPDRFTGSGSGTDF
TLTISSLQAEDVAVYYCKQSYSLRTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

```
XENCS541 PD-1 X BTLA (Xtend)
```

**> 9C6_H1.1_L1_[BTLA]_Fab-1C11[PD-1]_H3.240_L3.148_scFv(GKPGS)4-IgG1_pI(-
)_Isosteric_A_/PVA_/S267K/L368D/K370S/M428L/N434S-
Fc(216)_IgG1_C220S/PVA_/S267K/S364K/E357Q/M428L/N434S**

Chain 1 – 9C6_H1.1_ IgG1_pI(-)_Isosteric_A_/PVA_/S267K/L368D/K370S/M428L/N434S (SEQ ID NOS 44464-
44468)
QVQLKESGAEVKKPGASVKVSCKVSGFSLTGYGVNWVRQAPGQGLEWMGMIWIDGSTDYNSKFQGRVTMTKDNSKST
VYMELSSLRSEDTAVYYCARDRPDGRAMDYWGQGTMVTVSS/ASTKGPSVFPLAPSSKSTSGGTAALGCLVKDYFPE
PVTVSWNSGALTSGVHTFPAVLQSSGLYSLSSVVTVPSSSLGTQTYICNVNHKPSDTKVDKKVEPKSCDKTHTCPPC
PAPPVAGPSVFLFPPKPKDTLMISRTPEVTCVVVDVKHEDPEVKFNWYVDGVEVHNAKTKPREEEYNSTYRVVSVLT
VLHQDWLNGKEYKCKVSNKALPAPIEKTISKAKGQPREPQVYTLPPSREEMTKNQVSLTCDVSGFYPSDIAVEWESD
GQPENNYKTTPPVLDSDGSFFLYSKLTVDKSRWEQGDVFSCSVLHEALHSHYTQKSLSLSPGK

FIG. 49BB

Chain 2 – 1C11[PD-1]_H3.240_L3.148_scFv(GKPGS)4_Fc(216)_IgG1_C220S/PVA_/S267K/S364K/E357Q/M428L/N434S (SEQ ID NOS 44469-44478 and linker disclosed as SEQ ID NO: 39202)
QVQLVQSGPELKKPGESVKVSCKASGYTFTHYGINWVRQPPGQGLEWMGWINTYTGEPYYAPGFQERFVFSIDTSQD
TAYLQINSLKAEDTAVYYCARDYYGSSPYWGQGTLVTVSS/GKPGSGKPGSGKPGSGKPGS/DVLMTQSPDSLAVSL
GERATINCKSSQSIVHSNGNTYLEWYQQKPGQSPKLLIYKVSNRFSGVPDRFSGSGSGTDFTLTISSLQAEDVAVYY
CFQGSHVPNTFGGGTKVEIK/EPKSSDKTHTCPPCPAPPVAGPSVFLFPPKPKDTLMISRTPEVTCVVVDVKHEDPE
VKFNWYVDGVEVHNAKTKPREEQYNSTYRVVSVLTVLHQDWLNGKEYKCKVSNKALPAPIEKTISKAKGQPREPQVY
TLPPSREQMTKNQVKLTCLVKGFYPSDIAVEWESNGQPENNYKTTPPVLDSDGSFFLYSKLTVDKSRWQQGNVFSCS
VLHEALHSHYTQKSLSLSPGK

Chain 3 – 9C6_L1 (SEQ ID NOS 44479-44483)
SIVMTQSPDSLAVSLGERATINCKASQSVSNDVAWYQQKPGQSPKLLIYYASNRYTGVPDRFTGSGYGTDFTLTISS
LQAEDVAVYFCQQDYSSPTFGGGTKLEIK/RTVAAPSVFIFPPSDEQLKSGTASVVCLLNNFYPREAKVQWKVDNAL
QSGNSQESVTEQDSKDSTYSLSSTLTLSKADYEKHKVYACEVTHQGLSSPVTKSFNRGEC XENCS542 PD-1 X ICOS (Xtend)

> [ICOS]_H0L0_Fab-1C11[PD-1]_H3.241_L3.148-scFv(GKPGS)4-IgG1_pI(-)_Isosteric_A_/PVA_/S267K/L368D/K370S/M428L/N434S-Fc(216)_IgG1_C220S/PVA_/S267K/S364K/E357Q/M428L/N434S

Chain 1 – [ICOS]_H0_IgG1_pI(-)_Isosteric_A_/PVA_/S267K/L368D/K370S/M428L/N434S (SEQ ID NOS 44484-44488)
QVQLVQSGAEVKKPGASVKVSCKASGYTFTGYYMHWVRQAPGQGLEWMGWINPHSGGTNYAQKFQGRVTMTRDTSIS
TAYMELSRLRSDDTAVYYCARTYYYDSSGYYHDAFDIWGQGTMVTVSS/ASTKGPSVFPLAPSSKSTSGGTAALGCLVKDYFP
EPVTVSWNSGALTSGVHTFPAVLQSSGLYSLSSVVTVPSSSLGTQTYICNVNHKPSDTKVDKKVEPKSCDKTHTCPPCPAPPVAGPSVFLFPP
KPKDTLMISRTPEVTCVVVDVKHEDPEVKFNWYVDGVEVHNAKTKPREEEYNSTYRVVSVLTVLHQDWLNGKEYKCKVSNKALPAPIEKTISK
AKGQPREPQVYTLPPSREEMTKNQVSLTCDVSGFYPSDIAVEWESDGQPENNYKTTPPVLDSDGSFFLYSKLTVDKSRWEQGDVFSCSVLHEA
LHSHYTQKSLSLSPGK

Chain 2 – 1C11[PD-1]_H3.241_L3.148_scFv(GKPGS)4_Fc(216)_IgG1_C220S/PVA_/S267K/S364K/E357Q/M428L/N434S (SEQ ID NOS 44489-44498 and linker disclosed as SEQ ID NO: 39202)
EVQLVQSGPELKKPGESVKVSCKASGYTFTHYGINWVRQPPGQGLEWMGWINTYTGEPYYAPGFQERFVFSIDTSQD
TAYLQINSLKAEDTAVYYCARDYYGSSPYWGQGTLVTVSS/GKPGSGKPGSGKPGSGKPGS/DVLMTQSPDSLAVSL
GERATINCKSSQSIVHSNGNTYLEWYQQKPGQSPKLLIYKVSNRFSGVPDRFSGSGSGTDFTLTISSLQAEDVAVYY
CFQGSHVPNTFGGGTKVEIK/EPKSSDKTHTCPPCPAPPVAGPSVFLFPPKPKDTLMISRTPEVTCVVVDVKHEDPE
VKFNWYVDGVEVHNAKTKPREEQYNSTYRVVSVLTVLHQDWLNGKEYKCKVSNKALPAPIEKTISKAKGQPREPQVY
TLPPSREQMTKNQVKLTCLVKGFYPSDIAVEWESNGQPENNYKTTPPVLDSDGSFFLYSKLTVDKSRWQQGNVFSCS
VLHEALHSHYTQKSLSLSPGK

Chain 3 – [ICOS]_L0 (SEQ ID NOS 44499-44503)
DIQMTQSPSSVSASVGDRVTITCRASQGISRLLAWYQQKPGKAPKLLIYVASSLQSGVPSRFSGSGSGTDFTLTISS
LQPEDFATYYCQQANSFPWTFGQGTKVEIK/RTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSPVTKSFNRGEC

FIG. 49CC

XENCS543 PD-1 X ICOS (Xtend)

> [ICOS]_H0.66_L0_Fab-1C11[PD-1]_H3.241_L3.148-scFv(GKPGS)4-IgG1_pI(-
)_Isosteric_A_/PVA_/S267K/L368D/K370S/M428L/N434S-
Fc(216)_IgG1_C220S/PVA_/S267K/S364K/E357Q/M428L/N434S Chain 1 – [ICOS]_H0.66_ IgG1_pI(-)_Isosteric_A_/PVA_/S267K/L368D/K370S/M428L/N434S (SEQ ID NOS 44504-44508)

QVQLVQSGAEVKKPGASVKVSCKASGYTFTGYYMHWVRQAPGQGLEWMGWINPHSGETIYAQKFQGRVTMTRDTSIS
TAYMELSSLRSEDTAVYYCARTYYYDTSGYYHDAFDVWGQGTMVTVSS/ASTKGPSVFPLAPSSKSTSGGTAALGCL
VKDYFPEPVTVSWNSGALTSGVHTFPAVLQSSGLYSLSSVVTVPSSSLGTQTYICNVNHKPSDTKVDKKVEPKSCDK
THTCPPCPAPPVAGPSVFLFPPKPKDTLMISRTPEVTCVVVDVKHEDPEVKFNWYVDGVEVHNAKTKPREEEYNSTY
RVVSVLTVLHQDWLNGKEYKCKVSNKALPAPIEKTISKAKGQPREPQVYTLPPSREEMTKNQVSLTCDVSGFYPSDI
AVEWESDGQPENNYKTTPPVLDSDGSFFLYSKLTVDKSRWEQGDVFSCSVLHEALHSHYTQKSLSLSPGK

Chain 2 – 1C11[PD-
1]_H3.241_L3.148_scFv(GKPGS)4_Fc(216)_IgG1_C220S/PVA_/S267K/S364K/E357Q/M428L/N434S (SEQ ID NOS 44509-44518 and linker disclosed as SEQ ID NO: 39202)

EVQLVQSGPELKKPGESVKVSCKASGYTFTHYGINWVRQPPGQGLEWMGWINTYTGEPYYAPGFQERFVFSIDTSQD
TAYLQINSLKAEDTAVYYCARDYYGSSPYWGQGTLVTVSS/GKPGSGKPGSGKPGSGKPGS/DVLMTQSPDSLAVSL
GERATINCKSSQSIVHSNGNTYLEWYQQKPGQSPKLLIYKVSNRFSGVPDRFSGSGSGTDFTLTISSLQAEDVAVYY
CFQGSHVPNTFGGGTKVEIK/EPKSSDKTHTCPPCPAPPVAGPSVFLFPPKPKDTLMISRTPEVTCVVVDVKHEDPE
VKFNWYVDGVEVHNAKTKPREEQYNSTYRVVSVLTVLHQDWLNGKEYKCKVSNKALPAPIEKTISKAKGQPREPQVY
TLPPSREQMTKNQVKLTCLVKGFYPSDIAVEWESNGQPENNYKTTPPVLDSDGSFFLYSKLTVDKSRWQQGNVFSCS
VLHEALHSHYTQKSLSLSPGK

Chain 3 – [ICOS]_L0 (SEQ ID NOS 44519-44523)
DIQMTQSPSSVSASVGDRVTITCRASQGISRLLAWYQQKPGKAPKLLIYVASSLQSGVPSRFSGSGSGTDFTLTISS
LQPEDFATYYCQQANSFPWTFGQGTKVEIK/RTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSPVTKSFNRGEC XENCS544 PD-1 X CTLA-4 (Xtend)

> [CTLA-4]_H3_L0.22_Fab-1C11[PD-1]_H3.241_L3.148_scFv(GKPGS)4-IgG1_pI(-
)_Isosteric_A_/PVA_/S267K/L368D/K370S/M428L/N434S-
Fc(216)_IgG1_C220S/PVA_/S267K/S364K/E357Q/M428L/N434S Chain 1 - [CTLA-4]_H3_ IgG1_pI(-)_Isosteric_A_/PVA_/S267K/L368D/K370S/M428L/N434S (SEQ ID NOS 44524-44528)

EVQLVESGGGLVKPGGSLRLSCAASGFTFSSYTMHWVRQAPGKGLEWVSFISYDGNNKYYADSVKGRFTISRDNAKN
SLYLQMNSLRAEDTAVYYCARTGWLGPFDYWGQGTLVTVSS/ASTKGPSVFPLAPSSKSTSGGTAALGCLVKDYFPE
PVTVSWNSGALTSGVHTFPAVLQSSGLYSLSSVVTVPSSSLGTQTYICNVNHKPSDTKVDKKVEPKSCDKTHTCPPC
PAPPVAGPSVFLFPPKPKDTLMISRTPEVTCVVVDVKHEDPEVKFNWYVDGVEVHNAKTKPREEEYNSTYRVVSVLT
VLHQDWLNGKEYKCKVSNKALPAPIEKTISKAKGQPREPQVYTLPPSREEMTKNQVSLTCDVSGFYPSDIAVEWESD
GQPENNYKTTPPVLDSDGSFFLYSKLTVDKSRWEQGDVFSCSVLHEALHSHYTQKSLSLSPGK

FIG. 49DD

Chain 2 - 1C11[PD-1]_H3.241_L3.148_scFv(GKPGS)4_Fc(216)_IgG1_C220S/PVA_/S267K/S364K/E357Q/M428L/N434S
(SEQ ID NOS 44529-44538 and linker disclosed as SEQ ID NO: 39202)
EVQLVQSGPELKKPGESVKVSCKASGYTFTHYGINWVRQPPGQGLEWMGWINTYTGEPYYAPGFQERFVFSIDTSQDTAYLQ
INSLKAEDTAVYYCARDYYGSSPYWGQGTLVTVSS/GKPGSGKPGSGKPGSGKPGS/DVLMTQSPDSLAVSLGERATINCKS
SQSIVHSNGNTYLEWYQQKPGQSPKLLIYKVSNRFSGVPDRFSGSGSGTDFTLTISSLQAEDVAVYYCFQGSHVPNTFGGGT
KVEIK/EPKSSDKTHTCPPCPAPPVAGPSVFLFPPKPKDTLMISRTPEVTCVVVDVKHEDPEVKFNWYVDGVEVHNAKTKPR
EEQYNSTYRVVSVLTVLHQDWLNGKEYKCKVSNKALPAPIEKTISKAKGQPREPQVYTLPPSREQMTKNQVKLTCLVKGFYP
SDIAVEWESNGQPENNYKTTPPVLDSDGSFFLYSKLTVDKSRWQQGNVFSCSVLHEALHSHYTQKSLSLSPGK

Chain 3 - [CTLA-4]_L0.22 (SEQ ID NOS 44539-44543)
EIVLTQSPGTLSLSPGERATLSCRASQSVSSSYLAWYQQKPGQAPRLLIYGAFSRATGIPDRFSGSGSGTDFTLTISRLEPE
DFAVYYCQQYGSSPWTFGQGTKVEIK/RTVAAPSVFIFPPSDEQLKSGTASVVCLLNNFYPREAKVQWKVDNALQSGNSQES
VTEQDSKDSTYSLSSTLTLSKADYEKHKVYACEVTHQGLSSPVTKSFNRGEC XENCS545 PD-1 X LAG-3 (Xtend)

> 7G8_H3.30_L1.34_[LAG-3]_Fab-1C11[PD-1]_H3.241_L3.148_scFv(GKPGS)4-IgG1_pI(-)_Isosteric_A_/PVA_/S267K/L368D/K370S/M428L/N434S-Fc(216)_IgG1_C220S/PVA_/S267K/S364K/E357Q/M428L/N434S

Chain 1 – 7G8_H3.30_ IgG1_pI(-)_Isosteric_A_/PVA_/S267K/L368D/K370S/M428L/N434S (SEQ ID NOS 44544-44548)
EVQLVESGGGLVQPGGSLRLSCAASGFTFDDAWMSWVRQAPGKGLEWVAEISTKANNHATYYAESVKGRFTISRDDSKSSVY
LQMNSLRAEDTAVYYCTRLATWDWYFDVWGQGTTVTVSS/ASTKGPSVFPLAPSSKSTSGGTAALGCLVKDYFPEPVTVSWN
SGALTSGVHTFPAVLQSSGLYSLSSVVTVPSSSLGTQTYICNVNHKPSDTKVDKKVEPKSCDKTHTCPPCPAPPVAGPSVFL
FPPKPKDTLMISRTPEVTCVVVDVKHEDPEVKFNWYVDGVEVHNAKTKPREEEYNSTYRVVSVLTVLHQDWLNGKEYKCKVS
NKALPAPIEKTISKAKGQPREPQVYTLPPSREEMTKNQVSLTCDVSGFYPSDIAVEWESDGQPENNYKTTPPVLDSDGSFFL
YSKLTVDKSRWEQGDVFSCSVLHEALHSHYTQKSLSLSPGK

Chain 2 –1C11[PD-1]_H3.241_L3.148_scFv(GKPGS)4_Fc(216)_IgG1_C220S/PVA_/S267K/S364K/E357Q/M428L/N434S
(SEQ ID NOS 44549-44558 and linker disclosed as SEQ ID NO: 39202)
EVQLVQSGPELKKPGESVKVSCKASGYTFTHYGINWVRQPPGQGLEWMGWINTYTGEPYYAPGFQERFVFSIDTSQDTAYLQ
INSLKAEDTAVYYCARDYYGSSPYWGQGTLVTVSS/GKPGSGKPGSGKPGSGKPGS/DVLMTQSPDSLAVSLGERATINCKS
SQSIVHSNGNTYLEWYQQKPGQSPKLLIYKVSNRFSGVPDRFSGSGSGTDFTLTISSLQAEDVAVYYCFQGSHVPNTFGGGT
KVEIK/EPKSSDKTHTCPPCPAPPVAGPSVFLFPPKPKDTLMISRTPEVTCVVVDVKHEDPEVKFNWYVDGVEVHNAKTKPR
EEQYNSTYRVVSVLTVLHQDWLNGKEYKCKVSNKALPAPIEKTISKAKGQPREPQVYTLPPSREQMTKNQVKLTCLVKGFYP
SDIAVEWESNGQPENNYKTTPPVLDSDGSFFLYSKLTVDKSRWQQGNVFSCSVLHEALHSHYTQKSLSLSPGK

Chain 3 – 7G8_L1.34 (SEQ ID NOS 44559-44563)
DIVLTQSPSSLSASVGDRVTITCRASQSVDYDGDSYMNWYQQKPGKPPKLLIYAASELESGIPARFSGSGSGTDFTLTISSL
QPEDFATYYCQQSNEDPFTFGSGTKLEIK/RTVAAPSVFIFPPSDEQLKSGTASVVCLLNNFYPREAKVQWKVDNALQSGNS
QESVTEQDSKDSTYSLSSTLTLSKADYEKHKVYACEVTHQGLSSPVTKSFNRGEC

FIG. 49EE

XENCS546 PD-1 X LAG-3 (Xtend)

> 2A11_H1.144_L2.142_[LAG-3]_Fab-1C11[PD-1]_H3.241_L3.148_scFv(GKPGS)4-IgG1_pI(-)_Isosteric_A_/PVA_/S267K/L368D/K370S/M428L/N434S-Fc(216)_IgG1_C220S/PVA_/S267K/S364K/E357Q/M428L/N434S

Chain 1 – 2A11_H1.144_ IgG1_pI(-)_Isosteric_A_/PVA_/S267K/L368D/K370S/M428L/N434S (SEQ ID NOS 44564-44568)
EVQLVQSGAEVKKPGATVKISCKASGFNIKDYFMHWVQQAPGKGLEWMGWIDPELGDTEYAPKFQGRVTITADTSTN
TAYMELSSLRSEDTAVYYCYARGVYQALDYWGQGTLVTVSS/ASTKGPSVFPLAPSSKSTSGGTAALGCLVKDYFPE
PVTVSWNSGALTSGVHTFPAVLQSSGLYSLSSVVTVPSSSLGTQTYICNVNHKPSDTKVDKKVEPKSCDKTHTCPPC
PAPPVAGPSVFLFPPKPKDTLMISRTPEVTCVVVDVKHEDPEVKFNWYVDGVEVHNAKTKPREEEYNSTYRVVSVLT
VLHQDWLNGKEYKCKVSNKALPAPIEKTISKAKGQPREPQVYTLPPSREEMTKNQVSLTCDVSGFYPSDIAVEWESD
GQPENNYKTTPPVLDSDGSFFLYSKLTVDKSRWEQGDVFSCSVLHEALHSHYTQKSLSLSPGK

Chain 2 – 1C11[PD-1]_H3.241_L3.148_scFv(GKPGS)4_Fc(216)_IgG1_C220S/PVA_/S267K/S364K/E357Q/M428L/N434S (SEQ ID NOS 44569-44578 and linker disclosed as SEQ ID NO: 39202)
EVQLVQSGPELKKPGESVKVSCKASGYTFTHYGINWVRQPPGQGLEWMGWINTYTGEPYYAPGFQERFVFSIDTSQD
TAYLQINSLKAEDTAVYYCARDYYGSSPYWGQGTLVTVSS/GKPGSGKPGSGKPGSGKPGS/DVLMTQSPDSLAVSL
GERATINCKSSQSIVHSNGNTYLEWYQQKPGQSPKLLIYKVSNRFSGVPDRFSGSGSGTDFTLTISSLQAEDVAVYY
CFQGSHVPNTFGGGTKVEIK/EPKSSDKTHTCPPCPAPPVAGPSVFLFPPKPKDTLMISRTPEVTCVVVDVKHEDPE
VKFNWYVDGVEVHNAKTKPREEQYNSTYRVVSVLTVLHQDWLNGKEYKCKVSNKALPAPIEKTISKAKGQPREPQVY
TLPPSREQMTKNQVKLTCLVKGFYPSDIAVEWESNGQPENNYKTTPPVLDSDGSFFLYSKLTVDKSRWQQGNVFSCS
VLHEALHSHYTQKSLSLSPGK

Chain 3 – 2A11_L2.142 (SEQ ID NOS 44579-44583)
DIQMTQSPAFLSVTPGEKVTITCQASQDIGNYLNWFQQKPGQTVKLLIYFTSYLHSGVPSRFSGSGSGTDYTFTISS
LEAEDAATYFCQQGNTLPYTFGGGTKVEIK/RTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSPVTKSFNRGEC XENCS547 PD-1 X TIM-3 (Xtend)

> 3H3_H1_L2.1_Fab-1C11[PD-1]_H3.241_L3.148-scFv(GKPGS)4-IgG1_pI(-)_Isosteric_A_/PVA_/S267K/L368D/K370S/M428L/N434S-Fc(216)_IgG1_C220S/PVA_/S267K/S364K/E357Q/M428L/N434S

Chain 1 – 3H3_H1_ IgG1_pI(-)_Isosteric_A_/PVA_/S267K/L368D/K370S/M428L/N434S (SEQ ID NOS 44584-44588)
QVTLKESGPVLVKPTETLTLTCTVSGFSLNGYGVNWVRQPPGKGLEWLAMIWGDGSTDYNSALKSRLTISKDNSKSQ
VVLTMTNMDPVDTATYYCARSYYTSDEDYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSDTKVDKKVEPKSCDKTHTCPPCP
APPVAGPSVFLFPPKPKDTLMISRTPEVTCVVVDVKHEDPEVKFNWYVDGVEVHNAKTKPREEEYNSTYRVVSVLTV
LHQDWLNGKEYKCKVSNKALPAPIEKTISKAKGQPREPQVYTLPPSREEMTKNQVSLTCDVSGFYPSDIAVEWESDG
QPENNYKTTPPVLDSDGSFFLYSKLTVDKSRWEQGDVFSCSVLHEALHSHYTQKSLSLSPGK

FIG. 49FF

Chain 2 – 1C11[PD-1]_H3.241_L3.148_scFv(GKPGS)4_Fc(216)_IgG1_C220S/PVA_/S267K/S364K/E357Q/M428L/N434S (SEQ ID NOS 44589-44598 and linker disclosed as SEQ ID NO: 39202)
EVQLVQSGPELKKPGESVKVSCKASGYTFT<u>HYGIN</u>WVRQPPGQGLEWMG<u>WINTYTGEPYYAPGFQER</u>FVFSIDTSQD
TAYLQINSLKAEDTAVYYCARD<u>YYGSSPY</u>WGQGTLVTVSS/<u>GKPGSGKPGSGKPGSGKPGS</u>/DVLMTQSPDSLAVSL
GERATINCK<u>SSQSIVHSNGNTYLE</u>WYQQKPGQSPKLLIY<u>KVSNRFS</u>GVPDRFSGSGSGTDFTLTISSLQAEDVAVYY
C<u>FQGSHVPNT</u>FGGGTKVEIK/EPKSSDKTHTCPPCPAPPVAGPSVFLFPPKPKDTLMISRTPEVTCVVVDVKHEDPE
VKFNWYVDGVEVHNAKTKPREEQYNSTYRVVSVLTVLHQDWLNGKEYKCKVSNKALPAPIEKTISKAKGQPREPQVY
TLPPSREQMTKNQVKLTCLVKGFYPSDIAVEWESNGQPENNYKTTPPVLDSDGSFFLYSKLTVDKSRWQQGNVFSCS
VLHEALHSHYTQKSLSLSPGK

Chain 3 – 3H3_L2.1 (SEQ ID NOS 44599-44603)
DIVMTQSPDSLAVSLGERATINCK<u>SSQSLLNSRTRKNYLA</u>WYQQKPGQSPKLLIY<u>WASTRES</u>GVPDRFTGSGSGTDF
TLTISSLQAEDVAVYYC<u>KQSYSLRT</u>FGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC XENCS548 PD-1 X BTLA (Xtend)

> 9C6_H1.1_L1_[BTLA]_Fab-1C11[PD-1]_H3.241_L3.148_scFv(GKPGS)4-IgG1_pI(-)_Isosteric_A_/PVA_/S267K/L368D/K370S/M428L/N434S-Fc(216)_IgG1_C220S/PVA_/S267K/S364K/E357Q/M428L/N434S

Chain 1 – 9C6_H1.1_IgG1_pI(-)_Isosteric_A_/PVA_/S267K/L368D/K370S/M428L/N434S (SEQ ID NOS 44604-44608)
QVQLKESGAEVKKPGASVKVSCKVSGFSLT<u>GYGVN</u>WVRQAPGQGLEWMG<u>MIWIDGSTDYNSKFQG</u>RVTMTKDNSKST
VYMELSSLRSEDTAVYYCARD<u>RPDGRAMDY</u>WGQGTMVTVSS/ASTKGPSVFPLAPSSKSTSGGTAALGCLVKDYFPE
PVTVSWNSGALTSGVHTFPAVLQSSGLYSLSSVVTVPSSSLGTQTYICNVNHKPSDTKVDKKVEPKSCDKTHTCPPC
PAPPVAGPSVFLFPPKPKDTLMISRTPEVTCVVVDVKHEDPEVKFNWYVDGVEVHNAKTKPREEEYNSTYRVVSVLT
VLHQDWLNGKEYKCKVSNKALPAPIEKTISKAKGQPREPQVYTLPPSREEMTKNQVSLTCDVSGFYPSDIAVEWESD
GQPENNYKTTPPVLDSDGSFFLYSKLTVDKSRWEQGDVFSCSVLHEALHSHYTQKSLSLSPGK

Chain 2 – 1C11[PD-1]_H3.241_L3.148_scFv(GKPGS)4_Fc(216)_IgG1_C220S/PVA_/S267K/S364K/E357Q/M428L/N434S (SEQ ID NOS 44609-44618 and linker disclosed as SEQ ID NO: 39202)
EVQLVQSGPELKKPGESVKVSCKASGYTFT<u>HYGIN</u>WVRQPPGQGLEWMG<u>WINTYTGEPYYAPGFQER</u>FVFSIDTSQD
TAYLQINSLKAEDTAVYYCARD<u>YYGSSPY</u>WGQGTLVTVSS/<u>GKPGSGKPGSGKPGSGKPGS</u>/DVLMTQSPDSLAVSL
GERATINCK<u>SSQSIVHSNGNTYLE</u>WYQQKPGQSPKLLIY<u>KVSNRFS</u>GVPDRFSGSGSGTDFTLTISSLQAEDVAVYY
C<u>FQGSHVPNT</u>FGGGTKVEIK/EPKSSDKTHTCPPCPAPPVAGPSVFLFPPKPKDTLMISRTPEVTCVVVDVKHEDPE
VKFNWYVDGVEVHNAKTKPREEQYNSTYRVVSVLTVLHQDWLNGKEYKCKVSNKALPAPIEKTISKAKGQPREPQVY
TLPPSREQMTKNQVKLTCLVKGFYPSDIAVEWESNGQPENNYKTTPPVLDSDGSFFLYSKLTVDKSRWQQGNVFSCS
VLHEALHSHYTQKSLSLSPGK

Chain 3 – 9C6_L1 (SEQ ID NOS 44619-44623)
SIVMTQSPDSLAVSLGERATINCK<u>ASQSVSNDVA</u>WYQQKPGQSPKLLIY<u>YASNRYT</u>GVPDRFTGSGYGTDFTLTISS
LQAEDVAVYFC<u>QQDYSSPT</u>FGGGTKLEIK/RTVAAPSVFIFPPSDEQLKSGTASVVCLLNNFYPREAKVQWKVDNAL
QSGNSQESVTEQDSKDSTYSLSSTLTLSKADYEKHKVYACEVTHQGLSSPVTKSFNRGEC

FIG. 49GG

```
XENCS549 PD-1 X ICOS (Xtend)
```

> [ICOS]_H0L0_Fab-1C11[PD-1]_H3.241_L3.92-scFv(GKPGS)4-IgG1_pI(-
)_Isosteric_A_/PVA_/S267K/L368D/K370S/M428L/N434S-
Fc(216)_IgG1_C220S/PVA_/S267K/S364K/E357Q/M428L/N434S

Chain 1 – [ICOS]_H0_ IgG1_pI(-)_Isosteric_A_/PVA_/S267K/L368D/K370S/M428L/N434S (SEQ ID NOS 44624-44628)

QVQLVQSGAEVKKPGASVKVSCKASGYTFTGYYMHWVRQAPGQGLEWMGWINPHSGGTNYAQKFQGRVTMTRDTSIS
TAYMELSRLRSDDTAVYYCARTYYYDSSGYYHDAFDIWGQGTMVTVSS/ASTKGPSVFPLAPSSKSTSGGTAALGCLVKDYFP
EPVTVSWNSGALTSGVHTFPAVLQSSGLYSLSSVVTVPSSSLGTQTYICNVNHKPSDTKVDKKVEPKSCDKTHTCPPCPAPPVAGPSVFLFPP
KPKDTLMISRTPEVTCVVVDVKHEDPEVKFNWYVDGVEVHNAKTKPREEEYNSTYRVVSVLTVLHQDWLNGKEYKCKVSNKALPAPIEKTISK
AKGQPREPQVYTLPPSREEMTKNQVSLTCDVSGFYPSDIAVEWESDGQPENNYKTTPPVLDSDGSFFLYSKLTVDKSRWEQGDVFSCSVLHEA
LHSHYTQKSLSLSPGK

Chain 2 – 1C11[PD-1]_H3.241_L3.92_scFv(GKPGS)4_Fc(216)_IgG1_C220S/PVA_/S267K/S364K/E357Q/M428L/N434S (SEQ ID NOS 44629-44638 and linker disclosed as SEQ ID NO: 39202)

EVQLVQSGPELKKPGESVKVSCKASGYTFTHYGINWVRQPPGQGLEWMGWINTYTGEPYYAPGFQERFVFSIDTSQD
TAYLQINSLKAEDTAVYYCARDYYGSSPYWGQGTLVTVSS/GKPGSGKPGSGKPGSGKPGS/DIVMTQSPDSLAVSL
GERVTINCKASQSIVHSNGNTYLEWYQQKPGQPPKLLIYKVSNRFTGVPDRFSGSGSGTDFTLTISSLQAEDVAVYY
CFQGSHVPNTFGGGTKVEIK/EPKSSDKTHTCPPCPAPPVAGPSVFLFPPKPKDTLMISRTPEVTCVVVDVKHEDPE
VKFNWYVDGVEVHNAKTKPREEQYNSTYRVVSVLTVLHQDWLNGKEYKCKVSNKALPAPIEKTISKAKGQPREPQVY
TLPPSREQMTKNQVKLTCLVKGFYPSDIAVEWESNGQPENNYKTTPPVLDSDGSFFLYSKLTVDKSRWQQGNVFSCS
VLHEALHSHYTQKSLSLSPGK

Chain 3 – [ICOS]_L0 (SEQ ID NOS 44639-44643)

DIQMTQSPSSVSASVGDRVTITCRASQGISRLLAWYQQKPGKAPKLLIYVASSLQSGVPSRFSGSGSGTDFTLTISS
LQPEDFATYYCQQANSFPWTFGQGTKVEIK/RTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSPVTKSFNRGEC

```
XENCS550 PD-1 X ICOS (Xtend)
```

> [ICOS]_H0.66_L0_Fab-1C11[PD-1]_H3.241_L3.92-scFv(GKPGS)4-IgG1_pI(-
)_Isosteric_A_/PVA_/S267K/L368D/K370S/M428L/N434S-
Fc(216)_IgG1_C220S/PVA_/S267K/S364K/E357Q/M428L/N434S

Chain 1 – [ICOS]_H0.66_ IgG1_pI(-)_Isosteric_A_/PVA_/S267K/L368D/K370S/M428L/N434S (SEQ ID NOS 44644-44648)

QVQLVQSGAEVKKPGASVKVSCKASGYTFTGYYMHWVRQAPGQGLEWMGWINPHSGETIYAQKFQGRVTMTRDTSIS
TAYMELSSLRSEDTAVYYCARTYYYDTSGYYHDAFDVWGQGTMVTVSS/ASTKGPSVFPLAPSSKSTSGGTAALGCL
VKDYFPEPVTVSWNSGALTSGVHTFPAVLQSSGLYSLSSVVTVPSSSLGTQTYICNVNHKPSDTKVDKKVEPKSCDK
THTCPPCPAPPVAGPSVFLFPPKPKDTLMISRTPEVTCVVVDVKHEDPEVKFNWYVDGVEVHNAKTKPREEEYNSTY
RVVSVLTVLHQDWLNGKEYKCKVSNKALPAPIEKTISKAKGQPREPQVYTLPPSREEMTKNQVSLTCDVSGFYPSDI
AVEWESDGQPENNYKTTPPVLDSDGSFFLYSKLTVDKSRWEQGDVFSCSVLHEALHSHYTQKSLSLSPGK

FIG. 49HH

Chain 2 – 1C11[PD-1]_H3.241_L3.92_scFv(GKPGS)4_Fc(216)_IgG1_C220S/PVA_/S267K/S364K/E357Q/M428L/N434S (SEQ ID NOS 44649-44658 and linker disclosed as SEQ ID NO: 39202)
EVQLVQSGPELKKPGESVKVSCKASGYTFTHYGINWVRQPPGQGLEWMGWINTYTGEPYYAPGFQERFVFSIDTSQD
TAYLQINSLKAEDTAVYYCARDYYGSSPYWGQGTLVTVSS/GKPGSGKPGSGKPGSGKPGS/DIVMTQSPDSLAVSL
GERVTINCKASQSIVHSNGNTYLEWYQQKPGQPPKLLIYKVSNRFTGVPDRFSGSGSGTDFTLTISSLQAEDVAVYY
CFQGSHVPNTFGGGTKVEIK/EPKSSDKTHTCPPCPAPPVAGPSVFLFPPKPKDTLMISRTPEVTCVVVDVKHEDPE
VKFNWYVDGVEVHNAKTKPREEQYNSTYRVVSVLTVLHQDWLNGKEYKCKVSNKALPAPIEKTISKAKGQPREPQVY
TLPPSREQMTKNQVKLTCLVKGFYPSDIAVEWESNGQPENNYKTTPPVLDSDGSFFLYSKLTVDKSRWQQGNVFSCS
VLHEALHSHYTQKSLSLSPGK

Chain 3 – [ICOS]_L0 (SEQ ID NOS 44659-44663)
DIQMTQSPSSVSASVGDRVTITCRASQGISRLLAWYQQKPGKAPKLLIYVASSLQSGVPSRFSGSGSGTDFTLTISS
LQPEDFATYYCQQANSFPWTFGQGTKVEIK/RTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSPVTKSFNRGEC XENCS551 PD-1 X CTLA-4 (Xtend)

>[CTLA-4]_H3_L0.22_Fab-1C11[PD-1]_H3.241_L3.92_scFv(GKPGS)4-IgG1_pI(-)_Isosteric_A_/PVA_/S267K/L368D/K370S/M428L/N434S-Fc(216)_IgG1_C220S/PVA_/S267K/S364K/E357Q/M428L/N434S

Fab Chain 1 - [CTLA-4]_H3_IgG1_pI(-)_Isosteric_A_/PVA_/S267K/L368D/K370S/M428L/N434S (SEQ ID NOS 44664-44668)
EVQLVESGGGLVKPGGSLRLSCAASGFTFSSYTMHWVRQAPGKGLEWVSFISYDGNNKYYADSVKGRFTISRDNAKN
SLYLQMNSLRAEDTAVYYCARTGWLGPFDYWGQGTLVTVSS/ASTKGPSVFPLAPSSKSTSGGTAALGCLVKDYFPE
PVTVSWNSGALTSGVHTFPAVLQSSGLYSLSSVVTVPSSSLGTQTYICNVNHKPSDTKVDKKVEPKSCDKTHTCPPC
PAPPVAGPSVFLFPPKPKDTLMISRTPEVTCVVVDVKHEDPEVKFNWYVDGVEVHNAKTKPREEEYNSTYRVVSVLT
VLHQDWLNGKEYKCKVSNKALPAPIEKTISKAKGQPREPQVYTLPPSREEMTKNQVSLTCDVSGFYPSDIAVEWESD
GQPENNYKTTPPVLDSDGSFFLYSKLTVDKSRWEQGDVFSCSVLHEALHSHYTQKSLSLSPGK scFv Chain 2 - 1C11[PD-1]_H3.241_L3.92_scFv(GKPGS)4_Fc(216)_IgG1_C220S/PVA_/S267K/S364K/E357Q/M428L/N434S (SEQ ID NOS 44669-44678 and linker disclosed as SEQ ID NO: 39202)
EVQLVQSGPELKKPGESVKVSCKASGYTFTHYGINWVRQPPGQGLEWMGWINTYTGEPYYAPGFQERFVFSIDTSQD
TAYLQINSLKAEDTAVYYCARDYYGSSPYWGQGTLVTVSS/GKPGSGKPGSGKPGSGKPGS/DIVMTQSPDSLAVSL
GERVTINCKASQSIVHSNGNTYLEWYQQKPGQPPKLLIYKVSNRFTGVPDRFSGSGSGTDFTLTISSLQAEDVAVYY
CFQGSHVPNTFGGGTKVEIK/EPKSSDKTHTCPPCPAPPVAGPSVFLFPPKPKDTLMISRTPEVTCVVVDVKHEDPE
VKFNWYVDGVEVHNAKTKPREEQYNSTYRVVSVLTVLHQDWLNGKEYKCKVSNKALPAPIEKTISKAKGQPREPQVY
TLPPSREQMTKNQVKLTCLVKGFYPSDIAVEWESNGQPENNYKTTPPVLDSDGSFFLYSKLTVDKSRWQQGNVFSCS
VLHEALHSHYTQKSLSLSPGK

Light Chain 3 - [CTLA-4]_L0.22 (SEQ ID NOS 44679-44683)
EIVLTQSPGTLSLSPGERATLSCRASQSVSSSYLAWYQQKPGQAPRLLIYGAFSRATGIPDRFSGSGSGTDFTLTIS
RLEPEDFAVYYCQQYGSSPWTFGQGTKVEIK/RTVAAPSVFIFPPSDEQLKSGTASVVCLLNNFYPREAKVQWKVDNALQ
SGNSQESVTEQDSKDSTYSLSSTLTLSKADYEKHKVYACEVTHQGLSSPVTKSFNRGEC

FIG. 49II

XENCS552 PD-1 X LAG-3 (Xtend)

> 7G8_H3.30_L1.34_[LAG-3]_Fab-1C11[PD-1]_H3.241_L3.92_scFv(GKPGS)4-IgG1_pI(-
)_Isosteric_A_/PVA_/S267K/L368D/K370S/M428L/N434S-
Fc(216)_IgG1_C220S/PVA_/S267K/S364K/E357Q/M428L/N434S

Chain 1 – 7G8_H3.30_ IgG1_pI(-)_Isosteric_A_/PVA_/S267K/L368D/K370S/M428L/N434S (SEQ ID NOS 44684-44688)
EVQLVESGGGLVQPGGSLRLSCAASGFTFDDAWMSWVRQAPGKGLEWVAEISTKANNHATYYAESVKGRFTISRDDSKSSVY
LQMNSLRAEDTAVYYCTRLATWDWYFDVWGQGTTVTVSS/ASTKGPSVFPLAPSSKSTSGGTAALGCLVKDYFPEPVTVSWN
SGALTSGVHTFPAVLQSSGLYSLSSVVTVPSSSLGTQTYICNVNHKPSDTKVDKKVEPKSCDKTHTCPPCPAPPVAGPSVFL
FPPKPKDTLMISRTPEVTCVVVDVKHEDPEVKFNWYVDGVEVHNAKTKPREEEYNSTYRVVSVLTVLHQDWLNGKEYKCKVS
NKALPAPIEKTISKAKGQPREPQVYTLPPSREEMTKNQVSLTCDVSGFYPSDIAVEWESDGQPENNYKTTPPVLDSDGSFFL
YSKLTVDKSRWEQGDVFSCSVLHEALHSHYTQKSLSLSPGK

Chain 2 –1C11[PD-1]_H3.241_L3.92_scFv(GKPGS)4_Fc(216)_IgG1_C220S/PVA_/S267K/S364K/E357Q/M428L/N434S
(SEQ ID NOS 44689-44698 and linker disclosed as SEQ ID NO: 39202)
EVQLVQSGPELKKPGESVKVSCKASGYTFTHYGINWVRQPPGQGLEWMGWINTYTGEPYYAPGFQERFVFSIDTSQDTAYLQ
INSLKAEDTAVYYCARDYYGSSPYWGQGTLVTVSS/GKPGSGKPGSGKPGSGKPGS/DIVMTQSPDSLAVSLGERVTINCKA
SQSIVHSNGNTYLEWYQQKPGQPPKLLIYKVSNRFTGVPDRFSGSGSGTDFTLTISSLQAEDVAVYYCFQGSHVPNTFGGGT
KVEIK/EPKSSDKTHTCPPCPAPPVAGPSVFLFPPKPKDTLMISRTPEVTCVVVDVKHEDPEVKFNWYVDGVEVHNAKTKPR
EEQYNSTYRVVSVLTVLHQDWLNGKEYKCKVSNKALPAPIEKTISKAKGQPREPQVYTLPPSREQMTKNQVKLTCLVKGFYP
SDIAVEWESNGQPENNYKTTPPVLDSDGSFFLYSKLTVDKSRWQQGNVFSCSVLHEALHSHYTQKSLSLSPGK

Chain 3 – 7G8_L1.34 (SEQ ID NOS 44699-44703)
DIVLTQSPSSLSASVGDRVTITCRASQSVDYDGDSYMNWYQQKPGKPPKLLIYAASELESGIPARFSGSGSGTDFTLTISSL
QPEDFATYYCQQSNEDPFTFGSGTKLEIK/RTVAAPSVFIFPPSDEQLKSGTASVVCLLNNFYPREAKVQWKVDNALQSGNS
QESVTEQDSKDSTYSLSSTLTLSKADYEKHKVYACEVTHQGLSSPVTKSFNRGEC XENCS553 PD-1 X LAG-3 (Xtend)

> 2A11_H1.144_L2.142_[LAG-3]_Fab-1C11[PD-1]_H3.241_L3.92_scFv(GKPGS)4-IgG1_pI(-
)_Isosteric_A_/PVA_/S267K/L368D/K370S/M428L/N434S-
Fc(216)_IgG1_C220S/PVA_/S267K/S364K/E357Q/M428L/N434S

Chain 1 – 2A11_H1.144_ IgG1_pI(-)_Isosteric_A_/PVA_/S267K/L368D/K370S/M428L/N434S (SEQ ID NOS 44704-44708)
EVQLVQSGAEVKKPGATVKISCKASGFNIKDYFMHWVQQAPGKGLEWMGWIDPELGDTEYAPKFQGRVTITADTSTNTAYME
LSSLRSEDTAVYYCYARGVYQALDYWGQGTLVTVSS/ASTKGPSVFPLAPSSKSTSGGTAALGCLVKDYFPEPVTVSWNSGA
LTSGVHTFPAVLQSSGLYSLSSVVTVPSSSLGTQTYICNVNHKPSDTKVDKKVEPKSCDKTHTCPPCPAPPVAGPSVFLFPP
KPKDTLMISRTPEVTCVVVDVKHEDPEVKFNWYVDGVEVHNAKTKPREEEYNSTYRVVSVLTVLHQDWLNGKEYKCKVSNKA
LPAPIEKTISKAKGQPREPQVYTLPPSREEMTKNQVSLTCDVSGFYPSDIAVEWESDGQPENNYKTTPPVLDSDGSFFLYSK
LTVDKSRWEQGDVFSCSVLHEALHSHYTQKSLSLSPGK

FIG. 49JJ

Chain 2 – 1C11[PD-1]_H3.241_L3.92_scFv(GKPGS)4_Fc(216)_IgG1_C220S/PVA_/S267K/S364K/E357Q/M428L/N434S
(SEQ ID NOS 44709-44718 and linker disclosed as SEQ ID NO: 39202)
EVQLVQSGPELKKPGESVKVSCKASGYTFTHYGINWVRQPPGQGLEWMGWINTYTGEPYYAPGFQERFVFSIDTSQDTAYLQ
INSLKAEDTAVYYCARDYYGSSPYWGQGTLVTVSS/GKPGSGKPGSGKPGSGKPGS/DIVMTQSPDSLAVSLGERVTINCKA
SQSIVHSNGNTYLEWYQQKPGQPPKLLIYKVSNRFTGVPDRFSGSGSGTDFTLTISSLQAEDVAVYYCFQGSHVPNTFGGGT
KVEIK/EPKSSDKTHTCPPCPAPPVAGPSVFLFPPKPKDTLMISRTPEVTCVVVDVKHEDPEVKFNWYVDGVEVHNAKTKPR
EEQYNSTYRVVSVLTVLHQDWLNGKEYKCKVSNKALPAPIEKTISKAKGQPREPQVYTLPPSREQMTKNQVKLTCLVKGFYP
SDIAVEWESNGQPENNYKTTPPVLDSDGSFFLYSKLTVDKSRWQQGNVFSCSVLHEALHSHYTQKSLSLSPGK

Chain 3 – 2A11_L2.142 (SEQ ID NOS 44719-44723)
DIQMTQSPAFLSVTPGEKVTITCQASQDIGNYLNWFQQKPGQTVKLLIYFTSYLHSGVPSRFSGSGSGTDYTFTISSLEAED
AATYFCQQGNTLPYTFGGGTKVEIK/RTVAAPSVFIFPPSDEQLKSGTASVVCLLNNFYPREAKVQWKVDNALQSGNSQESV
TEQDSKDSTYSLSSTLTLSKADYEKHKVYACEVTHQGLSSPVTKSFNRGEC XENCS554 PD-1 X TIM-3 (Xtend)

> 3H3_H1_L2.1_Fab-1C11[PD-1]_H3.241_L3.92-scFv(GKPGS)4-IgG1_pI(-
)_Isosteric_A_/PVA_/S267K/L368D/K370S/M428L/N434S-
Fc(216)_IgG1_C220S/PVA_/S267K/S364K/E357Q/M428L/N434S

Chain 1 – 3H3_H1_ IgG1_pI(-)_Isosteric_A_/PVA_/S267K/L368D/K370S/M428L/N434S (SEQ ID NOS 44724-44728)
QVTLKESGPVLVKPTETLTLTCTVSGFSLNGYGVNWVRQPPGKGLEWLAMIWGDGSTDYNSALKSRLTISKDNSKSQVVLTM
TNMDPVDTATYYCARSYYTSDEDYWGQGTLVTVSS/ASTKGPSVFPLAPSSKSTSGGTAALGCLVKDYFPEPVTVSWNSGAL
TSGVHTFPAVLQSSGLYSLSSVVTVPSSSLGTQTYICNVNHKPSDTKVDKKVEPKSCDKTHTCPPCPAPPVAGPSVFLFPPK
PKDTLMISRTPEVTCVVVDVKHEDPEVKFNWYVDGVEVHNAKTKPREEEYNSTYRVVSVLTVLHQDWLNGKEYKCKVSNKAL
PAPIEKTISKAKGQPREPQVYTLPPSREEMTKNQVSLTCDVSGFYPSDIAVEWESDGQPENNYKTTPPVLDSDGSFFLYSKL
TVDKSRWEQGDVFSCSVLHEALHSHYTQKSLSLSPGK

Chain 2 – 1C11[PD-1]_H3.241_L3.92_scFv(GKPGS)4_Fc(216)_IgG1_C220S/PVA_/S267K/S364K/E357Q/M428L/N434S
(SEQ ID NOS 44729-44738 and linker disclosed as SEQ ID NO: 39202)
EVQLVQSGPELKKPGESVKVSCKASGYTFTHYGINWVRQPPGQGLEWMGWINTYTGEPYYAPGFQERFVFSIDTSQDTAYLQ
INSLKAEDTAVYYCARDYYGSSPYWGQGTLVTVSS/GKPGSGKPGSGKPGSGKPGS/DIVMTQSPDSLAVSLGERVTINCKA
SQSIVHSNGNTYLEWYQQKPGQPPKLLIYKVSNRFTGVPDRFSGSGSGTDFTLTISSLQAEDVAVYYCFQGSHVPNTFGGGT
KVEIK/EPKSSDKTHTCPPCPAPPVAGPSVFLFPPKPKDTLMISRTPEVTCVVVDVKHEDPEVKFNWYVDGVEVHNAKTKPR
EEQYNSTYRVVSVLTVLHQDWLNGKEYKCKVSNKALPAPIEKTISKAKGQPREPQVYTLPPSREQMTKNQVKLTCLVKGFYP
SDIAVEWESNGQPENNYKTTPPVLDSDGSFFLYSKLTVDKSRWQQGNVFSCSVLHEALHSHYTQKSLSLSPGK

Chain 3 – 3H3_L2.1 (SEQ ID NOS 44739-44743)
DIVMTQSPDSLAVSLGERATINCKSSQSLLNSRTRKNYLAWYQQKPGQSPKLLIYWASTRESGVPDRFTGSGSGTDFTLTIS
SLQAEDVAVYYCKQSYSLRTFGGGTKVEIK/RTVAAPSVFIFPPSDEQLKSGTASVVCLLNNFYPREAKVQWKVDNALQSGN
SQESVTEQDSKDSTYSLSSTLTLSKADYEKHKVYACEVTHQGLSSPVTKSFNRGEC

FIG. 49KK

XENCS555 PD-1 X BTLA (Xtend)

**> 9C6_H1.1_L1_[BTLA]_Fab-1C11[PD-1]_H3.241_L3.92_scFv(GKPGS)4-IgG1_pI(-
)_Isosteric_A_/PVA_/S267K/L368D/K370S/M428L/N434S-
Fc(216)_IgG1_C220S/PVA_/S267K/S364K/E357Q/M428L/N434S**

Chain 1 – 9C6_H1.1_ IgG1_pI(-)_Isosteric_A_/PVA_/S267K/L368D/K370S/M428L/N434S (SEQ ID NOS 44744-44748)
QVQLKESGAEVKKPGASVKVSCKVSGFSLTGYGVNWVRQAPGQGLEWMGMIWIDGSTDYNSKFQGRVTMTKDNSKST
VYMELSSLRSEDTAVYYCARDRPDGRAMDYWGQGTMVTVSS/ASTKGPSVFPLAPSSKSTSGGTAALGCLVKDYFPE
PVTVSWNSGALTSGVHTFPAVLQSSGLYSLSSVVTVPSSSLGTQTYICNVNHKPSDTKVDKKVEPKSCDKTHTCPPC
PAPPVAGPSVFLFPPKPKDTLMISRTPEVTCVVVDVKHEDPEVKFNWYVDGVEVHNAKTKPREEEYNSTYRVVSVLT
VLHQDWLNGKEYKCKVSNKALPAPIEKTISKAKGQPREPQVYTLPPSREEMTKNQVSLTCDVSGFYPSDIAVEWESD
GQPENNYKTTPPVLDSDGSFFLYSKLTVDKSRWEQGDVFSCSVLHEALHSHYTQKSLSLSPGK

**Chain 2 – 1C11[PD-
1]_H3.241_L3.92_scFv(GKPGS)4_Fc(216)_IgG1_C220S/PVA_/S267K/S364K/E357Q/M428L/N434S** (SEQ ID NOS
44749-44758 and linker disclosed as SEQ ID NO: 39202)
EVQLVQSGPELKKPGESVKVSCKASGYTFTHYGINWVRQPPGQGLEWMGWINTYTGEPYYAPGFQERFVFSIDTSQD
TAYLQINSLKAEDTAVYYCARDYYGSSPYWGQGTLVTVSS/GKPGSGKPGSGKPGSGKPGS/DIVMTQSPDSLAVSL
GERVTINCKASQSIVHSNGNTYLEWYQQKPGQPPKLLIYKVSNRFTGVPDRFSGSGSGTDFTLTISSLQAEDVAVYY
CFQGSHVPNTFGGGTKVEIK/EPKSSDKTHTCPPCPAPPVAGPSVFLFPPKPKDTLMISRTPEVTCVVVDVKHEDPE
VKFNWYVDGVEVHNAKTKPREEQYNSTYRVVSVLTVLHQDWLNGKEYKCKVSNKALPAPIEKTISKAKGQPREPQVY
TLPPSREQMTKNQVKLTCLVKGFYPSDIAVEWESNGQPENNYKTTPPVLDSDGSFFLYSKLTVDKSRWQQGNVFSCS
VLHEALHSHYTQKSLSLSPGK

Chain 3 – 9C6_L1 (SEQ ID NOS 44759-44763)
SIVMTQSPDSLAVSLGERATINCKASQSVSNDVAWYQQKPGQSPKLLIYYASNRYTGVPDRFTGSGYGTDFTLTISS
LQAEDVAVYFCQQDYSSPTFGGGTKLEIK/RTVAAPSVFIFPPSDEQLKSGTASVVCLLNNFYPREAKVQWKVDNAL
QSGNSQESVTEQDSKDSTYSLSSTLTLSKADYEKHKVYACEVTHQGLSSPVTKSFNRGEC

FIG. 50A

XENCS:556 (BO skeleton 1)

> [αXXX]_HXLX_Fab-1C11[PD-1]_H3.234_L3.144_scFv(GKPGS)4-IgG1_pI(-
)_Isosteric_A_/PVA_/S267K/L368D/K370S-Fc(216)_IgG1_C220S/PVA_/S267K/S364K/E357Q

Fab Chain 1 – [αXXX]_HX_IgG1_pI(-)_Isosteric_A_/PVA_/S267K/L368D/K370S (SEQ ID NO: 44764)
/ASTKGPSVFPLAPSSKSTSGGTAALGCLVKDYFPEPVTVSWNSGALTSGVHTFPAVLQSSGLYSLSSVVTVPSSSL
GTQTYICNVNHKPSDTKVDKKVEPKSCDKTHTCPPCPAPPVAGPSVFLFPPKPKDTLMISRTPEVTCVVVDVKHEDP
EVKFNWYVDGVEVHNAKTKPREEEYNSTYRVVSVLTVLHQDWLNGKEYKCKVSNKALPAPIEKTISKAKGQPREPQV
YTLPPSREEMTKNQVSLTCDVSGFYPSDIAVEWESDGQPENNYKTTPPVLDSDGSFFLYSKLTVDKSRWEQGDVFSC
SVMHEALHNHYTQKSLSLSPGK scFv Chain 2 – 1C11[PD-1]_H3.234_L3.144_scFv(GKPGS)4_Fc(216)_IgG1_C220S/PVA_/S267K/S364K/E357Q (SEQ
ID NOS 44765-44774 and linker disclosed as SEQ ID NO: 39202)
EVQLVQSGSELKKPGESVKVSCKASGYTFTHYGINWVRQPPGQGLEWMGWINTYTGEPYYAPGFQERFVFSLDTSQD
TAYLQINSLKAEDTAVYYCARDYYGSSPYWGQGTLVTVSS/GKPGSGKPGSGKPGSGKPGS/DIVMTQSPDSLAVSL
GERVTINCKASQSIVHSNGNTYLEWYQQKPGQPPKLLIYKVSNRFSGVPDRFSGSGSGTDFTLTISSVEAEDAATYY
CFQGSHVPNTFGQGTKVEIK/EPKSSDKTHTCPPCPAPPVAGPSVFLFPPKPKDTLMISRTPEVTCVVVDVKHEDPE
VKFNWYVDGVEVHNAKTKPREEQYNSTYRVVSVLTVLHQDWLNGKEYKCKVSNKALPAPIEKTISKAKGQPREPQVY
TLPPSREQMTKNQVKLTCLVKGFYPSDIAVEWESNGQPENNYKTTPPVLDSDGSFFLYSKLTVDKSRWQQGNVFSCS
VMHEALHNHYTQKSLSLSPGK

Light Chain 3 – [αXXX]_LX (SEQ ID NO: 44775)
/RTVAAPSVFIFPPSDEQLKSGTASVVCLLNNFYPREAKVQWKVDNALQSGNSQESVTEQDSKDSTYSLSSTLTLSK
ADYEKHKVYACEVTHQGLSSPVTKSFNRGEC XENCS557 (BO skeleton 2)

> [αXXX]_HXLX_Fab-1C11[PD-1]_H3.240_L3.148_scFv(GKPGS)4-IgG1_pI(-
)_Isosteric_A_/PVA_/S267K/L368D/K370S-Fc(216)_IgG1_C220S/PVA_/S267K/S364K/E357Q

Fab Chain 1 – [αXXX]_HX_ IgG1_pI(-)_Isosteric_A_/PVA_/S267K/L368D/K370S (SEQ ID NO: 44776)
/ASTKGPSVFPLAPSSKSTSGGTAALGCLVKDYFPEPVTVSWNSGALTSGVHTFPAVLQSSGLYSLSSVVTVPSSSL
GTQTYICNVNHKPSDTKVDKKVEPKSCDKTHTCPPCPAPPVAGPSVFLFPPKPKDTLMISRTPEVTCVVVDVKHEDP
EVKFNWYVDGVEVHNAKTKPREEEYNSTYRVVSVLTVLHQDWLNGKEYKCKVSNKALPAPIEKTISKAKGQPREPQV
YTLPPSREEMTKNQVSLTCDVSGFYPSDIAVEWESDGQPENNYKTTPPVLDSDGSFFLYSKLTVDKSRWEQGDVFSC
SVMHEALHNHYTQKSLSLSPGK

FIG. 50B scFv Chain 2 – 1C11[PD-1]_H3.240_L3.148_scFv(GKPGS)4_Fc(216)_IgG1_C220S/PVA_/S267K/S364K/E357Q (SEQ ID NOS 44777-44786 and linker disclosed as SEQ ID NO: 39202)
QVQLVQSGPELKKPGESVKVSCKASGYTFTHYGINWVRQPPGQGLEWMGWINTYTGEPYYAPGFQERFVFSIDTSQD
TAYLQINSLKAEDTAVYYCARDYYGSSPYWGQGTLVTVSS/GKPGSGKPGSGKPGSGKPGS/DVLMTQSPDSLAVSL
GERATINCKSSQSIVHSNGNTYLEWYQQKPGQSPKLLIYKVSNRFSGVPDRFSGSGSGTDFTLTISSLQAEDVAVYY
CFQGSHVPNTFGGGTKVEIK/EPKSSDKTHTCPPCPAPPVAGPSVFLFPPKPKDTLMISRTPEVTCVVVDVKHEDPE
VKFNWYVDGVEVHNAKTKPREEQYNSTYRVVSVLTVLHQDWLNGKEYKCKVSNKALPAPIEKTISKAKGQPREPQVY
TLPPSREQMTKNQVKLTCLVKGFYPSDIAVEWESNGQPENNYKTTPPVLDSDGSFFLYSKLTVDKSRWQQGNVFSCS
VMHEALHNHYTQKSLSLSPGK

Light Chain 3 – [αXXX]_LX (SEQ ID NO: 44787)
/RTVAAPSVFIFPPSDEQLKSGTASVVCLLNNFYPREAKVQWKVDNALQSGNSQESVTEQDSKDSTYSLSSTLTLSK
ADYEKHKVYACEVTHQGLSSPVTKSFNRGEC XENCS558 (BO skeleton 3)

> [αXXX]_HXLX_Fab-1C11[PD-1]_H3.241_L3.148_scFv(GKPGS)4-IgG1_pI(-)_Isosteric_A_/PVA_/S267K/L368D/K370S-Fc(216)_IgG1_C220S/PVA_/S267K/S364K/E357Q

Fab Chain 1 – [αXXX]_HX_IgG1_pI(-)_Isosteric_A_/PVA_/S267K/L368D/K370S (SEQ ID NO: 44788)
/ASTKGPSVFPLAPSSKSTSGGTAALGCLVKDYFPEPVTVSWNSGALTSGVHTFPAVLQSSGLYSLSSVVTVPSSSL
GTQTYICNVNHKPSDTKVDKKVEPKSCDKTHTCPPCPAPPVAGPSVFLFPPKPKDTLMISRTPEVTCVVVDVKHEDP
EVKFNWYVDGVEVHNAKTKPREEEYNSTYRVVSVLTVLHQDWLNGKEYKCKVSNKALPAPIEKTISKAKGQPREPQV
YTLPPSREEMTKNQVSLTCDVSGFYPSDIAVEWESDGQPENNYKTTPPVLDSDGSFFLYSKLTVDKSRWEQGDVFSC
SVMHEALHNHYTQKSLSLSPGK scFv Chain 2 – 1C11[PD-1]_H3.241_L3.148_scFv(GKPGS)4_Fc(216)_IgG1_C220S/PVA_/S267K/S364K/E357Q (SEQ ID NOS 44789-44798 and linker disclosed as SEQ ID NO: 39202)
EVQLVQSGPELKKPGESVKVSCKASGYTFTHYGINWVRQPPGQGLEWMGWINTYTGEPYYAPGFQERFVFSIDTSQD
TAYLQINSLKAEDTAVYYCARDYYGSSPYWGQGTLVTVSS/GKPGSGKPGSGKPGSGKPGS/DVLMTQSPDSLAVSL
GERATINCKSSQSIVHSNGNTYLEWYQQKPGQSPKLLIYKVSNRFSGVPDRFSGSGSGTDFTLTISSLQAEDVAVYY
CFQGSHVPNTFGGGTKVEIK/EPKSSDKTHTCPPCPAPPVAGPSVFLFPPKPKDTLMISRTPEVTCVVVDVKHEDPE
VKFNWYVDGVEVHNAKTKPREEQYNSTYRVVSVLTVLHQDWLNGKEYKCKVSNKALPAPIEKTISKAKGQPREPQVY
TLPPSREQMTKNQVKLTCLVKGFYPSDIAVEWESNGQPENNYKTTPPVLDSDGSFFLYSKLTVDKSRWQQGNVFSCS
VMHEALHNHYTQKSLSLSPGK

Light Chain 3 – [αXXX]_LX (SEQ ID NO: 44799)
/RTVAAPSVFIFPPSDEQLKSGTASVVCLLNNFYPREAKVQWKVDNALQSGNSQESVTEQDSKDSTYSLSSTLTLSK
ADYEKHKVYACEVTHQGLSSPVTKSFNRGEC XENCS559 (BO skeleton 4)

> [αXXX]_HXLX_Fab-1C11[PD-1]_H3.241_L3.92_scFv(GKPGS)4-IgG1_pI(-)_Isosteric_A_/PVA_/S267K/L368D/K370S-Fc(216)_IgG1_C220S/PVA_/S267K/S364K/E357Q

FIG. 50C

Fab Chain 1 – [αXXX]_HX_ IgG1_pI(-)_Isosteric_A_/PVA_/S267K/L368D/K370S (SEQ ID NO: 44800)
/ASTKGPSVFPLAPSSKSTSGGTAALGCLVKDYFPEPVTVSWNSGALTSGVHTFPAVLQSSGLYSLSSVVTVPSSSL
GTQTYICNVNHKPSDTKVDKKVEPKSCDKTHTCPPCPAPPVAGPSVFLFPPKPKDTLMISRTPEVTCVVVDVKHEDP
EVKFNWYVDGVEVHNAKTKPREEEYNSTYRVVSVLTVLHQDWLNGKEYKCKVSNKALPAPIEKTISKAKGQPREPQV
YTLPPSREEMTKNQVSLTCDVSGFYPSDIAVEWESDGQPENNYKTTPPVLDSDGSFFLYSKLTVDKSRWEQGDVFSC
SVMHEALHNHYTQKSLSLSPGK scFv Chain 2 – 1C11[PD-1]_H3.241_L3.92_scFv(GKPGS)4_Fc(216)_IgG1_C220S/PVA_/S267K/S364K/E357Q (SEQ ID NOS 44801-44810 and linker disclosed as SEQ ID NO: 39202)
EVQLVQSGPELKKPGESVKVSCKASGYTFTHYGINWVRQPPGQGLEWMGWINTYTGEPYYAPGFQERFVFSIDTSQD
TAYLQINSLKAEDTAVYYCARDYYGSSPYWGQGTLVTVSS/GKPGSGKPGSGKPGSGKPGS/DIVMTQSPDSLAVSL
GERVTINCKASQSIVHSNGNTYLEWYQQKPGQPPKLLIYKVSNRFTGVPDRFSGSGSGTDFTLTISSLQAEDVAVYY
CFQGSHVPNTFGGGTKVEIK/EPKSSDKTHTCPPCPAPPVAGPSVFLFPPKPKDTLMISRTPEVTCVVVDVKHEDPE
VKFNWYVDGVEVHNAKTKPREEQYNSTYRVVSVLTVLHQDWLNGKEYKCKVSNKALPAPIEKTISKAKGQPREPQVY
TLPPSREQMTKNQVKLTCLVKGFYPSDIAVEWESNGQPENNYKTTPPVLDSDGSFFLYSKLTVDKSRWQQGNVFSCS
VMHEALHNHYTQKSLSLSPGK

Light Chain 3 – [αXXX]_LX (SEQ ID NO: 44811)
/RTVAAPSVFIFPPSDEQLKSGTASVVCLLNNFYPREAKVQWKVDNALQSGNSQESVTEQDSKDSTYSLSSTLTLSK
ADYEKHKVYACEVTHQGLSSPVTKSFNRGEC

XENCS560 (BO skeleton 5)

> [αXXX]_HXLX_Fab-1C11[PD-1]_H3.234_L3.144_scFv(GKPGS)4-IgG1_pI(-)_Isosteric_A_/PVA_/S267K/L368D/K370S/M428L/N434S-Fc(216)_IgG1_C220S/PVA_/S267K/S364K/E357Q/M428L/N434S

Fab Chain 1 – [αXXX]_HX_IgG1_pI(-)_Isosteric_A_/PVA_/S267K/L368D/K370S/M428L/N434S (SEQ ID NO: 44812)
/ASTKGPSVFPLAPSSKSTSGGTAALGCLVKDYFPEPVTVSWNSGALTSGVHTFPAVLQSSGLYSLSSVVTVPSSSL
GTQTYICNVNHKPSDTKVDKKVEPKSCDKTHTCPPCPAPPVAGPSVFLFPPKPKDTLMISRTPEVTCVVVDVKHEDP
EVKFNWYVDGVEVHNAKTKPREEEYNSTYRVVSVLTVLHQDWLNGKEYKCKVSNKALPAPIEKTISKAKGQPREPQV
YTLPPSREEMTKNQVSLTCDVSGFYPSDIAVEWESDGQPENNYKTTPPVLDSDGSFFLYSKLTVDKSRWEQGDVFSC
SVLHEALHSHYTQKSLSLSPGK scFv Chain 2 – 1C11[PD-1]_H3.234_L3.144_scFv(GKPGS)4_Fc(216)_IgG1_C220S/PVA_/S267K/S364K/E357Q/M428L/N434S (SEQ ID NOS 44813-44822 and linker disclosed as SEQ ID NO: 39202)
EVQLVQSGSELKKPGESVKVSCKASGYTFTHYGINWVRQPPGQGLEWMGWINTYTGEPYYAPGFQERFVFSLDTSQD
TAYLQINSLKAEDTAVYYCARDYYGSSPYWGQGTLVTVSS/GKPGSGKPGSGKPGSGKPGS/DIVMTQSPDSLAVSL
GERVTINCKASQSIVHSNGNTYLEWYQQKPGQPPKLLIYKVSNRFSGVPDRFSGSGSGTDFTLTISSVEAEDAATYY
CFQGSHVPNTFGQGTKVEIK/EPKSSDKTHTCPPCPAPPVAGPSVFLFPPKPKDTLMISRTPEVTCVVVDVKHEDPE
VKFNWYVDGVEVHNAKTKPREEQYNSTYRVVSVLTVLHQDWLNGKEYKCKVSNKALPAPIEKTISKAKGQPREPQVY
TLPPSREQMTKNQVKLTCLVKGFYPSDIAVEWESNGQPENNYKTTPPVLDSDGSFFLYSKLTVDKSRWQQGNVFSCS
VLHEALHSHYTQKSLSLSPGK

FIG. 50D

Light Chain 3 – [αXXX]_LX (SEQ ID NO: 44823)
/RTVAAPSVFIFPPSDEQLKSGTASVVCLLNNFYPREAKVQWKVDNALQSGNSQESVTEQDSKDSTYSLSSTLTLSK
ADYEKHKVYACEVTHQGLSSPVTKSFNRGEC XENCS561 (BO skeleton 6)

**> [αXXX]_HXLX_Fab-1C11[PD-1]_H3.240_L3.148_scFv(GKPGS)4-IgG1_pI(-
)_Isosteric_A_/PVA_/S267K/L368D/K370S/M428L/N434S-
Fc(216)_IgG1_C220S/PVA_/S267K/S364K/E357Q/M428L/N434S**

Fab Chain 1 – [αXXX]_HX_IgG1_pI(-)_Isosteric_A_/PVA_/S267K/L368D/K370S/M428L/N434S (SEQ ID NO: 44824)
/ASTKGPSVFPLAPSSKSTSGGTAALGCLVKDYFPEPVTVSWNSGALTSGVHTFPAVLQSSGLYSLSSVVTVPSSSL
GTQTYICNVNHKPSDTKVDKKVEPKSCDKTHTCPPCPAPPVAGPSVFLFPPKPKDTLMISRTPEVTCVVVDVKHEDP
EVKFNWYVDGVEVHNAKTKPREEEYNSTYRVVSVLTVLHQDWLNGKEYKCKVSNKALPAPIEKTISKAKGQPREPQV
YTLPPSREEMTKNQVSLTCDVSGFYPSDIAVEWESDGQPENNYKTTPPVLDSDGSFFLYSKLTVDKSRWEQGDVFSC
SVLHEALHSHYTQKSLSLSPGK

**scFv Chain 2 – 1C11[PD-
1]_H3.240_L3.148_scFv(GKPGS)4_Fc(216)_IgG1_C220S/PVA_/S267K/S364K/E357Q/M428L/N434S** (SEQ ID NOS
44825-44834 and linker disclosed as SEQ ID NO: 39202)
QVQLVQSGPELKKPGESVKVSCKASGYTFT<u>HYGINW</u>VRQPPGQGLEWMG<u>WINTYTGEPYYAPGFQER</u>FVFSIDTSQD
TAYLQINSLKAEDTAVYYCARD<u>YYGSSPYW</u>GQGTLVTVSS/<u>GKPGSGKPGSGKPGSGKPGS</u>/DVLMTQSPDSLAVSL
GERATINCK<u>SSQSIVHSNGNTYLE</u>WYQQKPGQSPKLLIY<u>KVSNRF</u>SGVPDRFSGSGSGTDFTLTISSLQAEDVAVYY
CF<u>QGSHVPNTFGGG</u>TKVEIK/EPKSSDKTHTCPPCPAPPVAGPSVFLFPPKPKDTLMISRTPEVTCVVVDVKHEDPE
VKFNWYVDGVEVHNAKTKPREEQYNSTYRVVSVLTVLHQDWLNGKEYKCKVSNKALPAPIEKTISKAKGQPREPQVY
TLPPSREQMTKNQVKLTCLVKGFYPSDIAVEWESNGQPENNYKTTPPVLDSDGSFFLYSKLTVDKSRWQQGNVFSCS
VLHEALHSHYTQKSLSLSPGK

Liight Chain 3 – [αXXX]_LX (SEQ ID NO: 44835)
/RTVAAPSVFIFPPSDEQLKSGTASVVCLLNNFYPREAKVQWKVDNALQSGNSQESVTEQDSKDSTYSLSSTLTLSK
ADYEKHKVYACEVTHQGLSSPVTKSFNRGEC XENCS562 (BO skeleton 7)

**> [αXXX]_HXLX_Fab-1C11[PD-1]_H3.241_L3.148_scFv(GKPGS)4-IgG1_pI(-
)_Isosteric_A_/PVA_/S267K/L368D/K370S/M428L/N434S-
Fc(216)_IgG1_C220S/PVA_/S267K/S364K/E357Q/M428L/N434S**

Fab Chain 1 – [αXXX]_HX_IgG1_pI(-)_Isosteric_A_/PVA_/S267K/L368D/K370S/M428L/N434S (SEQ ID NO: 44836)
/ASTKGPSVFPLAPSSKSTSGGTAALGCLVKDYFPEPVTVSWNSGALTSGVHTFPAVLQSSGLYSLSSVVTVPSSSL
GTQTYICNVNHKPSDTKVDKKVEPKSCDKTHTCPPCPAPPVAGPSVFLFPPKPKDTLMISRTPEVTCVVVDVKHEDP
EVKFNWYVDGVEVHNAKTKPREEEYNSTYRVVSVLTVLHQDWLNGKEYKCKVSNKALPAPIEKTISKAKGQPREPQV
YTLPPSREEMTKNQVSLTCDVSGFYPSDIAVEWESDGQPENNYKTTPPVLDSDGSFFLYSKLTVDKSRWEQGDVFSC
SVLHEALHSHYTQKSLSLSPGK

FIG. 50E scFv Chain 2 – 1C11[PD-1]_H3.241_L3.148_scFv(GKPGS)4_Fc(216)_IgG1_C220S/PVA_/S267K/S364K/E357Q/M428L/N434S (SEQ ID NOS 44837-44846 and linker disclosed as SEQ ID NO: 39202)
EVQLVQSGPELKKPGESVKVSCKASGYTFTHYGINWVRQPPGQGLEWMGWINTYTGEPYYAPGFQERFVFSIDTSQD
TAYLQINSLKAEDTAVYYCARDYYGSSPYWGQGTLVTSS/GKPGSGKPGSGKPGSGKPGS/DVLMTQSPDSLAVSL
GERATINCKSSQSIVHSNGNTYLEWYQQKPGQSPKLLIYKVSNRFSGVPDRFSGSGSGTDFTLTISSLQAEDVAVYY
CFQGSHVPNTFGGGTKVEIK/EPKSSDKTHTCPPCPAPPVAGPSVFLFPPKPKDTLMISRTPEVTCVVVDVKHEDPE
VKFNWYVDGVEVHNAKTKPREEQYNSTYRVVSVLTVLHQDWLNGKEYKCKVSNKALPAPIEKTISKAKGQPREPQVY
TLPPSREQMTKNQVKLTCLVKGFYPSDIAVEWESNGQPENNYKTTPPVLDSDGSFFLYSKLTVDKSRWQQGNVFSCS
VLHEALHSHYTQKSLSLSPGK

Light Chain 3 – [αXXX]_LX (SEQ ID NO: 44847)
/RTVAAPSVFIFPPSDEQLKSGTASVVCLLNNFYPREAKVQWKVDNALQSGNSQESVTEQDSKDSTYSLSSTLTLSK
ADYEKHKVYACEVTHQGLSSPVTKSFNRGEC XENCS563 (BO skeleton 8)

>[αXXX]_HXLX_Fab-1C11[PD-1]_H3.241_L3.92_scFv(GKPGS)4-IgG1_pI(-)_Isosteric_A_/PVA_/S267K/L368D/K370S/M428L/N434S-Fc(216)_IgG1_C220S/PVA_/S267K/S364K/E357Q/M428L/N434S

Fab Chain 1 – [αXXX]_HX_IgG1_pI(-)_Isosteric_A_/PVA_/S267K/L368D/K370S/M428L/N434S (SEQ ID NO: 44848)
/ASTKGPSVFPLAPSSKSTSGGTAALGCLVKDYFPEPVTVSWNSGALTSGVHTFPAVLQSSGLYSLSSVVTVPSSSL
GTQTYICNVNHKPSDTKVDKKVEPKSCDKTHTCPPCPAPPVAGPSVFLFPPKPKDTLMISRTPEVTCVVVDVKHEDP
EVKFNWYVDGVEVHNAKTKPREEEYNSTYRVVSVLTVLHQDWLNGKEYKCKVSNKALPAPIEKTISKAKGQPREPQV
YTLPPSREEMTKNQVSLTCDVSGFYPSDIAVEWESDGQPENNYKTTPPVLDSDGSFFLYSKLTVDKSRWEQGDVFSC
SVLHEALHSHYTQKSLSLSPGK scFv Chain 2 – 1C11[PD-1]_H3.241_L3.92_scFv(GKPGS)4_Fc(216)_IgG1_C220S/PVA_/S267K/S364K/E357Q/M428L/N434S (SEQ ID NOS 44849-44858 and linker disclosed as SEQ ID NO: 39202)
EVQLVQSGPELKKPGESVKVSCKASGYTFTHYGINWVRQPPGQGLEWMGWINTYTGEPYYAPGFQERFVFSIDTSQD
TAYLQINSLKAEDTAVYYCARDYYGSSPYWGQGTLVTSS/GKPGSGKPGSGKPGSGKPGS/DIVMTQSPDSLAVSL
GERVTINCKASQSIVHSNGNTYLEWYQQKPGQPPKLLIYKVSNRFTGVPDRFSGSGSGTDFTLTISSLQAEDVAVYY
CFQGSHVPNTFGGGTKVEIK/EPKSSDKTHTCPPCPAPPVAGPSVFLFPPKPKDTLMISRTPEVTCVVVDVKHEDPE
VKFNWYVDGVEVHNAKTKPREEQYNSTYRVVSVLTVLHQDWLNGKEYKCKVSNKALPAPIEKTISKAKGQPREPQVY
TLPPSREQMTKNQVKLTCLVKGFYPSDIAVEWESNGQPENNYKTTPPVLDSDGSFFLYSKLTVDKSRWQQGNVFSCS
VLHEALHSHYTQKSLSLSPGK

Light Chain 3 – [αXXX]_LX (SEQ ID NO: 44859)
/RTVAAPSVFIFPPSDEQLKSGTASVVCLLNNFYPREAKVQWKVDNALQSGNSQESVTEQDSKDSTYSLSSTLTLSK
ADYEKHKVYACEVTHQGLSSPVTKSFNRGEC Binding avidity of XmAb20717 contributes to T cell activation

FIG. 73

>XENP015074 Numax_IgG1_PVA_/S267K Heavy Chain (SEQ ID NOS 44860-44864)
QVTLRESGPALVKPTQTLTLTCTFSGFSLSTAGMSVGWIRQPPGKALEWLADIWWDDKKHYNPSLKDRLTISKDTSK
NQVVLKVTNMDPADTATYYCARDMIFNFYFDVWGQGTTVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSNTKVDKKVEPKSCDKTHTCP
PCPAPPVAGPSVFLFPPKPKDTLMISRTPEVTCVVVDVKHEDPEVKFNWYVDGVEVHNAKTKPREEQYNSTYRVVSV
LTVLHQDWLNGKEYKCKVSNKALPAPIEKTISKAKGQPREPQVYTLPPSREEMTKNQVSLTCLVKGFYPSDIAVEWE
SNGQPENNYKTTPPVLDSDGSFFLYSKLTVDKSRWQQGNVFSCSVMHEALHNHYTQKSLSLSPGK

>XENP015074 Numax_IgG1_PVA_/S267K Light Chain (SEQ ID NOS 44865-44869)
DIQMTQSPSTLSASVGDRVTITCSASSRVGYMHWYQQKPGKAPKLLIYDTSKLASGVPSRFSGSGSGTEFTLTISSL
QPDDFATYYCFQGSGYPFTFGGGTKVEIK/RTVAAPSVFIFPPSDEQLKSGTASVVCLLNNFYPREAKVQWKVDNAL
QSGNSQESVTEQDSKDSTYSLSSTLTLSKADYEKHKVYACEVTHQGLSSPVTKSFNRGEC

FIG. 74

>XENP016432 Nivolumab_H0L0_IgG1_PVA_/S267K Heavy Chain (SEQ ID NOS 44870-44874)
QVQLVESGGGVVQPGRSLRLDCKASGITFSNSGMHWVRQAPGKGLEWVAVIWYDGSKRYYADSVKGRFTISRDNSKN
TLFLQMNSLRAEDTAVYYCATNDDYWGQGTLVTVSS/ASTKGPSVFPLAPSSKSTSGGTAALGCLVKDYFPEPVTVS
WNSGALTSGVHTFPAVLQSSGLYSLSSVVTVPSSSLGTQTYICNVNHKPSNTKVDKKVEPKSCDKTHTCPPCPAPPV
AGPSVFLFPPKPKDTLMISRTPEVTCVVVDVKHEDPEVKFNWYVDGVEVHNAKTKPREEQYNSTYRVVSVLTVLHQD
WLNGKEYKCKVSNKALPAPIEKTISKAKGQPREPQVYTLPPSREEMTKNQVSLTCLVKGFYPSDIAVEWESNGQPEN
NYKTTPPVLDSDGSFFLYSKLTVDKSRWQQGNVFSCSVMHEALHNHYTQKSLSLSPGK

>XENP016432 Nivolumab_H0L0_IgG1_PVA_/S267K Light Chain (SEQ ID NOS 44875-44879)
EIVLTQSPATLSLSPGERATLSCRASQSVSSYLAWYQQKPGQAPRLLIYDASNRATGIPARFSGSGSGTDFTLTISS
LEPEDFAVYYCQQSSNWPRTFGQGTKVEIK/RTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSPVTKSFNRGEC

FIG. 75

>XENP021461 Pembrolizumab_H0L0_IgG4_S228P Heavy Chain (SEQ ID NOS 44880-44884)
QVQLVQSGVEVKKPGASVKVSCKASGYTFTNYYMYWVRQAPGQGLEWMGGINPSNGGTNFNEKFKNRVTLTTDSSTT
TAYMELKSLQFDDTAVYYCARRDYRFDMGFDYWGQGTTVTVSS/ASTKGPSVFPLAPCSRSTSESTAALGCLVKDYF
PEPVTVSWNSGALTSGVHTFPAVLQSSGLYSLSSVVTVPSSSLGTKTYTCNVDHKPSNTKVDKRVESKYGPPCPPCP
APEFLGGPSVFLFPPKPKDTLMISRTPEVTCVVVDVSQEDPEVQFNWYVDGVEVHNAKTKPREEQFNSTYRVVSVLT
VLHQDWLNGKEYKCKVSNKGLPSSIEKTISKAKGQPREPQVYTLPPSQEEMTKNQVSLTCLVKGFYPSDIAVEWESN
GQPENNYKTTPPVLDSDGSFFLYSRLTVDKSRWQEGNVFSCSVMHEALHNHYTQKSLSLSLGK

>XENP021461 Pembrolizumab_H0L0_IgG4_S228P Light Chain (SEQ ID NOS 44885-44889)
EIVLTQSPATLSLSPGERATLSCRASKGVSTSGYSYLHWYQQKPGQAPRLLIYLASYLESGVPARFSGSGSGTDFTL
TISSLEPEDFAVYYCQHSRDLPLTFGGGTKVEIK/RTVAAPSVFIFPPSDEQLKSGTASVVCLLNNFYPREAKVQWK
VDNALQSGNSQESVTEQDSKDSTYSLSSTLTLSKADYEKHKVYACEVTHQGLSSPVTKSFNRGEC

FIG. 79

| Test Article | $C_{max}$ (µg/mL) | $V_d$ (mL/kg) | $t_{1/2}$ (days) | AUC∞ (day*µg/mL) | CL (mL/day/kg) | $V_{ss}$ (mL/kg) | MRTinf_pred (days) |
|---|---|---|---|---|---|---|---|
| XENP20053 | 42.92 | 48.1 | 3.8 | 185.5 | 11.1 | 53.4 | 4.8 |
| XmAb20717 | 27.57 | 73.0 | 9.0 | 227.9 | 808 | 107.5 | 12.2 |

FIG. 83

| XmAb20717 binding partner | Human | | | Cynomolgus Monkey | | |
|---|---|---|---|---|---|---|
| | $K_D$ (M) | $k_a$ (1/Ms) | $k_d$ (1/s) | $K_D$ (M) | $k_a$ (1/Ms) | $k_d$ (1/s) |
| CTLA4 | $4.1 \times 10^{-9}$ | $2.9 \times 10^5$ | $1.2 \times 10^{-3}$ | $2.3 \times 10^{-8}$ | $4.0 \times 10^5$ | $9.1 \times 10^{-3}$ |
| PD1 | $1.4 \times 10^{-9}$ | $3.1 \times 10^5$ | $4.3 \times 10^{-4}$ | $5.5 \times 10^{-9}$ | $1.9 \times 10^5$ | $1.1 \times 10^{-3}$ |

FIG. 89

| Receptor | $K_D$ (M) | |
|---|---|---|
| | XmAb20717 | XENP20053 |
| Human FcRn | $2.9 \times 10^{-7}$ | $7.5 \times 10^{-5}$ |
| Cynomolgus FcRn | $5.1 \times 10^{-7}$ | Low binding signal |
| Mouse FcRn | $4.6 \times 10^{-8}$ | $1.4 \times 10^{-7}$ |

FIG. 99

>XENP16434 YW243.55.S70_H0L0_IgG1_PVA_/S267K
XENP16434 YW243.55.S70_H0 Heavy Chain (SEQ ID NOS 44890-44894)
EVQLVESGGGLVQPGGSLRLSCAASGFTFSDSWIHWVRQAPGKGLEWVAWISPYGGSTYYADSVKGRFTI
SADTSKNTAYLQMNSLRAEDTAVYYCARRHWPGGFDYWGQGTLVTVSS/ASTKGPSVFPLAPSSKSTSGG
TAALGCLVKDYFPEPVTVSWNSGALTSGVHTFPAVLQSSGLYSLSSVVTVPSSSLGTQTYICNVNHKPSN
TKVDKKVEPKSCDKTHTCPPCPAPPVAGPSVFLFPPKPKDTLMISRTPEVTCVVVDVKHEDPEVKFNWYV
DGVEVHNAKTKPREEQYNSTYRVVSVLTVLHQDWLNGKEYKCKVSNKALPAPIEKTISKAKGQPREPQVY
TLPPSREEMTKNQVSLTCLVKGFYPSDIAVEWESNGQPENNYKTTPPVLDSDGSFFLYSKLTVDKSRWQQ
GNVFSCSVMHEALHNHYTQKSLSLSPGK

XENP16434 YW243.55.S70_L0 Light Chain (SEQ ID NOS 44895-44899)
DIQMTQSPSSLSASVGDRVTITCRASQDVSTAVAWYQQKPGKAPKLLIYSASFLYSGVPSRFSGSGSGTD
FTLTISSLQPEDFATYYCQQYLYHPATFGQGTKVEIK/RTVAAPSVFIFPPSDEQLKSGTASVVCLLNNF
YPREAKVQWKVDNALQSGNSQESVTEQDSKDSTYSLSSTLTLSKADYEKHKVYACEVTHQGLSSPVTKSF
NRGEC

FIG. 107

>XENP29154_TGN1412_hu5.11A1[CD28]_H1L1_IgG4_K447del

XENP29154_TGN1412_hu5.11A1[CD28]_H1_IgG4_K447del Heavy Chain (SEQ ID NOS 44900-44904)

EVQLVESGGGLVQPGGSLRLSCAASGFTFSDSWIHWVRQAPGKGLEWVAWISPYGGSTYYADSVKGRFTISADTSKN
TAYLQMNSLRAEDTAVYYCARRHWPGGFDYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCPAPP
VAGPSVFLFPPKPKDTLMISRTPEVTCVVVDVKHEDPEVKFNWYVDGVEVHNAKTKPREEQYNSTYRVVSVLTVLHQD
WLNGKEYKCKVSNKALPAPIEKTISKAKGQPREPQVYTLPPSREEMTKNQVSLTCLVKGFYPSDIAVEWESNGQPENNY
KTTPPVLDSDGSFFLYSKLTVDKSRWQQGNVFSCSVMHEALHNHYTQKSLSLSPGK

XENP29154 TGN1412_hu5.11A1[CD28]_ L1 Light Chain (SEQ ID NOS 44905-44909)

DIQMTQSPSSLSASVGDRVTITCRASQDVSTAVAWYQQKPGKAPKLLIYSASFLYSGVPSRFSGSGSGTDFTLTISSLQP
EDFATYYCQQYLYHPATFGQGTKVEIK/RTVAAPSVFIFPPSDEQLKSGTASVVCLLNNFYPREAKVQWKVDNALQSGN
SQESVTEQDSKDSTYSLSSTLTLSKADYEKHKVYACEVTHQGLSSPVTKSFNRGEC

FIG. 111

| XmAb22841 Binding Partner | Human | | | Cynomolgus Monkey | | |
|---|---|---|---|---|---|---|
| | $K_D$ (nM) | $k_a$ (1/Ms) | $k_d$ (1/s) | $K_D$ (nM) | $k_a$ (1/Ms) | $k_d$ (1/s) |
| CTLA4 | 4.6 | $1.6 \times 10^5$ | $7.3 \times 10^{-4}$ | 17.6 | $1.7 \times 10^5$ | $2.9 \times 10^{-3}$ |
| LAG3 | 1.4 | $8.1 \times 10^4$ | $1.2 \times 10^{-4}$ | 1.3 | $8.2 \times 10^5$ | $1.0 \times 10^{-3}$ |

FIG. 117

| Receptor | $K_D$ (M) | |
|---|---|---|
| | XmAb22841 | XENP22602 |
| Human FcRn | $1.4 \times 10^{-7}$ | $2.3 \times 10^{-6}$ |
| Cynomolgus monkey FcRn | $9.5 \times 10^{-8}$ | $1.2 \times 10^{-6}$ to $1.6 \times 10^{-7}$ [a] |
| Mouse FcRn | $6.3 \times 10^{-8}$ | $1.9 \times 10^{-7}$ |

BISPECIFIC AND MONOSPECIFIC ANTIBODIES USING NOVEL ANTI-PD-1 SEQUENCES

I. PRIORITY CLAIM

This application claims priority to U.S. Patent Application Nos. 62/583,438, filed Nov. 8, 2017; 62/598,938, filed Dec. 14, 2017 and 62/658,227, filed Apr. 16, 2018 all of which are expressly incorporated herein by reference in their entirety, with particular reference to the figures, legends, and claims therein.

II. SEQUENCE LISTING

The instant application contains a Sequence Listing which has been submitted electronically in ASCII format and is hereby incorporated by reference in its entirety. Said ASCII copy, created on May 7, 2019, is named 067461-5215-WO_SL_v2.txt and is 39,084,712 kilobytes in size.

III. BACKGROUND OF THE INVENTION

Checkpoint receptors such as CTLA-4, PD-1 (programmed cell death 1), TIM-3 (T cell immunoglobulin and mucin domain 3), LAG-3 (lymphocyte-activation gene 3), TIGIT (T cell immunoreceptor with Ig and ITIM domains), and others, inhibit the activation, proliferation, and/or effector activities of T cells and other cell types. Guided by the hypothesis that checkpoint receptors suppress the endogenous T cell response against tumor cells, preclinical and clinical studies of anti-CTLA4 and anti-PD1 antibodies, including nivolumab, pembrolizumab, ipilimumab, and tremelimumab, have indeed demonstrated that checkpoint blockade results in impressive anti-tumor responses, stimulating endogenous T cells to attack tumor cells, leading to long-term cancer remissions in a fraction of patients with a variety of malignancies. Unfortunately, only a subset of patients responds to these therapies, with response rates generally ranging from 10 to 30% and sometimes higher for each monotherapy, depending on the indication and other factors. Therapeutic combination of these agents, for example ipilimumab plus nivolumab, leads to even higher response rates, approaching 60% in some cases. Preclinical studies have shown additional synergies between anti-PD-1 antibodies and/or anti-CTLA-4 antibodies with blockade of more recently identified checkpoint receptors, including LAG-3, TIM-3, BTLA and TIGIT. While the potential of multiple checkpoint blockade is very promising, combination therapy with such agents is expected to carry a high financial burden. Moreover, autoimmune toxicities of combination therapies, for example nivolumab plus ipilimumab, are significantly elevated compared to monotherapy, causing many patients to halt the therapy.

A number of studies (Ahmadzadeh et al., Blood 114:1537 (2009), Matsuzaki et al., PNAS 107(17):7875-7880 (2010), Fourcade et al., Cancer Res. 72(4):887-896 (2012) and Gros et al., J. Clinical Invest. 124(5):2246 (2014)) examining tumor-infiltrating lymphocytes (TILs) have shown that TILs commonly express multiple checkpoint receptors. Moreover, it is likely that TILs that express multiple checkpoints are in fact the most tumor-reactive. In contrast, non-tumor reactive T cells in the periphery are more likely to express a single checkpoint. Checkpoint blockade with monospecific full-length antibodies is likely nondiscriminatory with regards to de-repression of tumor-reactive TILs versus autoantigen-reactive single expressing T cells that are assumed to contribute to autoimmune toxicities.

Accordingly, the invention is directed to bispecific antibodies that bind to human PD-1 and a second, different checkpoint inhibitor protein. Also provided are monospecific monoclonal antibodies that bind to human PD-1.

IV. BRIEF SUMMARY OF THE INVENTION

The present invention is directed to novel anti-PD-1 antigen binding domains (ABDs) and their uses in the creation of anti-PD-1 monovalent monoclonal antibodies and heterodimeric, bispecific antibodies that bind to PD-1 and a second target antigen selected from the group consisting of CTLA-4, LAG-3, TIM-3, TIGIT, BTLA and ICOS, and methods of making and using the antibodies.

Accordingly, in some aspects the invention provides anti-PD-1 monovalent monoclonal antibodies. In this aspect, the anti-PD-1 monoclonal antibody comprising: a) a heavy chain comprising, from N- to C-terminal, VH-CH1-hinge-CH2-CH3; and b) a light chain comprising, from N- to C-terminal, VL-CL; wherein the VHCDR1, VHCDR2, VHCDR3, VLCDR1, VLCDR2 and VLCDR3 are selected from the group consisting of the CDRs from XENP26940 in FIG. 24 and the CDRs from XNE28652 in FIG. 40.

In an additional aspect, the antibody has a VH and VL from XENP26940 depicted in FIG. 24.

In a further aspect, the antibody has a VH and VL from XENP28652 depicted in FIG. 40.

In either aspect, the hinge-CH2-CH3 can be an Fc domain selected from the group consisting of the Fc domain from human IgG1, IgG2, IgG3 and IgG4. When from IgG1, the Fc domain can be a variant human IgG1 domain, for example including the amino acid substitutions 427L/434S. Additionally, the variant IgG1 Fc domain can comprise ablation variants selected from those depicted in FIG. 5, and in particular the E233P/L234V/L235A/G236del/S267K substitutions. When the Fc domain is a variant human IgG4 domain it can comprise an S228P amino acid substitution.

In further aspects, the invention provides nucleic acid compositions comprising a first nucleic acid encoding the heavy chain and a second nucleic acid encoding the light chain. Also included are expression vector compositions comprising a first expression vector comprising the first nucleic acid and a second expression vector comprising said second nucleic acid, or a single expression vector comprising said first and second nucleic acids. Further included are host cells comprising the expression vector composition or expression vectors. Methods of making the anti-PD-1 antibodies are also included, comprising culturing the host cells under conditions wherein said antibody is expressed, and recovering said antibody. Furthermore, the invention provides methods of treating cancer in a patient in need thereof comprising administering the antibody to said patient.

In a further aspect, heterodimeric bispecific antibodies are provided. These antibodies comprise: a) a first monomer comprising: i) a single chain Fv domain (scFv) that binds human PD-1, wherein said scFv domain comprises: 1) a first variable heavy domain (VH1); 2) a scFv linker; and 3) a first variable light domain (VL1); and ii) a first variant Fc domain; b) a second monomer comprising: i) a heavy chain comprising a second variable heavy domain (VH2)-CH1-hinge-CH2-CH3; and c) a light chain comprising a second variable light domain (VL2) and a constant light domain (CL); wherein said first variable heavy domain and said first variable light domain form a first antigen binding domain (ABD1) and wherein said second variable heavy domain and said second variable light domain form a second ABD (ABD2) that binds to an antigen selected from human CTLA-4, human LAG-3, human TIM-3, human TIGIT, human BTLA and human ICOS. ABD1 can be any of the 1C11 VH and VL domains as outlined in FIGS. 13, 15, 16, 18, 20, 21, 24, 33 and 40.

In particular aspects, the ABD1 has sequences selected from the pairs consisting of 1C11[PD-1]_H3.234_L3.144 from XENP25806 in FIG. 15, 1C11[PD-1]_H3.240_L3.148 from XENP25812 from FIG. 15, 1C11[PD-1]_H3.241_L3.148 from XENP25813 in FIG. 15 and 1C11[PD-1]_H3.241_L3.92 from XENP25819 in FIG. 15.

In these aspects, the first monomer can comprise, from N- to C-terminal, VH1-scFv linker-VIA-hinge-variant Fc domain.

In further aspects, the first monomer can comprise, from N- to C-terminal, VL1-scFv linker-VH1-hinge-variant Fc domain.

In particular aspects, the ABD1 has sequences selected from the pairs consisting of 1C11[PD-1]_H3.234_L3.144 from XENP25806 in FIG. 15, 1C11[PD-1]_H3.240_L3.148 from XENP25812 from FIG. 15, 1C11[PD-1]_H3.241_L3.148 from XENP25813 in FIG. 15 and 1C11[PD-1]_H3.241_L3.92 from XENP25819 in FIG. 15, and the ABD2 binds to an antigen selected from human CTLA-4, human LAG-3, human TIM-3, human TIGIT, human BTLA and human ICOS.

In an additional aspect, the anti-CTLA-4 ABD2 has sequences selected from the pairs of SEQ ID NOs:38134 and 38138, 36739 and 36743, 36747 and 36751, 36755 and 36759, 36763 and 36767, 36771 and 36775, 36779 and 36783, 36787 and 36791, 36795 and 36799, 36803 and 36807, and 36811 and 36815 of the sequence listing.

In an additional aspect, the anti-LAG-3 ABD2 has sequences selected from the pairs of SEQ ID NOs:32755 and 32760, 36819 and 36823, 36827 and 36831, 36835 and 36839, 36843 and 36847, 36851 and 36855, 36859 and 36863, 36867 and 36871, 36875 and 36879, 36883 and 36887, 36891 and 36895, 36899 and 36903, 36907 and 36911, 36915 and 36919, 36923 and 36927, 36931 and 36935, 36939 and 36943, 36947 and 36951 and 36955 and 36959.

In an additional aspect, the anti-TIM-3 ABD2 has sequences selected from the pairs of SEQ ID NOs:36508 and 36513, 35757 and 37591, 37959 and 37599, 37603 and 37607, 37611 and 37615, 37619 and 37623, 37627 and 37631, 37635 and 37639, 37643 and 37647, 37651 and 37655, 37659 and 37663, 37667 and 37671, 37675 and 37679, 37683 and 37687 and 37691 and 37695.

In an additional aspect, the anti-TIGIT ABD2 has sequences selected from the pairs of SEQ ID NOs:37435 and 37439, 37443 and 37447, 37451 and 37455, 37459 and 37463, 37467 and 37471, 37475 and 37479, 37483 and 37487, 37491 and 37495, 37499 and 37503, 37507 and 37511, 37515 and 37519, 37523 and 37527, 37531 and 37535, 37539 and 37543, 37547 and 37551, 37555 and 37559, 37563 and 37567, 37571 and 37575 and 37579 and 37583.

In an additional aspect, the anti-ICOS ABD2 has sequences selected from the group consisting of: a) the pairs of SEQ ID NOs:26323 and 26328, 27477 and 27452 and 26353 and 26358 from the sequence listing from US2018/0127501; b) the VH and VL sequences of XENCS500 in FIG. 49; and c) the VH and VL sequences of XENCS501 in FIG. 49.

In an additional aspect, the anti-BTLA ABD2 has sequences selected from the pairs of SEQ ID NOs:20936 and 20941, 36707 and 36711, 36715 and 36719, 36723 and 36727 and 36761 and 36735.

In many aspects, the heterodimeric antibodies of the invention have a second variant IgG1 Fc domain comprises amino acid substitutions N208D/Q295E/N384D/Q418E/N421D, wherein said first and second variant IgG1 Fc domains each comprise amino acid substitutions E233P/L234V/L235A/G236del/S267K; and wherein said first variant IgG1 Fc domain comprises amino acid substitutions S364K/E357Q and second variant IgG1 Fc domain comprises amino acid substitutions L368D/K370S, wherein numbering is according to the EU index as in Kabat.

In further aspects, the invention provides nucleic acid compositions comprising: a) a first nucleic acid encoding said first monomer; b) a second nucleic acid encoding said second monomer; and c) a third nucleic acid encoding said light chain of any of claims 15 to 30.

In an additional aspect, the invention provides expression vector compositions comprising: a) a first expression vector comprising said first nucleic acid; b) a second expression vector comprising said second nucleic acid; and c) a third expression vector comprising said third nucleic acid. Also provided are host cells comprising the expression vector compositions, and methods of making the antibodies by culturing the host cells under conditions wherein said antibody is expressed, and recovering said antibody. Further provided are methods of treating cancer in a patient in need thereof comprising administering the heterodimeric bispecific antibodies of the invention to a patient.

V. BRIEF DESCRIPTION OF THE DRAWINGS

FIG. 1A to 1O depict several formats of the present invention. The first is the "bottle opener" format, with a first and a second anti-antigen binding domain. Additionally, mAb-Fv, mAb-scFv, Central-scFv, Central-Fv, one armed central-scFv, one scFv-mAb, scFv-mAb, a dual scFv format, DVD-Ig, Trident and mAb-(scFv2) are all shown. For all of the scFv domains depicted, they can be either N- to C-terminus variable heavy-(optional linker)-variable light, or the opposite. In addition, for the one armed scFv-mAb, the scFv can be attached either to the N-terminus of a heavy chain monomer or to the N-terminus of the light chain.

FIGS. 2A to 2D depicts the antigen sequences for a number of antigens of use in the invention, including both human and cynomolgus monkey in many cases, to facilitate the development of antigen binding domains that bind to both for ease of clinical development. Unless otherwise stated, all references to these antigens are to the human antigen. The sequence of human ICOS (sp|Q9Y6W8) is shown in SEQ ID NO: 26246 of WO/2018/045110. The sequence of human ICOS, extracellular domain (sp|Q9Y6W8|121-140) is SEQ ID NO: 26247 of WO/2018/045110.

FIG. 3A to 3F depict useful pairs of heterodimerization variant sets (including skew and pI variants). On FIG. 3E, there are variants for which there are no corresponding "monomer 2" variants; these are pI variants which can be used alone on either monomer, or included on the Fab side of a bottle opener, for example, and an appropriate charged scFv linker can be used on the second monomer that utilizes a scFv as the second antigen binding domain. Suitable charged linkers are shown in FIG. 7.

FIG. 4 depict a list of isosteric variant antibody constant regions and their respective substitutions. pI_(−) indicates lower pI variants, while pI_(+) indicates higher pI variants. These can be optionally and independently combined with other heterodimerization variants of the invention (and other variant types as well, as outlined herein).

FIG. 5 depict useful ablation variants that ablate FcγR binding (sometimes referred to as "knock outs" or "KO" variants). Generally, ablation variants are found on both monomers, although in some cases they may be on only one monomer.

FIGS. 6A and 6B show two particularly useful embodiments of the invention.

FIGS. 7A and 7B depict a number of charged scFv linkers that find use in increasing or decreasing the pI of heterodimeric antibodies that utilize one or more scFv as a component. The (+H) positive linker finds particular use herein, particularly with anti-CD3 vl and vh sequences shown herein. A single prior art scFv linker with a single charge is referenced as "Whitlow", from Whitlow et al., Protein Engineering 6(8):989-995 (1993). It should be noted that this linker was used for reducing aggregation and enhancing proteolytic stability in scFvs.

FIG. 8 depicts a list of engineered heterodimer-skewing Fc variants with heterodimer yields (determined by HPLC-CIEX) and thermal stabilities (determined by DSC). Not determined thermal stability is denoted by "n.d.".

FIG. 9 depicts the sequences for XENP21575, a chimeric anti-PD-1 antibody based on the variable regions of hybridoma done 1C11 and human IgG1 with E233P/L234V/L235A/G236del/S267K substitutions in the heavy chain. The CDRs are in bold, and the slashes indicate the borders of the variable domains. As noted herein and is true for every sequence herein containing CDRs, the exact identification of the CDR locations may be slightly different depending on numbering used as is shown in Table 1, and thus included herein are not only the CDRs that are underlined but also CDRs included within the VH and VL domains using other numbering systems. Additionally, each CDR has its own SEQ ID NO: in the sequence listing, and each VH and VL domain has its own SEQ ID NO: in the sequence listing.

FIG. 10 depicts blocking of PD-1/PD-L1 interaction on PD-1 transfected HEK293T cells by anti-PD-1 clone 1C11.

Figure 11:
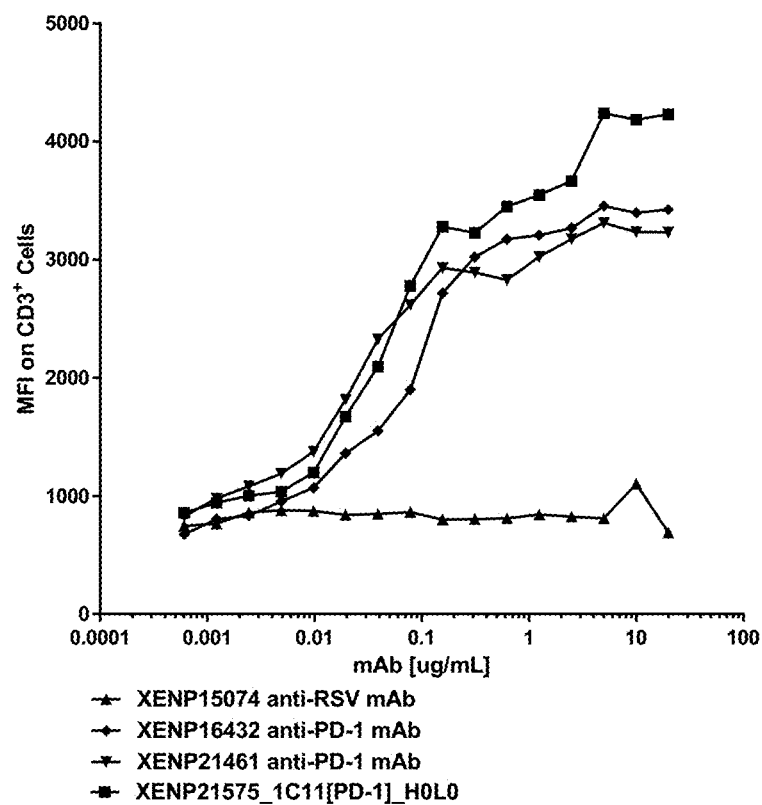

FIG. 11 depicts the binding of anti-PD-1 done 1C11 to SEB-stimulated T cells.

Figure 12A:
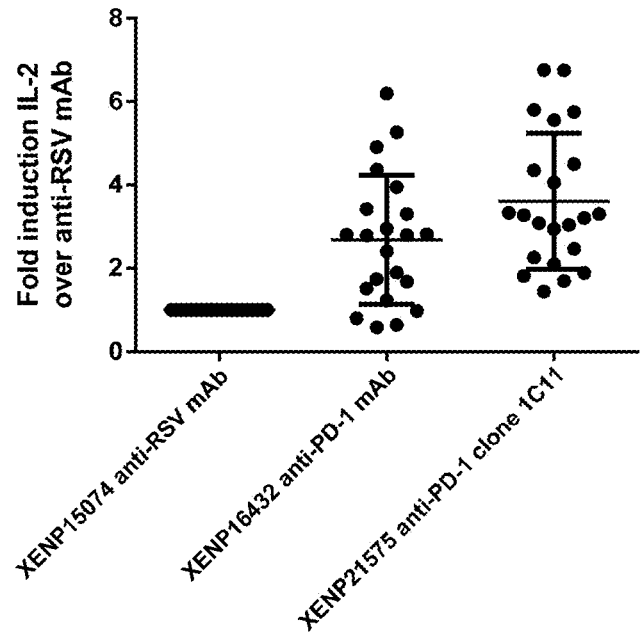
Figure 12B:
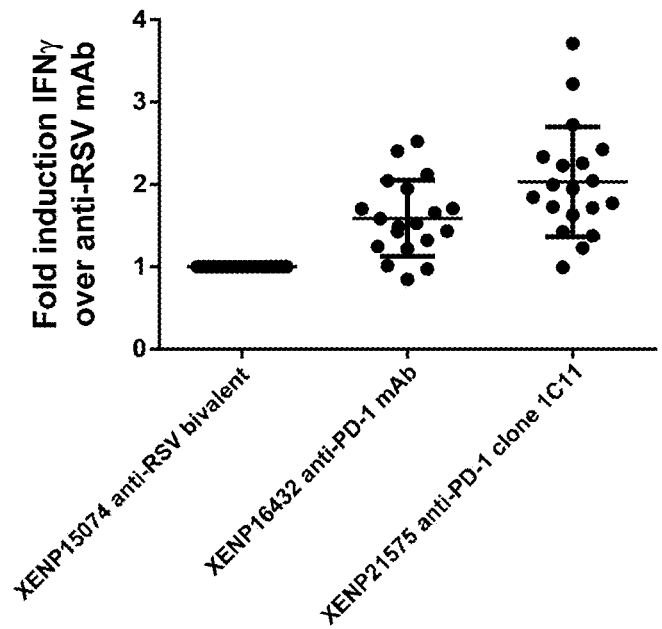

FIGS. 12A and 12B depict cytokine release assays (A: IL-2; B: IFNγ) after SEB stimulation of human PBMCs and treatment with anti-PD-1 done 1C11.

FIGS. 13A to 13C depict the sequences for illustrative Fab humanized variants of anti-PD-1 done 1C11 in the human IgG1 format with E233P/L234V/L235A/G236del/S267K substitutions in the heavy chain. The CDRs are in bold, and the slashes indicate the borders of the variable domains. As note herein and is true for every sequence herein containing CDRs, the exact identification of the CDR locations may be slightly different depending on numbering used as is shown in Table 1, and thus included herein are not only the CDRs that are underlined but also CDRs included within the VH and VL domains using other numbering systems. As will be appreciated by those in the art, the VH and VL domains can be formatted as Fab or scFvs. Additionally, each CDR has its own SEQ ID NO: in the sequence listing, and each VH and VL domain has its own SEQ ID NO: in the sequence listing.

Figure 14:
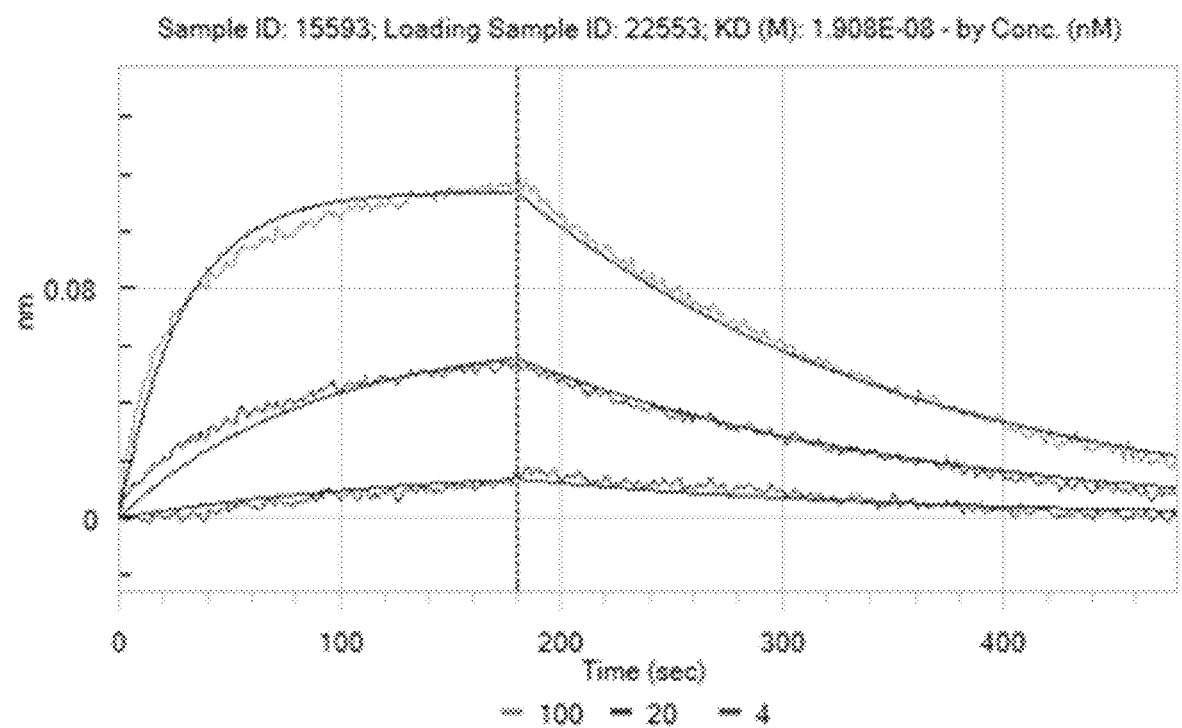

FIG. 14 depicts the affinity of XENP22553 for PD-1 as determined by Octet (as well as the associated sensorgram).

FIG. 15A to 15T depict sequences for illustrative scFv variants of anti-PD-1 done 1C11. The CDRs are underlined, the scFv linker is double underlined (in the sequences, the scFv linker is a positively charged scFv (GKPGS)4 linker, although as will be appreciated by those in the art, this linker can be replaced by other linkers, including uncharged or negatively charged linkers), and the slashes indicate the borders of the variable domains. As noted herein and is true for every sequence herein containing CDRs, the exact identification of the CDR locations may be slightly different depending on numbering used as is shown in Table 1 and thus included herein are not only the CDRs that are underlined but also CDRs included within the VH and VL domains using other numbering systems. Further, the naming convention illustrates the orientation of the scFv from N- to C-terminus; some of the sequences in this Figure are oriented as VH-scFv linker-VL (from N- to C-terminus), while some are oriented as VL-scFv linker-VH (from N- to C-terminus), although as will be appreciated by those in the art, these sequences may also be used in the opposition orientation from their depiction herein. Furthermore, as will be appreciated by those in the art, the VH and VL domains can be formatted as Fabs or scFvs. Additionally, each CDR has its own SEQ ID NO: in the sequence listing, and each VH and VL domain has its own SEQ ID NO: in the sequence listing.

FIGS. 16A and 16H depict sequences for illustrative variant anti-PD-1 mAbs with VH and VL domains from selected scFvs as described in Example XD. The CDRs are in bold, and the slashes indicate the borders of the variable domains. As noted herein and is true for every sequence herein containing CDRs, the exact identification of the CDR locations may be slightly different depending on numbering used as is shown in Table 1, and thus included herein are not only the CDRs that are underlined but also CDRs included within the VH and VL domains using other numbering systems. As will be appreciated by those in the art, the VH and VL domains can be formatted as Fabs or scFvs. Additionally, each CDR has its own SEQ ID NO: in the sequence listing, and each VH and VL domain has its own SEQ ID NO: in the sequence listing.

FIG. 17A to 17Q depict the stability of variant anti-PD-1 scFvs as determined by DSF and equilibrium dissociation constants (KD), association rates (ka), and dissociation rates (kd) of anti-PD-1 mAbs based on the VH/VL from the variant scFvs as determined by Octet. XENP for scFvs are in bold, and XENP for full-length mAb are in parentheses.

FIGS. 18A to 18G depict sequences for illustrative variant anti-PD-1 mAbs based on done 1C11. The CDRs are in bold, and the slashes indicate the borders of the variable domains. As noted herein and is true for every sequence herein containing CDRs, the exact identification of the CDR locations may be slightly different depending on numbering used as is shown in Table 1, and thus included herein are not only the CDRs that are underlined but also CDRs included within the VH and VL domains using other numbering systems. As will be appreciated by those in the art, the VH and VL domains can be formatted as Fabs or scFvs. Additionally, each CDR has its own SEQ ID NO: in the sequence listing, and each VH and VL domain has its own SEQ ID NO: in the sequence listing.

FIG. 19 depicts the of equilibrium dissociation constants (KD), association rates (ka), and dissociation rates (kd) of variant anti-PD-1 mAbs as determined by Octet.

FIGS. 20A to 20L depict sequences for variant heavy chains based on the heavy chain of XENP22553. The CDRs are in bold. As noted herein and is true for every sequence herein containing CDRs, the exact identification of the CDR locations may be slightly different depending on numbering used as is shown in Table 1, and thus included herein are not only the CDRs that are underlined but also CDRs included within the VH domain. As will be appreciated by those in the art, the VH domains can be used in Fabs or scFvs. Additionally, each CDR has its own SEQ ID NO: in the sequence listing, and each VH domain has its own SEQ ID NO: in the sequence listing.

FIGS. 21A to 21G depict sequences for variant light chains based on the light chain of XENP22553. The CDRs are in bold. As noted herein and is true for every sequence herein containing CDRs, the exact identification of the CDR locations may be slightly different depending on numbering used as is shown in Table 1, and thus included herein are not only the CDRs that are underlined but also CDRs included within the VL domains using other numbering systems. As will be appreciated by those in the art, the VL domains can be used in Fabs or scFvs. Additionally, each CDR has its own SEQ ID NO: in the sequence listing, and each VL domain has its own SEQ ID NO: in the sequence listing.

FIGS. 22A to 22E depict the of equilibrium dissociation constants (KD), association rates (ka), and dissociation rates (kd) of variant anti-PD-1 mAbs as determined by Octet. Variants are defined by heavy chain and light chain XenDs as depicted in FIGS. 20A-20L and FIGS. 21A-21G.

FIG. 23 depicts the of equilibrium dissociation constants (KD), association rates (ka), and dissociation rates (kd) of variant anti-PD-1 mAbs as determined by Octet. Variants are defined by heavy chain and light chain XenDs as depicted in FIG. 20 and FIG. 21.

FIGS. 24A to 24J depict sequences for additional illustrative variant anti-PD-1 mAbs based on done 1C11. The CDRs are underlined, and the slashes indicate the borders of the variable domains. As noted herein and is true for every sequence herein containing CDRs, the exact identification of the CDR locations may be slightly different depending on numbering used as is shown in Table 1, and thus included herein are not only the CDRs that are underlined but also CDRs included within the VH and VL domains using other numbering systems. As will be appreciated by those in the art, the VH and VL domains can be formatted as Fabs or scFvs. Additionally, each CDR has its own SEQ ID NO: in the sequence listing, and each VH and VL domain has its own SEQ ID NO: in the sequence listing.

FIG. 25 depicts the of equilibrium dissociation constants (KD), association rates (ka), and dissociation rates (kd) of variant anti-PD-1 mAbs as determined by Octet.

FIG. 26 depicts the affinity (KD) of anti-PD-1 1C11 variants as determined by Biacore.

Figure 27:
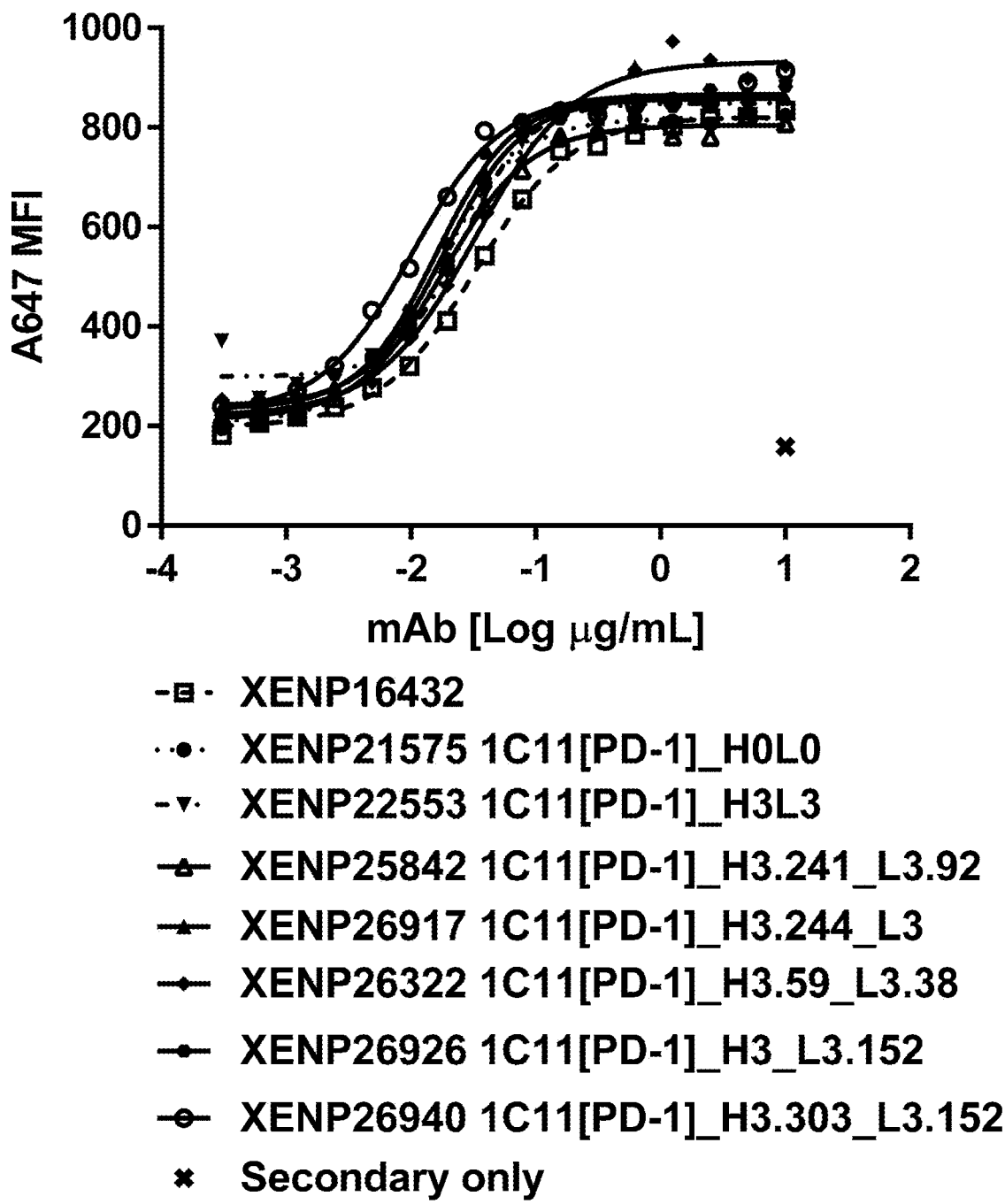

FIG. 27 depicts the binding of affinity optimized anti-PD-1 1C11 variants to SEB-stimulated T cells.

FIG. 28 depicts the blocking of PD-L1 and PD-L2 binding to PD-1 by anti-PD-1 1C11 variants as determined by normalized BLI-response in a tandem epitope binning assay using Octet.

Figure 29:
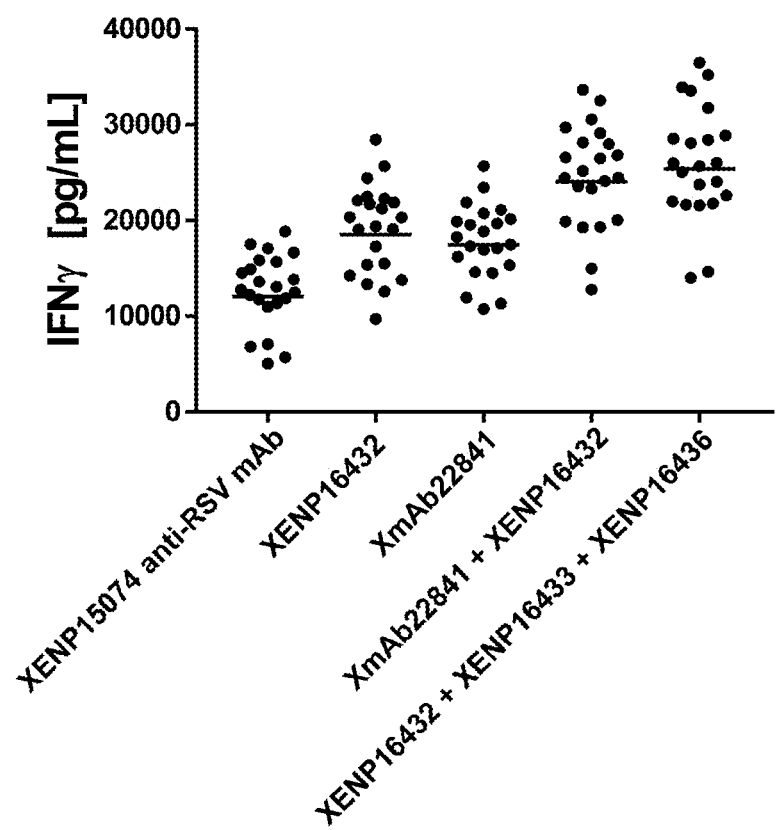

FIG. 29 depicts IFNγ secretion in an SEB-stimulated PBMC assay following incubation with the indicated test articles.

Figure 30:
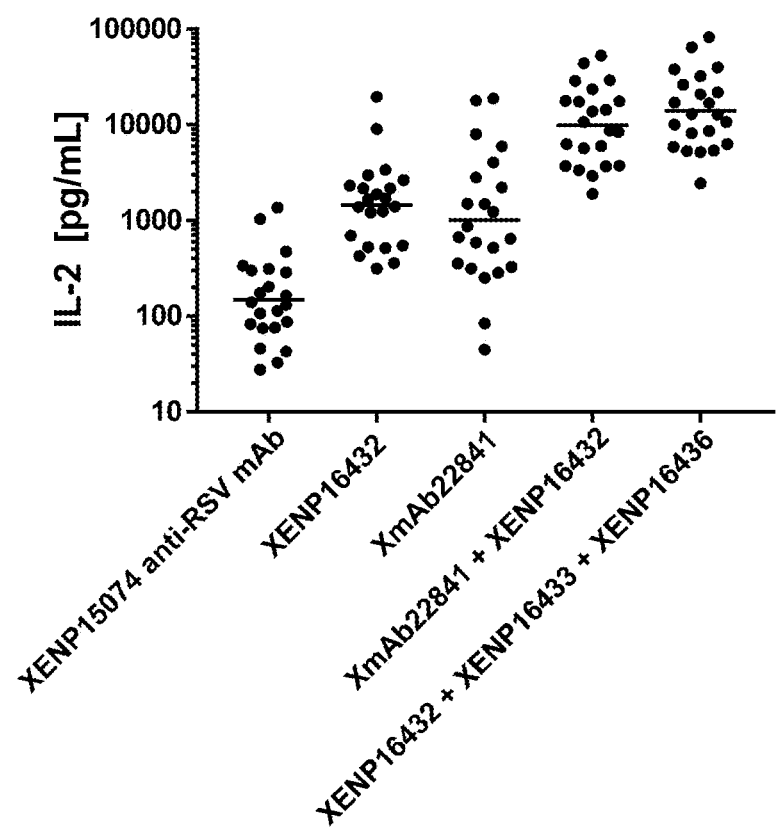

FIG. 30 depicts IFNγ secretion in an SEB-stimulated PBMC assay following incubation with the indicated test articles.

Figure 31:
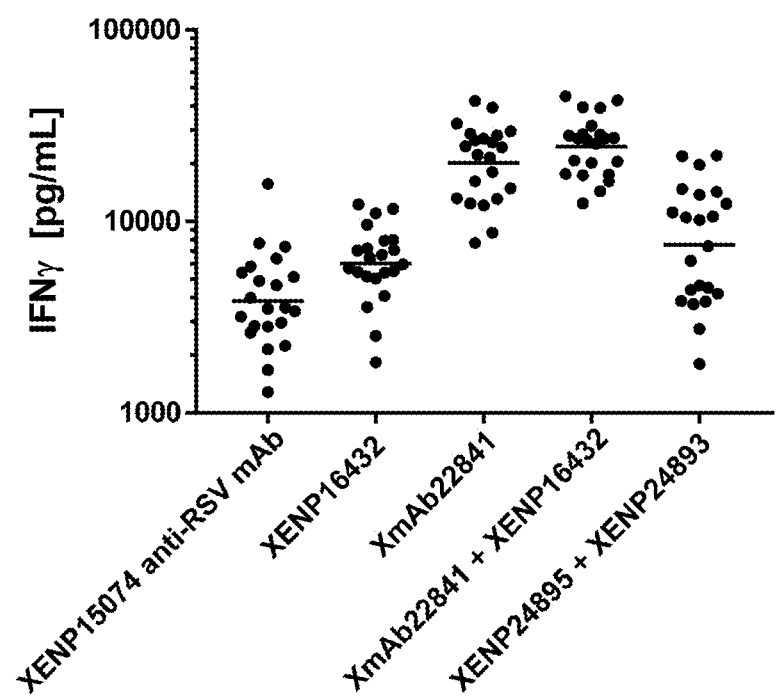

FIG. 31 depicts IFNγ secretion in an MLR assay following incubation with 20 μg/mL of the indicated test articles.

Figure 32:
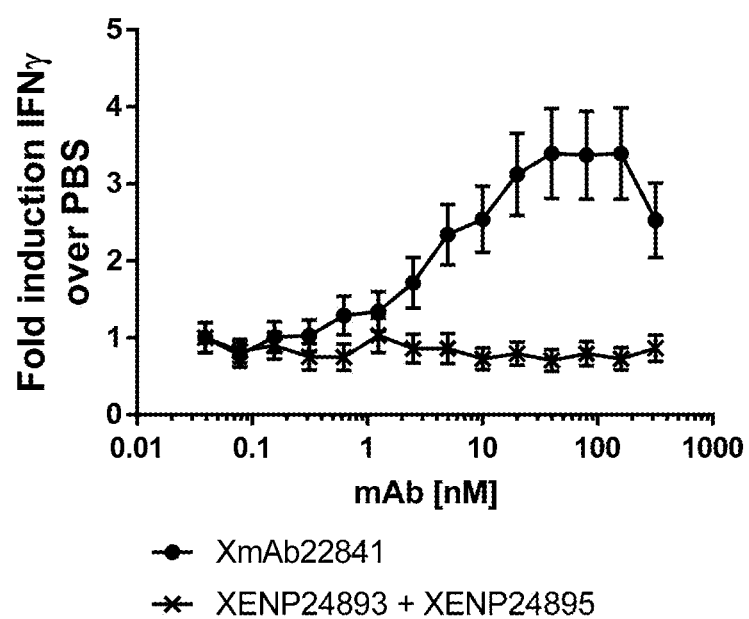

FIG. 32 depicts IFNγ secretion in an MLR assay following incubation with the indicated concentrations of the indicated test articles.

FIG. 33 depicts the sequences for XENP26842, a bivalent anti-PD-1 mAb with an ablation variant (E233P/L234V/L235A/G236de1/S267K, "IgG1_PVA_/S267k") and Xtend variant (M428L/N434S). The CDRs are underlined. As noted herein and is true for every sequence herein containing CDRs, the exact identification of the CDR locations may be slightly different depending on the numbering used as is shown in Table 1, and thus included herein are not only the CDRs that are underlined but also CDRs included within the $V_H$ and $V_L$ domains using other numbering systems. Additionally, each CDR has its own SEQ ID NO: in the sequence listing, and each VH and $V_L$ domain has its own SEQ ID NO: in the sequence listing.

Figure 34:
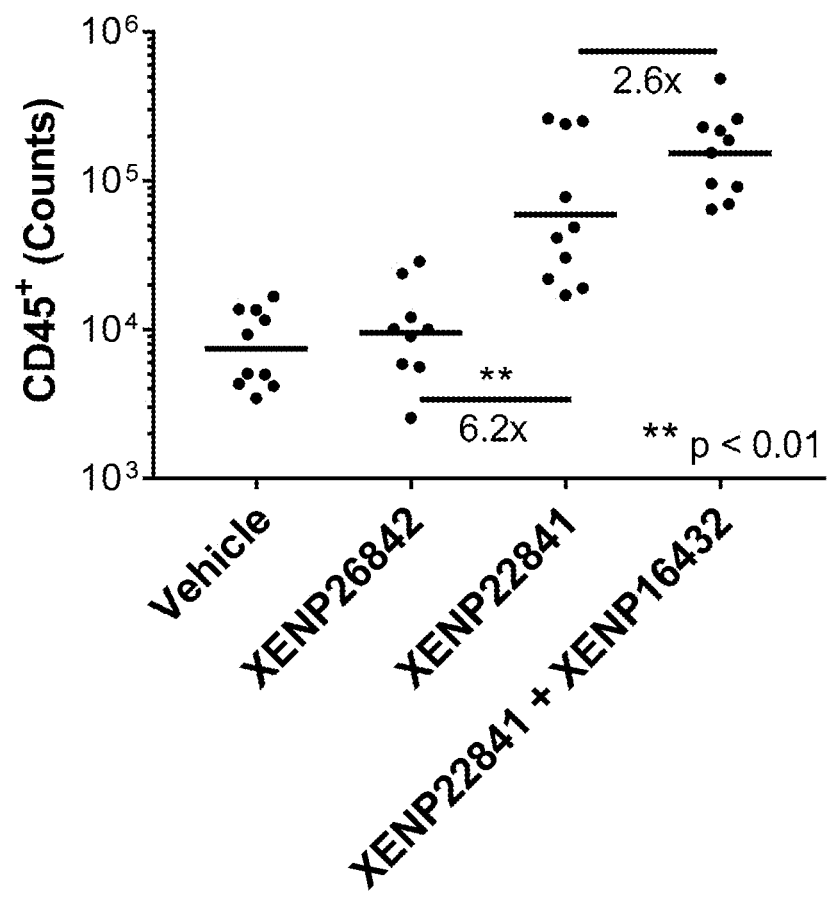

FIG. 34 depicts CD45$^+$ cell counts in whole blood of NSG mice on Day 14 after engraftment with human PBMCs on Day 0 and dosing with indicated test articles on Days 1 and 8.

Figure 35:
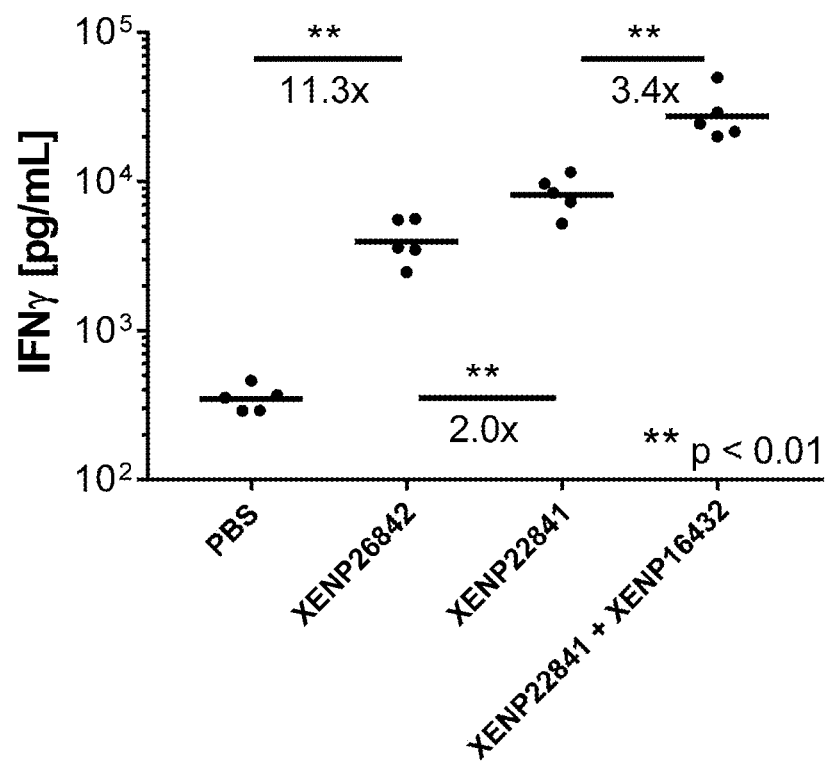

FIG. 35 depicts IFNγ concentration in serum of NSG mice on Day 7 after engraftment with human PBMCs on Day 0 and dosing with indicated test articles on Day 1.

Figure 36A:
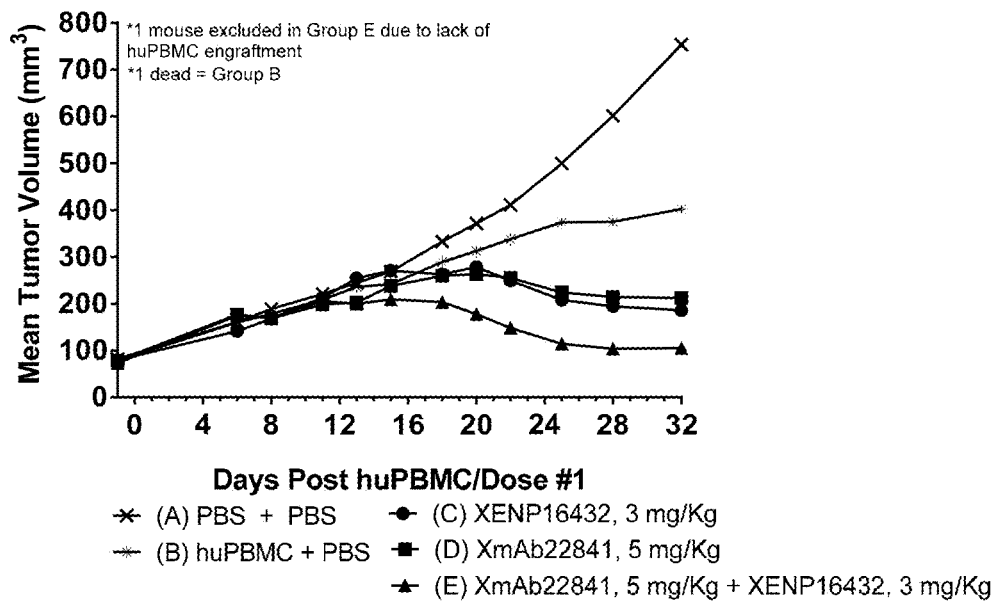
Figure 36B:
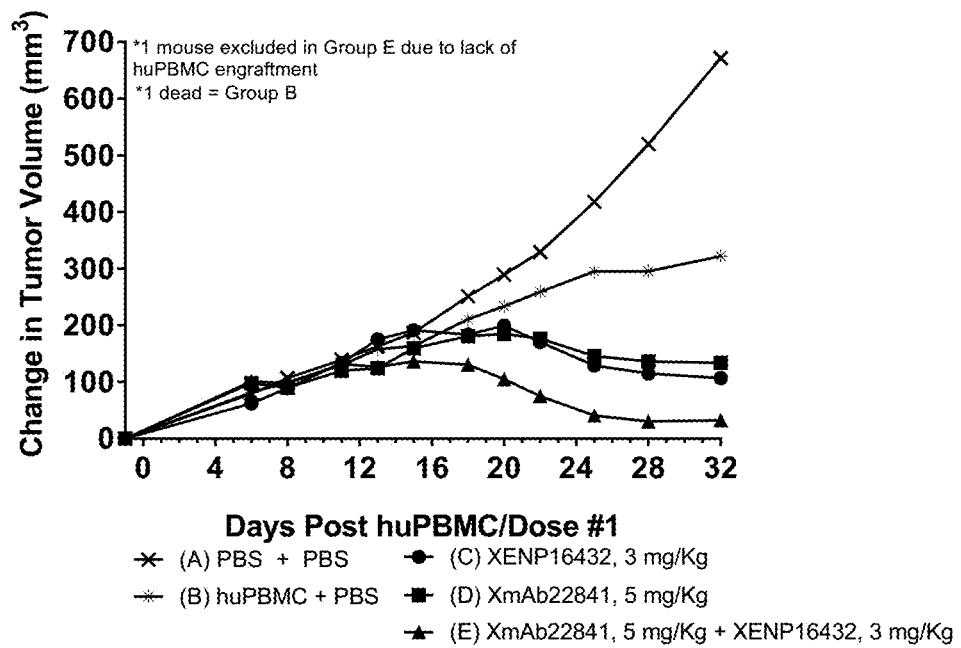
Figure 37A:
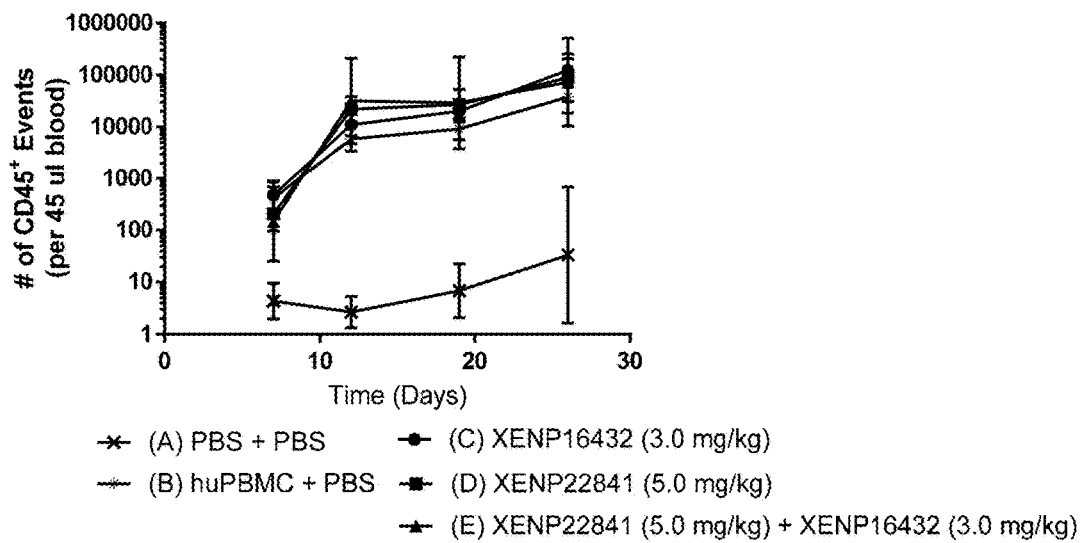
Figure 37B:
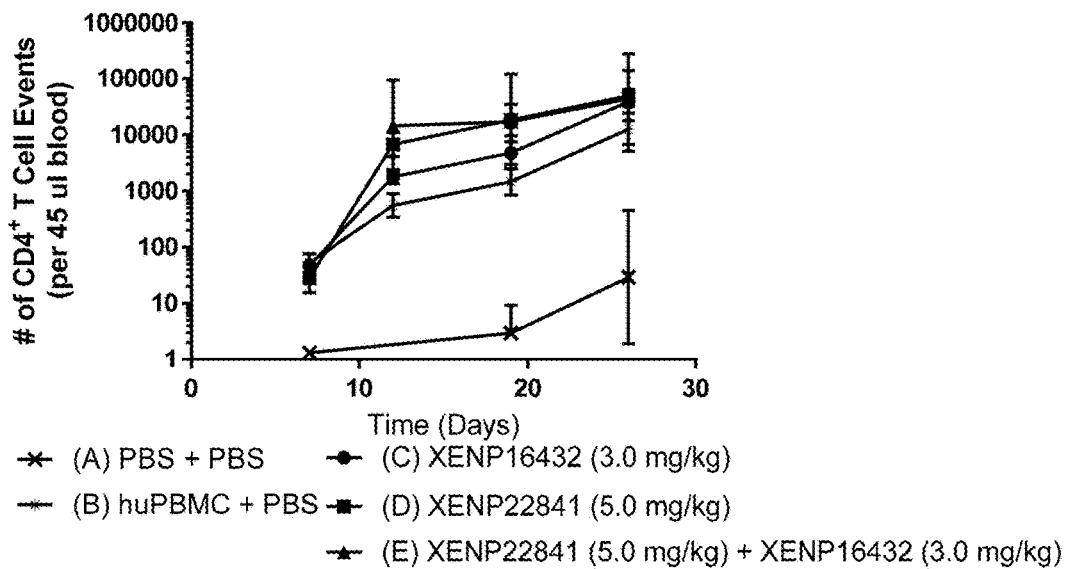
Figure 37C:
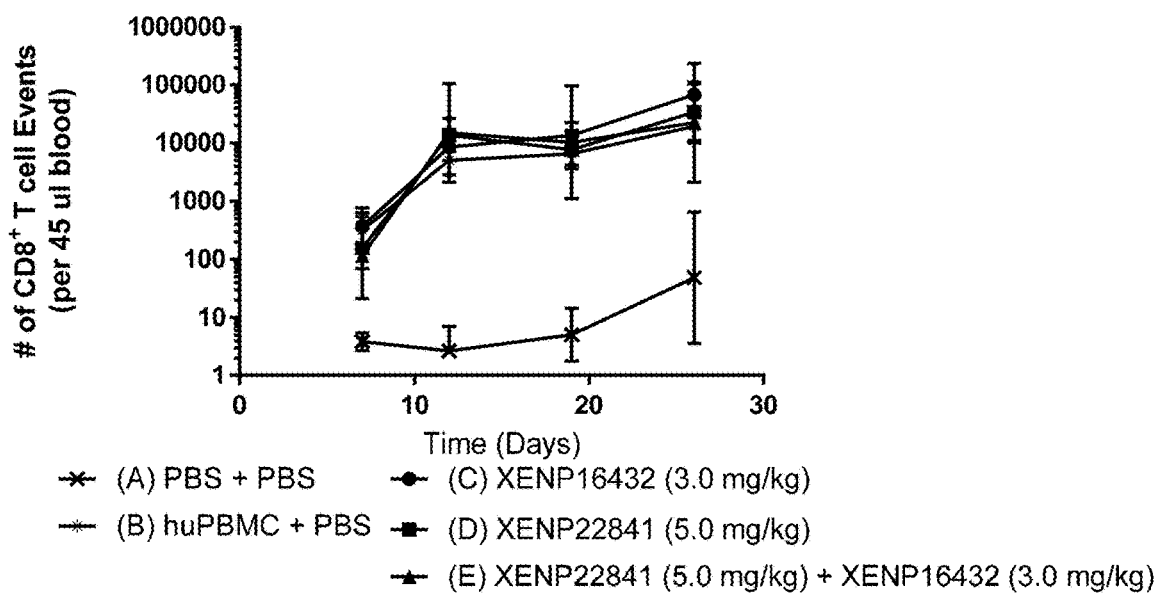
Figure 37D:
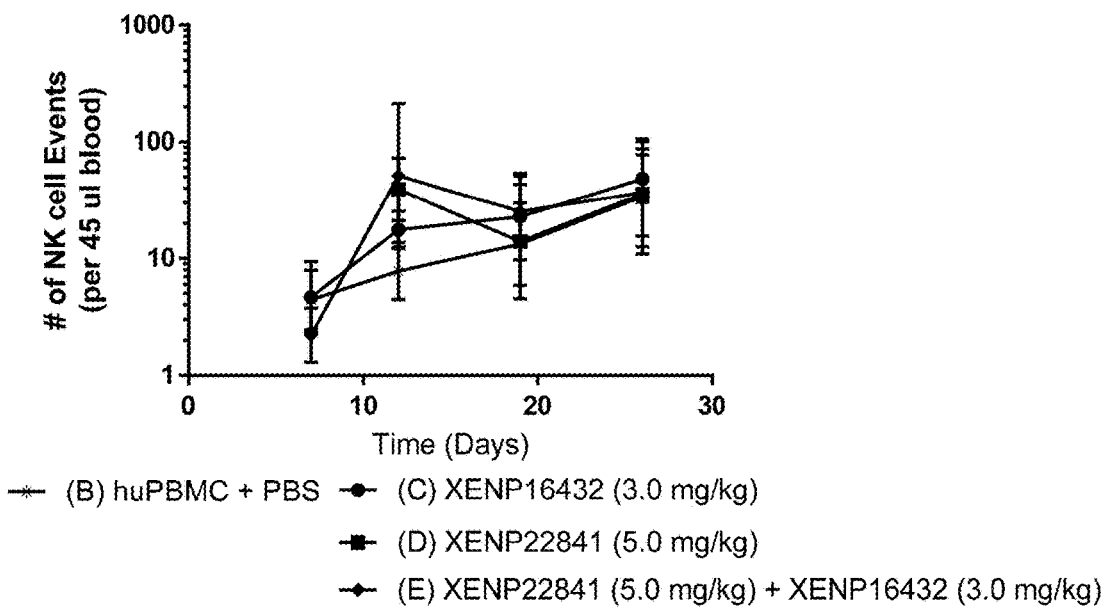

FIGS. 36A and 36B depict A) the mean tumor volume and B) change in tumor volume in NSG mice engrafted with pp65-expressing MCF-7 cells, following engraftment with pp65 reactive huPBMC and treatment with indicated test articles.

FIGS. 37A to 37D depict A) CD45$^+$ cell, B) CD4$^+$ T cell, C) CD8$^+$ T cell, and D) NK cell counts in the whole blood of NSG mice engrafted with pp65-expressing MCF-7 cells following engraftment with pp65 reactive huPBMC and treatment with indicated test articles.

Figure 38:
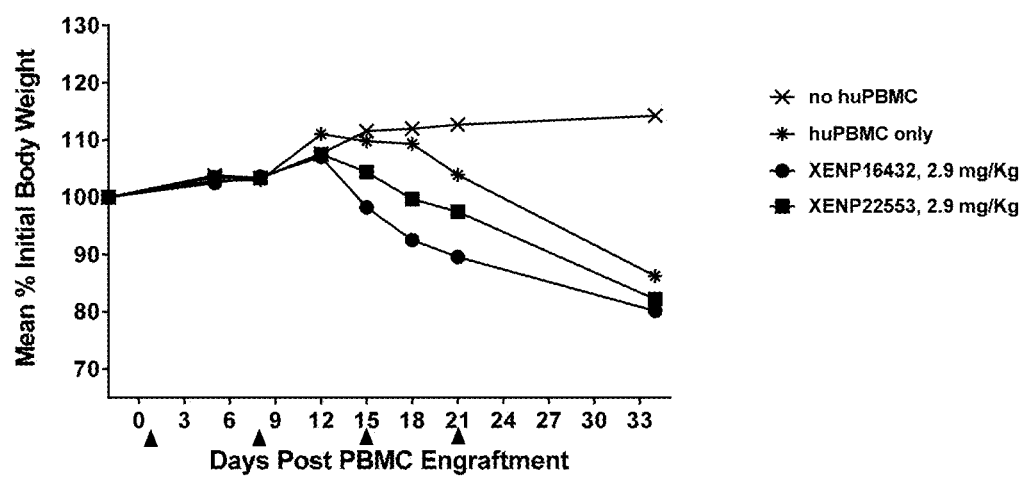

FIG. 38 depicts the change in weight over time (as a percentage of initial body weight) in huPBMC-engrafted NSG mice dosed with the indicated test articles.

Figure 39A:
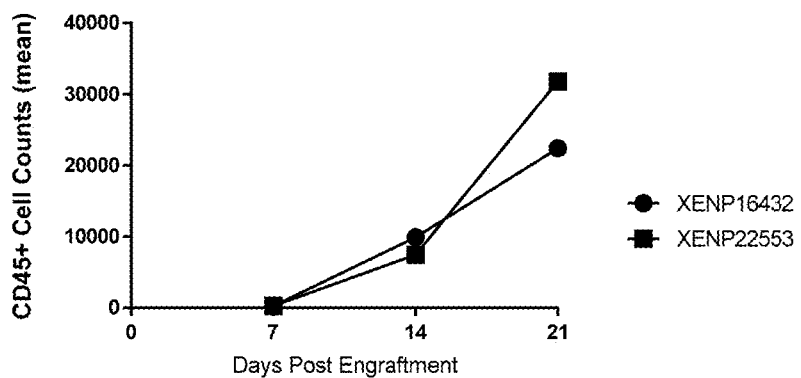
Figure 39B:
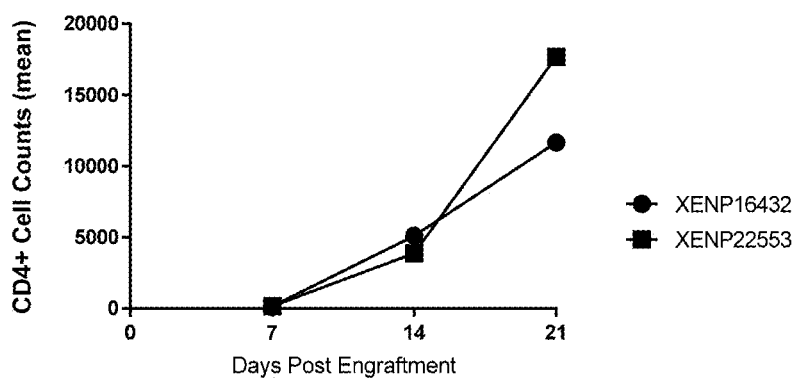
Figure 39C:
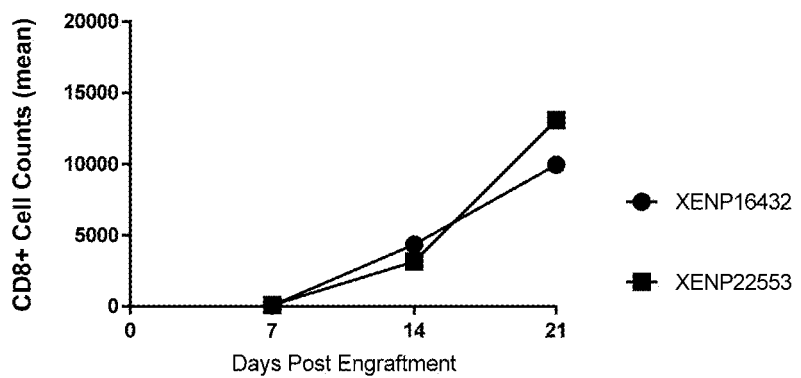

FIGS. 39A to 39C depict A) human CD45$^+$, B) human CD4$^+$ T cell, and C) human CD8$^+$ T cell counts in huPBMC-engrafted NSG mice following dosing with the indicating test articles.

FIGS. 40A to 40BB depict sequences for additional illustrative variant anti-PD-1 mAbs based on done 1C11. The CDRs are underlined, and the slashes indicate the borders of the variable domains. As noted herein and is true for every sequence herein containing CDRs, the exact identification of the CDR locations may be slightly different depending on numbering used as is shown in Table 1, and thus included herein are not only the CDRs that are underlined but also CDRs included within the $V_H$ and $V_L$ domains using other numbering systems. As will be appreciated by those in the art, the $V_H$ and $V_L$ domains can be formatted as Fabs or scFvs. Additionally, these sequences can include the M428L/N434S Xtend mutations. Additionally, each CDR has its own SEQ ID NO: in the sequence listing, and each $V_H$ and $V_L$ domain has its own SEQ ID NO: in the sequence listing.

FIG. 41 depicts the affinity/dissociation constants ($K_D$), association rates ($k_a$), and dissociation rates ($k_d$) of anti-PD-1 1C11 variants for human PD-1 as determined by Octet.

FIG. 42 depicts the affinity/dissociation constants ($K_D$), association rates ($k_a$), and dissociation rates ($k_d$) of anti-PD-1 1C11 variants for human PD-1 as determined by Octet.

FIG. 43 depicts the affinity/dissociation constants ($K_D$), association rates ($k_a$), and dissociation rates ($k_d$) of anti-PD-1 1C11 variants for human PD-1 as determined by Octet.

FIG. 44 depicts the affinity/dissociation constants ($K_D$), association rates ($k_a$), and dissociation rates ($k_d$) of anti-PD-1 1C11 variants for human PD-1 as determined by Octet.

FIG. 45 depicts the affinity/dissociation constants ($K_D$), association rates ($k_a$), and dissociation rates ($k_d$) of anti-PD-1 1C11 variants for human PD-1 and cynomolgus PD-1 as determined by Octet.

Figure 46:
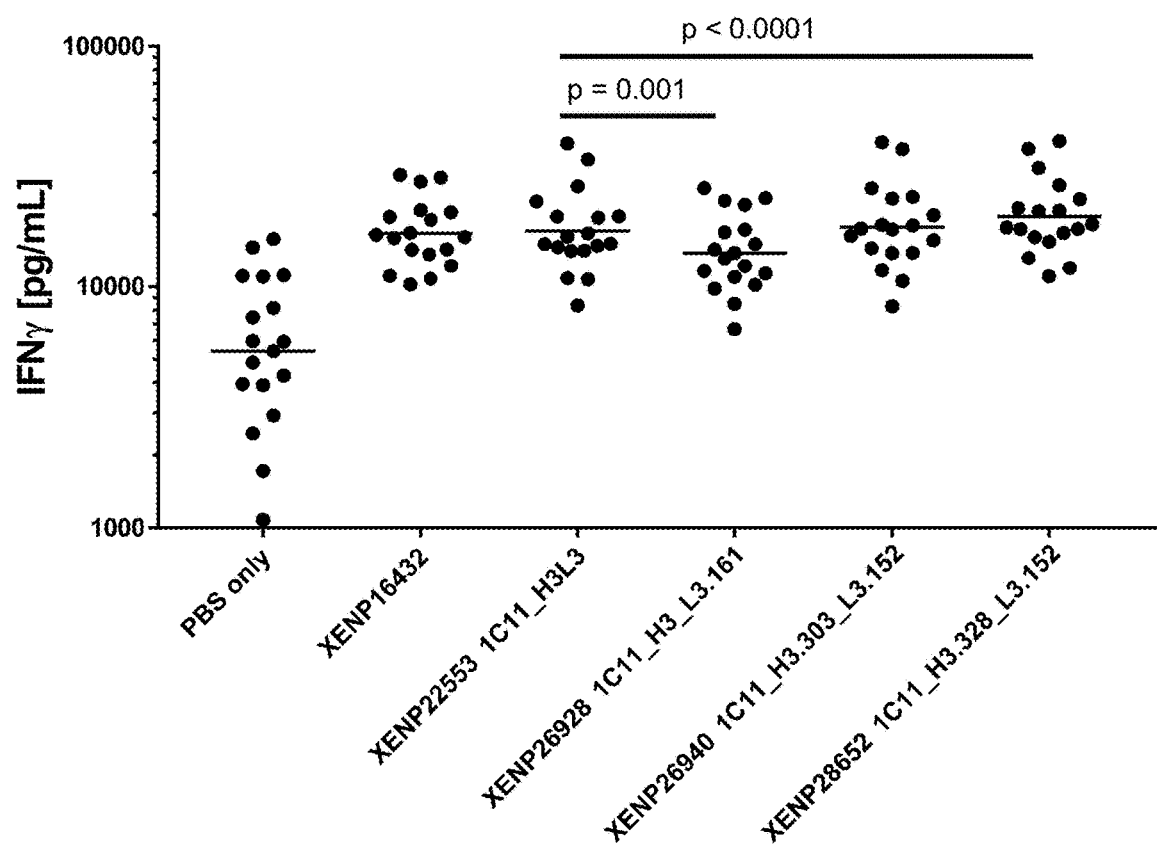

FIG. 46 depicts the induction of IFNγ by indicated 1C11 variants (as well as PBS and anti-PD-1 XENP16432 based on nivolumab as controls) in an SEB-stimulated PBMC assay. p-values are from paired t-test, comparing IFNγ secretion by PBMCs from the same donor.

Figure 47:
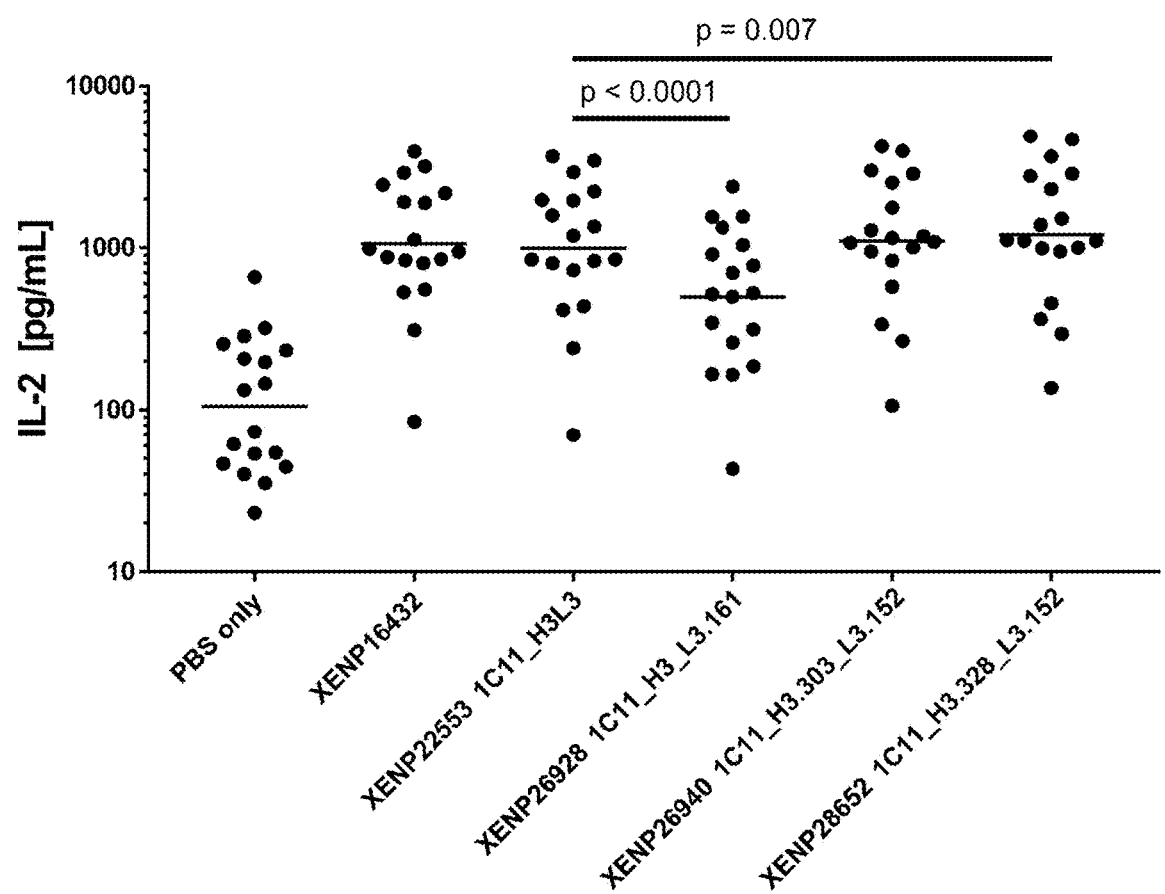

FIG. 47 depicts the induction of IL-2 by indicated 1C11 variants (as well as PBS and anti-PD-1 XENP16432 based on nivolumab as controls) in an SEB-stimulated PBMC assay. p-values are from paired t-test, comparing IL-2 secretion by PBMCs from the same donor.

Figure 48:
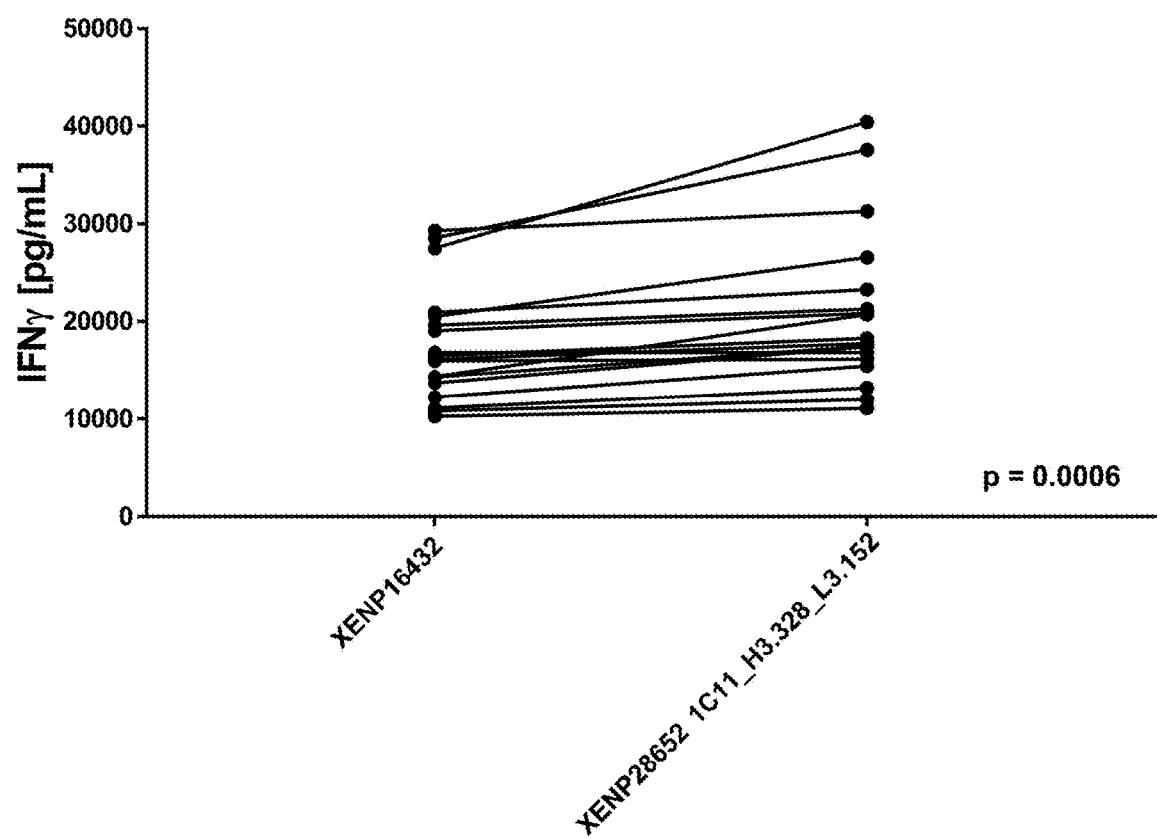

FIG. 48 depicts the induction of IFNγ by indicated anti-PD-1 mAb XENP16432 based on nivolumab and XENP28652 in an SEB-stimulated PBMC assay. p-values are from paired t-test, comparing IFNγ secretion by PBMCs from the same donor.

FIGS. 49A to 49KK show the sequences of a number of heterodimeric antibodies of the present invention in the "bottle opener" format, named using "XENCS" numbering. Three polypeptide chains are shown for each ("Fab chain, scFv chain and light chain"), with the CDRs underlined, linkers double underlined, and the junction between domains indicated by a "/". Each of these has its own sequence and thus identifier.

FIGS. 50A to 50E show the sequences of several useful "bottle opener" format "skeletons", with the Fvs of the scFv side directed to several particular anti-PD-1 ABDs, but without the Fv sequences for the "Fab" side. As will be appreciated by those in the art and outlined below, these "skeleton" sequences can be used with any Fab sequences outlined herein and contained within the sequence listing (e.g. a $V_H$ attached to the "Fab side heavy chain" or "Fab monomer" and a $V_L$ attached to the constant light chain). It should also be noted that these bottle opener skeleton sequences find use in the Central-scFv format of FIG. 1F (sometimes also referred to as the "2+1" format), with the addition of a second $V_H$ and CH1 domain as described herein. The Fab chain of each starts with a "/" delineating the beginning of the CH1 domain, such that a $V_H$ domain from an ABD as described herein is N-terminally fused to form a full length heavy chain, with the corresponding $V_L$ domain from the ABD being N-terminally fused to the '/" delineating the beginning of the CL domain in the light chain, such that a Fab is formed with the Fab chain and the light chain. The scFv chain is outlined for particular anti-PD-1 ABDs, with the CDRs underlined, the scFv linker double underlined, and "/" to indicate the junctions of domains. BO skeletons 1 to 4 (XENCS556 to 559) are identical to BO skeletons 5-8 (XENCS560 to 563) except the later include the 428L/434S "XTend®" Fc variants.

Figure 51:
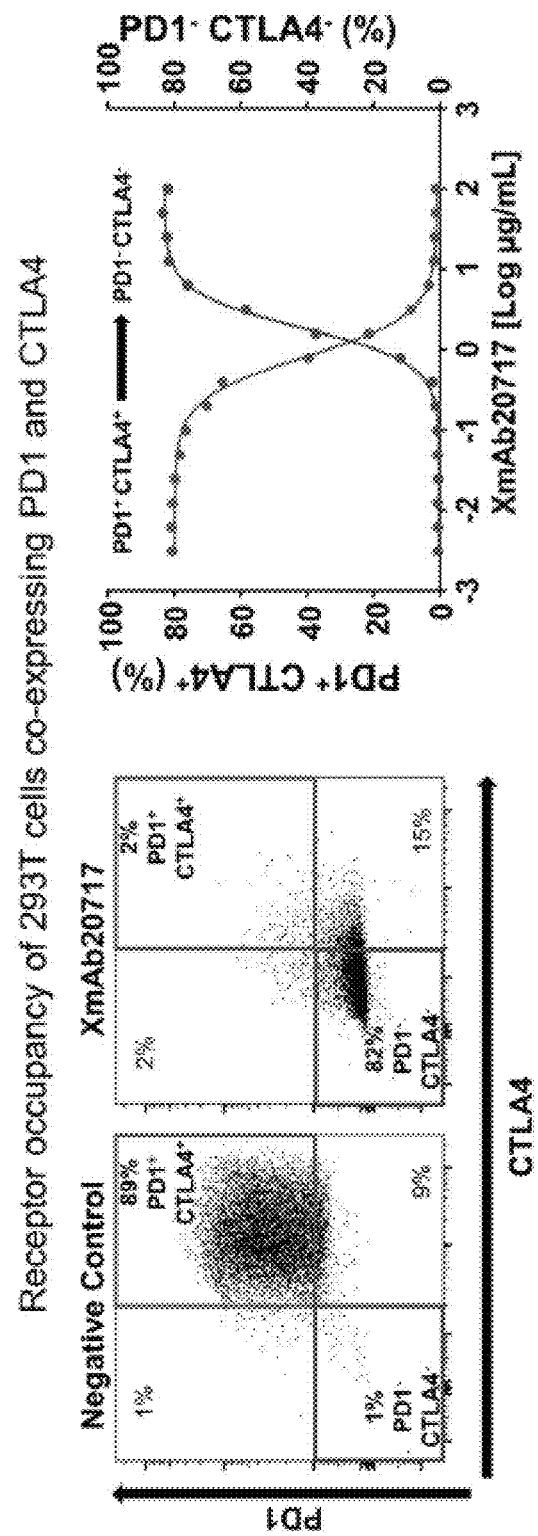

FIG. 51 shows that subject bispecific antibody XmAb20717 (anti-CTLA-4 x anti-PD-1) selectively target 293 T Cells that co-express PD1 and CTLA4.

Figure 52:
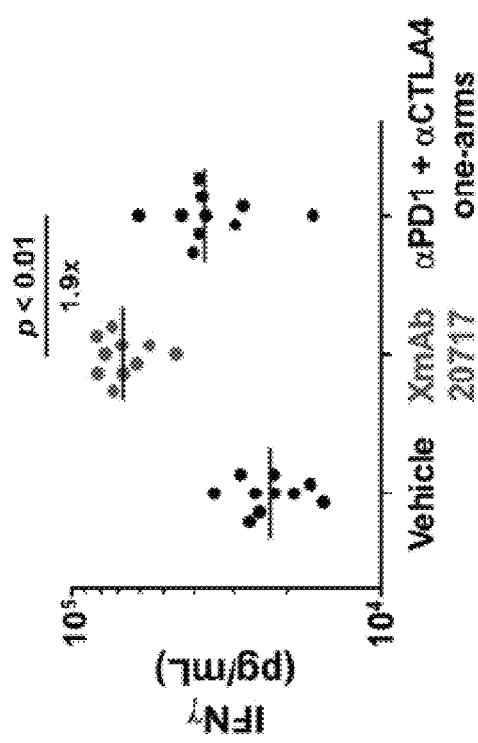

FIG. 52 shows that the binding avidity of XmAB20717 contributes to T cell activiation. In particular, IFNγ levels on Day 14 are shown after human PBMCs were engrated into NSG mice on Day 0 followed by dosing with the indicated test articles on Day 1.

Figure 53:
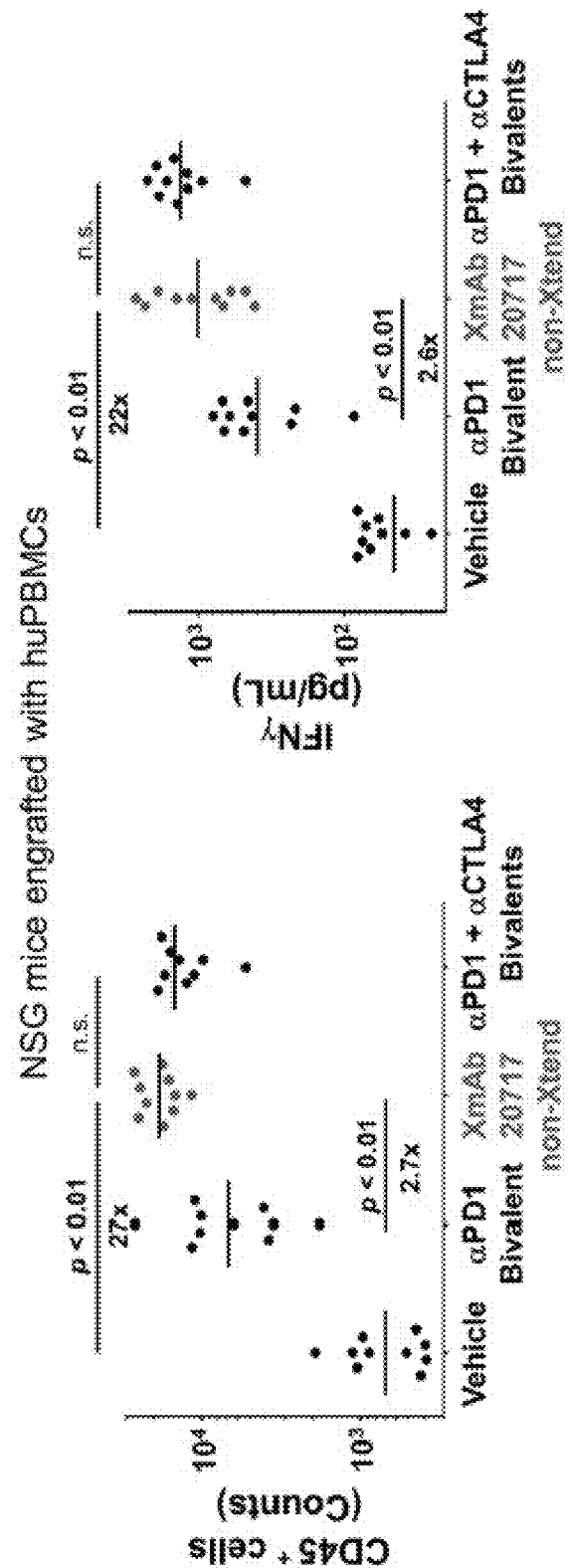

FIG. 53 shows that XmAB20717 promotes superior T cell activation compared to an anti-PD1 bivalent antibody. In particular, CD45+ cell counts and IFNγ levels on Day 14 are shown after human PBMCs were engrated into NSG mice on Day 0 followed by dosing with the indicated test articles on Day 1.

Figure 54:
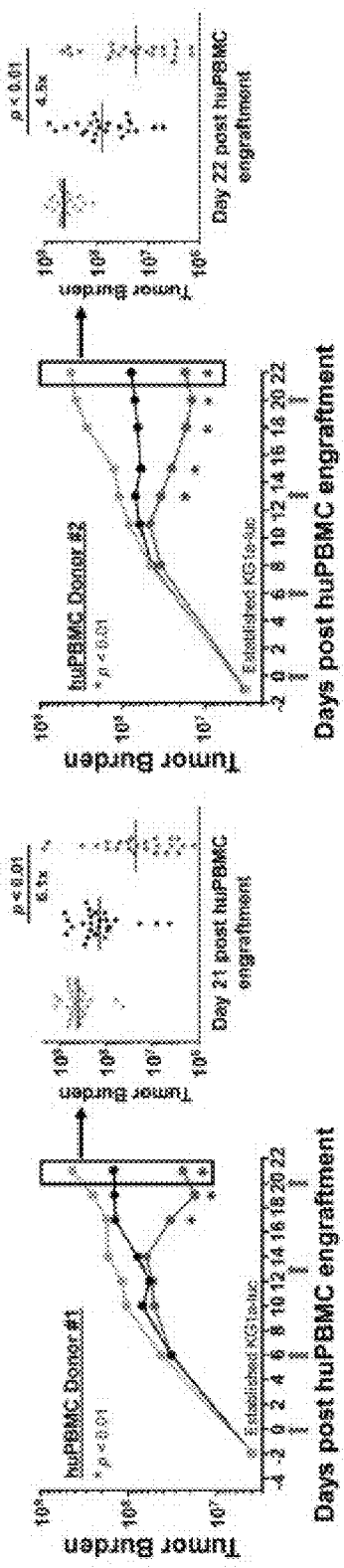

FIG. 54 is graphs showing that XmAb20717 enhances allogeneic anti-tumor responses in mice. NSG mice were engrafted with KG1a-luc followed by engaftment with huPBMCs. Tumor burden presented is derived from the geometric mean flux acquired by IVIS imaging of KG1a-luc.

Figure 55:
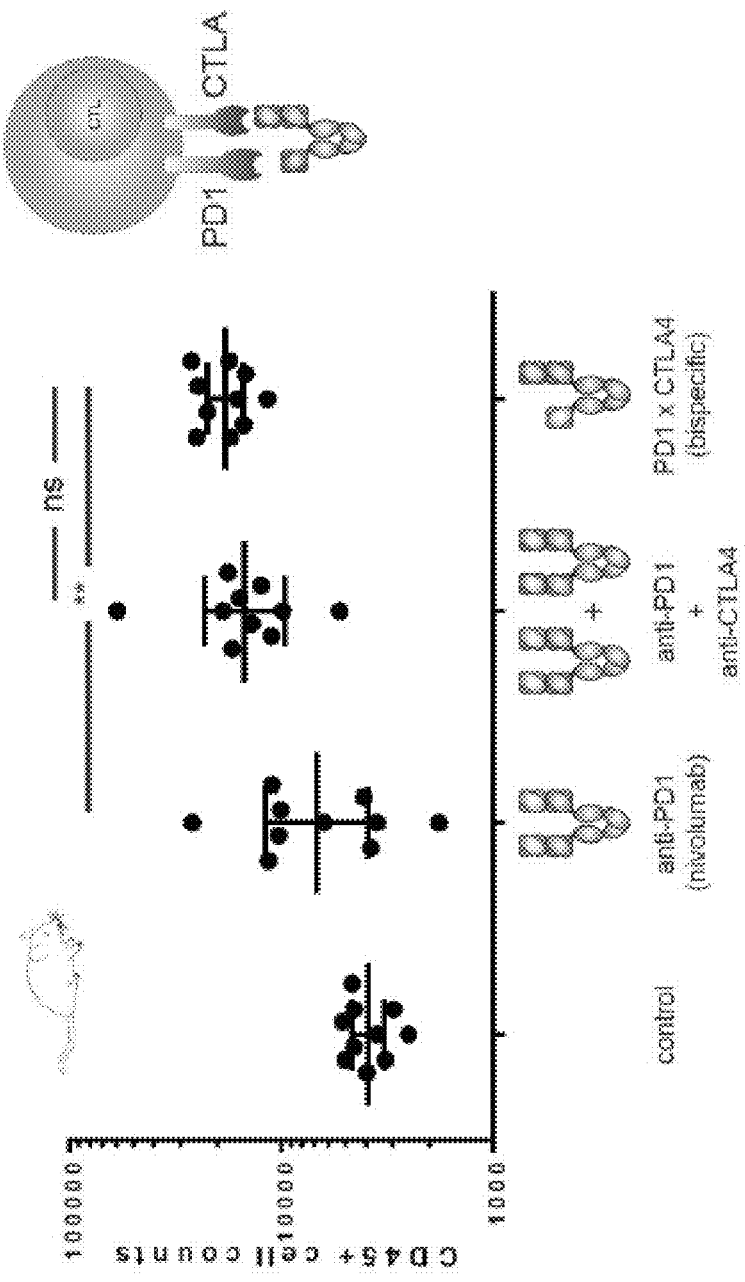

FIG. 55 is a graph showing that PD1 x CTLA4 bispecific antibodies are highly active in a mouse model for checkpoint blockade, as measured in CD45+ cell counts.

Figure 56:
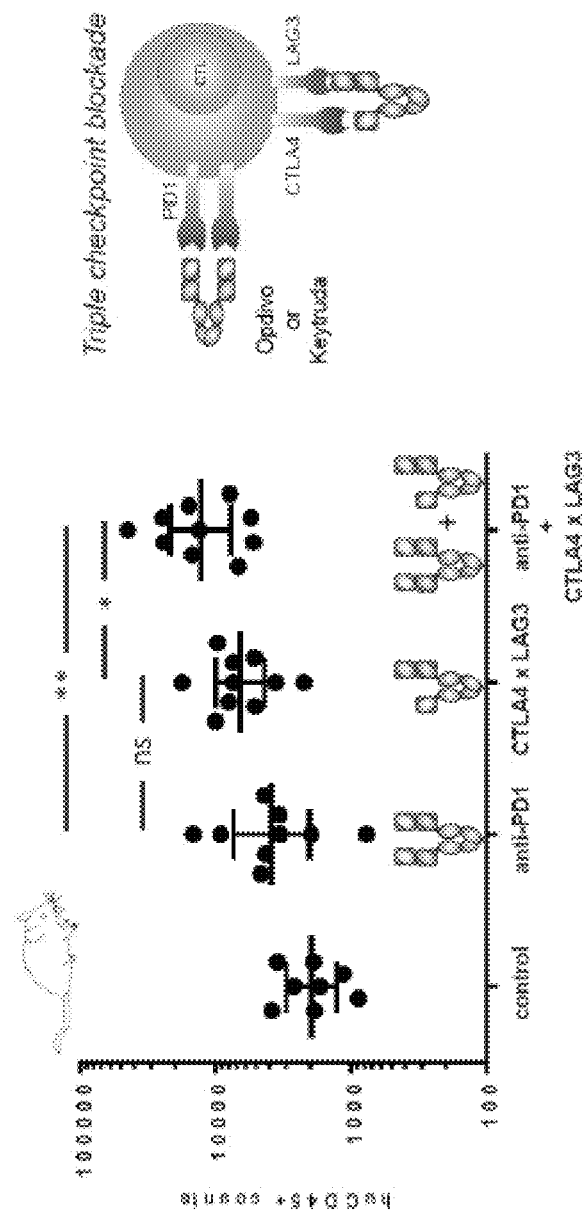

FIG. 56 is a graph showing that CTLA4 x LAG3 bispecific is active and combines with anti-PD-1 for triple blockade for a mouse model for checkpoint blockade.

Figure 57A:
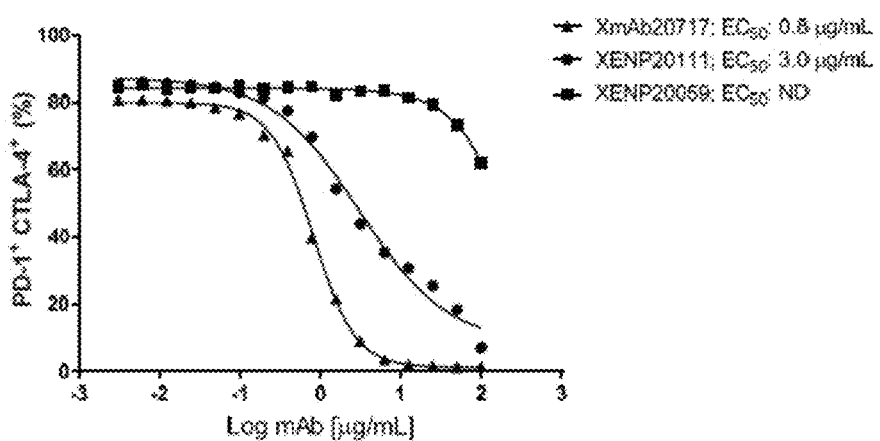
Figure 57B:
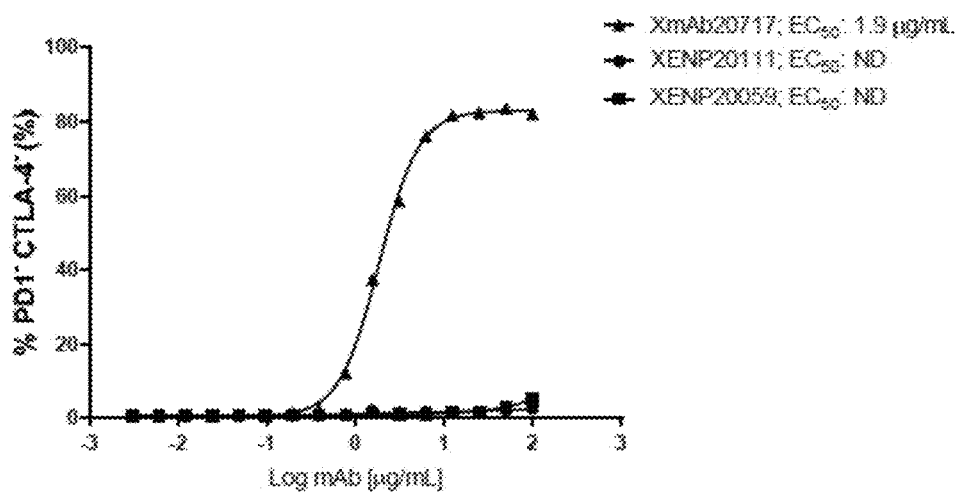

FIGS. 57A and 57B depict checkpoint receptor occupancy by the indicated test articles as indicated by percentage of populations of HEK293T cells expressing both CTLA-4 and PD-1 with unoccupied CTLA-4 and/or LAG-3 receptors as shown by staining.

Figure 58:
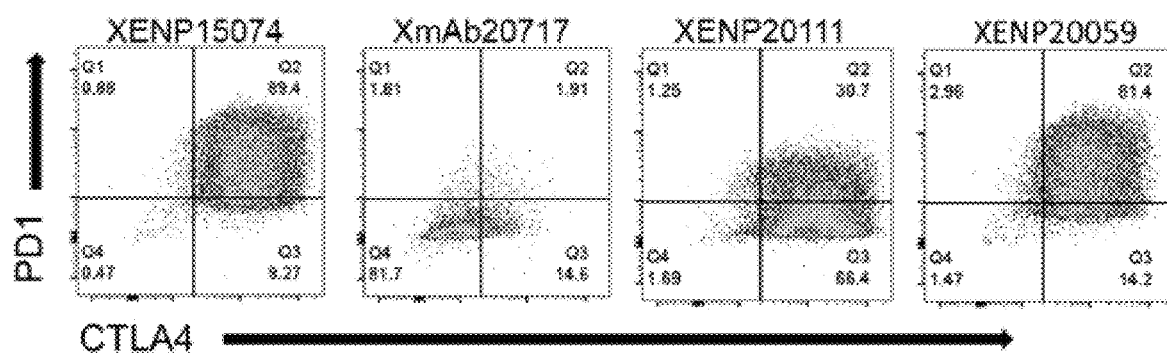

FIG. 58 shows FACS scatter plots depicting populations of (Q1) CTLA-4-PD-1+, (Q2) CTLA-4+PD-1+, (Q3) CTLA-4−PD-1+, and (Q4) CTLA-4−PD-1− cells following treatment with the indicated test articles.

Figure 59A:
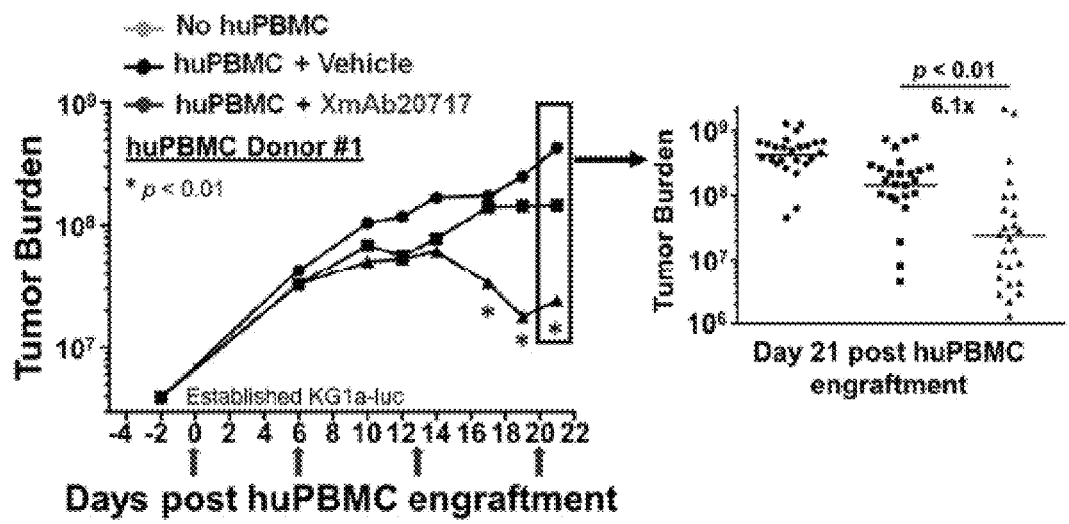
Figure 59B:
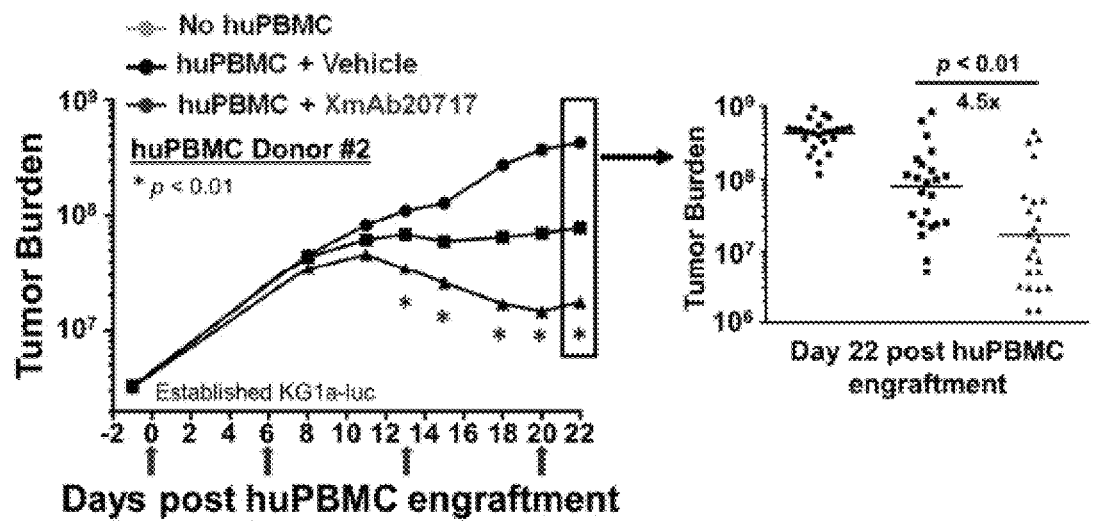

FIGS. 59A and 59B depict tumor burden (derived from the geometric mean flux acquired by IVIS imaging of KG1a-luc) in NSG mice engrafted with KG1a-luc followed by engraftment with huPBMCs following treatment with XmAb20717.

Figure 60:
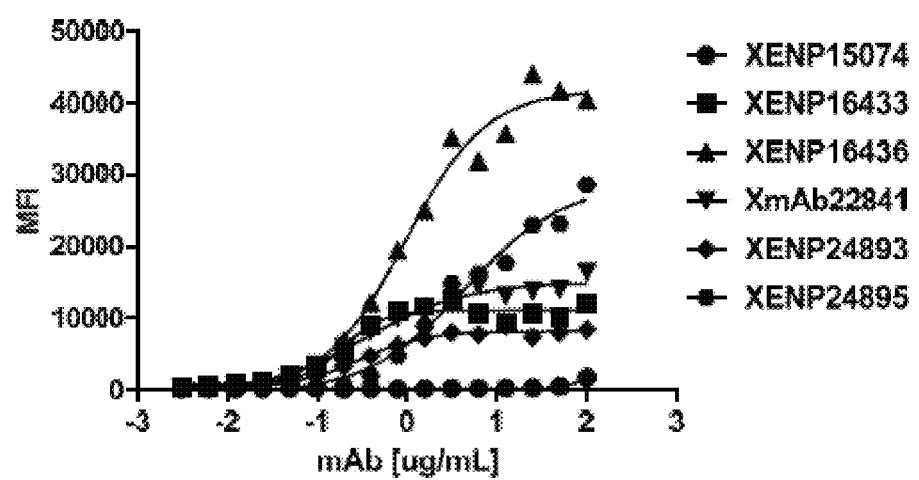
Figure 61A:
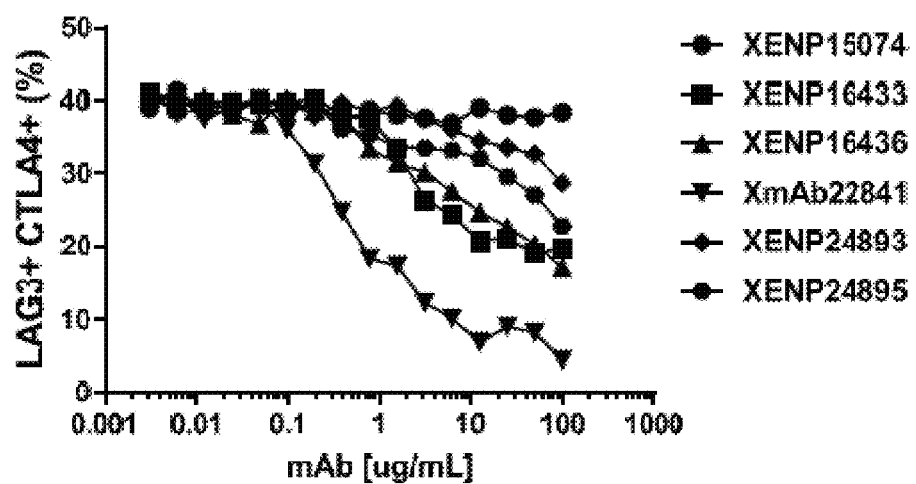
Figure 61B:
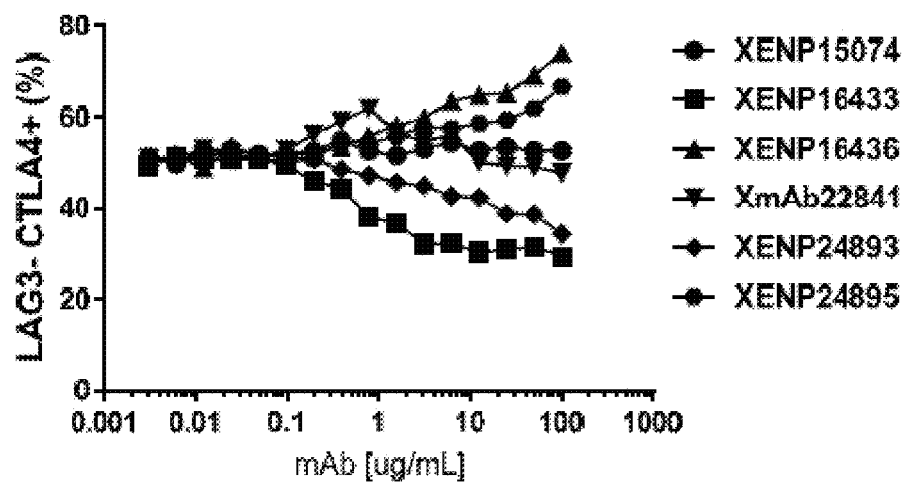
Figure 61C:
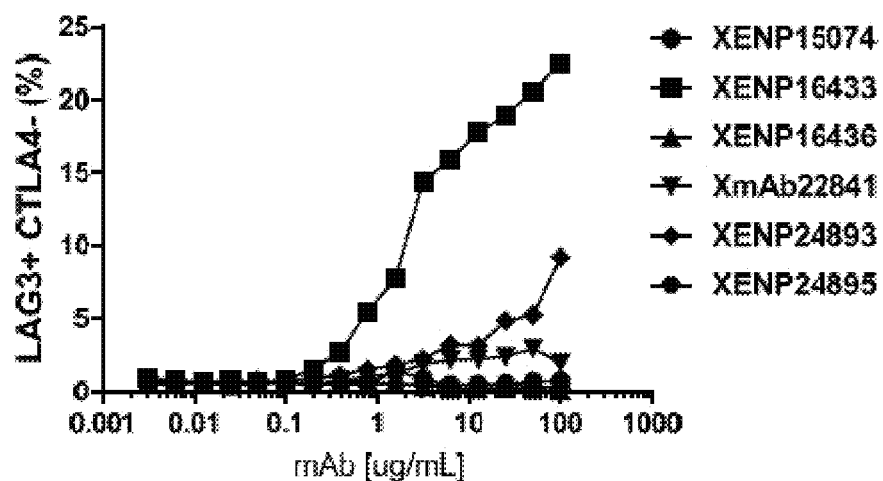
Figure 61D:
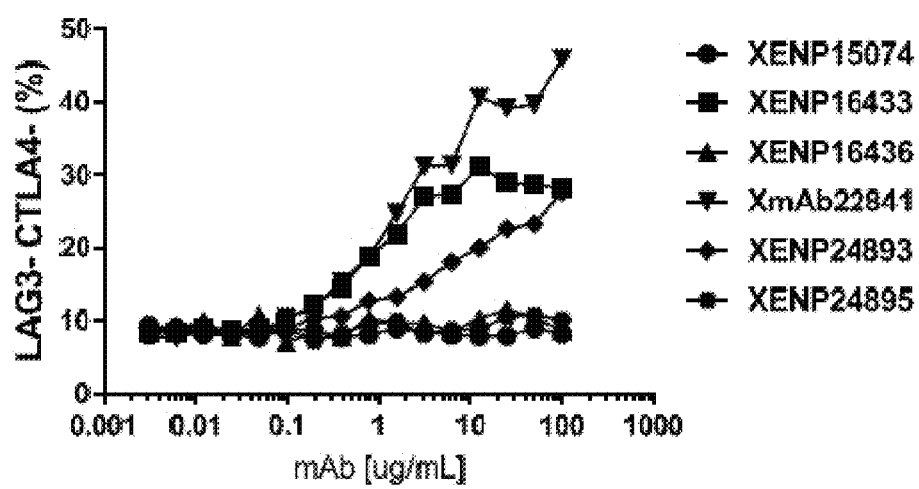

FIG. 60 depicts the binding of XmAb22841 to HEK293T cells expressing CTLA-4 and LAG-3.

FIGS. 61A to 61D depict checkpoint receptor occupancy by the indicated test articles as indicated by percentage of populations of HEK293T cells expressing both CTLA-4 and LAG-3 with unoccupied CTLA-4 and/or LAG-3 receptors as shown by staining.

Figure 62A:
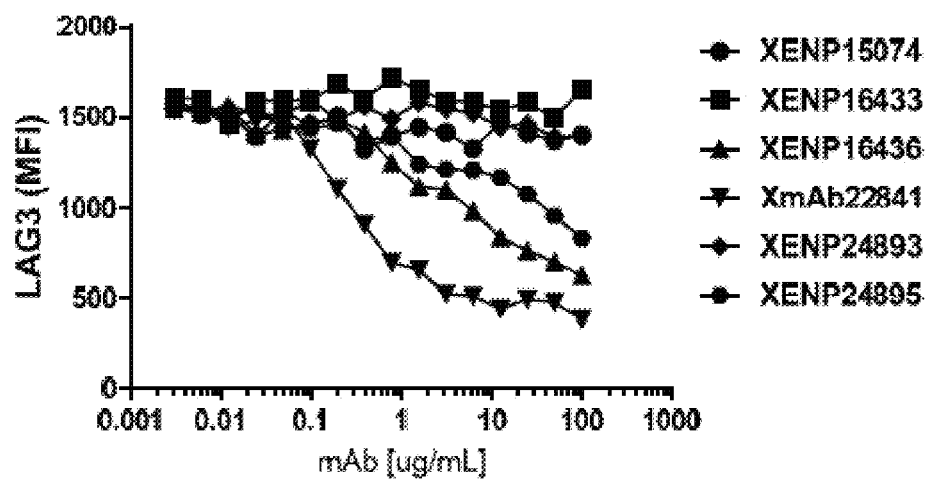
Figure 62B:
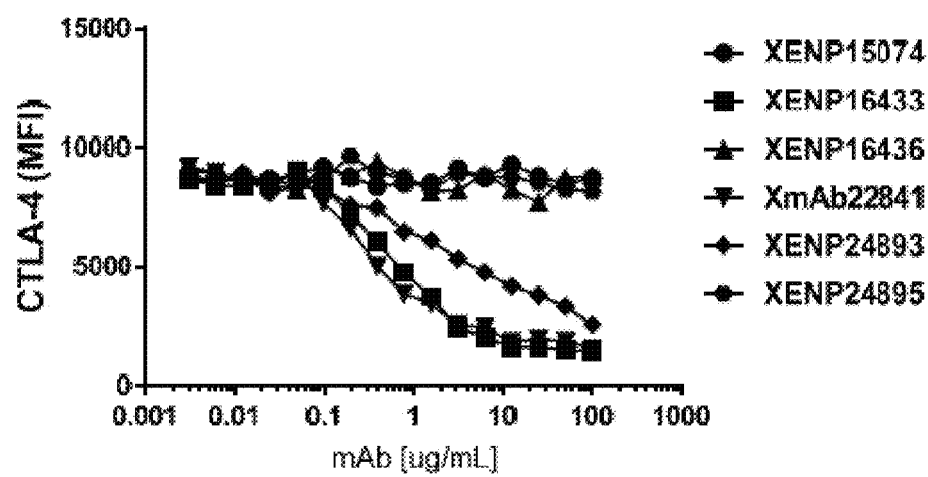
Figure 63A:
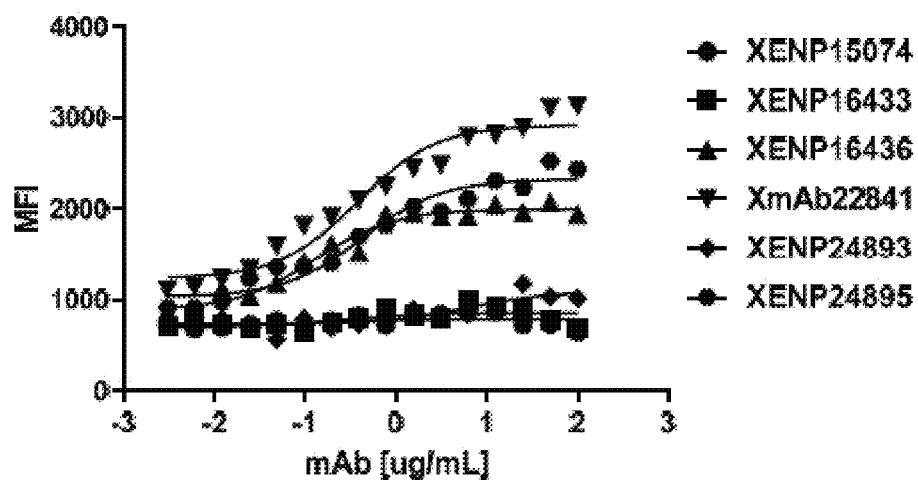
Figure 63B:
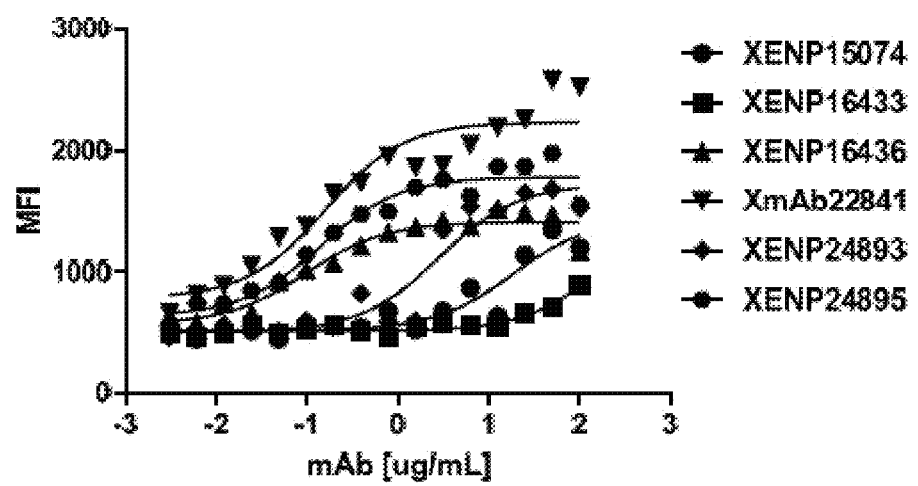
Figure 63C:
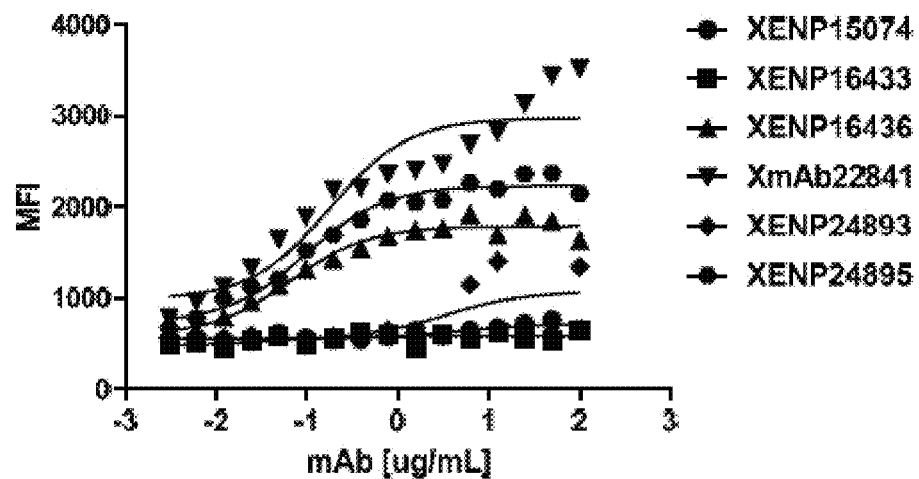
Figure 63D:
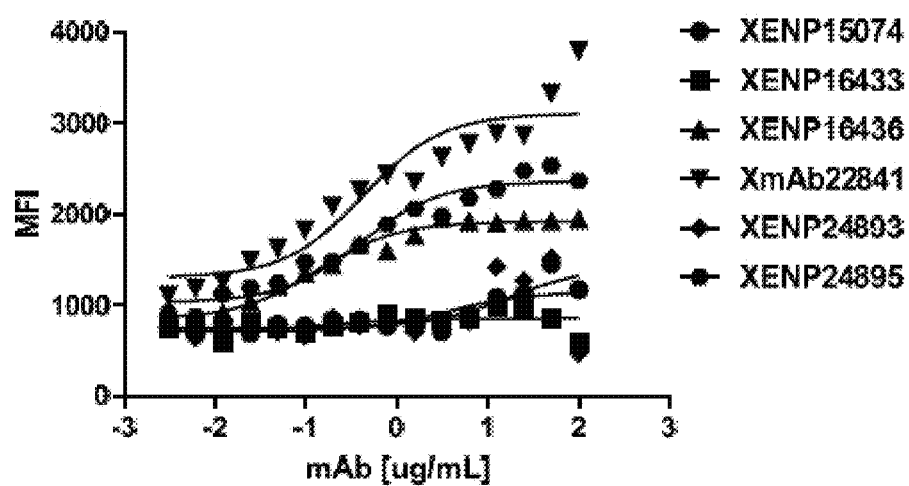
Figure 63E:
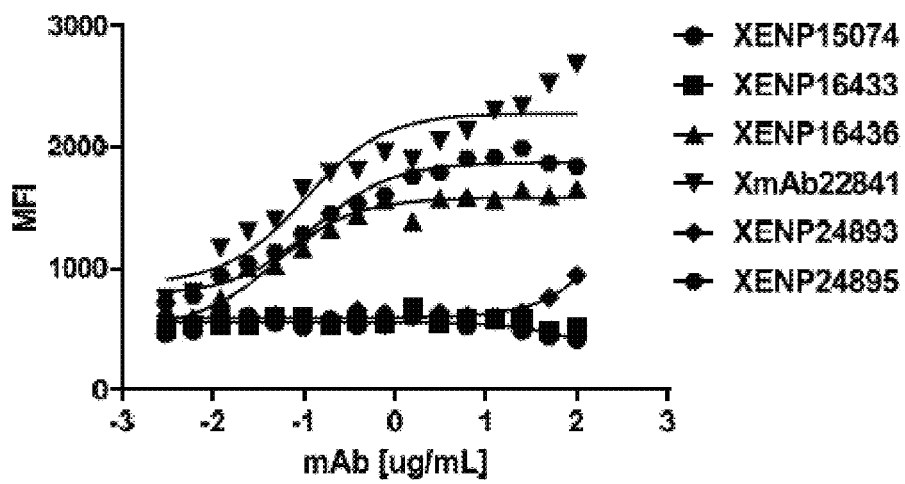
Figure 63F:
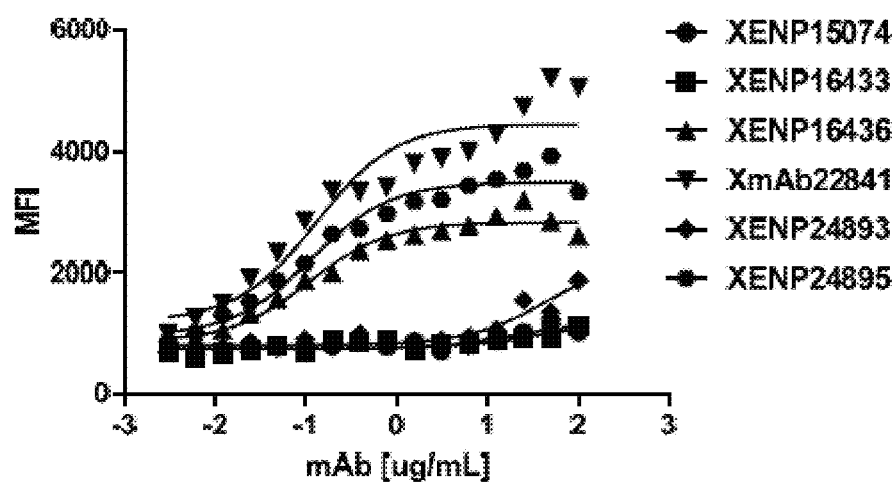

FIGS. 62A and 62B show the amount of unoccupied A) LAG-3 and B) CTLA-4 receptors on HEK293T cells expressing both CTLA-4 and LAG-3 following treatment with the indicated test articles.

FIGS. 63A to 63F depict binding of the indicated test articles to SEB-stimulated T cells from 6 separate PBMC donors (A-F).

Figure 64:
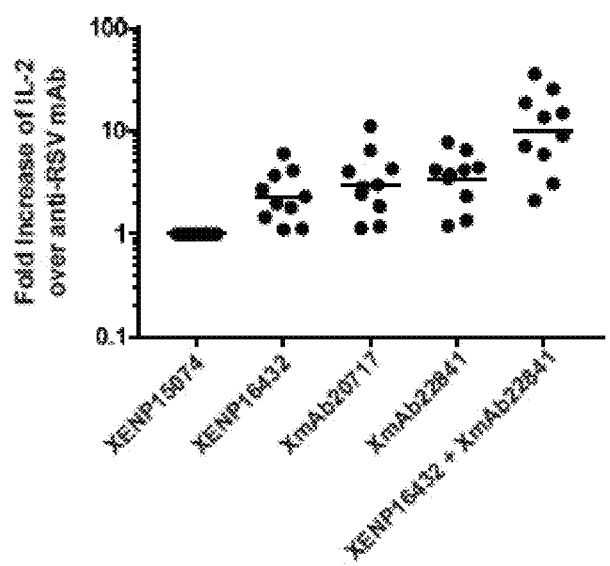

FIG. 64 depicts fold increase in IL-2 release by SEB-stimulated T cells following treatment with XENP16432, XmAb20717, XmAb22841, and XmAb22841 in combination with XENP16432 over treatment with anti-RSV mAb (XENP15074).

Figure 65:
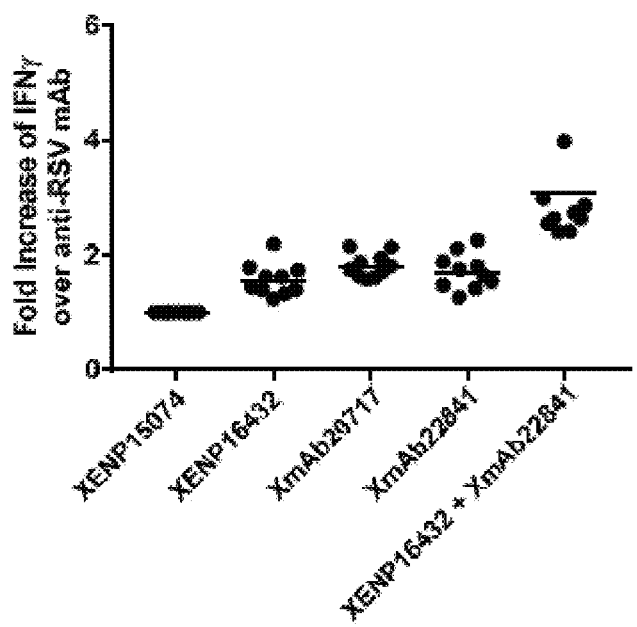

FIG. 65 depicts fold increase in IFNγ release by SEB-stimulated T cells following treatment with XENP16432, XmAb20717, XmAb22841, and XmAb22841 in combination with XENP16432 over treatment with anti-RSV mAb (XENP15074).

Figure 66:
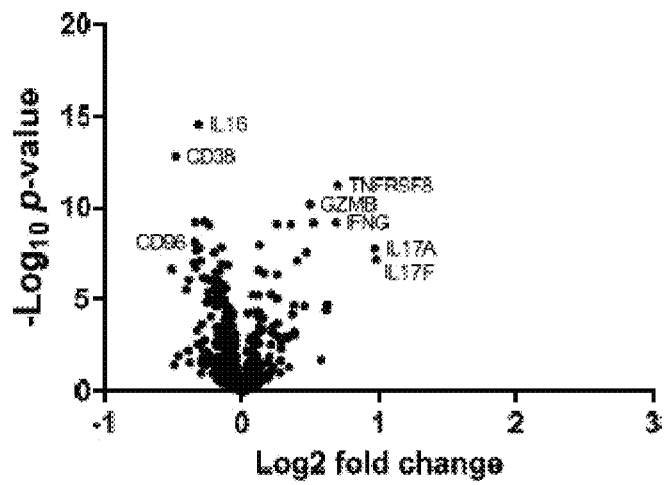

FIG. 66 depicts fold change (x-axis) in expression of immune-related genes by SEB-stimulated T cells following treatment with anti-PD-1 mAb (XENP16432) over treatment with anti-RSV mAb (XENP15074). The y-axis depicts the significance.

Figure 67:
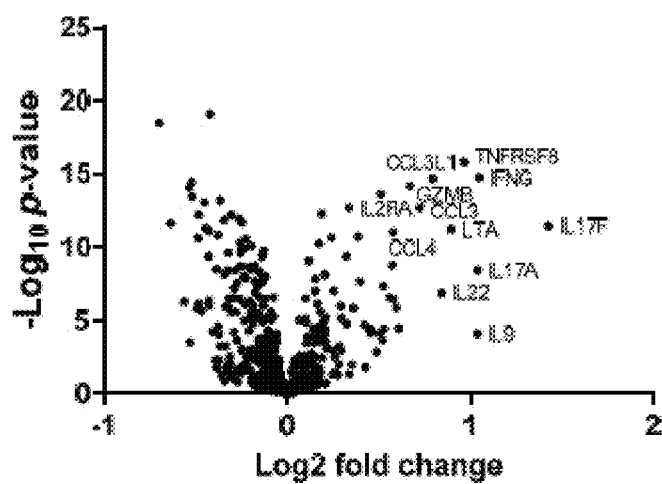

FIG. 67 depicts fold change (x-axis) in expression of immune-related genes by SEB-stimulated T cells following treatment with XmAb20717 over treatment with anti-RSV mAb (XENP15074).

Figure 68:
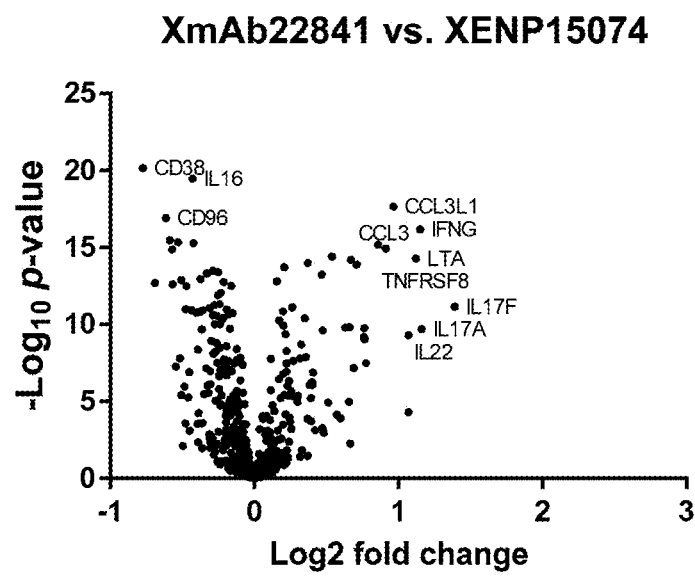

FIG. 68 depicts fold change (x-axis) in expression of immune-related genes by SEB-stimulated T cells following treatment with XmAb22841 over treatment with anti-RSV mAb (XENP15074).

Figure 69:
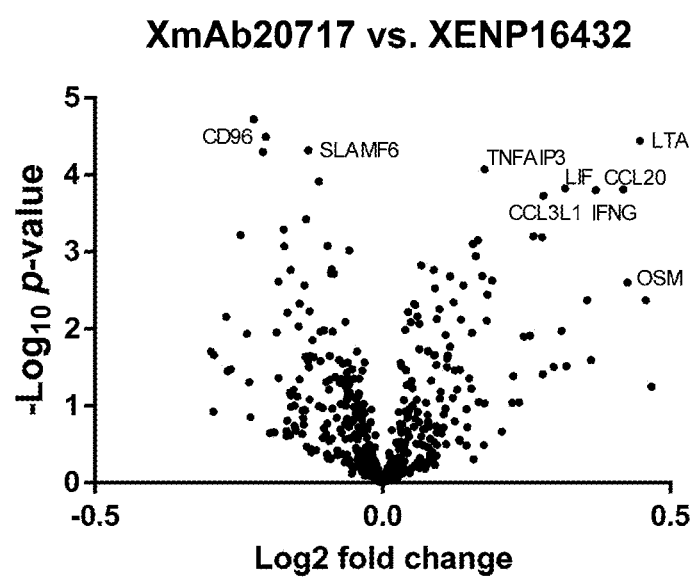

FIG. 69 depicts fold change (x-axis) in expression of immune-related genes by SEB-stimulated T cells following treatment with XmAb20717 over treatment with anti-PD-1 mAb (XENP16432).

Figure 70:
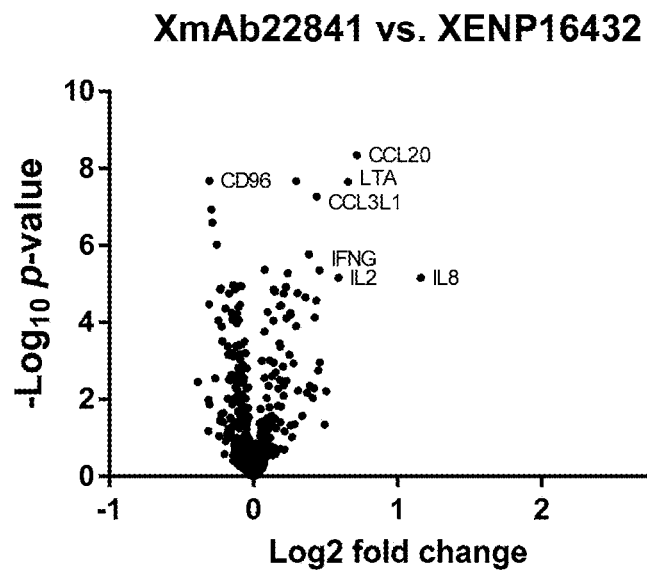

FIG. 70 depicts fold change (x-axis) in expression of immune-related genes by SEB-stimulated T cells following treatment with XmAb22841 over treatment with anti-PD-1 mAb (XENP16432).

Figure 71:
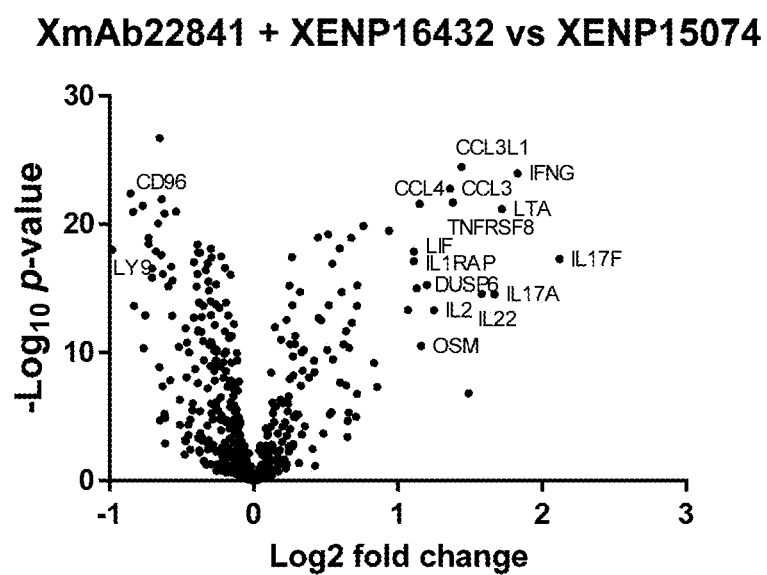

FIG. 71 depicts fold change (x-axis) in expression of immune-related genes by SEB-stimulated T cells following treatment with XmAb22841 in combination with anti-PD-1 mAb (XENP16432) over treatment with anti-RSV mAb (XENP15074).

Figure 72:
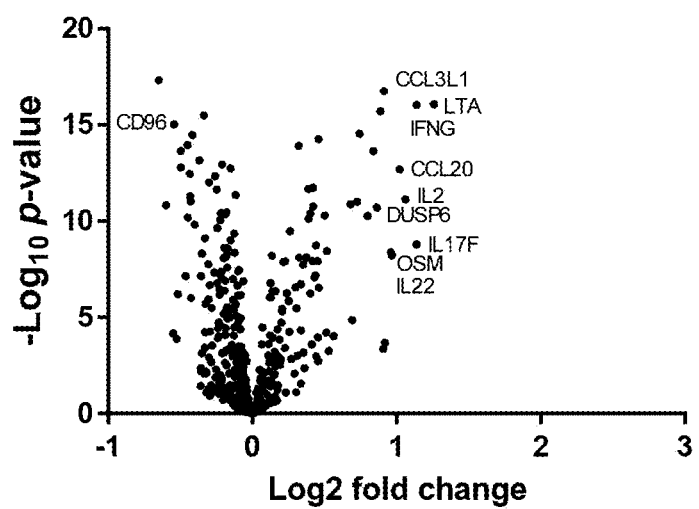

FIG. 72 depicts fold change (x-axis) in expression of immune-related genes by SEB-stimulated T cells following treatment with XmAb22841 in combination with anti-PD-1 mAb (XENP16432) over treatment with anti-PD-1 mAb (XENP16432) alone.

FIG. 73 depicts the sequence for an anti-RSV antibody. It is important to note that these sequences were generated based on human IgG1, with an ablation variant (E233P/L234V/L235A/G236del/S267K, "IgG1_PVA_/S267k"). The CDRs are underlined. As noted herein and is true for every sequence herein containing CDRs, the exact identification of the CDR locations may be slightly different depending on the numbering used as is shown in Table 1, and thus included herein are not only the CDRs that are underlined but also CDRs included within the VH and VL domains using other numbering systems.

FIG. 74 depicts the sequences for an anti-PD-1 antibody with the variable regions from nivolumab. It is important to note that these sequences were generated based on human IgG1, with an ablation variant (E233P/L234V/L235A/G236del/S267K, "IgG1_PVA_/S267k"). The CDRs are underlined. As noted herein and is true for every sequence herein containing CDRs, the exact identification of the CDR locations may be slightly different depending on the numbering used as is shown in Table 1, and thus included herein are not only the CDRs that are underlined but also CDRs included within the VH and VL domains using other numbering systems.

FIG. 75 depicts the sequences for an anti-PD-1 antibody with the variable regions from pembrolizumab. It is important to note that these sequences were generated based on human IgG4, with a S228P variant. The CDRs are underlined. As noted herein and is true for every sequence herein containing CDRs, the exact identification of the CDR locations may be slightly different depending on the numbering used as is shown in Table 1, and thus included herein are not only the CDRs that are underlined but also CDRs included within the VH and VL domains using other numbering systems.

Figure 76A:
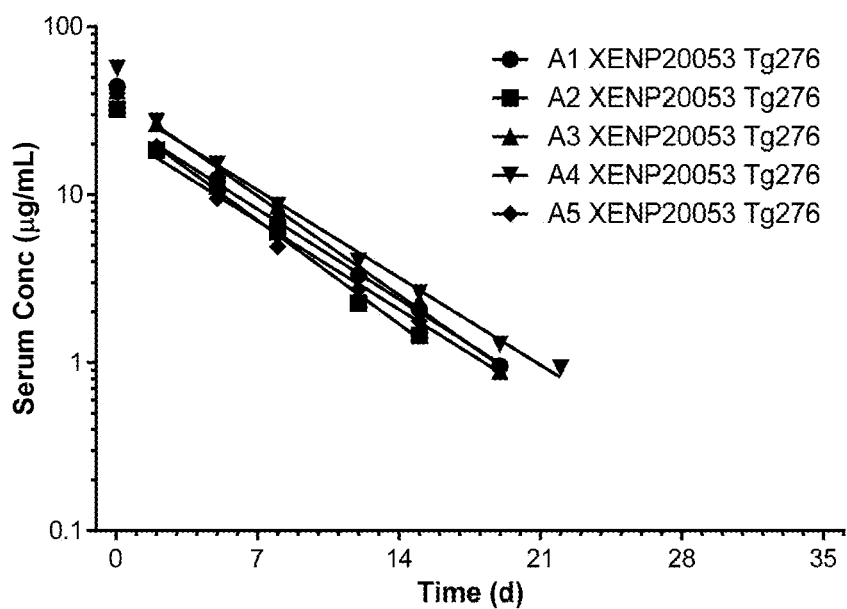
Figure 76B:
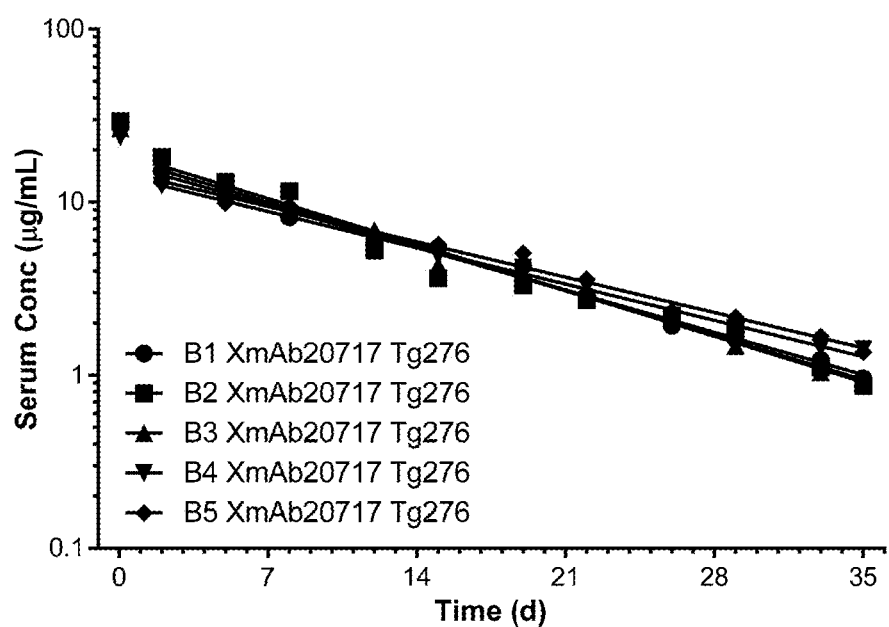

FIGS. 76A and 76B depict the pharmacokinetic profile for A) XENP20053 and B) XmAb20717 in individual mice following 2 mg/kg single i.v. administration in hFcRn (Tg276) mice.

Figure 77:
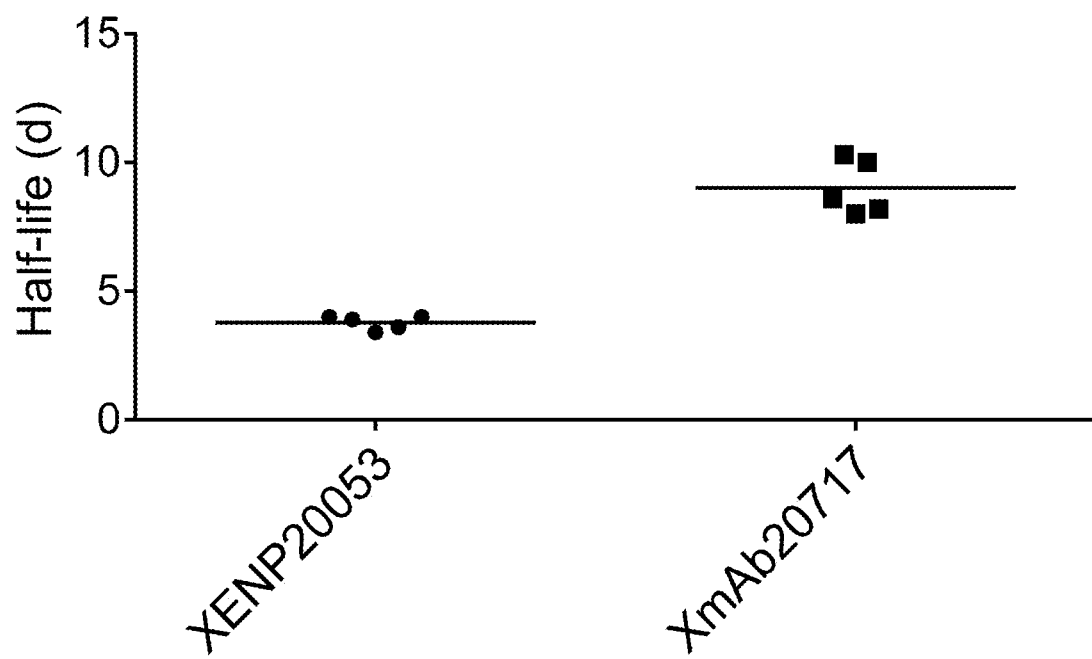

FIG. 77 depicts the half-life of XENP20053 and XmAb20717 (individual animals) following 2 mg/kg single dose i.v. administration in hFcRn (Tg276) mice.

Figure 78:
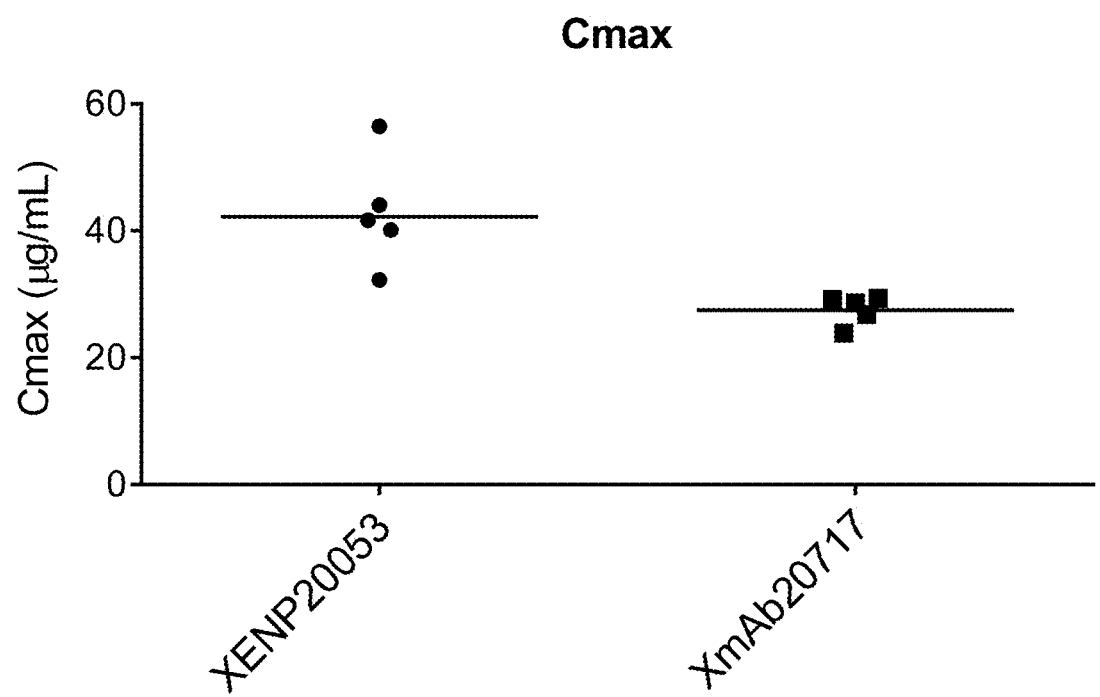
Figure 80A:
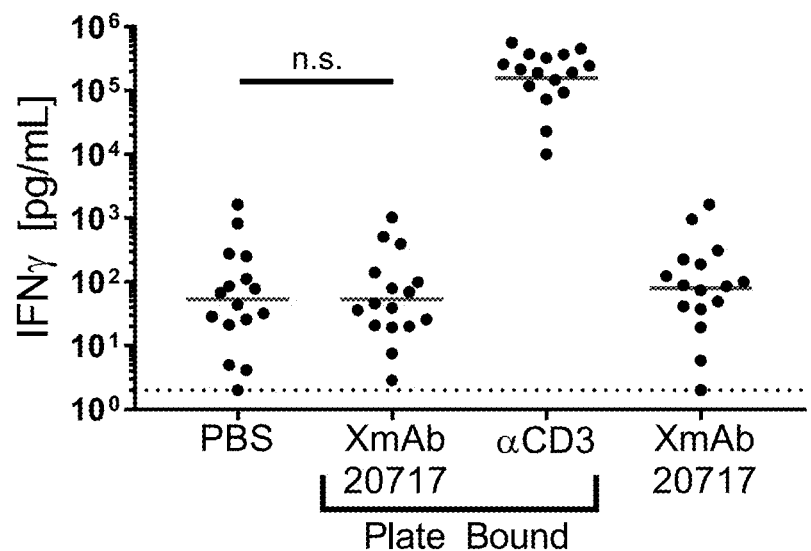
Figure 80B:
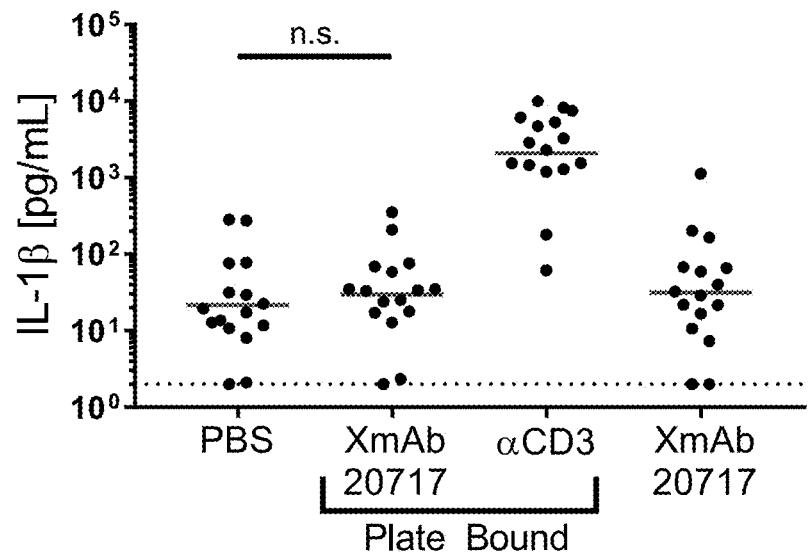
Figure 80C:
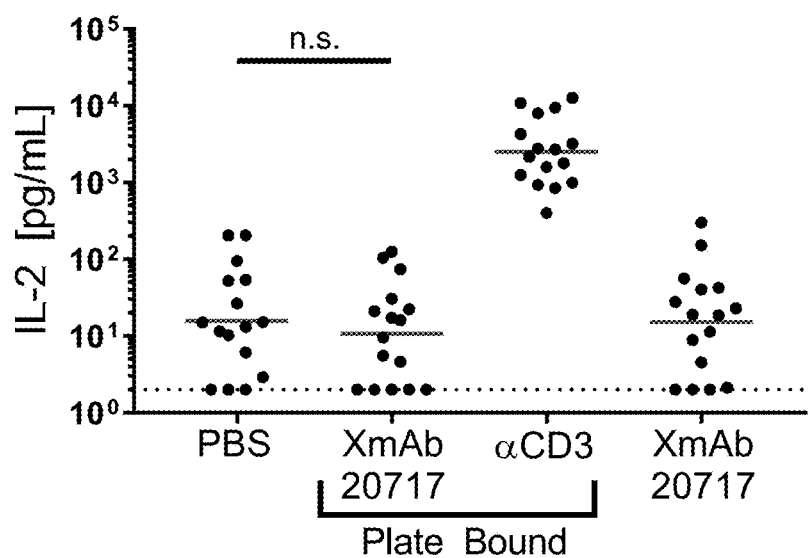
Figure 80D:
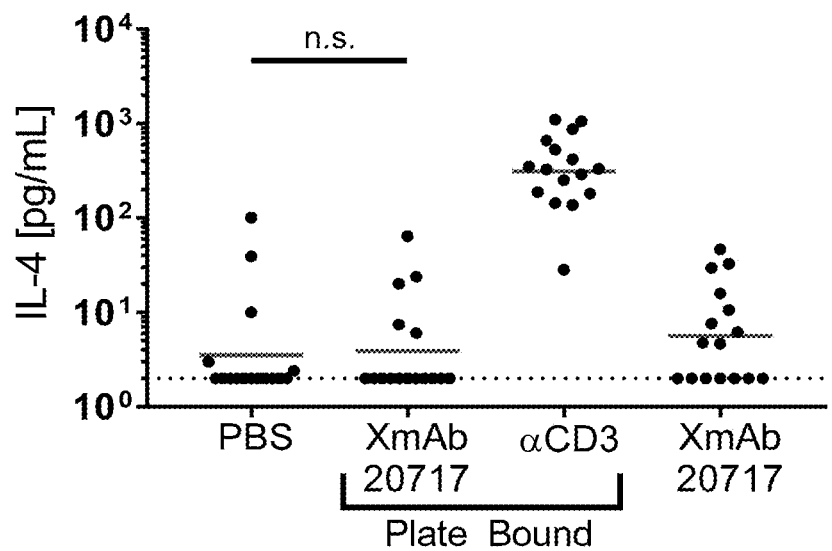
Figure 80E:
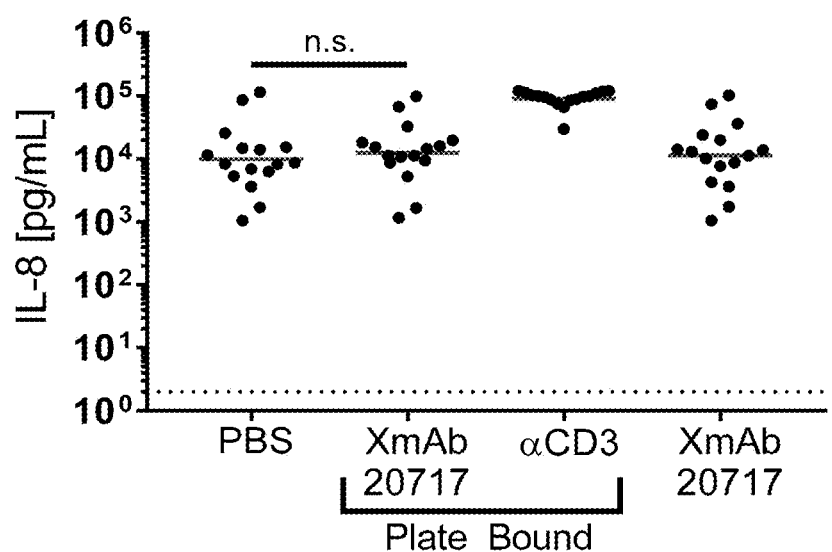
Figure 80F:
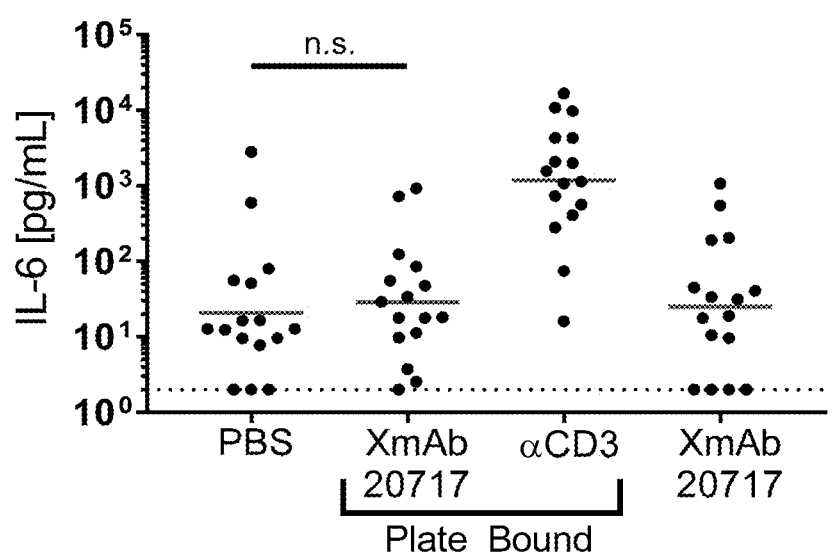
Figure 80G:
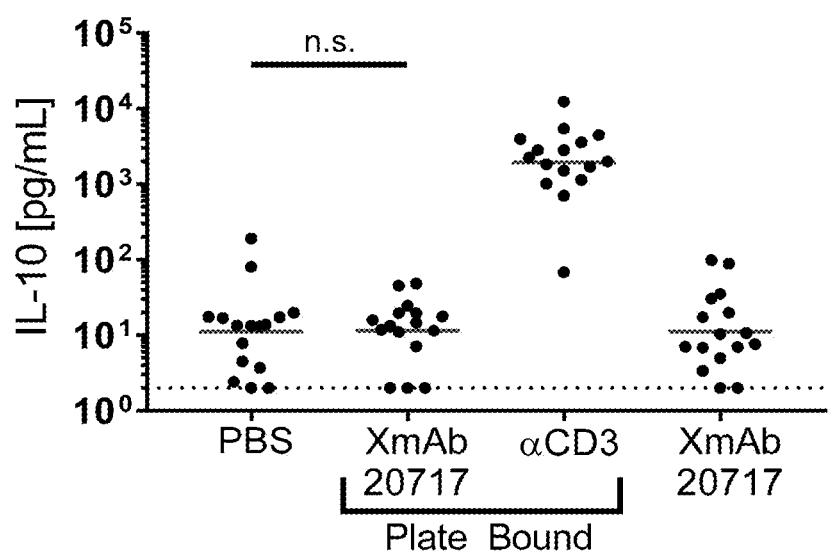
Figure 80H:
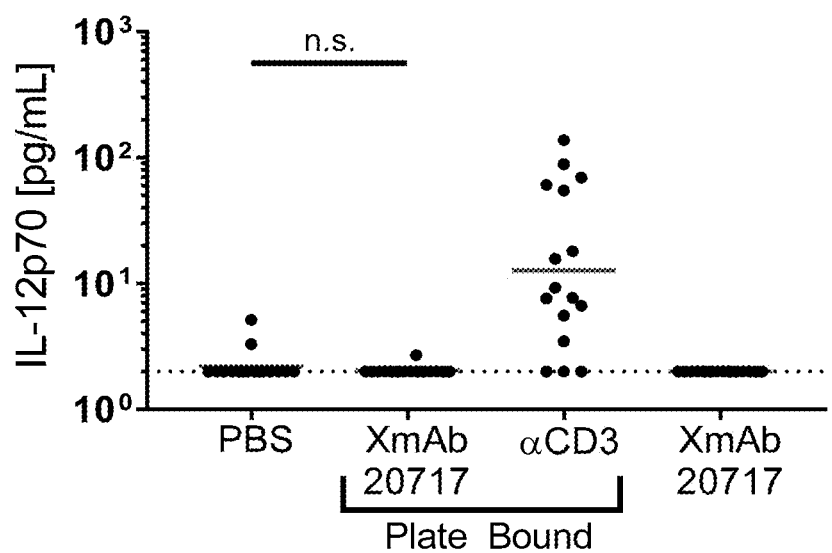
Figure 80I:
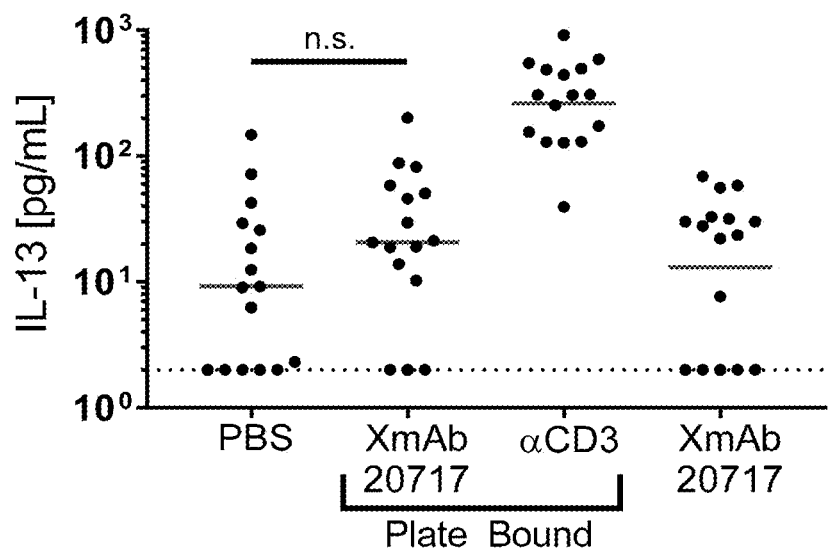
Figure 80J:
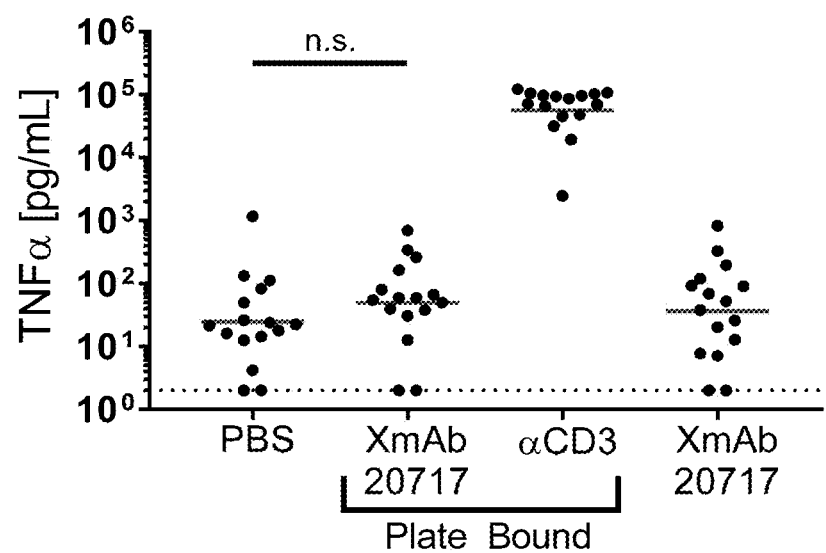

FIG. 78 depicts $C_{max}$ of XENP20053 and XmAb20717 (individual animals) following 2 mg/kg single dose i.v. administration in hFcRn (Tg276) mice.

FIG. 79 depicts the mean of selected PK parameters of XmAb20717 and XENP20053 following 2 mg/kg single dose i.v. administration in hFcRn (Tg276) mice.

FIGS. 80A to 80J depict the release of A) IFNγ, B) IL-1ß, C) IL-2, D) IL-4, E) IL-8, F) IL-6, G) IL-10, H) IL-12p70, I) IL-13, and J) TNFα from human PBMCs treated with PBS, plate-bound XmAb20717, soluble XmAb20717, and plate-bound anti-CD3 antibody (OKT3).

Figure 81A:
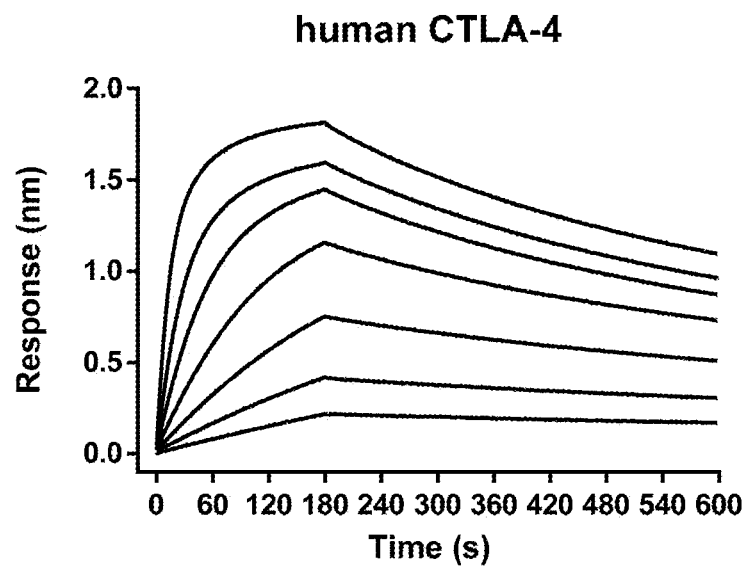
Figure 81B:
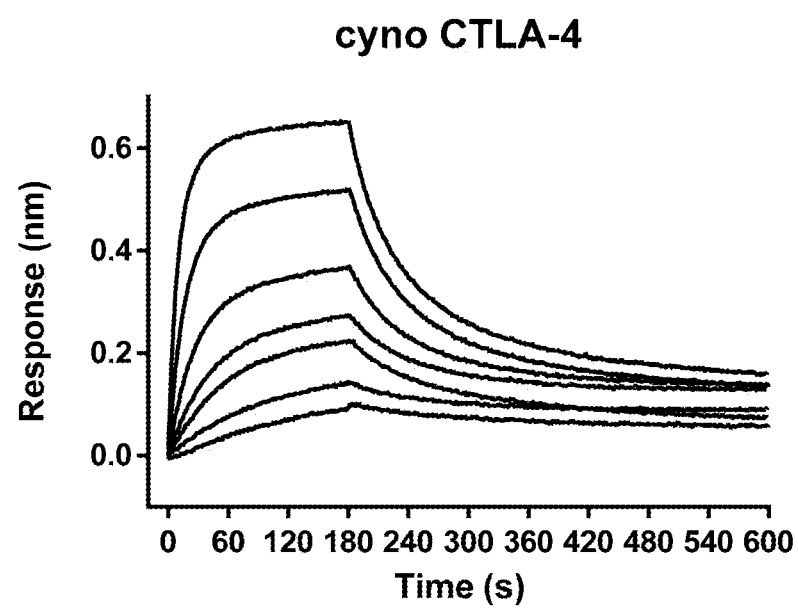

FIGS. 81A and 81B depict sensorgrams showing binding of XmAb20717 to A) human CTLA-4 and B) cynomolgus CTLA-4.

Figure 82A:
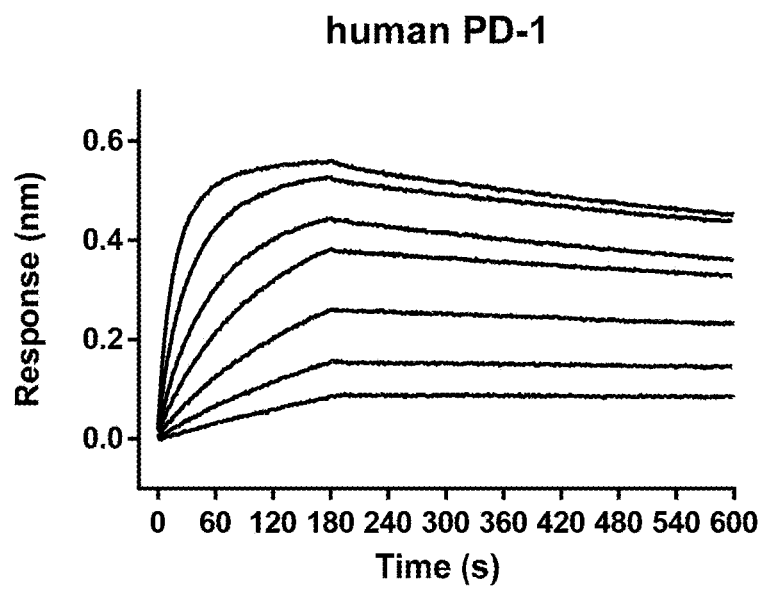
Figure 82B:
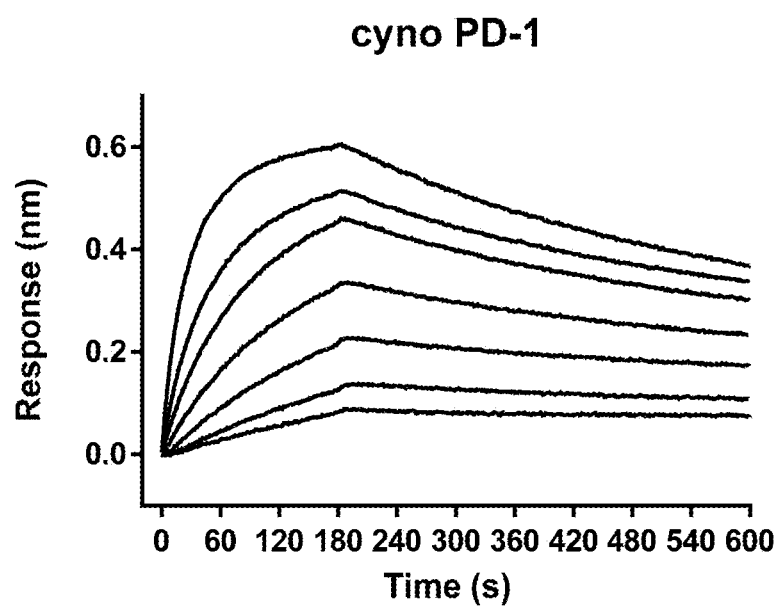

FIGS. 82A and 82B depict sensorgrams showing binding of XmAb20717 to A) human PD-1 and B) cynomolgus PD-1.

FIG. 83 depicts the equilibrium dissociation constants $(K_D)$, association rates $(k_a)$, and dissociation rates $(k_d)$ for binding of XmAb20717 to human and cynomolgus CTLA-4 and PD-1.

Figure 84:
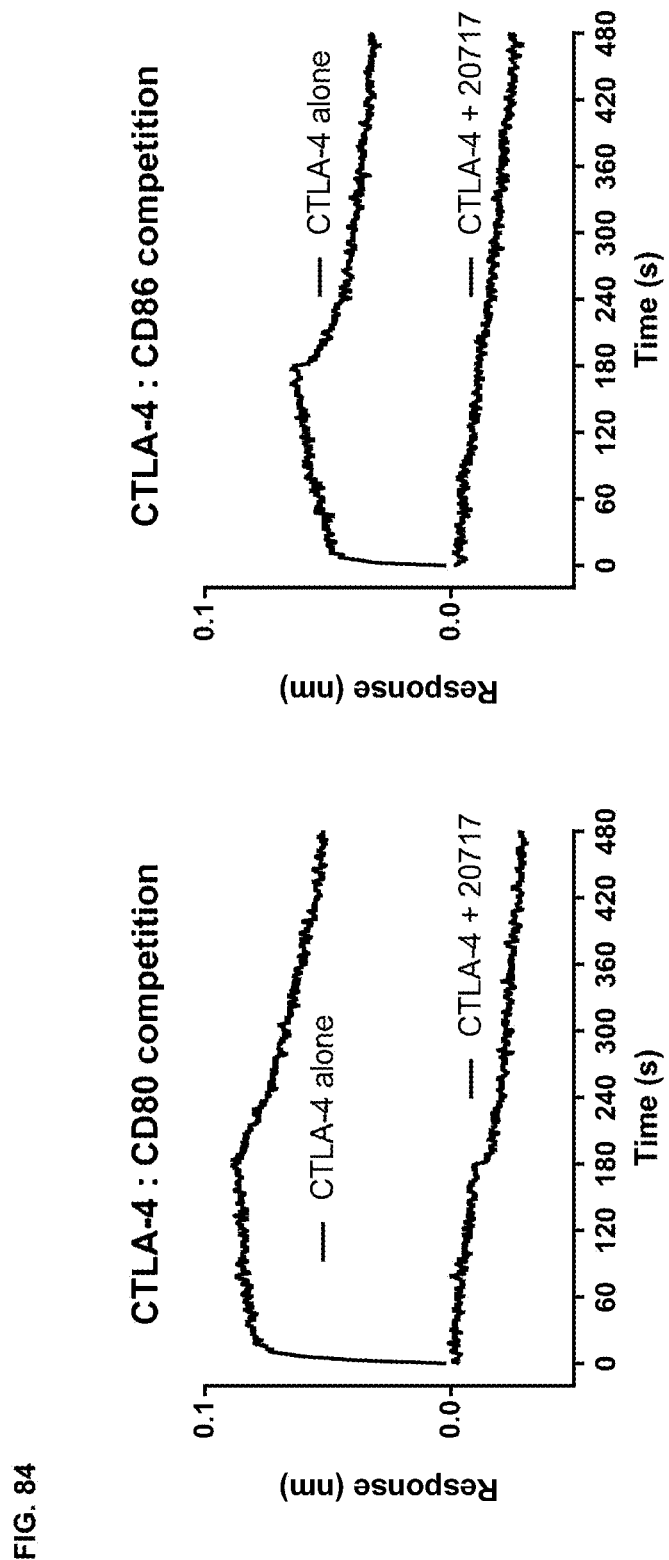

FIG. 84 depicts sensorgrams from competition binding experiments of CTLA-4 and ligands CD80 and CD86 with and without XmAb20717 pre-incubation.

Figure 85:
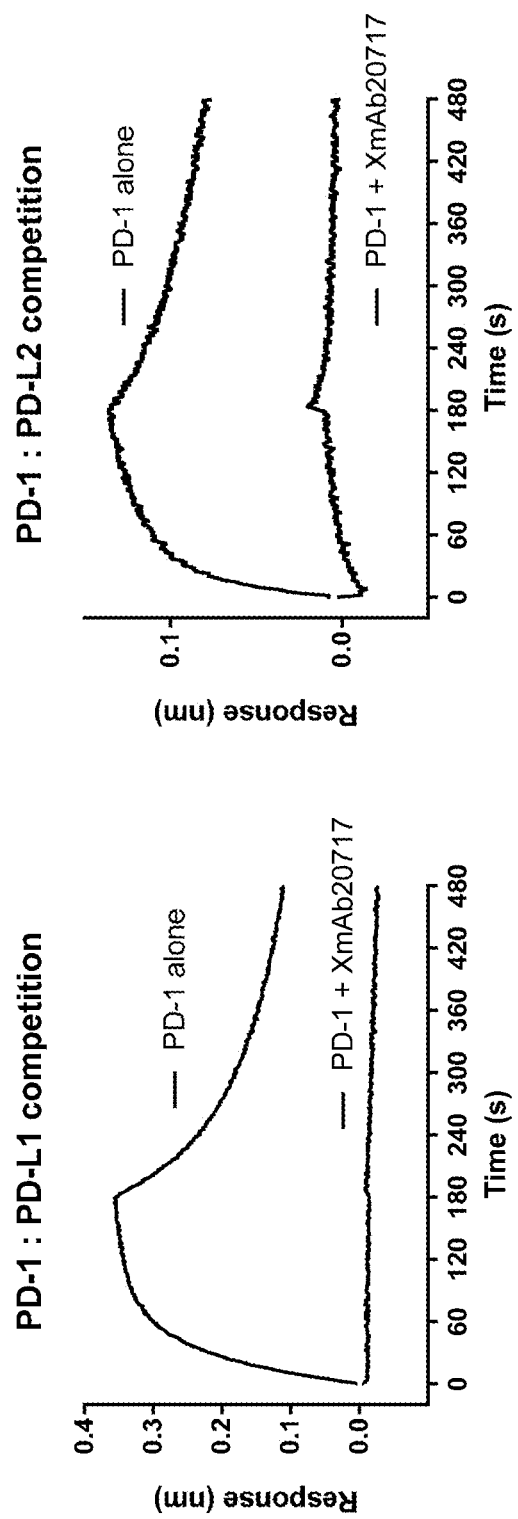

FIG. 85 depicts sensorgrams from competition binding experiments of PD-1 and ligands PD-L1 and PD-L2 with and without XmAb20717 pre-incubation.

Figure 86:
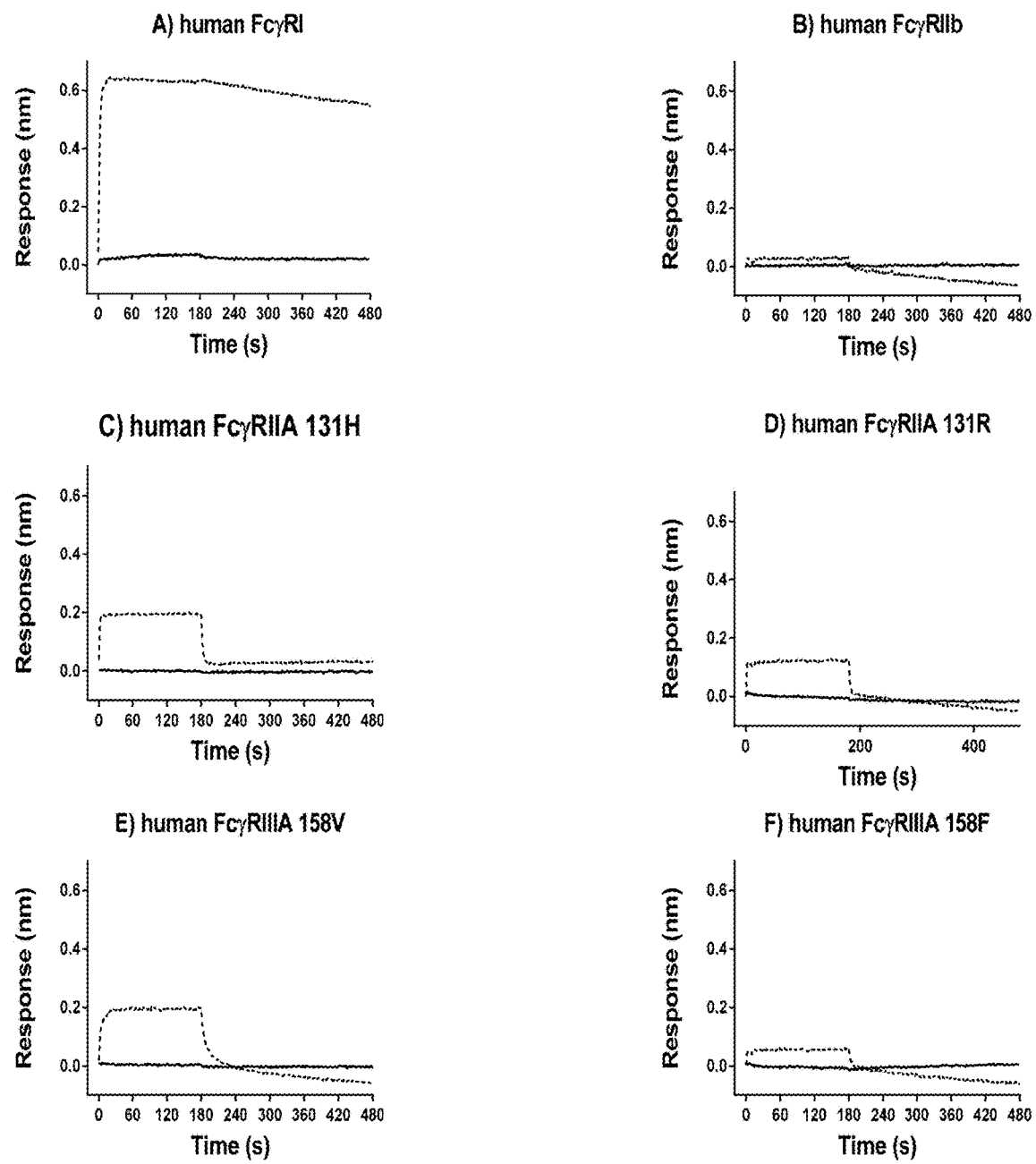

FIG. 86 depicts sensorgrams showing binding of XmAb20717 (solid line) and human IgG comparator (an anti-CD19 antibody with a native IgG1 constant region; dotted line) to A) human FcγRI, B) human FcγRIIb, C) human FcγRIIA (131H), D) human FcγRIIA (131R), E) human FcγRIIIA (158V), and F) human FcγRIIIA (158F).

Figure 87:
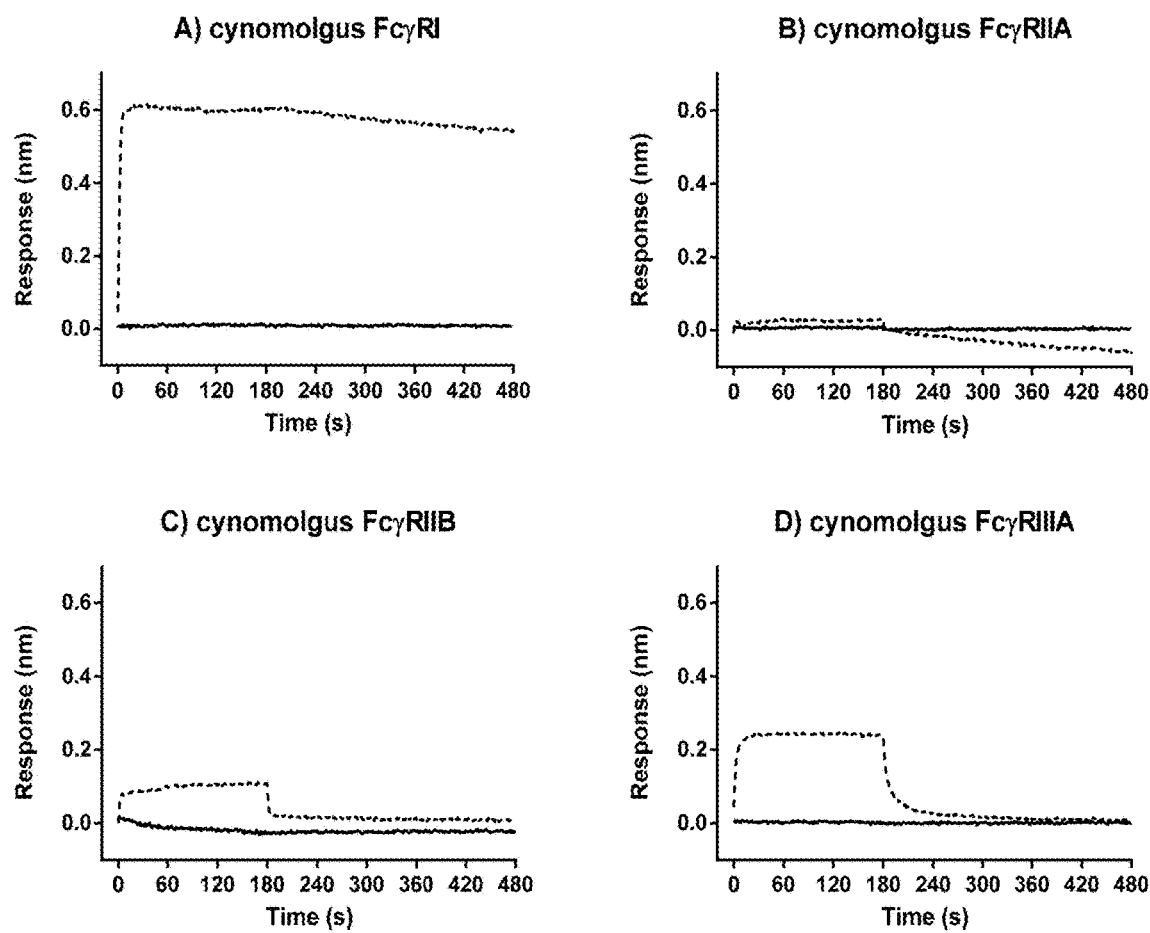

FIG. 87 depicts sensorgrams showing binding of XmAb20717 (solid line) and human IgG comparator (an anti-CD19 antibody with a native IgG1 constant region; dotted line) to A) cynomolgus FcγRI, B) cynomolgus FcγRIIA, C) cynomolgus FcγRIIb, and D) cynomolgus RcγRIIIA.

Figure 88:
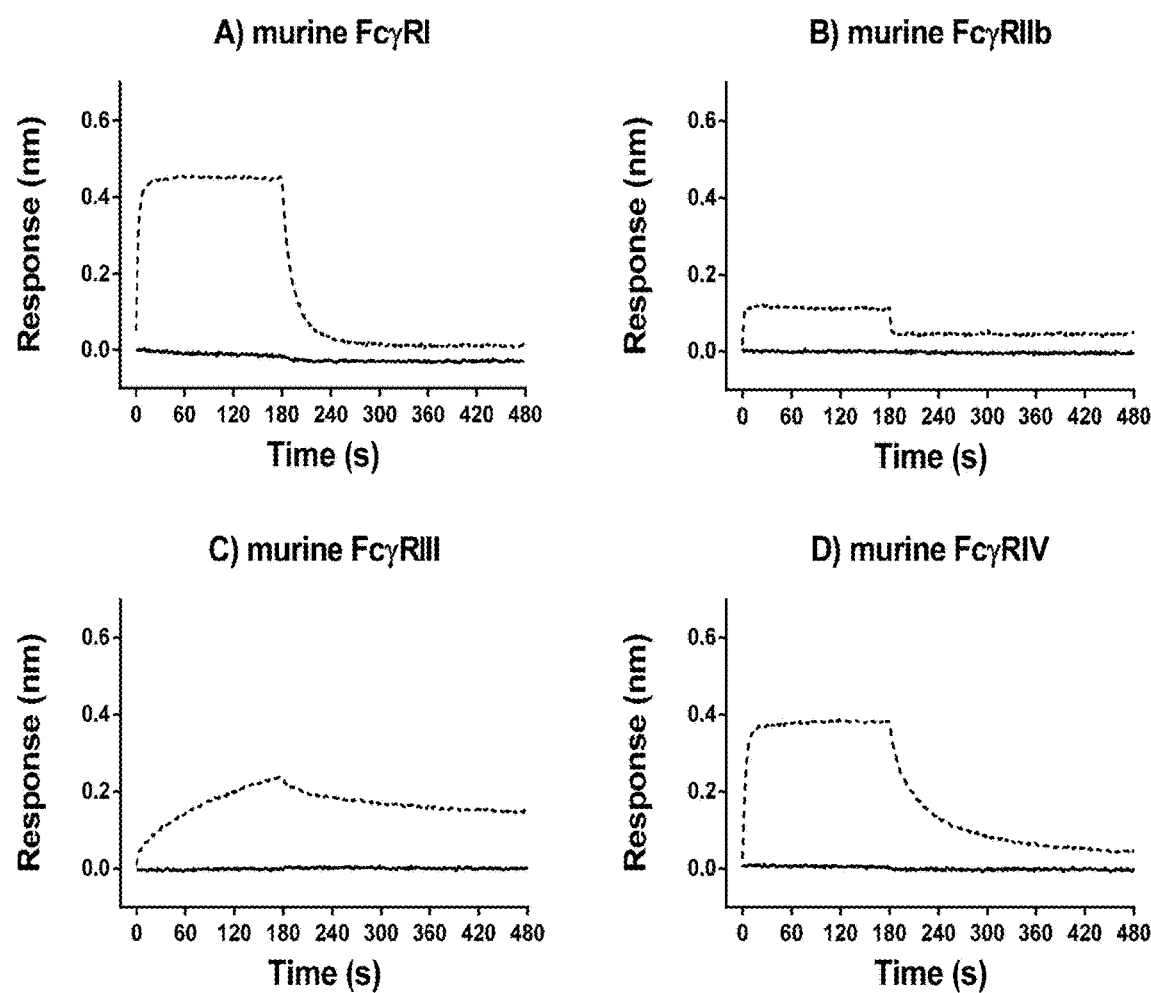

FIG. 88 depicts sensorgrams showing binding of XmAb20717 (solid line) and human IgG comparator (an anti-CD19 antibody with a native IgG1 constant region; dotted line) to A) murine FcγRI, B) murine FcγRIIb, C) murine FcγRIII, and D) murine FcγRIV.

FIG. 89 depicts equilibrium dissociation constants $(K_D)$ for binding of XmAb20717 and XENP20053 to human, cynomolgus, and mouse FcRn at pH 6.0.

Figure 90:
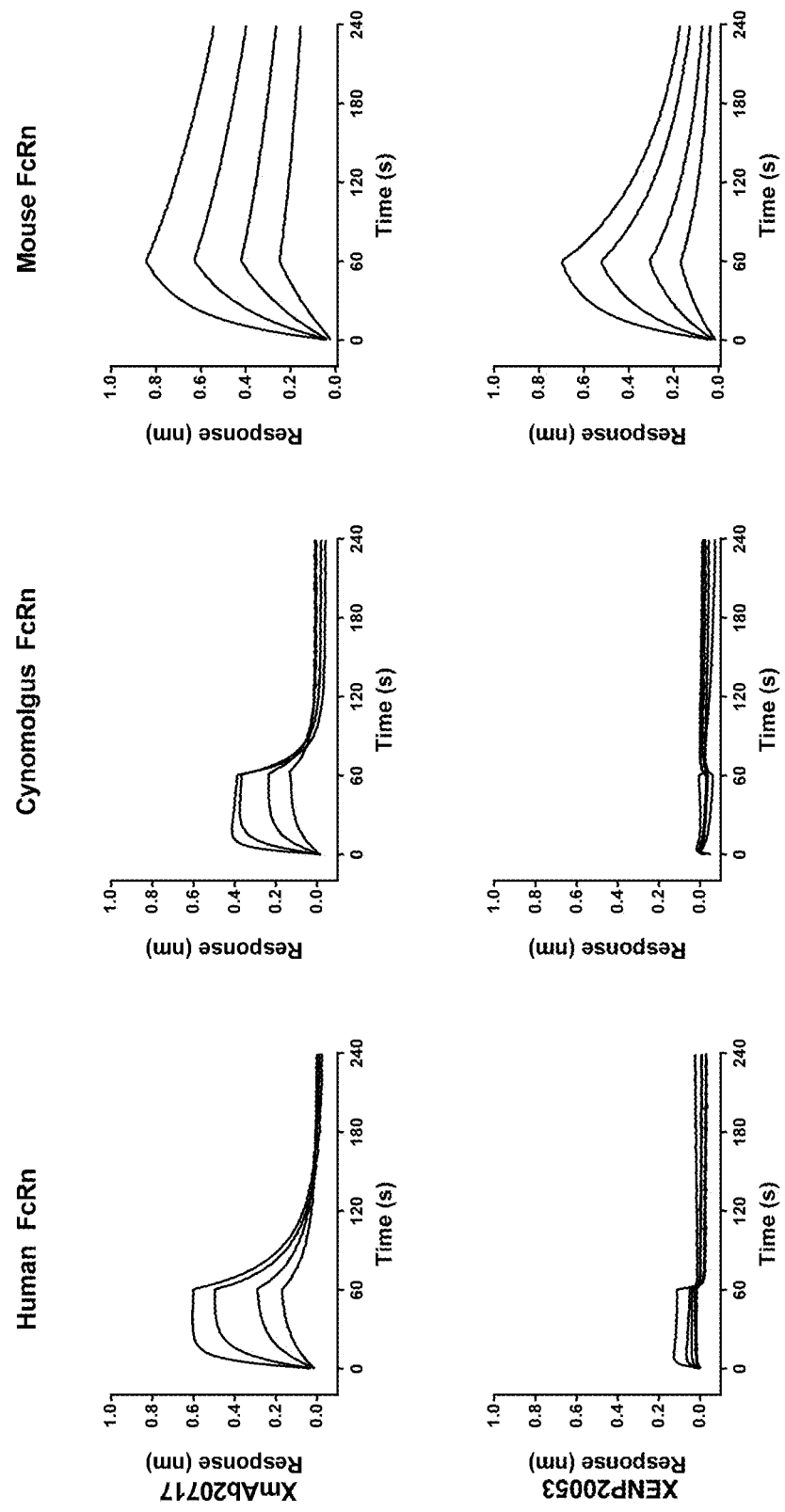

FIG. 90 depicts sensorgrams showing binding of XmAb20717 and XENP20053 to human, cynomolgus, and mouse FcRn (1000, 500, 250, and 125 nM) at pH 6.0.

Figure 91:
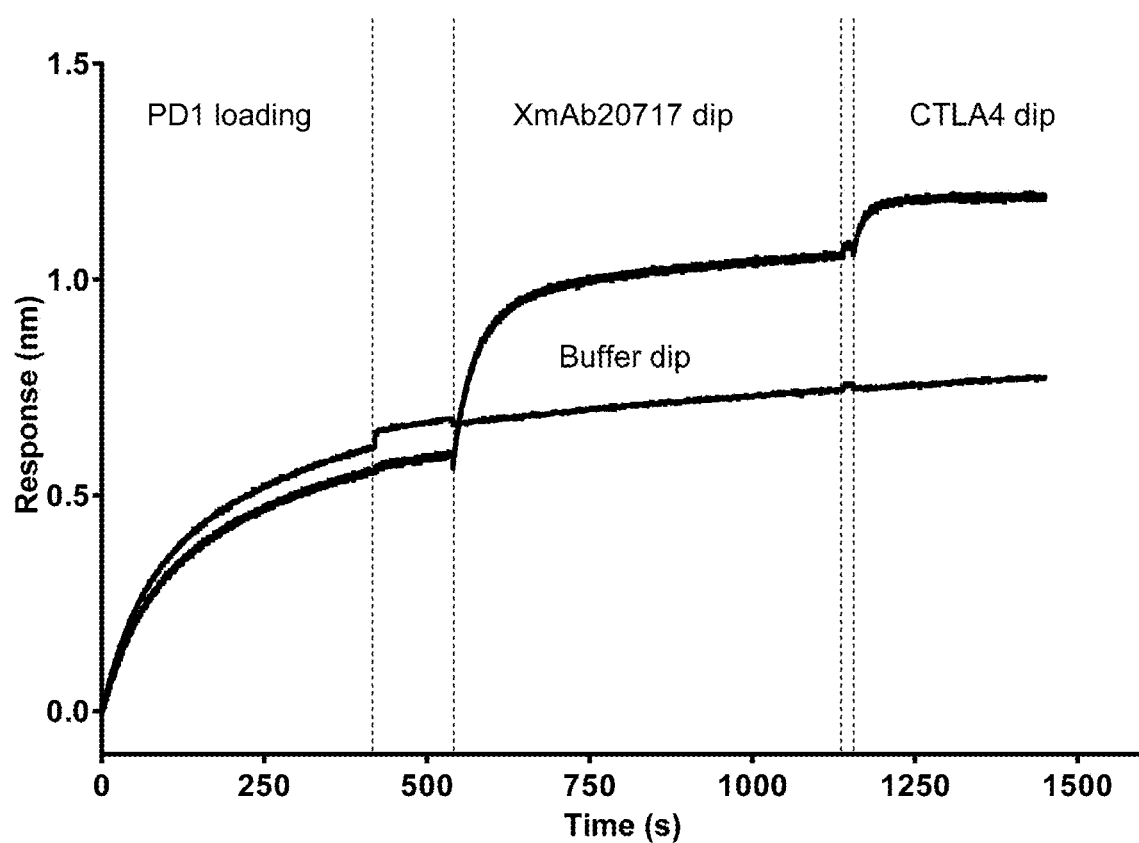

FIG. 91 depicts in-tandem BLI experiment showing biosensors loaded with PD-1 and dipped into XmAb20717 or buffer followed by a final dip into CTLA-4 antigen.

Figure 92:
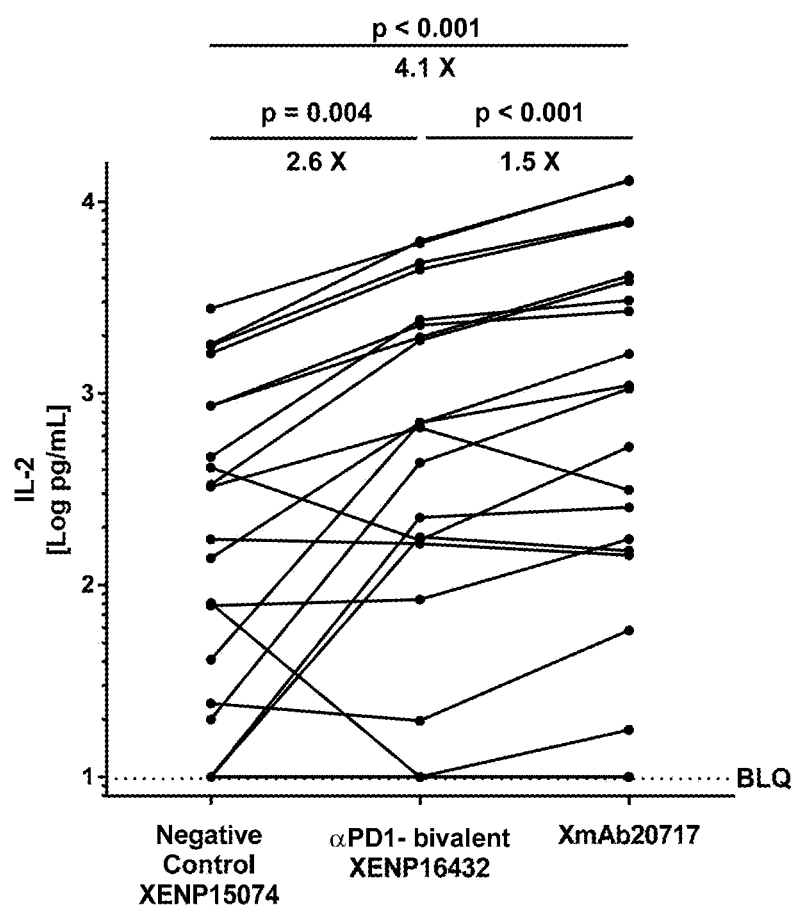

FIG. 92 depicts IL-2 secretion by SEB-stimulated human PBMCs following treatment with anti-RSV mAb XENP15074, anti-PD-1 mAb XENP16432, and XmAb20717. Each point represented a unique human donor.

Figure 93:
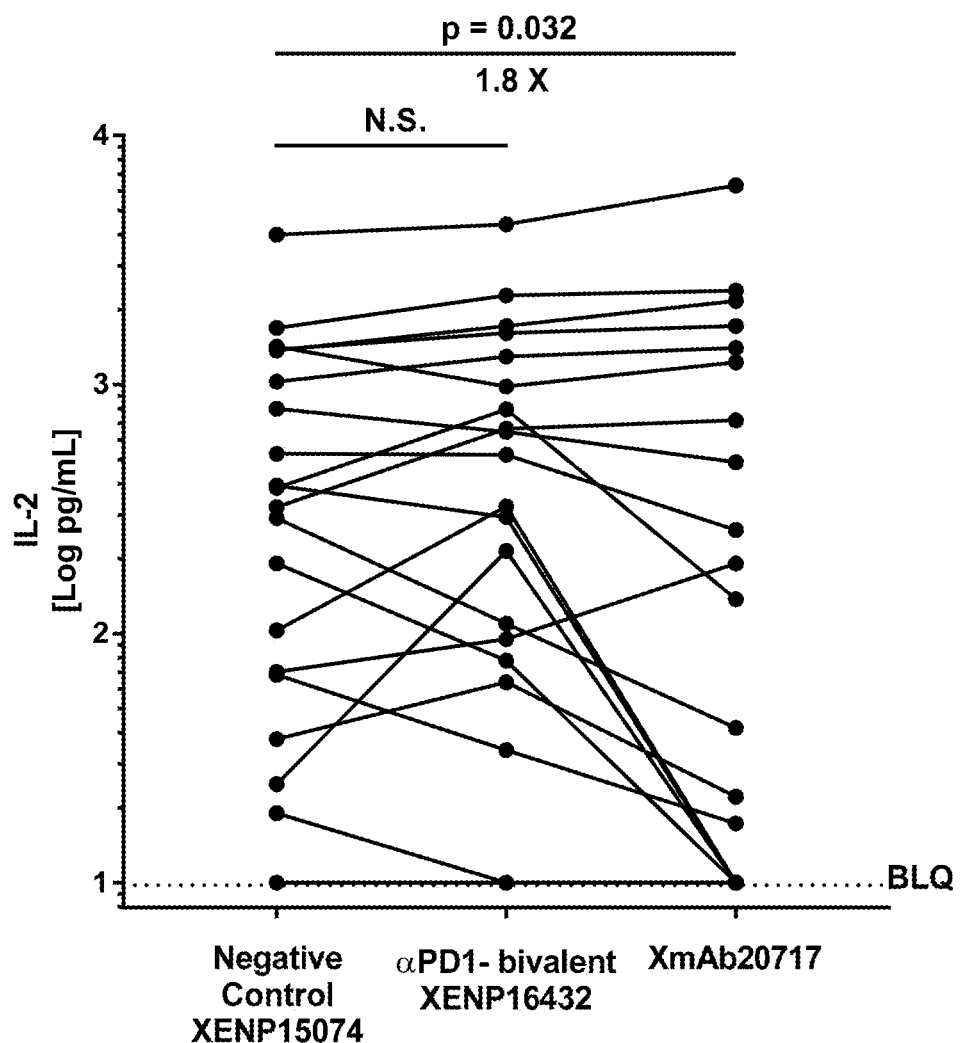

FIG. 93 depicts IL-2 secretion by unstimulated human PBMCs following treatment with anti-RSV mAb XENP15074, anti-PD-1 mAb XENP16432, and XmAb20717. Each point represented a unique human donor.

Figure 94:
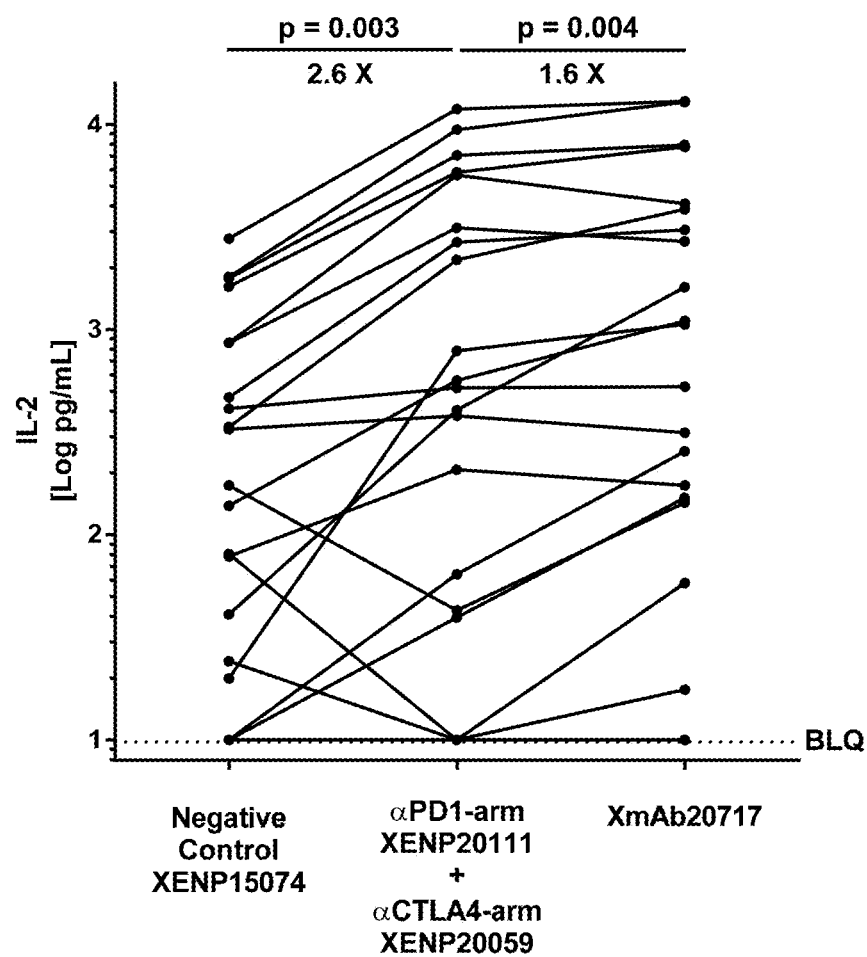

FIG. 94 depicts IL-2 secretion by unstimulated human PBMCs following treatment with anti-RSV mAb XENP15074, a combination of XENP20111 and XENP20059 (monovalent mAbs based on the anti-PD-1 and anti-CTLA-4 binding domains of XmAb20717), and XmAb20717. Each point represented a unique human donor.

Figure 95:
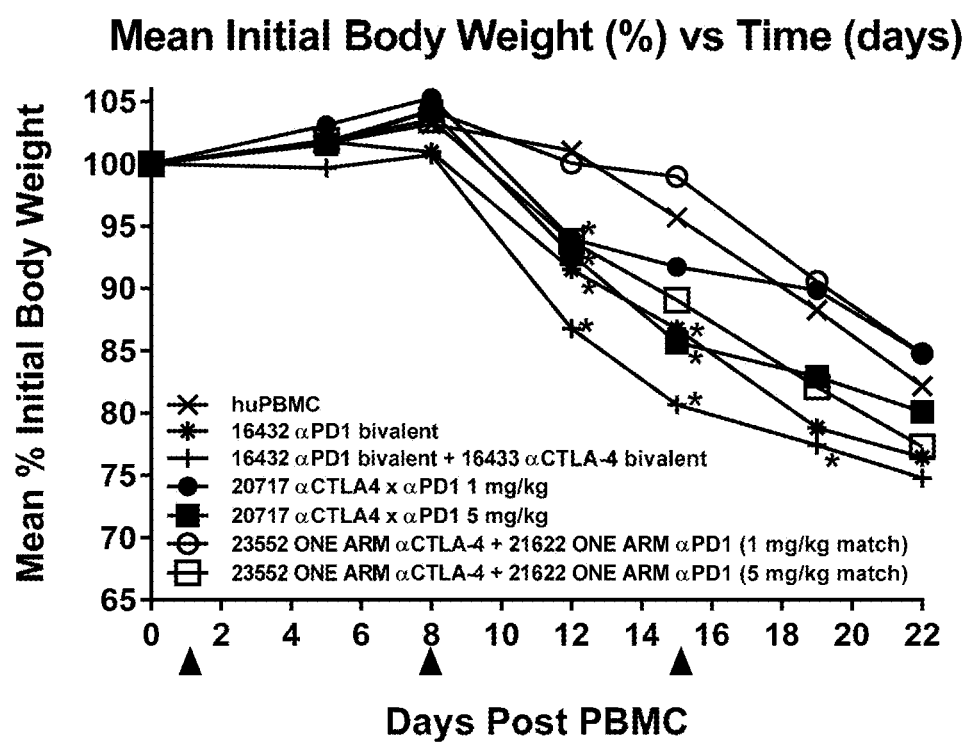

FIG. 95 depicts changes in body weight over time (as a percentage of initial body weight) in NSG mice engrafted i.v. OSP with human PBMCs and dosed with the indicated test articles. Dead mice were set to 70% initial body weight. * denotes $p<0.05$, unpaired Student's t-test, each group compared to huPBMCs. Triangles indicate dosing days.

Figure 96:
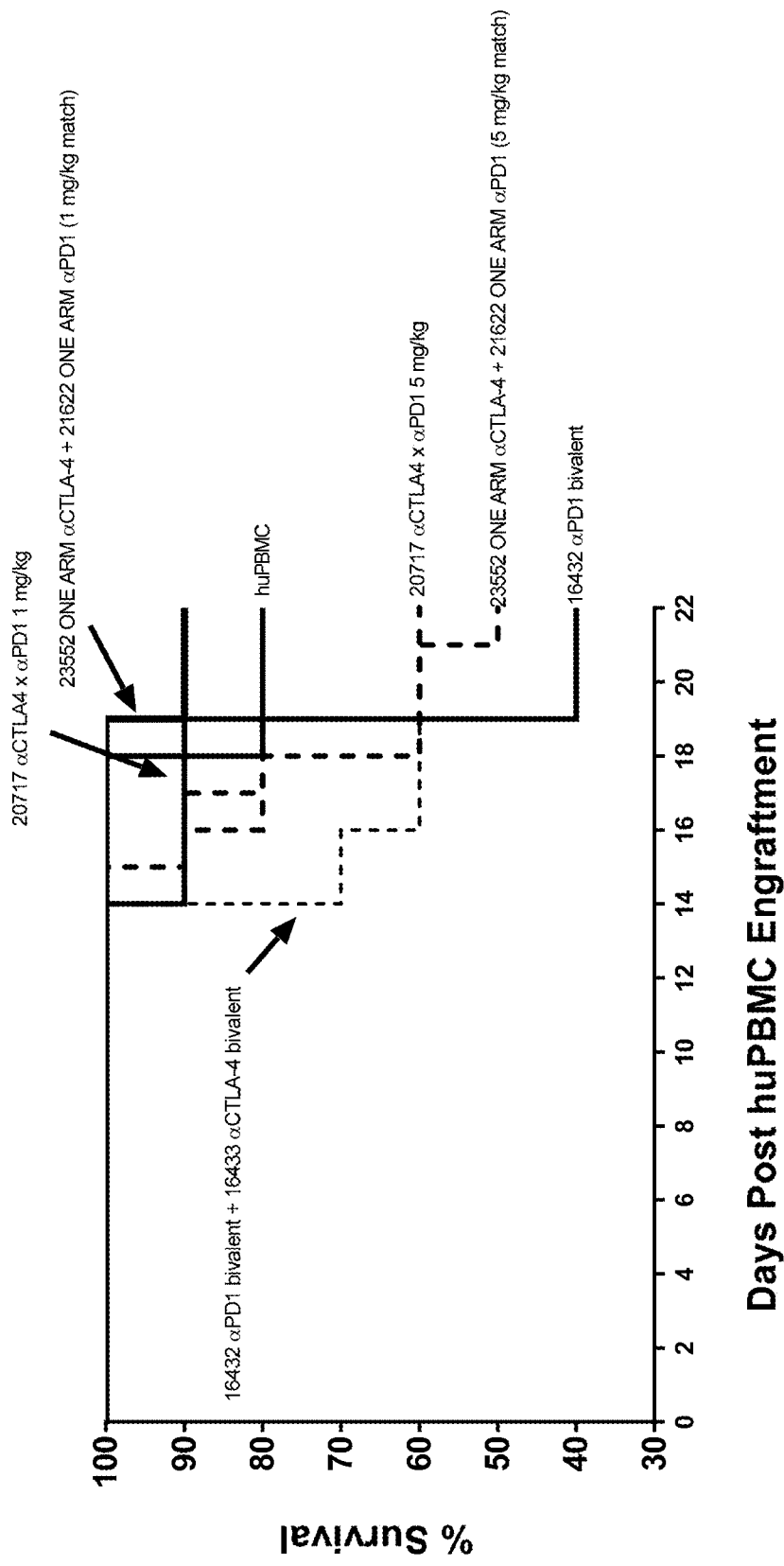

FIG. 96 depicts the survival of NSG mice engrafted i.v. OSP with human PBMCs and dosed with the indicated test articles.

Figure 97:
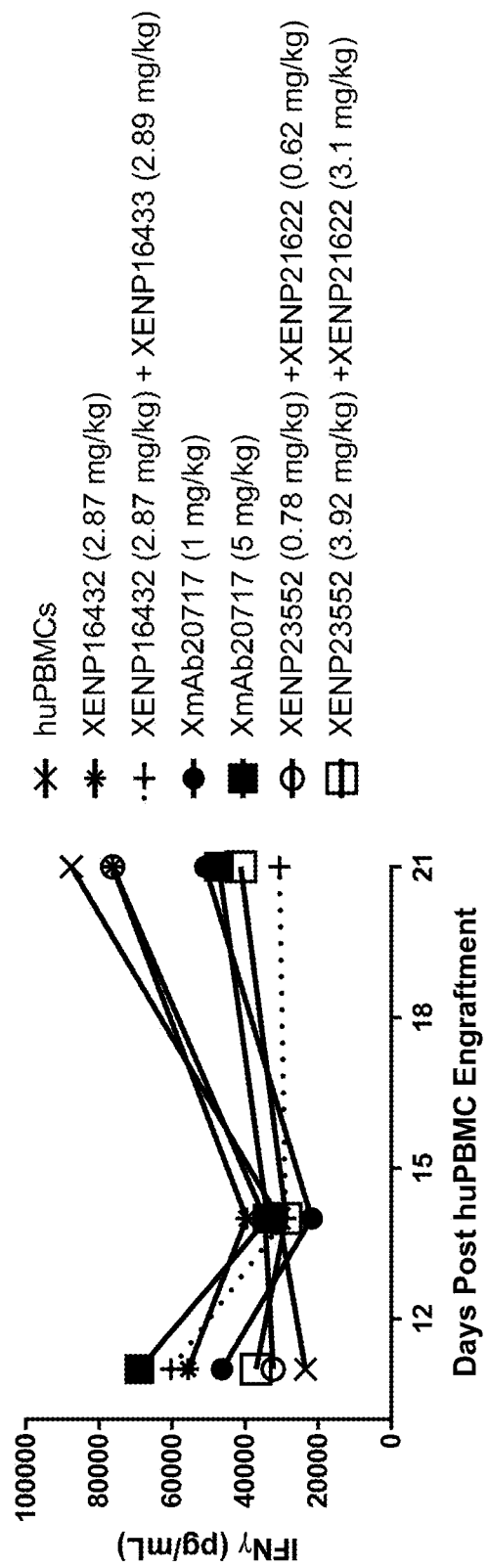

FIG. 97 depicts serum IFNγ concentration over time in NSG mice engrafted i.v. OSP with human PBMCs and dosed with the indicated test articles.

Figure 98A:
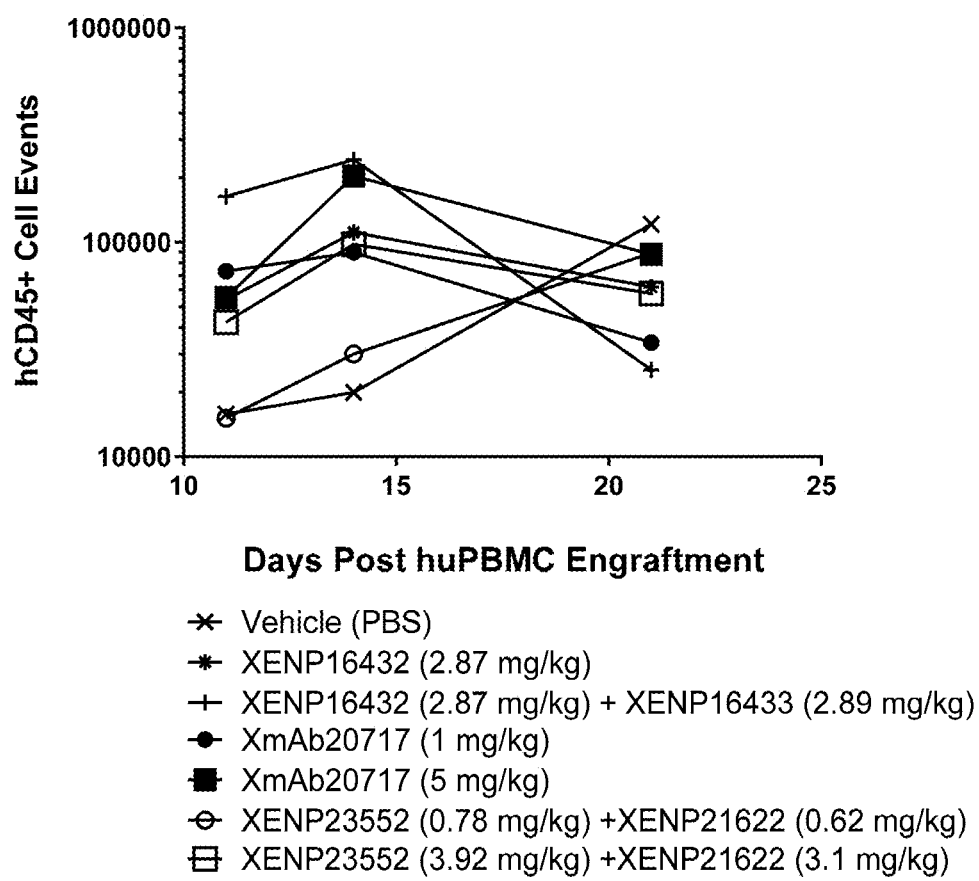
Figure 98B:
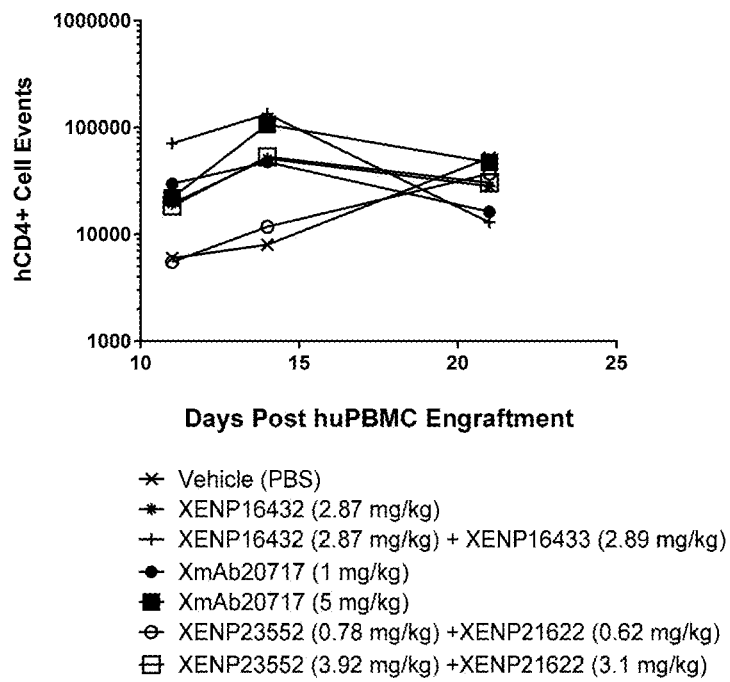
Figure 98C:
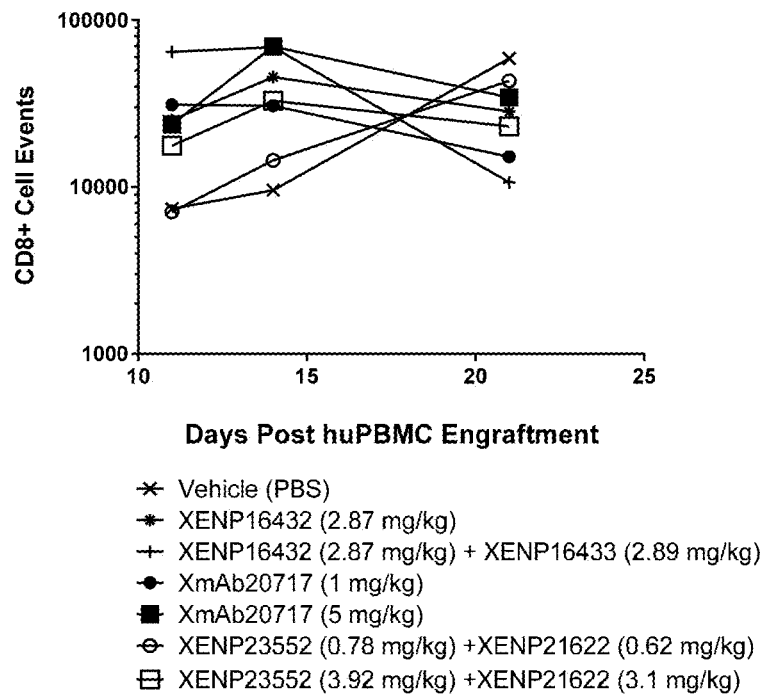

FIGS. 98A to 98C depicts A) human CD45$^+$ cell, B) human CD4$^+$ T cell, and C) human CD8$^+$ T cell counts over time in blood of NSG mice engrafted i.v. OSP with human PBMCs and dosed with the indicated test articles.

FIG. 99 depicts the sequences for XENP16434, a bivalent anti-PD-L1 mAb based on atezolizumab with an ablation variant (E233P/L234V/L235A/G236del/S267K, "IgG1_PVA_/S267k").

Figure 100:
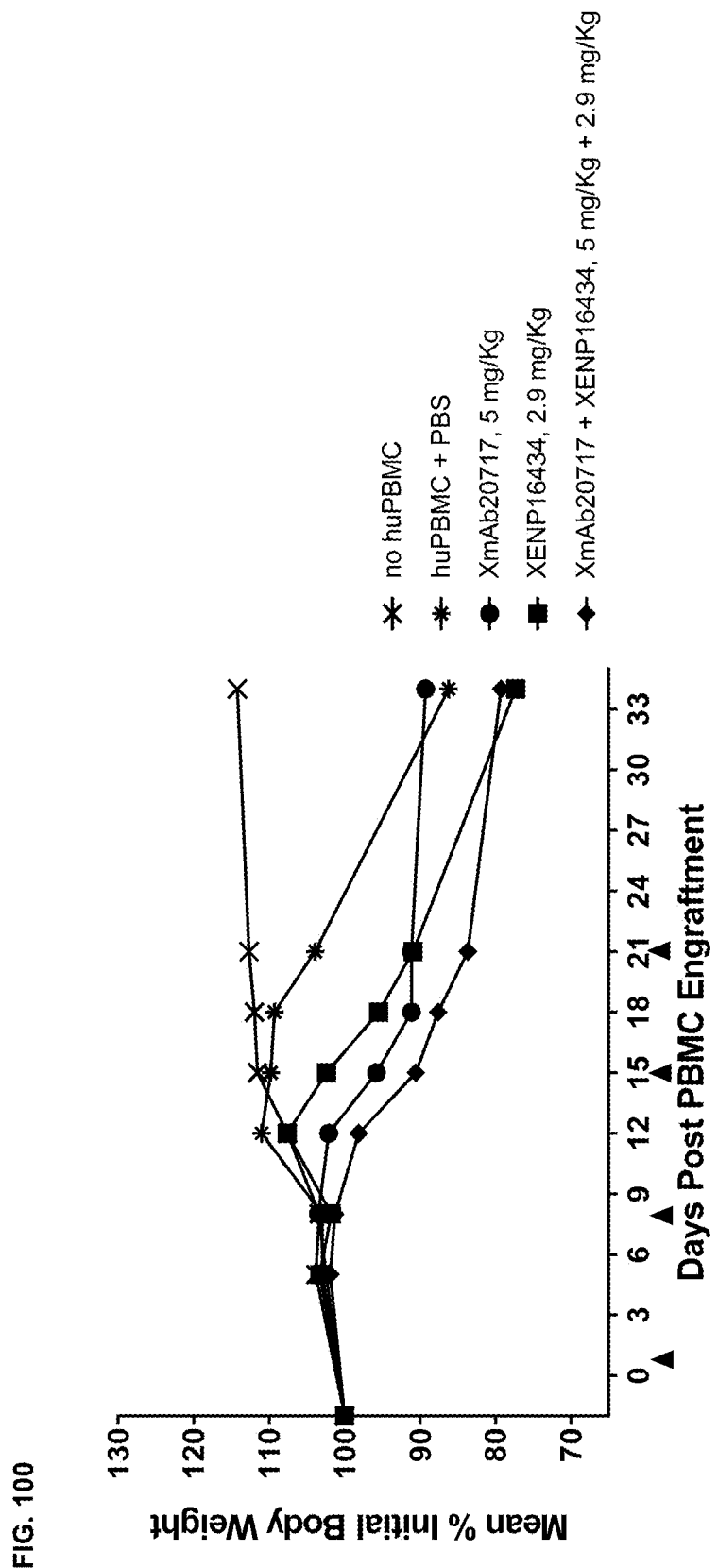

FIG. 100 depicts changes in body weight over time (as a percentage of initial body weight) in NSG mice engrafted i.v. OSP with human PBMCs and dosed with the indicated test articles. Dead mice were set to 70% initial body weight.

Figure 101:
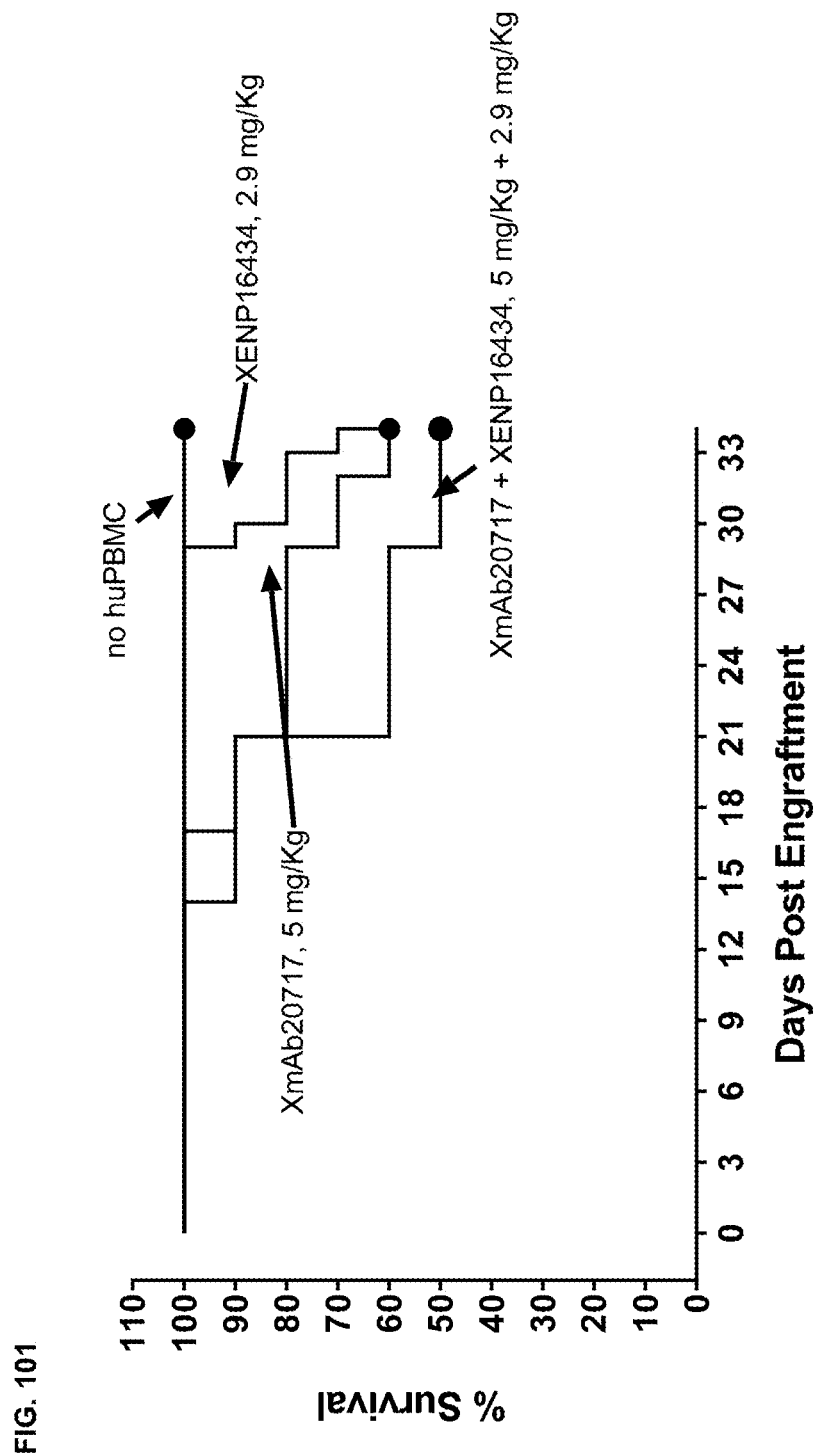

FIG. 101 depicts the survival of NSG mice engrafted i.v. OSP with human PBMCs and dosed with the indicated test articles.

Figure 102A:
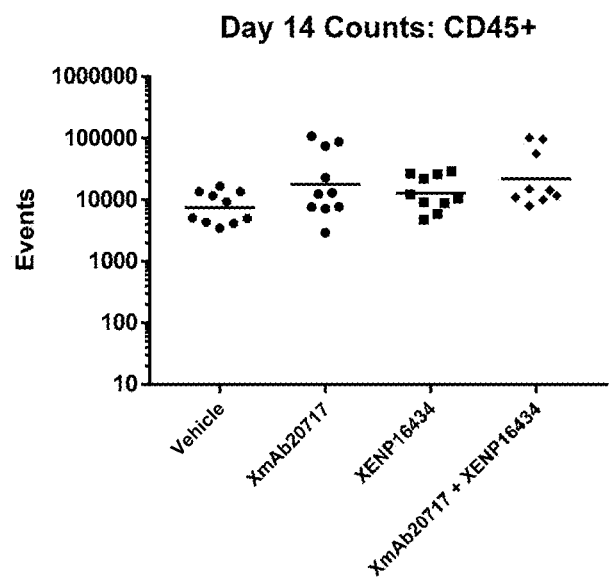
Figure 102B:
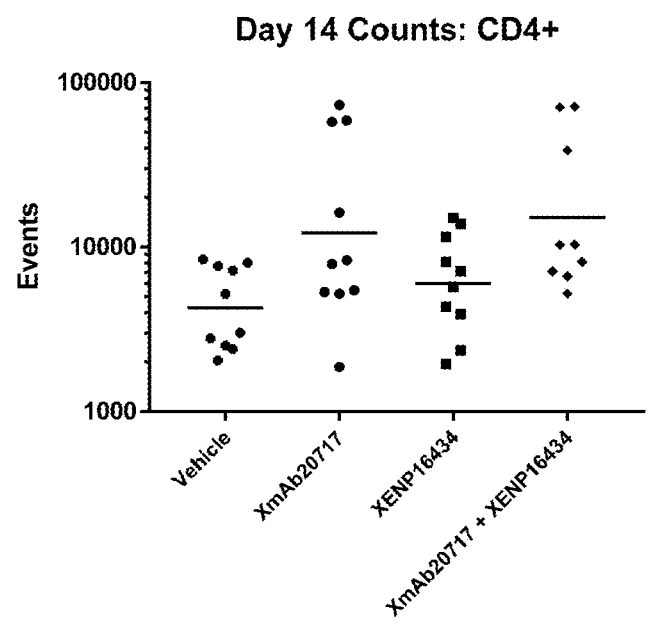
Figure 102C:
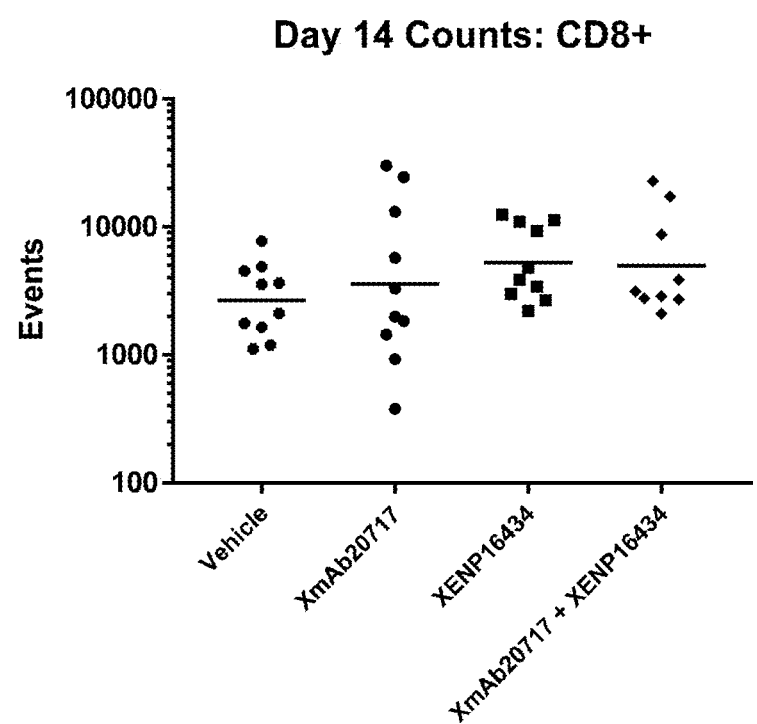

FIGS. 102A to 102C depicts A) human CD45⁺ cell, B) human CD4⁺ T cell, and C) human CD8⁺ T cell counts on Day 14 in blood of NSG mice engrafted i.v. OSP with human PBMCs and dosed with the indicated test articles.

Figure 103:
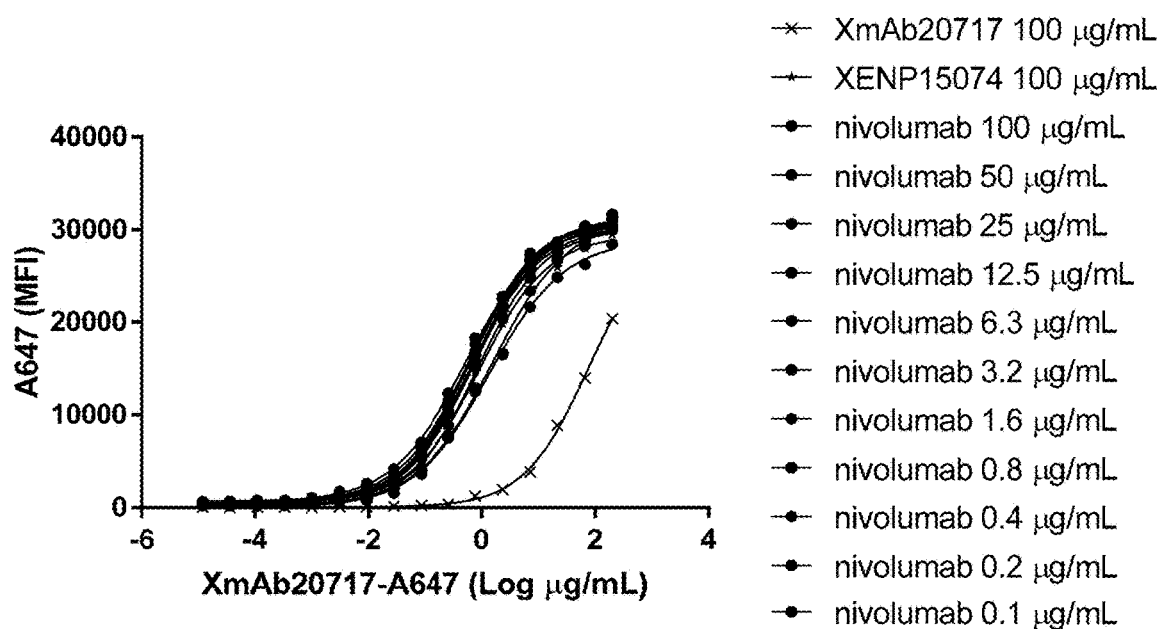

FIG. 103 depicts the binding of XmAb20717 to PD-1⁺ CTLA-4⁺ cells pretreated with the indicated concentrations of the indicated test articles.

Figure 104:
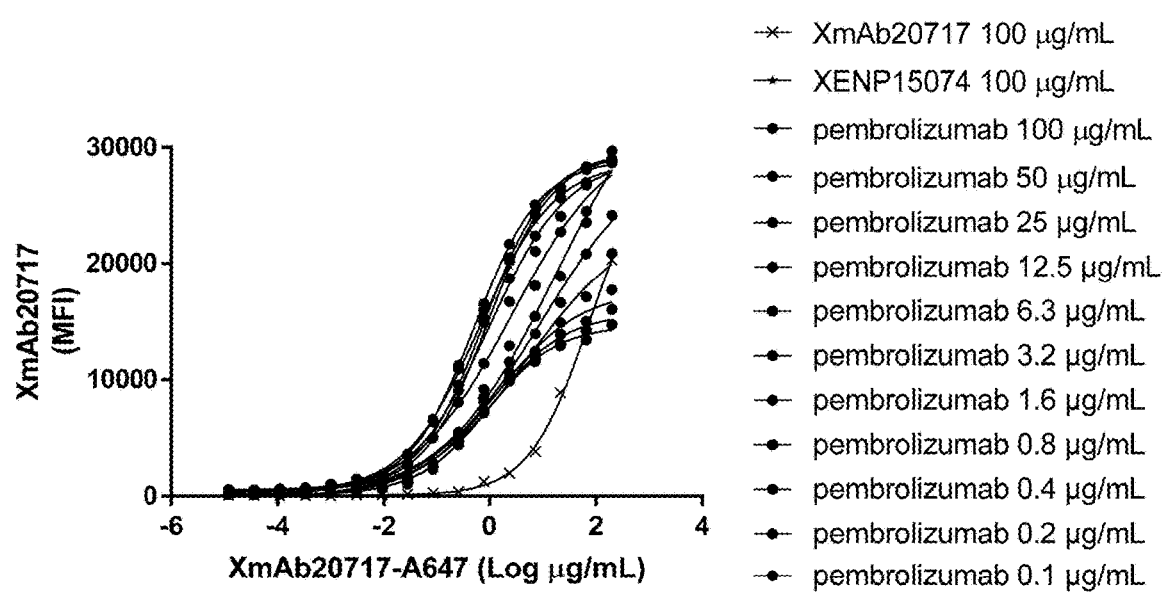

FIG. 104 depicts the binding of XmAb20717 to PD-1⁺ CTLA-4₊ cells pretreated with the indicated concentrations of the indicated test articles.

Figure 105:
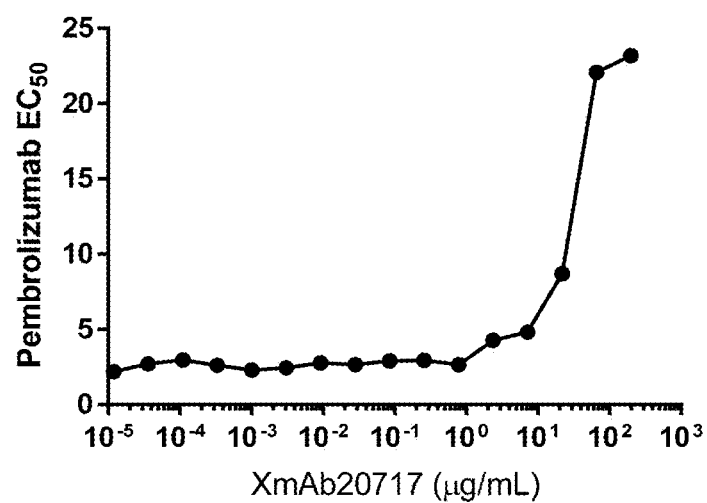
Figure 106A:
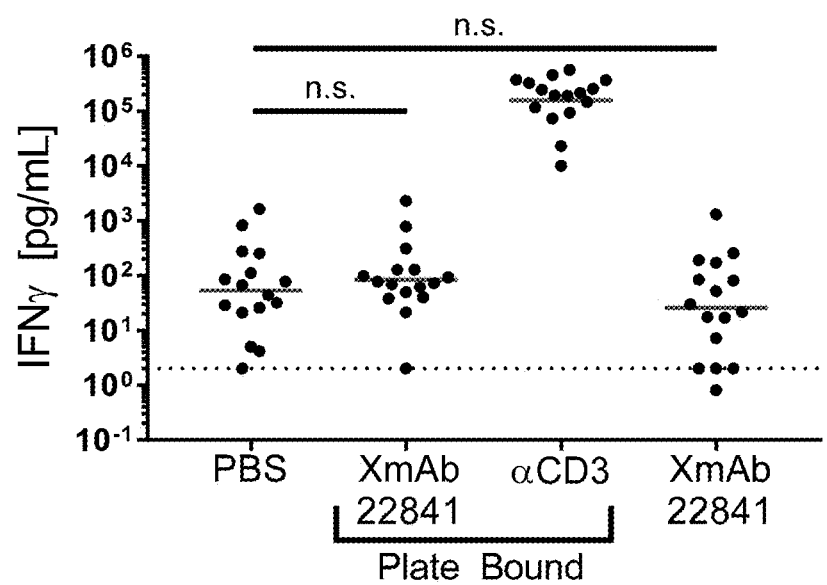
Figure 106B:
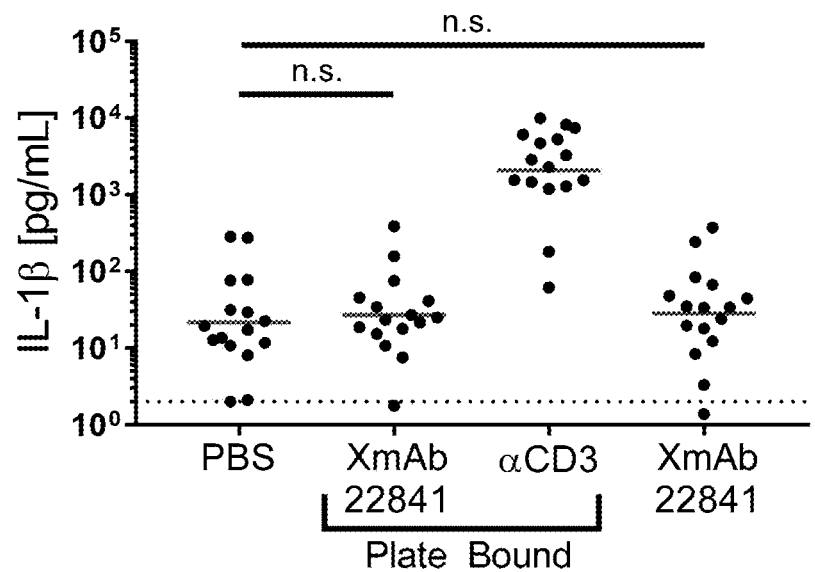
Figure 106C:
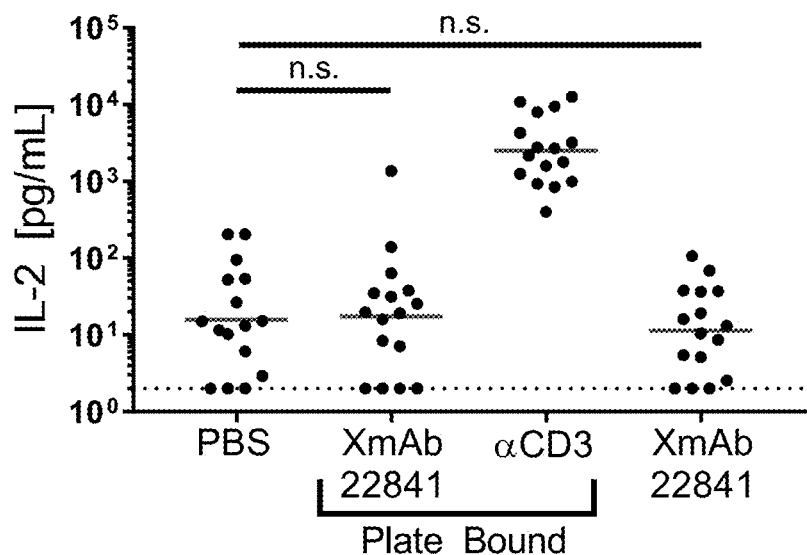
Figure 106D:
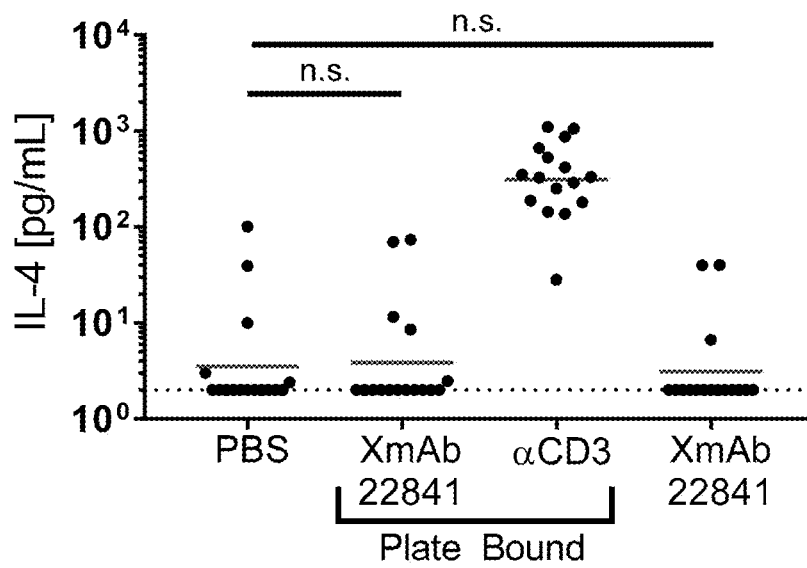
Figure 106E:
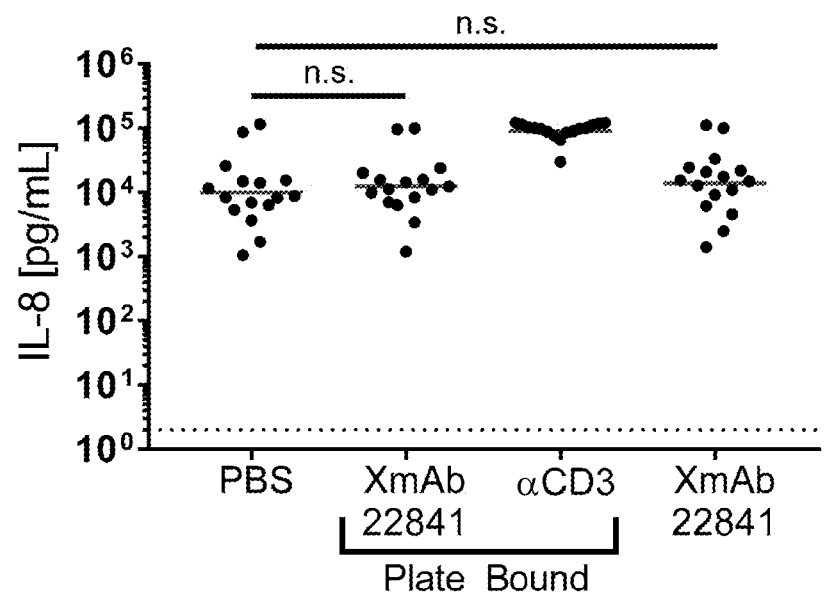
Figure 106F:
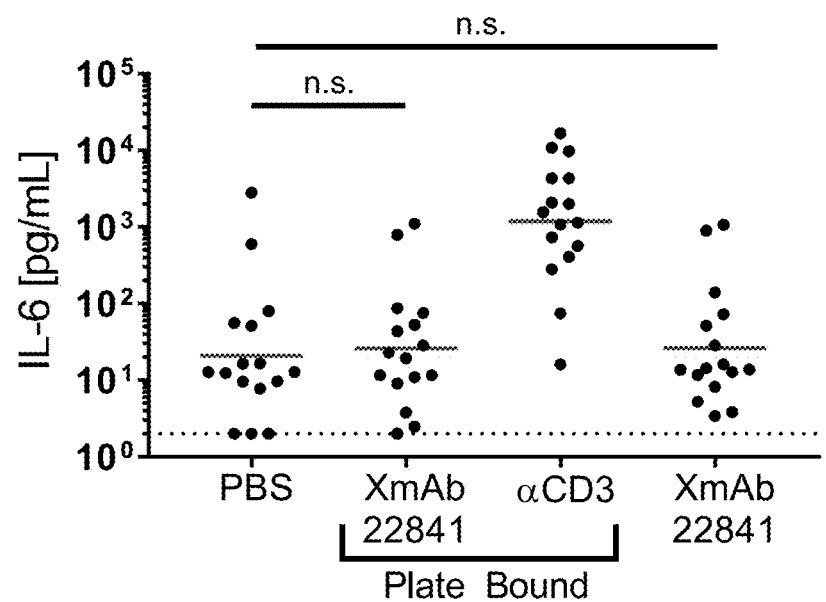
Figure 106G:
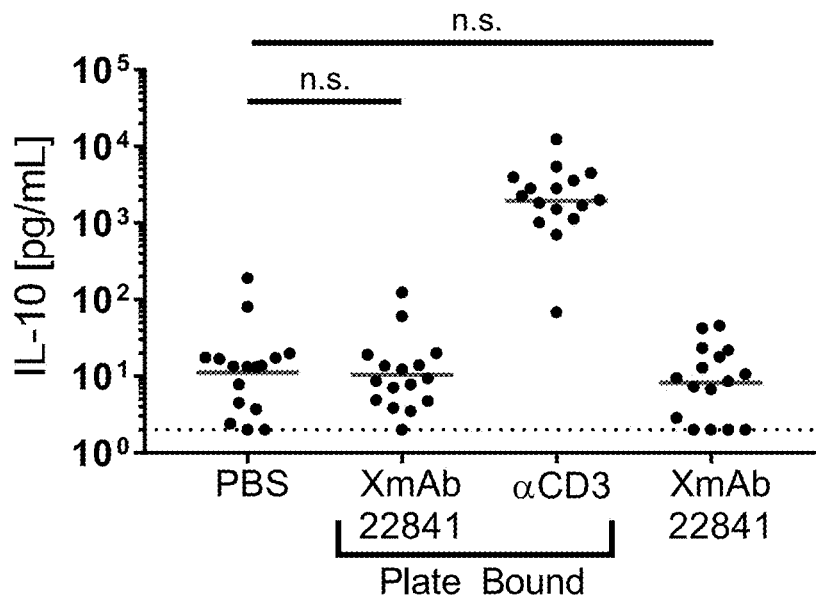
Figure 106H:
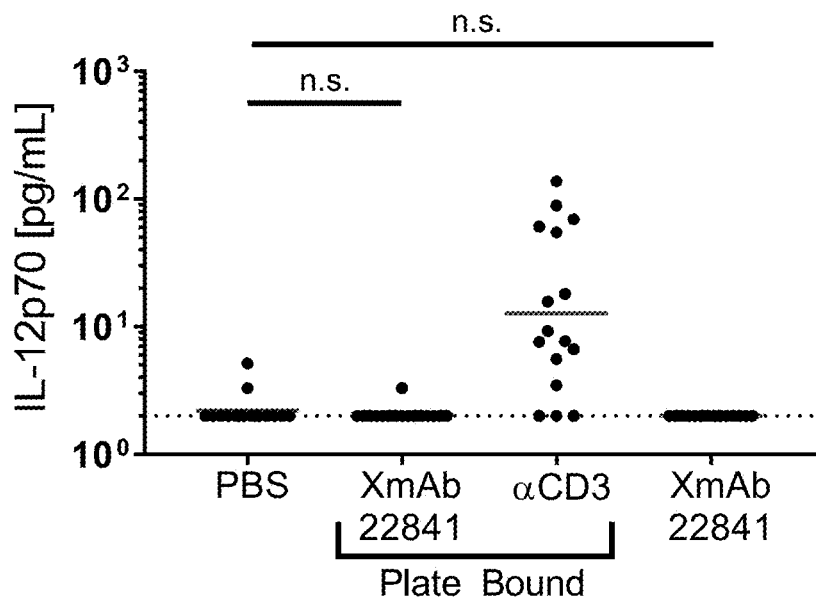
Figure 106I:
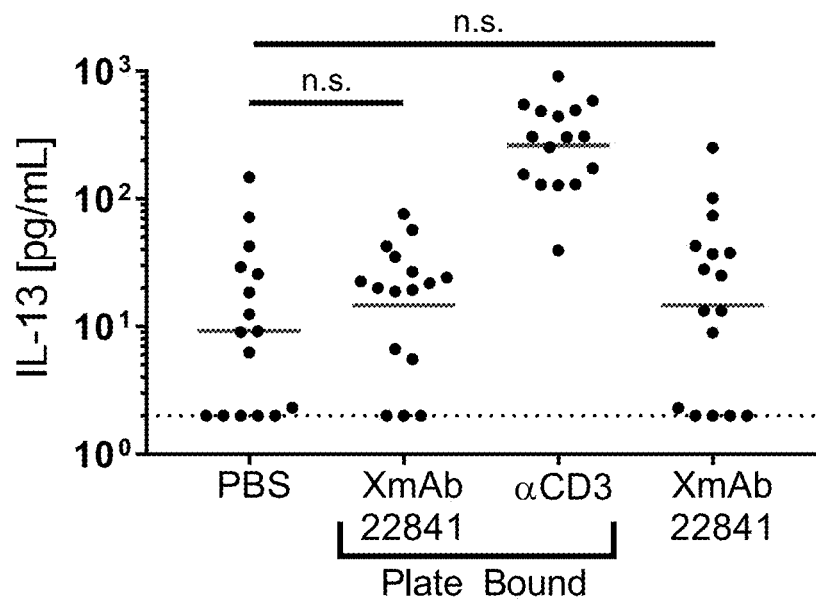
Figure 106J:
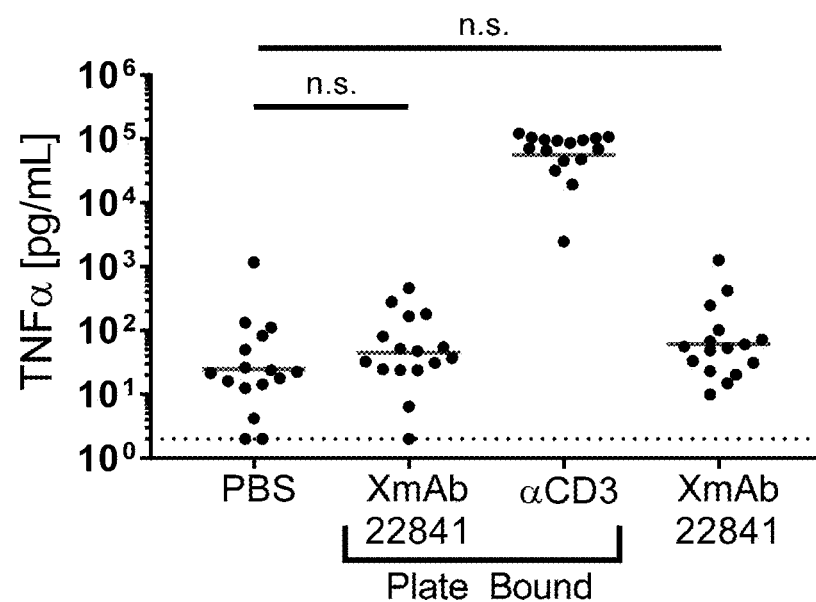
Figure 108A:
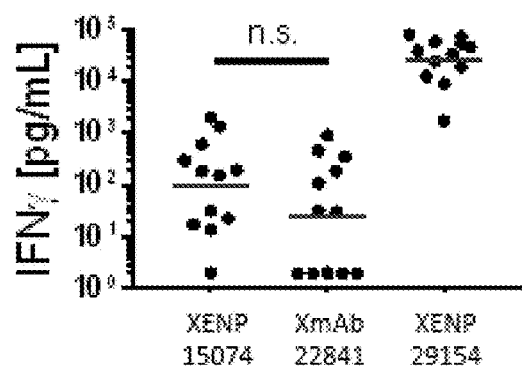
Figure 108B:
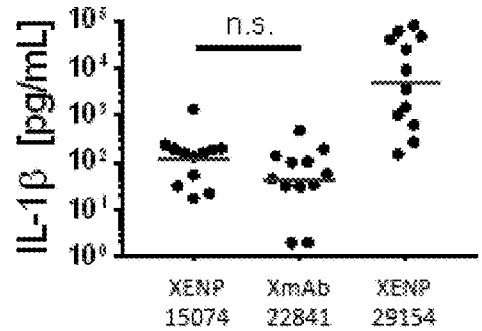
Figure 108C:
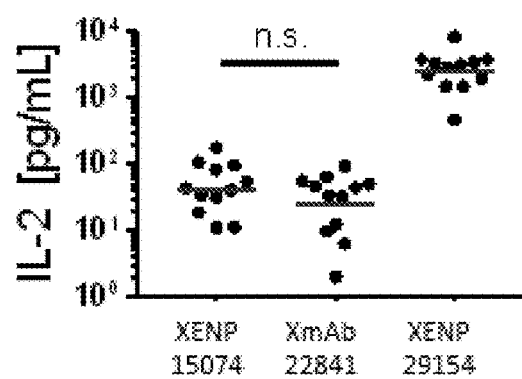
Figure 108D:
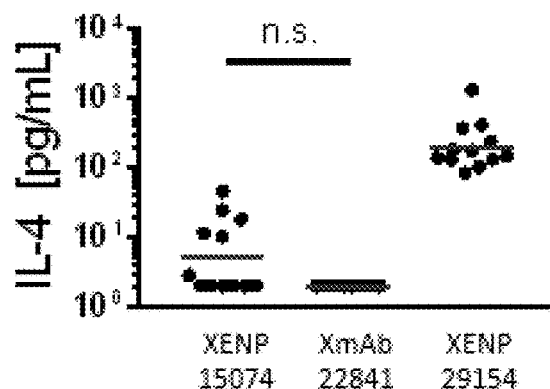
Figure 108E:
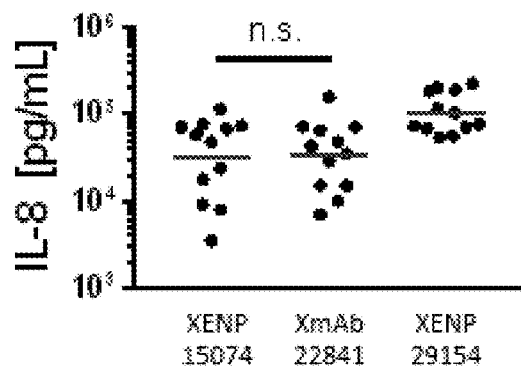
Figure 108F:
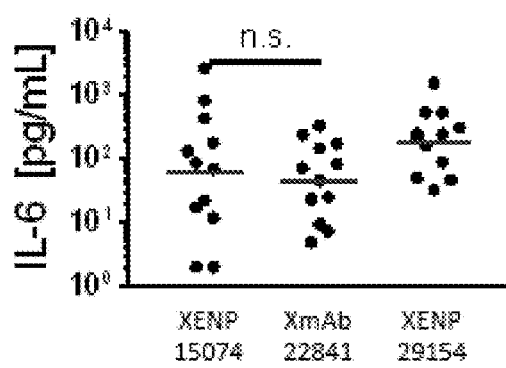
Figure 108G:
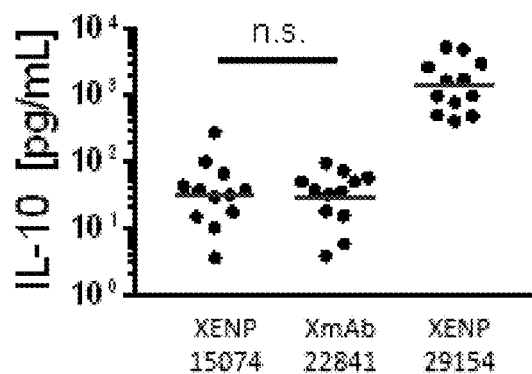
Figure 108H:
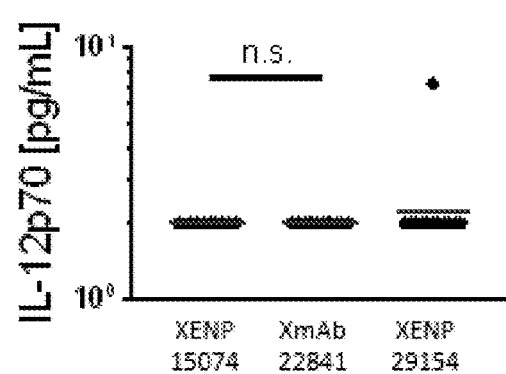
Figure 108I:
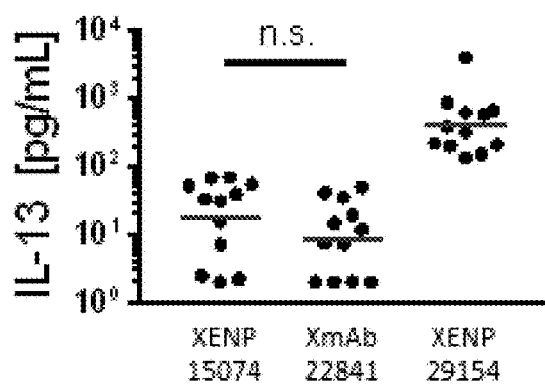
Figure 108J:
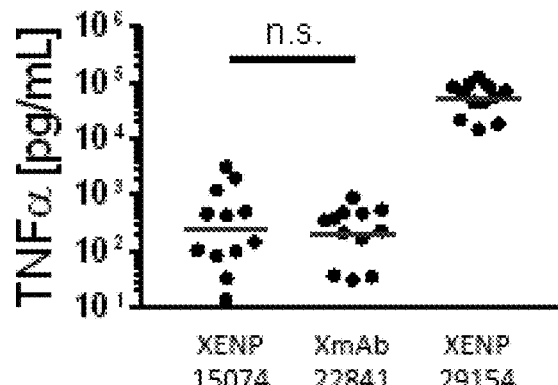

FIG. 105 depicts the EC₅₀ of pembrolizumab for blocking XmAb20717 binding to PD-1⁺CTLA-4⁺ cells. EC₅₀ values were derived from Prism software with curve fits using a least squares method.

FIGS. 106A to 106J depict the release of A) IFNγ, B) IL-1ß, C) IL-2, D) IL-4, E) IL-8, F) IL-6, G) IL-10, H) IL-12p70, I) IL-13, and J) TNFα from human PBMCs treated with PBS, plate-bound XmAb22841, soluble XmAb22841, and plate-bound anti-CD3 antibody (OKT3).

FIG. 107 depicts the sequences for XENP29154, which is in-house produced TGN1412.

FIGS. 108A to 108J depict the release of A) IFNγ, B) IL-1ß, C) IL-2, D) IL-4, E) IL-8, F) IL-6, G) IL-10, H) IL-12p70, I) IL-13, and J) TNFα from human PBMCs treated with air-dried XmAb22841, air-dried XENP15074 (isotype control), and air-dried XENP29154 (positive control).

Figure 109A:
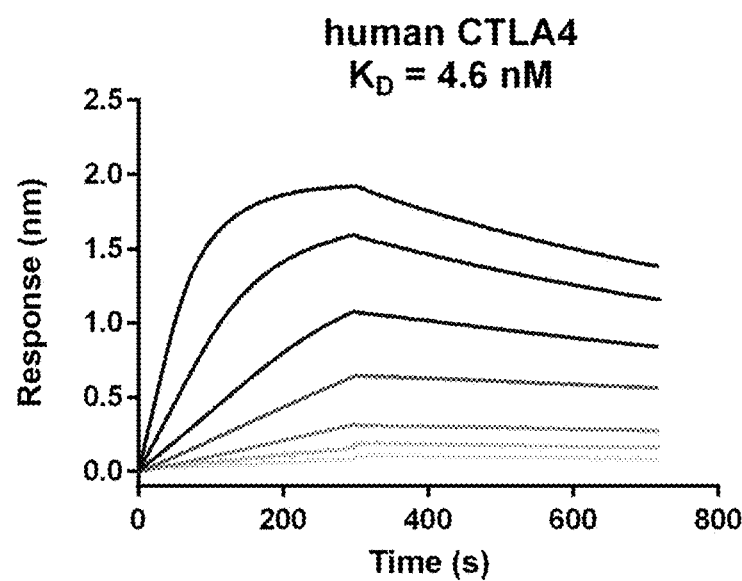
Figure 109B:
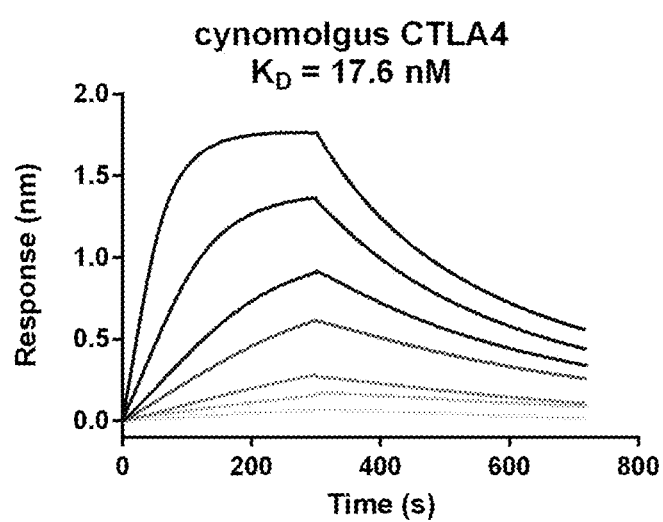

FIGS. 109A and 109B depict sensorgrams showing binding of XmAb22841 to A) human CTLA-4 and B) cynomolgus CTLA-4.

Figure 110A:
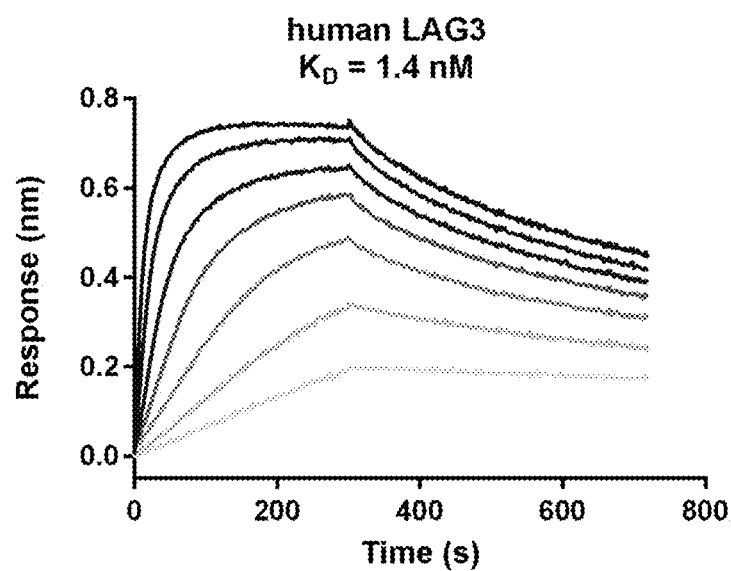
Figure 110B:
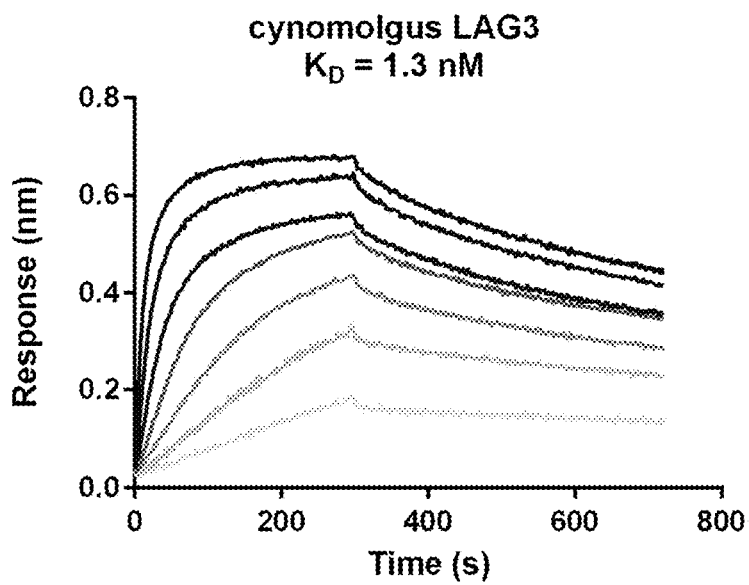

FIGS. 110A and 110B depict sensorgrams showing binding of XmAb22841 to A) human LAG-3 and B) cynomolgus LAG-3.

FIG. 111 depicts the equilibrium dissociation constants (KD), association rates ($k_a$), and dissociation rates ($k_d$) for binding of XmAb22841 to human and cynomolgus CTLA-4 and LAG-3.

Figure 112:
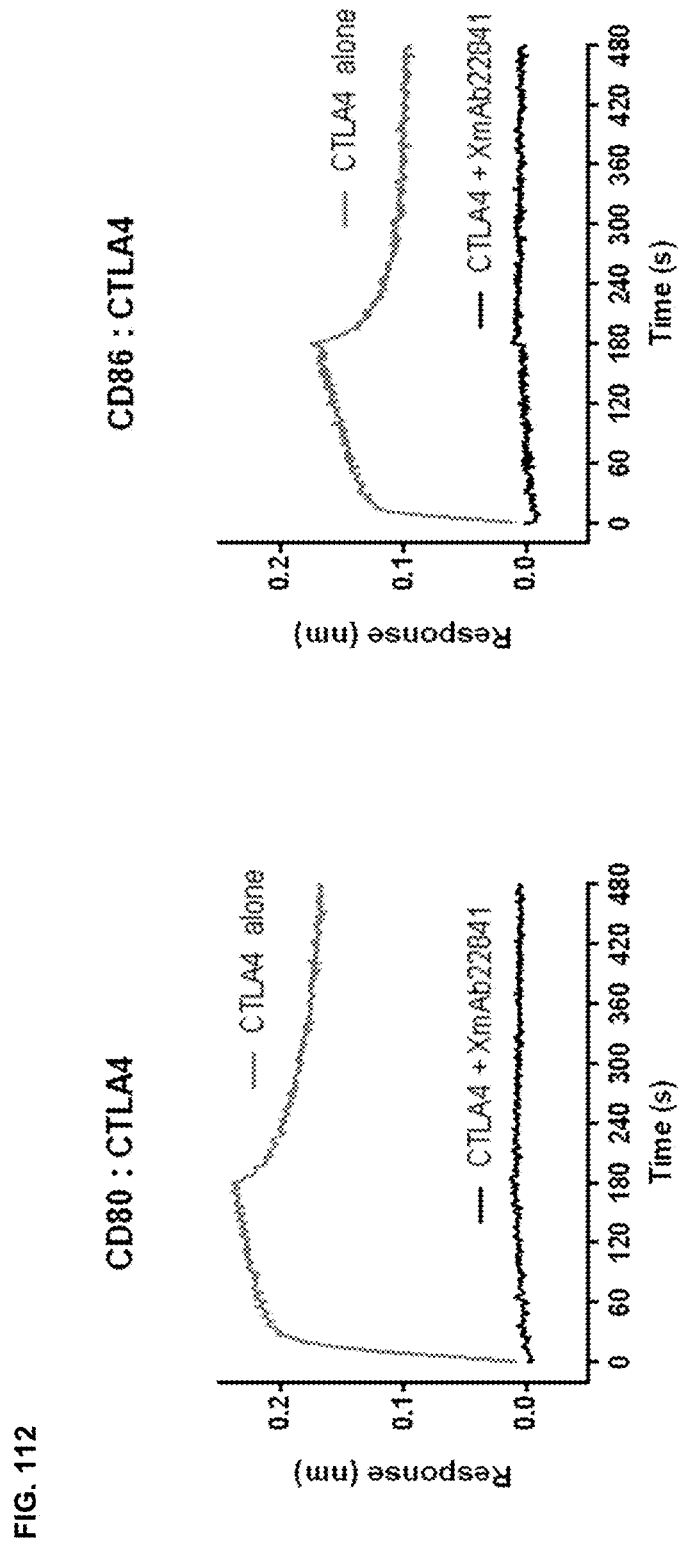

FIG. 112 depicts sensorgrams from competition binding experiments of CTLA-4 and ligands CD80 and CD86 with and without XmAb22841 pre-incubation.

Figure 113:
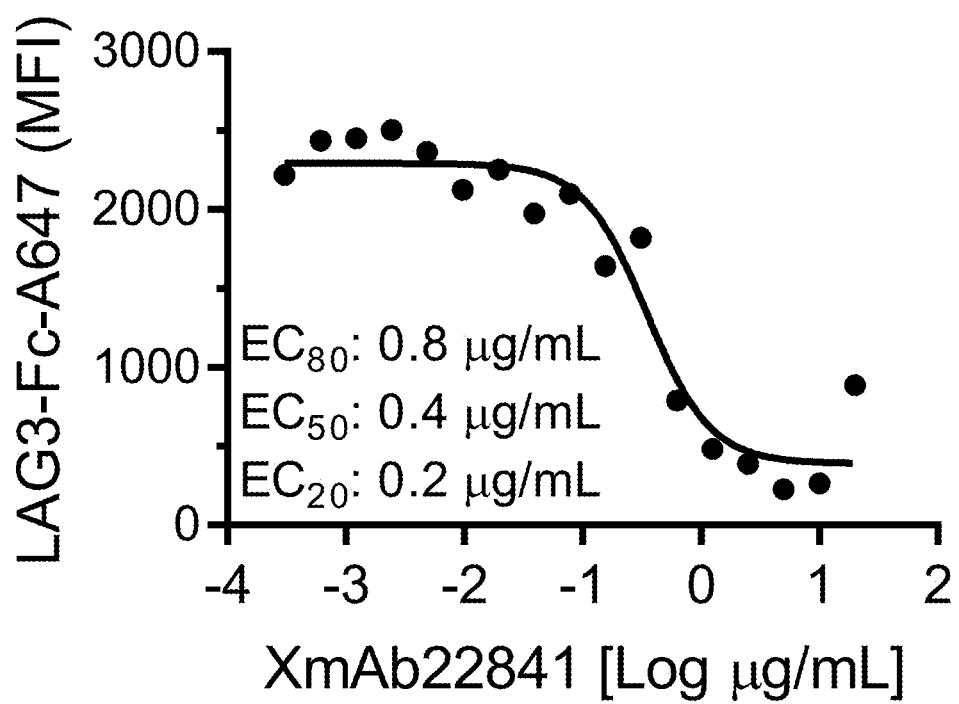

FIG. 113 depicts blocking of soluble LAG-3-Fc binding to cell-surface MHC Class II on Ramos cells by XmAb22841.

Figure 114:
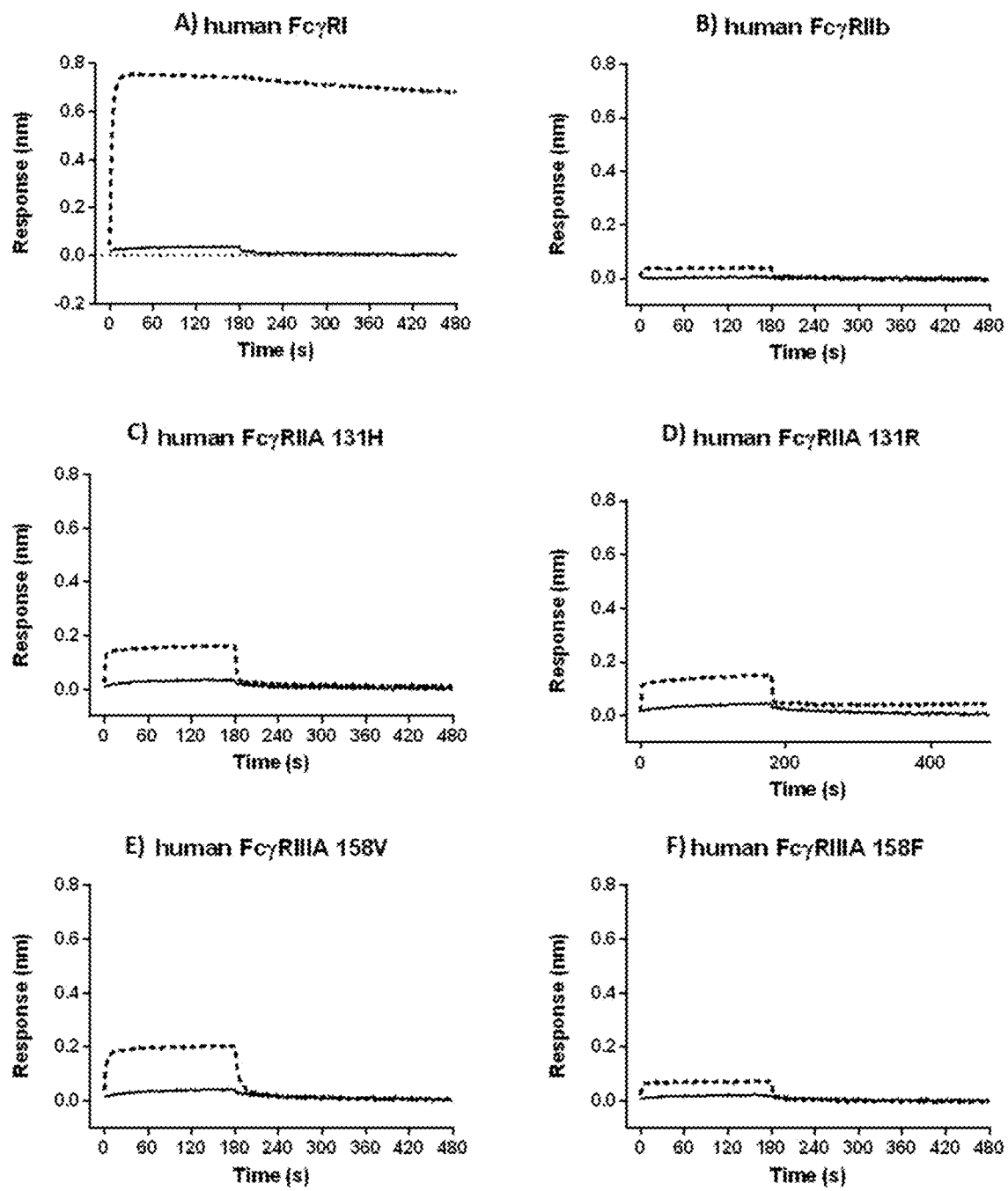

FIG. 114 depicts sensorgrams showing binding of XmAb22841 (solid line) and human IgG comparator (an anti-CD19 antibody with a native IgG1 constant region; dotted line) to A) human FcγRI, B) human FcγRIIb, C) human FcγRIIA (131H), D) human FcγRIIA (131R), E) human FcγRIIIA (158V), and F) human FcγRIIIA (158F).

Figure 115:
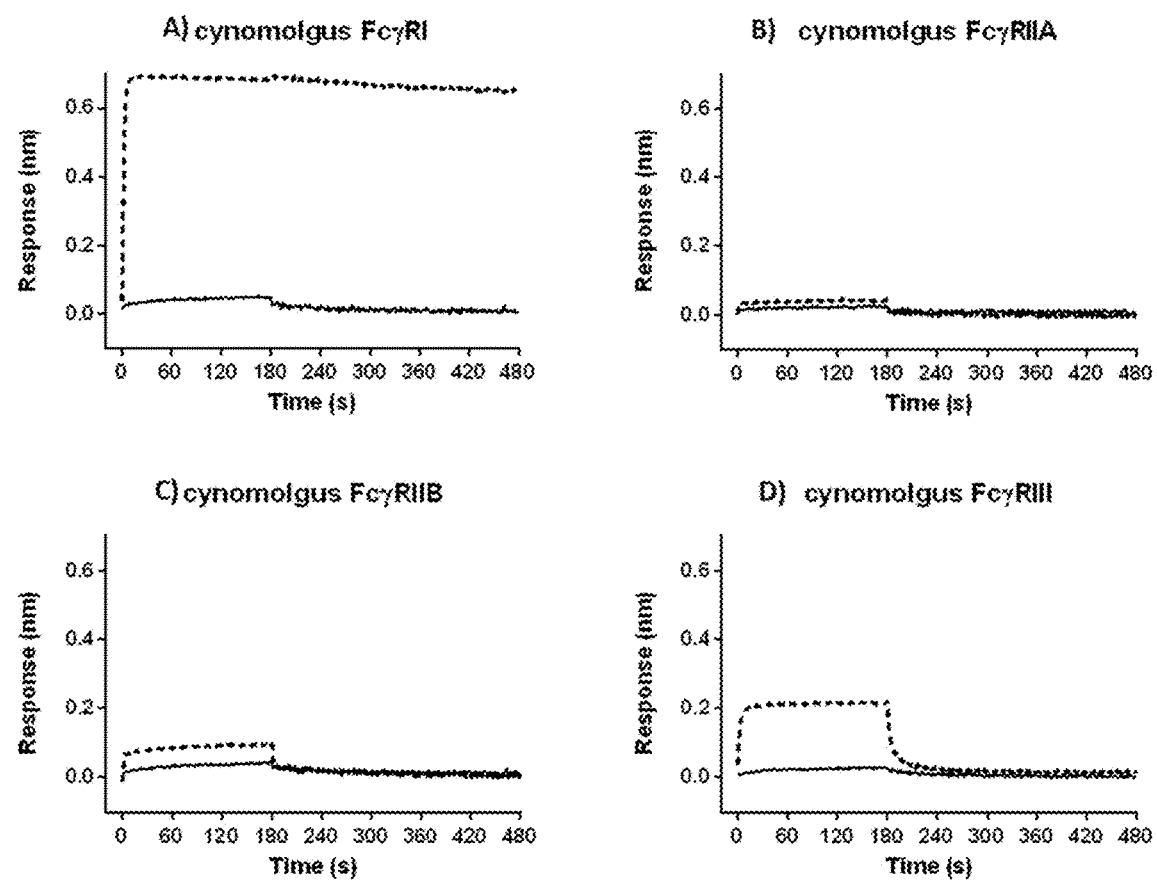

FIG. 115 depicts sensorgrams showing binding of XmAb22841 (solid line) and human IgG comparator (an anti-CD19 antibody with a native IgG1 constant region; dotted line) to A) cynomolgus FcγRI, B) cynomolgus FcγRIIA, C) cynomolgus FcγRIIb, and D) cynomolgus RcγRIIIA.

Figure 116:
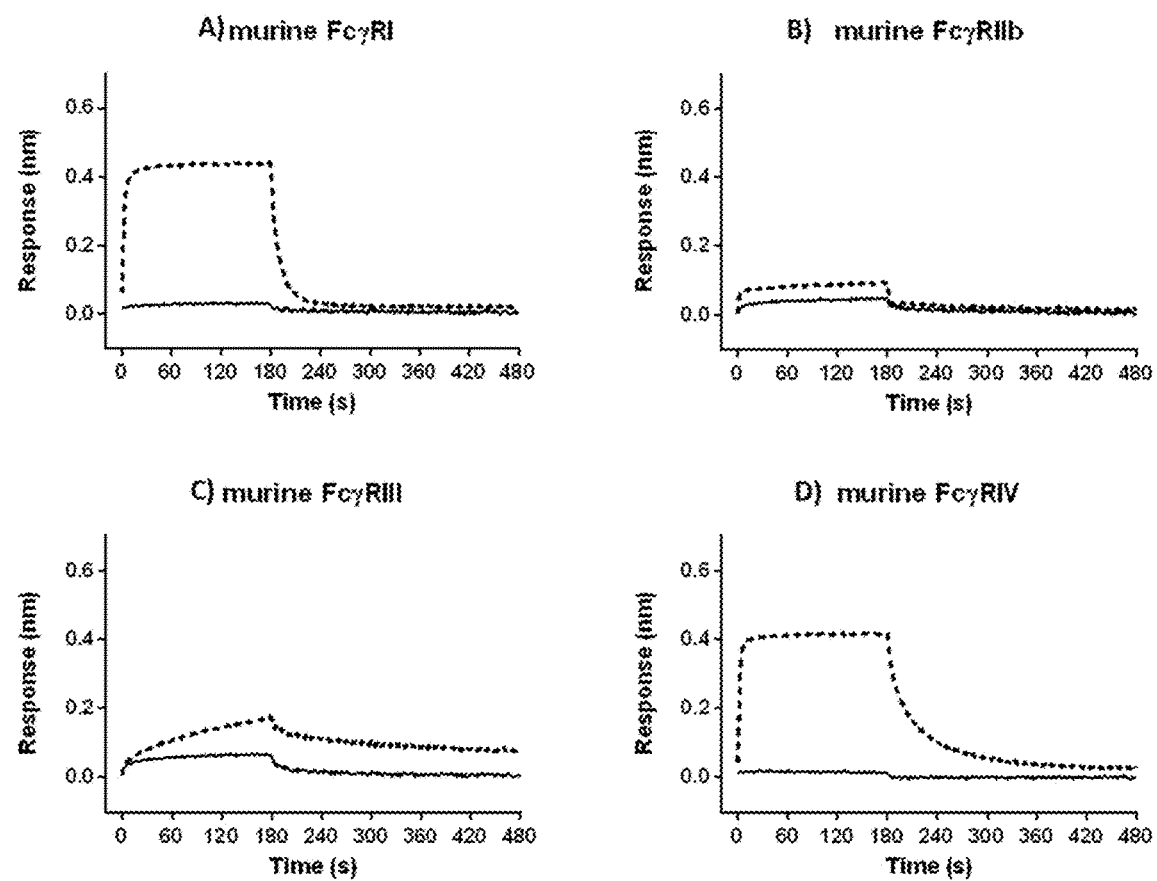

FIG. 116 depicts sensorgrams showing binding of XmAb22841 (solid line) and human IgG comparator (an anti-CD19 antibody with a native IgG1 constant region; dotted line) to A) murine FcγRI, B) murine FcγRIIb, C) murine FcγRIII, and D) murine FcγRIV.

FIG. 117 depicts equilibrium dissociation constants ($K_D$) for binding of XmAb22841 and XENP22602 to human, cynomolgus, and mouse FcRn at pH 6.0.

Figure 118:
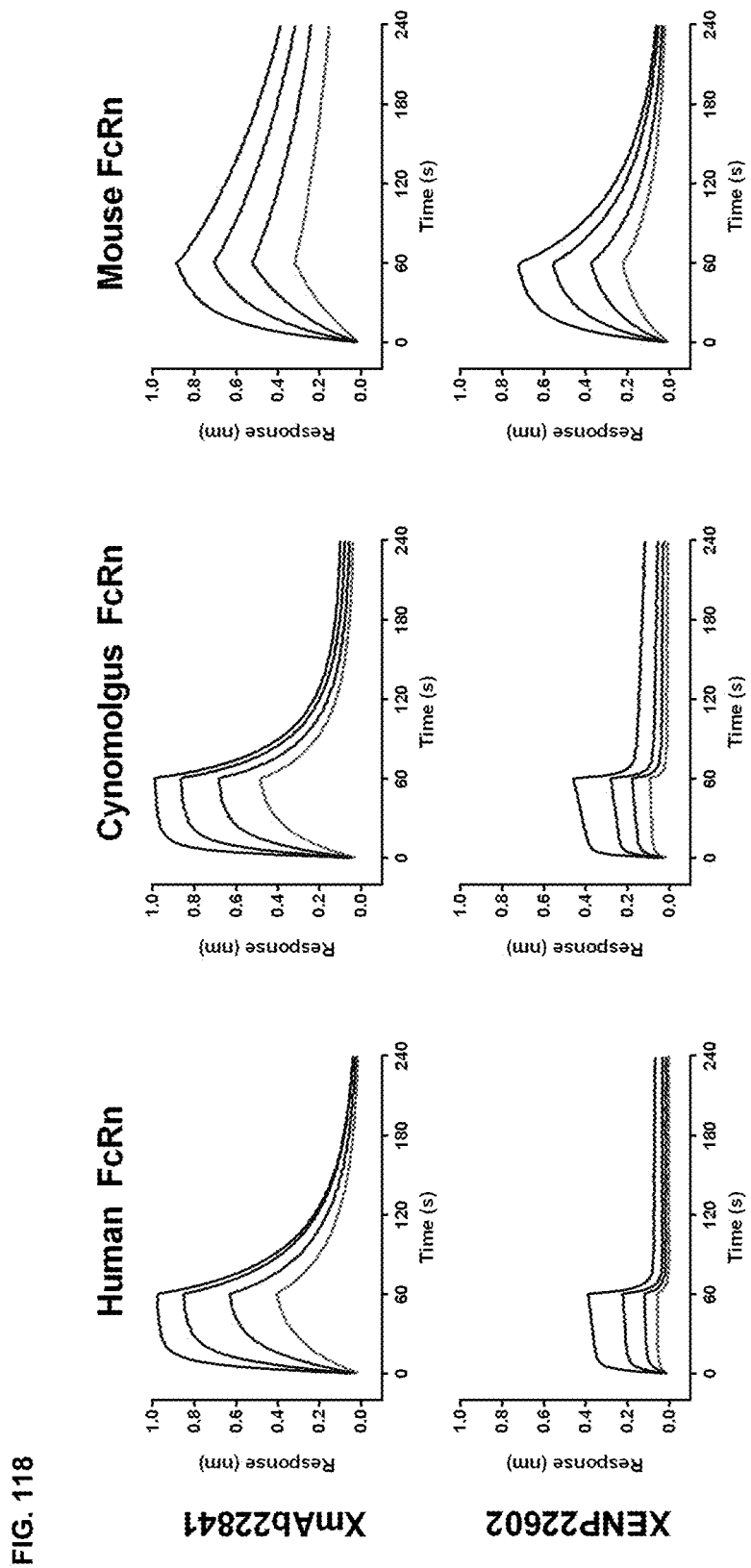

FIG. 118 depicts sensorgrams showing binding of XmAb22841 and XENP22602 to human, cynomolgus, and mouse FcRn (1000, 500, 250, and 125 nM) at pH 6.0.

Figure 119:
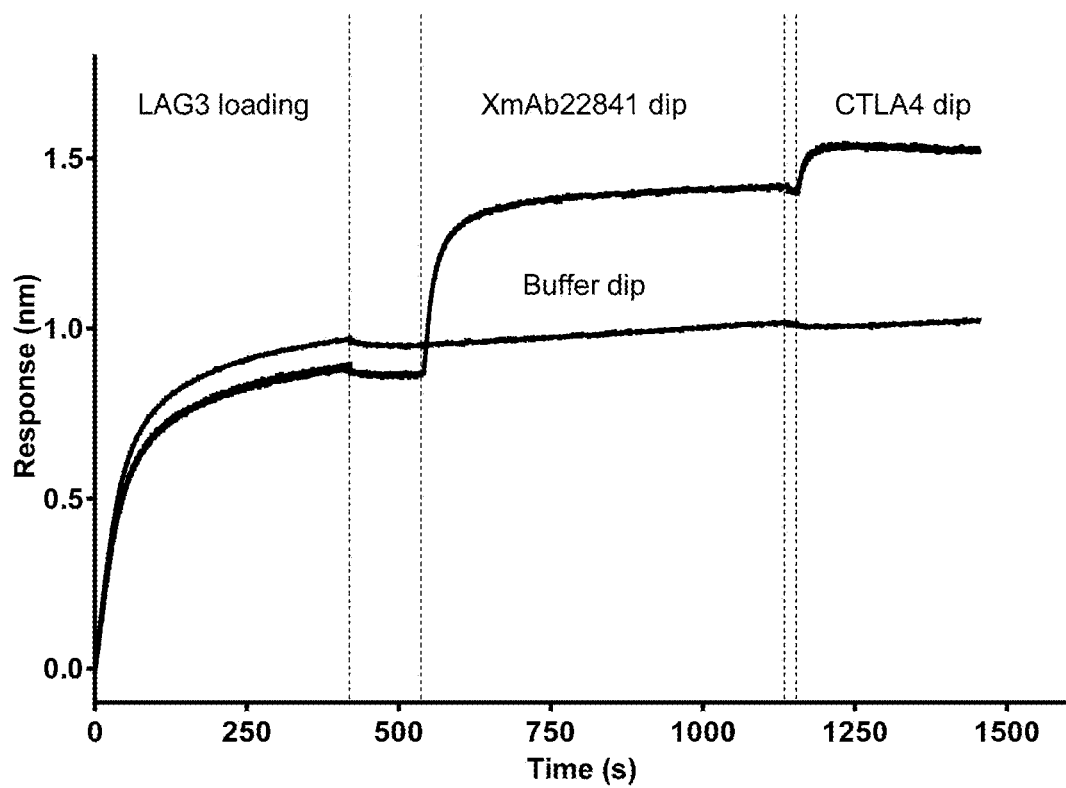

FIG. 119 depicts in-tandem BLI experiment showing biosensors loaded with LAG-3 and dipped into XmAb22841 or buffer followed by a final dip into CTLA-4 antigen.

Figure 120:
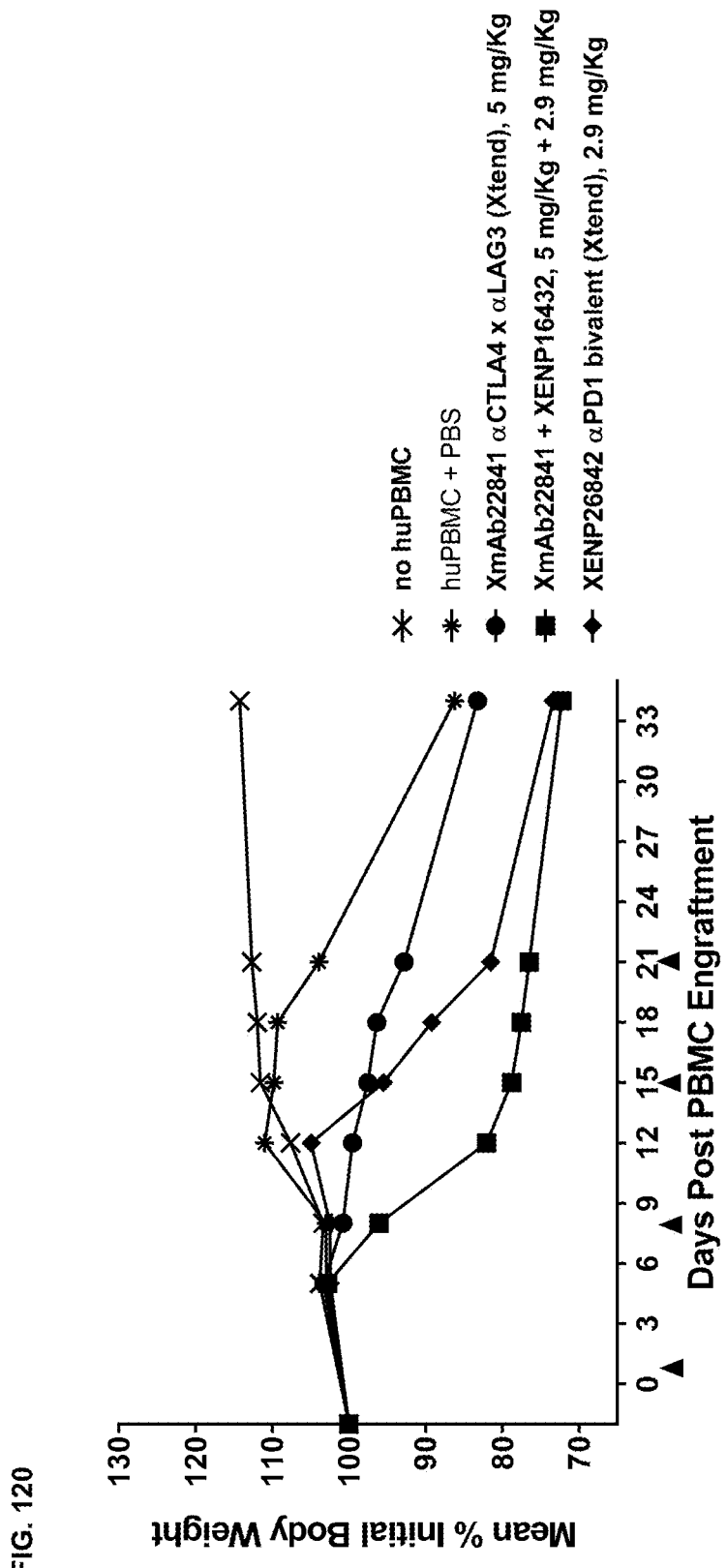

FIG. 120 depicts changes in body weight over time (as a percentage of initial body weight) in NSG mice engrafted i.v. OSP with human PBMCs and dosed with the indicated test articles. Dead mice were set to 70% initial body weight.

Figure 121:
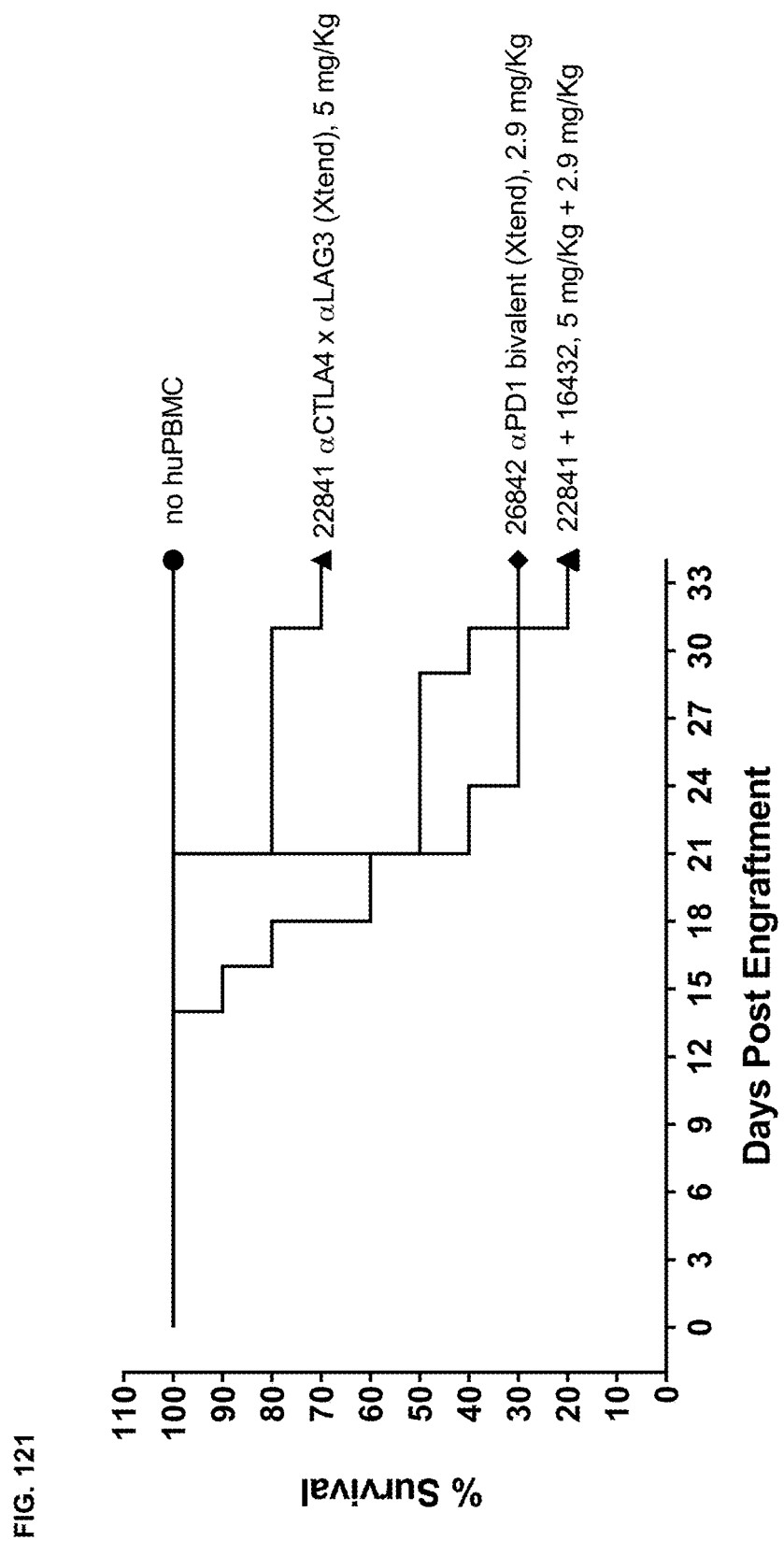

FIG. 121 depicts the survival of NSG mice engrafted i.v. OSP with human PBMCs and dosed with the indicated test articles.

Figure 122A:
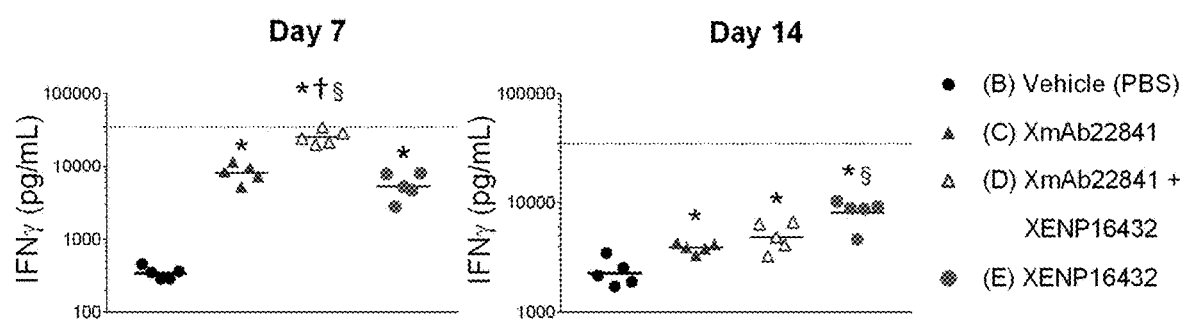
Figure 122B:
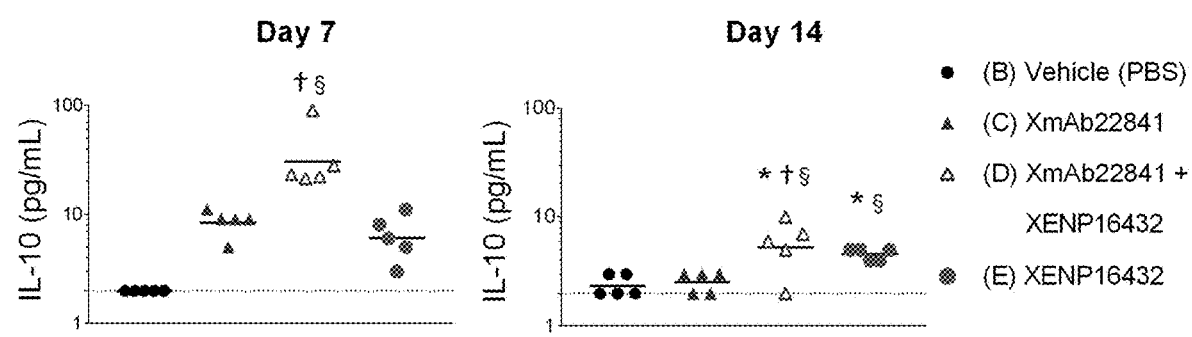

FIGS. 122A and 122B depict serum A) IFNγ concentration and B) IL-10 concentrations on Days 7 and 14 in serum of NSG mice engrafted i.v. OSP with human PBMCs and dosed with the indicated test articles.

VI. DETAILED DESCRIPTION OF THE INVENTION

A. Incorporation of Materials

1. Figures and Legends

All the figures, accompanying legends and sequences (with their identifiers and/or descriptions) of United States Patent Application Nos. 62/583,438, filed Nov. 8, 2017; 62/598,938, filed Dec. 14, 2017; 62/658,227, filed Apr. 16, 2018; 62/420,500, filed Nov. 10, 2016; 62/353,511, filed Jun. 22, 2016; 62/350,145, filed Jun. 14, 2016, Ser. No. 15/623,314, filed Jun. 14, 2017 and PCT/US17/37555, filed Jun. 14, 2017, all which are expressly and independently incorporated by reference herein in their entirety, particularly for the amino acid sequences depicted therein.

2. Sequences

Reference is made to the accompanying sequence listing as following: anti-PD-1 sequences suitable for use as ABDs include SEQ ID NOs: 6209-11464 (PD-1 scFv sequences, although the Fv sequences therein can be formatted as Fabs), SEQ ID NOs: 11465-17134 (PD-1 Fab sequences, although the Fv sequences therein can be formatted as scFvs), SEQ ID NOs: 33003-33072 (additional PD-1 Fab sequences, although the Fv sequences therein can be formatted as scFvs), SEQ ID NOs: 33073-35394 (additional PD-1 scFv sequences, although the Fv sequences therein can be formatted as Fabs) and SEQ ID NOs: 36127-36146 (PD-1 bivalent constructs, which can be formatted as either scFvs or Fabs). Anti-CTLA-4 sequences suitable for use as ABDs include SEQ ID NOs: 21-2918 (CTLA-4 scFv sequences, although the Fv sequences therein can be formatted as Fabs), SEQ ID NOs: 2919-6208 (CTLA-4 Fab sequences, although the Fv sequences therein can be formatted as scFvs), SEQ ID NOs: 36739-36818 (additional CTLA-4 Fab sequences, although the Fv sequences therein can be formatted as scFvs) and SEQ ID NOs: 35395-35416 (CTLA-4 one armed constructs, which can be formatted as either Fabs or scFvs). Anti-LAG-3 sequences suitable for use as ABDs include SEQ ID NOs: 17135-20764 (LAG-3 Fabs, although the Fv sequences therein can be formatted as scFvs), SEQ ID NOs:

36819-36962 (additional LAG-3 Fabs although the Fv sequences therein can be formatted as scFvs), SEQ ID NOs: 35417-35606 (additional LAG-3 Fabs although the Fv sequences therein can be formatted as scFvs), SEQ ID NOs: 25194-32793 (additional LAG-3 Fabs although the Fv sequences therein can be formatted as scFvs) and SEQ ID NOs: 32794-33002 (one armed LAG-3 constructs which can be formatted as either Fabs or scFvs). Anti-TIM-3 sequences suitable for use as ABDs include SEQ ID NOs: 20765-20884 (TIM-3 Fabs, although the Fv sequences therein can be formatted as scFvs), SEQ ID NOs: 37587-37698 (additional TIM-3 Fabs, the Fv sequences therein can be formatted as scFvs) and SEQ ID NOs: 36347-36706 (bivalent TIM-3 constructs which can be formatted as either Fabs or scFvs). Anti-BTLA sequences suitable for use as ABDs include SEQ ID NOs: 20885-21503 (BTLA Fabs although the Fv sequences therein can be formatted as scFvs) and SEQ ID NOs: 36707-36738 (additional BTLA Fabs although the Fv sequences therein can be formatted as scFvs). Anti-TIGIT sequences suitable for use as ABDs include SEQ ID NOs: 21504-21523 (TIGIT Fab although the Fv sequences therein can be formatted as scFvs) and SEQ ID NOs: 37435-37586 (additional TIGIT Fabs although the Fv sequences therein can be formatted as scFvs). As will be understood from those in the art, these sequence identifiers come in "pairs" for the variable heavy and light chains, as will be apparent from the sequence identifiers.

Bispecific antibodies of the invention include LAG3 X CTLA4 constructs of SEQ ID NOs: 35607-35866 and SEQ ID NOs: 21524-22620. PD-1 X CTLA4 constructs include those listed as SEQ ID NOs: 36167-36346 and SEQ ID NOs: 23316-23735. PD-1 X TIM3 constructs include those listed as SEQ ID NOs: 25174-25193. PD-1 X LAG3 constructs include those listed as SEQ ID NOs: 35867-36126 and SEQ ID NOs: 23736-25133. PD-1 X TIGIT constructs include those listed as SEQ ID NOs: 25134-25173. PD-1 X BTLA constructs include those listed as SEQ ID NOs: 22724-23315 and SEQ ID NOs: 36147-36166. CTLA4 X BTLA constructs include those listed as SEQ ID NOs: 22624-22723. Finally, the names for XENP23552, XENP22841, XENP22842, XENP22843, XENP22844, XENP22845, XENP22846, XENP22847, XENP22848, XENP22849, XENP22850, XENP22851, XENP22852, XENP22858, XENP22854, XENP22855 all should have included the "M428L/N434S" notation in the title, which were inadvertantly left off.

B. Nomenclature

The bispecific antibodies of the invention are listed in several different formats. Each polypeptide is given a unique "XENP" number (or in some cases, a "XENCS" number), although as will be appreciated in the art, a longer sequence might contain a shorter one. For example, the heavy chain of the scFv side monomer of a bottle opener format for a given sequence will have a first XENP number, while the scFv domain will have a different XENP number. Some molecules have three polypeptides, so the XENP number, with the components, is used as a name. Thus, the molecule XENP20717, which is in bottle opener format, comprises three sequences, generally referred to as "XENP20717 HC-Fab", XENP20717 HC-scFv" and "XENP20717 LC" or equivalents, although one of skill in the art would be able to identify these easily through sequence alignment. These XENP numbers are in the sequence listing as well as identifiers, and used in the Figures. In addition, one molecule, comprising the three components, gives rise to multiple sequence identifiers. For example, the listing of the Fab monomer has the full length sequence, the variable heavy sequence and the three CDRs of the variable heavy sequence; the light chain has a full length sequence, a variable light sequence and the three CDRs of the variable light sequence; and the scFv-Fc domain has a full length sequence, an scFv sequence, a variable light sequence, 3 light CDRs, a scFv linker, a variable heavy sequence and 3 heavy CDRs; note that all molecules herein with a scFv domain use a single charged scFv linker (+H), although others can be used. In addition, the naming nomenclature of particular variable domains uses a "Hx.xx_Ly.yy" type of format, with the numbers being unique identifiers to particular variable chain sequences. Thus, the variable domain of the Fab side of XENP22841 is "7G8_H3.30_L1.34", which indicates that the variable heavy domain H3.30 was combined with the light domain L1.34. In the case that these sequences are used as scFvs, the designation "7G8_H3.30_L1.34", indicates that the variable heavy domain H3.30 was combined with the light domain L1.34 and is in vh-linker-vl orientation, from N- to C-terminus. This molecule with the identical sequences of the heavy and light variable domains but in the reverse order would be named "7G8_L1.34_H3.30". Similarly, different constructs may "mix and match" the heavy and light chains as will be evident from the sequence listing and the Figures.

C. Definitions

In order that the application may be more completely understood, several definitions are set forth below. Such definitions are meant to encompass grammatical equivalents.

By "ablation" herein is meant a decrease or removal of activity. Thus for example, "ablating FcγR binding" means the Fc region amino acid variant has less than 50% starting binding as compared to an Fc region not containing the specific variant, with more than 70-80-90-95-98% loss of activity being preferred, and in general, with the activity being below the level of detectable binding in a Biacore, SPR or BLI assay. Of particular use in the ablation of FcγR binding are those shown in FIG. 5, which generally are added to both monomers.

By "ADCC" or "antibody dependent cell-mediated cytotoxicity" as used herein is meant the cell-mediated reaction wherein nonspecific cytotoxic cells that express FcγRs recognize bound antibody on a target cell and subsequently cause lysis of the target cell. ADCC is correlated with binding to FcγRIIIa; increased binding to FcγRIIIa leads to an increase in ADCC activity.

By "ADCP" or antibody dependent cell-mediated phagocytosis as used herein is meant the cell-mediated reaction wherein nonspecific phagocytic cells that express FcγRs recognize bound antibody on a target cell and subsequently cause phagocytosis of the target cell.

By "antigen binding domain" or "ABD" herein is meant a set of six Complementary Determining Regions (CDRs) that, when present as part of a polypeptide sequence, specifically binds a target antigen as discussed herein. Thus, a "checkpoint antigen binding domain" binds a target checkpoint antigen as outlined herein. As is known in the art, these CDRs are generally present as a first set of variable heavy CDRs (vhCDRs or VHCDR5) and a second set of variable light CDRs (vhCDRs or VLCDR5), each comprising three CDRs: vhCDR1, vhCDR2, vhCDR3 for the heavy chain and vlCDR1, vlCDR2 and vlCDR3 for the light. The CDRs are present in the variable heavy and variable light domains, respectively, and together form an Fv region. (See Table 1 and related discussion above for CDR numbering schemes). Thus, in some cases, the six CDRs of the antigen binding domain are contributed by a variable heavy and a variable light domain. In a "Fab" format, the set of 6 CDRs are contributed by two different polypeptide sequences, the variable heavy domain (vh or VH; containing the vhCDR1, vhCDR2 and vhCDR3) and the variable light domain (vl or VL; containing the vlCDR1, vlCDR2 and vlCDR3), with the C-terminus of the vh domain being attached to the N-terminus of the CH1 domain of the heavy chain and the C-terminus of the vl domain being attached to the N-terminus of the constant light domain (and thus forming the light chain). In a scFv format, the vh and vl domains are covalently attached, generally through the use of a linker (a "scFv linker") as outlined herein, into a single polypeptide sequence, which can be either (starting from the N-terminus) vh-linker-vl or vl-linker-vh, with the former being generally preferred (including optional domain linkers on each side, depending on the format used (e.g. from FIG. 1A-1O). In general, the C-terminus of the scFv domain is attached to the N-terminus of the hinge in the second monomer.

By "modification" herein is meant an amino acid substitution, insertion, and/or deletion in a polypeptide sequence or an alteration to a moiety chemically linked to a protein. For example, a modification may be an altered carbohydrate or PEG structure attached to a protein. By "amino acid modification" herein is meant an amino acid substitution, insertion, and/or deletion in a polypeptide sequence. For clarity, unless otherwise noted, the amino acid modification is always to an amino acid coded for by DNA, e.g. the 20 amino acids that have codons in DNA and RNA.

By "amino acid substitution" or "substitution" herein is meant the replacement of an amino acid at a particular position in a parent polypeptide sequence with a different amino acid. In particular, in some embodiments, the substitution is to an amino acid that is not naturally occurring at the particular position, either not naturally occurring within the organism or in any organism. For example, the substitution E272Y refers to a variant polypeptide, in this case an Fc variant, in which the glutamic acid at position 272 is replaced with tyrosine. For clarity, a protein which has been engineered to change the nucleic acid coding sequence but not change the starting amino acid (for example exchanging CGG (encoding arginine) to CGA (still encoding arginine) to increase host organism expression levels) is not an "amino acid substitution"; that is, despite the creation of a new gene encoding the same protein, if the protein has the same amino acid at the particular position that it started with, it is not an amino acid substitution.

By "amino acid insertion" or "insertion" as used herein is meant the addition of an amino acid sequence at a particular position in a parent polypeptide sequence. For example, –233E or 233E designates an insertion of glutamic acid after position 233 and before position 234. Additionally, –233ADE or A233ADE designates an insertion of AlaAspGlu after position 233 and before position 234.

By "amino acid deletion" or "deletion" as used herein is meant the removal of an amino acid sequence at a particular position in a parent polypeptide sequence. For example, E233- or E233 #, E233( ) or E233del designates a deletion of glutamic acid at position 233. Additionally, EDA233- or EDA233 # designates a deletion of the sequence GluAspAla that begins at position 233.

By "variant protein" or "protein variant", or "variant" as used herein is meant a protein that differs from that of a parent protein by virtue of at least one amino acid modification. The protein variant has at least one amino acid modification compared to the parent protein, yet not so many that the variant protein will not align with the parental protein using an alignment program such as that described below. In general, variant proteins (such as variant Fc domains, etc., outlined herein, are generally at least 75, 80, 85, 90, 91, 92, 93, 94, 95, 96, 97, 98 or 99% identical to the parent protein, using the alignment programs described below, such as BLAST.

As described below, in some embodiments the parent polypeptide, for example an Fc parent polypeptide, is a human wild type sequence, such as the heavy constant domain or Fc region from IgG1, IgG2, IgG3 or IgG4, although human sequences with variants can also serve as "parent polypeptides", for example the IgG1/2 hybrid of US Publication 2006/0134105 can be included. The protein variant sequence herein will preferably possess at least about 80% identity with a parent protein sequence, and most preferably at least about 90% identity, more preferably at least about 95-98-99% identity. Accordingly, by "antibody variant" or "variant antibody" as used herein is meant an antibody that differs from a parent antibody by virtue of at least one amino acid modification, "IgG variant" or "variant IgG" as used herein is meant an antibody that differs from a parent IgG (again, in many cases, from a human IgG sequence) by virtue of at least one amino acid modification, and "immunoglobulin variant" or "variant immunoglobulin" as used herein is meant an immunoglobulin sequence that differs from that of a parent immunoglobulin sequence by virtue of at least one amino acid modification. "Fc variant" or "variant Fc" as used herein is meant a protein comprising an amino acid modification in an Fc domain as compared to an Fc domain of human IgG1, IgG2 or IgG4.

The Fc variants of the present invention are defined according to the amino acid modifications that compose them. Thus, for example, N434S or 434S is an Fc variant with the substitution serine at position 434 relative to the parent Fc polypeptide, wherein the numbering is according to the EU index. Likewise, M428L/N434S defines an Fc variant with the substitutions M428L and N434S relative to the parent Fc polypeptide. The identity of the WT amino acid may be unspecified, in which case the aforementioned variant is referred to as 428L/434S. It is noted that the order in which substitutions are provided is arbitrary, that is to say that, for example, N434S/M428L is the same Fc variant as M428L/N434S, and so on. For all positions discussed in the present invention that relate to antibodies, unless otherwise noted, amino acid position numbering is according to the EU index. The EU index or EU index as in Kabat or EU numbering scheme refers to the numbering of the EU antibody. Kabat et al. collected numerous primary sequences of the variable regions of heavy chains and light chains. Based on the degree of conservation of the sequences, they classified individual primary sequences into the CDR and the framework and made a list thereof (see SEQUENCES OF IMMUNOLOGICAL INTEREST, 5th edition, NIH publication, No. 91-3242, E. A. Kabat et al., entirely incorporated by reference). See also Edelman et al., 1969, Proc Natl Acad Sci USA 63:78-85, hereby entirely incorporated by reference. The modification can be an addition, deletion, or substitution.

By "protein" herein is meant at least two covalently attached amino acids, which includes proteins, polypeptides, oligopeptides and peptides. In addition, polypeptides that make up the antibodies of the invention may include synthetic derivatization of one or more side chains or termini, glycosylation, PEGylation, circular permutation, cyclization, linkers to other molecules, fusion to proteins or protein domains, and addition of peptide tags or labels.

By "residue" as used herein is meant a position in a protein and its associated amino acid identity. For example, Asparagine 297 (also referred to as Asn297 or N297) is a residue at position 297 in the human antibody IgG1.

By "Fab" or "Fab region" as used herein is meant the polypeptide that comprises the VH, CH1, VL, and CL immunoglobulin domains, generally on two different polypeptide chains (e.g. VH-CH1 on one chain and VL-CL on the other). Fab may refer to this region in isolation, or this region in the context of a bispecific antibody of the invention. In the context of a Fab, the Fab comprises an Fv region in addition to the CH1 and CL domains.

By "Fv" or "Fv fragment" or "Fv region" as used herein is meant a polypeptide that comprises the VL and VH domains of an ABD. Fv regions can be formatted as both Fabs (as discussed above, generally two different polypeptides that also include the constant regions as outlined above) and scFvs, where the vl and vh domains are combined (generally with a linker as discussed herein) to form an scFv.

By "single chain Fv" or "scFv" herein is meant a variable heavy domain covalently attached to a variable light domain, generally using a scFv linker as discussed herein, to form a scFv or scFv domain. A scFv domain can be in either orientation from N- to C-terminus (vh-linker-vl or vl-linker-vh). In the sequences depicted in the sequence listing and in the figures, the order of the vh and vl domain is indicated in the name, e.g. H.X_L.Y means N- to C-terminal is vh-linker-vl, and L.Y_H.X is vl-linker-vh.

By "IgG subclass modification" or "isotype modification" as used herein is meant an amino acid modification that converts one amino acid of one IgG isotype to the corresponding amino acid in a different, aligned IgG isotype. For example, because IgG1 comprises a tyrosine and IgG2 a phenylalanine at EU position 296, a F296Y substitution in IgG2 is considered an IgG subclass modification.

By "non-naturally occurring modification" as used herein is meant an amino acid modification that is not isotypic. For example, because none of the human IgGs comprise a serine at position 434, the substitution 434S in IgG1, IgG2, IgG3, or IgG4 (or hybrids thereof) is considered a non-naturally occurring modification.

By "amino acid" and "amino acid identity" as used herein is meant one of the 20 naturally occurring amino acids that are coded for by DNA and RNA.

By "effector function" as used herein is meant a biochemical event that results from the interaction of an antibody Fc region with an Fc receptor or ligand. Effector functions include but are not limited to ADCC, ADCP, and CDC.

By "IgG Fc ligand" as used herein is meant a molecule, preferably a polypeptide, from any organism that binds to the Fc region of an IgG antibody to form an Fc/Fc ligand complex. Fc ligands include but are not limited to FcγRIs, FcγRIIs, FcγRIIIs, FcRn, C1q, C3, mannan binding lectin, mannose receptor, staphylococcal protein A, streptococcal protein G, and viral FcγR. Fc ligands also include Fc receptor homologs (FcRH), which are a family of Fc receptors that are homologous to the FcγRs (Davis et al., 2002, Immunological Reviews 190:123-136, entirely incorporated by reference). Fc ligands may include undiscovered molecules that bind Fc. Particular IgG Fc ligands are FcRn and Fc gamma receptors. By "Fc ligand" as used herein is meant a molecule, preferably a polypeptide, from any organism that binds to the Fc region of an antibody to form an Fc/Fc ligand complex.

By "Fc gamma receptor", "FcγR" or "FcgammaR" as used herein is meant any member of the family of proteins that bind the IgG antibody Fc region and is encoded by an FcγR gene. In humans this family includes but is not limited to FcγRI (CD64), including isoforms FcγRIa, FcγRIb, and FcγRIc; FcγRII (CD32), including isoforms FcγRIIa (including allotypes H131 and R131), FcγRIIb (including FcγRIIb-1 and FcγRIIb-2), and FcγRIIc; and FcγRIII (CD16), including isoforms FcγRIIIa (including allotypes V158 and F158) and FcγRIIIb (including allotypes FcγRIIb-NA1 and FcγRIIb-NA2) (Jefferis et al., 2002, Immunol Lett 82:57-65, entirely incorporated by reference), as well as any undiscovered human FcγRs or FcγR isoforms or allotypes. An FcγR may be from any organism, including but not limited to humans, mice, rats, rabbits, and monkeys. Mouse FcγRs include but are not limited to FcγRT (CD64), FcγRII (CD32), FcγRIII (CD16), and FcγRIII-2 (CD16-2), as well as any undiscovered mouse FcγRs or FcγR isoforms or allotypes.

By "FcRn" or "neonatal Fc Receptor" as used herein is meant a protein that binds the IgG antibody Fc region and is encoded at least in part by an FcRn gene. The FcRn may be from any organism, including but not limited to humans, mice, rats, rabbits, and monkeys. As is known in the art, the functional FcRn protein comprises two polypeptides, often referred to as the heavy chain and light chain. The light chain is beta-2-microglobulin and the heavy chain is encoded by the FcRn gene. Unless otherwise noted herein, FcRn or an FcRn protein refers to the complex of FcRn heavy chain with beta-2-microglobulin. A variety of FcRn variants used to increase binding to the FcRn receptor, and in some cases, to increase serum half-life. An "FcRn variant" is one that increases binding to the FcRn receptor, and suitable FcRn variants are shown below.

By "parent polypeptide" as used herein is meant a starting polypeptide that is subsequently modified to generate a variant. The parent polypeptide may be a naturally occurring polypeptide, or a variant or engineered version of a naturally occurring polypeptide. Accordingly, by "parent immunoglobulin" as used herein is meant an unmodified immunoglobulin polypeptide that is modified to generate a variant, and by "parent antibody" as used herein is meant an unmodified antibody that is modified to generate a variant antibody. It should be noted that "parent antibody" includes known commercial, recombinantly produced antibodies as outlined below. In this context, a "parent Fc domain" will be relative to the recited variant; thus, a "variant human IgG1 Fc domain" is compared to the parent Fc domain of human IgG1, a "variant human IgG4 Fc domain" is compared to the parent Fc domain human IgG4, etc.

By "Fc" or "Fc region" or "Fc domain" as used herein is meant the polypeptide comprising the CH2-CH3 domains of an IgG molecule, and in some cases, inclusive of the hinge. In EU numbering for human IgG1, the CH2-CH3 domain comprises amino acids 231 to 447, and the hinge is 216 to 230. Thus the definition of "Fc domain" includes both amino acids 231-447 (CH2-CH3) or 216-447 (hinge-CH2-CH3), or fragments thereof. An "Fc fragment" in this context may contain fewer amino acids from either or both of the N- and C-termini but still retains the ability to form a dimer with another Fc domain or Fc fragment as can be detected using standard methods, generally based on size (e.g. non-denaturing chromatography, size exclusion chromatography, etc.)

Human IgG Fc domains are of particular use in the present invention, and can be the Fc domain from human IgG1, IgG2 or IgG4.

A "variant Fc domain" contains amino acid modifications as compared to a parental Fc domain. Thus, a "variant human IgG1 Fc domain" is one that contains amino acid modifications (generally amino acid substitutions, although in the case of ablation variants, amino acid deletions are included) as compared to the human IgG1 Fc domain. In general, variant Fc domains have at least about 80, 85, 90, 95, 97, 98 or 99 percent identity to the corresponding parental human IgG Fc domain (using the identity algorithms discussed below, with one embodiment utilizing the BLAST algorithm as is known in the art, using default parameters). Alternatively, the variant Fc domains can have from 1, 2, 3, 4, 5, 6, 7, 8, 9, 10, 11,12, 13, 14, 15, 16, 17, 18, 19 or 20 amino acid modifications as compared to the parental Fc domain. Additionally, as discussed herein, the variant Fc domains herein still retain the ability to form a dimer with another Fc domain as measured using known techniques as described herein, such as non-denaturing gel electrophoresis.

By "heavy chain constant region" herein is meant the CH1-hinge-CH2-CH3 portion of an antibody (or fragments thereof), excluding the variable heavy domain; in EU numbering of human IgG1 this is amino acids 118-447 By "heavy chain constant region fragment" herein is meant a heavy chain constant region that contains fewer amino acids from either or both of the N- and C-termini but still retains the ability to form a dimer with another heavy chain constant region.

By "position" as used herein is meant a location in the sequence of a protein. Positions may be numbered sequentially, or according to an established format, for example the EU index for antibody numbering.

By "target antigen" as used herein is meant the molecule that is bound specifically by the antigen binding domain comprising the variable regions of a given antibody. As discussed below, in the present case the target antigens are checkpoint proteins.

By "strandedness" in the context of the monomers of the heterodimeric antibodies of the invention herein is meant that, similar to the two strands of DNA that "match", heterodimerization variants are incorporated into each monomer so as to preserve the ability to "match" to form heterodimers. For example, if some pI variants are engineered into monomer A (e.g. making the pI higher) then steric variants that are "charge pairs" that can be utilized as well do not interfere with the pI variants, e.g. the charge variants that make a pI higher are put on the same "strand" or "monomer" to preserve both functionalities. Similarly, for "skew" variants that come in pairs of a set as more fully outlined below, the skilled artisan will consider pI in deciding into which strand or monomer one set of the pair will go, such that pI separation is maximized using the pI of the skews as well.

By "target cell" as used herein is meant a cell that expresses a target antigen.

By "host cell" in the context of producing a bispecific antibody according to the invention herein is meant a cell that contains the exogeneous nucleic acids encoding the components of the bispecific antibody and is capable of expressing the bispecific antibody under suitable conditions. Suitable host cells are discussed below.

By "variable region" or "variable domain" as used herein is meant the region of an immunoglobulin that comprises one or more Ig domains substantially encoded by any of the Vκ, Vλ, and/or VH genes that make up the kappa, lambda, and heavy chain immunoglobulin genetic loci respectively, and contains the CDRs that confer antigen specificity. Thus, a "variable heavy domain" pairs with a "variable light domain" to form an antigen binding domain ("ABD"). In addition, each variable domain comprises three hypervariable regions ("complementary determining regions," "CDRs") (vhCDR1, vhCDR2 and vhCDR3 for the variable heavy domain and vlCDR1, vlCDR2 and vlCDR3 for the variable light domain) and four framework (FR) regions, arranged from amino-terminus to carboxy-terminus in the following order: FR1-CDR1-FR2-CDR2-FR3-CDR3-FR4.

By "wild type or WT" herein is meant an amino acid sequence or a nucleotide sequence that is found in nature, including allelic variations. A WT protein has an amino acid sequence or a nucleotide sequence that has not been intentionally modified.

The invention provides a number of antibody domains that have sequence identity to human antibody domains. Sequence identity between two similar sequences (e.g., antibody variable domains) can be measured by algorithms such as that of Smith, T. F. & Waterman, M. S. (1981) "Comparison Of Biosequences," Adv. Appl. Math. 2:482 [local homology algorithm]; Needleman, S. B. & Wunsch, CD. (1970) "A General Method Applicable To The Search For Similarities In The Amino Acid Sequence Of Two Proteins," J. Mol. Biol. 48:443 [homology alignment algorithm], Pearson, W. R. & Lipman, D. J. (1988) "Improved Tools For Biological Sequence Comparison," Proc. Natl. Acad. Sci. (U.S.A.) 85:2444 [search for similarity method]; or Altschul, S. F. et al, (1990) "Basic Local Alignment Search Tool," J. Mol. Biol. 215:403-10, the "BLAST" algorithm, see https://blast.ncbi.nlm.nih.gov/Blast.cgi. When using any of the aforementioned algorithms, the default parameters (for Window length, gap penalty, etc) are used. In one embodiment, sequence identity is done using the BLAST algorithm, using default parameters The antibodies of the present invention are generally isolated or recombinant. "Isolated," when used to describe the various polypeptides disclosed herein, means a polypeptide that has been identified and separated and/or recovered from a cell or cell culture from which it was expressed. Ordinarily, an isolated polypeptide will be prepared by at least one purification step. An "isolated antibody," refers to an antibody which is substantially free of other antibodies having different antigenic specificities. "Recombinant" means the antibodies are generated using recombinant nucleic acid techniques in exogenous host cells, and they can be isolated as well.

"Specific binding" or "specifically binds to" or is "specific for" a particular antigen or an epitope means binding that is measurably different from a non-specific interaction. Specific binding can be measured, for example, by determining binding of a molecule compared to binding of a control molecule, which generally is a molecule of similar structure that does not have binding activity. For example, specific binding can be determined by competition with a control molecule that is similar to the target.

Specific binding for a particular antigen or an epitope can be exhibited, for example, by an antibody having a KD for an antigen or epitope of at least about $10^{-4}$M, at least about $10^{-5}$ M, at least about $10^{-6}$M, at least about $10^{-7}$M, at least about $10^{-8}$M, at least about $10^{-9}$M, alternatively at least about $10^{-10}$ M, at least about $10^{-11}$ M, at least about $10^{-12}$M, or greater, where KD refers to a dissociation rate of a particular antibody-antigen interaction. Typically, an antibody that specifically binds an antigen will have a KD that is 20-, 50-, 100-, 500-, 1000-, 5,000-, 10,000- or more times greater for a control molecule relative to the antigen or epitope.

Also, specific binding for a particular antigen or an epitope can be exhibited, for example, by an antibody having a KA or Ka for an antigen or epitope of at least 20-, 50-, 100-, 500-, 1000-, 5,000-, 10,000- or more times greater for the epitope relative to a control, where KA or Ka refers to an association rate of a particular antibody-antigen interaction. Binding affinity is generally measured using a Biacore, SPR or BLI assay.

D. Antibodies

The present invention relates to the generation of bispecific checkpoint antibodies that bind two different checkpoint antigens as discussed herein. As is discussed below, the term "antibody" is used generally. Antibodies that find use in the present invention can take on a number of formats as described herein, including traditional antibodies as well as antibody derivatives, fragments and mimetics, described herein and depicted in the figures.

Traditional antibody structural units typically comprise a tetramer. Each tetramer is typically composed of two identical pairs of polypeptide chains, each pair having one "light" (typically having a molecular weight of about 25 kDa) and one "heavy" chain (typically having a molecular The hypervariable region generally encompasses amino acid residues from about amino acid residues 24-34 (LCDR1; "L" denotes light chain), 50-56 (LCDR2) and 89-97 (LCDR3) in the light chain variable region and around about 31-35B (HCDR1; "H" denotes heavy chain), 50-65 (HCDR2), and 95-102 (HCDR3) in the heavy chain variable region; Kabat et al., SEQUENCES OF PROTEINS OF IMMUNOLOGICAL INTEREST, 5th Ed. Public Health Service, National Institutes of Health, Bethesda, Md. (1991) and/or those residues forming a hypervariable loop (e.g. residues 26-32 (LCDR1), 50-52 (LCDR2) and 91-96 (LCDR3) in the light chain variable region and 26-32 (HCDR1), 53-55 (HCDR2) and 96-101 (HCDR3) in the heavy chain variable region; Chothia and Lesk (1987) J. Mol. Biol. 196:901-917. Specific CDRs of the invention are described below.

As will be appreciated by those in the art, the exact numbering and placement of the CDRs can be different among different numbering systems. However, it should be understood that the disclosure of a variable heavy and/or variable light sequence includes the disclosure of the associated (inherent) CDRs. Accordingly, the disclosure of each variable heavy region is a disclosure of the vhCDRs (e.g. vhCDR1, vhCDR2 and vhCDR3) and the disclosure of each variable light region is a disclosure of the vlCDRs (e.g. vlCDR1, vlCDR2 and vlCDR3). A useful comparison of CDR numbering is as below, see Lafranc et al., Dev. Comp. Immunol. 27(1):55-77 (2003):

TABLE 1

|  | Kabat + Chothia | IMGT | Kabat | AbM | Chothia | Contact | Xencor |
|---|---|---|---|---|---|---|---|
| vhCDR1 | 26-35 | 27-38 | 31-35 | 26-35 | 26-32 | 30-35 | 27-35 |
| vhCDR2 | 50-65 | 56-65 | 50-65 | 50-58 | 52-56 | 47-58 | 54-61 |
| vhCDR3 | 95-102 | 105-117 | 95-102 | 95-102 | 95-102 | 93-101 | 103-116 |
| vlCDR1 | 24-34 | 27-38 | 24-34 | 24-34 | 24-34 | 30-36 | 27-38 |
| vlCDR2 | 50-56 | 56-65 | 50-56 | 50-56 | 50-56 | 46-55 | 56-62 |
| vlCDR3 | 89-97 | 105-117 | 89-97 | 89-97 | 89-97 | 89-96 | 97-105 | weight of about 50-70 kDa). Human light chains are classified as kappa and lambda light chains. The present invention is directed to bispecific antibodies that generally are based on the IgG class, which has several subclasses, including, but not limited to IgG1, IgG2, IgG3, and IgG4. In general, IgG1, IgG2 and IgG4 are used more frequently than IgG3. It should be noted that IgG1 has different allotypes with polymorphisms at 356 (D or E) and 358 (L or M). The sequences depicted herein use the 356E/358M allotype, however the other allotype is included herein. That is, any sequence inclusive of an IgG1 Fc domain included herein can have 356D/358L replacing the 356E/358M allotype.

In addition, many of the antibodies herein have at least one of the cysteines at position 220 replaced by a serine; generally this is the on the "scFv monomer" side for most of the sequences depicted herein, although it can also be on the "Fab monomer" side, or both, to reduce disulfide formation. Specifically included within the sequences herein are one or both of these cysteines replaced (C220S).

Thus, "isotype" as used herein is meant any of the subclasses of immunoglobulins defined by the chemical and antigenic characteristics of their constant regions. It should be understood that therapeutic antibodies can also comprise hybrids of isotypes and/or subclasses. For example, as shown in US Publication 2009/0163699, incorporated by reference, the present invention the use of human IgG1/G2 hybrids.

Throughout the present specification, the Kabat numbering system is generally used when referring to a residue in the variable domain (approximately, residues 1-107 of the light chain variable region and residues 1-113 of the heavy chain variable region) and the EU numbering system for Fc regions (e.g., Kabat et al., supra (1991)).

Another type of Ig domain of the heavy chain is the hinge region. By "hinge" or "hinge region" or "antibody hinge region" or "hinge domain" herein is meant the flexible polypeptide comprising the amino acids between the first and second constant domains of an antibody. Structurally, the IgG CH1 domain ends at EU position 215, and the IgG CH2 domain begins at residue EU position 231. Thus for IgG the antibody hinge is herein defined to include positions 216 (E216 in IgG1) to 230 (p230 in IgG1), wherein the numbering is according to the EU index as in Kabat. In some cases, a "hinge fragment" is used, which contains fewer amino acids at either or both of the N- and C-termini of the hinge domain. As noted herein, pI variants can be made in the hinge region as well.

The light chain generally comprises two domains, the variable light domain (containing the light chain CDRs and together with the variable heavy domains forming the Fv region), and a constant light chain region (often referred to as CL or Cx).

Another region of interest for additional substitutions, outlined herein, is the Fc region.

The present invention provides a large number of different CDR sets. In this case, a "full CDR set" comprises the three variable light and three variable heavy CDRs, e.g. vlCDR1, vlCDR2, vlCDR3, vhCDR1, vhCDR2 and vhCDR3. These can be part of a larger variable light or variable heavy domain, respectfully. In addition, as more fully outlined herein, the variable heavy and variable light domains can be on separate polypeptide chains, when a heavy and light chain is used (for example when Fabs are used), or on a single polypeptide chain in the case of scFv sequences.

The CDRs contribute to the formation of the antigen-binding, or more specifically, epitope binding site of antibodies. "Epitope" refers to a determinant that interacts with a specific antigen binding site in the variable region of an antibody molecule known as a paratope. Epitopes are groupings of molecules such as amino acids or sugar side chains and usually have specific structural characteristics, as well as specific charge characteristics. A single antigen may have more than one epitope.

The epitope may comprise amino acid residues directly involved in the binding (also called immunodominant component of the epitope) and other amino acid residues, which are not directly involved in the binding, such as amino acid residues which are effectively blocked by the specifically antigen binding peptide; in other words, the amino acid residue is within the footprint of the specifically antigen binding peptide.

Epitopes may be either conformational or linear. A conformational epitope is produced by spatially juxtaposed amino acids from different segments of the linear polypeptide chain. A linear epitope is one produced by adjacent amino acid residues in a polypeptide chain. Conformational and nonconformational epitopes may be distinguished in that the binding to the former but not the latter is lost in the presence of denaturing solvents.

An epitope typically includes at least 3, and more usually, at least 5 or 8-10 amino acids in a unique spatial conformation. Antibodies that recognize the same epitope can be verified in a simple immunoassay showing the ability of one antibody to block the binding of another antibody to a target antigen, for example "binning." As outlined below, the invention not only includes the enumerated antigen binding domains and antibodies herein, but those that compete for binding with the epitopes bound by the enumerated antigen binding domains.

Thus, the present invention provides different antibody domains. As described herein and known in the art, the heterodimeric antibodies of the invention comprise different domains within the heavy and light chains, which can be overlapping as well. These domains include, but are not limited to, the Fc domain, the CH1 domain, the CH2 domain, the CH3 domain, the hinge domain, the heavy constant domain (CH1-hinge-Fc domain or CH1-hinge-CH2-CH3), the variable heavy domain, the variable light domain, the light constant domain, Fab domains and scFv domains.

Thus, the "Fc domain" includes the —CH2-CH3 domain, and optionally a hinge domain (—H—CH2-CH3). For IgG, the Fc domain comprises immunoglobulin domains CH2 and CH3 (Cγ2 and Cγ3) and the lower hinge region between CH1 (Cγ1) and CH2 (Cγ2). Although the boundaries of the Fc region may vary, the human IgG heavy chain Fc region is usually defined to include residues C226 or P230 to its carboxyl-terminus, wherein the numbering is according to the EU index as in Kabat. Accordingly, "CH" domains in the context of IgG are as follows: "CH1" refers to positions 118-215 according to the EU index as in Kabat. "Hinge" refers to positions 216-230 according to the EU index as in Kabat. "CH2" refers to positions 231-340 according to the EU index as in Kabat, and "CH3" refers to positions 341-447 according to the EU index as in Kabat. Thus, the "Fc domain" includes the —CH2-CH3 domain, and optionally a hinge domain (hinge-CH2-CH3). In the embodiments herein, when a scFv is attached to an Fc domain, it is generally the C-terminus of the scFv construct that is attached to all or part of the hinge of the Fc domain; for example, it is generally attached to the sequence EPKS which is the beginning of the hinge. In some embodiments, as is more fully described below, amino acid modifications are made to the Fc region, for example to alter binding to one or more FcγR receptors or to the FcRn receptor, and to enable heterodimer formation and purification, as outlined herein.

The heavy chain comprises a variable heavy domain and a constant domain, which includes a CH1-optional hinge-Fc domain comprising a CH2-CH3. The light chain comprises a variable light chain and the light constant domain. A scFv comprises a variable heavy chain, an scFv linker, and a variable light domain. In most of the constructs and sequences outlined herein, the C-terminus of the variable heavy chain is attached to the N-terminus of the scFv linker, the C-terminus of which is attached to the N-terminus of a variable light chain (N-vh-linker-vl-C) although that can be switched (N-vl-linker-vh-C).

Some embodiments of the invention comprise at least one scFv domain, which, while not naturally occurring, generally includes a variable heavy domain and a variable light domain, linked together by a scFv linker. As outlined herein, while the scFv domain is generally from N- to C-terminus oriented as vh-scFv linker-vl, this can be reversed for any of the scFv domains (or those constructed using vh and vl sequences from Fabs), to vl-scFv linker-vh, with optional linkers at one or both ends depending on the format (see generally FIG. 1A-1O).

As shown herein, there are a number of suitable linkers (for use as either domain linkers or scFv linkers) that can be used to covalently attach the recited domains, including traditional peptide bonds, generated by recombinant techniques. In some embodiments, the linker peptide may predominantly include the following amino acid residues: Gly, Ser, Ala, or Thr. The linker peptide should have a length that is adequate to link two molecules in such a way that they assume the correct conformation relative to one another so that they retain the desired activity. In one embodiment, the linker is from about 1 to 50 amino acids in length, preferably about 1 to 30 amino acids in length. In one embodiment, linkers of 1 to 20 amino acids in length may be used, with from about 5 to about 10 amino acids finding use in some embodiments. Useful linkers include glycine-serine polymers, including for example (GS)n, (GSGGS)n (SEQ ID NO: 37756), (GGGGS)n (SEQ ID NO: 37757), and (GGGS)n (SEQ ID NO: 37758), where n is an integer of at least one (and generally from 3 to 4), glycine-alanine polymers, alanine-serine polymers, and other flexible linkers. Alternatively, a variety of nonproteinaceous polymers, including but not limited to polyethylene glycol (PEG), polypropylene glycol, polyoxyalkylenes, or copolymers of polyethylene glycol and polypropylene glycol, may find use as linkers.

Other linker sequences may include any sequence of any length of CL/CH1 domain but not all residues of CL/CH1 domain; for example the first 5-12 amino acid residues of the CL/CH1 domains. Linkers can be derived from immunoglobulin light chain, for example Cκ or Cλ. Linkers can be derived from immunoglobulin heavy chains of any isotype, including for example Cγ1, Cγ2, Cγ3, Cγ4, Cα1, Cα2, Cδ, Cε, and Cμ. Linker sequences may also be derived from other proteins such as Ig-like proteins (e.g. TCR, FcR, KIR), hinge region-derived sequences, and other natural sequences from other proteins.

In some embodiments, the linker is a "domain linker", used to link any two domains as outlined herein together. For example, in FIG. 1F, there may be a domain linker that attaches the C-terminus of the CH1 domain of the Fab to the N-terminus of the scFv, with another optional domain linker attaching the C-terminus of the scFv to the CH2 domain (although in many embodiments the hinge is used as this domain linker). While any suitable linker can be used, many embodiments utilize a glycine-serine polymer as the domain linker, including for example (GS)n, (GSGGS)n (SEQ ID NO: 37756), (GGGGS)n (SEQ ID NO: 37757), and (GGGS)n (SEQ ID NO: 37758), where n is an integer of at least one (and generally from 3 to 4 to 5) as well as any peptide sequence that allows for recombinant attachment of the two domains with sufficient length and flexibility to allow each domain to retain its biological function. In some cases, and with attention being paid to "strandedness", as outlined below, charged domain linkers, as used in some embodiments of scFv linkers can be used.

In some embodiments, the linker is a scFv linker, used to covalently attach the vh and vl domains as discussed herein. In many cases, the scFv linker is a charged scFv linker, a number of which are shown in FIGS. 7A-7B. Accordingly, the present invention further provides charged scFv linkers, to facilitate the separation in pI between a first and a second monomer. That is, by incorporating a charged scFv linker, either positive or negative (or both, in the case of scaffolds that use scFvs on different monomers), this allows the monomer comprising the charged linker to alter the pI without making further changes in the Fc domains. These charged linkers can be substituted into any scFv containing standard linkers. Again, as will be appreciated by those in the art, charged scFv linkers are used on the correct "strand" or monomer, according to the desired changes in pI. For example, as discussed herein, to make triple F format heterodimeric antibody, the original pI of the Fv region for each of the desired antigen binding domains are calculated, and one is chosen to make an scFv, and depending on the pI, either positive or negative linkers are chosen.

Charged domain linkers can also be used to increase the pI separation of the monomers of the invention as well, and thus those included in FIGS. 7A-7B can be used in any embodiment herein where a linker is utilized.

In particular, the formats depicted in FIG. 1 are antibodies, usually referred to as "heterodimeric antibodies", meaning that the protein has at least two associated Fc sequences self-assembled into a heterodimeric Fc domain and at least two Fv regions, whether as Fabs or as scFvs.

E. Chimeric and Humanized Antibodies

In certain embodiments, the antibodies of the invention comprise a heavy chain variable region from a particular germline heavy chain immunoglobulin gene and/or a light chain variable region from a particular germline light chain immunoglobulin gene. For example, such antibodies may comprise or consist of a human antibody comprising heavy or light chain variable regions that are "the product of" or "derived from" a particular germline sequence. A human antibody that is "the product of" or "derived from" a human germline immunoglobulin sequence can be identified as such by comparing the amino acid sequence of the human antibody to the amino acid sequences of human germline immunoglobulins and selecting the human germline immunoglobulin sequence that is closest in sequence (i.e., greatest % identity) to the sequence of the human antibody (using the methods outlined herein). A human antibody that is "the product of" or "derived from" a particular human germline immunoglobulin sequence may contain amino acid differences as compared to the germline sequence, due to, for example, naturally-occurring somatic mutations or intentional introduction of site-directed mutation. However, a humanized antibody typically is at least 90% identical in amino acids sequence to an amino acid sequence encoded by a human germline immunoglobulin gene and contains amino acid residues that identify the antibody as being derived from human sequences when compared to the germline immunoglobulin amino acid sequences of other species (e.g., murine germline sequences). In certain cases, a humanized antibody may be at least 95, 96, 97, 98 or 99%, or even at least 96%, 97%, 98%, or 99% identical in amino acid sequence to the amino acid sequence encoded by the germline immunoglobulin gene. Typically, a humanized antibody derived from a particular human germline sequence will display no more than 10-20 amino acid differences from the amino acid sequence encoded by the human germline immunoglobulin gene (prior to the introduction of any skew, pI and ablation variants herein; that is, the number of variants is generally low, prior to the introduction of the variants of the invention). In certain cases, the humanized antibody may display no more than 5, or even no more than 4, 3, 2, or 1 amino acid difference from the amino acid sequence encoded by the germline immunoglobulin gene (again, prior to the introduction of any skew, pI and ablation variants herein; that is, the number of variants is generally low, prior to the introduction of the variants of the invention).

In one embodiment, the parent antibody has been affinity matured, as is known in the art. Structure-based methods may be employed for humanization and affinity maturation, for example as described in U.S. Ser. No. 11/004,590. Selection based methods may be employed to humanize and/or affinity mature antibody variable regions, including but not limited to methods described in Wu et al., 1999, J. Mol. Biol. 294:151-162; Baca et al., 1997, J. Biol. Chem. 272(16):10678-10684; Rosok et al., 1996, J. Biol. Chem. 271(37): 22611-22618; Rader et al., 1998, Proc. Natl. Acad. Sci. USA 95: 8910-8915; Krauss et al., 2003, Protein Engineering 16(10):753-759, all entirely incorporated by reference. Other humanization methods may involve the grafting of only parts of the CDRs, including but not limited to methods described in U.S. Ser. No. 09/810,510; Tan et al., 2002, J. Immunol. 169:1119-1125; De Pascalis et al., 2002, J. Immunol. 169:3076-3084, all entirely incorporated by reference.

VII. HETERODIMERIC ANTIBODIES

Accordingly, in some embodiments the present invention provides heterodimeric checkpoint antibodies that rely on the use of two different heavy chain variant Fc sequences, that will self-assemble to form heterodimeric Fc domains and heterodimeric antibodies.

The present invention is directed to novel constructs to provide heterodimeric antibodies that allow binding to more than one checkpoint antigen or ligand, e.g. to allow for bispecific binding. The heterodimeric antibody constructs are based on the self-assembling nature of the two Fc domains of the heavy chains of antibodies, e.g. two "monomers" that assemble into a "dimer". Heterodimeric antibodies are made by altering the amino acid sequence of each monomer as more fully discussed below. Thus, the present invention is generally directed to the creation of heterodimeric checkpoint antibodies which can co-engage antigens in several ways, relying on amino acid variants in the constant regions that are different on each chain to promote heterodimeric formation and/or allow for ease of purification of heterodimers over the homodimers.

Thus, the present invention provides bispecific antibodies. An ongoing problem in antibody technologies is the desire for "bispecific" antibodies that bind to two different antigens simultaneously, in general thus allowing the different antigens to be brought into proximity and resulting in new functionalities and new therapies. In general, these antibodies are made by including genes for each heavy and light chain into the host cells. This generally results in the formation of the desired heterodimer (A-B), as well as the two homodimers (A-A and B-B (not including the light chain heterodimeric issues)). However, a major obstacle in the formation of bispecific antibodies is the difficulty in purifying the heterodimeric antibodies away from the homodimeric antibodies and/or biasing the formation of the heterodimer over the formation of the homodimers.

There are a number of mechanisms that can be used to generate the heterodimers of the present invention. In addition, as will be appreciated by those in the art, these mechanisms can be combined to ensure high heterodimerization. Thus, amino acid variants that lead to the production of heterodimers are referred to as "heterodimerization variants". As discussed below, heterodimerization variants can include steric variants (e.g. the "knobs and holes" or "skew" variants described below and the "charge pairs" variants described below) as well as "pI variants", which allows purification of homodimers away from heterodimers. As is generally described in WO2014/145806, hereby incorporated by reference in its entirety and specifically as below for the discussion of "heterodimerization variants", useful mechanisms for heterodimerization include "knobs and holes" ("KIH"; sometimes herein as "skew" variants (see discussion in WO2014/145806), "electrostatic steering" or "charge pairs" as described in WO2014/145806, pI variants as described in WO2014/145806, and general additional Fc variants as outlined in WO2014/145806 and below.

In the present invention, there are several basic mechanisms that can lead to ease of purifying heterodimeric antibodies; one relies on the use of pI variants, such that each monomer has a different pI, thus allowing the isoelectric purification of A-A, A-B and B-B dimeric proteins. Alternatively, some scaffold formats, such as the "triple F" format, also allows separation on the basis of size. As is further outlined below, it is also possible to "skew" the formation of heterodimers over homodimers. Thus, a combination of steric heterodimerization variants and pI or charge pair variants find particular use in the invention.

In general, embodiments of particular use in the present invention rely on sets of variants that include skew variants, which encourage heterodimerization formation over homodimerization formation, coupled with pI variants, which increase the pI difference between the two monomers to facilitate purification of heterodimers away from homodimers.

Additionally, as more fully outlined below, depending on the format of the heterodimer antibody, pI variants can be either contained within the constant and/or Fc domains of a monomer, or charged linkers, either domain linkers or scFv linkers, can be used. That is, scaffolds that utilize scFv(s) such as the Triple F format can include charged scFv linkers (either positive or negative), that give a further pI boost for purification purposes. As will be appreciated by those in the art, some Triple F formats are useful with just charged scFv linkers and no additional pI adjustments, although the invention does provide pI variants that are on one or both of the monomers, and/or charged domain linkers as well. In addition, additional amino acid engineering for alternative functionalities may also confer pI changes, such as Fc, FcRn and KO variants.

In the present invention that utilizes pI as a separation mechanism to allow the purification of heterodimeric proteins, amino acid variants can be introduced into one or both of the monomer polypeptides; that is, the pI of one of the monomers (referred to herein for simplicity as "monomer A") can be engineered away from monomer B, or both monomer A and B change be changed, with the pI of monomer A increasing and the pI of monomer B decreasing. As discussed, the pI changes of either or both monomers can be done by removing or adding a charged residue (e.g. a neutral amino acid is replaced by a positively or negatively charged amino acid residue, e.g. glycine to glutamic acid), changing a charged residue from positive or negative to the opposite charge (e.g. aspartic acid to lysine) or changing a charged residue to a neutral residue (e.g. loss of a charge; lysine to serine.). A number of these variants are shown in the Figures.

Accordingly, this embodiment of the present invention provides for creating a sufficient change in pI in at least one of the monomers such that heterodimers can be separated from homodimers. As will be appreciated by those in the art, and as discussed further below, this can be done by using a "wild type" heavy chain constant region and a variant region that has been engineered to either increase or decrease its pI (wt A−+B or wt A−−B), or by increasing one region and decreasing the other region (A+−B—or A−B+).

Thus, in general, a component of some embodiments of the present invention are amino acid variants in the constant regions of antibodies that are directed to altering the isoelectric point (pI) of at least one, if not both, of the monomers of a dimeric protein to form "pI antibodies" by incorporating amino acid substitutions ("pI variants" or "pI substitutions") into one or both of the monomers. As shown herein, the separation of the heterodimers from the two homodimers can be accomplished if the pIs of the two monomers differ by as little as 0.1 pH unit, with 0.2, 0.3, 0.4 and 0.5 or greater all finding use in the present invention.

As will be appreciated by those in the art, the number of pI variants to be included on each or both monomer(s) to get good separation will depend in part on the starting pI of the components, for example in the triple F format, the starting pI of the scFv and Fab of interest. That is, to determine which monomer to engineer or in which "direction" (e.g. more positive or more negative), the Fv sequences of the two target antigens are calculated and a decision is made from there. As is known in the art, different Fvs will have different starting pIs which are exploited in the present invention. In general, as outlined herein, the pIs are engineered to result in a total pI difference of each monomer of at least about 0.1 logs, with 0.2 to 0.5 being preferred as outlined herein.

Furthermore, as will be appreciated by those in the art and outlined herein, in some embodiments, heterodimers can be separated from homodimers on the basis of size.

Figure 1A:
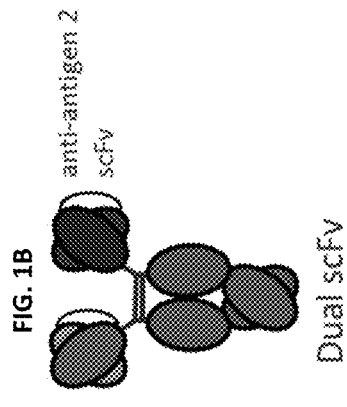
Figure 1B:
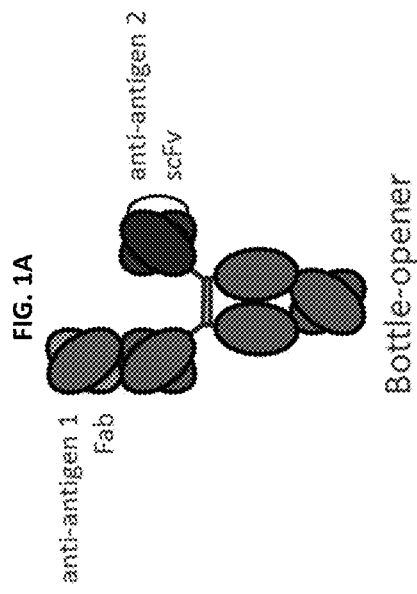
Figure 1C:
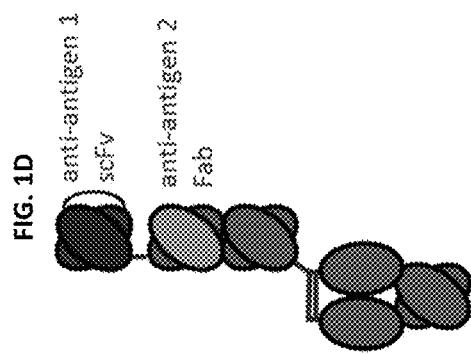
Figure 1D:
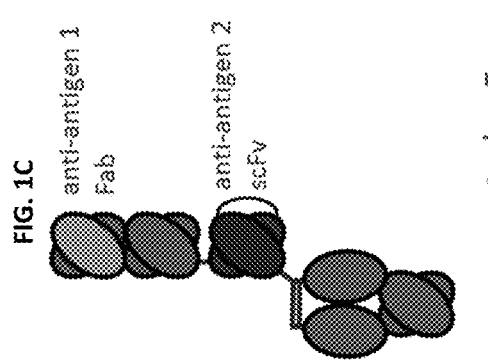
Figure 1N:
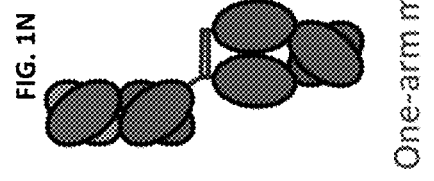
Figure 1M:
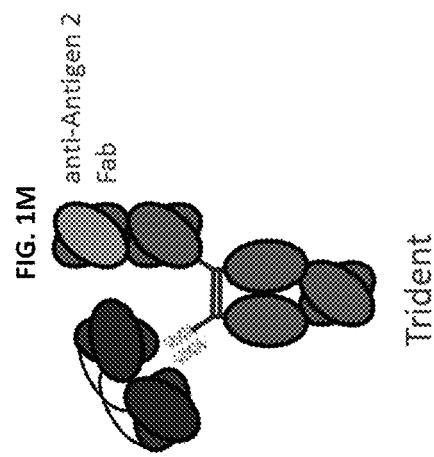
Figure 1O:
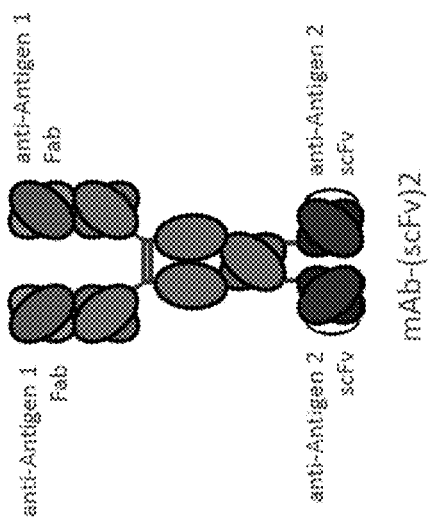

As shown in FIG. 1A-1O for example, several of the formats allow separation of heterodimers and homodimers on the basis of size.

A. Heterodimerization Variants

The present invention provides heterodimeric proteins, including heterodimeric antibodies in a variety of formats, which utilize heterodimeric variants to allow for heterodimeric formation and/or purification away from homodimers.

There are a number of suitable pairs of sets of heterodimerization skew variants. These variants come in "pairs" of "sets". That is, one set of the pair is incorporated into the first monomer and the other set of the pair is incorporated into the second monomer. It should be noted that these sets do not necessarily behave as "knobs in holes" variants, with a one-to-one correspondence between a residue on one monomer and a residue on the other; that is, these pairs of sets form an interface between the two monomers that encourages heterodimer formation and discourages homodimer formation, allowing the percentage of heterodimers that spontaneously form under biological conditions to be over 90%, rather than the expected 50% (25% homodimer A/A: 50% heterodimer A/B:25% homodimer B/B).

B. Steric Variants

In some embodiments, the formation of heterodimers can be facilitated by the addition of steric variants. That is, by changing amino acids in each heavy chain, different heavy chains are more likely to associate to form the heterodimeric structure than to form homodimers with the same Fc amino acid sequences. Suitable steric variants are included in in the Figures.

One mechanism is generally referred to in the art as "knobs and holes", referring to amino acid engineering that creates steric influences to favor heterodimeric formation and disfavor homodimeric formation can also optionally be used; this is sometimes referred to as "knobs and holes", as described in U.S. Ser. No. 61/596,846, Ridgway et al., Protein Engineering 9(7):617 (1996); Atwell et al., J. Mol. Biol. 1997 270:26; U.S. Pat. No. 8,216,805, all of which are hereby incorporated by reference in their entirety. The Figures identify a number of "monomer A-monomer B" pairs that rely on "knobs and holes". In addition, as described in Merchant et al., Nature Biotech. 16:677 (1998), these "knobs and hole" mutations can be combined with disulfide bonds to skew formation to heterodimerization.

An additional mechanism that finds use in the generation of heterodimers is sometimes referred to as "electrostatic steering" as described in Gunasekaran et al., J. Biol. Chem. 285(25):19637 (2010), hereby incorporated by reference in its entirety. This is sometimes referred to herein as "charge pairs". In this embodiment, electrostatics are used to skew the formation towards heterodimerization. As those in the art will appreciate, these may also have have an effect on pI, and thus on purification, and thus could in some cases also be considered pI variants. However, as these were generated to force heterodimerization and were not used as purification tools, they are classified as "steric variants". These include, but are not limited to, D221E/P228E/L368E paired with D221R/P228R/K409R (e.g. these are "monomer corresponding sets) and C220E/P228E/368E paired with C220R/E224R/P228R/K409R.

Additional monomer A and monomer B variants that can be combined with other variants, optionally and independently in any amount, such as pI variants outlined herein or other steric variants that are shown in FIG. 37 of US 2012/0149876, the figure and legend and SEQ ID NOs of which are incorporated expressly by reference herein.

In some embodiments, the steric variants outlined herein can be optionally and independently incorporated with any pI variant (or other variants such as Fc variants, FcRn variants, etc.) into one or both monomers, and can be independently and optionally included or excluded from the proteins of the invention.

A list of suitable skew variants is found in FIGS. 3A-3F and FIG. 8 showing some pairs of particular utility in many embodiments. Of particular use in many embodiments are the pairs of sets including, but not limited to, S364K/E357Q: L368D/K370S; L368D/K370S: S364K; L368E/K370S: S364K; T411T/E360E/Q362E: D401K; L368D/K370S: S364K/E357L, K370S: S364K/E357Q and T366S/L368A/Y407V: T366W (optionally including a bridging disulfide, T366S/L368A/Y407V/Y349C: T366W/S354C). In terms of nomenclature, the pair "S364K/E357Q: L368D/K370S" means that one of the monomers has the double variant set S364K/E357Q and the other has the double variant set L368D/K370S; as above, the "strandedness" of these pairs depends on the starting pI.

C. pI (Isoelectric Point) Variants for Heterodimers

In general, as will be appreciated by those in the art, there are two general categories of pI variants: those that increase the pI of the protein (basic changes) and those that decrease the pI of the protein (acidic changes). As described herein, all combinations of these variants can be done: one monomer may be wild type, or a variant that does not display a significantly different pI from wild-type, and the other can be either more basic or more acidic. Alternatively, each monomer is changed, one to more basic and one to more acidic.

Preferred combinations of pI variants are shown in FIG. 4. As outlined herein and shown in the figures, these changes are shown relative to IgG1, but all isotypes can be altered this way, as well as isotype hybrids. In the case where the heavy chain constant domain is from IgG2-4, R133E and R133Q can also be used.

In one embodiment, for example in the FIGS. 1A, E, F, G, H and I formats, a preferred combination of pI variants has one monomer (the negative Fab side) comprising 208D/295E/384D/418E/421D variants (N208D/Q295E/N384D/Q418E/N421D when relative to human IgG1) and a second monomer (the positive scFv side) comprising a positively charged scFv linker, including (GKPGS)4 (SEQ ID NO: 37755). However, as will be appreciated by those in the art, the first monomer includes a CH1 domain, including position 208. Accordingly, in constructs that do not include a CH1 domain (for example for antibodies that do not utilize a CH1 domain on one of the domains, for example in a dual scFv format or a "one armed" format such as those depicted in FIG. 1B, C or D), a preferred negative pI variant Fc set includes 295E/384D/418E/421D variants (Q295E/N384D/Q418E/N421D when relative to human IgG1).

Accordingly, in some embodiments, one monomer has a set of substitutions from FIG. 4 and the other monomer has a charged linker (either in the form of a charged scFv linker because that monomer comprises an scFv or a charged domain linker, as the format dictates, which can be selected from those depicted in FIGS. 7A-7B).

1. Isotypic Variants

In addition, many embodiments of the invention rely on the "importation" of pI amino acids at particular positions from one IgG isotype into another, thus reducing or eliminating the possibility of unwanted immunogenicity being introduced into the variants. A number of these are shown in FIG. 21 of US Publ. 2014/0370013, hereby incorporated by reference. That is, IgG1 is a common isotype for therapeutic antibodies for a variety of reasons, including high effector function. However, the heavy constant region of IgG1 has a higher pI than that of IgG2 (8.10 versus 7.31). By introducing IgG2 residues at particular positions into the IgG1 backbone, the pI of the resulting monomer is lowered (or increased) and additionally exhibits longer serum half-life. For example, IgG1 has a glycine (pI 5.97) at position 137, and IgG2 has a glutamic acid (pI 3.22); importing the glutamic acid will affect the pI of the resulting protein. As is described below, a number of amino acid substitutions are generally required to significant affect the pI of the variant antibody. However, it should be noted as discussed below that even changes in IgG2 molecules allow for increased serum half-life.

In other embodiments, non-isotypic amino acid changes are made, either to reduce the overall charge state of the resulting protein (e.g. by changing a higher pI amino acid to a lower pI amino acid), or to allow accommodations in structure for stability, etc. as is more further described below.

In addition, by pI engineering both the heavy and light constant domains, significant changes in each monomer of the heterodimer can be seen. As discussed herein, having the pIs of the two monomers differ by at least 0.5 can allow separation by ion exchange chromatography or isoelectric focusing, or other methods sensitive to isoelectric point.

D. Calculating pI

The pI of each monomer can depend on the pI of the variant heavy chain constant domain and the pI of the total monomer, including the variant heavy chain constant domain and the fusion partner. Thus, in some embodiments, the change in pI is calculated on the basis of the variant heavy chain constant domain, using the chart in the FIG. 19 of US Pub. 2014/0370013. As discussed herein, which monomer to engineer is generally decided by the inherent pI of the Fv and scaffold regions. Alternatively, the pI of each monomer can be compared.

E. pI Variants that Also Confer Better FcRn In Vivo Binding

In the case where the pI variant decreases the pI of the monomer, they can have the added benefit of improving serum retention in vivo.

Although still under examination, Fc regions are believed to have longer half-lives in vivo, because binding to FcRn at pH 6 in an endosome sequesters the Fc (Ghetie and Ward, 1997 Immunol Today. 18(12): 592-598, entirely incorporated by reference). The endosomal compartment then recycles the Fc to the cell surface. Once the compartment opens to the extracellular space, the higher pH, ~7.4, induces the release of Fc back into the blood. In mice, Dall'Acqua et al. showed that Fc mutants with increased FcRn binding at pH 6 and pH 7.4 actually had reduced serum concentrations and the same half life as wild-type Fc (Dall'Acqua et al. 2002, J. Immunol. 169:5171-5180, entirely incorporated by reference). The increased affinity of Fc for FcRn at pH 7.4 is thought to forbid the release of the Fc back into the blood. Therefore, the Fc mutations that will increase Fc's half-life in vivo will ideally increase FcRn binding at the lower pH while still allowing release of Fc at higher pH. The amino acid histidine changes its charge state in the pH range of 6.0 to 7.4. Therefore, it is not surprising to find His residues at important positions in the Fc/FcRn complex.

Recently it has been suggested that antibodies with variable regions that have lower isoelectric points may also have longer serum half-lives (Igawa et al., 2010 PEDS. 23(5): 385-392, entirely incorporated by reference). However, the mechanism of this is still poorly understood. Moreover, variable regions differ from antibody to antibody. Constant region variants with reduced pI and extended half-life would provide a more modular approach to improving the pharmacokinetic properties of antibodies, as described herein.

F. Additional Fc Variants for Additional Functionality

In addition to pI amino acid variants, there are a number of useful Fc amino acid modification that can be made for a variety of reasons, including, but not limited to, altering binding to one or more FcγR receptors, altered binding to FcRn receptors, etc.

Accordingly, the proteins of the invention can include amino acid modifications, including the heterodimerization variants outlined herein, which includes the pI variants and steric variants. Each set of variants can be independently and optionally included or excluded from any particular heterodimeric protein.

G. FcγR Variants

Accordingly, there are a number of useful Fc substitutions that can be made to alter binding to one or more of the FcγR receptors. Substitutions that result in increased binding as well as decreased binding can be useful. For example, it is known that increased binding to FcγRIIIa results in increased ADCC (antibody dependent cell-mediated cytotoxicity; the cell-mediated reaction wherein nonspecific cytotoxic cells that express FcγRs recognize bound antibody on a target cell and subsequently cause lysis of the target cell). Similarly, decreased binding to FcγRIIb (an inhibitory receptor) can be beneficial as well in some circumstances. Amino acid substitutions that find use in the present invention include those listed in U.S. Ser. No. 11/124,620 (particularly FIG. 41), Ser. Nos. 11/174,287, 11/396,495, 11/538,406, all of which are expressly incorporated herein by reference in their entirety and specifically for the variants disclosed therein. Particular variants that find use include, but are not limited to, 236A, 239D, 239E, 332E, 332D, 239D/332E, 267D, 267E, 328F, 267E/328F, 236A/332E, 239D/332E/330Y, 239D, 332E/330L, 243A, 243L, 264A, 264V and 299T.

In addition, there are additional Fc substitutions that find use in increased binding to the FcRn receptor and increased serum half life, as specifically disclosed in U.S. Ser. No. 12/341,769, hereby incorporated by reference in its entirety, including, but not limited to, 434S, 434A, 428L, 308F, 259I, 428L/434S, 259I/308F, 436I/428L, 436I or V/434S, 436V/428L and 259I/308F/428L.

H. Ablation Variants

Similarly, another category of functional variants are "FcγR ablation variants" or "Fc knock out (FcKO or KO)" variants. In these embodiments, for some therapeutic applications, it is desirable to reduce or remove the normal binding of the Fc domain to one or more or all of the Fcγ receptors (e.g. FcγR1, FcγRIIa, FcγRIIb, FcγRIIIa, etc.) to avoid additional mechanisms of action. That is, for example, in many embodiments, particularly in the use of bispecific checkpoint antibodies desirable to ablate FcγRIIIa binding to eliminate or significantly reduce ADCC activity such that one of the Fc domains comprises one or more Fcγ receptor ablation variants. These ablation variants are depicted in FIG. 5, and each can be independently and optionally included or excluded, with preferred aspects utilizing ablation variants selected from the group consisting of G236R/L328R, E233P/L234V/L235A/G236del/S239K, E233P/L234V/L235A/G236del/S267K, E233P/L234V/L235A/G236del/S239K/A327G, E233P/L234V/L235A/G236del/S267K/A327G and E233P/L234V/L235A/G236del. It should be noted that the ablation variants referenced herein ablate FcγR binding but generally not FcRn binding.

As is known in the art, the Fc domain of human IgG1 has the highest binding to the Fcγ receptors, and thus ablation variants can be used when the constant domain (or Fc domain) in the backbone of the heterodimeric antibody is IgG1. Alternatively, or in addition to ablation variants in an IgG1 background, mutations at the glycosylation position 297 (generally to A or S) can significantly ablate binding to FcγRIIIa, for example. Human IgG2 and IgG4 have naturally reduced binding to the Fcγ receptors, and thus those backbones can be used with or without the ablation variants.

I. Combination of Heterodimeric and Fc Variants

As will be appreciated by those in the art, all of the recited heterodimerization variants (including skew and/or pI variants) can be optionally and independently combined in any way, as long as they retain their "strandedness" or "monomer partition". In addition, all of these variants can be combined into any of the heterodimerization formats.

In the case of pI variants, while embodiments finding particular use are shown in the Figures, other combinations can be generated, following the basic rule of altering the pI difference between two monomers to facilitate purification.

In addition, any of the heterodimerization variants, skew and pI, are also independently and optionally combined with Fc ablation variants, Fc variants, FcRn variants, as generally outlined herein. Preferred combinations are shown in FIGS. 6A-6B.

Antigen Binding Domains to Target Antigens

The bispecific antibodies of the invention have two different antigen binding domains (ABDs) that bind to two different target antigens ("target pairs"), in either bivalent, bispecific formats or trivalent, bispecific formats as generally shown in FIG. 1A-1O. In the present invention, the bispecific heterodimeric antibodies target human PD-1 on one side and a second antigen on the other side selected from CTLA-4, TIM-3, LAG-3, TIGIT, ICOS and BTLA, the sequences of which are shown in FIG. 2. Accordingly, suitable bispecific antibodies bind PD-1 and CTLA-4, PD-1 and TIM-3, PD-1 and LAG-3, PD-1 and TIGIT, PD-1 and BTLA and PD-1 and ICOS. Note that generally these bispecific antibodies are named "anti-PD-1 X anti-CTLA-4", or generally simplistically or for ease (and thus interchangeably) as "PD-1 X CTLA-4", etc. for each pair. Note that unless specified herein, the order of the antigen list in the name does not confer structure; that is a PD-1 X CTLA-4 bottle opener antibody can have the scFv bind to PD-1 or CTLA-4, although in some cases, the order specifies structure as indicated.

As is more fully outlined herein, these combinations of ABDs can be in a variety of formats, as outlined below, generally in combinations where one ABD is in a Fab format and the other is in an scFv format. As discussed herein and shown in FIG. 1A-1O, some formats use a single Fab and a single scFv (FIGS. 1A, C and D), and some formats use two Fabs and a single scFv (FIGS. 1E, F, G, H and I).

VIII. ANTIGEN BINDING DOMAINS

As discussed herein, the bispecific heterodimeric antibodies of the invention include two antigen binding domains (ABDs), each of which bind to a different target protein. As outlined herein, these heterodimeric antibodies can be bispecific and bivalent (each antigen is bound by a single ABD, for example, in the format depicted in FIG. 1A), or bispecific and trivalent (one antigen is bound by a single ABD and the other is bound by two ABDs, for example as depicted in FIG. 1F).

In addition, in general, one of the ABDs comprises a scFv as outlined herein, in an orientation from N- to C-terminus of vh-scFv linker-vl or vl-scFv linker-vh. One or both of the other ABDs, according to the format, generally is a Fab, comprising a vh domain on one protein chain (generally as a component of a heavy chain) and a vl on another protein chain (generally as a component of a light chain).

The invention provides a number of ABDs that bind to a number of different target proteins, as outlined below. As will be appreciated by those in the art, any set of 6 CDRs or vh and vl domains can be in the scFv format or in the Fab format, which is then added to the heavy and light constant domains, where the heavy constant domains comprise variants (including within the CH1 domain as well as the Fc domain). The scFv sequences contained in the sequence listing utilize a particular charged linker, but as outlined herein, uncharged or other charged linkers can be used, including those depicted in FIGS. 7A-7B.

In addition, as discussed above, the numbering used in the Sequence Listing for the identification of the CDRs is Kabat, however, different numbering can be used, which will change the amino acid sequences of the CDRs as shown in Table 1.

For all of the variable heavy and light domains listed herein, further variants can be made. As outlined herein, in some embodiments the set of 6 CDRs can have from 0, 1, 2, 3, 4 or 5 amino acid modifications (with amino acid substitutions finding particular use), as well as changes in the framework regions of the variable heavy and light domains, as long as the frameworks (excluding the CDRs) retain at least about 80, 85 or 90% identity to a human germline sequence selected from those listed in FIG. 1 of U.S. Pat. No. 7,657,380, which Figure and Legend is incorporated by reference in its entirety herein. Thus, for example, the identical CDRs as described herein can be combined with different framework sequences from human germline sequences, as long as the framework regions retain at least 80, 85 or 90% identity to a human germline sequence selected from those listed in FIG. 1 of U.S. Pat. No. 7,657,380. Alternatively, the CDRs can have amino acid modifications (e.g. from 1, 2, 3, 4 or 5 amino acid modifications in the set of CDRs (that is, the CDRs can be modified as long as the total number of changes in the set of 6 CDRs is less than 6 amino acid modifications, with any combination of CDRs being changed; e.g. there may be one change in vlCDR1, two in vhCDR2, none in vhCDR3, etc.)), as well as having framework region changes, as long as the framework regions retain at least 80, 85 or 90% identity to a human germline sequence selected from those listed in FIG. 1 of U.S. Pat. No. 7,657,380.

A. PD-1 Antigen Binding Domains

In the embodiments of the invention, one of the ABDs binds human PD-1. WO 2017/218707, hereby expressly incorporated by reference in its entirety, and specifically for Figures, Legends and SEQ identifiers that depict anti-PD-1 sequences, outlines a large number of anti-PD-1 ABDs, that can be used in combination with ABDs to other checkpoint inhibitors. However, the present disclosure is directed to additional anti-PD-1 ABDs based on the 1C11 done, shown in FIGS. 13, 15, 16, 18, 20, 21, 24, 33 and 40.

As is known in the art, stability of variable domains can change based on the format. That is, VH and VL domains that are identified and/or useful in a Fab format may not be as stable in an scFv format, and thus sometimes additional engineering occurs to increase stability (e.g. Tm).

In useful embodiments, the invention provides anti-PD-1 ABDs comprising a VHCDR1 comprising the amino acid sequence HYG(M/I)N; a VHCDR2 comprising the amino acid sequence WINT(Y/H)TGEP(T/Y)YA(D/P)GF(T/Q)(G/E); a VHCDR3 comprising the amino acid sequence DY(F/Y)GSSPY; a VLCDR1 comprising the amino acid sequence VLCDR1 R(S/A)SQSIV(F/H)SNGNTYLE; a VLCDR2 comprising the amino acid sequence KVSNRF(S/T); and a VHCDR3 comprising the amino acid sequence FQGSHVPN. As is known, amino acids depicted as "(S/T)" means that either amino acid can be at this position.

In useful embodiments, the bispecific antibodies of the invention include an ABD to human PD-1. In these embodiments, the six CDRs that confer binding to PD-1 are selected from those depicted in any of FIGS. 13,15, 16,18, 20, 21, 24, 33 and 40. Alternatively in these embodiments, the VH and VL domains that confer binding to PD-1 are selected from those depicted in any of FIGS. 13, 15, 16,18, 20, 21, 24, 33 and 40.

In some embodiments, the bispecific antibodies of the invention include an ABD to PD-1 in a Fab format. In some embodiments, the ABD to PD-1 contains the 6 CDRs of any ABDs of FIGS. 13,16, 18, 20, 21, 24, 33 and 40, or the VH and VL domains from any ABD of FIGS. 13,16, 18, 20, 21, 24, 33 and 40.

Of particular use in many embodiments that have a Fab ABD to PD-1 is the ABD of XENP26940 1C11[PD-1]_H3.303_L3.152 of FIGS. 24A-24J. Thus, the six CDRs and/or the VH and VL domains from XENP026940 can be used in the constructs of the invention.

Of particular use in many embodiments that have a Fab ABD to PD-1 is the ABD of XENP28652 1C11[PD-1]_H3.328_L3.153 of FIG. 40. Thus, the six CDRs and/or the VH and VL domains from XENP28652 can be used in the constructs of the invention.

In some embodiments, the bispecific antibodies of the invention include an ABD to PD-1 in a scFv format. In some embodiments, the ABD to PD-1 contains the 6 CDRs of any ABDs of FIG. 15A-15T, or the VH and VL domains from any ABD of FIG. 15A-15T.

Of particular use in many embodiments that have a scFv ABD to PD-1 is the ABD of XENP025806 1C11[PD-1]_H3.234_L3.144 as depicted in FIG. 15A-15T. Thus, the six CDRs and/or the VH and VL domains from XENP025806 can be used in the constructs of the invention.

Of particular use in many embodiments that have a scFv ABD to PD-1 is the ABD of XENP025812 1C11[PD-1]_H3.240_L3.148 as depicted in FIG. 15A-15T. Thus, the six CDRs and/or the VH and VL domains from XENP025812 can be used in the constructs of the invention.

Of particular use in many embodiments that have a scFv ABD to PD-1 is the ABD of XENP025813 1C11[PD-1]_H3.241_L3.148 as depicted in FIG. 15A-15T. Thus, the six CDRs and/or the VH and VL domains from XENP025813 can be used in the constructs of the invention.

Of particular use in many embodiments that have a scFv ABD to PD-1 is the ABD of XENP025819 1C11[PD-1]_H3.241_L3.92 as depicted in FIG. 15A-15T. Thus, the six CDRs and/or the VH and VL domains from XENP025819 can be used in the constructs of the invention.

B. CTLA-4 Antigen Binding Domains

As will be appreciated by those in the art, any number of anti-CTLA-4 ABD sequences can be used in combination with the scFv anti-PD-1 sequences of the invention in the creation of bispecific antibodies. Anti-CTLA-4 sequences suitable for use as ABDs include SEQ ID NOs: 21-2918 (CTLA-4 scFv sequences, although the Fv sequences therein can be formatted as Fabs), SEQ ID NOs: 2919-6208 (CTLA-4 Fab sequences, although the Fv sequences therein can be formatted as scFvs), SEQ ID NOs: 36739-36818 (additional CTLA-4 Fab sequences, although the Fv sequences therein can be formatted as scFvs) and SEQ ID NOs: 35395-35416 (CTLA-4 one armed constructs, which can be formatted as either Fabs or scFvs). As will be understood from those in the art, these sequence identifiers come in "pairs" for the variable heavy and light chains, as will be apparent from the sequence identifiers.

In some embodiments, an anti-CTLA-4 Fab is selected from the pairs of SEQ ID NOs:36739 and 36743, 36747 and 36751, 36755 and 36759, 36763 and 36767, 36771 and 36775, 36779 and 36783, 36787 and 36791, 36795 and 36799, 36803 and 36807 and 36811 and 36815 of the sequence listing.

Of particular interest in the present invention are the sequences of the Fab CTLA-4 ABD of CTLA-4 H3_L0.22, including the VH (SEQ ID NO:38134, with VHCDRs (SEQ ID NOs:38135, 38136 and 38137) and VL (SEQ ID NO:38138 with VLCDRs (SEQ ID NOs:38139, 38140 and 38141).

C. LAG-3 Antigen Binding Domains

As will be appreciated by those in the art, any number of anti-LAG-3 ABD sequences can be used in combination with the scFv anti-PD-1 sequences of the invention in the creation of bispecific antibodies. Anti-LAG-3 sequences suitable for use as ABDs include SEQ ID NOs: 17135-20764 (LAG-3 Fabs, although the Fv sequences therein can be formatted as scFvs), SEQ ID NOs: 36819-36962 (additional LAG-3 Fabs although the Fv sequences therein can be formatted as scFvs), SEQ ID NOs: 35417-35606 (additional LAG-3 Fabs although the Fv sequences therein can be formatted as scFvs), SEQ ID NOs: 25194-32793 (additional LAG-3 Fabs although the Fv sequences therein can be formatted as scFvs) and SEQ ID NOs: 32794-33002 (one armed LAG-3 constructs which can be formatted as either Fabs or scFvs). As will be understood from those in the art, these sequence identifiers come in "pairs" for the variable heavy and light chains, as will be apparent from the sequence identifiers.

In some embodiments, an anti-LAG-3 Fab is selected from the pairs of SEQ ID NOs:36819 and 36823, 36827 and 36831, 36835 and 36839, 36843 and 36847, 36851 and 36855, 36859 and 36863, 36867 and 36871, 36875 and 36879, 36883 and 36887, 36891 and 36895, 36899 and 36903, 36907 and 36911, 36915 and 36919, 36923 and 36927, 36931 and 36935, 36939 and 36943, 36947 and 36951 and 36955 and 36959.

Of particular interest in the present invention are the sequences of the LAG-3 Fab ABD of XENP22594, including the VH (SEQ ID NO:32755, with VHCDRs (SEQ ID NOs:32756, 32757 and 32758) and VL (SEQ ID NO:32760 with VLCDRs (SEQ ID NOs:32761, 32762 and 32763).

Of particular interest in the present invention are the sequences of the LAG-3 Fab ABD of XENP22656, including the VH (SEQ ID NO:28815, with VHCDRs (SEQ ID NOs:28816, 28817, and 28118) and VL (SEQ ID NO:28820, with VLCDRs (SEQ ID NOs:28821, 28822 and 28823).

D. TIM-3 Antigen Binding Domains

As will be appreciated by those in the art, any number of anti-TIM-3 ABD sequences can be used in combination with the scFv anti-PD-1 sequences of the invention in the creation of bispecific antibodies. Anti-TIM-3 sequences suitable for use as ABDs include SEQ ID NOs: 20765-20884 (TIM-3

Fabs, although the Fv sequences therein can be formatted as scFvs), SEQ ID NOs: 37587-37698 (additional TIM-3 Fabs, the Fv sequences therein can be formatted as scFvs) and SEQ ID NOs: 36347-36706 (bivalent TIM-3 constructs which can be formatted as either Fabs or scFvs). As will be understood from those in the art, these sequence identifiers come in "pairs" for the variable heavy and light chains, as will be apparent from the sequence identifiers.

In some embodiments, the anti-TIM-3 ABD is selected from the pairs of SEQ ID NOs:35757 and 37591, 37959 and 37599, 37603 and 37607, 37611 and 37615, 37619 and 37623, 37627 and 37631, 37635 and 37639, 37643 and 37647, 37651 and 37655, 37659 and 37663, 37667 and 37671, 37675 and 37679, 37683 and 37687 and 37691 and 37695.

Of particular interest in the present invention are the Fab sequences of the anti-TIM-3 ABD of XENP21189, including the VH (SEQ ID NO:36508, with VHCDRs (SEQ ID NOs:36509, 36510 and 36511) and VL (SEQ ID NO:36513, with VLCDRs (SEQ ID NOs:36514, 36515 and 36516).

E. BTLA Antigen Binding Domains

As will be appreciated by those in the art, any number of anti-BTLA ABD sequences can be used in combination with the scFv anti-PD-1 sequences of the invention in the creation of bispecific antibodies. Anti-BTLA sequences suitable for use as ABDs include SEQ ID NOs: 20885-21503 (BTLA Fabs although the Fv sequences therein can be formatted as scFvs) and SEQ ID NOs: 36707-36738 (additional BTLA Fabs although the Fv sequences therein can be formatted as scFvs). As will be understood from those in the art, these sequence identifiers come in "pairs" for the variable heavy and light chains, as will be apparent from the sequence identifiers.

In some embodiments, the anti-BTLA ABD of use in the invention are selected from the pairs of SEQ ID NOs:36707 and 36711, 36715 and 36719, 36723 and 36727 and 36761 and 36735.

Of particular interest in the present invention are the Fab sequences of the anti-BTLA ABD of XENP20269, including the VH (SEQ ID NO:20936, with VHCDRs (SEQ ID NOs:20937, 20938 and 20939) and VL (SEQ ID NO:20941, with VLCDRs (SEQ ID NOs:20942, 20943 and 20944).

F ICOS Antigen Binding Domains

As will be appreciated by those in the art, any number of anti-ICOS ABD sequences can be used in combination with the scFv anti-PD-1 sequences of the invention in the creation of bispecific antibodies. Anti-ICOS sequences suitable for use as ABDs include many as disclosed in US2018/0127501, expressly incorporated by reference in its entirety and specifically for the legends and FIGS. 19, 20 and 24, the sequences depicted therein, as well as SEQ ID NOs:27869-28086 from US2018/0127501 which contain a number of ICOS Fab sequences (heavy chain VH1-CH1 and light chain VL1-CL) as indicated in the naming nomenclature. As will be understood from those in the art, these sequence identifiers come in "pairs" for the variable heavy and light chains, as will be apparent from the sequence identifiers.

In some embodiments, the anti-ICOS ABD of use in the invention are selected from the pairs of SEQ ID NOs:26323 and 26328, 27477 and 27452 and 26353 and 26358 from the sequence listing from US2018/0127501.

Of particular interest in the present invention are the Fab sequences of the anti-ICOS ABD from XENCS500 in FIGS. 49A-49KK, with $V_H$_ICOS_H0_L0 and VL_ICOS_H0_L0.

Of particular interest in the present invention are the Fab sequences of the anti-ICOS ABD from XENCS501 in FIGS. 49A-49KK, with VH_ICOS_H0.66_L0 and VL_ICOS_H0.66_L0.

G. TIGIT Antigen Binding Domains

Anti-TIGIT sequences suitable for use as ABDs include SEQ ID NOs: 21504-21523 and SEQ ID NOs: 37435-37586 (as will be understood from those in the art, these sequence identifiers come in "pairs" for the variable heavy and light chains, as will be apparent from the sequence identifiers), as well as TIGIT ABDs selected from the pairs of SEQ ID NOs:37435 and 37439, 37443 and 37447, 37451 and 37455, 37459 and 37463, 37467 and 37471, 37475 and 37479, 37483 and 37487, 37491 and 37495, 37499 and 37503, 37507 and 37511, 37515 and 37519, 37523 and 37527, 37531 and 37535, 37539 and 37543, 37547 and 37551, 37555 and 37559, 37563 and 37567, 37571 and 37575 and 37579 and 37583.

IX. MONOVALENT ANTI-PD-1 ANTIBODIES

In addition, as will be appreciated by those in the art, the novel Fv sequences outlined herein can also be used in both monospecific antibodies (e.g. "traditional monoclonal antibodies") or non-heterodimeric bispecific formats. Accordingly, the present invention provides monoclonal (monospecific) antibodies comprising the 6 CDRs and/or the vh and vl sequences from the figures, generally with IgG1, IgG2, IgG3 or IgG4 constant regions, with IgG1, IgG2 and IgG4 (including IgG4 constant regions comprising a S228P amino acid substitution) finding particular use in some embodiments. That is, any sequence herein with a "H_L" designation can be linked to the constant region of a human IgG1 antibody.

A. Anti-PD-1 Monoclonal Antibodies

As will be appreciated by those in the art, the novel Fv sequences outlined herein can also be used in both mono-specific antibodies (e.g. "traditional monoclonal antibodies") or non-heterodimeric bispecific formats. Accordingly, the present invention provides monoclonal (monospecific) antibodies comprising the 6 CDRs and/or the vh and vl sequences from the figures, generally with IgG1, IgG2, IgG3 or IgG4 constant regions, with IgG1, IgG2 and IgG4 (including IgG4 constant regions comprising a S228P amino acid substitution) finding particular use in some embodiments. That is, any sequence herein with a "H_L" designation can be linked to the constant region of a human IgG1 antibody.

In some embodiments, the monoclonal antibody is selected from those depicted in FIGS. 13, 16,18, 20, 21, 24, 33 and 40.

In some embodiments, antibodies comprising a VH and VL domain from XENP26940 1C11[PD-1]_H3.303_L3.152 of FIGS. 24A-24J. Thus, the six CDRs and/or the VH and VL domains from XENP026940 can be used in the creation of monoclonal antibodies. In some embodiments, the VH and VL from XENP026940 can be used with a IgG1 constant domain. In some embodiments, the VH and VL from XENP026940 can be used with a IgG1 constant domain, that may contain additional Fc variants, in particular the 428L/434S FcRn variants. In some embodiments, the VH and VL from XENP026940 can be used with a IgG4 constant domain, particularly with a S228P amino acid substitution. In some embodiments, the antibody is XENP26940.

In some embodiments, antibodies comprising a VH and VL domain from XENP28652 1C11[PD-1]_H3.328_L3.153 of FIG. 40. Thus, the six CDRs and/or the VH and VL domains from XENP28652 can be used in the creation of monoclonal antibodies. In some embodiments, the VH and VL from XENP28652 can be used with a IgG1 constant domain. In some embodiments, the VH and VL from XENP28652 can be used with a IgG1 constant domain, that may contain additional Fc variants, in particular the 428L/434S FcRn variants. In some embodiments, the VH and VL from XENP28652 can be used with a IgG4 constant domain, particularly with a S228P amino acid substitution. In some embodiments, the antibody is XENP28652.

X. USEFUL FORMATS OF THE INVENTION

As will be appreciated by those in the art and discussed more fully below, the bispecific heterodimeric antibodies of the present invention can take on a wide variety of configurations, as are generally depicted in FIG. 1. Some figures depict "single ended" configurations, where there is one type of specificity on one "arm" of the molecule and a different specificity on the other "arm". Other figures depict "dual ended" configurations, where there is at least one type of specificity at the "top" of the molecule and one or more different specificities at the "bottom" of the molecule. Thus, the present invention is directed to novel immunoglobulin compositions that co-engage a different first and a second antigen.

As will be appreciated by those in the art, the heterodimeric formats of the invention can have different valencies as well as be bispecific. That is, heterodimeric antibodies of the invention can be bivalent and bispecific, wherein one checkpoint target is bound by one ABD and the other checkpoint target is bound by a second ABD. The heterodimeric antibodies can also be trivalent and bispecific, wherein the first antigen is bound by two ABDs and the second antigen by a second ABD.

A. Bottle Opener Format

One heterodimeric scaffold that finds particular use in the present invention is the "triple F" or "bottle opener" scaffold format as shown in FIG. 1. In this embodiment, one heavy chain of the antibody contains a single chain Fv ("scFv", as defined herein) and the other heavy chain is a "regular" Fab format, comprising a variable heavy chain and a light chain. This structure is sometimes referred to herein as "triple F" format (scFv-Fab-Fc) or the "bottle-opener" (BO) format, due to a rough visual similarity to a bottle-opener (see FIG. 1A). The two chains are brought together by the use of amino acid variants in the constant regions (e.g. the Fc domain, the CH1 domain and/or the hinge region) that promote the formation of heterodimeric antibodies as is described more fully below.

There are several distinct advantages to the present "triple F" format. As is known in the art, antibody analogs relying on two scFv constructs often have stability and aggregation problems, which can be alleviated in the present invention by the addition of a "regular" heavy and light chain pairing. In addition, as opposed to formats that rely on two heavy chains and two light chains, there is no issue with the incorrect pairing of heavy and light chains (e.g. heavy 1 pairing with light 2, etc.).

Many of the embodiments outlined herein rely in general on the bottle opener format that comprises a first monomer comprising an scFv (sometimes referred to herein as the "scFv monomer" or "scFv chain" of the BO format), comprising a variable heavy and a variable light domain, covalently attached using an scFv linker (charged, in many but not all instances), where the scFv is covalently attached to the N-terminus of a first Fc domain usually through a domain linker (which, as outlined herein can either be un-charged or charged and can be exogeneous or endogeneous (e.g. all or part of the native hinge domain). Thus the scFv monomer can have, from N-terminal to C-terminal, a structure selected from VH1-scFv linker-VL1-optional linker-CH2-CH3, VL1-scFv linker-VH1-optional linker-CH2-CH3, VH1-scFv linker-VL1-hinge-CH2-CH3 and VL1-scFv linker-VH1-hinge-CH2-CH3. The second monomer of the bottle opener format is a heavy chain (VH2-CH1-hinge-CH2-CH3), and the composition further comprises a light chain (VL2-CL).

In addition, the Fc domains of the bottle opener format generally comprise skew variants (e.g. a set of amino acid substitutions as shown in FIG. 3A-3F and FIG. 8, with particularly useful skew variants being selected from the group consisting of S364K/E357Q: L368D/K370S; L368D/K370S: S364K; L368E/K370S: S364K; T411T/E360E/Q362E: D401K; L368D/K370S: S364K/E357L, K370S: S364K/E357Q, T366S/L368A/Y407V: T366W and T366S/L368A/Y407V/Y349C: T366W/S354C), optionally ablation variants (including those shown in FIG. 5), optionally charged scFv linkers (including those shown in FIGS. 7A-7B) and the heavy chain comprises pI variants (including those shown in FIG. 4).

In some embodiments, the bottle opener format includes skew variants, pI variants, and ablation variants. Accordingly, some embodiments include bottle opener formats that comprise: a) a first monomer (the "scFv monomer") that comprises a charged scFv linker (with the +H sequence of FIGS. 7A-7B being preferred in some embodiments), the skew variants S364K/E357Q, the ablation variants E233P/L234V/L235A/G236del/S267K, and an Fv that binds to PD-1 as outlined herein; b) a second monomer (the "Fab monomer") that comprises the skew variants L368D/K370S, the pI variants N208D/Q295E/N384D/Q418E/N421D, the ablation variants E233P/L234V/L235A/G236del/S267K, and a variable heavy domain that, with the variable light domain, makes up an Fv that binds to a second antigen as outlined herein; and c) a light chain.

A number of suitable combinations are outlined in WO2017/218707 for this format. Generally, the present invention is directed to the use of new anti-PD-1 ABDs based on a newly identified done, 1C11. In this case, the heterodimeric antibodies bind to PD-1 and a second target antigen selected from the group consisting of CTLA-4, LAG-3, TIM-3, BTLA, TIGIT (all of which are classified as checkpoint receptors) and ICOS (which is an activator).

In some embodiments, the anti-PD-1 ABD is the scFv side of the bottle opener format. Thus, suitable ABD pairs include (scFv first, Fab second), PD-1 X CTLA-4, PD-1 X LAG-3, PD-1 X TIM-3, PD-1 X BTLA, PD-1 X TIGIT and PD-1 X ICOS. Suitable CDR sets as well as ABDs are described below, with particularly useful combinations similarly described below.

In some embodiments, the bottle opener format includes skew variants, pI variants, ablation variants and FcRn variants. Accordingly, some embodiments include bottle opener formats that comprise: a) a first monomer (the "scFv monomer") that comprises a charged scFv linker (with the +H sequence of FIGS. 7A-7B being preferred in some embodiments), the skew variants S364K/E357Q, the ablation variants E233P/L234V/L235A/G236del/S267K, the FcRn variants M428L/N434S and an Fv that binds to PD-1 as outlined herein; b) a second monomer (the "Fab monomer") that comprises the skew variants L368D/K370S, the pI variants N208D/Q295E/N384D/Q418E/N421D, the ablation variants E233P/L234V/L235A/G236del/S267K, the FcRn variants M428L/N434S and a variable heavy domain that, with the variable light domain, makes up an Fv that binds to anantigen as outlined herein; and c) a light chain.

Specifically, FIGS. 50A-50E shows some bottle opener "skeleton" sequences that have a PD-1 scFv monomer but are missing the Fab sequences that can be used on the other side. That is, Fv sequences for the Fab portion of any ABD for CTLA-4, TIM-3, LAG-3, BTLA-, TIGIT and ICOS as discussed herein.

Specific bottle opener embodiments are outlined below.

B. mAb-Fv

One heterodimeric scaffold that finds particular use in the present invention is the mAb-Fv format shown in FIG. 1. In this embodiment, the format relies on the use of a C-terminal attachment of an "extra" variable heavy domain to one monomer and the C-terminal attachment of an "extra" variable light domain to the other monomer, thus forming a third antigen binding domain, wherein the Fab portions of the two monomers bind a target antigen as outlined herein and the "extra" scFv domain binds PD-1.

In this embodiment, the first monomer comprises a first heavy chain, comprising a first variable heavy domain and a first constant heavy domain comprising a first Fc domain, with a first variable light domain covalently attached to the C-terminus of the first Fc domain using a domain linker (vh1-CH1-hinge-CH2-CH3-[optional linker]-v12). The second monomer comprises a second variable heavy domain of the second constant heavy domain comprising a second Fc domain, and a third variable heavy domain covalently attached to the C-terminus of the second Fc domain using a domain linker (vj1-CH1-hinge-CH2-CH3-[optional linker]-vh2. The two C-terminally attached variable domains make up a Fv that binds PD-1. This embodiment further utilizes a common light chain comprising a variable light domain and a constant light domain that associates with the heavy chains to form two identical Fabs that bind a target antigen. As for many of the embodiments herein, these constructs include skew variants, pI variants, ablation variants, additional Fc variants, etc. as desired and described herein.

In addition, the Fc domains of the mAb-Fv format comprise skew variants (e.g. a set of amino acid substitutions as shown in FIGS. 3 and 8, with particularly useful skew variants being selected from the group consisting of S364K/E357Q: L368D/K370S; L368D/K370S: S364K; L368E/K370S: S364K; T411T/E360E/Q362E: D401K; L368D/K370S: S364K/E357L, K370S: S364K/E357Q, T366S/L368A/Y407V: T366W and T366S/L368A/Y407V/Y349C: T366W/S354C), optionally ablation variants (including those shown in FIG. 5), optionally charged scFv linkers (including those shown in FIG. 7) and the heavy chain comprises pI variants (including those shown in FIG. 4).

In some embodiments, the mAb-Fv format includes skew variants, pI variants, and ablation variants. Accordingly, some embodiments include mAb-Fv formats that comprise: a) a first monomer that comprises the skew variants S364K/E357Q, the ablation variants E233P/L234V/L235A/G236del/S267K, and a first variable heavy domain that, with the first variable light domain of the light chain, makes up an Fv, and a second variable heavy domain; b) a second monomer that comprises the skew variants L368D/K370S, the pI variants N208D/Q295E/N384D/Q418E/N421D, the ablation variants E233P/L234V/L235A/G236del/S267K, and a first variable heavy domain that, with the first variable light domain, makes up the Fv, and a second variable light chain, that together with the second variable heavy domain forms an Fv (ABD) that binds to PD-1; and c) a light chain comprising a first variable light domain and a constant light domain.

In some embodiments, the mAb-Fv format includes skew variants, pI variants, ablation variants and FcRn variants. Accordingly, some embodiments include mAb-Fv formats that comprise: a) a first monomer that comprises the skew variants S364K/E357Q, the ablation variants E233P/L234V/L235A/G236del/S267K, the FcRn variants M428L/N434S and a first variable heavy domain that, with the first variable light domain of the light chain, makes up an Fv that binds to an antigen, and a second variable heavy domain; b) a second monomer that comprises the skew variants L368D/K370S, the pI variants N208D/Q295E/N384D/Q418E/N421D, the ablation variants E233P/L234V/L235A/G236del/S267K, the FcRn variants M428L/N434S and a first variable heavy domain that, with the first variable light domain, makes up the Fv that binds to the antigen as outlined herein, and a second variable light chain, that together with the second variable heavy domain of the first monomer forms an Fv (ABD) that binds PD-1; and c) a light chain comprising a first variable light domain and a constant light domain.

C. mAb-scFv

One heterodimeric scaffold that finds particular use in the present invention is the mAb-scFv format shown in FIG. 1. In this embodiment, the format relies on the use of a C-terminal attachment of a scFv to one of the monomers, thus forming a third antigen binding domain, wherein the Fab portions of the two monomers bind one of the antigens outlined herein and the "extra" scFv domain binds PD-1. Thus, the first monomer comprises a first heavy chain (comprising a variable heavy domain and a constant domain), with a C-terminally covalently attached scFv comprising a scFv variable light domain, an scFv linker and a scFv variable heavy domain in either orientation (vh1-CH1-hinge-CH2-CH3-[optional linker]-vh2-scFv linker-v12 or vh1-CH1-hinge-CH2-CH3-[optional linker]-v12-scFv linker-vh2). This embodiment further utilizes a common light chain comprising a variable light domain and a constant light domain, that associates with the heavy chains to form two identical Fabs that bind the antigen. As for many of the embodiments herein, these constructs include skew variants, pI variants, ablation variants, additional Fc variants, etc. as desired and described herein.

In addition, the Fc domains of the mAb-scFv format comprise skew variants (e.g. a set of amino acid substitutions as shown in FIGS. 3 and 8, with particularly useful skew variants being selected from the group consisting of S364K/E357Q: L368D/K370S; L368D/K370S: S364K; L368E/K370S: S364K; T411T/E360E/Q362E: D401K; L368D/K370S: S364K/E357L, K370S: S364K/E357Q, T366S/L368A/Y407V: T366W and T366S/L368A/Y407V/Y349C: T366W/S354C), optionally ablation variants (including those shown in FIG. 5), optionally charged scFv linkers (including those shown in FIG. 7) and the heavy chain comprises pI variants (including those shown in FIG. 4).

In some embodiments, the mAb-scFv format includes skew variants, pI variants, and ablation variants. Accordingly, some embodiments include mAb-scFv formats that comprise: a) a first monomer that comprises the skew variants S364K/E357Q, the ablation variants E233P/L234V/L235A/G236del/S267K, and a variable heavy domain that, with the variable light domain of the common light chain, makes up an Fv that binds to a target antigen as outlined herein, and a scFv domain that binds to PD-1; b) a second monomer that comprises the skew variants L368D/K370S, the pI variants N208D/Q295E/N384D/Q418E/N421D, the ablation variants E233P/L234V/L235A/G236del/S267K, and a variable heavy domain that, with the variable light domain of the common light chain, makes up an Fv that binds to the target antigen as outlined herein; and c) a common light chain comprising a variable light domain and a constant light domain.

In some embodiments, the mAb-scFv format includes skew variants, pI variants, ablation variants and FcRn variants. Accordingly, some embodiments include mAb-scFv formats that comprise: a) a first monomer that comprises the skew variants S364K/E357Q the ablation variants E233P/L234V/L235A/G236del/S267K, the FcRn variants M428L/N434S and a variable heavy domain that, with the variable light domain of the common light chain, makes up an Fv that binds to an antigen as outlined herein, and a scFv domain that binds to PD-1; b) a second monomer that comprises the skew variants L368D/K370S, the pI variants N208D/Q295E/N384D/Q418E/N421D, the ablation variants E233P/L234V/L235A/G236del/S267K, the FcRn variants M428L/N434S and a variable heavy domain that, with the variable light domain of the common light chain, makes up an Fv that binds to an antigen as outlined herein; and c) a common light chain comprising a variable light domain and a constant light domain.

D. Central-scFv

One heterodimeric scaffold that finds particular use in the present invention is the Central-scFv format shown in FIG. 1 (also sometimes referred to as the "2+1" format). In this embodiment, the format relies on the use of an inserted scFv domain thus forming a third antigen binding domain, wherein the Fab portions of the two monomers bind a target antigen and the "extra" scFv domain binds PD-1. The scFv domain is inserted between the Fc domain and the CH1-Fv region of one of the monomers, thus providing a third antigen binding domain. This can actually be thought of as an addition to the bottle opener format, wherein there is an additional VH-CH1 domain added to the N-terminus of the scFv, which utilizes a common light chain.

In this embodiment, one monomer comprises a first heavy chain comprising a first variable heavy domain, a CH1 domain (and optional hinge) and Fc domain, with a scFv comprising a scFv variable light domain, an scFv linker and a scFv variable heavy domain. The scFv is covalently attached between the C-terminus of the CH1 domain of the heavy constant domain and the N-terminus of the first Fc domain using optional domain linkers (vh1-CH1-[optional linker]-vh2-scFv linker-v12-[optional linker including the hinge]-CH2-CH3, or the opposite orientation for the scFv, vh1-CH1-[optional linker]-v12-scFv linker-vh2-[optional linker including the hinge]-CH2-CH3). The other monomer is a standard Fab side. This embodiment further utilizes a common light chain comprising a variable light domain and a constant light domain, that associates with the heavy chains to form two identical Fabs that bind a target antigen. As for many of the embodiments herein, these constructs include skew variants, pI variants, ablation variants, additional Fc variants, etc. as desired and described herein.

In addition, the Fc domains of the central scFv format comprise skew variants (e.g. a set of amino acid substitutions as shown in FIGS. 3 and 8, with particularly useful skew variants being selected from the group consisting of S364K/E357Q: L368D/K370S; L368D/K370S: S364K; L368E/K370S: S364K; T411T/E360E/Q362E: D401K; L368D/K370S: S364K/E357L, K370S: S364K/E357Q, T366S/L368A/Y407V: T366W and T366S/L368A/Y407V/Y349C: T366W/S354C), optionally ablation variants (including those shown in FIG. 5), optionally charged scFv linkers (including those shown in FIG. 7) and the heavy chain comprises pI variants (including those shown in FIG. 4).

In some embodiments, the central-scFv format includes skew variants, pI variants, and ablation variants. Accordingly, some embodiments include central scFv formats that comprise: a) a first monomer that comprises the skew variants S364K/E357Q, the ablation variants E233P/L234V/L235A/G236del/S267K, and a variable heavy domain that, with the variable light domain of the light chain, makes up an Fv that binds to a target antigen as outlined herein, and an scFv domain that binds to PD-1; b) a second monomer that comprises the skew variants L368D/K370S, the pI variants N208D/Q295E/N384D/Q418E/N421D, the ablation variants E233P/L234V/L235A/G236del/S267K, and a variable heavy domain that, with variable light domain of the light chain, makes up an Fv that binds to a target antigen as outlined herein; and c) a light chain comprising a variable light domain and a constant light domain.

In some embodiments, the central-scFv format includes skew variants, pI variants, ablation variants and FcRn variants. Accordingly, some embodiments include central scFv formats that comprise: a) a first monomer that comprises the skew variants S364K/E357Q, the ablation variants E233P/L234V/L235A/G236del/S267K, the FcRn variants M428L/N434S and a variable heavy domain that, with the variable light domain of the light chain, makes up an Fv that binds to a target antigen as outlined herein, and an scFv domain that binds to PD-1; b) a second monomer that comprises the skew variants L368D/K370S, the pI variants N208D/Q295E/N384D/Q418E/N421D, the ablation variants E233P/L234V/L235A/G236del/S267K, the FcRn variants M428L/N434S and a variable heavy domain that, with variable light domain of the light chain, makes up an Fv that binds to SSTR2 as outlined herein; and c) a light chain comprising a variable light domain and a constant light domain.

E. Central-Fv

One heterodimeric scaffold that finds particular use in the present invention is the Central-Fv format shown in FIG. 1G. In this embodiment, the format relies on the use of an inserted Fv domain (i.e., the central Fv domian) thus forming a third antigen binding domain, wherein the Fab portions of the two monomers bind a target antigen and the "central Fv" domain binds PD-1. The scFv domain is inserted between the Fc domain and the CH1-Fv region of the monomers, thus providing a third antigen binding domain, wherein each monomer contains a component of the scFv (e.g. one monomer comprises a variable heavy domain and the other a variable light domain).

In this embodiment, one monomer comprises a first heavy chain comprising a first variable heavy domain, a CH1 domain, and Fc domain and an additional variable light domain. The light domain is covalently attached between the C-terminus of the CH1 domain of the heavy constant domain and the N-terminus of the first Fc domain using domain linkers (vh1-CH1-[optional linker]-v12-hinge-CH2-CH3). The other monomer comprises a first heavy chain comprising a first variable heavy domain, a CH1 domain and Fc domain and an additional variable heavy domain (vh1-CH1-[optional linker]-vh2-hinge-CH2-CH3). The light domain is covalently attached between the C-terminus of the CH1 domain of the heavy constant domain and the N-terminus of the first Fc domain using domain linkers.

This embodiment further utilizes a common light chain comprising a variable light domain and a constant light domain, that associates with the heavy chains to form two identical Fabs that bind a target antigen. As for many of the embodiments herein, these constructs include skew variants, pI variants, ablation variants, additional Fc variants, etc. as desired and described herein.

F. One Armed Central-scFv

One heterodimeric scaffold that finds particular use in the present invention is the one armed central-scFv format shown in FIG. 1. In this embodiment, one monomer comprises just an Fc domain, while the other monomer uses an inserted scFv domain thus forming the second antigen binding domain. In this format, either the Fab portion binds a target antigen and the scFv binds PD-1 or vice versa. The scFv domain is inserted between the Fc domain and the CH1-Fv region of one of the monomers.

In this embodiment, one monomer comprises a first heavy chain comprising a first variable heavy domain, a CH1 domain and Fc domain, with a scFv comprising a scFv variable light domain, an scFv linker and a scFv variable heavy domain. The scFv is covalently attached between the C-terminus of the CH1 domain of the heavy constant domain and the N-terminus of the first Fc domain using domain linkers. The second monomer comprises an Fc domain. This embodiment further utilizes a light chain comprising a variable light domain and a constant light domain, that associates with the heavy chain to form a Fab. As for many of the embodiments herein, these constructs include skew variants, pI variants, ablation variants, additional Fc variants, etc. as desired and described herein.

In addition, the Fc domains of the one armed central-scFv format generally include skew variants (e.g. a set of amino acid substitutions as shown in FIGS. 3 and 8, with particularly useful skew variants being selected from the group consisting of S364K/E357Q: L368D/K370S; L368D/K370S: S364K; L368E/K370S: S364K; T411T/E360E/Q362E: D401K; L368D/K370S: S364K/E357L, K370S: S364K/E357Q, T366S/L368A/Y407V: T366W and T366S/L368A/Y407V/Y349C: T366W/S354C), optionally ablation variants (including those shown in FIG. 5), optionally charged scFv linkers (including those shown in FIG. 7) and the heavy chain comprises pI variants (including those shown in FIG. 4).

In some embodiments, the one armed central-scFv format includes skew variants, pI variants, and ablation variants. Accordingly, some embodiments of the one armed central-scFv formats comprise: a) a first monomer that comprises the skew variants S364K/E357Q the ablation variants E233P/L234V/L235A/G236del/S267K, and a variable heavy domain that, with the variable light domain of the light chain, makes up an Fv that binds to a target antigen as outlined herein, and a scFv domain that binds to PD-1; b) a second monomer that includes an Fc domain having the skew variants L368D/K370S, the pI variants N208D/Q295E/N384D/Q418E/N421D, the ablation variants E233P/L234V/L235A/G236del/S267K; and c) a light chain comprising a variable light domain and a constant light domain.

In some embodiments, the one armed central-scFv format includes skew variants, pI variants, ablation variants and FcRn variants. Accordingly, some embodiments of the one armed central-scFv formats comprise: a) a first monomer that comprises the skew variants S364K/E357Q, the ablation variants E233P/L234V/L235A/G236del/S267K, the FcRn variants M428L/N434S and a variable heavy domain that, with the variable light domain of the light chain, makes up an Fv that binds to a target antigen as outlined herein, and a scFv domain that binds to PD-1; b) a second monomer that includes an Fc domain having the skew variants L368D/K370S, the pI variants N208D/Q295E/N384D/Q418E/N421D, the ablation variants E233P/L234V/L235A/G236del/S267K, and the FcRn variants M428L/N434S; and c) a light chain comprising a variable light domain and a constant light domain.

G. One Armed scFv-mAb

One heterodimeric scaffold that finds particular use in the present invention is the one armed scFv-mAb format shown in FIG. 1. In this embodiment, one monomer comprises just an Fc domain, while the other monomer uses a scFv domain attached at the N-terminus of the heavy chain, generally through the use of a linker: vh-scFv linker-vl-[optional domain linker]-CH1-hinge-CH2-CH3 or (in the opposite orientation) vl-scFv linker-vh-[optional domain linker]-CH1-hinge-CH2-CH3. In this format, the Fab portions each bind a target antigen and the scFv binds PD-1. This embodiment further utilizes a light chain comprising a variable light domain and a constant light domain, that associates with the heavy chain to form a Fab. As for many of the embodiments herein, these constructs include skew variants, pI variants, ablation variants, additional Fc variants, etc. as desired and described herein.

In addition, the Fc domains of the one armed scFv-mAb format generally include skew variants (e.g. a set of amino acid substitutions as shown in FIGS. 3 and 8, with particularly useful skew variants being selected from the group consisting of S364K/E357Q: L368D/K370S; L368D/K370S: S364K; L368E/K370S: S364K; T411T/E360E/Q362E: D401K; L368D/K370S: S364K/E357L, K370S: S364K/E357Q, T366S/L368A/Y407V: T366W and T366S/L368A/Y407V/Y349C: T366W/S354C), optionally ablation variants (including those shown in FIG. 5), optionally charged scFv linkers (including those shown in FIG. 7) and the heavy chain comprises pI variants (including those shown in FIG. 4).

In some embodiments, the one armed scFv-mAb format includes skew variants, pI variants, and ablation variants. Accordingly, some embodiments of the one armed scFv-mAb formats comprise: a) a first monomer that comprises the skew variants S364K/E357Q, the ablation variants E233P/L234V/L235A/G236del/S267K, and a variable heavy domain that, with the variable light domain of the light chain, makes up an Fv that binds to a target antigen as outlined herein, and a scFv domain that binds to PD-1; b) a second monomer that includes an Fc domain having the skew variants L368D/K370S, the pI variants N208D/Q295E/N384D/Q418E/N421D, the ablation variants E233P/L234V/L235A/G236del/S267K; and c) a light chain comprising a variable light domain and a constant light domain.

In some embodiments, the one armed scFv-mAb format includes skew variants, pI variants, ablation variants and FcRn variants. Accordingly, some embodiments one armed scFv-mAb formats comprise: a) a first monomer that comprises the skew variants S364K/E357Q, the ablation variants E233P/L234V/L235A/G236del/S267K, the FcRn variants M428L/N434S and a variable heavy domain that, with the variable light domain of the light chain, makes up an Fv that binds to a target antigen as outlined herein, and a scFv domain that binds to PD-1; b) a second monomer that includes an Fc domain having the skew variants L368D/K370S, the pI variants N208D/Q295E/N384D/Q418E/N421D, the ablation variants E233P/L234V/L235A/G236del/S267K, and the FcRn variants M428L/N434S; and c) a light chain comprising a variable light domain and a constant light domain.

H. scFv-mAb

One heterodimeric scaffold that finds particular use in the present invention is the mAb-scFv format shown in FIG. 1E. In this embodiment, the format relies on the use of a N-terminal attachment of a scFv to one of the monomers, thus forming a third antigen binding domain, wherein the Fab portions of the two monomers bind a target antigen and the "extra" scFv domain binds PD-1.

In this embodiment, the first monomer comprises a first heavy chain (comprising a variable heavy domain and a constant domain), with a N-terminally covalently attached scFv comprising a scFv variable light domain, an scFv linker and a scFv variable heavy domain in either orientation ((vh1-scFv linker-vl1-[optional domain linker]-vh2-CH1-hinge-CH2-CH3) or (with the scFv in the opposite orientation) ((vl1-scFv linker-vh1-[optional domain linker]-vh2-CH1-hinge-CH2-CH3)). This embodiment further utilizes a common light chain comprising a variable light domain and a constant light domain that associates with the heavy chains to form two identical Fabs that bind the target. As for many of the embodiments herein, these constructs include skew variants, pI variants, ablation variants, additional Fc variants, etc. as desired and described herein.

In addition, the Fc domains of the scFv-mAb format generally include skew variants (e.g. a set of amino acid substitutions as shown in FIGS. 3 and 8, with particularly useful skew variants being selected from the group consisting of S364K/E357Q: L368D/K370S; L368D/K370S: S364K; L368E/K370S: S364K; T411T/E360E/Q362E: D401K; L368D/K370S: S364K/E357L, K370S: S364K/E357Q, T366S/L368A/Y407V: T366W and T366S/L368A/Y407V/Y349C: T366W/S354C), optionally ablation variants (including those shown in FIG. 5), optionally charged scFv linkers (including those shown in FIG. 7) and the heavy chain comprises pI variants (including those shown in FIG. 4).

In some embodiments, the scFv-mAb format includes skew variants, pI variants, and ablation variants. Accordingly, some embodiments include scFv-mAb formats that comprise: a) a first monomer that comprises the skew variants S364K/E357Q, the ablation variants E233P/L234V/L235A/G236del/S267K, and a variable heavy domain that, with the variable light domain of the common light chain, makes up an Fv that binds to the target as outlined herein, and a scFv domain that binds to PD-1; b) a second monomer that comprises the skew variants L368D/K370S, the pI variants N208D/Q295E/N384D/Q418E/N421D, the ablation variants E233P/L234V/L235A/G236del/S267K, and a variable heavy domain that, with the variable light domain of the common light chain, makes up an Fv that binds to the target antigen as outlined herein; and c) a common light chain comprising a variable light domain and a constant light domain.

In some embodiments, the scFv-mAb format includes skew variants, pI variants, ablation variants and FcRn variants. Accordingly, some embodiments include scFv-mAb formats that comprise: a) a first monomer that comprises the skew variants S364K/E357Q, the ablation variants E233P/L234V/L235A/G236del/S267K, the FcRn variants M428L/N434S and a variable heavy domain that, with the variable light domain of the common light chain, makes up an Fv that binds to the target antigen as outlined herein, and a scFv domain that binds to PD-1; b) a second monomer that comprises the skew variants L368D/K370S, the pI variants N208D/Q295E/N384D/Q418E/N421D, the ablation variants E233P/L234V/L235A/G236del/S267K, the FcRn variants M428L/N434S and a variable heavy domain that, with the variable light domain of the common light chain, makes up an Fv that binds to the target as outlined herein; and c) a common light chain comprising a variable light domain and a constant light domain.

I. Dual scFv Formats

The present invention also provides dual scFv formats as are known in the art and shown in FIG. 1B. In this embodiment, the SSTR2 x CD3 heterodimeric bispecific antibody is made up of two scFv-Fc monomers (both in either (vh-scFv linker-vl-[optional domain linker]-CH2-CH3) format or (vl-scFv linker-vh-[optional domain linker]-CH2-CH3) format, or with one monomer in one orientation and the other in the other orientation.

In some embodiments, the dual scFv format includes skew variants, pI variants, and ablation variants. Accordingly, some embodiments include dual scFv formats that comprise: a) a first monomer that comprises the skew variants S364K/E357Q, the ablation variants E233P/L234V/L235A/G236del/S267K, and a first scFv that binds either PD-1 or the target antigen; and b) a second monomer that comprises the skew variants L368D/K370S, the pI variants N208D/Q295E/N384D/Q418E/N421D, the ablation variants E233P/L234V/L235A/G236del/S267K, and a second scFv that binds either PD-1 or the other target antigen.

In some embodiments, the dual scFv format includes skew variants, pI variants, ablation variants and FcRn variants. In some embodiments, the dual scFv format includes skew variants, pI variants, and ablation variants. Accordingly, some embodiments include dual scFv formats that comprise: a) a first monomer that comprises the skew variants S364K/E357Q, the ablation variants E233P/L234V/L235A/G236del/S267K, the FcRn variants M428L/N434S and a first scFv; and b) a second monomer that comprises the skew variants L368D/K370S, the pI variants N208D/Q295E/N384D/Q418E/N421D, the ablation variants E233P/L234V/L235A/G236del/S267K, the FcRn variants M428L/N434S and a second scFv.

XI. PARTICULAR EMBODIMENTS OF THE INVENTION

As will be appreciated by those in the art, the invention provides a large number of possible combinations of anti-PD-1 scFv sequences with the ABDs for different target antigens in the different formats of the invention.

In some embodiments, any PD-1 ABD of FIGS. 13, 15, 16,18, 20, 21, 24, 33 and 40 can be combined with any anti-TIM-3 ABD, any anti-CTLA-4 ABD, any anti-ICOS ABD, any anti-TIM-3 ABD, any anti-LAG-3 ABD or any anti-BTLA ABD, in any format of FIG. 1. Of particular use are anti-PD-1 scFv sequences of FIG. 15 in combination with Fab ABDs of the sequence listing for these ABDs. In some embodiments, these combinations are made using the "backbone" sequences for the bottle opener format as depicted in FIG. 162 of US Publication No. 2016/0355608 (which can also be used for the Central-scFv format), or using the "backbone" sequences for the "mAb-scFv" format as depicted in FIG. 163 of US Publication No. 2016/0355608, both Figures of which (and the accompanying legends) are expressly incorporated by reference herein.

A. PD-1 X CTLA-4 Bottle Opener Embodiments

In some embodiments, the invention provides bispecific heterodimeric antibodies that bind to both human PD-1 and human CTLA-4. As will be appreciated by those in the art, there are a large number of possible combinations of anti-PD-1 scFv sequences with the ABDs for CTLA-4.

In some embodiments, the PD-1 ABD is the scFv and the CTLA-4 ABD is the Fab construct. In these embodiments, any scFv ABD from FIG. 15 A-15T can be combined with any anti-CTLA-4 ABD sequence. Anti-CTLA-4 ABDs sequences suitable for use in the present invention include SEQ ID NOs: 21-2918 (CTLA-4 scFv sequences, although the Fv sequences therein can be formatted as Fabs), SEQ ID NOs: 2919-6208 (CTLA-4 Fab sequences, although the Fv sequences therein can be formatted as scFvs), SEQ ID NOs: 36739-36818 (additional CTLA-4 Fab sequences, although the Fv sequences therein can be formatted as scFvs) and SEQ ID NOs: 35395-35416 (CTLA-4 one armed constructs, which can be formatted as either Fabs or scFvs). As will be understood from those in the art, these sequence identifiers come in "pairs" for the variable heavy and light chains, as will be apparent from the sequence identifiers.

In some embodiments, heterodimeric antibodies of the invention are made in the bottle opener format using a PD-1 ABD from FIG. 15 as the scFv and the CTLA-4 ABD as the Fab Fv, when the CTLA-4 ABD is selected from a pair from SEQ ID NOs:2919-6208 and SEQ ID NOs:35395-35416 of the present sequencing listing. In some embodiments, the VH domain of the CTLA-4 Fab is added to SEQ ID NO:471, the VL of the CTLA-4 Fab is added to SEQ ID NO:473 and the PD-1 scFv is added to SEQ ID NO:472 of US2016/0355608. In some embodiments, the VH domain of the CTLA-4 Fab is added to SEQ ID NO:474, the $V_L$ of the CTLA-4 Fab is added to SEQ ID NO:476 and the PD-1 scFv is added to SEQ ID NO:475 of US2016/0355608. In some embodiments, the VH domain of the CTLA-4 Fab is added to SEQ ID NO:477, the VL of the CTLA-4 Fab is added to SEQ ID NO:479 and the PD-1 scFv is added to SEQ ID NO:478 of US2016/0355608. In some embodiments, the VH domain of the CTLA-4 Fab is added to SEQ ID NO:480, the VL of the CTLA-4 Fab is added to SEQ ID NO:482 and the PD-1 scFv is added to SEQ ID NO:481 of US2016/0355608.

In some embodiments, the CTLA-4 Fab comprises a variable heavy domain of SEQ ID NO:38134 and a variable light domain of SEQ ID NO:38138.

In some embodiments, an anti-CTLA-4 Fab is selected from any of SEQ ID NOs: 2919-6208 and SEQ ID NOs: 36739-36818 herein, with the CTLA-4 Fab comprising a variable heavy domain of SEQ ID NO:38134 and a variable light domain of SEQ ID NO:38138 finding particular use. In these embodiments, the remainder of the heterodimeric antibody is XENCS556 from FIG. 50; that is, the VH from the CTLA-4 Fab is added N-terminally to the Fab Chain of XENCS556 and the VL from the CTLA-4 Fab is added N-terminally to the Light Chain of XENCS556.

In some embodiments, an anti-CTLA-4 Fab is selected from any of SEQ ID NOs: 2919-6208 and SEQ ID NOs: 36739-36818 herein, with the CTLA-4 Fab comprising a variable heavy domain of SEQ ID NO:38134 and a variable light domain of SEQ ID NO:38138 finding particular use. In these embodiments, the remainder of the heterodimeric antibody is XENCS557 from FIG. 50; that is, the VH from the CTLA-4 Fab is added N-terminally to the Fab Chain of XENCS557 and the VL from the CTLA-4 Fab is added N-terminally to the Light Chain of XENCS557.

In some embodiments, an anti-CTLA-4 Fab is selected from any of SEQ ID NOs: 2919-6208 and SEQ ID NOs: 36739-36818 herein, with the CTLA-4 Fab comprising a variable heavy domain of SEQ ID NO:38134 and a variable light domain of SEQ ID NO:38138 finding particular use. In these embodiments, the remainder of the heterodimeric antibody is XENCS558 from FIG. 50; that is, the VH from the CTLA-4 Fab is added N-terminally to the Fab Chain of XENCS558 and the VL from the CTLA-4 Fab is added N-terminally to the Light Chain of XENCS558.

In some embodiments, an anti-CTLA-4 Fab is selected from any of SEQ ID NOs: 2919-6208 and SEQ ID NOs: 36739-36818 herein, with the CTLA-4 Fab comprising a variable heavy domain of SEQ ID NO:38134 and a variable light domain of SEQ ID NO:38138 finding particular use. In these embodiments, the remainder of the heterodimeric antibody is XENCS559 from FIG. 50; that is, the VH from the CTLA-4 Fab is added N-terminally to the Fab Chain of XENCS559 and the VL from the CTLA-4 Fab is added N-terminally to the Light Chain of XENCS559.

In some embodiments, an anti-CTLA-4 Fab is selected from any of SEQ ID NOs: 2919-6208 and SEQ ID NOs: 36739-36818 herein, with the CTLA-4 Fab comprising a variable heavy domain of SEQ ID NO:38134 and a variable light domain of SEQ ID NO:38138 finding particular use. In these embodiments, the remainder of the heterodimeric antibody is XENCS560 from FIG. 50; that is, the VH from the CTLA-4 Fab is added N-terminally to the Fab Chain of XENCS560 and the VL from the CTLA-4 Fab is added N-terminally to the Light Chain of XENCS560.

In some embodiments, an anti-CTLA-4 Fab is selected from any of SEQ ID NOs: 2919-6208 and SEQ ID NOs: 36739-36818 herein, with the CTLA-4 Fab comprising a variable heavy domain of SEQ ID NO:38134 and a variable light domain of SEQ ID NO:38138 finding particular use. In these embodiments, the remainder of the heterodimeric antibody is XENCS561 from FIG. 50; that is, the VH from the CTLA-4 Fab is added N-terminally to the Fab Chain of XENCS561 and the VL from the CTLA-4 Fab is added N-terminally to the Light Chain of XENCS561.

In some embodiments, an anti-CTLA-4 Fab is selected from any of SEQ ID NOs: 2919-6208 and SEQ ID NOs: 36739-36818 herein, with the CTLA-4 Fab comprising a variable heavy domain of SEQ ID NO:38134 and a variable light domain of SEQ ID NO:38138 finding particular use. In these embodiments, the remainder of the heterodimeric antibody is XENCS562 from FIG. 50; that is, the VH from the CTLA-4 Fab is added N-terminally to the Fab Chain of XENCS562 and the VL from the CTLA-4 Fab is added N-terminally to the Light Chain of XENCS562.

In some embodiments, an anti-CTLA-4 Fab is selected from any of SEQ ID NOs: 2919-6208 and SEQ ID NOs: 36739-36818 herein, with the CTLA-4 Fab comprising a variable heavy domain of SEQ ID NO:38134 and a variable light domain of SEQ ID NO:38138 finding particular use. In these embodiments, the remainder of the heterodimeric antibody is XENCS563 from FIG. 50; that is, the VH from the CTLA-4 Fab is added N-terminally to the Fab Chain of XENCS563 and the VL from the CTLA-4 Fab is added N-terminally to the Light Chain of XENCS563.

In some embodiments, an anti-CTLA-4 Fab is selected from the pairs of SEQ ID NOs:36739 and 36743, 36747 and 36751, 36755 and 36759, 36763 and 36767, 36771 and 36775, 36779 and 36783, 36787 and 36791, 36795 and 36799, 36803 and 36807 and 36811 and 36815 of the sequence listing. In these embodiments, the remainder of the heterodimeric antibody is XENCS556 from FIG. 50; that is, the VH from the CTLA-4 Fab is added N-terminally to the Fab Chain of XENCS556 and the VL from the CTLA-4 Fab is added N-terminally to the Light Chain of XENCS556.

In some embodiments, an anti-CTLA-4 Fab is selected from the pairs of SEQ ID NOs:36739 and 36743, 36747 and 36751, 36755 and 36759, 36763 and 36767, 36771 and 36775, 36779 and 36783, 36787 and 36791, 36795 and 36799, 36803 and 36807 and 36811 and 36815 of the sequence listing. In these embodiments, the remainder of the heterodimeric antibody is XENCS557 from FIG. 50; that is, the VH from the CTLA-4 Fab is added N-terminally to the Fab Chain of XENCS557 and the VL from the CTLA-4 Fab is added N-terminally to the Light Chain of XENCS557.

In some embodiments, an anti-CTLA-4 Fab is selected from the pairs of SEQ ID NOs:36739 and 36743, 36747 and 36751, 36755 and 36759, 36763 and 36767, 36771 and 36775, 36779 and 36783, 36787 and 36791, 36795 and 36799, 36803 and 36807 and 36811 and 36815 of the sequence listing. In these embodiments, the remainder of the heterodimeric antibody is XENCS558 from FIG. 50; that is, the VH from the CTLA-4 Fab is added N-terminally to the Fab Chain of XENCS558 and the VL from the CTLA-4 Fab is added N-terminally to the Light Chain of XENCS558.

In some embodiments, an anti-CTLA-4 Fab is selected from the pairs of SEQ ID NOs:36739 and 36743, 36747 and 36751, 36755 and 36759, 36763 and 36767, 36771 and 36775, 36779 and 36783, 36787 and 36791, 36795 and 36799, 36803 and 36807 and 36811 and 36815 of the sequence listing. In these embodiments, the remainder of the heterodimeric antibody is XENCS559 from FIG. 50; that is, the VH from the CTLA-4 Fab is added N-terminally to the Fab Chain of XENCS559 and the VL from the CTLA-4 Fab is added N-terminally to the Light Chain of XENCS559.

In some embodiments, an anti-CTLA-4 Fab is selected from the pairs of SEQ ID NOs:36739 and 36743, 36747 and 36751, 36755 and 36759, 36763 and 36767, 36771 and 36775, 36779 and 36783, 36787 and 36791, 36795 and 36799, 36803 and 36807 and 36811 and 36815 of the sequence listing. In these embodiments, the remainder of the heterodimeric antibody is XENCS560 from FIG. 50; that is, the VH from the CTLA-4 Fab is added N-terminally to the Fab Chain of XENCS560 and the VL from the CTLA-4 Fab is added N-terminally to the Light Chain of XENCS560.

In some embodiments, an anti-CTLA-4 Fab is selected from the pairs of SEQ ID NOs:36739 and 36743, 36747 and 36751, 36755 and 36759, 36763 and 36767, 36771 and 36775, 36779 and 36783, 36787 and 36791, 36795 and 36799, 36803 and 36807 and 36811 and 36815 of the sequence listing. In these embodiments, the remainder of the heterodimeric antibody is XENCS561 from FIG. 50; that is, the VH from the CTLA-4 Fab is added N-terminally to the Fab Chain of XENCS561 and the VL from the CTLA-4 Fab is added N-terminally to the Light Chain of XENCS561.

In some embodiments, an anti-CTLA-4 Fab is selected from the pairs of SEQ ID NOs:36739 and 36743, 36747 and 36751, 36755 and 36759, 36763 and 36767, 36771 and 36775, 36779 and 36783, 36787 and 36791, 36795 and 36799, 36803 and 36807 and 36811 and 36815 of the sequence listing. In these embodiments, the remainder of the heterodimeric antibody is XENCS562 from FIG. 50; that is, the VH from the CTLA-4 Fab is added N-terminally to the Fab Chain of XENCS562 and the VL from the CTLA-4 Fab is added N-terminally to the Light Chain of XENCS562.

In some embodiments, an anti-CTLA-4 Fab is selected from the pairs of SEQ ID NOs:36739 and 36743, 36747 and 36751, 36755 and 36759, 36763 and 36767, 36771 and 36775, 36779 and 36783, 36787 and 36791, 36795 and 36799, 36803 and 36807 and 36811 and 36815 of the sequence listing. In these embodiments, the remainder of the heterodimeric antibody is XENCS563 from FIG. 50; that is, the VH from the CTLA-4 Fab is added N-terminally to the Fab Chain of XENCS563 and the VL from the CTLA-4 Fab is added N-terminally to the Light Chain of XENCS563.

In some embodiments, the PD-1 X CTLA-4 heterodimeric antibody of the invention is selected from the group consisting of XENCS502, XENCS509, XENCS516, XENCS523, XENCS530, XENCS537, XENCS544 and XENCS551.

B. PD-1 X ICOS Bottle Opener Embodiments

In some embodiments, the invention provides bispecific heterodimeric antibodies that bind to both human PD-1 and human ICOS. As will be appreciated by those in the art, there are a large number of possible combinations of anti-PD-1 scFv sequences with the ABDs for ICOS.

In some embodiments, the PD-1 ABD is the scFv and the ICOS ABD is the Fab construct. In these embodiments, any scFv ABD from FIG. 15A-15T can be combined with any anti-ICOS ABD sequence. Anti-ICOS sequences suitable for use as ABDs include many as disclosed in US2018/0127501, expressly incorporated by reference in its entirety and specifically for the legends and FIGS. 19, 20 and 24, the sequences depicted therein, as well as SEQ ID NOs:27869-28086 from US2018/0127501 which contain a number of ICOS Fab sequences (heavy chain VH1-CH1 and light chain VL1-CL) as indicated in the naming nomenclature. Additionally included are the anti-ICOS ABDs of the VH/VL pairs of SEQ ID NOs:26323 and 26328, 27477 and 27452 and 26353 and 26358 from the sequence listing from US2018/0127501. As will be understood from those in the art, these sequence identifiers come in "pairs" for the variable heavy and light chains, as will be apparent from the sequence identifiers.

Of particular interest in the present invention are the Fab sequences of the anti-ICOS ABD from XENCS500 in FIGS. 49A-49KK, with VH_ICOS_H0_L0 and VL_ICOS_H0_L0. Of particular interest in the present invention are the Fab sequences of the anti-ICOS ABD from XENCS501 in FIGS. 49A-49KK, with VH_ICOS_H0.66_L0 and VL_ICOS_H0.66_L0.

In some embodiments, the VH domain of the ICOS Fab is added to SEQ ID NO:471, the VL of the ICOS Fab is added to SEQ ID NO:473 and the PD-1 scFv is added to SEQ ID NO:472 of US2016/0355608. In some embodiments, the VH domain of the ICOS Fab is added to SEQ ID NO:474, the VL of the ICOS Fab is added to SEQ ID NO:476 and the PD-1 scFv is added to SEQ ID NO:475 of US2016/0355608. In some embodiments, the VH domain of the ICOS Fab is added to SEQ ID NO:477, the VL of the ICOS Fab is added to SEQ ID NO:479 and the PD-1 scFv is added to SEQ ID NO:478 of US2016/0355608. In some embodiments, the VH domain of the ICOS Fab is added to SEQ ID NO:480, the VL of the ICOS Fab is added to SEQ ID NO:482 and the PD-1 scFv is added to SEQ ID NO:481 of US2016/0355608.

In some embodiments, an anti-ICOS Fab is selected from VH/VL pairs of SEQ ID NOs:26323 and 26328, 27477 and 27452 and 26353 and 26358 from the sequence listing from US2018/0127501, with the Fab sequences of the anti-ICOS ABD from XENCS500 in FIGS. 49A-49KK (VH_ICOS_H0_L0 and VL_ICOS_H0_L0) and the anti-ICOS ABD from XENCS501 in FIGS. 49A-49KK (VH_ICOS_H0.66_L0 and VL_ICOS_H0.66_L0) finding particular use. In these embodiments, the remainder of the heterodimeric antibody is XENCS556 from FIG. 50; that is, the VH from the ICOS Fab is added N-terminally to the Fab Chain of XENCS556 and the VL from the ICOS Fab is added N-terminally to the Light Chain of XENCS556.

In some embodiments, an anti-ICOS Fab is selected from VH/VL pairs of SEQ ID NOs:26323 and 26328, 27477 and 27452 and 26353 and 26358 from the sequence listing from US2018/0127501, with the Fab sequences of the anti-ICOS ABD from XENCS500 in FIGS. 49A-49KK (VH_ICOS_H0_L0 and VL_ICOS_H0_L0) and the anti-ICOS ABD from XENCS501 in FIGS. 49A-49KK (VH_ICOS_H0.66_L0 and VL_ICOS_H0.66_L0) finding particular use. In these embodiments, the remainder of the heterodimeric antibody is XENCS557 from FIG. 50; that is, the VH from the ICOS Fab is added N-terminally to the Fab Chain of XENCS557 and the VL from the ICOS Fab is added N-terminally to the Light Chain of XENCS557.

In some embodiments, an anti-ICOS Fab is selected from VH/VL pairs of SEQ ID NOs:26323 and 26328, 27477 and 27452 and 26353 and 26358 from the sequence listing from US2018/0127501, with the Fab sequences of the anti-ICOS ABD from XENCS500 in FIGS. 49A-49KK (VH_ICOS_H0_L0 and VL_ICOS_H0_L0) and the anti-ICOS ABD from XENCS501 in FIGS. 49A-49KK (VH_ICOS_H0.66_L0 and VL_ICOS_H0.66_L0) finding particular use. In these embodiments, the remainder of the heterodimeric antibody is XENCS558 from FIG. 50; that is, the VH from the ICOS Fab is added N-terminally to the Fab Chain of XENCS558 and the VL from the ICOS Fab is added N-terminally to the Light Chain of XENCS558.

In some embodiments, an anti-ICOS Fab is selected from VH/VL pairs of SEQ ID NOs:26323 and 26328, 27477 and 27452 and 26353 and 26358 from the sequence listing from US2018/0127501, with the Fab sequences of the anti-ICOS ABD from XENCS500 in FIGS. 49A-49KK (VH_ICOS_H0_L0 and VL_ICOS_H0_L0) and the anti-ICOS ABD from XENCS501 in FIGS. 49A-49KK (VH_ICOS_H0.66_L0 and VL_ICOS_H0.66_L0) finding particular use. In these embodiments, the remainder of the heterodimeric antibody is XENCS559 from FIG. 50; that is, the VH from the ICOS Fab is added N-terminally to the Fab Chain of XENCS559 and the VL from the ICOS Fab is added N-terminally to the Light Chain of XENCS559.

In some embodiments, an anti-ICOS Fab is selected from VH/VL pairs of SEQ ID NOs:26323 and 26328, 27477 and 27452 and 26353 and 26358 from the sequence listing from US2018/0127501, with the Fab sequences of the anti-ICOS ABD from XENCS500 in FIGS. 49A-49KK (VH_ICOS_H0_L0 and VL_ICOS_H0_L0) and the anti-ICOS ABD from XENCS501 in FIGS. 49A-49KK (VH_ICOS_H0.66_L0 and VL_ICOS_H0.66_L0) finding particular use. In these embodiments, the remainder of the heterodimeric antibody is XENCS560 from FIG. 50; that is, the VH from the ICOS Fab is added N-terminally to the Fab Chain of XENCS560 and the VL from the ICOS Fab is added N-terminally to the Light Chain of XENCS560.

In some embodiments, an anti-ICOS Fab is selected from VH/VL pairs of SEQ ID NOs:26323 and 26328, 27477 and 27452 and 26353 and 26358 from the sequence listing from US2018/0127501, with the Fab sequences of the anti-ICOS ABD from XENCS500 in FIGS. 49A-49KK (VH_ICOS_H0_L0 and VL_ICOS_H0_L0) and the anti-ICOS ABD from XENCS501 in FIGS. 49A-49KK (VH_ICOS_H0.66_L0 and VL_ICOS_H0.66_L0) finding particular use. In these embodiments, the remainder of the heterodimeric antibody is XENCS561 from FIG. 50; that is, the VH from the ICOS Fab is added N-terminally to the Fab Chain of XENCS561 and the VL from the ICOS Fab is added N-terminally to the Light Chain of XENCS561.

In some embodiments, an anti-ICOS Fab is selected from VH/VL pairs of SEQ ID NOs:26323 and 26328, 27477 and 27452 and 26353 and 26358 from the sequence listing from US2018/0127501, with the Fab sequences of the anti-ICOS ABD from XENCS500 in FIGS. 49A-49KK (VH_ICOS_H0_L0 and VL_ICOS_H0_L0) and the anti-ICOS ABD from XENCS501 in FIGS. 49A-49KK (VH_ICOS_H0.66_L0 and VL_ICOS_H0.66_L0) finding particular use. In these embodiments, the remainder of the heterodimeric antibody is XENCS562 from FIG. 50; that is, the VH from the ICOS Fab is added N-terminally to the Fab Chain of XENCS562 and the VL from the ICOS Fab is added N-terminally to the Light Chain of XENCS562.

In some embodiments, an anti-ICOS Fab is selected from VH/VL pairs of SEQ ID NOs:26323 and 26328, 27477 and 27452 and 26353 and 26358 from the sequence listing from US2018/0127501, with the Fab sequences of the anti-ICOS ABD from XENCS500 in FIGS. 49A-49KK (VH_ICOS_H0_L0 and VL_ICOS_H0_L0) and the anti-ICOS ABD from XENCS501 in FIGS. 49A-49KK (VH_ICOS_H0.66_L0 and VL_ICOS_H0.66_L0) finding particular use. In these embodiments, the remainder of the heterodimeric antibody is XENCS563 from FIG. 50; that is, the VH from the ICOS Fab is added N-terminally to the Fab Chain of XENCS563 and the VL from the ICOS Fab is added N-terminally to the Light Chain of XENCS563.

In some embodiments, the PD-1 X ICOS heterodimeric antibody of the invention is selected from the group consisting of XENCS500, XENCS501, XENCS507, XENCS508, XENCS514, XENCS515, XENCS521, XENCS522, XENCS528, XENCS529, XENCS535, XENCS526, XENCS542, XENCS543, XENCS549 and XENCS550.

C. PD-1 X LAG-3 Bottle Opener Embodiments

In some embodiments, the invention provides bispecific heterodimeric antibodies that bind to both human PD-1 and human LAG-3. As will be appreciated by those in the art, there are a large number of possible combinations of anti-PD-1 scFv sequences with the ABDs for LAG-3.

In some embodiments, the PD-1 ABD is the scFv and the LAG-3 ABD is the Fab construct. In these embodiments, any scFv ABD from FIG. 15A-15T can be combined with any anti-LAG-3 ABD sequence. Anti-LAG-3 sequences suitable for use as ABDs include SEQ ID NOs: 17135-20764; SEQ ID NOs: 36819-36962; SEQ ID NOs: 35417-35606; SEQ ID NOs: 25194-32793; SEQ ID NOs: 32794-33002 (as will be understood from those in the art, all of these sequence identifiers come in "pairs" for the variable heavy and light chains, as will be apparent from the sequence identifiers); anti-LAG-3 Fabs selected the pairs of SEQ ID NOs:36819 and 36823, 36827 and 36831, 36835 and 36839, 36843 and 36847, 36851 and 36855, 36859 and 36863, 36867 and 36871, 36875 and 36879, 36883 and 36887, 36891 and 36895, 36899 and 36903, 36907 and 36911, 36915 and 36919, 36923 and 36927, 36931 and 36935, 36939 and 36943, 36947 and 36951 and 36955 and 36959; as well as the sequences of the LAG-3 Fab ABD of XENP22594, including the VH (SEQ ID NO:32755, with VHCDRs (SEQ ID NOs:32756, 32757 and 32758) and VL (SEQ ID NO:32760 with VLCDRs (SEQ ID NOs:32761, 32762 and 32763) and the sequences of the LAG-3 Fab ABD of XENP22656, including the VH (SEQ ID NO:28815, with VHCDRs (SEQ ID NOs:28816, 28817, and 28118) and VL (SEQ ID NO:28820, with VLCDRs (SEQ ID NOs:28821, 28822 and 28823).

In some embodiments, the VH domain of the LAG-3 Fab is added to SEQ ID NO:471, the VL of the LAG-3 Fab is added to SEQ ID NO:473 and the PD-1 scFv is added to SEQ ID NO:472 of US2016/0355608. In some embodiments, the VH domain of the LAG-3 Fab is added to SEQ ID NO:474, the VL of the LAG-3 Fab is added to SEQ ID NO:476 and the PD-1 scFv is added to SEQ ID NO:475 of US2016/0355608. In some embodiments, the VH domain of the LAG-3 Fab is added to SEQ ID NO:477, the VL of the LAG-3 Fab is added to SEQ ID NO:479 and the PD-1 scFv is added to SEQ ID NO:478 of US2016/0355608. In some embodiments, the VH domain of the LAG-3 Fab is added to SEQ ID NO:480, the VL of the LAG-3 Fab is added to SEQ ID NO:482 and the PD-1 scFv is added to SEQ ID NO:481 of US2016/0355608.

In some embodiments, the anti-LAG-3 Fab is selected from the pairs of SEQ ID NOs:36819 and 36823, 36827 and 36831, 36835 and 36839, 36843 and 36847, 36851 and 36855, 36859 and 36863, 36867 and 36871, 36875 and 36879, 36883 and 36887, 36891 and 36895, 36899 and 36903, 36907 and 36911, 36915 and 36919, 36923 and 36927, 36931 and 36935, 36939 and 36943, 36947 and 36951 and 36955 and 36959; with the VH/VL of XENP22594 (VH SEQ ID NO:32755 and VL SEQ ID NO:32760) and the VH/VL of XENP22656 (VH SEQ ID NO:28815 VL SEQ ID NO:28820) finding particular use.

In some embodiments, the anti-LAG-3 Fab is selected from the pairs of SEQ ID NOs:36819 and 36823, 36827 and 36831, 36835 and 36839, 36843 and 36847, 36851 and 36855, 36859 and 36863, 36867 and 36871, 36875 and 36879, 36883 and 36887, 36891 and 36895, 36899 and 36903, 36907 and 36911, 36915 and 36919, 36923 and 36927, 36931 and 36935, 36939 and 36943, 36947 and 36951 and 36955 and 36959; with the VH/VL of XENP22594 (VH SEQ ID NO:32755 and VL SEQ ID NO:32760) and the VH/VL of XENP22656 (VH SEQ ID NO:28815 VL SEQ ID NO:28820) finding particular use. In these embodiments, the remainder of the heterodimeric antibody is XENCS556 from FIG. 50; that is, the VH from the LAG-3 Fab is added N-terminally to the Fab Chain of XENCS556 and the VL from the LAG-3 Fab is added N-terminally to the Light Chain of XENCS556.

In some embodiments, the anti-LAG-3 Fab is selected from the pairs of SEQ ID NOs:36819 and 36823, 36827 and 36831, 36835 and 36839, 36843 and 36847, 36851 and 36855, 36859 and 36863, 36867 and 36871, 36875 and 36879, 36883 and 36887, 36891 and 36895, 36899 and 36903, 36907 and 36911, 36915 and 36919, 36923 and 36927, 36931 and 36935, 36939 and 36943, 36947 and 36951 and 36955 and 36959; with the VH/VL of XENP22594 (VH SEQ ID NO:32755 and VL SEQ ID NO:32760) and the VH/VL of XENP22656 (VH SEQ ID NO:28815 VL SEQ ID NO:28820) finding particular use. In these embodiments, the remainder of the heterodimeric antibody is XENCS557 from FIG. 50; that is, the VH from the LAG-3 Fab is added N-terminally to the Fab Chain of XENCS557 and the VL from the LAG-3 Fab is added N-terminally to the Light Chain of XENCS557.

In some embodiments, the anti-LAG-3 Fab is selected from the pairs of SEQ ID NOs:36819 and 36823, 36827 and 36831, 36835 and 36839, 36843 and 36847, 36851 and 36855, 36859 and 36863, 36867 and 36871, 36875 and 36879, 36883 and 36887, 36891 and 36895, 36899 and 36903, 36907 and 36911, 36915 and 36919, 36923 and 36927, 36931 and 36935, 36939 and 36943, 36947 and 36951 and 36955 and 36959; with the VH/VL of XENP22594 (VH SEQ ID NO:32755 and VL SEQ ID NO:32760) and the VH/VL of XENP22656 (VH SEQ ID NO:28815 VL SEQ ID NO:28820) finding particular use. In these embodiments, the remainder of the heterodimeric antibody is XENCS558 from FIG. 50; that is, the VH from the LAG-3 Fab is added N-terminally to the Fab Chain of XENCS558 and the VL from the LAG-3 Fab is added N-terminally to the Light Chain of XENCS558.

In some embodiments, the anti-LAG-3 Fab is selected from the pairs of SEQ ID NOs:36819 and 36823, 36827 and 36831, 36835 and 36839, 36843 and 36847, 36851 and 36855, 36859 and 36863, 36867 and 36871, 36875 and 36879, 36883 and 36887, 36891 and 36895, 36899 and 36903, 36907 and 36911, 36915 and 36919, 36923 and 36927, 36931 and 36935, 36939 and 36943, 36947 and 36951 and 36955 and 36959; with the VH/VL of XENP22594 (VH SEQ ID NO:32755 and VL SEQ ID NO:32760) and the VH/VL of XENP22656 (VH SEQ ID NO:28815 VL SEQ ID NO:28820) finding particular use. In these embodiments, the remainder of the heterodimeric antibody is XENCS559 from FIG. 50; that is, the VH from the LAG-3 Fab is added N-terminally to the Fab Chain of XENCS559 and the VL from the LAG-3 Fab is added N-terminally to the Light Chain of XENCS559.

In some embodiments, the anti-LAG-3 Fab is selected from the pairs of SEQ ID NOs:36819 and 36823, 36827 and 36831, 36835 and 36839, 36843 and 36847, 36851 and 36855, 36859 and 36863, 36867 and 36871, 36875 and 36879, 36883 and 36887, 36891 and 36895, 36899 and 36903, 36907 and 36911, 36915 and 36919, 36923 and 36927, 36931 and 36935, 36939 and 36943, 36947 and 36951 and 36955 and 36959; with the VH/VL of XENP22594 (VH SEQ ID NO:32755 and VL SEQ ID NO:32760) and the VH/VL of XENP22656 (VH SEQ ID NO:28815 VL SEQ ID NO:28820) finding particular use. In these embodiments, the remainder of the heterodimeric antibody is XENCS560 from FIG. 50; that is, the VH from the LAG-3 Fab is added N-terminally to the Fab Chain of XENCS560 and the VL from the LAG-3 Fab is added N-terminally to the Light Chain of XENCS560.

In some embodiments, the anti-LAG-3 Fab is selected from the pairs of SEQ ID NOs:36819 and 36823, 36827 and 36831, 36835 and 36839, 36843 and 36847, 36851 and 36855, 36859 and 36863, 36867 and 36871, 36875 and 36879, 36883 and 36887, 36891 and 36895, 36899 and 36903, 36907 and 36911, 36915 and 36919, 36923 and 36927, 36931 and 36935, 36939 and 36943, 36947 and 36951 and 36955 and 36959; with the VH/VL of XENP22594 (VH SEQ ID NO:32755 and VL SEQ ID NO:32760) and the VH/VL of XENP22656 (VH SEQ ID NO:28815 VL SEQ ID NO:28820) finding particular use. In these embodiments, the remainder of the heterodimeric antibody is XENCS561 from FIG. 50; that is, the VH from the LAG-3 Fab is added N-terminally to the Fab Chain of XENCS561 and the VL from the LAG-3 Fab is added N-terminally to the Light Chain of XENCS561.

In some embodiments, the anti-LAG-3 Fab is selected from the pairs of SEQ ID NOs:36819 and 36823, 36827 and 36831, 36835 and 36839, 36843 and 36847, 36851 and 36855, 36859 and 36863, 36867 and 36871, 36875 and 36879, 36883 and 36887, 36891 and 36895, 36899 and 36903, 36907 and 36911, 36915 and 36919, 36923 and 36927, 36931 and 36935, 36939 and 36943, 36947 and 36951 and 36955 and 36959; with the VH/VL of XENP22594 (VH SEQ ID NO:32755 and VL SEQ ID NO:32760) and the VH/VL of XENP22656 (VH SEQ ID NO:28815 VL SEQ ID NO:28820) finding particular use. In these embodiments, the remainder of the heterodimeric antibody is XENCS562 from FIG. 50; that is, the VH from the LAG-3 Fab is added N-terminally to the Fab Chain of XENCS562 and the VL from the LAG-3 Fab is added N-terminally to the Light Chain of XENCS562.

In some embodiments, the anti-LAG-3 Fab is selected from the pairs of SEQ ID NOs:36819 and 36823, 36827 and 36831, 36835 and 36839, 36843 and 36847, 36851 and 36855, 36859 and 36863, 36867 and 36871, 36875 and 36879, 36883 and 36887, 36891 and 36895, 36899 and 36903, 36907 and 36911, 36915 and 36919, 36923 and 36927, 36931 and 36935, 36939 and 36943, 36947 and 36951 and 36955 and 36959; with the VH/VL of XENP22594 (VH SEQ ID NO:32755 and VL SEQ ID NO:32760) and the VH/VL of XENP22656 (VH SEQ ID NO:28815 VL SEQ ID NO:28820) finding particular use. In these embodiments, the remainder of the heterodimeric antibody is XENCS563 from FIG. 50; that is, the VH from the LAG-3 Fab is added N-terminally to the Fab Chain of XENCS563 and the VL from the LAG-3 Fab is added N-terminally to the Light Chain of XENCS563.

In some embodiments, the PD-1 X LAG-3 heterodimeric antibody of the invention is selected from the group consisting of XENCS503, XENCS504, XENCS510, XENCS511, XENCS517, XENCS518, XENCS521, XENCS524, XENCS525, XENCS531, XENCS532, XENCS538, XENCS539, XENCS545, XENCS546, XENCS552 and XENCS553.

D. PD-1 X TIM-3 Bottle Opener Embodiments

In some embodiments, the invention provides bispecific heterodimeric antibodies that bind to both human PD-1 and human TIM-3. As will be appreciated by those in the art, there are a large number of possible combinations of anti-PD-1 scFv sequences with the ABDs for TIM-3.

In some embodiments, the PD-1 ABD is the scFv and the TIM-3 ABD is the Fab construct. In these embodiments, any scFv ABD from FIG. 15A-15T can be combined with any anti-TIM-3 ABD sequence. Anti-TIM-3 sequences suitable for use as ABDs include SEQ ID NOs: 20765-20884; SEQ ID NOs: 37587-37698; SEQ ID NOs: 36347-36706 (as will be understood from those in the art, these sequence identifiers come in "pairs" for the variable heavy and light chains, as will be apparent from the sequence identifiers), anti-TIM-3 ABDs selected from the pairs of SEQ ID NOs:35757 and 37591, 37959 and 37599, 37603 and 37607, 37611 and 37615, 37619 and 37623, 37627 and 37631, 37635 and 37639, 37643 and 37647, 37651 and 37655, 37659 and 37663, 37667 and 37671, 37675 and 37679, 37683 and 37687 and 37691 and 37695; as well as the Fab sequences of the anti-TIM-3 ABD of XENP21189 (VH SEQ ID NO:36508 and VL SEQ ID NO:36513) finding particular use.

In some embodiments, the VH domain of the TIM-3 Fab is added to SEQ ID NO:471, the VL of the TIM-3 Fab is added to SEQ ID NO:473 and the PD-1 scFv is added to SEQ ID NO:472 of US2016/0355608. In some embodiments, the VH domain of the TIM-3 Fab is added to SEQ ID NO:474, the VL of the TIM-3 Fab is added to SEQ ID NO:476 and the PD-1 scFv is added to SEQ ID NO:475 of US2016/0355608. In some embodiments, the VH domain of the TIM-3 Fab is added to SEQ ID NO:477, the VL of the TIM-3 Fab is added to SEQ ID NO:479 and the PD-1 scFv is added to SEQ ID NO:478 of US2016/0355608. In some embodiments, the VH domain of the TIM-3 Fab is added to SEQ ID NO:480, the VL of the TIM-3 Fab is added to SEQ ID NO:482 and the PD-1 scFv is added to SEQ ID NO:481 of US2016/0355608.

Anti-TIM-3 sequences suitable for use as ABDs include SEQ ID NOs: 20765-20884; SEQ ID NOs: 37587-37698; SEQ ID NOs: 36347-36706 (as will be understood from those in the art, these sequence identifiers come in "pairs" for the variable heavy and light chains, as will be apparent from the sequence identifiers), anti-TIM-3 ABDs selected from the pairs of SEQ ID NOs:35757 and 37591, 37959 and 37599, 37603 and 37607, 37611 and 37615, 37619 and 37623, 37627 and 37631, 37635 and 37639, 37643 and 37647, 37651 and 37655, 37659 and 37663, 37667 and 37671, 37675 and 37679, 37683 and 37687 and 37691 and 37695; as well as the Fab sequences of the anti-TIM-3 ABD of XENP21189 (VH SEQ ID NO:36508 and VL SEQ ID NO:36513) finding particular use. In these embodiments, the remainder of the heterodimeric antibody is XENCS556 from FIG. 50; that is, the VH from the TIM-3 Fab is added N-terminally to the Fab Chain of XENCS556 and the VL from the TIM-3 Fab is added N-terminally to the Light Chain of XENCS556.

Anti-TIM-3 sequences suitable for use as ABDs include SEQ ID NOs: 20765-20884; SEQ ID NOs: 37587-37698; SEQ ID NOs: 36347-36706 (as will be understood from those in the art, these sequence identifiers come in "pairs" for the variable heavy and light chains, as will be apparent from the sequence identifiers), anti-TIM-3 ABDs selected from the pairs of SEQ ID NOs:35757 and 37591, 37959 and 37599, 37603 and 37607, 37611 and 37615, 37619 and 37623, 37627 and 37631, 37635 and 37639, 37643 and 37647, 37651 and 37655, 37659 and 37663, 37667 and 37671, 37675 and 37679, 37683 and 37687 and 37691 and 37695; as well as the Fab sequences of the anti-TIM-3 ABD of XENP21189 (VH SEQ ID NO:36508 and VL SEQ ID NO:36513) finding particular use. In these embodiments, the remainder of the heterodimeric antibody is XENCS557 from FIG. 50; that is, the VH from the TIM-3 Fab is added N-terminally to the Fab Chain of XENCS557 and the VL from the TIM-3 Fab is added N-terminally to the Light Chain of XENCS557.

Anti-TIM-3 sequences suitable for use as ABDs include SEQ ID NOs: 20765-20884; SEQ ID NOs: 37587-37698; SEQ ID NOs: 36347-36706 (as will be understood from those in the art, these sequence identifiers come in "pairs" for the variable heavy and light chains, as will be apparent from the sequence identifiers), anti-TIM-3 ABDs selected from the pairs of SEQ ID NOs:35757 and 37591, 37959 and 37599, 37603 and 37607, 37611 and 37615, 37619 and 37623, 37627 and 37631, 37635 and 37639, 37643 and 37647, 37651 and 37655, 37659 and 37663, 37667 and 37671, 37675 and 37679, 37683 and 37687 and 37691 and 37695; as well as the Fab sequences of the anti-TIM-3 ABD of XENP21189 (VH SEQ ID NO:36508 and VL SEQ ID NO:36513) finding particular use. In these embodiments, the remainder of the heterodimeric antibody is XENCS558 from FIG. 50; that is, the VH from the TIM-3 Fab is added N-terminally to the Fab Chain of XENCS558 and the VL from the TIM-3 Fab is added N-terminally to the Light Chain of XENCS558.

Anti-TIM-3 sequences suitable for use as ABDs include SEQ ID NOs: 20765-20884; SEQ ID NOs: 37587-37698; SEQ ID NOs: 36347-36706 (as will be understood from those in the art, these sequence identifiers come in "pairs" for the variable heavy and light chains, as will be apparent from the sequence identifiers), anti-TIM-3 ABDs selected from the pairs of SEQ ID NOs:35757 and 37591, 37959 and 37599, 37603 and 37607, 37611 and 37615, 37619 and 37623, 37627 and 37631, 37635 and 37639, 37643 and 37647, 37651 and 37655, 37659 and 37663, 37667 and 37671, 37675 and 37679, 37683 and 37687 and 37691 and 37695; as well as the Fab sequences of the anti-TIM-3 ABD of XENP21189 (VH SEQ ID NO:36508 and VL SEQ ID NO:36513) finding particular use. In these embodiments, the remainder of the heterodimeric antibody is XENCS559 from FIG. 50; that is, the VH from the TIM-3 Fab is added N-terminally to the Fab Chain of XENCS559 and the VL from the TIM-3 Fab is added N-terminally to the Light Chain of XENCS559.

Anti-TIM-3 sequences suitable for use as ABDs include SEQ ID NOs: 20765-20884; SEQ ID NOs: 37587-37698; SEQ ID NOs: 36347-36706 (as will be understood from those in the art, these sequence identifiers come in "pairs" for the variable heavy and light chains, as will be apparent from the sequence identifiers), anti-TIM-3 ABDs selected from the pairs of SEQ ID NOs:35757 and 37591, 37959 and 37599, 37603 and 37607, 37611 and 37615, 37619 and 37623, 37627 and 37631, 37635 and 37639, 37643 and 37647, 37651 and 37655, 37659 and 37663, 37667 and 37671, 37675 and 37679, 37683 and 37687 and 37691 and 37695; as well as the Fab sequences of the anti-TIM-3 ABD of XENP21189 (VH SEQ ID NO:36508 and VL SEQ ID NO:36513) finding particular use. In these embodiments, the remainder of the heterodimeric antibody is XENCS560 from FIG. 50; that is, the VH from the TIM-3 Fab is added N-terminally to the Fab Chain of XENCS560 and the VL from the TIM-3 Fab is added N-terminally to the Light Chain of XENCS560.

Anti-TIM-3 sequences suitable for use as ABDs include SEQ ID NOs: 20765-20884; SEQ ID NOs: 37587-37698; SEQ ID NOs: 36347-36706 (as will be understood from those in the art, these sequence identifiers come in "pairs" for the variable heavy and light chains, as will be apparent from the sequence identifiers), anti-TIM-3 ABDs selected from the pairs of SEQ ID NOs:35757 and 37591, 37959 and 37599, 37603 and 37607, 37611 and 37615, 37619 and 37623, 37627 and 37631, 37635 and 37639, 37643 and 37647, 37651 and 37655, 37659 and 37663, 37667 and 37671, 37675 and 37679, 37683 and 37687 and 37691 and 37695; as well as the Fab sequences of the anti-TIM-3 ABD of XENP21189 (VH SEQ ID NO:36508 and VL SEQ ID NO:36513) finding particular use. In these embodiments, the remainder of the heterodimeric antibody is XENCS561 from FIG. 50; that is, the VH from the TIM-3 Fab is added N-terminally to the Fab Chain of XENCS561 and the VL from the TIM-3 Fab is added N-terminally to the Light Chain of XENCS561.

Anti-TIM-3 sequences suitable for use as ABDs include SEQ ID NOs: 20765-20884; SEQ ID NOs: 37587-37698; SEQ ID NOs: 36347-36706 (as will be understood from those in the art, these sequence identifiers come in "pairs" for the variable heavy and light chains, as will be apparent from the sequence identifiers), anti-TIM-3 ABDs selected from the pairs of SEQ ID NOs:35757 and 37591, 37959 and 37599, 37603 and 37607, 37611 and 37615, 37619 and 37623, 37627 and 37631, 37635 and 37639, 37643 and 37647, 37651 and 37655, 37659 and 37663, 37667 and 37671, 37675 and 37679, 37683 and 37687 and 37691 and 37695; as well as the Fab sequences of the anti-TIM-3 ABD of XENP21189 (VH SEQ ID NO:36508 and VL SEQ ID NO:36513) finding particular use. In these embodiments, the remainder of the heterodimeric antibody is XENCS562 from FIG. 50; that is, the VH from the TIM-3 Fab is added N-terminally to the Fab Chain of XENCS562 and the VL from the TIM-3 Fab is added N-terminally to the Light Chain of XENCS562.

Anti-TIM-3 sequences suitable for use as ABDs include SEQ ID NOs: 20765-20884; SEQ ID NOs: 37587-37698; SEQ ID NOs: 36347-36706 (as will be understood from those in the art, these sequence identifiers come in "pairs" for the variable heavy and light chains, as will be apparent from the sequence identifiers), anti-TIM-3 ABDs selected from the pairs of SEQ ID NOs:35757 and 37591, 37959 and 37599, 37603 and 37607, 37611 and 37615, 37619 and 37623, 37627 and 37631, 37635 and 37639, 37643 and 37647, 37651 and 37655, 37659 and 37663, 37667 and 37671, 37675 and 37679, 37683 and 37687 and 37691 and 37695; as well as the Fab sequences of the anti-TIM-3 ABD of XENP21189 (VH SEQ ID NO:36508 and VL SEQ ID NO:36513) finding particular use. In these embodiments, the remainder of the heterodimeric antibody is XENCS563 from FIG. 50; that is, the VH from the TIM-3 Fab is added N-terminally to the Fab Chain of XENCS563 and the VL from the TIM-3 Fab is added N-terminally to the Light Chain of XENCS563.

In some embodiments, the PD-1 X TIM-3 heterodimeric antibody of the invention is selected from the group consisting of XENCS505, XENCS512, XENCS519, XENCS526, XENCS533, XENCS540, XENCS547 and XENCS554.

E. PD-1 X TIGIT Bottle Opener Embodiments

In some embodiments, the invention provides bispecific heterodimeric antibodies that bind to both human PD-1 and human TIGIT. As will be appreciated by those in the art, there are a large number of possible combinations of anti-PD-1 scFv sequences with the ABDs for TIGIT.

In some embodiments, the PD-1 ABD is the scFv and the TIGIT ABD is the Fab construct. In these embodiments, any scFv ABD from FIG. 15A-15T can be combined with any anti-TIGIT ABD sequence. Anti-TIGIT sequences suitable for use as ABDs include SEQ ID NOs: 21504-21523 and SEQ ID NOs: 37435-37586 (as will be understood from those in the art, these sequence identifiers come in "pairs" for the variable heavy and light chains, as will be apparent from the sequence identifiers), as well as TIGIT ABDs selected from the pairs of SEQ ID NOs:37435 and 37439, 37443 and 37447, 37451 and 37455, 37459 and 37463, 37467 and 37471, 37475 and 37479, 37483 and 37487, 37491 and 37495, 37499 and 37503, 37507 and 37511, 37515 and 37519, 37523 and 37527, 37531 and 37535, 37539 and 37543, 37547 and 37551, 37555 and 37559, 37563 and 37567, 37571 and 37575 and 37579 and 37583.

In some embodiments, the VH domain of the TIGIT Fab is added to SEQ ID NO:471, the VL of the TIGIT Fab is added to SEQ ID NO:473 and the PD-1 scFv is added to SEQ ID NO:472 of US2016/0355608. In some embodiments, the VH domain of the TIGIT Fab is added to SEQ ID NO:474, the VL of the TIGIT Fab is added to SEQ ID NO:476 and the PD-1 scFv is added to SEQ ID NO:475 of US2016/0355608. In some embodiments, the VH domain of the TIGIT Fab is added to SEQ ID NO:477, the VL of the TIGIT Fab is added to SEQ ID NO:479 and the PD-1 scFv is added to SEQ ID NO:478 of US2016/0355608. In some embodiments, the VH domain of the TIGIT Fab is added to SEQ ID NO:480, the VL of the TIGIT Fab is added to SEQ ID NO:482 and the PD-1 scFv is added to SEQ ID NO:481 of US2016/0355608.

Anti-TIGIT sequences suitable for use as ABDs include SEQ ID NOs: 21504-21523 and SEQ ID NOs: 37435-37586 (as will be understood from those in the art, these sequence identifiers come in "pairs" for the variable heavy and light chains, as will be apparent from the sequence identifiers), as well as TIGIT ABDs selected from the pairs of SEQ ID NOs:37435 and 37439, 37443 and 37447, 37451 and 37455, 37459 and 37463, 37467 and 37471, 37475 and 37479, 37483 and 37487, 37491 and 37495, 37499 and 37503, 37507 and 37511, 37515 and 37519, 37523 and 37527, 37531 and 37535, 37539 and 37543, 37547 and 37551, 37555 and 37559, 37563 and 37567, 37571 and 37575 and 37579 and 37583. In these embodiments, the remainder of the heterodimeric antibody is XENCS556 from FIG. 50; that is, the VH from the TIGIT Fab is added N-terminally to the Fab Chain of XENCS556 and the VL from the TIGIT Fab is added N-terminally to the Light Chain of XENCS556.

Anti-TIGIT sequences suitable for use as ABDs include SEQ ID NOs: 21504-21523 and SEQ ID NOs: 37435-37586 (as will be understood from those in the art, these sequence identifiers come in "pairs" for the variable heavy and light chains, as will be apparent from the sequence identifiers), as well as TIGIT ABDs selected from the pairs of SEQ ID NOs:37435 and 37439, 37443 and 37447, 37451 and 37455, 37459 and 37463, 37467 and 37471, 37475 and 37479, 37483 and 37487, 37491 and 37495, 37499 and 37503, 37507 and 37511, 37515 and 37519, 37523 and 37527, 37531 and 37535, 37539 and 37543, 37547 and 37551, 37555 and 37559, 37563 and 37567, 37571 and 37575 and 37579 and 37583. In these embodiments, the remainder of the heterodimeric antibody is XENCS557 from FIG. 50; that is, the VH from the TIGIT Fab is added N-terminally to the Fab Chain of XENCS557 and the VL from the TIGIT Fab is added N-terminally to the Light Chain of XENCS557.

Anti-TIGIT sequences suitable for use as ABDs include SEQ ID NOs: 21504-21523 and SEQ ID NOs: 37435-37586 (as will be understood from those in the art, these sequence identifiers come in "pairs" for the variable heavy and light chains, as will be apparent from the sequence identifiers), as well as TIGIT ABDs selected from the pairs of SEQ ID NOs:37435 and 37439, 37443 and 37447, 37451 and 37455, 37459 and 37463, 37467 and 37471, 37475 and 37479, 37483 and 37487, 37491 and 37495, 37499 and 37503, 37507 and 37511, 37515 and 37519, 37523 and 37527, 37531 and 37535, 37539 and 37543, 37547 and 37551, 37555 and 37559, 37563 and 37567, 37571 and 37575 and 37579 and 37583. In these embodiments, the remainder of the heterodimeric antibody is XENCS558 from FIG. 50; that is, the VH from the TIGIT Fab is added N-terminally to the Fab Chain of XENCS558 and the VL from the TIGIT Fab is added N-terminally to the Light Chain of XENCS558.

Anti-TIGIT sequences suitable for use as ABDs include SEQ ID NOs: 21504-21523 and SEQ ID NOs: 37435-37586 (as will be understood from those in the art, these sequence identifiers come in "pairs" for the variable heavy and light chains, as will be apparent from the sequence identifiers), as well as TIGIT ABDs selected from the pairs of SEQ ID NOs:37435 and 37439, 37443 and 37447, 37451 and 37455, 37459 and 37463, 37467 and 37471, 37475 and 37479, 37483 and 37487, 37491 and 37495, 37499 and 37503, 37507 and 37511, 37515 and 37519, 37523 and 37527, 37531 and 37535, 37539 and 37543, 37547 and 37551, 37555 and 37559, 37563 and 37567, 37571 and 37575 and 37579 and 37583. In these embodiments, the remainder of the heterodimeric antibody is XENCS559 from FIG. 50; that is, the VH from the TIGIT Fab is added N-terminally to the Fab Chain of XENCS559 and the VL from the TIGIT Fab is added N-terminally to the Light Chain of XENCS559.

Anti-TIGIT sequences suitable for use as ABDs include SEQ ID NOs: 21504-21523 and SEQ ID NOs: 37435-37586 (as will be understood from those in the art, these sequence identifiers come in "pairs" for the variable heavy and light chains, as will be apparent from the sequence identifiers), as well as TIGIT ABDs selected from the pairs of SEQ ID NOs:37435 and 37439, 37443 and 37447, 37451 and 37455, 37459 and 37463, 37467 and 37471, 37475 and 37479, 37483 and 37487, 37491 and 37495, 37499 and 37503, 37507 and 37511, 37515 and 37519, 37523 and 37527, 37531 and 37535, 37539 and 37543, 37547 and 37551, 37555 and 37559, 37563 and 37567, 37571 and 37575 and 37579 and 37583. In these embodiments, the remainder of the heterodimeric antibody is XENCS560 from FIG. 50; that is, the VH from the TIGIT Fab is added N-terminally to the Fab Chain of XENCS560 and the VL from the TIGIT Fab is added N-terminally to the Light Chain of XENCS560.

Anti-TIGIT sequences suitable for use as ABDs include SEQ ID NOs: 21504-21523 and SEQ ID NOs: 37435-37586 (as will be understood from those in the art, these sequence identifiers come in "pairs" for the variable heavy and light chains, as will be apparent from the sequence identifiers), as well as TIGIT ABDs selected from the pairs of SEQ ID NOs:37435 and 37439, 37443 and 37447, 37451 and 37455, 37459 and 37463, 37467 and 37471, 37475 and 37479, 37483 and 37487, 37491 and 37495, 37499 and 37503, 37507 and 37511, 37515 and 37519, 37523 and 37527, 37531 and 37535, 37539 and 37543, 37547 and 37551, 37555 and 37559, 37563 and 37567, 37571 and 37575 and 37579 and 37583. In these embodiments, the remainder of the heterodimeric antibody is XENCS561 from FIG. 50; that is, the VH from the TIGIT Fab is added N-terminally to the Fab Chain of XENCS561 and the VL from the TIGIT Fab is added N-terminally to the Light Chain of XENCS561.

Anti-TIGIT sequences suitable for use as ABDs include SEQ ID NOs: 21504-21523 and SEQ ID NOs: 37435-37586 (as will be understood from those in the art, these sequence identifiers come in "pairs" for the variable heavy and light chains, as will be apparent from the sequence identifiers), as well as TIGIT ABDs selected from the pairs of SEQ ID NOs:37435 and 37439, 37443 and 37447, 37451 and 37455, 37459 and 37463, 37467 and 37471, 37475 and 37479, 37483 and 37487, 37491 and 37495, 37499 and 37503, 37507 and 37511, 37515 and 37519, 37523 and 37527, 37531 and 37535, 37539 and 37543, 37547 and 37551, 37555 and 37559, 37563 and 37567, 37571 and 37575 and 37579 and 37583. In these embodiments, the remainder of the heterodimeric antibody is XENCS562 from FIG. 50; that is, the VH from the TIGIT Fab is added N-terminally to the Fab Chain of XENCS562 and the VL from the TIGIT Fab is added N-terminally to the Light Chain of XENCS562.

Anti-TIGIT sequences suitable for use as ABDs include SEQ ID NOs: 21504-21523 and SEQ ID NOs: 37435-37586 (as will be understood from those in the art, these sequence identifiers come in "pairs" for the variable heavy and light chains, as will be apparent from the sequence identifiers), as well as TIGIT ABDs selected from the pairs of SEQ ID NOs:37435 and 37439, 37443 and 37447, 37451 and 37455, 37459 and 37463, 37467 and 37471, 37475 and 37479, 37483 and 37487, 37491 and 37495, 37499 and 37503, 37507 and 37511, 37515 and 37519, 37523 and 37527, 37531 and 37535, 37539 and 37543, 37547 and 37551, 37555 and 37559, 37563 and 37567, 37571 and 37575 and 37579 and 37583. In these embodiments, the remainder of the heterodimeric antibody is XENCS563 from FIG. 50; that is, the VH from the TIGIT Fab is added N-terminally to the Fab Chain of XENCS563 and the VL from the TIGIT Fab is added N-terminally to the Light Chain of XENCS563.

F. PD-1 X BTLA Bottle Opener Embodiments

In some embodiments, the PD-1 ABD is the scFv and the BTLA ABD is the Fab construct. In these embodiments, any scFv ABD from FIG. 15A-15T can be combined with any anti-BTLA ABD sequence Anti-BTLA sequences suitable for use as ABDs include SEQ ID NOs: 20885-21503 and SEQ ID NOs: 36707-36738 (s will be understood from those in the art, these sequence identifiers come in "pairs" for the variable heavy and light chains, as will be apparent from the sequence identifiers); anti-BTLA ABD selected from the pairs of SEQ ID NOs:36707 and 36711, 36715 and 36719, 36723 and 36727 and 36761 and 36735; with the Fab anti-BTLA ABD of XENP20269 (VH SEQ ID NO:20936 and VL SEQ ID NO:20941) finding particular use.

In some embodiments, the VH domain of the BTLA Fab is added to SEQ ID NO:471, the VL of the BTLA Fab is added to SEQ ID NO:473 and the PD-1 scFv is added to SEQ ID NO:472 of US2016/0355608. In some embodiments, the VH domain of the BTLA Fab is added to SEQ ID NO:474, the VL of the BTLA Fab is added to SEQ ID NO:476 and the PD-1 scFv is added to SEQ ID NO:475 of US2016/0355608. In some embodiments, the VH domain of the BTLA Fab is added to SEQ ID NO:477, the VL of the BTLA Fab is added to SEQ ID NO:479 and the PD-1 scFv is added to SEQ ID NO:478 of US2016/0355608. In some embodiments, the VH domain of the BTLA Fab is added to SEQ ID NO:480, the VL of the BTLA Fab is added to SEQ ID NO:482 and the PD-1 scFv is added to SEQ ID NO:481 of US2016/0355608.

Anti-BTLA sequences suitable for use as ABDs include SEQ ID NOs: 20885-21503 and SEQ ID NOs: 36707-36738 (s will be understood from those in the art, these sequence identifiers come in "pairs" for the variable heavy and light chains, as will be apparent from the sequence identifiers); anti-BTLA ABD selected from the pairs of SEQ ID NOs: 36707 and 36711, 36715 and 36719, 36723 and 36727 and 36761 and 36735; with the Fab anti-BTLA ABD of XENP20269 (VH SEQ ID NO:20936 and VL SEQ ID NO:20941) finding particular use. In these embodiments, the remainder of the heterodimeric antibody is XENCS556 from FIG. 50; that is, the VH from the BTLA Fab is added N-terminally to the Fab Chain of XENCS556 and the VL from the BTLA Fab is added N-terminally to the Light Chain of XENCS556.

Anti-BTLA sequences suitable for use as ABDs include SEQ ID NOs: 20885-21503 and SEQ ID NOs: 36707-36738 (s will be understood from those in the art, these sequence identifiers come in "pairs" for the variable heavy and light chains, as will be apparent from the sequence identifiers); anti-BTLA ABD selected from the pairs of SEQ ID NOs: 36707 and 36711, 36715 and 36719, 36723 and 36727 and 36761 and 36735; with the Fab anti-BTLA ABD of XENP20269 (VH SEQ ID NO:20936 and VL SEQ ID NO:20941) finding particular use. In these embodiments, the remainder of the heterodimeric antibody is XENCS557 from FIG. 50; that is, the VH from the BTLA Fab is added N-terminally to the Fab Chain of XENCS557 and the VL from the BTLA Fab is added N-terminally to the Light Chain of XENCS557.

Anti-BTLA sequences suitable for use as ABDs include SEQ ID NOs: 20885-21503 and SEQ ID NOs: 36707-36738 (s will be understood from those in the art, these sequence identifiers come in "pairs" for the variable heavy and light chains, as will be apparent from the sequence identifiers); anti-BTLA ABD selected from the pairs of SEQ ID NOs: 36707 and 36711, 36715 and 36719, 36723 and 36727 and 36761 and 36735; with the Fab anti-BTLA ABD of XENP20269 (VH SEQ ID NO:20936 and VL SEQ ID NO:20941) finding particular use. In these embodiments, the remainder of the heterodimeric antibody is XENCS558 from FIG. 50; that is, the VH from the BTLA Fab is added N-terminally to the Fab Chain of XENCS558 and the VL from the BTLA Fab is added N-terminally to the Light Chain of XENCS558.

Anti-BTLA sequences suitable for use as ABDs include SEQ ID NOs: 20885-21503 and SEQ ID NOs: 36707-36738 (s will be understood from those in the art, these sequence identifiers come in "pairs" for the variable heavy and light chains, as will be apparent from the sequence identifiers); anti-BTLA ABD selected from the pairs of SEQ ID NOs: 36707 and 36711, 36715 and 36719, 36723 and 36727 and 36761 and 36735; with the Fab anti-BTLA ABD of XENP20269 (VH SEQ ID NO:20936 and VL SEQ ID NO:20941) finding particular use. In these embodiments, the remainder of the heterodimeric antibody is XENCS559 from FIG. 50; that is, the VH from the BTLA Fab is added N-terminally to the Fab Chain of XENCS559 and the VL from the BTLA Fab is added N-terminally to the Light Chain of XENCS559.

Anti-BTLA sequences suitable for use as ABDs include SEQ ID NOs: 20885-21503 and SEQ ID NOs: 36707-36738 (s will be understood from those in the art, these sequence identifiers come in "pairs" for the variable heavy and light chains, as will be apparent from the sequence identifiers); anti-BTLA ABD selected from the pairs of SEQ ID NOs: 36707 and 36711, 36715 and 36719, 36723 and 36727 and 36761 and 36735; with the Fab anti-BTLA ABD of XENP20269 (VH SEQ ID NO:20936 and VL SEQ ID NO:20941) finding particular use. In these embodiments, the remainder of the heterodimeric antibody is XENCS560 from FIG. 50; that is, the VH from the BTLA Fab is added N-terminally to the Fab Chain of XENCS560 and the VL from the BTLA Fab is added N-terminally to the Light Chain of XENCS560.

Anti-BTLA sequences suitable for use as ABDs include SEQ ID NOs: 20885-21503 and SEQ ID NOs: 36707-36738 (s will be understood from those in the art, these sequence identifiers come in "pairs" for the variable heavy and light chains, as will be apparent from the sequence identifiers); anti-BTLA ABD selected from the pairs of SEQ ID NOs: 36707 and 36711, 36715 and 36719, 36723 and 36727 and 36761 and 36735; with the Fab anti-BTLA ABD of XENP20269 (VH SEQ ID NO:20936 and VL SEQ ID NO:20941) finding particular use. In these embodiments, the remainder of the heterodimeric antibody is XENCS561 from FIG. 50; that is, the VH from the BTLA Fab is added N-terminally to the Fab Chain of XENCS561 and the VL from the BTLA Fab is added N-terminally to the Light Chain of XENCS561.

Anti-BTLA sequences suitable for use as ABDs include SEQ ID NOs: 20885-21503 and SEQ ID NOs: 36707-36738 (s will be understood from those in the art, these sequence identifiers come in "pairs" for the variable heavy and light chains, as will be apparent from the sequence identifiers); anti-BTLA ABD selected from the pairs of SEQ ID NOs: 36707 and 36711, 36715 and 36719, 36723 and 36727 and 36761 and 36735; with the Fab anti-BTLA ABD of XENP20269 (VH SEQ ID NO:20936 and VL SEQ ID NO:20941) finding particular use. In these embodiments, the remainder of the heterodimeric antibody is XENCS562 from FIG. 50; that is, the VH from the BTLA Fab is added N-terminally to the Fab Chain of XENCS562 and the VL from the BTLA Fab is added N-terminally to the Light Chain of XENCS562.

Anti-BTLA sequences suitable for use as ABDs include SEQ ID NOs: 20885-21503 and SEQ ID NOs: 36707-36738 (s will be understood from those in the art, these sequence identifiers come in "pairs" for the variable heavy and light chains, as will be apparent from the sequence identifiers); anti-BTLA ABD selected from the pairs of SEQ ID NOs: 36707 and 36711, 36715 and 36719, 36723 and 36727 and 36761 and 36735; with the Fab anti-BTLA ABD of XENP20269 (VH SEQ ID NO:20936 and VL SEQ ID NO:20941) finding particular use. In these embodiments, the remainder of the heterodimeric antibody is XENCS563 from FIG. 50; that is, the VH from the BTLA Fab is added N-terminally to the Fab Chain of XENCS563 and the VL from the BTLA Fab is added N-terminally to the Light Chain of XENCS563.

XII. NUCLEIC ACIDS OF THE INVENTION

The invention further provides nucleic acid compositions encoding the heterodimeric bispecific antibodies of the invention as well as the monospecific antibodies outlined herein.

As will be appreciated by those in the art, the nucleic acid compositions will depend on the format and scaffold of the heterodimeric protein. Thus, for example, when the format requires three amino acid sequences, such as for the triple F format (e.g. a first amino acid monomer comprising an Fc domain and a scFv, a second amino acid monomer comprising a heavy chain and a light chain), three nucleic acid sequences can be incorporated into one or more expression vectors for expression. Similarly, some formats (e.g. dual scFv formats such as disclosed in FIG. 1) only two nucleic acids are needed; again, they can be put into one or two expression vectors.

As is known in the art, the nucleic acids encoding the components of the invention can be incorporated into expression vectors as is known in the art, and depending on the host cells used to produce the heterodimeric antibodies of the invention. Generally the nucleic acids are operably linked to any number of regulatory elements (promoters, origin of replication, selectable markers, ribosomal binding sites, inducers, etc.). The expression vectors can be extra-chromosomal or integrating vectors.

The nucleic acids and/or expression vectors of the invention are then transformed into any number of different types of host cells as is well known in the art, including mammalian, bacterial, yeast, insect and/or fungal cells, with mammalian cells (e.g. CHO cells), finding use in many embodiments.

In some embodiments, nucleic acids encoding each monomer and the optional nucleic acid encoding a light chain, as applicable depending on the format, are each contained within a single expression vector, generally under different or the same promoter controls. In embodiments of particular use in the present invention, each of these two or three nucleic acids are contained on a different expression vector. As shown herein and in 62/025,931, hereby incorporated by reference, different vector ratios can be used to drive heterodimer formation. That is, surprisingly, while the proteins comprise first monomer:second monomer:light chains (in the case of many of the embodiments herein that have three polypeptides comprising the heterodimeric antibody) in a 1:1:2 ratio, these are not the ratios that give the best results.

The heterodimeric antibodies of the invention are made by culturing host cells comprising the expression vector(s) as is well known in the art. Once produced, traditional antibody purification steps are done, including an ion exchange chromatography step. As discussed herein, having the pIs of the two monomers differ by at least 0.5 can allow separation by ion exchange chromatography or isoelectric focusing, or other methods sensitive to isoelectric point. That is, the inclusion of pI substitutions that alter the isoelectric point (pI) of each monomer so that such that each monomer has a different pI and the heterodimer also has a distinct pI, thus facilitating isoelectric purification of the "triple F" heterodimer (e.g., anionic exchange columns, cationic exchange columns). These substitutions also aid in the determination and monitoring of any contaminating dual scFv-Fc and mAb homodimers post-purification (e.g., IEF gels, cIEF, and analytical IEX columns).

XIII. BIOLOGICAL AND BIOCHEMICAL FUNCTIONALITY OF THE HETERODIMERIC CHECKPOINT ANTIBODIES

Generally the bispecific antibodies of the invention are administered to patients with cancer, and efficacy is assessed, in a number of ways as described herein. Thus, while standard assays of efficacy can be run, such as cancer load, size of tumor, evaluation of presence or extent of metastasis, etc., immuno-oncology treatments can be assessed on the basis of immune status evaluations as well. This can be done in a number of ways, including both in vitro and in vivo assays. For example, evaluation of changes in immune status (e.g. presence of ICOS+ CD4+ T cells following ipi treatment) along with "old fashioned" measurements such as tumor burden, size, invasiveness, LN involvement, metastasis, etc. can be done. Thus, any or all of the following can be evaluated: the inhibitory effects of the checkpoints on CD4+ T cell activation or proliferation, CD8+ T (CTL) cell activation or proliferation, CD8+ T cell-mediated cytotoxic activity and/or CTL mediated cell depletion, NK cell activity and NK mediated cell depletion.

In some embodiments, assessment of treatment is done by evaluating immune cell proliferation, using for example, CFSE dilution method, Ki67 intracellular staining of immune effector cells, and 3H-Thymidine incorporation method, In some embodiments, assessment of treatment is done by evaluating the increase in gene expression or increased protein levels of activation-associated markers, including one or more of: CD25, CD69, CD137, ICOS, PD1, GITR, OX40, and cell degranulation measured by surface expression of CD107A.

In general, gene expression assays are done as is known in the art.

In general, protein expression measurements are also similarly done as is known in the art.

In some embodiments, assessment of treatment is done by assessing cytotoxic activity measured by target cell viability detection via estimating numerous cell parameters such as enzyme activity (including protease activity), cell membrane permeability, cell adherence, ATP production, co-enzyme production, and nucleotide uptake activity. Specific examples of these assays include, but are not limited to, Trypan Blue or PI staining, 51Cr or 35S release method, LDH activity, MTT and/or WST assays, Calcein-AM assay, Luminescent based assay, and others.

In some embodiments, assessment of treatment is done by assessing T cell activity measured by cytokine production, measure either intracellularly in culture supernatant using cytokines including, but not limited to, IFNγ, TNFα, GM-CSF, IL2, IL6, IL4, IL5, IL10, IL13 using well known techniques.

XIV. EXAMPLES

A. Example 1 Investigating In Vitro Binding of XmAb22841

1. 1A: XmAb20717 Simultaneously Occupies PD-1 and CTLA-4 Expressed on the Surface of Cells HEK293T cells stably expressing CTLA-4 (Crown Bioscience, Santa Clara, Calif.) were transfected with a pCMV6-AC-GFP vector encoding PD-1 (OriGene, Rockville, Md.). 3 days after transfection, cells were treated with indicated test articles for 30 minutes at 4° C. Following incubation, cells were washed two times and stained with Pacific Blue-conjugated XENP20111 (a one-armed scFv-Fc based on the anti-PD-1 arm from XmAb20717) and APC-conjugated XENP20059 (a one-armed Fab-Fc based on the anti-CTLA-4 arm from XmAb20717) for 30 minutes at 4° C. and assayed by flow cytometry. FIGS. 57A-57B and FIG. 58 show receptor occupancy following treatment with the various test articles as depicted by percentage of various populations of GFP+ (CTLA-4+PD-1+) HEK293T cells with unoccupied CTLA-4 and/or PD-1 receptors as indicated by staining. For example, occupancy of CTLA-4 receptors decreases the percentage of PD-1$^+$CTLA-4$^+$ and PD-1$^-$CTLA-4$^+$ populations and increases the percentage of PD-1$^+$CTLA-4$^-$ and PD-1$^-$ CTLA-4$^-$ populations. FIGS. 57A-57B shows the prevalence of PD-1$^+$CTLA-4$^+$ and PD-1$^-$ CTLA-4$^-$. FIG. 58 shows scatter plots depicting the prevalence of various populations following treatment with 12.5 µg/mL of indicated test articles. The data show that XmAb20717 selectively targets cells simultaneously expressing PD-1 and CTLA-4.

B. Example 2: XmAb20717 Enhances Allogeneic Anti-Tumor Responses in Mice

NOD SCID gamma (NSG) mice were engrafted with KG1A-luc cancer cells on Day 0. On Day 21, human PBMCs were engrafted into the intraperitoneally into the mice. After PBMC engraftment, indicated test articles were dosed weekly by intraperitoneal injection (control mice were dosed with PBS) for 4 weeks (or 4 total doses). Tumor growth was monitored by measuring total flux per mouse using an in vivo imaging system (IVIS® Lumina III) and data are shown (days post 1$^{st}$ dose) in
FIGS. 59A-59B.

C. Example 3: Investigating In Vitro Binding of XmAb22841

1. XmAb22841 Binding to HEK293T Expressing CTLA-4 and LAG-3

HEK293T cells stably expressing CTLA-4 (Crown Bioscience, Santa Clara, Calif.) were transfected with a pCMV6-AC-GFP vector encoding LAG-3 (OriGene, Rockville, Md.). 3 days after transfection, cells were incubated with of the following test articles at the indicated concentrations for 30 minutes at 4° C.: XmAb22841; XENP16433, a bivalent mAb based on the parental done from which the anti-CTLA-4 arm of XmAb22841 was derived; XENP16436, a bivalent mAb based on the parental done from which the anti-LAG-3 arm of XmAb22841 was derived; XENP24893, a one-armed scFv-Fc based on the anti-CTLA-4 arm from XmAb22841; XENP24895, a one-armed Fab-Fc based on the anti-LAG-3 arm from XmAb22841; and XENP15074, a bivalent anti-RSV mAb as a control. Following incubation, cells were washed two times and binding was detected with an anti-human-Fc-A647 conjugated secondary antibody (Jackson Immunoresearch, West Grove, Pa.). MFI indicating binding of test articles to GFP+ cells (i.e. CTLA-4+LAG-3+) are depicted in FIG. 60.

2. Occupancy of CTLA-4 and LAG-3 on HEK293T Expressing CTLA-4 and LAG-3 by XmAb22841

HEK293T cells stably expressing CTLA-4 (Crown Bioscience, Santa Clara, Calif.) were transfected with a pCMV6-AC-GFP vector encoding LAG-3 (OriGene, Rockville, Md.). 3 days after transfection, cells were treated with the following test articles for 30 minutes at 4° C.: XmAb22841, XENP16433, XENP16436, XENP24893, XENP24895, and XENP15074. Following incubation, cells were washed two times and stained with Pacific Blue-conjugated XENP24895 and A647-conjugated XENP23552. FIGS. 61A-61D show receptor occupancy following treatment with the various test articles as depicted by percentage of various populations of GFP+ (CTLA-4+LAG-3+) HEK293T cells with unoccupied CTLA-4 and/or LAG-3 receptors as indicated by staining. For example, occupancy of CTLA-4 receptors decreases the percentage of LAG-3+ CTLA-4+ and LAG-3-CTLA-4+ populations and increases the percentage of LAG-3+CTLA-4- and LAG-3-CTLA-4- populations. FIGS. 62A-62B respectively show the amount of unoccupied LAG-3 and CTLA-4 receptors on GFP+ cells following treatment with test articles as indicated by XENP24895 and XENP23552 binding.

3. XmAb22841 Binding to SEB-Stimulated T Cells

Binding of XmAb22841 to T cells was measured in an SEB-stimulated PBMC assay. Staphylococcal Enterotoxin B (SEB) is a superantigen that causes T cell activation and proliferation in a manner similar to that achieved by activation via the T cell receptor (TCR), including expression of checkpoint receptors such as LAG-3 and CTLA-4. Accordingly, human PBMCs from 6 donors were stimulated with 500 ng/mL SEB for 3 days. Cells were then treated with indicated concentrations of the indicated test articles for 30 minutes. Following incubation, cells were washed and stained with an anti-human-Fc-A647 antibody (Jackson Immunoresearch). MFI indicating binding of test articles to CD3+ T cells are depicted in FIGS. 63A-63F respectively for each donor.

The data show that, in PBMCs from each of the donors, XmAb22841 binds more avidly to CD3+ T cells compared to monospecific controls, demonstrating that binding to human T cells is significantly better by bispecific antibody XmAb22841, where each arm monovalently binds a different antigen, than by monospecific antibodies.

D. Example 4: Investigating Cytokine Release and Immune-Related Gene Expression Profiles Following Treatment with Bispecific Checkpoint Antibodies Human PBMCs were stimulated with 100 ng/mL SEB for 2 days. Following stimulation, cells were washed twice then restimulated with 100 ng/mL SEB and 20 µg/mL indicated test articles. Cell supernatant was collected 24 hours post treatment and assayed for IL-2 and IFNγ by a multiplexed assay on MULTI-SPOT 384-Well Spot plates (Meso Scale Discovery, Rockville, Md.). RNA was extracted from cells and assayed by nCounter® PanCancer Immune Profiling Panel (NanoString Technologies, Seattle, Wash.) which assays 770 target genes covering immune response.

FIG. 64 and FIG. 65 respectively depicts the fold increase in IL-2 and IFNγ following treatment by anti-PD-1 mAb (XENP16432), XmAb20717, and XmAb22841 as well as XmAb22841 in combination with anti-PD-1 mAb, in comparison to anti-RSV mAb (XENP15074). Notably, combination of XmAb22841 with anti-PD-1 mAb resulted in significantly more cytokine release than by either alone, demonstrating the advantage of a triple immune checkpoint blockade. FIG. 66 to FIG. 72 show the fold change in expression of various genes (as determined by Nanostring nCounter®) between the bispecific checkpoint antibodies, anti-PD-1 mAb, and anti-RSV mAb.

E. Example 5: Generation of Anti-PD-1 Clone 1C11

1. Generation and Screening of Anti-PD-1 Hybridoma

To develop additional PD-1 targeting arms, monoclonal antibodies were first generated by hybridoma technology through ImmunoPrecise, through their Standard Method and Rapid Prime Method. For the Standard Method, antigen(s) was injected into 3 BALB/c mice. 7-10 days before being sacrificed for hybridoma generation, the immunized mice received an antigen boost. Antibody titre is evaluated by ELISA on the antigen and the best responding mice are chosen for fusion. A final antigen boost is given 4 days prior to fusion. Lymphocytes from the mice are pooled, purified then fused with SP2/0 myeloma cells. Fused cells are grown on HAT selective Single-Step cloning media for 10-12 days at which point the hybridomas were ready for screening. For the Rapid Prime method, antigen(s) was injected into 3 BALB/c mice. After 19 days, lymphocytes from all the mice are pooled, purified then fused with SP2/0 myeloma cells. Fused cells were grown on HAT selective Single-Step cloning media for 10-12 days at which point the hybridomas were ready for screening. Antigen(s) used were mouse Fc fusion of human PD-1 (huPD-1-mFc), mouse Fc fusion of cyno PD-1 (cynoPD-1-mFc), His-tagged human PD-1 (huPD-1-His), His-tagged cyno PD-1 (cynoPD-1-His) or mixtures thereof.

Anti-PD-1 hybridoma clones generated as described above were subject to two rounds of screening using Octet, a BioLayer Interferometry (BLI)-based method. Experimental steps for Octet generally included the following: Immobilization (capture of ligand or test article onto a biosensor); Association (dipping of ligand- or test article-coated biosensors into wells containing serial dilutions of the corresponding test article or ligand); and Dissociation (returning of biosensors to well containing buffer) in order to determine the affinity of the test articles. A reference well containing buffer alone was also included in the method for background correction during data processing.

For the first round, anti-mouse Fc (AMC) biosensors were used to capture the clones with dips into 500 nM of bivalent human and cyno PD-1-Fc-His. For the second round, clones identified in the first round that were positive for both human and cyno PD-1 were captured onto AMC biosensors and dipped into 500 nM monovalent human and cyno PD-1-His.

2. Characterization of Clone 1C11

One hybridoma clone identified in Example 1 was clone 1C11. DNA encoding the VH and VL of hybridoma clone 1C11 were generated by gene synthesis and subcloned using standard molecular biology techniques into expression vector pTT5 containing human IgG1 constant region with E233P/L234V/L235A/G236del/S267K substitutions to generate XENP21575, sequences for which are depicted in FIG. 9.

3. PD-L1 Blocking with Clone 1C11

Blocking of checkpoint receptor/ligand interaction is necessary for T cell activation. The blocking ability of XENP21575 was investigated in a cell binding assay, with XENP16432 (anti-PD-1 mAb with variable regions of nivolumab), XENP21461 (anti-PD-1 mAb with variable regions of pembrolizumab), and XENP15074 (anti-RSV Mab with variable regions of motavizumab) as controls. HEK293T cells transfected to express PD-1 were incubated with XENP21575, as well as control antibodies. Following incubation, a murine Fc fusion of PD-L1 was added and allowed to incubate. Binding of PD-L1-mFc to HEK293T cells was detected with an anti-murine IgG secondary antibody, data for which are depicted in FIG. 10. The data shows that PD-L1 blocking by XENP21575 was similar to blocking by XENP16432 and XENP21461.

4. T Cell Surface Binding of Clone 1C11

Binding of anti-PD-1 clone 1C11 to T cells was measured in an SEB-stimulated PBMC assay. Staphylococcal Enterotoxin B (SEB) is a superantigen that causes T cell activation and proliferation in a manner similar to that achieved by activation via the T cell receptor (TCR), including expression of checkpoint receptors such as PD-1. Human PBMCs were stimulated with 100 ng/mL for 3 days. Following stimulation, PBMCs were incubated with the indicated test articles at indicated concentrations at 4° C. for 30 min. PBMCs were stained with anti-CD3-FITC (UCHT1) and APC labeled antibody for human immunoglobulin κ light chain. The binding of the test articles to T cells as indicated by APC MFI on FITC+ cells is depicted in FIG. 11.

5. T Cell Activation by Clone 1C11

T cell activation by clone 1C11, as indicated by cytokine secretion, was investigated in an SEB-stimulated PBMC assay. Human PBMCs were stimulated with 500 ng/mL SEB for 2 days. Cells were then washed twice in culture medium and stimulated with 500 ng/mL SEB in combination with indicated amounts of indicated test articles for 24 hours. Supernatants were then assayed for IL-2 and IFNγ by cells, data for which are depicted in FIG. 12A-12B.

6. Humanization of Clone 1C11

Clone 1C11 humanized using string content optimization (see, e.g., U.S. Pat. No. 7,657,380, issued Feb. 2, 2010). DNA encoding the heavy and light chains were generated by gene synthesis and subcloned using standard molecular biology techniques into the expression vector pTT5. Sequences for illustrative humanized variants of clone 1C11 in bivalent antibody format are depicted in FIGS. 13A-13C.

The affinity of XENP22553 was determined using Octet as generally described in Examples. In particular, anti-human Fc (AHC) biosensors were used to capture the test article with dips into multiple concentrations of histidine-tagged PD-1. The affinity result and corresponding sensorgram are depicted in FIG. 14.

7. Stability Optimization of a Humanized Variant of Clone 1C11 in the scFv Format The variable regions of anti-PD-1 clone 1C11 humanized variant H3L3 (as in XENP22553) were engineered for improved stability (while maintaining affinity) in the context of an scFv, for example, for use in a bispecific antibody. DNA encoding an scFv with the variable heavy and variable light regions of XENP22553 were generated by gene synthesis and subcloned using standard molecular biology techniques into the expression vector pTT5. The C-terminus of the scFv included a polyhistidine tag for purification. A library of scFv variants was then constructed by standard mutagenesis, illustrative sequences for which are depicted in FIG. 15A-15T (although polyhistidine tags have been removed).

Stability of scFv-His was evaluated using Differential Scanning Fluorimetry (DSF). DSF experiments were performed using a Bio-Rad CFX Connect Real-Time PCR Detection System. Proteins were mixed with SYPRO Orange fluorescent dye and diluted to 0.2 mg/mL in PBS. The final concentration of SYPRO Orange was 10X. After an initial 10 minute incubation period of 25° C., proteins were heated from 25 to 95° C. using a heating rate of 1° C./min. A fluorescence measurement was taken every 30 sec. Melting temperatures (Tm) were calculated using the instrument software. Stability results are depicted in FIG. 17A-17Q. The data show that melting temperature (Tm) increased by up to 19° C.

To determine the affinity of the variants, the variable regions from the scFvs were formatted as Fabs in a bivalent IgG1 with E233P/L234V/L235A/G236del/S267K substitutions. Illustrative sequences are depicted in FIGS. 16A-16H. DNA encoding the heavy and light chains were generated by gene synthesis and subcloned using standard molecular biology techniques into pTT5 expression vector containing IgG1 constant regions, and transiently transfected into HEK293E cells. Affinity screens of supernatant were performed using Octet. Anti-human Fc (AHC) biosensors were used to capture 1:2 dilutions of each supernatant to a density of 2.0 nm, and dipped into PD-1-His for KD determination. Affinity results are depicted in FIG. 17A-17Q.

8. Affinity Optimization of a Humanized Variant of Done 1C11 in the Fab Format

The variable regions of anti-PD-1 clone 1C11 humanized variant H3L3 (as in XENP22553) was generated in the Fab format and engineered for optimized affinity, for example, for use as a bivalent, monospecific antibody or for use in a bispecific antibody.

In a first library, variable heavy and light regions from scFvs generated in Example 4D found to have increased affinity were combined to generate bivalent IgG1 format with E233P/L234V/L235A/G236del/S267K substitutions, illustrative sequences for which are depicted in FIGS. 20A-20L. DNA encoding the heavy and light chains were generated by gene synthesis and subcloned using standard molecular biology techniques into pTT5 expression vector containing IgG1 constant regions, and transiently transfected into HEK293E cells. Antibodies were purified by Protein A chromatography, and affinity screens were performed using Octet. AHC biosensors were used to capture antibodies, and dipped into multiple concentrations of PD-1-His for KD determination. Affinity results are depicted in FIG. 19.

In a second library, additional variants were constructed by standard mutagenesis on the expression vectors encoding either the heavy or light chains of XENP22553. Illustrative sequences for the additional heavy chain and light chain variants are depicted in FIGS. 20A-20L and FIGS. 21A-21G. Expression vectors containing DNA encoding the additional heavy chain variants and DNA encoding the light chain of XENP22553, or DNA encoding the heavy chain of XENP22553 and DNA encoding the additional light chain variants were transiently transfected into HEK293E cells. Affinity screens of supernatant were performed using Octet. Anti-human Fc (AHC) biosensors were used to capture 1:2 dilutions of each supernatant to a density of 2.0 nm, and dipped into PD-1-His for KD determination. Affinity results are depicted in FIGS. 22A-22E. In a follow-up screen, DNA encoding selected antibodies were transfected into HEK293E cells, and antibodies were purified by Protein A chromatography and screened for affinity using Octet. Anti-human Fc (AHC) biosensors were used to capture antibodies, and dipped into multiple concentrations of PD-1-His for KD determination, results for which are depicted in FIG. 23.

Another library was generated as generally described above. Illustrative sequences for resulting antibodies are depicted in FIGS. 24A-24J. DNA encoding selected antibodies were transfected into HEK293E cells, and antibodies were purified by Protein A chromatography and screened for affinity using Octet. Anti-human Fc (AHC) biosensors were used to capture antibodies, and dipped into multiple concentrations of PD-1-His for KD determination, results for which are depicted in FIG. 25.

9. Affinity Screen of Affinity Optimized 1C11 Variants as Determined by Biacore

Affinity of 1C11 variants generated as described above and control mAbs based on nivolumab (XENP16432) and pembrolizumab (XENP21461) were determined using Biacore, a surface plasmon resonance (SPR)-based technology. Experimental steps for Biacore generally included the following: Immobilization (capture of ligand onto a sensor chip); Association (flowing of various concentrations of analyte over sensor chip); and Dissociation (flowing buffer over the sensor chips) in order to determine the affinity of the test articles. A reference flow with buffer alone was also included in the method for background correction during data processing. Binding affinities and kinetic rate constants were obtained by analyzing the processed data using a 1:1 binding model. In particular, anti-PD-1 mAbs were captured onto Protein A sensor chips, and then multiple concentrations of histidine-tagged human PD-1 or histidine tagged cyno PD-1 were flowed over the sensor chips. The resulting dissociation constants (KD) are depicted in FIG. 26.

10. T Cell Surface Binding of Affinity Optimized 1C11 Variants

Binding of affinity optimized 1C11 variants to T cells was measured in an SEB-stimulated PBMC assay. Human PBMCs were stimulated with 500 ng/mL SEB for 3 days. Following stimulation, PBMCs were incubated with the indicated test articles at indicated concentrations 30 min. PBMCs were stained with anti-CD3-FITC (UCHT1) and A647 labeled antibody for human Fc. The binding of the test articles to T cells as indicated by A647 MFI on FITC+ cells is depicted in FIG. 27.

11. Blocking of PD-L1 and PD-L2 Binding to PD-1 by Affinity Optimized 1C11 Variants The ability of affinity optimized 1C11 variants to block PD-L1 and PD-L2 binding to PD-1 was investigated in a tandem epitope binning assay using the Octet HTX instrument. Experimental steps for Octet were as generally described in Examples. In particular, murine Fc fusion of human PD-1 was loaded onto AMC (anti-mouse Fc capture) biosensors prior to dipping into 100 nM of a first test article (as indicated on the left side of the table depicted in FIG. 28) and then into 100 nM of a second test article (as indicated on the top of the table depicted in FIG. 28). Test articles included affinity optimized variants of humanized done 1C11 and Fc fusions of PD-L1 and PD-L2 (RnD Systems, Minneapolis, Minn.). The BLI-response of each test article pair was normalized against the response from dipping the biosensor into HBS-EP buffer and then dipping into the test article. The normalized BLI-responses of each pair of test articles are depicted in. If the second test article provided a normalized BLI-response less than 0.4, the binding of the second test article to PD-1 was considered to be blocked by the first test article. If the second test article provided a normalized BLI-response between 0.4 and 0.6, the blocking is considered borderline. If the second test article provided a normalized BLI-response greater than 0.6, the binding of the second test article to PD-1 was considered to not be blocked by the first test article. The data show that each of the anti-PD-1 1C11 variants blocked PD-L1 and PD-L2 binding to PD-1.

F. Example 6: Further Engineering Affinity Optimized 1C11 Variants

We engineered further 1C11 variants to modulate PD-1 affinity using the aforementioned approaches as well as by mixing and matching substitutions that appeared to best modulate affinity. In addition, we combined variant 1C11 variable heavy chains with variant 1C11 variable light chains demonstrating favorable affinity modulation. Illustrative sequences for resulting antibodies are depicted in FIGS. 40A-40BB.

1. Affinity Screen of Additional Affinity-Engineered 1C11 Variants

Affinity of the additional affinity-engineered 1C11 variants were determined using Octet, as generally described above. In particular, AHC biosensor was used to capture the 1C11 variants and dipped into multiple concentrations of His-tagged human PD-1 (as well as His-tagged cynomolgus PD-1 for the data depicted in FIG. 41). The resulting dissociation constants (KD), association rates (ka), and dissociation rates (kd) are depicted in FIG. 41 to FIG. 45, where each Figure depicts separate experimental sets.

2. Induction of Cytokine Secretion by 1C11 Variants in an SEB-Stimulated PBMC Assay While there was technical variability between experiments as well as between data obtained from Octet or Biacore, the affinity of 1C11_H3L3 (as determined by Octet) was generally in the range of 15-19 nM (from 4/6 experiments). From the various rounds of engineering, we obtained 1C11 variants having much tighter affinities (e.g. XENP26940 having affinity ranging from 0.51-0.74 nM; and XENP28652 having an affinity of 0.77 nM as determined by Octet) as well as variants having much weaker affinities (e.g. XENP26928 having an affinity of 333 nM as determined by Octet) for human PD-1. Accordingly, we investigated T cell activation by the variants with differing affinities, as indicated by cytokine secretion, in an SEB-stimulated PBMC assay. PBMC from 18 unique donors were stimulated with 100 ng/mL SEB for 2 days. Cells were then washed and restimulated with SEB and 20 µg/mL of the test articles. Data depicting IFNγ and IL-2 secretion are depicted respectively in FIG. 46 and FIG. 47. The data suggest a correlation between activity of the 1C11 variants and their affinity as indicated by the weaker binding affinity of XENP26928 and a corresponding weaker induction of cytokine secretion.

In summary, we identified novel anti-PD-1 mAb 1C11, which when humanized as 1C11_H3L3 (XENP22533) has a similar affinity compared to an anti-PD-1 mAb XENP16432 based on nivolumab (respectively 8.6 nM and 4.5 nM as determined by Biacore; respectively –18 nM and 10 nM as determined by Octet). Despite the similar affinity, XENP22533 binds T cells more tightly than XENP16432 as depicted in FIG. 11. We engineered XENP22533 to produce variants with modulated affinities over two orders of magnitude toward PD-1 as measured by Octet. This "affinity ladder" should prove useful in identifying the optimal affinity toward PD-1 that can best navigate the complex physiological behaviors of PD-1 receptor recycling, antibody: antigen complex lifetime, and antibody serum half-life. These factors will be explored in future in vivo mouse tumor models.

G. Example 7: Triple Checkpoint Blockade with XmAb22841 and αPD-1 Enhances Cytokine Secretion from SEB-Stimulated Cells Human PBMCs were stimulated with 100 ng/mL SEB for 2 days. Cells were washed two times and restimulated with 100 ng/mL SEB and 20 µg/mL indicated test articles for 24 hours. Cell supernatants were collected and assayed for IFNγ and IL-2 secretion as depicted in FIG. 29 and FIG. 30. The data show that triple checkpoint blockade enabled by a combination of XmAb22841 and XENP16432 (a bivalent αPD-1 mAb with ablated effector function based on nivolumab) enhance cytokine secretion beyond either XENP16432 or XmAb22841 alone. Notably, the combination of XmAb22841 and XENP16432 enhances cytokine secretion to a similar level as triple checkpoint blockade by a combination of XENP16432, XENP16433 (a bivalent αCTLA-4 mAb with ablated effector function based on ipilimumab), and XENP16436 (a bivalent αLAG-3 mAb with ablated effector function based on 25F7).

H. Example 8: Avidity of XmAb22841 is Responsible for Cytokine Release from MLR PBMCs from 2 unique donors were mixed (400,000 cells/donor) and incubated with the 20 µg/mL of the indicated test articles for 5 days. Following incubation, cells were assayed for IFNγ as depicted in FIG. 31. In a similar experiment, mixed PBMCs were incubated with various concentrations of indicated test articles for 5 days, and fold induction of IFNγ over PBS are depicted in FIG. 32. The data show that XmAb22841 enhances IFNγ secretion beyond a combination of XENP24895 (one-arm monovalent mAb based on anti-LAG-3 arm of XmAb22841) and XENP24893 (one-arm monovalent mAb based on anti-CTLA-4 arm of XmAb22841) demonstrating that avidity enabled by bivalent binding is necessary for enhancing cytokine release.

I. Example 9: Triple Checkpoint Blockade with XmAb22841 and αPD-1 Enhance GVHD in NSG Mice NOD SCID gamma (NSG) mice (10 per group) were engrafted via IV-OSP with 10×106 human PBMCs on Day 0. On Day 1, mice were dosed with XENP26842 (a bivalent αPD-1 mAb based on nivolumab with ablated effector function and M428L/N434S Xtend mutations; sequence depicted in FIG. 33), XmAb22841, a combination of XmAb22841 and XENP16432, or PBS for 4 weeks (4 total doses). Blood was drawn on Day 7, 14, and 21 to count various lymphocyte populations as depicted in FIG. 34 (for Day 14) and serum concentrations of IFNγ as depicted in FIG. 35 (for Day 7).

J. Example 10: Triple Checkpoint Blockade with XmAb22841 and αPD-1 Enhances Anti-Tumor Response in Mice NOD SCID gamma (NSG) mice (10 per group) were engrafted intradermally with 3×106 pp65-expressing MCF-7 cells in the rear flank on Day–14. On Day 0, mice were engrafted intraperitoneally with 5×106 human PBMCs from an HLA matched CMV+ donor that screened positive for T cell pp65 reactivity (or PBS for control mice). Mice were treated weekly with XENP16432, XmAb22841, a combination of XmAb22841 and XENP16432, or PBS (for control mice) for 4 weeks (4 total doses). Tumor volumes were monitored by caliper measurements, data for which are shown (days post 1st dose) in FIGS. 36A-36B. Blood was drawn on Day 7, 12, 19, and 26 and analyzed by flow cytometry to count various lymphocyte populations as depicted in FIGS. 37A-37D. The data show that lymphocyte counts (in particular CD8+ T cells) were similar with or without the various checkpoint inhibitors. However, treatment with the various test articles resulted in notably decreased tumor volume indicating enhanced anti-tumor response from de-repression of T cell activity by checkpoint blockade. Furthermore, the data show that triple checkpoint blockade enabled by the combination treatment with XmAb22841 (targeting CTLA-4 and LAG-3) and XENP16432 (targeting PD-1) synergistically enhanced anti-tumor response over treatment with either XmAb22841 or XENP16432 alone.

K. Example 11: Anti-PD-1 mAb 1C11 Enhances GVHD in PBMC-Engrafted NSG-Mice

In a GVHD study, we investigated the effect of humanized anti-PD-1 mAb 1C11_H3L3 (XENP22553). NSG mice were engrafted i.v. with 10×106 human PBMCs on Day 0, followed by treatment on Days 1, 8, 15, and 21 with the following test articles: PBS control, XENP16432 (an anti-PD-1 antibody based on nivolumab with E233P/L234V/L235A/G236del/S267K ablation variants), and XENP22553. FIG. 38 depicts the change in body weight of mice (as a percentage of initial body weight) over time, and FIGS. 39A-39C depicts human CD45+ cell, CD4+ T cell, and CD8+ T cell counts in mice blood over time.

L. Example 12: Xtend Fc Domain Extends the Half-Life of Anti-PD-1 x Anti-CTLA-4 Bispecific Antibody in hFcRn Transgenic Mice Tg276 transgenic hFcRn mice (hemizygous for hFcRn; n=5) were treated with 2 mg/kg XmAb20717 or XENP20053 (non-Xtend analog of XmAb20717) on Day 0. Whole blood samples were collected 1 hour post-treatment and on Days 2, 5, 8, 12, 15, 19, 22, 16, 29, 33, and 35. Test article concentration was detected using human PD-1 and human CTLA-4 antigen. PK interpretative analysis was performed using Phoenix WinNonlin software (Version 6.4.0.768) with PK parameters for non-compartmental analysis of free drug serum concentration versus time. Pharmacokinetic profile of XmAb20717 and XENP20053 in are depicted in FIGS. 76A-76B; half-life are depicted in FIG. 77; and Cmax are depicted in FIG. 78. Additional PK parameters are summarized in FIG. 79.

M. Example 13: XmAb20717 does not Induce Cytokine Release in Naive T Cells P BMCs were thawed overnight and treated with 20 μg/mL of indicated soluble or plate bound test articles for 24 hours. Anti-CD3 antibody was done OKT3. Cell supernatants were then collected and assayed with V-PLEX Proinflammatory Panel 1 Human Kit (Meso Scale, Rockville, Md.). Each point represents a unique human donor tested in technical singlet. Paired t tests were used to determine statistical significance (n.s. signifies a p-value >0.05). The data depicted in FIGS. 80A-80J show that XmAb20717 does not induce cytokine release (A: IFNγ; B: IL-1ß; C: IL-2; D: IL-4; E: IL-8; F: IL-6; G: IL-10; H: IL-12p70; I: IL-13; J: TNFα) in naive T cells.

N. Example 14: Further Characterization of Binding by XmAb20717

1. XmAb20717 Binds Human and Cynomolgus CTLA-4 and PD-1

Binding of XmAb20717 to human and cynomolgus CTLA-4 and PD-1 was characterized using Octet, a BioLayer Interferometry (BLI)-based method. Binding affinities were obtained by analyzing the processed data globally using a 1:1 binding model. Octet sensorgrams are shown in FIGS. 81A-81B and FIGS. 82A-82B. The resulting equilibrium dissociation constants (KD), association rate constants (ka), and dissociation constants (kd) are presented in FIG. 83. Affinities for both human and cynomolgus CTLA-4 were measured at approximately 4.1 and 23 nM respectively. Binding affinities for human and cyno PD-1 were 1.4 and 5.5 nM respectively.

2. XmAb20717 Competes for Binding with Ligands of CTLA-4 and PD-1

Binding of CD80 and CD86 to CTLA-4 with and without XmAb20717 and binding of PD-L1 and PD-L2 to PD-1 with and without XmAb20717 was characterized using Octet, a BioLayer Interferometry (BLI)-based method. Octet sensorgrams are shown in FIG. 84 and FIG. 85. In all cases, 100 nM CTLA-4 and 100 nM PD-1 show a binding signal with their ligands (CD80/CD86 and PDL1/PDL2 respectively). In the presence of excess XmAb20717, pre-incubated with CTLA-4 or PD-1 at room temperature for 1 hour prior to the experiment, there is no binding signal observed to any ligands due to the competition of XmAb20717 with CTLA-4 and PD-1 for their ligands CD80/CD86 and PD-L1/PD-L2, respectively.

3. XmAb20717 does not Bind FcγR

Binding of XmAb20717 to human, cynomolgus, and mouse FcγRs was characterized using Octet, a BioLayer Interferometry (BLI)-based method. A comparator antibody was also tested using similar methods: anti-CD19 antibody with a native IgG1 constant region. Octet sensorgrams are shown in FIG. 86 to FIG. 88. While the expected binding patterns for a native human IgG1 antibody were observed for the comparator antibody, no binding for any of the FcγRs was detected for XmAb20717.

4. XmAb20717 Binds Human, Cynomolgus, and Mouse FcRn at pH 6.0

Binding of XmAb20717 to human, cynomolgus, and mouse FcRn at pH 6.0 was characterized using Octet, a BioLayer Interferometry (BLI)-based method. A comparator antibody was also tested using similar methods: XENP20053, an anti-PD1 x anti-CTLA4 bispecific antibody containing the same variable regions and engineered constant regions as XmAb20717 but lacking the amino acid substitutions XmAb20717 contains for enhancing FcRn binding. Binding affinities were obtained by analyzing the processed data globally using a 1:1 Langmuir model. Octet sensorgrams are shown FIG. 90. The resulting equilibrium dissociation constants (KD) are presented FIG. 89. Affinities measured for XmAb20717 are tighter than those measured for the comparator, indicating that the Fc substitutions contained in XmAb20717 improve the affinity for FcRn at pH 6.0, the physiologically relevant pH for endosome trafficking.

5. XmAb20717 Simultaneously Binds PD-1 and CTLA-4

Binding of XmAb20717 to both PD1 and CTLA4 antigens was tested using an in-tandem dip approach using BLI technology on the Octet HTX instrument. First, biosensors were loaded with PD-1, then dipped into either XmAb20717 or buffer as a control, and finally, into CTLA-4. FIG. 91 shows the binding sensorgrams which indicate that XmAb20717 can bind to both antigens simultaneously. The XmAb20717 sensorgram continues to increase in signal during the final CTLA4 antigen dip while the control sensorgram with no XmAb20717 loaded remains flat.

O. Example 15: Further In Vitro Characterization of XmAb20717

1. XmAb20717 Promotes Greater IL-2 Secretion from SEB-Stimulated PBMCs Compared to an Anti-PD-1 Antibody PBMCs from 22 unique donors were stimulated with 500 ng/mL SEB for 48 h.

Cells were then washed two times in culture medium and re-stimulated with 500 ng/mL SEB plus 20 μg/mL of indicated test articles for 18 h. Culture supernatants were collected and assayed for IL-2 concentration by ELISA, data for which are depicted in FIG. 92.

2. XmAb20717 Suppresses IL-2 Secretion from Unstimulated Human PBMCs Compared to an Anti-PD-1 Antibody Unstimulated PBMCs from 22 unique donors were treated with 20 μg/mL of indicated test articles for 72 h. Culture supernatants were collected and assayed for IL-2 concentration by ELISA, data for which are depicted in FIG. 93.

3. XmAb20717 Promotes Greater IL-2 Secretion from Human Lymphocytes Compared to a Mixture of Component Arms that Comprises XmAb20717

PBMCs from 22 unique donors were stimulated with 500 ng/mL SEB for 48 hours (data from XENP15074 and XENP20717 replicated from FIG. 92). Cells were then washed two times in culture medium and re-stimulated with 500 ng/mL SEB and 20 μg/mL of indicated test articles for 18 hours. Culture supernatants were collected and assayed for IL-2 abundance by ELISA, data for which are depicted in FIG. 94.

P. Example 16: Further Analysis of In Vivo Studies in Murine Models

We further analyzed data from a GVHD study described in an earlier example. FIG. 95 depicts the mean change in body weight of mice (as a percentage of initial body weight) over time. FIG. 96 depicts the survival of mice over time. FIG. 97 depicts the mean IFNγ level over time in the mice. FIGS. 98A-98C depicts human CD45+ cell, CD4+ T cell, and CD8+ T cell counts in mice blood over time.

Q. Example 17: XmAb20717 Combines with PD-L1 Blockade in a GVHD Model

In another GVHD study, we investigated the combination of XmAb20717 with PD-L1 blockade (anti-PD-L1 mAb). NSG mice were engrafted i.v. with 10×106 human PBMCs on Day 0, followed by treatment on Days 1, 8, 15, and 21 with the following test articles: PBS control, XmAb20717, XENP16434 (an anti-PD-L1 antibody based on atezolizumab with E233P/L234V/L235A/G236del/S267K ablation variants; sequences depicted in FIG. 99), and XmAb20717 in combination with XENP16434. FIG. 100 depicts the change in body weight of mice (as a percentage of initial body weight) over time, FIG. 101 depicts the survival of mice over time, and FIGS. 102A-102C depicts human CD45+ cell, CD4+ T cell, and CD8+ T cell counts in mice blood on Day 14.

R. Example 18: Interaction of XmAb20717 with Comparator Anti-PD-1 Antibodies To determine if pembrolizumab or nivolumab can interfere with the binding activity of XmAb20717, 293T cells stably expressing PD-1-GFP and CTLA-4 were treated with nivolumab or pembrolizumab (16-point 2-fold serial dilutions beginning at 100 μg/mL) for 30 minutes at 4° C. The cells were washed twice with 200 4 ice-cold FACS buffer (3% FBS in PBS), and stained with XmAb20717 conjugated to Alexa647 (16 point 3-fold serial dilutions beginning at 200 μg/mL) on ice for 30 minutes. Cells were then analyzed by FACS for binding by XmAb20717, data for which are depicted in FIG. 103 and FIG. 104. Data depicted in FIG. 103 indicate that nivolumab does not significantly interfere with binding of XmAb20717 to PD-1+CTLA-4+ cells. Data depicted in FIG. 104 indicate that pembrolizumab does interfere with the binding of XmAb20717 to PD-1+CTLA-4+ cells; however, data depicted in FIG. 105 indicate that interference by pembrolizumab can be overcome with high concentrations of XmAb20717. This suggests that XmAb20717 may be administered in a subject in combination with or subsequent to treatment with nivolumab or pembrolizumab.

S. Example 19: XmAb22841 does not Induce Cytokine Release in Naive T Cells and is not Superagonistic PBMCs were thawed overnight and treated with 20 μg/mL of indicated soluble or plate bound test articles for 24 hours. Anti-CD3 antibody was done OKT3. Cell supernatants were then collected and assayed with V-PLEX Proinflammatory Panel 1 Human Kit (Meso Scale, Rockville, Md.). Each point represents a unique human donor tested in technical singlet. Paired t tests were used to determine statistical significance (n.s. signifies a p-value >0.05). The data depicted in FIGS. 106A-106J show that XmAb22841 does not induce cytokine release (A: IFNγ; B: IL-18; C: IL-2; D: IL-4; E: IL-8; F: IL-6; G: IL-10; H: IL-12p70; I: IL-13; J: TNFα) in naive T cells.

Superagonstic properties of XmAb22841 was also assessed by air-drying per the Stebbings protocol (Stebbings R. et al. 2007). Air-drying of test articles was achieved by drying in a SpeedVac™ for 2 hours at room temperature. Human PBMCs were treated for 24 hours with 10 μg of air-dried XmAb22841, and activity was compared to 10 μg of air-dried XENP15074 (anti-RSV negative isotype control) or the superagonist TGN1412 (XENP29154; sequences for which are depicted in FIG. 107). TGN1412 did not possess any activity when bound to the assay plate using an aqueous adsorption method; however, air-dried TGN1412 promoted IFNγ, IL-1β, IL-2, IL-4, IL-6, IL-8, IL-10, IL-13, and TNF cytokine secretion from unstimulated human PBMC. In comparison, the cytokine levels in PBMCs treated with air-dried XmAb22841 remained similar to the negative control of air-dried XENP15074 (data shown in FIGS. 108A-108J).

T. Example 20: Further Characterization of Binding by XmAb22841

1. XmAb22841 Binds Human and Cynomolgus CTLA-4 and LAG-3

Binding of XmAb22841 to human and cynomolgus CTLA-4 and LAG-3 was characterized using Octet, a Bio-Layer Interferometry (BLI)-based method. Binding affinities were obtained by analyzing the processed data globally using a 1:1 binding model. Octet sensorgrams are shown in FIGS. 109A-109B and FIGS. 110A-11B. The resulting equilibrium dissociation constants (KD), association rate constants (ka), and dissociation constants (kd) are presented in FIG. 111. Affinities for both human and cynomolgus CTLA-4 were measured at approximately 4.6 and 17.6 nM respectively. Binding affinities for human and cyno LAG-3 were 1.4 and 1.3 nM respectively.

2. XmAb22841 Competes for Binding with Ligands of CTLA-4 and LAG-3

Binding of CD80 and CD86 to CTLA-4 with and without XmAb22841 was characterized using Octet, a BioLayer Interferometry (BLI)-based method. Octet sensorgrams are shown in FIG. 112. In both cases, 100 nM CTLA-4 show a binding signal with their ligands (CD80/CD86). In the presence of excess XmAb22841, pre-incubated with CTLA-4 at room temperature for 1 hour prior to the experiment, there is no binding signal observed to any ligands due to the competition of XmAb22841 with CTLA-4 for its ligands CD80/CD86.

Soluble LAG-3 binds to MHC Class II expressed on the surface of cancer del lines. Therefore, we determined if XmAb22841 can block soluble LAG-3 binding to MHCII+ Ramos cells when complexed to XmAb22841. As depicted in FIG. 113, XmAb22841 dose-dependently blocked binding of soluble LAG-3 antigen to Ramos cells.

3. XmAb22841 does not Bind FcγR

Binding of XmAb22841 to human, cynomolgus, and mouse FcγRs was characterized using Octet, a BioLayer Interferometry (BLI)-based method. A comparator antibody was also tested using similar methods: anti-CD19 antibody with a native IgG1 constant region. Octet sensorgrams are shown in FIG. 114 to FIG. 116. While the expected binding patterns for a native human IgG1 antibody were observed for the comparator antibody, no binding for any of the FcγRs was detected for XmAb22841.

4. XmAb22841 Binds Human, Cynomolgus, and Mouse FcRn at pH 6.0

Binding of XmAb22841 to human, cynomolgus, and mouse FcRn at pH 6.0 was characterized using Octet, a BioLayer Interferometry (BLI)-based method. A comparator antibody was also tested using similar methods: XENP22602, an anti-CTLA-4 x anti-LAG-3 bispecific antibody containing the same variable regions and engineered constant regions as XmAb22841 but lacking the amino acid substitutions XmAb22841 contains for enhancing FcRn binding. Binding affinities were obtained by analyzing the processed data globally using a 1:1 Langmuir model. Octet sensorgrams are shown FIG. 118. The resulting equilibrium dissociation constants (KD) are presented FIG. 117. Affinities measured for XmAb22841 are tighter than those measured for the comparator, indicating that the Fc substitutions contained in XmAb22841 improve the affinity for FcRn at pH 6.0, the physiologically relevant pH for endosome trafficking.

5. XmAb22841 Simultaneously Binds CTLA-4 and LAG-3 approach using BLI technology on the Octet HTX instrument. First, biosensors were loaded with LAG3, then dipped into either XmAb22841 or buffer as a control, and finally, into CTLA4. FIG. 119 shows the binding sensorgrams which indicate that XmAb22841 can bind to both antigens simultaneously. The XmAb22841 sensorgram continues to increase in signal during the final CTLA4 antigen dip while the control sensorgram with no XmAb22841 loaded remains flat.

U. Example 21: Further Analysis of GVHD by XmAb22841 and PD-1 Blockade

We further analyzed data from a GVHD study investigating triple-checkpoint blockade by XmAb22841 and PD-1 blockade described in an earlier example. FIG. 120 depicts the mean change in body weight of mice (as a percentage of initial body weight) over time. FIG. 121 depicts the survival of mice over time. FIGS. 122A-122B depicts the IFNγ and IL-10 concentrations on Days 7 and 14.

SEQUENCE LISTING

The patent contains a lengthy "Sequence Listing" section. A copy of the "Sequence Listing" is available in electronic form from the USPTO web site (https://seqdata.uspto.gov/?pageRequest=docDetail&DocID=US11312770B2). An electronic copy of the "Sequence Listing" will also be available from the USPTO upon request and payment of the fee set forth in 37 CFR 1.19(b)(3).

What is claimed is:

1. A method for treating cancer comprising administering to a patient in need thereof:
   a) a heterodimeric bispecific antibody that binds CTLA-4 and LAG-3; and
   b) an anti-PD-1 antibody,
   wherein said heterodimeric bispecific antibody comprises:
   i) a first monomer comprising
      A) a single chain Fv domain (scFv) that binds human CTLA-4, wherein said scFv domain comprises:
      1) a first variable heavy domain (VH1);
      2) a scFv linker; and
      3) a first variable light domain (VL1); and
      B) a first variant Fc domain;
   ii) a second monomer comprising a VH2-CH1-hinge-CH2-CH3 heavy chain, wherein VH2 is a second variable heavy domain and CH2-CH3 is a second variant Fc domain; and
   c) a light chain comprising a second variable light domain (VL2) and a constant light domain (CL);
   wherein said VH2 and said VL2 bind LAG-3, wherein said VH1 comprises a vhCDR1 comprising the amino acid sequence of SEQ ID NO:35616, a vhCDR2 comprising the amino acid sequence SEQ ID NO:35617 and a vhCDR3 comprising the amino acid sequence of SEQ ID NO:35618, said VL1 comprises a vlCDR1 comprising the amino acid sequence of SEQ ID NO:35619, a vlCDR2 comprising the amino acid sequence SEQ ID NO:35620 and a vlCDR3 comprising the amino acid sequence of SEQ ID NO:35621, and wherein said VH2 comprises a vhCDR1 comprising the amino acid sequence of SEQ ID NO:35609, a vhCDR2 comprising the amino acid sequence SEQ ID NO:35610 and a vhCDR3 comprising the amino acid sequence of SEQ ID NO:35611, said VL2 comprises a vlCDR1 comprising the amino acid sequence of SEQ ID NO:35624, a vlCDR2 comprising the amino acid sequence SEQ ID NO:35625 and a vlCDR3 comprising the amino acid sequence of SEQ ID NO:35626.

2. A method according to claim 1, wherein said VH1 comprises SEQ ID NO:35613, VL1 comprises SEQ ID NO:35614, VH2 comprises SEQ ID NO:35608 and VL2 has SEQ ID NO:35623.

3. A method for treating cancer comprising administering to a patient in need thereof:
   a) a heterodimeric bispecific antibody that binds CTLA-4 and LAG-3; and
   b) an anti-PD-1 antibody,
wherein said heterodimeric bispecific antibody comprises:
   i) a first monomer comprising
      A) a single chain Fv domain (scFv) that binds human CTLA-4, wherein said scFv domain comprises:
         1) a first variable heavy domain (VH1);
         2) a scFv linker; and
         3) a first variable light domain (VL1); and
      B) a first variant Fc domain;
   ii) a second monomer comprising a VH2-CH1-hinge-CH2-CH3 heavy chain, wherein VH2 is a second variable heavy domain and CH2-CH3 is a second variant Fc domain; and
   c) a light chain comprising a second variable light domain (VL2) and a constant light domain (CL);
wherein said VH2 and said VL2 bind LAG-3,
wherein said first monomer comprises SEQ ID NO:35612, said second monomer comprises SEQ ID NO:35607 and said light chain comprises SEQ ID NO:35622.

4. A method for treating cancer comprising administering to a patient in need thereof:
   a) a heterodimeric bispecific antibody comprising:
      i) a first monomer comprising SEQ ID NO:35612;
      ii) a second monomer comprising SEQ ID NO:35607; and
      iii) a light chain comprising SEQ ID NO:35622; and
   b) an anti-PD-1 antibody.

* * * * *

UNITED STATES PATENT AND TRADEMARK OFFICE
CERTIFICATE OF CORRECTION

PATENT NO. : 11,312,770 B2
APPLICATION NO. : 16/184895
DATED : April 26, 2022
INVENTOR(S) : Bernett et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 238 days.

Signed and Sealed this
Eighteenth Day of February, 2025

Coke Morgan Stewart
*Acting Director of the United States Patent and Trademark Office*